(12) United States Patent
Hacohen et al.

(10) Patent No.: US 11,939,637 B2
(45) Date of Patent: *Mar. 26, 2024

(54) MOLECULAR BIOMARKERS FOR CANCER IMMUNOTHERAPY

(71) Applicants: Massachusetts Institute of Technology, Cambridge, MA (US); The General Hospital Corporation, Boston, MA (US)

(72) Inventors: Nir Hacohen, Brookline, MA (US); Michael S. Rooney, Cambridge, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 205 days.

This patent is subject to a terminal disclaimer.

(21) Appl. No.: 17/179,956

(22) Filed: Feb. 19, 2021

(65) Prior Publication Data

US 2021/0262039 A1 Aug. 26, 2021

Related U.S. Application Data

(62) Division of application No. 15/537,839, filed as application No. PCT/US2015/067143 on Dec. 21, 2015, now Pat. No. 10,975,442.

(60) Provisional application No. 62/124,473, filed on Dec. 19, 2014.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57407* (2013.01); *C12Q 2600/106* (2013.01); *C12Q 2600/156* (2013.01); *C12Q 2600/158* (2013.01); *G01N 2333/96436* (2013.01); *G01N 2800/52* (2013.01)

(58) Field of Classification Search
CPC .................................................. C12Q 1/6886
USPC ....................................................... 424/142.1
See application file for complete search history.

(56) References Cited

U.S. PATENT DOCUMENTS

| | | | |
|---|---|---|---|
| 3,854,480 A | 12/1974 | Zaffaroni |
| 3,870,790 A | 3/1975 | Lowey et al. |
| 4,210,644 A | 7/1980 | Ewing et al. |
| 4,226,859 A | 10/1980 | Stach |
| 4,369,172 A | 1/1983 | Schor et al. |
| 4,379,454 A | 4/1983 | Campbell et al. |
| 4,452,775 A | 6/1984 | Kent |
| 4,554,101 A | 11/1985 | Hopp |
| 4,588,585 A | 5/1986 | Mark et al. |
| 4,603,112 A | 7/1986 | Paoletti et al. |
| 4,656,127 A | 4/1987 | Mundy |
| 4,675,189 A | 6/1987 | Kent et al. |
| 4,683,195 A | 7/1987 | Mullis et al. |
| 4,683,202 A | 7/1987 | Mullis |
| 4,690,915 A | 9/1987 | Rosenberg |
| 4,722,848 A | 2/1988 | Paoletti et al. |
| 4,743,249 A | 5/1988 | Loveland |
| 4,751,180 A | 6/1988 | Cousens et al. |
| 4,769,330 A | 9/1988 | Paoletti et al. |
| 4,816,540 A | 3/1989 | Onishi |
| 4,842,866 A | 6/1989 | Horder et al. |
| 4,844,893 A | 7/1989 | Honsik et al. |
| 4,906,169 A | 3/1990 | Chien et al. |
| 4,935,233 A | 6/1990 | Bell et al. |
| 4,973,468 A | 11/1990 | Chiang et al. |
| 5,023,084 A | 6/1991 | Chien et al. |
| 5,035,891 A | 7/1991 | Runkel et al. |
| 5,110,587 A | 5/1992 | Paoletti et al. |
| 5,133,974 A | 7/1992 | Paradissis et al. |
| 5,174,993 A | 12/1992 | Paoletti |
| 5,185,146 A | 2/1993 | Altenburger |
| 5,198,223 A | 3/1993 | Gale et al. |
| 5,204,253 A | 4/1993 | Sanford et al. |
| 5,217,720 A | 6/1993 | Sekigawa et al. |
| 5,279,833 A | 1/1994 | Rose |
| 5,364,773 A | 11/1994 | Paoletti et al. |
| 5,407,686 A | 4/1995 | Patel et al. |
| 5,422,119 A | 6/1995 | Casper |
| 5,494,807 A | 2/1996 | Paoletti et al. |
| 5,541,171 A | 7/1996 | Rhodes et al. |

(Continued)

FOREIGN PATENT DOCUMENTS

CN 103180730 A 6/2013
EP 1486567 A1 12/2004

(Continued)

OTHER PUBLICATIONS

U.S. Appl. No. 16/094,786, filed Oct. 18, 2018, 2019-0346442, Published.
U.S. Appl. No. 13/108,610, filed May 16, 2011, 2011-0293637, now U.S. Pat. No. 9,115,402, Granted.
U.S. Appl. No. 14/794,449, filed Jul. 8, 2015, 2016-00008447, Abandoned.
U.S. Appl. No. 15/187,174, filed Jun. 20, 2016, 2016-0331822, Abandoned.
U.S. Appl. No. 15/800,732, filed Nov. 1, 2017, 2018-0055922, Abandoned.
U.S. Appl. No. 16/181,098, filed Nov. 5, 2018, 2019-0060432, Published.

(Continued)

*Primary Examiner* — Sean E Aeder
(74) *Attorney, Agent, or Firm* — Foley Hoag LLP; DeAnn F. Smith; Thi K. Dio

(57) ABSTRACT

In one aspect, provided herein is a method comprising: (a) (i) determining cytolytic activity in a tumor from the subject; and/or (ii) determining genetic alterations associated with cytolytic activity in the tumor; and (b) administering an immunotherapeutic agent to the subject if (i) cytolytic activity is detected in the tumor and/or (ii) a genetic alteration associated with induction of cytolytic activity, tumor resistance to cytolytic activity and/or suppression of cytolytic activity is detected in the tumor.

12 Claims, 156 Drawing Sheets

(56) References Cited

U.S. PATENT DOCUMENTS

| | | |
|---|---|---|
| 5,580,859 A | 12/1996 | Felgner et al. |
| 5,589,466 A | 12/1996 | Felgner et al. |
| 5,658,785 A | 8/1997 | Johnson |
| 5,686,281 A | 11/1997 | Roberts |
| 5,705,190 A | 1/1998 | Broad et al. |
| 5,736,152 A | 4/1998 | Dunn |
| 5,756,101 A | 5/1998 | Paoletti et al. |
| 5,762,938 A | 6/1998 | Paoletti et al. |
| 5,766,597 A | 6/1998 | Paoletti et al. |
| 5,766,882 A | 6/1998 | Falkner et al. |
| 5,770,212 A | 6/1998 | Falkner et al. |
| 5,811,104 A | 9/1998 | Dale et al. |
| 5,833,975 A | 11/1998 | Paoletti et al. |
| 5,843,728 A | 12/1998 | Seed et al. |
| 5,849,303 A | 12/1998 | Wasmoen et al. |
| 5,849,589 A | 12/1998 | Tedder et al. |
| 5,851,828 A | 12/1998 | Seed et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 5,942,235 A | 8/1999 | Paoletti |
| 5,989,562 A | 11/1999 | Wasmoen et al. |
| 5,990,091 A | 11/1999 | Tartaglia et al. |
| 5,994,136 A | 11/1999 | Naldini et al. |
| 6,004,777 A | 12/1999 | Tartaglia et al. |
| 6,004,811 A | 12/1999 | Seed et al. |
| 6,013,516 A | 1/2000 | Verma et al. |
| 6,090,393 A | 7/2000 | Fischer |
| 6,130,066 A | 10/2000 | Tartaglia et al. |
| 6,156,567 A | 12/2000 | Fischer |
| 6,159,477 A | 12/2000 | Audonnet et al. |
| 6,165,782 A | 12/2000 | Naldini et al. |
| 6,214,353 B1 | 4/2001 | Paoletti et al. |
| 6,228,846 B1 | 5/2001 | Audonnet et al. |
| 6,258,595 B1 | 7/2001 | Gao et al. |
| 6,265,189 B1 | 7/2001 | Paoletti et al. |
| 6,277,558 B1 | 8/2001 | Hudson |
| 6,284,240 B1 | 9/2001 | Seed et al. |
| 6,309,647 B1 | 10/2001 | Paoletti et al. |
| 6,312,682 B1 | 11/2001 | Kingsman et al. |
| 6,352,694 B1 | 3/2002 | June et al. |
| 6,392,013 B1 | 5/2002 | Seed et al. |
| 6,406,705 B1 | 6/2002 | Davis et al. |
| 6,410,014 B1 | 6/2002 | Seed et al. |
| 6,428,953 B1 | 8/2002 | Naldini et al. |
| 6,475,769 B1 | 11/2002 | Wilson et al. |
| 6,489,458 B2 | 12/2002 | Hackett et al. |
| 6,534,055 B1 | 3/2003 | June et al. |
| 6,537,540 B1 | 3/2003 | Burstein et al. |
| 6,537,594 B1 | 3/2003 | Paoletti et al. |
| 6,569,457 B2 | 5/2003 | Ullah et al. |
| 6,638,534 B1 | 10/2003 | Ishibashi et al. |
| 6,682,743 B2 | 1/2004 | Mayr |
| 6,713,068 B1 | 3/2004 | Audonnet et al. |
| 6,753,162 B1 | 6/2004 | Seed et al. |
| 6,761,893 B2 | 7/2004 | Chaplin et al. |
| 6,780,407 B1 | 8/2004 | Paoletti et al. |
| 6,780,417 B2 | 8/2004 | Kaslow et al. |
| 6,793,926 B1 | 9/2004 | Rasty et al. |
| 6,797,514 B2 | 9/2004 | Berenson et al. |
| 6,821,515 B1 | 11/2004 | Cleland et al. |
| 6,867,041 B2 | 3/2005 | Berenson et al. |
| 6,869,794 B2 | 3/2005 | Vogels et al. |
| 6,887,466 B2 | 5/2005 | June et al. |
| 6,893,865 B1 | 5/2005 | Lockert et al. |
| 6,905,680 B2 | 6/2005 | June et al. |
| 6,905,681 B1 | 6/2005 | June et al. |
| 6,905,874 B2 | 6/2005 | Berenson et al. |
| 6,913,752 B2 | 7/2005 | Chaplin et al. |
| 6,913,922 B1 | 7/2005 | Bout et al. |
| 6,923,973 B1 | 8/2005 | Cox et al. |
| 6,924,128 B2 | 8/2005 | Allen |
| 6,936,466 B2 | 8/2005 | Feldhaus |
| 6,943,019 B2 | 9/2005 | Wilson et al. |
| 6,953,690 B1 | 10/2005 | Gao et al. |
| 6,955,808 B2 | 10/2005 | Curiel |
| 6,974,695 B2 | 12/2005 | Vogels et al. |
| 6,991,797 B2 | 1/2006 | Andersen et al. |
| 7,029,848 B2 | 4/2006 | Vogels et al. |
| 7,045,313 B1 | 5/2006 | Moss et al. |
| 7,097,842 B2 | 8/2006 | Suter et al. |
| 7,115,391 B1 | 10/2006 | Chen et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,172,893 B2 | 2/2007 | Rabinowitz et al. |
| 7,175,843 B2 | 2/2007 | June et al. |
| 7,189,536 B2 | 3/2007 | Chaplin et al. |
| 7,198,784 B2 | 4/2007 | Kingsman et al. |
| 7,232,566 B2 | 6/2007 | June et al. |
| 7,255,862 B1 | 8/2007 | Tartaglia et al. |
| 7,259,015 B2 | 8/2007 | Kingsman et al. |
| 7,283,337 B2 | 10/2007 | Sakai et al. |
| 7,303,910 B2 | 12/2007 | Bebbington et al. |
| 7,335,364 B2 | 2/2008 | Chaplin et al. |
| 7,351,585 B2 | 4/2008 | Mitrophanous et al. |
| 7,384,644 B2 | 6/2008 | Chaplin et al. |
| 7,445,924 B2 | 11/2008 | Chaplin et al. |
| 7,459,270 B2 | 12/2008 | Chaplin et al. |
| 7,572,631 B2 | 8/2009 | Berenson et al. |
| 7,572,821 B2 | 8/2009 | Sun et al. |
| 7,608,279 B2 | 10/2009 | Parisot et al. |
| 7,628,980 B2 | 12/2009 | Suter et al. |
| 7,705,120 B2 | 4/2010 | Lillie et al. |
| 7,708,949 B2 | 5/2010 | Stone et al. |
| 7,741,465 B1 | 6/2010 | Eshhar et al. |
| 7,767,449 B1 | 8/2010 | Paoletti |
| 7,892,533 B2 | 2/2011 | Suter et al. |
| 7,897,156 B2 | 3/2011 | Ackermann et al. |
| 7,923,017 B2 | 4/2011 | Chaplin et al. |
| 7,939,086 B2 | 5/2011 | Chaplin et al. |
| 7,964,395 B2 | 6/2011 | Chaplin et al. |
| 7,964,396 B2 | 6/2011 | Chaplin et al. |
| 7,964,398 B2 | 6/2011 | Chaplin et al. |
| 7,985,739 B2 | 7/2011 | Kay et al. |
| 8,034,334 B2 | 10/2011 | Dudley et al. |
| 8,088,379 B2 | 1/2012 | Robbins et al. |
| 8,163,293 B2 | 4/2012 | Chaplin |
| 8,211,422 B2 | 7/2012 | Eshhar et al. |
| 8,227,432 B2 | 7/2012 | Hackett et al. |
| 8,236,560 B2 | 8/2012 | Chaplin et al. |
| 8,268,325 B2 | 9/2012 | Chaplin et al. |
| 8,268,329 B2 | 9/2012 | Chaplin et al. |
| 8,278,036 B2 | 10/2012 | Kariko et al. |
| 8,309,098 B2 | 11/2012 | Howley et al. |
| 8,372,622 B2 | 2/2013 | Suter et al. |
| 8,399,645 B2 | 3/2013 | Campana et al. |
| 8,404,658 B2 | 3/2013 | Hajjar et al. |
| 8,454,972 B2 | 6/2013 | Nabel et al. |
| 8,470,598 B2 | 6/2013 | Chaplin et al. |
| 8,557,779 B2 | 10/2013 | Sugiyama |
| 8,648,104 B2 | 2/2014 | Du et al. |
| 8,697,854 B2 | 4/2014 | Schendel et al. |
| 8,796,414 B2 | 8/2014 | Johnston |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,115,402 B2 | 8/2015 | Hacohen et al. |
| 9,556,237 B2 | 1/2017 | Schmaljohn et al. |
| 9,909,159 B2 | 3/2018 | Marras et al. |
| 9,962,453 B2 | 5/2018 | Georges |
| 10,202,640 B2 | 2/2019 | Davis et al. |
| 10,426,824 B1 | 10/2019 | Hacohen et al. |
| 10,801,070 B2 | 10/2020 | Clement et al. |
| 10,835,585 B2 | 11/2020 | Fritsch et al. |
| 10,975,442 B2 | 4/2021 | Hacohen et al. |
| 10,993,997 B2 | 5/2021 | Hacohen et al. |
| 11,421,016 B2 | 8/2022 | Nguyen et al. |

(56) References Cited

U.S. PATENT DOCUMENTS

| | | |
|---|---|---|
| 11,452,768 B2 | 9/2022 | Hacohen et al. |
| 11,549,149 B2 | 1/2023 | Fritsch |
| 2003/0104008 A1 | 6/2003 | Loosmore et al. |
| 2004/0013648 A1 | 1/2004 | Kingsman et al. |
| 2004/0018971 A1 | 1/2004 | Fikes et al. |
| 2004/0053304 A1 | 3/2004 | Markowitz |
| 2006/0008468 A1 | 1/2006 | Chiang et al. |
| 2006/0163385 A1 | 7/2006 | Link et al. |
| 2006/0252077 A1 | 11/2006 | Buzby |
| 2006/0258607 A1 | 11/2006 | Jarosch et al. |
| 2007/0003442 A1 | 1/2007 | Link et al. |
| 2007/0025970 A1 | 2/2007 | Kingsman et al. |
| 2007/0055049 A1 | 3/2007 | Grey et al. |
| 2007/0083334 A1 | 4/2007 | Mintz et al. |
| 2007/0134197 A1 | 6/2007 | Eichner et al. |
| 2007/0184489 A1 | 8/2007 | Griffiths et al. |
| 2007/0195127 A1 | 8/2007 | Ahn et al. |
| 2008/0003142 A1 | 1/2008 | Link et al. |
| 2008/0014222 A1 | 1/2008 | Simmons et al. |
| 2008/0014589 A1 | 1/2008 | Link et al. |
| 2008/0071706 A1 | 3/2008 | Honda et al. |
| 2008/0254008 A1 | 10/2008 | Dropulic et al. |
| 2009/0005254 A1 | 1/2009 | Griffiths et al. |
| 2009/0026082 A1 | 1/2009 | Rothberg et al. |
| 2009/0028888 A1 | 1/2009 | Bergeron et al. |
| 2009/0055944 A1 | 2/2009 | Korman et al. |
| 2009/0111106 A1 | 4/2009 | Mitrophanous et al. |
| 2009/0131543 A1 | 5/2009 | Weitz et al. |
| 2009/0136494 A1 | 5/2009 | Ponath et al. |
| 2009/0186042 A1 | 7/2009 | Johnston et al. |
| 2009/0220980 A1 | 9/2009 | Hoon et al. |
| 2009/0304711 A1 | 12/2009 | Pardoll et al. |
| 2010/0137143 A1 | 6/2010 | Rothberg et al. |
| 2010/0137163 A1 | 6/2010 | Link et al. |
| 2010/0158951 A1 | 6/2010 | Randolph et al. |
| 2010/0203531 A1 | 8/2010 | Sarkaria et al. |
| 2010/0210529 A1 | 8/2010 | van der Burg et al. |
| 2010/0282617 A1 | 11/2010 | Rothberg et al. |
| 2010/0286057 A1 | 11/2010 | Walensky et al. |
| 2010/0297071 A1 | 11/2010 | Ishibashi et al. |
| 2010/0304989 A1 | 12/2010 | Von Hoff et al. |
| 2011/0097312 A1 | 4/2011 | Molldrem |
| 2011/0223149 A1 | 9/2011 | Nash et al. |
| 2011/0257890 A1 | 10/2011 | Weinschenk et al. |
| 2011/0293571 A1 | 12/2011 | Widdowson et al. |
| 2011/0293637 A1 | 12/2011 | Hacohen et al. |
| 2012/0082691 A1 | 4/2012 | Rammensee et al. |
| 2012/0219947 A1 | 8/2012 | Yurkovetsky et al. |
| 2012/0244133 A1 | 9/2012 | Rosenberg et al. |
| 2012/0288539 A1 | 11/2012 | Eber |
| 2012/0295960 A1 | 11/2012 | Palfi et al. |
| 2013/0071414 A1 | 3/2013 | Dotti et al. |
| 2013/0210014 A1 | 8/2013 | Sharman |
| 2013/0295110 A1 | 11/2013 | Binder et al. |
| 2014/0056986 A1 | 2/2014 | Desai et al. |
| 2014/0178438 A1 | 6/2014 | Sahin et al. |
| 2014/0256595 A1 | 9/2014 | Link et al. |
| 2014/0322716 A1 | 10/2014 | Robins |
| 2015/0079119 A1 | 3/2015 | Johnston |
| 2015/0125463 A1 | 5/2015 | Cogswell et al. |
| 2015/0140041 A1 | 5/2015 | Vitiello |
| 2015/0224182 A1 | 8/2015 | Hunt et al. |
| 2015/0278441 A1 | 10/2015 | Min et al. |
| 2016/0008447 A1 | 1/2016 | Hacohen et al. |
| 2016/0101170 A1 | 4/2016 | Hacohen et al. |
| 2016/0130641 A1 | 5/2016 | Wang et al. |
| 2016/0213771 A1 | 7/2016 | Sampson et al. |
| 2016/0310584 A1 | 10/2016 | Fritsch et al. |
| 2016/0326593 A1 | 11/2016 | Clement et al. |
| 2016/0331822 A1 | 11/2016 | Hacohen et al. |
| 2016/0339090 A1 | 11/2016 | Hacohen et al. |
| 2017/0022251 A1 | 1/2017 | Rammensee et al. |
| 2017/0067090 A1 | 3/2017 | Zhang et al. |
| 2017/0160269 A1 | 6/2017 | Linnemann et al. |
| 2017/0199961 A1 | 7/2017 | Yelensky et al. |
| 2017/0233821 A1 | 8/2017 | Lianidou et al. |
| 2017/0298441 A1 | 10/2017 | Wu et al. |
| 2018/0000913 A1 | 1/2018 | Hacohen et al. |
| 2018/0055922 A1 | 3/2018 | Hacohen et al. |
| 2018/0127803 A1 | 5/2018 | Lei et al. |
| 2018/0153975 A1 | 6/2018 | Fritsch et al. |
| 2019/0060428 A1 | 2/2019 | Fritsch |
| 2019/0060432 A1 | 2/2019 | Hacohen et al. |
| 2019/0099475 A1 | 4/2019 | Benz et al. |
| 2019/0376147 A1 | 12/2019 | Fritsch |
| 2020/0016251 A1 | 1/2020 | Hacohen et al. |
| 2020/0069783 A1 | 3/2020 | Hacohen et al. |
| 2020/0101147 A1 | 4/2020 | Zeng |
| 2020/0330571 A1 | 10/2020 | Fritsch et al. |
| 2020/0368337 A1 | 11/2020 | Fritsch et al. |
| 2020/0407804 A1 | 12/2020 | Clement et al. |
| 2021/0220455 A1 | 7/2021 | Hacohen et al. |
| 2021/0262039 A1 | 8/2021 | Hacohen et al. |
| 2021/0379168 A1 | 12/2021 | Hacohen et al. |
| 2023/0149345 A1 | 5/2023 | Elmaleh et al. |

FOREIGN PATENT DOCUMENTS

| | | |
|---|---|---|
| EP | 1680681 B1 | 11/2011 |
| EP | 2390363 A1 | 11/2011 |
| EP | 2569633 A2 | 3/2013 |
| EP | 2574346 A1 | 4/2013 |
| FR | 2650840 A1 | 2/1991 |
| JP | 2003/517274 A | 5/2003 |
| JP | 2003/523365 A | 8/2003 |
| JP | 2003/535024 A | 11/2003 |
| JP | 2005/505271 A | 2/2005 |
| JP | 2005/529187 A | 9/2005 |
| JP | 2006/526628 A | 11/2006 |
| JP | 2009/532350 A | 9/2009 |
| JP | 2009/532664 A | 9/2009 |
| JP | 2010/533184 A | 10/2010 |
| JP | 2012/522500 A | 9/2012 |
| JP | 2013/530943 A | 8/2013 |
| WO | WO-91/02087 A1 | 2/1991 |
| WO | WO-91/06309 A1 | 5/1991 |
| WO | WO-92/15712 A1 | 9/1992 |
| WO | WO-1992/15322 A1 | 9/1992 |
| WO | WO-1992/15672 A1 | 9/1992 |
| WO | WO-93/24640 A2 | 12/1993 |
| WO | WO-1995/27780 A1 | 10/1995 |
| WO | WO-1995/30018 A2 | 11/1995 |
| WO | WO-96/18372 A2 | 6/1996 |
| WO | WO-00/20587 A2 | 4/2000 |
| WO | WO-00/66153 A1 | 11/2000 |
| WO | WO-2001/89788 A2 | 11/2001 |
| WO | WO-2003/020763 A2 | 3/2003 |
| WO | WO-2003/057171 A2 | 7/2003 |
| WO | WO-2003/086459 A1 | 10/2003 |
| WO | WO-2003/106692 A2 | 12/2003 |
| WO | WO-2004/002627 A2 | 1/2004 |
| WO | WO-2004/026897 A1 | 4/2004 |
| WO | WO-2004/030615 A2 | 4/2004 |
| WO | WO-2004/033685 A1 | 4/2004 |
| WO | WO-2004/044004 A2 | 5/2004 |
| WO | WO-2004/058801 A2 | 7/2004 |
| WO | WO-2004/074322 A1 | 9/2004 |
| WO | WO-2004/091763 A2 | 10/2004 |
| WO | WO-2005/021151 A1 | 3/2005 |
| WO | WO-2005/087261 A2 | 9/2005 |
| WO | WO-2005/113595 A2 | 12/2005 |
| WO | WO-2005/114215 A2 | 12/2005 |
| WO | WO-2006/000830 A2 | 1/2006 |
| WO | WO-2006/040551 A2 | 4/2006 |
| WO | WO-2006/040554 A1 | 4/2006 |
| WO | WO-2006/096571 A2 | 9/2006 |
| WO | WO-2006/121168 A1 | 11/2006 |
| WO | WO-2006/125962 A2 | 11/2006 |
| WO | WO-2007/015540 A1 | 2/2007 |
| WO | WO-2007/059033 A1 | 5/2007 |
| WO | WO-2007/089541 A2 | 8/2007 |
| WO | WO-2007/095033 A2 | 8/2007 |
| WO | WO-2007/101227 A2 | 9/2007 |
| WO | WO-2007/124090 A2 | 11/2007 |

(56) References Cited

FOREIGN PATENT DOCUMENTS

| WO | WO-2007/133710 A2 | 11/2007 |
|---|---|---|
| WO | WO-2008/011344 A2 | 1/2008 |
| WO | WO-2008/038002 A2 | 4/2008 |
| WO | WO-2008/039818 A2 | 4/2008 |
| WO | WO-2008/063227 A2 | 5/2008 |
| WO | WO-2008/096831 A1 | 8/2008 |
| WO | WO-2008/109075 A2 | 9/2008 |
| WO | WO-2009/014708 A2 | 1/2009 |
| WO | WO-2009/025117 A1 | 2/2009 |
| WO | WO-2009/032477 A2 | 3/2009 |
| WO | WO-2009/043520 A1 | 4/2009 |
| WO | WO-2009/126306 A2 | 10/2009 |
| WO | WO-2010/033949 A1 | 3/2010 |
| WO | WO-2010/045345 A2 | 4/2010 |
| WO | WO-2010/093784 A2 | 8/2010 |
| WO | WO-2011/051489 A2 | 5/2011 |
| WO | WO-2011/079176 A2 | 6/2011 |
| WO | WO-2011/134944 A2 | 11/2011 |
| WO | WO-2011/143656 A2 | 11/2011 |
| WO | WO-2011/146862 A1 | 11/2011 |
| WO | WO-2012/027379 A2 | 3/2012 |
| WO | WO-2012/079000 A1 | 6/2012 |
| WO | WO-2012/095639 A2 | 7/2012 |
| WO | WO-2012/101112 A1 | 8/2012 |
| WO | WO-2012/159643 A1 | 11/2012 |
| WO | WO-2012/159754 A2 | 11/2012 |
| WO | WO-2013/026027 A1 | 2/2013 |
| WO | WO-2013/036201 A1 | 3/2013 |
| WO | WO-2013/039889 A1 | 3/2013 |
| WO | WO-2013/040371 A2 | 3/2013 |
| WO | WO-2013/086464 A1 | 6/2013 |
| WO | WO-2013/123031 A2 | 8/2013 |
| WO | WO-2013/133405 A1 | 9/2013 |
| WO | WO-2013/166321 A1 | 11/2013 |
| WO | WO-2013/173223 A1 | 11/2013 |
| WO | WO-2013/176915 A1 | 11/2013 |
| WO | WO-2013164754 A2 | 11/2013 |
| WO | WO-2014/009535 A2 | 1/2014 |
| WO | WO-2014/011987 A1 | 1/2014 |
| WO | WO-2014/012051 A1 | 1/2014 |
| WO | WO-2014/018863 A1 | 1/2014 |
| WO | WO-2014/047561 A1 | 3/2014 |
| WO | WO-2014/056986 A1 | 4/2014 |
| WO | WO-2014/059173 A2 | 4/2014 |
| WO | WO-2014/083173 A1 | 6/2014 |
| WO | WO-2014/085802 A1 | 6/2014 |
| WO | WO-2014/133567 A1 | 9/2014 |
| WO | WO-2014/133568 A1 | 9/2014 |
| WO | WO-2014/134165 A1 | 9/2014 |
| WO | WO-2014/150924 A2 | 9/2014 |
| WO | WO-2014/168874 A2 | 10/2014 |
| WO | WO-2014/172606 A1 | 10/2014 |
| WO | WO-2014/183649 A1 | 11/2014 |
| WO | WO-2014/184744 A1 | 11/2014 |
| WO | WO-2014/191128 A1 | 12/2014 |
| WO | WO-2014/197369 A1 | 12/2014 |
| WO | WO-2015/085233 A1 | 6/2015 |
| WO | WO-2015/094995 A2 | 6/2015 |
| WO | WO-2015/095811 A2 | 6/2015 |
| WO | WO-2016/020710 A1 | 2/2016 |
| WO | WO-2016/100975 A1 | 6/2016 |
| WO | WO-2016/164833 A1 | 10/2016 |
| WO | WO-2016/187508 A2 | 11/2016 |
| WO | WO-2016/201049 A2 | 12/2016 |
| WO | WO-2017/173321 A1 | 10/2017 |
| WO | WO-2017/184590 A1 | 10/2017 |
| WO | WO-2018/140391 A1 | 8/2018 |

OTHER PUBLICATIONS

U.S. Appl. No. 16/188,737, filed Nov. 13, 2018, 2016-0101170, now U.S. Pat. No. 10,426,824, Granted.
U.S. Appl. No. 16/381,791, filed Apr. 11, 2019, 2020-0069783, Published.
U.S. Appl. No. 16/528,195, filed Jul. 31, 2019, 2020-0016251, Published.
U.S. Appl. No. 15/037,394, filed May 18, 2016, 2016-0298185, Published.
U.S. Appl. No. 14/877,125, filed Oct. 7, 2015, 2016-0101170, Published.
U.S. Appl. No. 17/089,408, filed Nov. 4, 2020, 2021-0220455, Published.
U.S. Appl. No. 15/102,129, filed Jun. 6, 2016, 2016-0310584, Abandoned.
U.S. Appl. No. 16/813,371, filed Mar. 9, 2020, 2020-0330571, Published.
U.S. Appl. No. 15/038,504, filed May 23, 2016, 2016-0326593, now U.S. Pat. No. 10,801,070, Granted.
U.S. Appl. No. 17/017,045, filed Sep. 10, 2020, 2020-0407804, Published.
U.S. Appl. No. 15/105,961, filed Jun. 17, 2016, 2016-0339090, Published.
U.S. Appl. No. 15/537,785, filed Jun. 19, 2017, 2018-0000913, now U.S. Pat. No. 10,993,997, Granted.
U.S. Appl. No. 17/217,864, filed Mar. 30, 2021, 2021-0379168, Published.
U.S. Appl. No. 15/537,839, filed Jun. 19, 2017, 2019-0127803, now U.S. Pat. No. 10,975,442, Granted.
U.S. Appl. No. 17/179,956, filed Feb. 19, 2021, 2021-0262039, Published.
U.S. Appl. No. 15/575,328, filed Nov. 17, 2017, 2018-0153975, now U.S. Pat. No. 10,835,585, Granted.
U.S. Appl. No. 16/859,252, filed Apr. 27, 2020, 2020-0368337, Published.
U.S. Appl. No. 15/513,127, filed Mar. 21, 2017, 2017-0298441, Abandoned.
U.S. Appl. No. 15/735,566, filed Dec. 11, 2017, 2019-0060428, Abandoned.
U.S. Appl. No. 16/480,535, filed Jul. 24, 2019, 2019-0376147, now U.S. Pat. No. 11,549,149, Allowed.
"A Phase 1 Study of Nivolumab in Subjects With Advanced or Recurrent Malignancies," National Library of Medicine, First posted: Aug. 8, 2008 and last updated Mar. 24, 2020. https://clinicaltrials.gov/ct2/show/NCT00730639, Clinical Trials Identifier NCT00730639.
"CT-011 and p53 Genetic Vaccine for Advance Solid Tumor," National Library of Medicine, updated:2011_06_30, XP002738554, https://clinicaltrials.gov/archive/NCT01386502/2011_06_30, Clinical Trials Identifier NCT01386502.
"Dose-escalation Study of Combination and Ipilimumab in Subjects With Unresectable Stage III or Stage IV Malignant Melanoma," National Library of Medicine, First posted: Dec. 2, 2009 and last updated Mar. 22, 2021. https://www.clinicaltrials.gov/ct2/show/NCT01024231, Clinical Trials Identifier NCT01024231.
"Monoclonal Antibody Therapy and Vaccine Therapy in Treating Patients with Stage IV Melanoma That Has Been Removed By Surgery," National Library of Medicine, 2010, XP002738553, https:clinicaltrials.gov/archive/NCT01176474/2010_08_05.
"Neon Therapeutics' Personal Neoantigen Vaccine Study Demonstrates Prolonged Progression-Free Survival in Advanced or Metastatic Melanoma, Non-Small Cell Lung and Bladder Cancers," published by Globe Newswire on Jul. 15, 2019 ("Neon Press Release 2019").
"Single-cell sequencing: A brief overview of how to derive a genome or transcriptome from a single cell," Nature Methods, 18(11) (2014).
"Study of Pembrolizumab in Participants With Progressive Locally Advanced or Metastatic Carcinoma, Melanoma, or Non-small Cell Lung Carcinoma (P07990/MK-3475-001/KEYNOTE-001) (KEYNOTE-001)," National Library of Medicine, First posted: Feb. 15, 2011 and last updated Dec. 13, 2019 https://clinicaltrials.gov/ct2/show/NCT01295827, Clinical Trials Identifier NCT01295827.
Acknowledgment of Receipt dated Jun. 28, 2017 for Response to Notices of Opposition of EP2569633.
Adam Piore., "Custom Cancer Vaccines," Feb. 27, 2019 edition of MIT Technology Review.

(56) References Cited

OTHER PUBLICATIONS

Akinleye et al., "Ibrutinib and novel BTK inhibitors in clinical development," Journal of Hematology & Oncology, 6(59): 1-9 (2013).
Albert et al., "Direct Selection of Human Genomic Loci by Microarray Hybridization," Nat Methods, 4(11): 903-905 (2007).
Alderton G. "Research Highlights" from vol. 13 of *Nature Reviews, Cancer* (Apr. 2013).
Allocca et al., "Novel adeno-associated virus serotypes efficiently transduce murine Photoreceptors," Journal of Virology, 81(20): 11372-11380 (2007).
Almeida et al., "CTdatabase: a knowledge-base of high-throughput and curated data on cancer-testis antigens," Nucleic acids research, 37:D816-819 (2008).
Alyea et al., "Toxicity and Efficacy of Defined Doses of CD4+ Donor Lymphocytes for Treatment of Relapse After Allogeneic Bone Marrow Transplant," Blood, 91(10):3671-3680 (1998).
Anderson et al., "Next Generation DNA Sequencing and the Future of Genomic Medicine," Genes, 1: 38-69 (2010).
Andreatta et al., "Gapped sequence alignment using artificial neural networks: application to the MHC class I system," Bioinformatics 32(4):511-517 (2016).
Annunziata et al., "Frequent Engagement of the Classical and Alternative NF-KB Pathways by Diverse Genetic Abnormalities in Multiple Myeloma," Cancer Cell, 12(2): 115-130 (2007).
Applicant's Authorization and Release Form of the Massachusetts General Hospital, Aug. 12, 2008; and Supplemental Release to Applicant of the Partners Healthcare System, Aug. 13, 2008.
Aranda et al. "Motely Malignancies" p. 1565 from vol. 19, No. 12 of *Nature Medicine* (Dec. 2013), entitled "Notable advances 2013".
Attia et al., "Autoimmunity Correlates With Tumor Regression in Patients With Metastatic Melanoma Treated with Anti-Cytotoxic T-Lymphocyte Antigen-4," J Clin Oncol, 23.(25): 6043-6053 (2005).
Austen et al., "Mutations in the ATM Gene Lead to Impaired Overall and Treatment-Free Survival that is Independent of IGVH Mutation Status in Patients with B-CLL," Blood, 106(9): 3175-3182 (2005).
Azvolinsky et al., "PD-1 Inhibitor MK-3475 Again Shows Promise in Advanced Melanoma," Cancer Network, 2013. [Retrieved online] http://www.cancernetwork.com/melanoma/pd-1-inhibitor-mk-3475-again-shows-promise-advanced-melanoma.
Bachireddy et al., "Reversal of in situ T cell exhaustion during effective human anti-leukemia responses to donor lymphocyte infusion," Blood, 123(9):1412-1421 (2013).
Backert et al., "Immunoinformatics and epitope prediction in the age of genomic medicine," Genome Medicine, 7:119 (2015).
Balakrishnan et al, "Novel Somatic and Germline Mutations in Cancer Candidate Genes in Glioblastoma, Melanoma, and Pancreatic Carcinoma," Cancer Res, 67: 3545-3550 (2007).
Baskar et al., "Autologous Lymphoma Vaccines Induce Human T Cell Responses Against Multiple, Unique Epitopes," J Clin Invest, 113:1498-1510 (2004).
Bassani-Sternberg et al., "Mass Spectrometry of Human Leukocyte Antigen Class I Peptidomes Reveals Strong Effects of Protein Abundance and Turnover on Antigen Presentation," Mol Cell Proteomics, 14:658-673 (2015).
Baurain et al., "High Frequency of Autologous Anti-Melanoma CTL Directed Against an Antigen Generated by a Point Mutation in a New Helicase Gene," J Immunol, 164: 6057-6066 (2000).
Baylin, "A decade of exploring the cancer epigenome-biological and translational implications," Nat Rev Cancer, 11:726-734 (2005).
Beck et al., "Enterocolitis in Patients With Cancer After Antibody Blockade of Cytotoxicity TLymphocyte-Associated Antigen 4," J Clin Oncol, 24(15): 2283-2289 (2006).
Bediaga et al., "DNA methylation epigenotypes in breast cancer molecular subtypes," Breast Cancer Research, 12:R77 (2010).
Behrends et al., "Network organization of the human autophagy system." Nature, 466(7302):68-76 (2010).

Bellucci et al., "Complete Response to Donor Lymphocyte Infusion in Multiple Myeloma is Associated with Antibody Responses to Highly Expressed Antigens," Blood, 103: 656-663 (2004).
Bentley et al., "Accurate Whole Human Genome Sequencing using Reversible Terminator Chemistry," Nature, 456(7218): 53-59 (2008).
Berg et al., "Detection of artifacts and peptide modifications in liquid chromatography/mass spectrometry data using two-dimensional signal intensity map data visualization," Rapid Commun Mass Spectrom, 20(10):1558-1562 (2006).
Berger et al., "Melanoma genome sequencing reveals frequent PREX2 mutations," Nature, 485(7399):502 (2012).
Bettelli et al., "TH-17 cells in the circle of immunity and autoimmunity," Nat Immunol, 8:345-350 (2007).
Blackwell HE, Grubbs RH (1998). "Highly Efficient Synthesis of Covalently Cross-Linked Peptide Helices by Ring-Closing Metathesis". Angewandte Chemie International Edition. 37(23): 3281-3284.
Boen et al., "Identification of T Cell Ligands in a Library of Peptides Covalently Attached to HLA-DR4," J Immunol, 165:2040-2047 (2000).
Boisgerault et al., "Definition of the HLA-A29 peptide ligand motif allows prediction of potential T-cell epitopes from the retinal soluble antigen, a candidate autoantigen in birdshot retinopathy," PNAS, 93:3466-3470 (1996).
Boisguerin et al., "Translation of genomis-guided RNA-based personalised cancer vaccaines: towards the bedside," British J Cancer, 111:1469-1475 (2014).
Boon et al., "Human T Cell Responses Against Melanoma," Annu Rev Immunol, 24: 175-208 (2006).
Boon, "Toward a Genetic Analysis of Tumor Rejection Antigens," Adv Cancer Res, 58:177-210 (1992).
Bourdetsky et al., The nature and extent of contributions by defective ribosome products to the HLA peptidome, PNAS, III, E1591-E1599 (2014).
Bowerman et al., "Engineering the binding properties of the T cell receptor:peptide:MHC ternary complex that governs T cell activity," Mol Immunol, 46(15):3000-3008 (2009).
Brandle et al., "A Mutated HLA-A2 Molecule Recognized by Autologous Cytotoxic T Lymphocytes on a Human Renal Cell Carcinoma," J Exp Med, 183: 2501-2508 (1996).
Bremel et al., "An integrated approach to epitope analysis I: Dimensional reduction, visualization and prediction of MHC binding using amino acid principal components and regression approaches," Immunome Res, 6:7 (2010).
Brinckerhoff et al., "Melanoma Vaccines," Curr Opin Oncol, 12:163-173 (2000).
Broad Institute Article, Jan. 29, 2009, "Turning Cancer's Strength Into Weakness," (2009).
Brochier et al., "Large-scale eradication of rabies using recombinant vaccinia-rabies vaccine," Nature, 354:520-552 (1991).
Brown et al., "Neo-antigens predicted by tumor genome meta-analysis correlate with increased patient survival," Genome Res, 24(5):743-750 (2014).
Burger et al., "Safety and activity of ibrutinib plus rituximab for patients with high-risk chronic lymphocytic leukaemia: a single-arm, phase 2 study," Lancet Oncology, 15(10):1090-1099 (2014).
Böhmet al., DNA vector constructs that prime hepatitis B surface antigen-specific cytotoxic T lymphocyte and antibody responses in mice after intramuscular injection. Journal of immunological methods 193(1): 29-40 (1996).
Cai et al., "Mutated BCR-ABL Generates Immunogenic T-Cell Epitopes in CML Patients," Clinical Cancer Research, 18(20):5761-5772 (2012).
Cai et al., "Peptides Derived From Mutated BCR-ABL Elicit T Cell Immunity In CML Patients," BLOOD, 116(21): 388-388 (2010).
Callahan et al., "Nivolumab Plus Ipilimumab in Patients With Advanced Melanoma: Updated Survival, Response, and Safety Data in a phase I Dose-Escalation Study," J Clin Oncol, 36(4): 391-398 (2018).
Cancer Genome Atlas Network, "Comprehensive molecular characterization of human colon and rectal cancer," Nature, 487:330-337 (2012).

(56) References Cited

OTHER PUBLICATIONS

Cancer Genome Atlas Network, "Comprehensive molecular portraits of human breast tumours," Nature, 490:61-70 (2012).
Cancer Genome Atlas Research Network, "Comprehensive genomic characterization defines human glioblastoma genes and core pathways," Nature, 455(7216):1061-1068 (2008).
Cancer Genome Atlas Research Network, "Comprehensive genomic characterization of squamous cell lung cancers," Nature, 489, 519-525 (2012).
Cancer Genome Atlas Research Network, "Comprehensive molecular characterization of clear cell renal cell carcinoma," Nature, 499:43-49 (2013).
Cancer Genome Atlas Research Network, "Genomic and epigenomic landscapes of adult de novo acute myeloid leukemia," New England Journal of Medicine, 368(22):2059-2074 (2013).
Cancer Genome Atlas Research Network, "Integrated genomic analyses of ovarian carcinoma," Nature, 474: 609-615 (2011).
Cardarella et al., "Clinical, Pathologic, and Biologic Features Associated with BRAF Mutations in Non-Small Cell Lung Cancer," Clin Cancer Res, 19(16):4532-4540 (2013).
Carlino et al., "Immune checkpoint inhibitors in melanoma," Lancet, 398: 1002-1014 (2021).
Caron et al., "Analysis of MHC immunopeptidomes using mass spectrometry," Mol Cell Proteomics (2015), doi: 10.1074/mcp.OI 15.052431.
Carpten et al., "A transforming mutation in the pleckstrin homology domain of AKT1 in cancer," Nature, 448(26):439-444 (2004).
Carreno et al., "A dendritic cell vaccine increases the breadth and diversity of melanoma neoantigen-specific T cells," Science, 348(6239):803-808 (2015).
Carter et al., "Identification and validation of cell surface antigens for antibody targeting in oncology," Endocrine—Related Cancer, 11:659-687 (2004).
Certified Priority Document for U.S. Appl. No. 61/334,866, filed May 14, 2010.
Chang et al., "Peptide length-based prediction of peptide-MHC class II binding," Bioinformatics, 22(22): 2761-2767 (2006).
Chang et al., "Use of tumor genomic profiling to reveal mechanisms of resistance to the BTK inhibitor ibrutinib in chronic lymphocytic leukemia (CLL)," J Clin Oncol, 31(15S):Abstract 7014 (2013).
Chatila, "The Regulatory T Cell Transcriptosome: E Pluribus Unum," Immunity, 27(5):693-695 (2007).
Chen et al., Molecular Pharmaceutics, 3:109-111 (2010).
Chianese-Bullock et al., "Multi-peptide vaccines vialed as peptide mixtures can be stable reagents for use in peptide-based immune therapies," Vaccine, 27(11):1764-1770 (2009).
Chiari et al., "Two Antigens Recognized by Autologous Cytolytic T Lymphocytes on a Melanoma Result from a Single Point Mutation in an Essential Housekeeping Gene," Cancer Res, 59: 5785-5792 (1999).
Chinese Office Action dated Jun. 12, 2017 in corresponding CN Application No. 2014800322910.
Chowell et al., "TCR contact residue hydrophobicity is a hallmark of immunogenic CD8(+) T cell epitopes," PNAS, 112:E1754-E1762 (2015).
Christianson et al., "Defining human ERAD networks through an integrative mapping strategy," Nat Cell Biol, 14:93-105 (2012).
Ciofani et al., "A Validated Regulatory Network for Th17 Cell Specification," Cell, 151(2):289-303 (2012).
Clinical trial NCT 01970358, Patrick Ott, A Phase I Study With a Personalized NeoAntigen Cancer Vaccine in Melanoma, p. 1-6, Retrieved from https://clinicaltrials.gov/ct2/show/NCT01970358 downloaded Jun. 20, 2017.
CNBC news article posted online on Mar. 1, 2019 entitled "Bill Gates: These breakthrough technologies are going to profoundly change the world".
Coffman et al., "Vaccine Adjuvants: Putting Innate Immunity to Work," Immunity 33:492-503 (2010).

Consolidated Table of Documents filed in Opposition to date in Response to Notices of Opposition of EP2569633 dated Jun. 28, 2017.
Coulie et al., "Genes Coding for Antigens Recognized on Human Tumors by Autologous Cytolytic T Lymphocytes," Annals of New York Academy of Sciences: 113-119 (1993).
Coulie et al., "Tumour antigens recognized by T lymphocytes: at the core of cancer immunotherapy," Nature Review, 14: 135-146 (2014).
Dai et al., "Prediction of soluble heterologous protein expression levels in *Escherichia coli* from sequence-based features and its potential in biopharmaceutical process development," Pharmaceutical Bioprocessing, 2(3): 253-266 (2014).
Dana-Farber Cancer Institute; Feb. 20, 2013 publication of the Dana-Farber Cancer Institute entitled, Inside the Institute; and the article "Study tracks evolution of leukemia."
Datasheet for the decision of May 31, 2007, Boards of Appeal of The European Patent Office, T 1396/06.
De Plaen et al., "Immunogenic (tum-) Variants of Mouse Tumor P815: Cloning of the Gene of Tum-Antigen P91A and Identification of the Tum-Mutation," PNAS, 85: 2274-2278 (1988).
Declaration by Professor John Haanen, M.D., Ph.D. on Mar. 8, 2019.
Declaration by Stephen Johnston filed during the prosecution of granted U.S. Pat. No. 8,796,414 Nov. 20, 2013.
Declaration of Dr Nir Hacohen on Feb. 16, 2014.
Declaration of Dr. John C. Castle executed on Nov. 9, 2016.
DeKosky et al., "High-throughput sequencing of the paired human immunoglobulin heavy and light chain repertoire," Nature Biotech 166-170 (2013).
Dengjel et al., "Glycan side chains on naturally presented MHC class II ligands," J. Mass Spectrom, 40:100-104 (2005).
Dermer et al., "Another Anniversary for the War on Cancer," Biotech, 12:320 (1994).
Di Nicolantonio et al., "Wild-Type Is Required for Response to Panitumumab or Cetuximab in Metastatic Colorectal Cancer," Journal of Clinical Oncology. 26(35):5705-5712 (2008).
Diaz et al., "The molecular evolution of acquired resistance to targeted EGFR blockade in colorectal cancers," Nature, 486: 537-540 (2012).
Ding et al., "Genome remodelling in a basal-like breast cancer metastasis and xenograft," Nature, 464:999-1005 (2010).
Donkena et al., "Oxidative Stress and DNA Methylation in Prostate Cancer," Obstetrics and Gynecology International, 2010(Article ID 302051):14 pages (2010).
Dressman et al., "Gene expression profiles of multiple breast cancer phenotypes and response to neoadjuvant chemotherapy," Clin Cancer Res, 12(3):819-826 (2006).
Du et al., "The Significance and Therapeutic Potential of GATA3 Expression and Mutation in Breast Cancer: A Systematic Review," Med Res Rev, 35(6):1300-1315 (2015).
Duarte "Milestone 21 Individualized neoantigen vaccines" Nature Milestones, Nov. 2020: S3-S25.
Dudley et al., "Cancer Regression and Autoimmunity in Patients After Clonal Repopulation with Antitumor Lymphocytes," Science, 298: 850-854 (2002).
Dössinger et al., "MHC multimer-guided and cell culture-independent isolation of functional T cell receptors from single cells facilitates TCR identification for immunotherapy," PloS one, 8(4):e61384 (2013).
Eichmann et al., "Identification and characterisation of peptide binding motifs of six autoimmune disease-associated human leukocyte antigen-class I molecules including HLA-B*39:06," Tissue Antigens 84(4):378-388 (2014).
Elias et al., Target-decoy search strategy for increased confidence in large-scale protein identifications by mass spectrometry, Nat Meth, 4:207-214 (2007).
Engelhard, "Structure of peptides associated with MHC class I molecules," Curr Opin Immunol, 6(1):13-23 (1994).
Erlich et al., "Next-generation sequencing for HLA typing of class I loci," BMC Genomics, 12:42 (2011).
Estep et al., "Mutation Analysis of BRAF, MEK1 and MEK2 in 15 Ovarian Cancer Cell Lines: Implications for Therapy," PLOS ONE, 12:e1279 (2007).

(56) References Cited

OTHER PUBLICATIONS

Extended European Search Report dated Apr. 11, 2016, which issued during prosecution of EP Application No. 15198284.0.
Extended European Search Report for EP Application No. 19219395.1 dated Jul. 23, 2020.
Extended European Search Report for EP Application No. 22162718.5 dated Jul. 1, 2022.
Extended European Search Report for EP Application No. EP 20179960 dated Nov. 9, 2020.
Extended European Search Report received for EP patent application No. EP11781409, dated Apr. 10, 2014.
Extended Search Report in Corresponding European Application No. 11781409.5, dated Apr. 14, 2014.
Extracts from the USPTO patent register.
Eyers et al., "CONSeQuence: prediction of reference peptides for absolute quantitative proteomics using consensus machine learning approaches," Mol Cell Proteomics (2011); 10(11):M110.003384. doi: 10.1074/mcp.MI 10.003384. Epub Aug. 3, 2011.
Ezzell, "Cancer 'Vaccines': An idea whose time has come?," J NIH Res, 7:46 (1995).
Fackler et al., "Quantitative Multiplex Methylation-Specific PCR Assay for the Detection of Promoter Hypermethylation in Multiple Genes in Breast Cancer," Cancer Research, 64(13): 4442-4452 (2004).
Filatreau et al., "Technische Universitat Berlin, Fakultat III—Prozesswissenschaften Direct comparasion of T cell receptor avidity of auto-antigen specific conventional and regulatory T cells," Abstract, 1-6.
Final Office Action for U.S. Appl. No. 15/735,566, "Formulations for Neoplasia Vaccines and Methods of Preparing Thereof," dated Feb. 3, 2021.
Final Office Action for U.S. Appl. No. 15/800,732, "Compositions and Methods of Identifying Tumor Specific Neoantigens," dated Dec. 17, 2020.
Final Office Action for U.S. Appl. No. 16/813,371, "Formulations for Neoplasia Vaccines," dated Oct. 13, 2020.
Final Rejection for U.S. Appl. No. 14/794,449, "Compositions and Methods of Identifying Tumor Specific Neoantigens," dated Apr. 5, 2019.
Final Rejection for U.S. Appl. No. 14/877,125, "Compositions and Methods for Personalized Neoplasia Vaccines," dated May 24, 2019.
Final Rejection for U.S. Appl. No. 13/108,610, "Compositions and Methods of Identifying Tumor Specific Neoantigens," dated May 12, 2014.
Final Rejection for U.S. Appl. No. 14/794,449, "Compositions and Methods of Identifying Tumor Specific Neoantigens," dated Sep. 13, 2017.
Final Rejection for U.S. Appl. No. 14/877,125, "Compositions and Methods for Personalized Neoplasia Vaccines," dated Oct. 25, 2017.
Final Rejection for U.S. Appl. No. 15/038,504, "Compositions and Methods for Diagnosing, Evaluating and Treating Cancer by Means of the DNA Methyl," dated Apr. 30, 2018.
Final Rejection for U.S. Appl. No. 15/038,504, "Compositions and Methods for Diagnosing, Evaluating and Treating Cancer by Means of the DNA Methyl," dated Dec. 21, 2018.
Final Rejection for U.S. Appl. No. 15/102,129, "Formulations for Neoplasia Vaccines," dated Aug. 15, 2019.
Final Rejection for U.S. Appl. No. 15/102,129, "Formulations for Neoplasia Vaccines," dated Sep. 14, 2018.
Final Rejection for U.S. Appl. No. 15/105,961, "Combination Therapy With Neoantigen Vaccine," dated Aug. 23, 2019.
Final Rejection for U.S. Appl. No. 15/105,961, "Combination Therapy With Neoantigen Vaccine," dated Jul. 5, 2018.
Final Rejection for U.S. Appl. No. 15/187,174, "Compositions and Methods of Identifying Tumor Specific Neoantigens," dated May 25, 2017.
Final Rejection for U.S. Appl. No. 15/187,174, "Compositions and Methods of Identifying Tumor Specific Neoantigens," dated Oct. 12, 2018.

Final Rejection for U.S. Appl. No. 15/513,127, "Use of Clonal Evolution Analysis for Ibrutinib Resistance in Chronic Lymphocytic Leukemia Patients," dated May 17, 2019.
Final Rejection for U.S. Appl. No. 15/537,785, "Methods for Profiling the T Cell Repertoire," dated Jul. 18, 2019.
Final Rejection for U.S. Appl. No. 15/537,839, "Molecular Biomarkers for Cancer Immunotherapy," dated May 1, 2020.
Final Rejection for U.S. Appl. No. 15/575,328, " Shared Neoantigens," dated Oct. 23, 2019.
Final Rejection for U.S. Appl. No. 16/181,098, "Compositions and Methods of Identifying Tumor Specific Neoantigens," dated Jun. 17, 2019.
Fritsch et al., "HLA-Binding Properties of Tumor Neoepitopes in Humans," Cancer Immunol Res, 2(6):522-529 (2014).
Fritsch et al., "Personal Neoantigen Cancer Vaccines: A Road Not Fully Paved," Cancer Immunology Research, 8: 1465-9 (2020).
Fritsch et al., "Personal neoantigen cancer vaccines: The momentum builds," Oncoimmunology, 3(6):e29311 (2014).
Fruci et al., "Altered expression of endoplasmic reticulum aminopeptidases ERAPI and ERAP2 in transformed non-lymphoid human tissues," J Cell Physiol, 216(3):742-749 (2008).
Furman et al., "Ibrutinib resistance in chronic lymphocytic leukemia," New Engl J Med, 370(24):2352 (2014).
Fusaro et al., "Prediction of high-responding peptides for targeted protein assays by mass spectrometry" Nat Biotechnol, 27(2):190-198 (2009).
Ganesan et al., "Tumor-Infiltrating Regulatory T Cells Inhibit Endogenous Cytotoxic T Cell Responses to Lung Adenocarcinoma," The Journal of Immunology, 191(4): 2009-2017 (2013).
Garcia-Marco et al., "Frequent Somatic Deletion of the 13q12.3 locus Encompassing BRCA2 in Chronic Lymphocytic Leukemia," Blood, 88: 1568-1575 (1996).
Gascoigne et al., "Allelic exclusion of the T cell receptor a-chain: developmental regulation of post-translational event," Semin Immunol, 11:337-347 (1999).
Gaynor et al., "GATA3 Mutations Found in Breast Cancers May Be Associated with Aberrant Nuclear Localization, Reduced Transactivation and Cell Invasiveness", Hormones and Cancer, 4: 123-139 (2013).
Gazdar, "Activating and resistance mutations of EGFR in non-small-cell lung cancer: role in clinical response to EGFR tyrosine kinase inhibitors," Oncogene, 28:S24-S31 (2009).
Gibney et al., "Safety and efficacy of adjuvant anti-PD1 therapy (nivolumab) in combination with vaccine in resected high-risk metastatic melanoma.," J Clin Oncol, Abstract 9056 (2013).
Gilboa, "The Makings of a Tumor Rejection Antigen," Immunity, 11: 263-270 (1999).
Gnirke et al., "Solution Hybrid Selection with Ultra-Long Oligonucleotides for Massively Parallel Targeted Sequencing," Nat Biotechnol, 27(2): 182-189 (2009).
Goh et al., "Mining the Structural Genomics Pipeline: Identification of Protein Properties that Affect High-throughput Experimental Analysis," Journal of Molecular Biology, 336(1): 115-130 (2004).
Gotter et al., "Medullary Epithelial Cells of the Human Thymus Express a Highly Diverse Selection of Tissue-specific Genes Colocalized in Chromosomal Clusters," J Exp Med, 199(2): 155-166 (2004).
Goya et al., "SNVMix:predicting single nucleotide variants from next-generation sequencing of tumors," Bioinformatics, Original Paper, 26(6): 730-736 (2010).
Greenman et al., "Patterns of somatic mutation in human cancer genomes," Nature, 446:153-158 (2007).
Guasp et al., "The Peptidome of Behcet's Disease-Associated HLA-B*51 :01 Includes Two Subpeptidomes Differentially Shaped by Endoplasmic Reticulum Aminopeptidase 1," Arthritis Rheumatol, 68:505-515 (2016).
Gubin et al., "Checkpoint blockade cancer immunotherapy targets tumor-specific mutant antigens," Nature, 515:577-581 (2014).
Gueguen et al., "An Antigen Recognized by Autologous CTLs on a Human Bladder Carcinoma," J Immunol, 160(12): 6188-6194 (1998).
Guo et al., "Different length peptids bind to HLA-Aw68 similarity at their ends but bulge on in the middle, " Nature, 360:364-366 (1992).

(56) References Cited

OTHER PUBLICATIONS

Guruprasad et al., "Correlation between stability of a protein and its dipeptide composition: a novel approach for predicting in vivo stability of a protein from its primary sequence," Protein Eng, 4(2):155-161 (1990).
Haanen et al., "Immunotherapy of melanoma," Euro J Canc Supp 11:97-105 (2013).
Hacohen et al., "Getting Personal with Neoantigen-Based Therapeutic Cancer Vaccines," Cancer Immunol. Res, 1(1):11-15 (2013).
Hamid et al., "Safety and Tumor Responses with Lambrolizumab (Anti-PD-1) in Melanoma," The New England Journal of Medicine, 369(2):134-144 (2013).
Han et al., "Linking T-Cell Receptor Sequence to Fucntional Phenotype at the Single-Cell Level," Nat Biotechnol, 32:684-692 (2014).
Harndahl et al., "Peptide-MHC class I stability is a better predictor than peptide affinity of CTL immunogenicity," Eur J Immunol, 42:1405-1416 (2012).
Harndahl et al., "Real-time, High-Throughput Measurements of Peptide-MHC-I Dissociation Using a Scintillation Proximity Assay," J Immunol Methods, 374:5-12 (2011).
Herbst et al., "Predictive Correlates of Response to the Anti-PD-L1 Antibody MPDL3280A in Cancer Patients," Nature, 515(7528):563-567 (2014).
Herman et al., "Differences in the Recognition by CTL of Peptides Presented by the HLAB*4402 and the HLA-B*4403 Molecules Which Differ by a Single Amino Acid," Tissue Antigens, 53: 111-121 (1999).
Hersey et al., "Phase I/II study of treatment with dendritic cell vaccines in patient with disseminated melanoma," Cancer Immunol Immunoother, 53:125-134 (2004).
Hickman et al., "Toward a Definition of Self: Proteomic Evaluation of the Class I Peptide Repertoire," J Immunol, 172:2944-2952 (2004).
History of Changes for Study: NCT01176461, Vaccine Therapy and Monoclonal Antibody Therapy in Treating Patients with Stage III or Stage IV Melanoma That Cannot Be Ren by Surgery, (6 pages) (2010).
Hocker et al., "Ultraviolet Radiation and Melanoma: A Systematic Review and Analysis of Reported Sequence Variants," Hum Mutat, 28(6): 578-588 (2007).
Hodi et al., "Biologic Activity of Cytotoxic T Lymphocyte-Associated Antigen 4 Antibody Blockade in Previously Vaccinated Metastatic Melanoma and Ovarian Carcinoma Patients," PNAS, 100: 4712-4717 (2003).
Hodi et al., "Immunologic and Clinical Effects of Antibody Blockade of Cytotoxic T Lymphocyte-Associated Antigen 4 in Previously Vaccinated Cancer Patients," PNAS, 105: 3005-3010 (2008).
Hodi et al., "Improved Survival with Ipilimumab in Patients with Metastatic Melanoma," New Engl J Med, 363:711-723 (2010).
Hofmann et al., "Presence of the BCR-ABL mutation Glu255Lys prior to STI571 (imatinib) treatment in patients with Ph+ acute lymphoblastic leukemia," Blood, 102(2): 659-661 (2003).
Hombrink et al., "Identification of Biological Relevant Minor Histocompatibility Antigens within the B-lymphocyte-Derived HLA-Ligandome Using a Reverse Immunology Approach," Clin Cancer Res, 21(9):2177-2186 (2015).
Hoof et al., "NetMHCpan, a method for MHC class I binding prediction beyond humans," Immunogenetics, 61:1-13 (2009).
Huang et al., "T Cells Associated With Tumor Regression Recognize Frameshifted Products of the CDKN2A Tumor Suppressor Gene Locus and a Mutated HLA Class I Gene Product," J Immunol, 172(10):6057-6064 (2004).
Humphries et al., "Lineage tracing reveals multipotent stem cells maintain human adenomas and the pattern of clonal expansion in tumor evolution," PNAS, 110(27):e2490-e2499 (2013).
Hunt et al., "Characterization of peptides bound to the class I MHC molecule HLA-A2.1 by mass spectrometry," Science, 255:1261-1263 (1992).

IEDB Analysis Resource for MHC-I binding predictions (printed Oct. 2019).
IEDB Analysis Resource for MHC-II binding predictions (printed Oct. 2019).
Illumina, "Immunotherapy, the Next Generation of Cancer Treatment, NGS-guided assessment of interactions between tumors and the immune system leads to new discoveries in immuno-oncology," (2016).
Intellectual Property Policy for Partners-Affiliated Hospitals and Institutions, Aug. 15, 2002.
International Preliminary Report on Patentability for International Application No. PCT/US2011/036665 dated Nov. 20, 2012.
International Preliminary Report on Patentability for International Application No. PCT/US2014/033185 dated Oct. 22, 2015.
International Preliminary Report on Patentability for International Application No. PCT/US2014/067146 dated May 31, 2016.
International Preliminary Report on Patentability for International Application No. PCT/US2014/068746 dated Jun. 7, 2016.
International Preliminary Report on Patentability for International Application No. PCT/US2014/068893 dated Jun. 7, 2016.
International Preliminary Report on Patentability for International Application No. PCT/US2014/071707 dated Jun. 21, 2016.
International Preliminary Report on Patentability for International Application No. PCT/US2015/067143 dated Jun. 20, 2017.
International Preliminary Report on Patentability for International Application No. PCT/US2017/028122 dated Oct. 23, 2018.
International Search Report and Written Opinion for International Application No. PCT/US/2015/051340 dated Dec. 21, 2015.
International Search Report and Written Opinion for International Application No. PCT/US/2016/033452 dated May 20, 2016.
International Search Report and Written Opinion for International Application No. PCT/US/2016/036605 dated Jan. 16, 2017.
International Search Report and Written Opinion for International Application No. PCT/US2011/036665 dated Jul. 2, 2012.
International Search Report and Written Opinion for International Application No. PCT/US2014/033185 dated Nov. 5, 2014.
International Search Report and Written Opinion for International Application No. PCT/US2014/067146 dated Mar. 31, 2015.
International Search Report and Written Opinion for International Application No. PCT/US2015/067143 dated Apr. 12, 2016.
International Search Report and Written Opinion for International Application No. PCT/US2017/028122 dated Apr. 18, 2016.
International Search Report and Written Opinion for International Application No. PCT/US2018/014831 dated Apr. 4, 2018.
International Search Report for International Application No. PCT/US2014/068746 dated Mar. 23, 2015.
International Search Report for International Application No. PCT/US2014/068893 dated Apr. 9, 2015.
International Search Report for International Application No. PCT/US2014/071707 dated Sep. 10, 2015.
Invention Agreement of the Dana-Farber Cancer Institute, Jul. 1, 1997.
Ishihama et al., "Exponentially Modified Protein Abundance Index (emPAI) for Estimation of Absolute Protein Amount in Proteomics by the Number of Sequenced Peptides per Protein," Mol Cell Proteomics, 4:1265-1272 (2005).
Japanese Office Action dated Jan. 22, 2018, which issured during prosecution of JP 2016-507587.
Japanese Office Action from Application No. 2013-510360 dated Apr. 28, 2015.
Jarmalavicius et al., "High Immunogenicity of the Human Leukocyte Antigen Peptidomes of Melanoma Tumor Cells," J Biol Chem, 287(40):33401-33411 (2012).
Jeffery et al., "The Influence of HLA Class I Alleles and Heterozygosity on the Outcome of Human T Cell Lymphotropic Virus Type I Infection," J Immunol, 165:7278-7284 (2000).
Ji et al., "An immune-active tumor microenvironment favors clinical response to ipilimumab," Cancer Immunol Immunother, 61(7):1019-1031 (2011).
Jiang et al., "GATA3 Mutations Define a Unique Subtype of Luminal-Like Breast Cancer With Improved Survival," Canc 120:1329-1337 (2014).

(56) References Cited

OTHER PUBLICATIONS

Jocham et al., "Adjuvant Autologous Renal Tumour Cell Vaccine and Risk of Tumour Progression in Patients with Renal-Cell Carcinoma After Radical Nephrectomy: Phase III, Randomised Controlled Trial," Lancet, 363: 594-599 (2004).
Johnson et al., "Discovery of Naturally Processed and HLA-Presented Class I Peptides from Vaccinia Virus Infection using Mass Spectrometry for Vaccine Development," Vaccine, 28(1):38-47 (2009).
Jorgensen et al., "NetMHC stab—predicting stability of peptide-MHC-I complexes; impacts for cytotoxic T lymphocyte epitope discovery." Immunology 141:18-26 (2014).
Jun et al., "Progress in T cell adoptive Immunotherapy for Malignant Solid Tumors," Chin Med Biotechnol, 3(1):1-7 (2008).
Kalaora et al., "Use of HLA peptidomics and whole exome sequencing to identify human immunogenic neo-antigens," Oncotarget, 7(5):5110-5117 (2016).
Kanduri et al., "Differential genome-wide array-based methylation profiles in prognostic subsets of chronic lymphocytic leukemia," Blood, 115(2):296-305 (2010).
Kantoff et al., "Sipuleucel-T Immunotherapy for Castration-Resistant Prostate Cancer," The New England Journal of Medicine, 363: 411-422 (2010).
Kanzler et al., "Therapeutic Targeting of Innate Immunity with Toll-like Receptor Agonists and Antagonists," Nat Med, 13: 552-559 (2007).
Kawakami et al., "Identification of human tumor antigens and its implications for diagnosis and treatment of cancer," Cancer Sci, 95(10): 784-791 (2004).
Keats et al., "Promiscuous Mutations Activate the Noncanonical NF-KB Pathway in Multiple Myeloma," Cancer Cell, 12: 131-144 (2007).
Kenter et al., "Phase I Immunotherapeutic Trial with Long Peptides Spanning the E6 and E7 Sequences of High-Risk Human Papillomavirus 16 in End-Stage Cervical Cancer Patients Show Low Toxicity and Robust Immunogenicity," Clin. Cancer Research, 14(1):169-177 (2008).
Keogh et al., "Identification of New Epitopes from Four Different Tumor-Associated Antigens: Recognition of Naturally Processed Epitopes Correlates with HLA-A☐00201-Binding Affinity," J Immunol, 167:787-796 (2001).
Keskin et al., "Direct identification of an HPV-16 tumor antigen from cervical cancer biopsy specimens," Front Immunol, 2:75 (2011).
Keskin et al., "Neoantigen vaccine generates intratumoral T cell responses in phase lb glioblastoma trial," Nature, 565(7738):234-239 (2019).
Keskin et al., "Physical detection of influenza A epitopes identifies a stealth subset on human lung epithelium evading natural CD8 immunity," PNAS, 112(7):2151-2156 (2015).
Kesmir et al., "Prediction of proteasome cleavage motifs by neural networks," Protein Eng, 15(4):287-296 (2002).
Kessler et al., "Identification of T-cell epitopes for cancer immunotherapy," Leukemia, 21:1859-1874 (2007).
Khalili et al., "In silico prediction of tumor antigens derived from functional missense mutations of the cancer gene census," Oncoimmunology, 1(8):1281-1289 (2012).
Khammari et al., "Treatment of metastatic melanoma with autologous melan-A/mart-1-specific cytotoxic t lymphocyte clones," Journal of Investigative Dermatology, 129(12): 2835-2842 (2009).
Kim et al., "Derivation of an amino acid similarity matrix for peptide:MHC binding and its application as a Bayesian prior," BMC Bioinformatics, 10:1-11 (2009).
Kim et al., "Inactivating mutations of caspase-8 in colorectal carcinomas," Gastroenterology, 125:708-715 (2003).
Kim et al., "mTOR inhibitors radiosensitize PTEN-deficient non-small-cell lung cancer cells harboring an EGFR activating mutation by inducing autophagy," J Cell Biochem, 114(6):1248-1256 (2013).
Kim et al., "Positional Bias of MHC Class I Restricted T-Cell Epitopes in Viral Antigens Is Likely due to a Bias in Conservation," PLoS Comput Biol, 9:el002884 (2013).

Kirstensen et al., "The Antigenicity of the Tumor Cell—Context Matters," The New England Journal of Medicine, 376(5): 491-493 (2017).
Klug et al., "Characterization of MHC Ligands for Peptide Based Tumor Vaccination," Current Pharmaceutical Design, 15(28): 3221-3236 (2009).
Kobayashi et al., "DNA methylation profiling reveals novel biomarkers and important roles for DNA methyltransferases in prostate cancer," Genome Research, 21:1017-1027 (2011).
Koh et al., "Immunological consequences of using three different clinical/laboratory techniques of emulsifying peptide-based vaccines in incomplete Freund's adjuvant," J Translational Med, 4:42 (2006).
Komarova et al., "Evolution of Ibrutinib Resistance in Chronic Lymphcytic Leukemia (CLL)," Proceedings of the National Academy of Sciences, 111(38):13906-13911 (2014).
Kornher et al., "Mutation Detection Using Nucleotide Analogs That Alter Electrophoretic Mobility," Nucleic Acids Res, 17(19): 7779-7784 (1989).
Kreiter et al., "Targeting the tumor mutanome for personalized vaccination therapy," OncoImmunology, 1(5):768-769 (2012).
Krieg, "Therapeutic potential of Toll-like receptor 9 activation," Nature reviews Drug discovery, 5(6):471-484 (2006).
Kronenberger et al., "A Polyvalent Cellular Vaccine Induces T-cell Responses Against Specific Self-antigens Overexpressed in Chronic Lymphocytic B-cell Leukemia," J Immunother, 31(8): 723-730 (2008).
Kronke et al. "Lenalidomide causes selective degradation of IKZFI and IKZF3 in multiple myeloma cells." Science, 343(6168): 301-305 (2014).
Kronke et al. "Lenalidomide induces ubiquitination and degradation of CKla in del(5q) MDS," Nature, 523(7559):183-188 (2015).
Kuppuswamy et al., "Single Nucleotide Primer Extension to Detect Genetic Diseases: Experimental Application to Hemophilia B (Factor IX) and Cystic Fibrosis Genes," PNAS, 88(4): 1143-1147 (1991).
Kyte et al., "A Simple Method for Displaying the Hydropathic Character of a Protein," J. Mol. Biol., 157: 105-132 (1982).
Ladetto et al., "Real-Time Polymerase Chain Reaction in Multiple Myeloma: Quantitative Analysis of Tumor Contamination of Stem Cell Harvests," Exp Hematol, 30: 529-536 (2002).
Landau et al., "Chronic lymphocytic leukemia: molecular heterogeneity revealed by high-throughput genomics," Genome Med, 5:47 (2013).
Landau et al., "Increased Local Disorder of DNA Methylation Forms the Basis of High Intra-Leukemic Epigenetic Heterogeneity and Enhances CLL Evolution," Blood, 122:596 (2013).
Landau et al., "The evolutionary landscape of chronic lymphocytic leukemia treated with ibrutinib targeted therapy," Nat Commun, 8(1):2185 (2017).
Larsen et al., "Large-scale validation of methods for cytotoxic T-lymphocyte epitope prediction," BMC Bioinformatics, 8:424-424 (2007).
Lata et al., "MHCBN 4.0: A database of MHC/TAP binding peptides and T-cell epitopes," BMC Research Notes, 2(1): 61 (2009).
Lavranos Declaration dated Jan. 12, 2022.
Lavranos Declaration dated Jan. 17, 2022.
Le et al., "Next-Generation Cancer Vaccine Approaches: Integrating Lessons Learned From Current Successes With Promising Biotechnologic Advances," J Natl Compr Cancer Network, 11:766-772 (2013).
Lee et al., "Monocyte-derived dendritic cells from HLA-matched allogenic donors showed a greater ability to induce leukemic cell-specific T cells in comparison to leukemic cell-derived dendritic cells or monocyte-derived dendritic cells from AML patients," Leukemia Research, 32: 1653-1660 (2008).
Lee, "Identification of Neo-antigens for a Cancer Vaccine by Transcriptome Analysis", PhD Thesis, Arizona State University (2012).
Lemmel et al., "Differential quantitative analysis of MHC ligands by mass spectrometry using stable isotope labeling," Nature Biotechnology, 22(4):450-454 (2004).

(56) References Cited

OTHER PUBLICATIONS

Letter from Mathys & Squire dated Jun. 28, 2017 accompanying Response to Notices of Opposition of EP2569633.
Letter from Mathys & Squire dated Jun. 29, 2017+B245:B256.
Lewin et al., "DNA is the Genetic Material: Mutations Change the Sequence of DNA, " Genes IV, 4:68-69 (1990).
Lewintre et al., "Analysis of chronic lymphotic leukemia transcriptomic profile: differences between molecular subgroups," Leuk Lymphoma, 50:68-79 (2009).
Ley et al., "DNA sequencing of a cytogenetically normal acute myeloid leukaemia genome," Nature, 456: 66-72 (2008).
Ley et al., "DNMT3A Mutations in Acute Myeloid Leukemia", The New England Journal of Medicine, 363: 2423-2433 (2010).
Li et al., "Cancer Genome Sequencing and Its Implications for Personalized Cancer Vaccines," Cancers 3(4):4191-4211 (2011).
Lin et al., "Evaluation of MHC-II Peptide Binding Prediction Servers: Applications for Vaccine Research," BMC Bioinformatics, 9: S22 (2008).
Linard et al., "A ras-Mutated Peptide Targeted by CTL Infiltrating a Human Melanoma Lesion," J Immunol, 168:4802-4808 (2002).
Linardou et al., "Assessment of somatic k-RAS mutations as a mechanism associated with resistance to EGFR-targeted agents: a systematic review and meta-analysis of studies in advanced non-small-cell lung cancer and metastatic colorectal cancer," Lancet Oncol, 9(10):962-972 (2008).
Linardou et al., "Somatic EGFR mutations and efficacy of tyrosine kinase inhibitors in NSCLC," Nat Rev Clin Oncol, 6(6):352-366 (2009).
Lindhout et al., "Site-specific enzymatic polysialylation of therapeutic proteins using bacterial enzymes," PNAS, 108(18):7397-7402 (2011).
Linnemann et al., "High-throughput epitope discovery reveals frequent recognition of neo-antigens by CD4+ T cells in human melanoma," Nat Med, 21:81-85 (2015).
Linnemann et al., "High-throughput identification of antigen-specific TCRs by TCR gene capture," Nat Med, 19(11): 1534-1541 (2013).
Liu et al., "Athlates:accurate typing of human leukocyte antigen through exome sequencing," Nucleic Acids Res, 41(14):e142 (2013).
Llano et al., "Best-Characterized HIV-1 CTL Epitopes: The 2013 Update," HIV Mol Immunol, 3-25 (2013).
Lorente et al., "Diversity of Natural Self-Derived Ligands Presented by Different HLA Class I Molecules in Transporter Antigen Processing-Deficient Cells," PLoS ONE 8:e59118 (2013).
Loveridge et al., "The genetic contribution to human T-cell receptor repertoire," Immunology, 74:246-250 (1991).
Lucas et al., "About human tumor antigens to be used in immunotherapy," Semin Immunol, 20(5):301-307 (2008).
Lundegaard et al., "NetMHC-3.0: accurate web accessible predictions of human, mouse and monkey MHC class I affinities for peptides of length 8-11," Nucleic Acids Research, 36: W509.W512 (2008).
Lundegaard et al., "State of the art and challenges in sequence based T-cell epitope prediction," Immunome Research, 6(Suppl 2): S3 (2010).
Luo et al. "Machine learning methods for Predicting hla-Peptide Binding activity," Bioinformatics and Biology Insights, 9(s3):21-29 (2015).
Ma, "Novor: Real-Time Peptide de Novo Sequencing Software," J Am Soc Mass Spectrom, 26:1885-1894 (2015).
Macconaill et al., Profiling Critical Cancer Gene Mutations in Clinical Tumor Samples, PLoS One, 4(11):e7887 (2009).
Machiels et al., "Peptide-Based Cancer Vaccines," Seminars in Oncology, 29(5):494-502 (2002).
Mackall et al., "Targeting tumor specific translocations in sarcomas in pediatric patients for immunotherapy," Clinical Orthopaedics and Related Research, 373:25-31 (2000).
Maeurer et al., "New treatment options for patients with melanoma: review of melanoma-derived T-cell epitopebased peptide vaccines," Melanom Research, 6:11-24 (1996).
Maker et al., "Intrapatient Dose Escalation of Anti-CTLA-4 Antibody in Patients With Metastatic Melanoma," J Immunother, 29: 455-463 (1997).
Malavolta et al., "Interpretation of the dissolution of insoluble peptide sequences based on the acid-base properties of the solvent," Protein Sci, 15(6):1476-1488 (2006).
Malcikova et al., "Identification of somatic hypermutations in the TP53 gene in B-cell chronic lymphocytic leukemia," Molecular Immunol, 45(5):1525-1529 (2008).
Mandelboim et al., "Regression of Established Murine Carcinoma Metastases Following Vaccination with Tumor-Associated Antigen Peptides," Nature Medicine, 1(11):1179-1183 (1995).
Mandruzzato et al., "A CASP-8 Mutation Recognized by Cytolytic T Lymphocytes on a Human Head and Neck Carcinoma," J Exp Med, 186: 785-793 (1997).
Mardis et al., "Cancer genome sequencing: a review," Human Molecular Genetics, 18(2): R163-R168 (2009).
Mardis et al., "Recurring Mutations Found by Sequencing an Acute Myeloid Leukemia Genome," New Engl J Med, 361:1058-1066 (2009).
Mardis, "The impact of next-generation sequencing technology on genetics," Trends in Genetics, 24(3):133-141 (2007).
Margulies et al., "Genome Sequencing in Open Microfabricated High Density Picoliter Reactors," Nature, 15:437(7057): 376-380 (2005).
Marijt et al., "Hematopoiesis-Restricted Minor Histocompatibility Antigens HA-1- or HA -2- specific T Cells can Induce Complete Remissions of Relapsed Leukemia," PNAS, 100: 2742-2747 (2003).
Marina et al., "Serologic Markers of Effective Tumor Immunity Against Chronic Lymphocytic Leukemia Include Nonmutated B-Cell Antigens," Cancer Res, 70(4): 1344-1355 (2010).
Mark et al., "Site-specific mutagenesis of the human fibroblast interferon gene," PNAS, 81(18):5662-5666 (1984).
McCleskey et al., "GATA-3 Expression in Advanced Breast Cancer: Prognostic Value and Organ-Specific Relapse," Amer J Clin Pathol 144:756-763 (2015).
McGranahan et al., "Clonal neoantigens elicit T cell immunoreactivity and sensitivity to immune checkpoint blockade," Science, 351(6280: 1463-1469 (2016).
McMurtrey et al., "Toxoplasma gondii peptide ligands open the gate of the HLA class I binding groove," eLife 5:e12556 (2016).
Melief., "Cancer Immunotherapy by Dendritic Cells" Immunity, 29: 372-383 (2008).
Melief., "Precision T-cell therapy targets tumours," Nature, 547(7662): 165-167 (2017).
Men et al., "Assessment of Immunogenicity of Human Melan-A Peptide Analogues in HLA-A*0201/Kb Transgenic Mice," J Immunol, 162:3566-3573 (1999).
Meyerson et al., "Advances in understanding cancer genomes through second-generation sequencing," Nat Rev Genetics, 11:685-696 (2010).
Mikeska et al., "The implications of heterogeneous DNA methylation for the accurate quantification of methylation," Epigenomics, 2(4):561-573 (2010).
Milner et al., "The Effect of Proteasome Inhibition on the Generation of the Human Leukocyte Antigen (HLA) Peptidome," Mol Cell Proteomics, 12:1853-1864 (2013).
Milner et al., "The Turnover Kinetics of Major Histocompatibility Complex Peptides of Human Cancer Cells*," Mol Cell Proteomics, 5:357-365 (2006).
Miyamoto et al, "GATA binding protein 3 is down-regulated in bladder cancer yet strong expression is an independent predictor of poor prognosis in invasive tumor," Human Pathology, 43:2033-2040 (2012).
Mkrtichyan et al., "B117 Defining a novel mechanism of a-PD1 synergy with vaccine to induce potent anti-tumor effects," Clinical Exp. Metastasis, 28, Abstract #B117(247-248): 157-259 (2011).
Mommen et al., "Expanding the detectable HLA peptide repertoire using electron-transfer/higher-energy collision dissociation (EThcD)," PNAS III, 4507-4512 (2014).
Mommen et al., "Sampling From the Proteome to the Human Leukocyte Antigen-DR (HLA-DR) Ligandome Proceeds Via High Specificity," Mol Cell Proteomics MCP, 15:1412-1423 (2016).

(56) References Cited

OTHER PUBLICATIONS

Mosmann et al., "TH1 and TH2 Cells: Different Patterns of Lymphokine Secretion Lead to Different Functional Properties," Ann Rev Immunol, 7:145-173 (1989).
Mullally et al., "Beyond HLA: The Significance of Genomic Variation for Allogeneic Hematopoietic Stem Cell Transplantation," Blood, 109: 1355-1362 (2007).
Muntel et al., "Abundance-based Classifier for the Prediction of Mass Spectrometric Peptide Detectability Upon Enrichment (PPA)," Mol Cell Proteomics, 14:430-440 (2015).
Murphy et al., "Antigen Presentation to T Lymphocytes," Janeway's Immunobiology, 7th Edition, 5:182-83 & 197 (2008).
Ng et al., "Dereplication and de novo sequencing of nonribosomal peptides," Nat Meth, 6:596-599 (2009).
Nielsen et al., "NetMHCpan-3.0; improved prediction of binding to MHC class I molecules integrating information from multiple receptor and peptide length datasets," Genome Medicine, 8:33 (2016).
Nielsen et al., "The role of the proteasome in generating cytotoxic T-cell epitopes: insights obtained from improved predictions of proteasomal cleavage," Immunogenetics, 57:33-41 (2005).
Niwa et al., "Bimodal protein solubility distribution revealed by an aggregation analysis of the entire ensemble of *Escherichia coli* proteins," PNAS, 106(11): 4201-4206 (2009).
Non-Final Office Action for U.S. Appl. No. 13/108,610, "Compositions and Methods of Identifying Tumor Specific Neoantigens," dated Aug. 15, 2013.
Non-Final Office Action for U.S. Appl. No. 13/108,610, "Compositions and Methods of Identifying Tumor Specific Neoantigens," dated Dec. 3, 2014.
Non-Final Office Action for U.S. Appl. No. 14/794,449, "Compositions and Methods of Identifying Tumor Specific Neoantigens," dated Dec. 29, 2016.
Non-Final Office Action for U.S. Appl. No. 14/794,449, "Compositions and Methods of Identifying Tumor Specific Neoantigens," dated Jul. 24, 2018.
Non-Final Office Action for U.S. Appl. No. 14/877,125, "Compositions and Methods for Personalized Neoplasia Vaccines," dated Mar. 27, 2017.
Non-Final Office Action for U.S. Appl. No. 14/877,125, "Compositions and Methods for Personalized Neoplasia Vaccines," dated Nov. 2, 2018.
Non-Final Office Action for U.S. Appl. No. 15/038,504, "Compositions and Methods for Diagnosing, Evaluating and Treating Cancer By Means of the DNA Methyl," dated Sep. 6, 2017.
Non-Final Office Action for U.S. Appl. No. 15/102,129, "Formulations for Neoplasia Vaccines," dated Apr. 26, 2019.
Non-Final Office Action for U.S. Appl. No. 15/102,129, "Formulations for Neoplasia Vaccines," dated Dec. 17, 2018.
Non-Final Office Action for U.S. Appl. No. 15/102, 129, "Formulations for Neoplasia Vaccines," dated Jul. 28, 2017.
Non-Final Office Action for U.S. Appl. No. 15/102,129, "Formulations for Neoplasia Vaccines," dated Mar. 7, 2018.
Non-Final Office Action for U.S. Appl. No. 15/105,961, "Combination Therapy With Neoantigen Vaccine," dated Jan. 21, 2021.
Non-Final Office Action for U.S. Appl. No. 15/105,961, "Combination Therapy With Neoantigen Vaccine," dated Jan. 8, 2019.
Non-Final Office Action for U.S. Appl. No. 15/105,961, "Combination Therapy With Neoantigen Vaccine," dated Nov. 20, 2017.
Non-Final Office Action for U.S. Appl. No. 15/187,174, "Compositions and Methods of Identifying Tumor Specific Neoantigens," dated Dec. 5, 2016.
Non-Final Office Action for U.S. Appl. No. 15/187,174, "Compositions and Methods of Identifying Tumor Specific Neoantigens," dated Jan. 22, 2018.
Non-Final Office Action for U.S. Appl. No. 15/513,127, "Use of Clonal Evolution Analysis for Ibrutinib Resistance in Chronic Lymphocytic Leukemia Patients," dated Dec. 4, 2020.
Non-Final Office Action for U.S. Appl. No. 15/513,127, "Use of Clonal Evolution Analysis for Ibrutinib Resistance in Chronic Lymphocytic Leukemia Patients," dated Nov. 26, 2018.
Non-Final Office Action for U.S. Appl. No. 15/537,785, "Methods for Profiling the T Cell Repertoire," dated Dec. 21, 2018.
Non-Final Office Action for U.S. Appl. No. 15/575,328, "Shared Neoantigens," dated Jun. 27, 2019.
Non-Final Office Action for U.S. Appl. No. 16/181,098, "Compositions and Methods of Identifying Tumor Specific Neoantigens," dated Jan. 31, 2019.
Non-Final Office Action for U.S. Appl. No. 16/181,098, "Compositions and Methods of Identifying Tumor Specific Neoantigens," dated Oct. 29, 2020.
Non-Final Rejection for U.S. Appl. No. 14/877,125, " Compositions and Methods for Personalized Neoplasia Vaccines," dated Feb. 3, 2020.
Non-Final Rejection for U.S. Appl. No. 15/038,504, "Compositions and Methods for Diagnosing, Evaluating and Treating Cancer by Means of the DNA Methylation Status," dated Feb. 4, 2020.
Non-Final Rejection for U.S. Appl. No. 15/105,961, "Combination Therapy With Neoantigen Vaccine," dated Jun. 2, 2020.
Non-Final Rejection for U.S. Appl. No. 15/513,127, "Use of Clonal Evolution Analysis for Ibrutinib Resistance in Chronic Lymphocytic Leukemia Patients," dated Oct. 29, 2019.
Non-Final Rejection for U.S. Appl. No. 15/537,785, "Methods for Profiling the T Cell Repertoire," dated May 11, 2020.
Non-Final Rejection for U.S. Appl. No. 15/537,839, "Molecular Biomarkers for Cancer Immunotherapy," dated Oct. 8, 2019.
Non-Final Rejection for U.S. Appl. No. 15/735,566, "Formulations for Neoplasia Vaccines and Methods of Preparing Thereof," dated May 28, 2020.
Non-Final Rejection for U.S. Appl. No. 15/800,732, "Compositions and Methods of Identifying Tumor Specific Neoantigens," dated Apr. 10, 2020.
Notice of Allowance for U.S. Appl. No. 13/108,610, "Compositions and Methods of Identifying Tumor Specific Neoantigens," dated Jun. 11, 2015.
Notice of Allowance for U.S. Appl. No. 13/108,610, "Compositions and Methods of Identifying Tumor Specific Neoantigens," dated May 12, 2015.
Notice of Allowance for U.S. Appl. No. 15/102,129, "Formulations for Neoplasia Vaccines," dated Oct. 12, 2018.
Notice of Allowance for U.S. Appl. No. 15/575,328, "Shared Neoantigens," dated Jan. 23, 2020.
Notice of Allowance for U.S. Appl. No. 16/188,737, "Compositions and Methods of Identifying Tumor Specific Neoantigens," dated Jul. 25, 2019.
Notice of Opposition to European Patent No. EP2569633—Agenus Inc. (Opponent) dated Nov. 9, 2016.
Notice of Opposition to European Patent No. EP2569633—Dr. Christian Muller (Opponent) dated Nov. 9, 2016.
Notice of Opposition to European Patent No. EP2569633—Gritstone Oncology, Inc. (Opponent) dated Nov. 7, 2016.
Notice of Opposition to European Patent No. EP2569633—James Poole Limited (Opponent) dated Nov. 9, 2016.
Notice of Opposition to European Patent No. EP2569633—Strawman Limited (Opponent) dated Nov. 10, 2016.
Novellino et al., "A listing of human tumor antigens recognized by T cells: Mar. 2004 update," Cancer Immunol Immunother, 54(3):187-207 (2005).
Nyren et al., "Solid Phase DNA Minisequencing by an Enzymatic Luminometric Inorganic Pyrophosphate Detection Assay," Anal Biochem, 208(1): 171-175 (1993).
O'Mahony et al., "A Pilot Study of CTLA-4 Blockade after Cancer Vaccine Failure in Patients with Advanced Malignancy" Clin Canc Res 13(3):958-964 (2007).
O'Shea et al., "Signal transduction and Th17 cell differentiation," Microbes Infect, 11(5):599-611 (2009).
Oakes et al., "Evolution of DNA Methylation Is Linked to Genetic Aberrations in Chronic Lymphocytic Leukemia," Cancer Discov, 4(3):348-361 (2014).
Oakes et al., "Heterogeneity and Evolution of DNA Methylation in Chronic Lymphocytic Leukemia," Blood, 122(21):1626 (2013).

(56) References Cited

OTHER PUBLICATIONS

Oates et al., "D(2)P(2): database of disordered protein predictions," Nucleic Acids Res, 41:D508-D516 (2013).
Ofran et al., "Identification of Human Minor Histocompatibility Antigens (MHA) by Combining Bioinformatic Prediction of Peptide Epitopes with Validation of T Cell Reactivity in Patient Blood Samples after Allogeneic Hematopoietic Stem Cell Transplantation," Biol Bone Marrow Transplant, 14:1 (Abstract #2) (2008).
Ohashi et al., "Lung cancers with aquired resistance to EGFR inhibitors occasionally harbor BRAF gene mutations but lack mutations in KRAS, NRAS, or MEK1," PNAS, E2127-E2133 (2012).
Opavsky et al., CpG Island Methylation in a Mouse Model of Lymphoma Is Driven by the Genetic Configuration of Tumor Cells, PLOS Genetics, 3(9):e167 (2007).
Opposition Letter—Agenus Inc. (Opponent) in European Patent 2569633, dated Nov. 9, 2016.
Opposition Letter—Dr. Christian Muller (Opponent) in European Patent No. 2569633, dated Nov. 9, 2016.
Opposition Letter—Gritstone Oncology Inc. (Opponent) in European Application No. 11781409.5 dated Nov. 7, 2016.
Opposition Letter—James Poole Limited (Opponent) in European Patent No. 2569633, dated Nov. 9, 2016.
Opposition Letter—Strawman Limited (Opponent) in European Patent No. 2569633 dated Nov. 10, 2016.
Osorio et al., "Stability Analysis of Antimicrobial Peptides in Solvation Conditions by Molecular Dynamics," Adv Comp Bio, 232:127-131 (2014).
Ott et al., "A Phase Ib Trial of Personalized Neoantigen Therapy Plus Anti-PD-1 in Patients with Advanced Melanoma, Non-small Cell Lung Cancer, or Bladder Cancer," Cell, 183(2):347-362 (2020).
Ott et al., "An Immunogenic personal neoantigen vaccine for patients with melanoma," Nature, 547:217-221 (2017).
Ott et al., "Vaccines and Melanoma," Hematol Oncol Clin N Am, 28(3):559-569 (2014).
PAIR Assignment Register extract (accessed Oct. 20, 2016).
PAIR Screenshot Patent Assignment Abstract of Title of U.S. Appl. No. 13/108,610, filed May 16, 2011.
Pan et al., "Epigenomic Evaluation in diffuse Large B-Cell Lymphomas," Blood, Nov. 15, 2013, 122(21) XP55174946.
Parker et al., "Scheme for Ranking Potential HLA-A2 Binding Peptides Based on Independent Binding of Individual Peptide Side-Chains," J Immunol, 152(1): 163-175 (1994).
Parkhurst et al., "Improved induction of melanoma-reactive CTL with peptides from the melanoma antigen gp100 modified at HLA-A*0201-binding residues", The Journal of Immunology, 157: 2539-2548 (1996).
Parmiani et al., "Unique Human Tumor Antigens: Immunobiology and Use in Clinical Trials," J Immunol, 178: 1975-1979 (2007).
Pasmant et al., "Characterization of a Germ-Line Deletion, Including the Entire INK4/ARF Locus, in a Melanoma-Neural System Tumor Family: Identification of ANRIL, an Antisense Noncoding RNA Whose Expression Coclusters with ARF," Cancer Res, 67(8):3963-3969 (2007).
Peters et al., "A Community Resource Benchmarking Predictions of Peptide Binding to MHC-I Molecules," PLoS Computational Biology, 2(6): e65 (2006).
Peters et al., "Accurate whole-genome sequencing and haplotyping from 10 to 20 human cells," Nature 487:190-195 (2012).
Peters et al., "The Immune Epitope Database and Analysis Resource: From Vision to Blueprint," PLoS Biol, 3(3): e91 (2005).
Peters et al., "The many faces of TH-17 Cells," Curr Opin Immunol, 23(6):702-706 (2011).
Phan et al., "Cancer regression and autoimmunity induced by cytotoxic T lymphocyte-associated antigen 4 blockade in patients with metastatic melanoma," PNAS, 100(14):8372-8377 (2003).
Pietras, "Biologic Basis of Sequential and Combination Therapies for Hormone-Responsive Breast Cancer," Oncologist, 11:704-717 (2006).
Pilla et al., "Multipeptide vaccination in cancer patient," Expert Opin Biol Ther, 9(8):1043-1055 (2009).
Piros et al., "Market Opportunity for Molecular Diagnostics in Personalized Cancer Therapy," Handbook of Clinical Nanomedicine: Law, Business, Regulation, Safety and Risk, Chapter 14: 1-29 (2016).
Pleasance et al., "A comprehensive catalogue of somatic mutations from a human cancer genome," Nature, 463:191-196 (2010).
Pleasance et al., "A small-cell lung cancer genome with complex signatures of tobacco exposure," Nature, 463: 184-190 (2010).
Policy Reallocating Ownership of Intellectual Property Covered by the Intellectual Property Policy, Sep. 18, 2002.
Poster entitled "Disease-related biomarkers are associated with extended progression-free survival after treatment with Neo-PV-01 in combination with anti-PD1 in patients with metastatic cancers" presented at The Society for Immunotherapy of Cancer Annual Meeting Nov. 6-10, 2019 ("SITC 2019 poster").
Prezant et al., "Trapped-Oligonucleotide Nucleotide Incorporation (TONI) Assay, a Simple Method for Screening Point Mutations," Hum Mutat, 1(2): 159-164 (1992).
Prints-outs from the UniProtKB database concerning the CEP170, PARVA and FLT3 genes.
Pritchard et al., "Exome Sequencing to Predict Neoantigens in Melanoma," Cancer Immunol Res, 3:992-998 (2015).
Provan et al., "Eradication of Polymerase Chain Reaction-Detectable Chronic Lymphocytic Leukemia Cells is Associated with Improved Outcome After Bone Marrow Transplantation," Blood, 88: 2228-2235 (1996).
Public Pair Assignment Data Screenshot of U.S. Appl. No. 61/334,866, filed May 14, 2010.
Rajasagi et al., "Systematic Identification of Personal Mutated Tumor-Specific Neoantigens in CLL," Blood, 120(21):954 (2012).
Rajasagi et al., "Systematic identification of personal tumor-specific neoantigens in chronic lymphocytic leukemia," Blood, 124(3):453-462 (2014).
Rammensee et al., "Cancer Vaccines: Some Basic Considerations," Genomic and Personalized Medicine, 5:573-589 (2009).
Rammensee et al., "MHC ligands and peptide motifs: first listing," Immunogenetics, 41:178 (1995).
Rammensee et al., "SYFPEITHI: Database for MHC Ligands and Peptide Motifs," Immunogenetics, 50(3-4): 213-219 (1999).
Rammensee et al., "Towards Patient-Specific Tumor Antigen Selection for Vaccination," Immunological Reviews, Blackwell Publishing Munksgaard, 188:164-176 (2002).
Rappsilber et al., "Protocol for micro-purification, enrichment, pre-fractionation and storage of peptides for proteomics using StageTips," Nat Protoc, 2(8):1896-1906 (2007).
Reche et al., "Elicitation from virus-naive individuals of cytotoxic T lymphocytes directed against conserved HIV-1 epitopes," Med Immunol, 5:1 (2006).
Reck et al., "First-Line Immunotherapy for Non-Smalll-Cell Lung Cancer," Journal of Clinical Oncology, 40(6): 586-597 (2022).
Reifenberger et al., "Frequent Alterations of Ras Signaling Pathway Genes in Sporadic Malignant Melanomas," Int J Cancer, 109: 377-384 (2004).
Response to Notices of Opposition of EP2569633, dated Jun. 28, 2017.
Ressing et al., "Human CTL epitopes encoded by human papillomavirus type 16 E6 and E7 identified through in vivo and in vitro immunogenicity studies of HLA-A*0201-binding peptides.," J Immunol, 154(11):5934-5943 (1995).
Restifo et al., "Adoptive immunotherapy for cancer: harnessing the T cell response," Nat Rev Immunol, 12(4):269-281 (2015).
Restriction Requirement for U.S. Appl. No. 13/108,610, "Compositions and Methods of Identifying Tumor Specific Neoantigens," dated Mar. 7, 2013.
Restriction Requirement for U.S. Appl. No. 14/794,449, "Compositions and Methods of Identifying Tumor Specific Neoantigens," dated Oct. 26, 2016.
Restriction Requirement for U.S. Appl. No. 14/877,125, "Compositions and Methods for Personalized Neoplasia Vaccines," dated Nov. 18, 2016.

(56) References Cited

OTHER PUBLICATIONS

Restriction Requirement for U.S. Appl. No. 15/038,504, "Compositions and Methods for Diagnosing, Evaluating and Treating Cancer By Means of the DNA Methyl," dated Jun. 22, 2017.
Restriction Requirement for U.S. Appl. No. 15/102,129, "Formulations for Neoplasia Vaccines," dated May 8, 2017.
Restriction Requirement for U.S. Appl. No. 15/105,961, "Combination Therapy With Neoantigen Vaccine," dated Jul. 13, 2017.
Restriction Requirement for U.S. Appl. No. 15/187,174, "Compositions and Methods of Identifying Tumor Specific Neoantigens," dated Sep. 9, 2016.
Restriction Requirement for U.S. Appl. No. 15/513,127, "Use of Clonal Evolution Analysis for Ibrutinib Resistance in Chronic Lymphocytic Leukemia Patients," dated Aug. 13, 2018.
Restriction Requirement for U.S. Appl. No. 15/537,785, "Methods for Profiling the T Cell Repertoire," dated Mar. 22, 2018.
Restriction Requirement for U.S. Appl. No. 15/537,839, "Molecular Biomarkers for Cancer Immunotherapy," dated Jun. 20, 2019.
Restriction Requirement for U.S. Appl. No. 15/575,328, "Shared Neoantigens," dated Feb. 7, 2019.
Ribas et al., "Antitumor Activity in Melanoma and Anti-Self Responses in a Phase I Trial with the Anti-Cytotoxic T Lymphocyte-Associated Antigen 4 Monoclonal Antibody CP-675,206," J Clin Oncol, 23(35): 8968-8977 (2005).
Rizvi et al., "Mutational landscape determines sensitivity to PD-1 blockade in non-small cell lung cancer," Science, 348(6230):124-128 (2015).
Robbins et al., "A mutated beta-catenin gene encodes a melanoma-specific antigen recognized by tumor infiltrating lymphocytes," J Exp Med, 183(3):1185-1192 (1996).
Robinson et al., "The IPD and FMGT/HLA database: allele variant databases," Nucleic Acids Res, 43:D423-D431 (2015).
Rock et al., "Re-examining class-I presentation and the DRIP hypothesis," Trends Immunol, 35(4):144-152 (2014).
Rondon et al., "Graft-versus-Leukemia Effect After Allogeneic Bone Marrow Transplantation for Chronic Lymphocytic Leukemia," Bone Marrow Transplant, 18: 669-672 (1996).
Rooney et al., "Molecular and Genetic Properties of Tumors Associated with Local Immune Cytolytic Activity," Cell, 160(1-2):48-61 (2015).
Rosenberg et al., "Cancer Immunotherapy: Moving Beyond Current Vaccines," Nat Med, 10: 909-915 (2004).
Rubin et al., "Mutation patterns in cancer genomes," PNAS, 106(51):21766-21770 (2009).
Rubinfeld et al., "Stabilization of Beta-Catenin by Genetic Defects in Melanoma Cell Lines," Science, 275(5307):1790-1792 (1997).
Ruggles et al., "An analysis of the sensitivity of proteogenomic mapping of somatic mutations and novel splicing events in cancer," Cell Proteomics, 15(3):1060-1071 (2015).
Sabbatini et al., "Phase I trial of overlapping long peptides from a tumor self-antigen and Poly-ICLC shows rapid induction of integrated immune response in ovarian cancer patients," Clin Cancer Res, 18:6497-6508 (2012).
Sahin et al., "Personalized RNA mutanome vaccines mobilize poly-specific therapeutic immunity against cancer," Nature, 547(7662):222-226 (2017).
Sanderson et al., "Autoimmunity in a Phase I Trial of a Fully Human Anti-Cytotoxic T-Lymphocyte Antigen-4 Monoclonal Antibody With Multiple Melanoma Peptides and Montanide ISA 51 for Patients With Resected Stages III and IV Melanoma," J Clin Oncol, 23(4):741-750 (2005).
Saterdal et al., "Frameshift-mutation-derived peptides as tumor-specific antigens in inherited and spontaneous colorectal cancer," Proceedings of the National Academy of Sciences 98(23): 13255-13260 (2001).
Sato et al., "Intraepithelial CD8+ tumor-infiltrating lymphocytes and a high CD8+/regulatory T cell ratio are associated with favorable prognosis in ovarian cancer," PNAS, 102(51):1838-18543 (2005).
Saveanu et al., "Concerted peptide trimming by human ERAPI and ERAP2 aminopeptidase complexes in the endoplasmic reticulum," Nat Immunol, 6:689-697 (2005).
Saxova et al., "Predicting proteasomal cleavage sites: a comparison of available methods," Int Immunol, 15:781-787 (2003).
Schaffner et al., "Somatic ATM Mutations Indicate a Pathogenic Role of ATM in B-Cell Chronic Lymphocytic Leukemia," Blood, 94: 748-753 (1999).
Scheibenbogen et al., "Analysis of the T Cell Response to Tumor and Viral Peptide Antigens by an IFNy-Elispot Assay," Int. J. Cancer, 71:932-936 (1997).
Schietinger et al., "Specificity in cancer immunotherapy," Semin. Immunol, 20(5)276-285 (2008).
Schuh et al., "Monitoring chronic lymphocytic leukemia progression by whole genome sequencing reveals heterogeneous clonal evolution patterns," Blood, 120(20):4191-4196 (2012).
Schumacher et al., "Neoantigens in cancer immunotherapy," Science, 348:69-74 (2015).
Schwitalle et al., "Immunogenic peptides generated by frameshift mutations in DNA mismatch repair-deficient cancer cells," Cancer Immunity, 4(1):14 (2004).
Searle et al., "Using Data Independent Acquisition (DIA) to Model High-responding Peptides for Targeted Proteomics Experiments," Mol Cell Proteomics, 14:2331-2340 (2015).
Segal et al., "Epitope Landscape in Breast and Colorectal Cancer," Cancer Res, 68: 889-892 (2008).
Sensi et al., "Unique Tumor Antigenesis: Evidence for Immune Control of Genome Integrity and Immunogenic for T Cell-Mediated Patient-Specific Immunotherapy," Clin Cancer Res, 12(7): 5023-5032 (2006).
Sette et al., "Peptide binding to the most frequent HLA-A class I alleles measured by quantitative molecular binding assays," Molecular Immunology, 31(11): 813-822 (1994).
Sette et al., "The relationship between class I binding affinity and immunogenicity of potential cytotoxic T cell epitopes," J Immunol, 153:5586-5592 (1994).
Shames et al., "A Genome-Wide Screen for Promoter Methylation in Lung Cancer Identifies Novel Methylation Markers for Multiple Malignancies," PLOS Med, 3(12):e486 (2006).
Sharma et al., "A Chromatin-Mediated Reversible Drug-Tolerant State in Cancer Cell Subpopulations," Cell, 141:69-80 (2010).
Sharma et al., "Novel cancer immunotherapy agents with survival benefit: recent successes and next steps," Nat Rev Cancer, 11(11):805-812 (2011).
Shastri et al., "Presentation of endogenous peptide/MHC class I complexes is profoundly influenced by specific C-terminal flanking residues," J Immunol, 155:4339 (1995).
Shen et al., "Integrated genetic and epigenetic analysis identifies three different subclasses of colon cancer," PNAS, 104(47):18654-18659 (2007).
Shendure et al., "Next-generation DNA sequencing," Nat Biotechnol, 26(10):1135-1145 (2008).
Shimizu et al., "Production of human cells expressing individual transferred HLA-A,-B,-C genes using an HLA-A,-B,-C null human cell line," J Immunol, 142(9):3320-3328 (1989).
Shimizu et al., "Transfer of cloned human class I major histocompatibility complex genes into HLA mutant human lymphoblastoid cells," Mol Cell Biol, 6(4):1074-1087 (1986).
Shrock et al., "Tumor mutational burden is predictive of response to immune checkpoint inhibitors in MSI-high metastatic colorectal cancer," Annals of Oncology, 30: 1096-1103 (2019).
Shukla et al., "Topics in Cancer Genomics," Graduate Theses and Dissertations, Paper 13796 (2014). [accessed online] https://search.proquest.com/docview/1558874754.
Sidney et al., "Measurement of MHC/Peptide Interactions by Gel Filtration or Monoclonal Antibody Capture," Curr Protoc Immunol: 18.3.1-18.3.36 (2013).
Sidney et al., "Measurement of MHC/Peptide Interactions by Gel Filtration" Curr Prot Immunol, 31(1):18.3.1-18.3.19 (1999).
Siegmund et al., "Inferring clonal expansion and cancer stem cell dynamics from DNA methylation patterns in colorectal cancers," PNAS, 106(12):4828-4833 (2009).

(56) References Cited

OTHER PUBLICATIONS

Sigalotti et al., "Intratumor Heterogeneity of Cancer/Testis Antigens Expression in Human Cutaneous Melanoma Is Methylation-Regulated and Functionally Reverted by 5-Aza-2'-deoxycytidine, " Cancer Research, 64(24): 9167-9171 (2004).
Singh et al., "CIMT 2010: Report on the eighth annual meeting of the association for cancer immunotherapy, May 26-28, 2010, Mainz, Germany," Cancer Immunol. Immunother., 60: 443-450 (2011).
Singh-Jasuga et al., "Correlation of T-cell response, clinical activity and regulatory T-cell levels in renal cell carcinoma patients treated with IMA901, a novel multi-peptide vaccine," J Clin Conology, 25:18S, Abstract #3017 (2007).
Sjoblom et al., "The Consensus Coding Sequences of Human Breast and Colorectal Cancers," Science, 314(5797):268-274 (2006).
Smialowsky et al., "Protein solubility: sequence based prediction and experimental verification," Bioinformatics, 23(19):2356-3542 (2007).
Snyder et al., "Genetic Basis for Clinical Response to CTLA-4 Blockade in Melanoma," New Engl J Med, 371(23):2189-2199 (2014).
Snyder et al., "Immunogenic peptide discovery in cancer genomes," Cuff Opin Genet Dev, 30: 7-16 (2015).
Soiffer et al., "Vaccination with irradiated autologous melanoma cells engineered to secrete human granulocyte-macrophage colony-stimulating factor generates potent antitumor immunity in patients with metastatic melanoma," PNAS, 95(22):13141-13146 (1998).
Soiffer et al., "Vaccination With Irradiated, Autologous Melanoma Cells Engineered to Secrete Granulocyte-Macrophage Colony-Stimulating Factor by Adenoviral-Mediated Gene Transfer Augments Antitumor Immunity in Patients With Metastatic Melanoma," J Clin Oncol, 21(17):3343-3350 (2003).
Sokolov., "Primer Extension Technique for the Detection of Single Nucleotide in Genomic DNA," Nucleic Acids Res. 18(12): 3671 (1990).
Somasundaram et al., "Human Leukocyte Antigen-A2-Restricted CTL Responses to Mutated BRAF Peptides in Melanoma Patients," Cancer Res, 66(6): 3287-3293 (2006).
Song et al., "Full screening and accurate subtyping of HLA-A*02 alleles through group-specific amplification and mono-allelic sequencing." Cell Mol Immunol, 10:490-496 (2013).
Soung et al., "Capase-8 gene is frequently inactivated by the frameshift somatic mutation 1225_1226delTG in hepatocellular carcinomas," Oncogene, 24:141-147 (2005).
Sowa et al., "Defining the Human Deubiquitinating Enzyme Interaction Landscape," Cell, 138(2):389-403 (2009).
Spitler, "Cancer Vaccines: The Interferon Analogy," Cancer Biother, 10:1-3 (1995).
Srivastava et al., "Modeling the Repertoire of True Tumor-Specific MHC I Epitopes in a Human Tumor," PLOS ONE, 4(7):e6094 (2009).
Srivastava, "Therapeutic Cancer Vaccines," Curr Opin Immunol, 18: 201-205 (2006).
Stankovic et al., "Microarray Analysis Reveals that TP53- and ATM-Mutant B-CLLs Share a Defect in Activating Proapoptotic Responses after DNA Damage but are Distinguished byMajor Differences in Activating Prosurvival Responses," Blood, 103: 291-300 (2004).
Stranzl et al., "NetCTLpan: pan-specific MHC class I pathway epitope predictions," Immunogenetics, 62(6):357-368 (2010).
Stratton et al., "The Cancer Genome," Nature, 458(7239):719-724 (2009).
Su et al., "Immunological and Clinical Responses in Metastatic Renal Cancer Patients Vaccinated with Tumor RNA-Transfected Dendritic Cells," Cancer Res, 63: 2127-2133 (2003).
Su et al., "Next-generation sequencing and its applications in molecular diagnostics" Exp Rev Mol Diagn, 11(3):333-343 (2011).
Submission in opposition proceedings of EP 2569633, dated Jun. 28, 2017.
Sun et al., Material bionics and Thinking Innovation, 176-177 (2012).
Supplementary Materials from Third Party Observation in EP Application No. 15198284.0.
Syvanen et al., "A Primer-Guided Nucleotide Incorporatiopn Assay in the Genotyping of Apoliprotein E," Genomics, 8(4): 684-692 (1990).
Syvanen et al., "Identification of Individuals by Analysis of Biallelic DNA Markers, Using PCR and Solid-Phase Minisequencing," Am J Hum Genet, 52(1): 46-59 (1993).
Table S4 Somatic mutations Identified in Breast or Colorectal Cancers filed on Nov. 7, 2016 in Notice of Opposition by Gritstone Oncology Inc. to EP 2569633.
Table S5 Breast CAN-genes, filed on Nov. 7, 2016, in Notice of Opposition by Gritstone Oncology Inc., to EP Patent No. 2569633.
Table S6 Colorectal CAN-genes, filed on Nov. 7, 2016 in Notice of Opposition by Gritstone Oncology Inc. to EP Patent No. 2569633.
Tang et al., "NeoantigenR: An annotation based pipeline for tumor neoantigen identification from sequencing data," bioRxiv preprint first posted online Aug. 8, 2017.
Thomas et al., "High-Throughput Oncogene Mutation Profiling in Human Cancer," Nat Genet, 39: 347-351 (2007).
Thompson et al., "Aberrations of the B-Cell Receptor B29 (CD79b) Gene in Chronic Lymphocytic Leukemia," Blood, 90(4):1387-1394 (1997).
Thon et al., "Personalized treatment strategies in glioblastoma: MGMT promoter methylation status," Onco Targets and Therapy, 6:1363-1372 (2013).
Thornton et al., "Characterisation of TP53 Abnormalities in Chronic Lymphocytic Leukaemia," Hematol J, 5: 47-54 (2004).
Timmerman et al., "Idiotype-Pulsed Dendritic Cell Vaccination for B-Cell Lymphoma: Clinical and Immune Responses in 35 Patients," Blood, 99: 1517-1526 (2002).
Tjernberg et al., "DMSO-Related Effects in Protein Characterization," Journal of Biomolecular Screening, 11(2): 131-137 (2006).
Tong et al., "Methods and protocols for prediction of immunogenic epitopes", Briefings In Bioinformatics, 8(2): 96-108 (2008).
Topalian et al., "Five-Year Survival and Correlates Among Patients With Advanced Melanoma, Renal Cell Carcinoma, or Non-Small Cell Lung Cancer Treated With Nivolumab," JAMA Oncol., 5(10): 1411-1420 (2019).
Topalian et al., "Safety, Activity, and Immune Correlates of Anti-PD-1 Antibody in Cancer," N Engl J Med, 366(26):2443-2454 (2012).
Topalian et al., "Targeting the PD-1/B7-H1(PD-L1) pathway to activate anti-tumor immunity," Current Opinion in Immunology, 24:207-212 (2012).
Tourdot et al., "A general strategy to enhance immunogenicity of low-affinity HLA-A2.1—associated peptides: implication in the identificatiioonn of cryptic tumor epitopes," Eur. J. Immunol, 30:3411-3421 (2000).
Toze et al., "Myeloablative Allografting for Chronic Lymphocytic Leukemia: Evidence for Potent Graft-versus-Leukemia Effect Associated with Graft-versus-Host Disease," Bone Marrow Transplant, 36: 825-830 (2005).
Trolle et al., "Automated benchmarking of peptide-MHC class I binding predictions," Bioinformatics, 31(13):2174-2181 (2015).
Trolle et al., "The Length Distribution of Class I-Restricted T Cell Epitopes Is Determined by Both Peptide Supply and MHC Allele-Specific Binding Preference," J Immunol (2016), doi: 10.4049/jimmunol.1501721.
Tumeh et al., "PD-1 blockade induces responses by inhibiting adaptive immune resistance," Nature, 515(7528):568-571 (2014).
Turchaninova et al., "Pairing of T-cell receptor chains via emulsion PCR," Eur J Immunol, 43:2507-2515 (2013).
Turke et al., "Preexistence and Clonal Selection of MET Amplification in EGFR Mutant NSCLC," Cancer Cell, 17: 77-88 (2010).
Tynan et al., "T cell receptor recognition of a "super-bulged" major histocompatibility complex class I-bound peptide," Nat Immunol, 6:1114-1122 (2005).
U.S. Final Office Action dated May 25, 2017 and issued in U.S. Appl. No. 15/187,174.
U.S. Final Rejection dated Sep. 13, 2017 and issued in U.S. Appl. No. 14/794,449.

(56) References Cited

OTHER PUBLICATIONS

U.S. Non-Final Office Action dated Jan. 22, 2018 and issued in U.S. Appl. No. 15/187,174.
U.S. Non-Final Office Action dated Mar. 7, 2019 and issued in U.S. Appl. No. 15/037,394.
U.S. Non-Final Office Action dated Oct. 2, 2020 and issued in U.S. Appl. No. 15/037,394.
U.S. Non-Final Office Action dated Dec. 5, 2016 and issued in U.S. Appl. No. 15/187,174.
U.S. Non-Final Office Action dated Dec. 29, 2016 and issued in U.S. Appl. No. 14/794,449.
Udeshi et al., "Methods for quantification of in vivo changes in protein ubiquitination following proteasome and deubiquitinase inhibition," Mol Cell Proteomics, 11:148-159 (2012).
Ueda et al., "Germ Line and Somatic Mutations of BRAF V599E in Ovarian Carcinoma," Int J Gynecol Cancer, 17: 794-797 (2007).
Ugozzoli et al., "Detection of Specific Alleles by Using Allele-Specific Primer Extension Followed by Capture on Solid Support," Genet Anal Tech AppL, 9(4): 107-112 (1992).
UniProtKB Printouts—Q5SW79 filed on Nov. 2016 in Muller Opposition to EP 2569633.
Van Buuren et al., "High sensitivity of cancer exome-based CD8 T cell neo-antigen identification," OncoImmunology, 3(5):e28836 (2014).
Van de Roemer et al., "P1737:IVAC: Individualized vaccines for cancer," Immunology 137(Suppl. 1):715, Sep. 2012.
Van Den Broeke et al., "Identification and Epitope Enhancement of a PAX-FKHR Fusion Protein Breakpoint Epitope in Alveolar Rhabdomyosarcoma Cells Created by a Tumorigenic Chromosomal Translocation Inducing CTL Capable of Lysing Human Tumors," American Association for Cancer Research, 66(3):1818-1823 (2006).
Van der Bruggen et al., "A Gene Encoding an Antigen Recognized by Cytolytic T Lymphocytes on a Human Melanoma," Science, 254: 1643-1647 (1991).
Van Pel et al., "Tumor Cell Variants Obtained by a Mutageneis of a Lewis Lung Carcinoma Cell Line: Immune Rejection by Syngeneic Mice," PNAS, 76(10): 5282-5285 (1979).
Van Trappen et al., "Somatic Mitochondrial DNA Mutations in Primary and Metastatic Ovarian Cancer," Gynecol Oncol, 104: 129-133 (2007).
Vandenberghe et al., "Heparin binding directs activation of T cells against adeno-associated virus serotype 2 capsid," Nature Medicine, 12(8): 967-971 (2006).
Vandrovcova et al., "Somatic BRAF-V600E Mutations in Familial Colorectal Cancer," Cancer Epidemio Biomarkers Prev, 15(11):2270-2273 (2006).
Varley et al., "Intra-tumor heterogeneity of MLH1 promoter methylation revealed by deep single molecule bisulfite sequencing," Nucleic Acids Research, 37(14):4603-4612 (2009).
Velez et al., "BNT221, an Autologous Neoantigen-Specific T cell Product for Adoptive Cell Therapy of Metastatic Ovarian Cancer" poster presented Oct. 2021 at SITC.
Verhoef et al., "Des-enkephalin-γ-endorphin (DEγE): Biotransformation in rat, dog and human plasma," Eur J Drug Metab Ph, 11(4):291-302 (1986).
Vita et al., "The immune epitope database (IEDB) 3.0," Nucleic Acids Res, 43:D405-D412 (2015).
Vita et al., "The Immune Epitope Database 2.0," Nucleic Acids Res, 38:D854-D862 (2010).
Vogel et al., "Mass Spectrometry Reveals Changes in MHC I Antigen Presentation After Lentivector Expression of a Gene Regulation System," Molecular Therapy—Nucleic Acids, 2:e75 (2013).
Vogelstein et al., "Cancer Genome Landscapes," Science, 339(6127): 1546-1558 (2013).
Volpe et al., "Alternative BCR/ABL Splice Variants in Philadelphia Chromosome-Positive Leukemias Result in Novel Tumor-Specific Fusion Proteins that May Represent Potential Targets for Immunotherapy Approaches," Cancer Res, 67(11):5300-5307 (2007).
Vonderheide et al., "Immunotherapy at Large: The road to personalized cancer vaccines," Nature Medicine 19(9) 1098-1100 (2013).

Walter et al., "DNA Methylation Profiling Defines Clinically Relevant Biological Subsets of Non-small Cell Lung Cancer," Clin Cancer Res, 18(8):2360-2373 (2012).
Walz et al., "The antigenic landscape of multiple myeloma: mass spectrometry (re)defines targets for T-cell-based immunotherapy," Blood 126:1203-1213 (2015).
Wang et al., Functional Polymeric Material, 1-44 (2010).
Wang, "Tumor Antigens Discovery: Perspectives for Cancer Therapy", Molecular Medicine, 3(11): 716-731 (1997).
Weber et al., "Safety, Efficacy, and Biomarkers of Nivolumab With Vaccine in Ipilimumab-Refractory or -Naive Melanoma," J Clin Oncol, 31:4311-4318 (2013).
Weinschenk et al., "Integrated Functional Genomics Approach for the Design of Patientindividual Antitumor Vaccines," Cancer Res, 62: 5818-5827 (2002).
Willmore-Payne et al., "Human Malignant Melanoma: Detectection of BRAF- and c-kit-Activating Mutations by High-Resolution Amplicon Melting Analysis," Hum Pathol, 36: 486-493 (2005).
Wolfel et al., "A p16INK4a-insensitive CDK4 mutant targeted by cytolytic T lymphocytes in a human melanoma," Science, 269(5228): 1281-1284 (1995).
Wood et al., "The Genomic Landscapes of Human Breast and Colorectal Cancers," Science, 318: 1108-1113 (2007).
Woodbury et al., "Introduction to Macromolecular Binding Equilibria," CRC Press, 13:978 (2007).
Wraith, "The Future of Immunotherapy: A 20-Year Perspective," Front Immunol, 8(1668): 1-6 (2017).
Wu et al., "Detection of a potent humoral response asscoiated with immune-induced remission of chronic myelogenous leukemia," J Clin Invest, 106(5):705-714 (2000).
Wu et al., "Graft-versus-Leukemia Target Antigens in Chronic Myelogenous Leukemia Are Expressed on Myeloid Progenitor Cells," Clin Cancer Res, 11(12):4504-4511 (2005).
Wu et al., "Heterogeneity of Breast Cancer Metastases: Comparison of Therapeutic Target Expression and Promoter Methylation Between Primary Tumors and Their Multifocal Metastases," Clinical Cancer Research, 14(7): 1938-1946 (2008).
Wu et al., "Induction of Tumor Immunity Following Allogeneic Stem Cell Transplantation," Adv Immunol, 90: 133-173 (2006).
Wu et al., "Mouse Model of Human Ovarian Endometrioid Adenocarcinoma Based on Somatic Defects in the Wnt/6-Catenin and PI3K/Pten Signaling Pathways," Cancer Cell, 11: 321-333 (2007).
Wu et al., "Reconstitution of T-Cell Receptor Repertoire Diversity Following T-Cell Depleted Allogeneic Bone Marrow Transplantation is Related to Hematopoietic Chimerism," Blood, 95: 352-359 (2000).
Wu et al., "Structure-based engineering of a monoclonal antibody for improved solubility," Protein Engineering, Design & Selection, 23(8): 643-651 (2010).
Yang et al., "Meta-analysis followed by replication identifies loci in or near CDKN1B, TET3, CD80, DRAM1, and ARID5B as associated with systemic lupus erythematosus in Asians," American journal of human genetics, 92:41-51 (2013).
Yao et al., "Advances in targeting cell surface signalling molecules for immune modulation," Nature Rev Drug Discov, 12:130-146 (2013).
Yee et al., "Adoptive T cell therapy using antigen-specific CD8 T cell clones for the treatment of patients with metastatic melanoma: In vivo persistence, migration, and antitumor effect of transferred T cells," PNAS, 99(25): 16168-16173 (2002).
Yewdell, "DRiPs solidify: progress in understanding endogenous MHC class I antigen processing," Trends Immunol, 32(11):548-558 (2011).
Yokoyama et al., "Matrilysin (MMP-7) Is a Novel Broadly Expressed Tumor Antigen Recognized by Antigen-Specific T Cells," Clin Cancer Res, 14(17): 5503-5511 (2008).
Yosef et al., "Dynamic regulatory network controlling TH17 cell differentiation," Nature, 496(7446):461-468 (2013).
Yoshitake et al., "Cross☐linking of GPI☐080, a possible regulatory molecule of cell adhesion, induces up☐regulation of CD11b/CD18 expression on neutrophil surfaces and shedding of L☐ selectin," Journal of leukocyte biology, 71(2):205-211 (2002).

(56) References Cited

OTHER PUBLICATIONS

You et al., "Understanding Prediction Systems for HLA-Binding Peptides and T-Cell Epitope Identification," Pattern Recognition in Bioinformatics, Lecture Notes in Computer Science, 4474: 337-348 (2007).
Zhang et al., "Dana-Farber repository for machine learning in immunology," J Immunol Methods, 374(1-2):18-25 (2011).
Zhang et al., "Graft-versus-Leukemia Antigen CML66 Elicits Coordinated B-Cell and T-Cell Immunity after Donor Lymphocyte Infusion," Clin Cancer Res, 16: 2729-2739 (2010).
Zhang et al., "Intratumoral T Cells, recurrence, and survival in epithelial ovarian cancer," New Engl J Med, 348(3):203-213 (2003).
Zhang et al., "The impact of next-generation sequencing on genomics," J Genet Genomics, 38(3):95-109 (2011).
Zhang et al., Oncology, 1-44 (2005).
Zhou et al., "Diverse CD8+ T-Cell Responses to Renal Cell Carcinoma Antigens in Patients Treated with an Autologous Granulocyte-Macrophage Colony-Stimulating Factor Gene-Transduced Renal Tumor Cell Vaccine," Cancer Res, 65: 1079-1088 (2005).
Zhou et al., "Transcriptional regulatory networks in Th17 cell differentiation," Curr Opin Immunol, 21(2):146-152 (2009).
Zhou et al., Persistance of Multiple Tumor-Specific T-Cell Clones is Associated with Complete Tumor Regression in a Melanoma Patient Receiving Adoptive Cell transfer Therapy, J Immunother, 28(1):53-62 (2005).
Acevedo et al., "Analysis of the mechanisms mediating tumor-specific changes in gene expression in human liver tumors," Cancer Res, 68(8):2641-2651 (2008).
Adams, "Toll-like receptor agonists in cancer therapy," Immunotherapy, 1(6):949-964 (2009).
Akiyama et al., "GATA-4 and GATA-5 transcription factor genes and potential downstream antitumor target genes are epigenetically silenced in colorectal and gastric cancer," Mol Cell Biol, 23:8429-8439 (2003).
Alarcon et al., "DNA vaccines: technology and application as anti-parasite and anti-microbial agents," Advances in Parasitology, 42:343-410 (1999).
Ali et al., "In situ regulation of DC subsets and T cells mediates tumor regression in mice," Cancer Immunotherapy. 1(8):1-10 (2009).
Ali et al., "Infection-mimicking materials to program dendritic cells in situ," Nat Mater, 8:151-8 (2009).
Allison, "The Mode of Action of Immunological Adjuvants," Dev Biol Stand, 92: 3-11 (1998).
Altman et al., "Phenotypic analysis of antigen-specific T lymphocytes," Science, 274(5284):94-6 (1996).
Alvarez, "Present and future evolution of advanced breast cancer therapy," Breast Cancer Research, 12(Suppl 2):S1 (2010).
Amara et al., "Control of a mucosal challenge and prevention of AIDS by a multiprotein DNA/MVA vaccine," Science, 292(5514):69-74 (2001).
Amato et al., "Vaccination of metastatic renal cancer patients with MVA-5T4: a randomized, double-blind, placebo-controlled phase III study," Clin Can Res, 16(22):5539-47 (2010).
Amato et al., "Vaccination of renal cell cancer patients with modified vaccinia ankara delivering tumor antigen 5T4 (TroVax) administered with interleukin 2: a phase II trial," Clin Cancer Res, 14(22):7504-10 (2008).
Anders et al., "HTSeq—A Python framework to work with high-throughput sequencing data," Bioinformatics, 31(2):166-169 (2015).
Andersen et al., "Parallel detection of antigen-specific T cell responses by combinatorial encoding of MHC multimers," Nature protocols, 7(5):891-902 (2012).
Antoine et al., "The complete genomic sequence of the modified vaccinia Ankara strain: comparison with other orthopoxviruses," Virology, 244(2):365-96 (1998).
Antonis et al., "Vaccination with recombinant modified vaccinia virus Ankara expressing bovine respiratory syncytial virus (bRSV) proteins protects calves against RSV challenge," Vaccine, 25(25):4818-4827 (2007).
Aucouturier et al., "Adjuvants designed for veterinary and human vaccines," Vaccine, 19(17-19):2666-2672 (2001).
Ausubel, "A botanical macroscope," Proceedings of the National Academy of Sciences, 106(31):12569-12570 (2009).
Avogadri et al. "Modulation of CTLA-4 and GITR for Cancer Immunotherapy," Curr Top Microbiol Immunol, 344:211 (2011).
Bachem et al., "Superior antigen cross-presentation and XCR1 expression define human CD11c+ CD141+ cells as homologues of mouse CD8+ dendritic cells," Journal of Experimental Medicine, 207(6):1273-1281 (2010).
Baden et al., "First-in-human evaluation of the safety and immunogenicity of a recombinant adenovirus serotype 26 HIV-1 Env vaccine (IPCAVD 001)," J Infect Dis, 207(2):240-247 (2012).
Balagaan et al., "Stable and efficient intraocular gene transfer using pseudotyped EIAV lentiviral vectors," J Gene Med, 8:275-285 (2005).
Balazsi et al., "Cellular decision making and biological noise: from microbes to mammals," Cell, 144(6):910-925 (2011).
Balch et al., "Final version of 2009 AJCC melanoma staging and classification," Journal of clinical oncology, 27(36):6199-6206 (2009).
Barbie et al., "Systematic RNA interference reveals that oncogenic KRAS-driven cancers require TBK1," Nature, 462:108-112 (2009).
Barretina et al., "The Cancer Cell Line Encyclopedia enables predictive modelling of anticancer drug sensitivity," Nature, 483:603-607 (2012).
Baylin, "DNA methylation and gene silencing in cancer," Nat Clin Pract Oncol 2, Suppl 1, S4-11 (2005).
Benson, "Tandem repeats finder: a program to analyze DNA sequences," Nucleic acids research, 27(2):573-580 (1999).
Benton et al., "Screening lambdagt recombinant clones by hybridization to single plaques in situ," Science, 196(4286):180-182 (1977).
Berger et al., "The genomic complexity of primary human prostate cancer," Nature, 470:214-220 (2011).
Berman et al., "Regions of focal DNA hypermethylation and long-range hypomethylation in colorectal cancer coincide with nuclear lamina-associated domains," Nat Genet, 44:40-46 (2012).
Bhardwaj et al., "TLR Agonists: Are They Good Adjuvants?," Cancer J, 16:382-391 (2010).
Bindea et al., "Spatiotemporal dynamics of intratumoral immune cells reveal the immune landscape in human cancer," Immunity, 39:782-795 (2013).
Bird, "DNA methylation patterns and epigenetic memory," Genes Dev, 16:6-21 (2002).
Birrell et al., "A genome-wide screen in *Saccharomyces cerevisiae* for genes affecting UV radiation sensitivity," Proceedings of the National Academy of Sciences 98(22):12608-12613 (2001).
Bishop et al., "APOBEC-mediated editing of viral RNA," Science, 305:645 (2004).
Bisht et al., "Severe acute respiratory syndrome coronavirus spike protein expressed by attenuated vaccinia virus protectively immunizes mice," Proc Natl Acad Sci, 101:6641-46 (2004).
Blanchard et al., "Modified vaccinia virus Ankara undergoes limited replication in human cells and lacks several immunomodulatory proteins: implications for use as a human vaccine," Journal of General Virology, 79(5):1159-1167 (1998).
Bock et al., "BiQ Analyzer: visualization and quality control for DNA methylation data from bisulfite sequencing," Bioinformatics, 21:4067-4068 (2005).
Bock et al., "Reference Maps of human ES and iPS cell variation enable high-throughput characterization of pluripotent cell lines," Cell, 144:439-452 (2011).
Bogunovic et al., "TLR4 engagement during TLR3-induced proinflammatory signaling in dendritic cells promotes IL-10-mediated suppression of antitumor immunity," Cancer Res, 71(16):5467-5476 (2011).
Boller et al. "Characterization of the antibody response specific for the human endogenous retrovirus HTDV/HERV-K," Journal of virology, 71(6):4581-4588 (1997).
Boni et al. "Adoptive transfer of allogeneic tumor-specific T cells mediates effective regression of large tumors across major histocompatibility barriers," Blood, 112(12):4746-4754 (2008).

(56) References Cited

OTHER PUBLICATIONS

Boquest et al., "Isolation and transcription profiling of purified uncultured human stromal stem cells: alteration of gene expression after in vitro cell culture," Molecular biology of the cell, 16(3):1131-1141 (2005).
Boscardin et al., "Antigen targeting to dendritic cells elicits long-lived T cell help for antibody responses," Journal of Experimental Medicine, 203(3):599-606 (2006).
Boyle et al., "Gel-free multiplexed reduced representation bisulfite sequencing for large-scale DNA methylation profiling," Genome Biol, 13:R92 (2012).
Boyle et al., "Tapasin-related protein TAPBPR is an additional component of the MHC class I presentation pathway," Proceedings of the National Academy of Sciences, 110: 3465-3470 (2013).
Bozic et al., "Dynamics of targeted cancer therapy," Trends Mol Med, 18:311-316 (2012).
Bozic et al., "Evolutionary dynamics of cancer in response to targeted combination therapy," Elife, 2:e00747 (2013).
Brahmer et al., "Safety and activity of anti-PD-L1 antibody in patients with advanced cancer," N Engl J Med, 366(26):2455-2465 (2012).
Brown et al., "Integrative genomic analysis implicates gain of PIK3CA at 3g26 and MYC at 8q24 in chronic lymphocytic leukemia," Clin Cancer Res, 8:3791-802 (2012).
Brunsvig et al., "Telomerase Peptide Vaccination: A Phase I/II Study in Patients with Non-Small Cell Lung Cancer," Cancer Immunol Immunother, 55(12): 1553-1564 (2006).
Buchschacher et al., "Human immunodeficiency virus vectors for inducible expression of foreign genes." Journal of virology, 66(5):2731-2739 (1992).
Buckwalter et al., "'It is the antigen(s), stupid' and other lessons from over a decade of vaccitherapy of human cancer," Seminar in Immunology, 20(5):296-300 (2008).
Buller et al., "Decreased virulence of recombinant vaccinia virus expression vectors is associated with a thymidine kinase-negative phenotype," Nature, 317:813-815 (1985).
Buller et al., "Deletion of the vaccinia virus growth factor gene reduces virus virulence," Journal of virology, 62(3):866-874 (1988).
Burger et al., "B cell receptor signaling in chronic lymphocytic leukemia," Trends Immunol, 34:592-601 (2013).
Burkhardt et al., "Autologous CLL cell vaccination early after transplant induces leukemia-specific T cells," The Journal of clinical investigation, 123(9):3756-3765 (2013).
Buser et al., "Unique composite hematolymphoid tumor consisting of a pro-T lymphoblastic lymphoma and an indeterminate dendritic cell tumor: evidence for divergent common progenitor cell differentiation," Pathobiology, 81:199-205 (2014).
Byrd et al., "Targeting BTK with ibrutinib in relapsed chronic lymphocytic leukemia," The New England journal of medicine, 369:32-42 (2013).
Bystryn et al., "Double-blind trial of a polyvalent, shed-antigen, melanoma vaccine," Clin Cancer Res, 7(7):1882-1887 (2001).
Cahill et al., "450K-array analysis of chronic lymphocytic leukemia cells reveals global DNA methylation to be relatively stable over time and similar in resting and proliferative compartments," Leukemia, 27:150-158 (2013).
Cancer Genome Atlas Research Network, "Comprehensive molecular characterization of gastric adenocarcinoma," Nature, 513:202-209 (2014).
Carreno et al., "IL-12p70-producing patient DC vaccine elicits Tcl-polarized immunity," Journal of Clinical Investigation, 123(8):3383-94 (2013).
Carter et al., "Absolute quantification of somatic DNA alterations in human cancer," Nat Biotechnol, 30:413-21 (2012).
Carter et al., "Accurate estimation of homologue-specific DNA concentration-ratios in cancer samples allows long-range haplotyping," Nature Precedings, 59-87 (2011).
Caskey et al., "Synthetic double-stranded RNA induces innate immune responses similar to a live viral vaccine in humans," The Journal of experimental medicine, 208(12):2357-2366 (2011).
Castle et al., "Exploiting the mutanome for tumor vaccination," Cancer research, 72(5):1081-1091 (2012).
CBOL Plant Working Group, "A DNA barcode for land plants," PNAS, 106(31):12794-12797 (2009).
Chang et al., "Immune selection of hot-spot beta 2-microglobulin gene mutations, HLA-A2 allospecificity loss, and antigen-processing machinery component down-regulation in melanoma cells derived from recurrent metastases following immunotherapy," Journal of immunology, 174:1462-1471 (2005).
Chapman et al., "Initial genome sequencing and analysis of multiple myeloma," Nature, 471:467-472 (2011).
Cheever, "Twelve immunotherapy drugs that could cure cancers," Immunological reviews, 222:357-368 (2008).
Chen et al., "Impact of replication timing on non-CpG and CpG substitution rates in mammalian genomes," Genome Res, 20:447-457 (2010).
Chen et al., "Langerhans Cell Sarcoma Arising from Chronic Lymphocytic Lymphoma/Small Lymphocytic Leukemia: Lineage Analysis and BRAF V600E Mutation Study," N Am J Sci, 5:386-91 (2013).
Chen et al., "Molecular mechanisms of T cell co-stimulation and co-inhibition," Nature reviews Immunology, 13:227-242 (2013).
Chen et al., "Recombinant modified vaccinia virus Ankara expressing the spike glycoprotein of severe acute respiratory syndrome coronavirus induces protective neutralizing antibodies primarily targeting the receptor binding region," Journal of virology, 79.5:2678-2688 (2005).
Chen et al., "Induction of CD8+ T cell responses to dominant and subdominant epitopes and protective immunity to Sendai virus infection by DNA vaccination," The Journal of Immunology, 160(5):2425-2432 (1998).
Child et al., "Insertional inactivation of the large subunit of ribonucleotide reductase encoded by vaccinia virus is associated with reduced virulence in vivo," Virology, 174(2):625-629 (1990).
Chim et al., "Epigenetic dysregulation of the Wnt signalling pathway in chronic lymphocytic leukaemia," J Clin Pathol, 61:1214-1219 (2008).
Chiron et al., "Cell-cycle reprogramming for PI3K inhibition overrides a relapse-specific C481S BTK mutation revealed by longitudinal functional genomics in mantle cell lymphoma," Cancer Discov, 4:1022-35 (2014).
Christian et al., "Targeting DNA double-strand breaks with TAL effector nucleases," Genetics, 186(2):757-761 (2010).
Chroboczek et al., "The Sequence of the Genome of Adenovirus Type 5 and Its Comparison with the Genome of Adenovirus Type 2," Virology, 186:280-285 (1992).
Church, "Genomes for all," Sci Am, 294(1):46-54 (2006).
Cibulskis et al., "ContEst: estimating cross-contamination of human samples in next-generation sequencing data," Bioinformatics, 27:2601-2602 (2011).
Cibulskis et al., "Sensitive detection of somatic point mutations in impure and heterogeneous cancer samples," Nat Biotechnol, 31:213-9 (2013).
Cleveland, "LOWESS: A program for smoothing scatterplots by robust locally weighted regression," The American Statistician, 35:54 (1981).
Conlon et al., "Mouse, but not Human STING, Binds and Signals in Response to the Vascular Disrupting Agent 5,6-Dimethylxanthenone-4- Acetic Acid," Journal of Immunology, 190:5216-25 (2013).
Corbett et al., "Aerosol immunization with NYVAC and MVA vectored vaccines is safe, simple, and immunogenic," Proc Natl Acad Sci, 105(6):2046-51 (2008).
Coulie et al., "A mutated intron sequence codes for an antigenic peptide recognized by cytolytic T lymphocytes on a human melanoma," Proc Natl Acad Sci USA, 92(17):7976-7980 (1995).
Cox et al., "Induction of cytotoxic T lymphocytes by recombinant canarypox (ALVAC) and attenuated vaccinia (NYVAC) viruses expressing the HIV-1 envelope glycoprotein," Virology, 195(2):845-850 (1993).
Crozat et al., "The XC chemokine receptor 1 is a conserved selective marker of mammalian cells homologous to mouse CD8α+ dendritic cells," Journal of Experimental Medicine, 207(6):1283-1292 (2010).

(56) References Cited

OTHER PUBLICATIONS

Daheshia et al., "Suppression of ongoing ocular inflammatory disease by topical administration of plasmid DNA encoding IL-10," The Journal of Immunology 159(4):1945-1952 (1997).
De et al., "Aberration in DNA methylation in B-cell lymphomas has a complex origin and increases with disease severity," PLoS Genet. 9:e1003137 (2013).
De Magalhaes et al., "Next-generation sequencing in aging research: emerging applications, problems, pitfalls and possible solutions," Ageing Research Reviews, 9(3):315-323 (2010).
DeLuca et al., "RNA-SeQC: RNA-seq metrics for quality control and process optimization," Bioinformatics, 28:1530-2 (2012).
DePristo et al., "A framework for variation discovery and genotyping using next-generation DNA sequencing data," Nature Genetics, 43:491-498 (2011).
Di Stasi et al., "Inducible apoptosis as a safety switch for adoptive cell therapy," New England Journal of Medicine, 365(18):1673-1683 (2011).
Didierlaurent et al., "Attenuated poxviruses expressing a synthetic HIV protein stimulate HLA-A2-restricted cytotoxic T-cell responses," Vaccine, 22(25-26):3395-3403 (2004).
Ding et al., "Somatic mutations affect key pathways in lung adenocarcinoma," Nature, 455:1069-1075 (2008).
Dohner et al., "Genomic aberrations and survival in chronic lymphocytic leukemia," The New England journal of medicine, 343:1910-1916 (2000).
Doody et al., "PRDMI/BLIMP-1 Modulates IFN—Dependent Control of the MHC Class I Antigen-Processing and Peptide-Loading Pathway," The Journal of Immunology, 179:7614-7623 (2007).
Dreicer et al., "MVA-MUC1-IL2 vaccine immunotherapy (TG4010) improves PSA doubling time in patients with prostate cancer with biochemical failure," Investigational new drugs, 27(4):379-386 (2009).
Dubey et al., "The immunodominant antigen of an ultraviolet-induced regressor tumor is generated by a somatic point mutation in the DEAD (SEQ ID No. 62) box helicase p68," The Journal of experimental medicine, 185(4):695-705 (1997).
DuPage et al., "Expression of tumour-specific antigens underlies cancer immunoediting," Nature, 482(7385):405-409 (2012).
Dupuis et al., "Dendritic Cells Internalize Vaccine Adjuvant after Intramuscular Injection," Cell Immunol, 186(1): 18-27 (1998).
Earl et al., "Immunogenicity of a highly attenuated MVA smallpox vaccine and protection against monkeypox," Nature, 428:182 (2004).
Eckhardt et al., "DNA methylation profiling of human chromosomes 6, 20 and 22, " Nat Genet, 38:1378-1385 (2006).
Eden et al., "Discovering motifs in ranked lists of DNA sequences," PLoS computational biology, 3, e39 (2007).
Eden et al., "GOrilla: a tool for discovery and visualization of enriched GO terms in ranked gene lists," BMC bioinformatics, 10:48 (2009).
Eggermont et al., "Ulceration and stage are predictive of interferon efficacy in melanoma: results of the phase III adjuvant trials EORTC 18952 and EORTC 18991," Eur J Cancer, 48(2):218-225 (2012).
Ehrlich, "DNA hypomethylation in cancer cells," Epigenomics, 1:239-259 (2009).
Engler et al., "A one pot, one step, precision cloning method with high throughput capability," PloS one 3(11):e3647 (2008).
Engler et al., "Golden gate shuffling: a one-pot DNA shuffling method based on type IIs restriction enzymes," PloS one, 4(5):e5553 (2009).
Escobar et al., "Bayesian density estimation and inference using mixtures," Journal of the American Statistical Association, 90:577-588 (1995).
Esteban, "Attenuated poxvirus vectors MVA and NYVAC as promising vaccine cadidates against HIV/AIDS," Human vaccines, 5(12):867-871 (2009).
Fais et al., "Chronic lymphocytic leukemia B cells express restricted sets of mutated and unmutated antigen receptors, " The Journal of clinical investigation, 102:1515-25 (1998).
Fan et al., "The multi substrate adapter Gabl regulates hepatocyte growth factor (scatter factor)-c-Met signaling for cell survival and DNA repair," Molecular and cellular biology, 21:4968-4984 (2001).
Fantom Consortium et al., "A promoter-level mammalian expression atlas," Nature, 507:462-470 (2014).
Farsaci et al., "Consequence of dose scheduling of sunitinib on host immune response elements and vaccine combination therapy," Int J Cancer, 130:1948-1959 (2012).
Felgner et al., "Lipofection: A Highly Efficient, Lipid-Mediated DNA-Transfection Procedure," PNAS, 84(21): 7413-7417 (1987).
Ferrier-Rembert et al., "Short-and long-term immunogenicity and protection induced by non-replicating smallpox vaccine candidates in mice and comparison with the traditional 1st generation vaccine," Vaccine, 26(14): 1794-1804 (2008).
Finke et al., "Sunitinib Reverses Type-1 Immune Suppression and Decreases T-Regulatory Cells in Renal Cell Carcinoma Patients," Clin Cancer Res, 14(20):6674-6682 (2008).
Fisher et al., "A scalable, fully automated process for construction of sequence-ready human exome targeted capture libraries," Genome Biol, 12:R1 (2011).
Flaherty et al., "From genes to drugs: targeted strategies for melanoma," Nat Rev Cancer, 12(5):349-361 (2012).
Flexner et al., "Prevention of vaccinia virus infection in imiminodeficient mice by vector-directed IL-2 expression," Nature, 330(6145):259-262 (1987).
Flynn et al., "Immunization with HIV Gag targeted to dendritic cells followed by recombinant New York vaccinia virus induces robust T-cell immunity in nonhuman primates," Proc Natl Acad Sci, 108(17):7131-7136 (2011).
Forconi et al., "Genome-wide DNA analysis identifies recurrent imbalances predicting outcome in chronic lymphocytic leukaemia with 17p deletion," British journal of haematology, 143:532-6 (2008).
Fransen et al., "Controlled local delivery of CTLA-4 blocking antibody induces CD8+ T-cell-dependent tumor eradication and decreases risk of toxic side effects," Clin Cancer Res, 19(19):5381-5389 (2013).
Frederick et al., "BRAF inhibition is associated with enhanced melanoma antigen expression and a more favorable tumor microenvironment in patients with metastatic melanoma," Clin Cancer Res, 19:1225-1231 (2013).
Friedberg et al., "Inhibition of Syk with fostamatinib disodium has significant clinical activity in non-Hodgkin lymphoma and chronic lymphocytic leukemia," Blood, 115:2578-2585 (2011).
Fritsch et al., "Translational repression of MCL-1 couples stress-induced eIF2 alpha phosphorylation to mitochondrial apoptosis initiation," The Journal of biological chemistry, 282:22551-62 (2007).
Furman et al., "Idelalisib and rituximab in relapsed chronic lymphocytic leukemia," The New England journal of medicine, 370:997-1007 (2014).
Fynan et al., "DNA vaccines: protective immunizations by parenteral, mucosal, and gene-gun inoculations," PNAS, 90 (24): 11478-82 (1993).
Gabrilovich et al., "IL-12 and Mutant P53 Peptide-Pulsed Dendritic Cells for the Specific Immunotherapy of Cancer," J Immunother Emphasis Tumor Immunol, 19(6): 414-418 (1996).
Gallego-Gomez et al., "Differences in virus-induced cell morphology and in virus maturation between MVA and other strains (WR, Ankara, and NYCBH) of vaccinia virus in infected human cells," Journal of virology, 77(19):10606-10622 (2003).
Gallois et al., "A needle in the 'cancer vaccine' haystack," Nature medicine, 16(8):854-856 (2010).
Gao et al., "Integrative analysis of complex cancer genomics and clinical profiles using the cBioPortal," Science signaling, 6(269):pi1 (2013).
Garimella et al., "Identification of novel molecular regulators of tumor necrosis factor-related apoptosis-inducing ligand (TRAIL)-induced apoptosis in breast cancer cells by RNAi screening," Breast cancer research, 16(2):R41 (2014).
Garofalo et al., "miR-221&222 regulate TRAIL resistance and enhance tumorigenicity through PTEN and TIMP3 downregulation," Cancer Cell, 16(6):498-509 (2009).

(56) References Cited

OTHER PUBLICATIONS

Garraway et al., "Lessons from the cancer genome," Cell, 153:17-37 (2013).
Gaucher et al., "Yellow fever vaccine induces integrated multilineage and polyfunctional immune responses," The Journal of experimental medicine, 205(13):3119-3131 (2008).
Gevaert et al., "Protein identification methods in proteomics," Electrophoresis: An International Journal, 21(6):1145-1154 (2000).
Gherardi et al., "Prime-boost immunization schedules based on influenza virus and vaccinia virus vectors potentiate cellular immune responses against human immunodeficiency virus Env protein systemically and in the genitorectal draining lymph nodes," Journal of virology, 77(12):7048-7057 (2003).
Ghiringhelli et al., "Metronomic cyclophosphamide regimen selectively depletes CD4+CD25+ regulatory T cells and restores T and NK effector functions in end stage cancer patients," Cancer Immunol Immunother, 56:641-648 (2007).
Giaever et al., "Functional profiling of the *Saccharomyces cerevisiae* genome," Nature, 418(6896):387-391 (2002).
Giannopoulos et al., "Peptide vaccination elicits leukemia-associated antigen-specific cytotoxic CD8+ T-cell responses in patients with chronic lymphocytic leukemia," Leukemia, 24(4):798-805 (2010).
Gibbs et al., "Abundant quantitative trait loci exist for DNA methylation and gene expression in human brain," PLoS genetics, 6:e1000952 (2010).
Gluzman, "SV40-transformed simian cells support the replication of early SV40 mutants," Cell, 23:175-182 (1981).
Goebel et al., "The complete DNA sequence of vaccinia virus," Virology, 179(1):247-266 (1990).
Gomez et al., "Efficient CD8+ T cell response to the HIV-env V3 loop epitope from multiple virus isolates by a DNA prime/vaccinia virus boost (rWR and rMVA strains) immunization regime and enhancement by the cytokine IFN-γ," Virus research, 105:11-22 (2004).
Gomez et al., "Head-to-head comparison on the immunogenicity of two HIV/AIDS vaccine candidates based on the attenuated poxvirus strains MVA and NYVAC co-expressing in a single locus the HIV-1BX08 gp120 and HIV-1IIIB Gag-Pol-Nef proteins of clade B," Vaccine, 25(15):2863-2885 (2007).
Gomez et al., "MVA and NYVAC as vaccines against emergent infectious diseases and cancer," Current gene therapy, 11(:3):189-217 (2011).
Gomez et al., "The poxvirus vectors MVA and NYVAC as gene delivery systems for vaccination against infectious diseases and cancer," Current gene therapy, 8(2):97-120 (2008).
Gomez et al., "Virus distribution of the attenuated MVA and NYVAC poxvirus strains in mice," Journal of General Virology, 88(9):2473-2478 (2007).
Greco et al., "Improving the safety of cell therapy with the TK-suicide gene," Front Pharmacol, 6:95 (2015).
Gregoriadis et al., "Improving the therapeutic efficacy of peptides and proteins: A role for polysialic acids," Int J Pharmaceutics, 300(1-2):125-30 (2005).
Gros et al., "PD-1 identifies the patient-specific CD8+ tumor-reactive repertoire infiltrating human tumors." The Journal of clinical investigation, 124(5):2246-2259 (2014).
Grunstein et al., "Colony hybridization: a method for the isolation of cloned DNAs that contain a specific gene," PNAS, 72(10):3961-3965 (1975).
GTEx Consortium, The Genotype-Tissue Expression (GTEx) project, Nature genetics, 45:580-585 (2013).
Guo et al., "Droplet microfluidics for high-throughput biological assays," Lab Chip, 12:2146-55 (2012).
Gupta et al., "Single-cell sequencing of T cell receptors: a perspective on the technological development and translational application," Adv Exp Med Biol 1255:29-50 (2020).
Guthals et al., "Shotgun Protein Sequencing with Meta-contig Assembly," Molecular and Cellular Proteomics, 1(10):1084-96 (2012).
Hadrup et al., "Parallel detection of antigen-specific T-eeil responses by multidimensional encoding of MHC multimers," Nature Methods, 6(7):520-26 (2009).
Halabi et al., "Prognostic model for predicting survival in men with hormone-refractory metastatic prostate cancer," Journal of Clinical Oncology, 21(7):1232-1237 (2003).
Hall, "Advanced sequencing technologies and their wider impact in microbiology," Journal of experimental biology, 210(9):1518-1525 (2007).
Hanahan et al., "Hallmarks of cancer: the next generation," Cell, 144:646-674 (2011).
Hansen et al., "Increased methylation variation in epigenetic domains across cancer types," Nat Genet, 43:768-775 (2011).
Hanzelmann et al., "GSVA: gene set variation analysis for microarray and RNA-Seq data," BMC bioinformatics, 14:7 (2013).
Harris et al., "Comparison of sequencing-based methods to profile DNA methylation and identification of monoallelic epigenetic modifications," Nat Biotechnol, 28:1097-1105 (2010).
Harris et al., "RNA editing enzyme APOBECI and some of its homologs can act as DNA mutators," Molecular cell, 1095):1247-1253 (2002).
Heemskerk et al., "The cancer antigenome," EMBO Journal, 32(2):194-203 (2013).
Hel et al., "Potentiation of simian immunodeficiency virus (SIV)-specific CD4+ and CD8+ T cell responses by a DNA-SIV and NYVAC-SIV prime/boost regimen," The Journal of Immunology, 167(12):7180-7191 (2001).
Herbeuval et al., "HAART reduces death ligand but not death receptors in lymphoid tissue of HIV-infected patients and simian immunodeficiency virus-infected macaques," AIDS, 23:35-40 (2009).
Herman et al., "ibrutinib-induced lymphocytosis in patients with chronic lymphocytic leukemia: correlative analyses from a phase II study," Leukemia, 28:2188 (2014).
Hinrichs et al., "Exploiting the curative potential of adoptive T-cell therapy for cancer," Immunological reviews, 257:56-71 (2014).
Hombrink et al., "High-Throughput Identification of Potential Minor Histocompatibility Antigens by MHC Tetramer-Based Screening: Feasibility and Limitations," Plos One, 6(8):1-11 (2011).
Honigberg et al., "The Bruton tyrosine kinase inhibitor PCI-32765 blocks B-cell activation and is efficacious in models of autoimmune disease and B-cell malignancy," PNAS, 107:13075-13080 (2010).
Horig et al., "Phase 1 clinical trial of a recombinant canarypoxvirus (ALVAC) vaccine expressing human carcinoembryonic antigen and the B7.1 co-stimulatory molecule," Cancer Immunol Immunother, 49:504-514 (2000).
Huang et al., "Mucosal priming with replicative Tiantan vaccinia and systemic boosting with DNA vaccine raised strong mucosal and systemic HIV-specific immune responses," Vaccine, 25(52):8874-8884 (2007).
Hutchings et al., "Combination of protein and viral vaccines induces potent cellular and humoral immune responses and enhanced protection from murine malaria challenge," Infect Immun, 75(12):5819-26 (2007).
Illingworth et al., "Orphan CpG islands identify numerous conserved promoters in the mammalian genome," PLoS Genet, 6(9):e1001134 (2010).
Inokuchi et al., "DCC protein expression in hematopoietic cell populations and its relation to leukemogenesis," J Clin Invest, 97:852-857 (1996).
Itoh et al., "Personalized peptide vaccines: A new therapeutic modality for cancer," Cancer Sci, 97:970-976 (2006).
Izeradjene et al., "Casein kinase II (CK2) enhances death-inducing signaling complex (DISC) activity in TRAIL-induced apoptosis in human colon carcinoma cell lines," Oncogene, 24:2050-2058 (2005).
Jaatinen et al., "Global gene expression profile of human cord blood-derived CD133+ cells," Stem Cells, 24:631-641 (2006).
Jemal et al., "Cancer statistics, 2007," CA: a cancer journal for clinicians, 57:43-66 (2007).
Jennewein et al., "Sumoylation of peroxisome proliferator-activated receptor gamma by apoptotic cells prevents lipopolysaccharide-induced NCoR removal from kappaB binding sites mediating transrepression of proinflammatory cytokines," Journal of immunology, 181:5646-5652 (2008).

(56) References Cited

OTHER PUBLICATIONS

Jensen et al., "Design and implementation of adoptive therapy with chimeric antigen receptor-modified T cells," Immunol Rev, 257(1):127-144 (2014).
Johann et al., "GLVR1, a receptor for gibbon ape leukemia virus, is homologous to a phosphate permease of Neurospora crassa and is expressed at high levels in the brain and thymus," Journal of Virology, 66(3):1635-1640 (1992).
Johnson et al., "Single-cell perforin and granzyme expression reveals the anatomical localization of effector CD8+ T cells in influenza virus-infected mice," PNAS, 100:2657-2662 (2003).
Jones et al., "Functions of DNA methylation: islands, start sites, gene bodies and beyond," Nat Rev Genet, 13:484-492 (2012).
Jones et al., "InterProScan 5: genome-scale protein function classification," Bioinformatics, 30:1236-1240 (2014).
Jones et al., "The epigenomics of cancer," Cell, 128:683-692 (2007).
Kandoth et al., "Mutational landscape and significance across 12 major cancer types," Nature, 502:333-339 (2013).
Kannan et al., "Vaccination strategies in follicular lymphoma," Current hematologic malignancy reports, 4(4):189-195 (2009).
Kantoff et al. "Overall survival analysis of a phase II randomized controlled trial of a Poxviral-based PSA-targeted immunotherapy in metastatic castration-resistant prostate cancer," Journal of Clinical Oncology, 28(7):1099-1105 (2010).
Karanikas et al., "High frequency of cytolytic T lymphocytes directed against a tumor-specific mutated antigen detectable with HLA tetramers in the blood of a lung carcinoma patient with long survival," Cancer Res, 61:3718-3724 (2001).
Karnani et al., "Pan-S replication patterns and chromosomal domains defined by genome-tiling arrays of ENCODE genomic areas," Genome research, 17:865-876 (2007).
Karolchik et al., "The UCSC Table Browser data retrieval tool," Nucleic acids research, 32:D493-496 (2004).
Kaufman et al., "Phase II randomized study of vaccine treatment of advanced prostate cancer (E7897): a trial of the Eastern Cooperative Oncology Group," Journal of Clinical Oncology, 22(11):2122-2132 (2004).
Kawai et al., "TLR signaling," Seminars in immunology, 19(1):24-32 (2007).
Kenter et al., "Vaccination against HPV-16 oncoproteins for vulvar intraepithelial neoplasia," New England Journal of Medicine, 361(19):1838-1847 (2009).
Khong et al., "Natural selection of tumor variants in the generation of 'tumor escape' phenotypes," Nature immunology, 3:999-1005 (2002).
Kim et al., "A Myc network accounts for similarities between embryonic stem and cancer cell transcription programs," Cell, 143:313-324 (2010).
Kim et al., "Anticancer flavonoids are mouse-selective STING agonists," ACS chemical biology, 8(7):1396-1401 (2013).
Kim et al., "TopHat2: accurate alignment of transcriptomes in the presence of insertions, deletions and gene fusions," Genome biology, 14:R36 (2013).
Kim et al., "TroVax, a recombinant modified vaccinia Ankara virus encoding 5T4: lessons learned and future development," Human vaccines, 6(10):784-791 (2010).
Kimmel et al., "[54] Identification and characterization of specific clones: Strategy for confirming the validity of presumptive clones," Methods in enzymology, 152:507-511 (1987).
Kirkwood et al., "High- and Low-dose Interferon Alpha-2b in High-isk Melanoma: First Analysis of Intergroup Trial E1690/S9111/C9190," J Clin Oncol, 18:2444-2458 (2000).
Kirkwood et al., "Interferon alfa-2b Adjuvant Therapy of High-Risk Resected Cutaneous Melanoma: The Eastern Cooperative Oncology Group Trial EST 1684," J Clin Oncol, 14:7-17 (1996).
Klebanoff et al., "Therapeutic cancer vaccines:are we there yet?," Immunol Rev, 239(1):27-44 (2011).
Klein et al., "Droplet Barcoding for Single-Cell Transcriptomics Applied to Embryonic Stem Cells," Cell, 161:1187-1201 (2015).
Kloor et al., "Immune evasion of microsatellite unstable colorectal cancers," International journal of cancer, 127:1001-1010 (2010).
Kobayashi et al., "Peptide epitope identification for tumor-reactive CD4 T cells," Current opinion in immunology, 20(2):221-227 (2008).
Koch, "Combining morphology and DNA barcoding resolves the taxonomy of Western Malagasy Liotrigona Moure, 1961," African Invertebrates, 51(2):413-421 (2010).
Kotwal et al., "Vaccinia virus encodes two proteins that are structurally related to members of the plasma serine protease inhibitor superfamily," Journal of virology, 63(2):600-606 (1989).
Kreiter et al., "Mutant MHC Class II epitopes drive therapeutic immune responses to cancer," Nature, 520:692 (2015).
Kreso et al., "Variable clonal repopulation dynamics influence chemotherapy response in colorectal cancer," Science, 339:543-548 (2013).
Kress et al., "DNA barcodes: Genes, genomics, and bioinformatics," PNAS, 105(8):2761-2762 (2008).
Kress et al., "Use of DNA barcodes to identify flowering plants," PNAS, 102(23):8369-8374 (2005).
Kulis et al., "Epigenomic analysis detects widespread gene-body DNA hypomethylation in chronic lymphocytic leukemia," Nat Genet, 44:1236-1242 (2012).
Kyte et al., "Telomerase Peptide Vaccination Combined with Temozolomide: A Clinical Trial in Stage IV Melanoma Patients," Clin Cancer Res, 17(13):4568-4580 (2011).
Lahaye et al., "DNA barcoding the floras of biodiversity hotspots," PNAS, 105(8):2923-2928 (2008).
Landan et al., "Epigenetic polymorphism and the stochastic formation of differentially methylated regions in normal and cancerous tissues," Nat Genet, 44:1207-1214 (2012).
Landau et al., "Clonal evolution in hematological malignancies and therapeutic implications," Leukemia, 28:34-43 (2014).
Landau et al., "Evolution and Impact of Subclonal Mutations in Chronic Lymphocytic Leukemia," Cell, 152:714-726 (2013).
Langmead et al., "Fast gapped-read alignment with Bowtie 2," Nat Meth, 9:357-359 (2012).
Langmead et al., "Ultrafast and memory-efficient alignment of short DNA sequences to the human genome," Genome Biology, 10:R25 (2009).
Lawrence et al., "Discovery and saturation analysis of cancer genes across 21 tumour types," Nature, 505:495-501 (2014).
Lawrence et al., "Mutational heterogeneity in cancer and the search for new cancer-associated genes," Nature, 499:214-218 (2013).
Le et al., "Evaluation of Ipilimumab in combination with allogeneic pancreatic tumor cells transfected with a GM-CSF gene in previously treated pancreatic cancer," J Immunother, 36(7):382-389 (2013).
Le Mercier et al., "Beyond CTLA-4 and PD-1, the generation Z of negative checkpoint regulators," Front Immunol, 6:418 (2015).
Lee et al., "Sequential amplification of cloned DNA as tandem multimers using class-IIS restriction enzymes," Genetic Analysis: Biomolecular Engineering, 13(6):139-145 (1996).
Leffers et al., "Immunization with a P53 synthetic long peptide vaccine induces P53☐specific immune responses in ovarian cancer patients, a phase II trial," Int J Cancer, 125(9):2104-2113 (2009).
Leffers et al., "Long-term clinical and immunological effects of p53?SLP® vaccine in patients with ovarian cancer," Int J Cancer, 130(1):105-112 (2012).
Leitner et al., "Immune responses induced by intramuscular or gene gun injection of protective deoxyribonucleic acid vaccines that express the circumsporozoite protein from Plasmodium berghei malaria parasites," J Immunol, 159(12):6112-6119 (1997).
Lemay et al., "Dok-3, a Novel Adapter Molecule Involved in the Negative Regulation of Immunoreceptor Signaling," Mol Cell Biol, 20:2743-2754 (2000).
Lennerz et al., "The Response of Autologous T Cells to a Human Melanoma is Dominated by Mutated Neoantigens," PNAS, 102(44):16013-16018 (2005).
Lewis et al., "DNA Vaccines: A Review," Advances in Virus Research, 54:129-88 (1999).
Li et al., "Fast and accurate short read alignment with Burrows-Wheeler Transform," Bioinformatics, 25(14):1754-1760 (2009).

(56) References Cited

OTHER PUBLICATIONS

Li et al., "Inactivating mutations of the chromatin remodeling gene ARID2 in hepatocellular carcinoma," Nature Genetics, 43:828-829 (2011).
Li et al., "Mapping short DNA sequencing reads and calling variants using mapping quality scores," Genome Res, 18:1851-1858 (2008).
Li et al., "RSEM: accurate transcript quantification from RNA-Seq data with or without a reference genome," BMC Bioinformatics, 12:323 (2011).
Li et al., "The Sequence Alignment/Map format and SAMtools," Bioinformatics, 25(16):2078-2079 (2009).
Li et al., "Fast and accurate long-read alignment with Burrows-Wheeler transform," Bioinformatics, 26(5):589-595 (2010).
Liggins et al., "MORC4, a novel member of the MORC family, is highly expressed in a subset of diffuse large B-cell lymphomas," Brit J Haematol, 138:479-486 (2007).
Lim et al., "Transcriptome analyses of mouse and human mammary cell subpopulations reveal multiple conserved genes and pathways," Breast Cancer Res, 12:R21 (2010).
Lin et al., "Relevance of the immunoglobulin VH somatic mutation status in patients with chronic lymphocytic leukemia treated with fludarabine, cyclophosphamide, and rituximab (FCR) or related chemoimmunotherapy regimens," Blood, 113:3168-71 (2009).
Link et al., "Electric control of droplets in microfluidic devices," Angew Chem Int Ed Engl, 45(16):2556-2560 (2006).
Liu et al., "Systematic identification of type I and type II interferon-induced antiviral factors," PNAS, 109(11):4239-4244 (2012).
Livak et al. "Methods for qPCR gene expression profiling applied to 1440 lymphoblastoid single cells," Methods, 59(1):71-79 (2013).
Llobet et al., "CK2 controls TRAIL and Fas sensitivity by regulating FLIP levels in endometrial carcinoma cells," Oncogene, 27:2513-2524 (2008).
Lohr et al., "Discovery and prioritization of somatic mutations in diffuse large B-cell lymphoma (DLBCL) by whole-exome sequencing," PNAS, 109(10):3879-3884 (2012).
Lu et al., "Mutated regions of nucleophosmin 1PPP1R3B Is Recognized by T Cells Used To Treat a Melanoma Patient Who Experienced a Durable Complete Tumor Regression," J Immunol, 190(12):6034-6042 (2013).
Luckow et al., "Trends in the Development of Baculovirus Expression Vectors," Nat Biotechnol, 6:47-55 (1988).
Lund et al., "Coordination of early protective immunity to viral infection by regulatory T cells," Science, 320(5880):1220-1224 (2008).
Lundegaard et al., "Prediction of epitopes using neural network based methods," J Immunol Methods, 374(1-2):26-34 (2011).
Mackett et al., "Vaccinia virus: a selectable eukaryotic cloning and expression vector," PNAS, 79:7415-7419 (1982).
Macosko et al., "Highly Parallel Genome-wide Expression Profiling of Individual Cells Using Nanoliter Droplets," Cell, 161(5):1202-1214 (2015).
Maegawa et al., "Age-related epigenetic drift in the pathogenesis of MDS and AML," Genome Res, 24:580-591 (2014).
Mandl et al., "Immunotherapy with MVA-BN@-HER2 induces HER-2-specific Th1 immunity and alters the intratumoral balance of effector and regulatory T cells," Cancer Immunol Immunother, 61(1):19-29 (2012).
Manghera et al., "Endogenous retrovirus-K promoter: a landing strip for inflammatory transcription factors?," Retrovirol, 10:16 (2013).
Mannino et al., "Liposome Mediated Gene Transfer," Biotechniques, 6(7): 682-690 (1988).
Marabelle et al., "Depleting tumor-specific Tregs at a single site eradicates disseminated tumors," J Clin Invest, 1123(6):2447-2463(2013).
Maratea et al. "Deletion and fusion analysis of the phage φX174 lysis gene E," Gene 40(1):39-46 (1985).
Marcais et al., "A fast, lock-free approach for efficient parallel counting of occurrences of k-mers," Bioinformatics, 27(6):764-770 (2011).
Marshall et al., "Phase I Study in Cancer Patients of a Replication-Defective Avipox Recombinant Vaccine That Expresses Human Carcinoembryonic Antigen," J Clin Oncol, 17:332-337 (1999).
Matsushita et al., "Cancer Exome Analysis Reveals a T Cell Dependent Mechanism of Cancer Immunoediting," Nature, 482(7385):400-404 (2012).
Maus et al., "Adoptive Immunotherapy for Cancer or Viruses," Annual Review of Immunology, 32:189-225 (2014).
Mayer et al., "A revised nomenclature for transcribed human endogenous retroviral loci," Mobile DNA, 2:7 (2011).
Mayr et al., "Abstammung, Eigenschaften und Verwendung des attenuierten Vaccinia-Stammes MVA (Translated Summary)," Infection, 3(1):6-14 (1975).
Mayr, "The smallpox vaccination strain MVA: marker, genetic structure, experience gained with the parenteral vaccination and behavior in organisms with a debilitated defence mechanism (author's transl)," Zentralbl Bakteriol 167(5-6):375-9 (1978).
Mazutis et al., "Single-cell analysis and sorting using droplet-based microfluidics," Nat Protoc, 8:870-891 (2013).
McCormack et al., "HLA-A*3101 and Carbamazepine-Induced Hypersensitivity Reactions in Europeans," New Engl J Med, 364:1134-1143 (2011).
McCurdy et al., "Modified Vaccinia Ankara: Potential as an Alternative Smallpox Vaccine," Clin Infect Dis, 38:1749-1753 (2004).
McDermott et al., "Immune Therapy for Kidney Cancer: A Second Dawn?," Semin Oncol, 40(4):492-498 (2013).
McFadden et al., "Genetic and clonal dissection of murine small cell lung carcinoma progression by genome sequencing." Cell, 156(6):1298-1311 (2014).
McKenna et al., "The Genome Analysis Toolkit: a MapReduce framework for analyzing next-generation DNA sequencing data," Genome Res, 20(9):1297-1303 (2010).
Medema et al., "Immune Escape of Tumors in Vivo by Expression of Cellular Flice-Inhibitory Protein," J Exp Med, 190:1033-1038 (1999).
Meissner et al., "Genome-scale DNA methylation maps of pluripotent and differentiated cells," Nature, 454:766-770 (2008).
Melief et al., "Immunotherapy of established (pre)malignant disease by synthetic long peptide vaccines," Nature Rev Cancer, 8:351-360 (2008).
Menke et al., "Genetic interactions between the Wilms' tumor 1 gene and the p53 gene," Cancer Res, 62(22):6615-6620 (2002).
Mermel et al., "GISTIC2.0 facilitates sensitive and confident localization of the targets of focal somatic number alteration in human cancers," Genome Biol, 12:R41 (2011).
Merrifield, "Solid Phase Peptide Synthesis. I. The Synthesis of a Tetrapeptide," J Am Chem Soc, 85(14):2149-2154 (1963).
Messmer et al., "In vivo measurements document the dynamic cellular kinetics of chronic lymphocytic leukemia B cells," J Clin Invest, 115(3):755-764 (2005).
Meyer et al., "Mapping of deletions in the genome of the highly attenuated vaccinia virus MVA and their influence on virulence," J Gen Virol, 72:1031-1038 (1991).
Midgley, "Vaccinia virus strain NYVAC induces substantially lower and qualitatively different human antibody responses compared with strains Lister and Dryvax," J Gen Virol, 89:2992-2997 (2008).
Miller et al., "Construction and properties of retrovirus packaging cells based on gibbon ape leukemia virus, " Virol, 65:2220-2224 (1991).
Missale et al., "HLA-A31- and HLA-Aw68-restricted cytotoxic T cell responses to a single hepatitis B virus nucleocapsid epitope during acute viral hepatitis," J Exp Med, 177(3):751-762 (1993).
Mkrtichyan et al., "Anti-PD-1 synergizes with cyclophosphamide to induce potent anti-tumor vaccine effects through novel mechanisms," European Journal of Immunology 41(10):2977-2986 (2011).
Mocellin et al., "Interferon Alpha Adjuvant Therapy in Patients With High-Risk Melanoma: A Systematic Review and Meta-analysis," JNCI, 102(7):493-501 (2010).
Mooij, "Differential CD4+ versus CD8+ T-Cell Responses Elicited by Different Poxvirus-Based Human Immunodeficiency Virus Type 1 Vaccine Candidates Provide Comparable Efficacies in Primates," J Virol, 82(6):2975-2988 (2008).

(56) References Cited

OTHER PUBLICATIONS

Mor et al., "Complexity of the cytokine and antibody response elicited by immunizing mice with Plasmodium yoelii circumsporozoite protein plasmid DNA," J Immunol, 155(4):2039-2046 (1995).
Morison et al., "A census of mammalian imprinting," Trends Genet, 21(8):457-465 (2005).
Morozov et al., "The Transmembrane Protein of the Human Endogenous Retrovirus—K (HERV-K) Modulates Cytokine Release and Gene Expression," PloS one 8(8):e70399 (2013).
Morton et al., "Prolonged Survival of Patients Receiving Active Immunotherapy With Canvaxin Therapeutic Polyvalent Vaccine After Complete Resection of Melanoma Metastatic to Regional Lymph Nodes," Ann Surg, 236(4):438-448 (2002).
Moss, "Reflections on the early development of poxvirus vectors," Vaccine, 31(39): 4220-4222 (2013).
Murphy et al., "Genetic construction, expression, and melanoma-selective cytotoxicity of a diphtheria toxin-related alpha-melanocyte-stimulating hormone fusion protein," PNAS, 83:8258-8262 (1986).
Murphy et al., "Phase I Clinical Trial: T-Cell Therapy for Prostate Cancer Using Autologous Dendritic Cells Pulsed with HLA-A0201-Specific Peptides from Prostate-Specific Membrane Antigen," Prostate, 29(6): 371-380 (1996).
Musey et al., "HIV-1 Vaccination Administered Intramuscularly Can Induce Both Systemic and Mucosal T Cell Immunity in HIV-1-Uninfected Individuals," J Immunol, 171(2):1094-1101 (2003).
Najera et al., "Cellular and Biochemical Differences between Two Attenuated Poxvirus Vaccine Candidates (MVA and NYVAC) and Role of the C7L Gene," J Virol, 80(12):6033-6047 (2006).
Nam et al., "Different contribution of co-stimulatory molecules B7.1 and B7.2 to the immune response to recombinant modified vaccinia virus ankara vaccine expressing prM/E proteins of Japanese encephalitis virus and two hepatitis B virus vaccines," Acta Virol, 51:125-30 (2007).
Nielsen et al., "NetMHCpan, a Method for Quantitative Predictions of Peptide Binding to Any HLA-A and -B Locus Protein of Known Sequence," PloS one, 2:e796 (2007).
Nishimura et al., "Distinct Role of Antigen-Specific T Helper Type 1 (Th1) and Th2 Cells in Tumor Eradication in Vivo," J Ex Med, 190(5):617-27 (1999).
Nocentini et al., "A new member of the tumor necrosis factor/nerve growth factor receptor family inhibits T cell receptor-induced apoptosis," PNAS, 94(12):6216-6221 (1997).
Novershtern et al., "Densely Interconnected Transcriptional Circuits Control Cell States in Human Hematopoiesis," Cell, 144(2):296-309 (2011).
Oh et al., "Neutrophil isolation protocol," J Vis Exp (2008).
Ohnishi et al., "Premature Termination of Reprogramming In Vivo Leads to Cancer Development through Altered Epigenetic Regulation." Cell, 156(4):663-677 (2014).
Okada et al., "Induction of CD8+ T-Cell Responses Against Novel Glioma-Associated Antigen Peptides and Clinical Activity by Vaccinations With α-Type 1 Polarized Dendritic Cells and Polyinosinic-Polycytidylic Acid Stabilized by Lysine and Carboxymethylcellulose in Patients With Recurrent Malignant Glioma," J Clin Oncol, 29(3):330-336 (2011).
Oshiumi et al., "DEAD/H BOX 3 (DDX3) helicase binds the RIG-I adaptor IPS-1 to up-regulate IFN-beta-inducing potential," Eur J Immunol, 40:940-948 (2010).
Ott et al., "CTLA-4 and PD-1/PD-L1 Blockade: New Immunotherapeutic Modalities with Durable Clinical Benefit in Melanoma Patients," Clin Cancer Res, 19(19):5300-5309 (2013).
Oudard et al., "A phase II study of the cancer vaccine TG4010 alone and in combination with cytokines in patients with metastatic renal clear-cell carcinoma: clinical and immunological findings," Cancer Immunol Immunother, 60(2): 261-271 (2011).
Padgett et al., "Creating seamless junctions independent of restriction sites in PCR cloning," Gene, 168:31-35 (1996).
Page et al., "Immune Modulation in Cancer with Antibodies," Annu Rev Med, 65:185-202 (2014).
Pages, et al., "Effector Memory T Cells, Early Metastasis, and Survival in Colorectal Cancer," New Engl J Med, 353:2654-2666 (2005).
Panicali et al., "Construction of live vaccines by using genetically engineered poxviruses: biological activity of recombinant vaccinia virus expressing influenza virus hemagglutinin," PNAS, 80(17):5364-5368 (1983).
Panicali et al., "Construction of poxviruses as cloning vectors: insertion of the thymidine kinase gene from herpes simplex virus into the DNA of infectious vaccinia virus," PNAS, 79(16):4927-4931 (1982).
Pantaleo et al., "Poxvirus vector-based HIV vaccines," Curr Opin HIV-AIDS, 5:391-396 (2010).
Paoletti, "Applications of pox virus vectors to vaccination: an update," PNAS, 93(21):11349-53 (1996).
Pei et al., "Genome-wide DNA methylation analysis reveals novel epigenetic changes in chronic lymphocytic leukemia," Epigenetics, 7:567-578 (2012).
Peng et al., "DOK3 Negatively Regulates LPS Responses and Endotoxin Tolerance, " PloS one 7:e39967 (2012).
Perez et al., "A new era in anticancer peptide vaccines," Cancer, 116(9):2071-2080 (2010).
Perez et al., "p63 consensus DNA-binding site: identification, analysis and application into a p63MH algorithm," Oncogene, 26:7363-7370 (2007).
Perkvs et al., "Poxvirus based vaccine candidates for cancer, AIDS, and other infectious diseases," J Leukocyte Biol, 58(1):1-13 (1995).
Perreau et al., "DNA/NYVAC Vaccine Regimen Induces HIV-Specific CD4 and CD8 T-Cell Responses in Intestinal Mucosa," J Virol, 85(19):9854-9862 (2011).
Petsch et al., "Protective efficacy of in vitro synthesized, specific mRNA vaccines against influenza A virus infection," Nat Biotechnol, 30(12):1210-1216 (2012).
Pieters et al., "On guard: coronin proteins in innate and adaptive immunity," Nat Rev Immunol, 13:510-518 (2013).
Pirard et al., "Interferon Alpha as Adjuvant Postsurgical Treatment of Melanoma: A Meta-Analysis," Dermatology, 208(1):43-48 (2004).
Poirot et al., "Multiplex genome edited T-cell manufacturing platform for "off-the-shelf" adoptive T-cell immunotherapies," Cancer Res, 75(18):3853 (2015).
Poulet, "Development and registration of recombinant veterinary vaccines: The example of the canarypox vector platform," Vaccine, 25(30):5606-5612 (2007).
Powell et al., "NCoR1 Mediates Papillomavirus E8E2C Transcriptional Repression," J Virol, 84:4451-4460 (2010).
Pujadas et al., "Regulated noise in the epigenetic landscape of development and disease," Cell, 148(6):1123-1131 (2012).
Qin et al., "Soft lithography for micro- and nanoscale patterning," Nat Protoc, 5:491-502 (2010).
Quesada et al., "Exome sequencing identifies recurrent mutations of the splicing factor SF3B1 gene in chronic lymphocytic leukemia," Nat Genet, 44:47-52 (2012).
Quezada et al., "CTLA4 blockade and GM-CSF combination immunotherapy alters the intratumor balance of effector and regulatory T cells," J Clin Invest, 116(7):1935-1945 (2006).
Ramos et al., "An Inducible Caspase 9 Suicide Gene to Improve the Safety of Mesenchymal Stromal Cell Therapies," Stem Cells, 28(6):1107-1115 (2010).
Ramskold et al., "Full-length mRNA-Seq from single-cell levels of RNA and individual circulating tumor cells," Nat Biotechnol, 30:777-782 (2012).
Rassenti et al., "Relative value of ZAP-70, CD38, and immunoglobulin mutation status in predicting aggressive disease in chronic lymphocytic leukemia," Blood, 112:1923-1930 (2008).
Raval et al., "Downregulation of Death-Associated Protein Kinase 1 (DAPK1) in Chronic Lymphocytic Leukemia," Cell, 129(5):879-890 (2007).
Ravi et al., "Sensitization of Tumor Cells to Apo2 Ligand/TRAIL-induced Apoptosis by Inhibition of Casein Kinase II," Cancer Res, 62(15):4180-4185 (2002).
Richter et al., "Mechanistic Determinants of Biotherapeutics Absorption Following SC Administration," The AAPS Journal, 14(3):559-568 (2012).

(56) References Cited

OTHER PUBLICATIONS

Rini et al., "Biology and Treatment of Advanced Renal Cell Carcinoma: A Global Perspective," Semin Oncol, 40(4):419-420 (2013).
Robbins et al., "Mining exomic sequencing data to identify mutated antigens recognized by adoptively transferred tumor-reactive T cells," Nat Med, 19(6):747-752 (2013).
Robinson et al., "A phase I-II trial of multiple-dose polyriboinosic-polyribocytidylic acid in patieonts with leukemia or solid tumors," J Natl Cancer Inst, 57(3):599-602 (1976).
Robinson et al., "DNA vaccines for viral infections: Basic studies and applications," Adv Virus Res, 55:1-74 (2000).
Robinson et al., "edgeR: a Bioconductor package for differential expression analysis of digital gene expression data," Bioinformatics, 26(1):139-140 (2010).
Robinson et al., "Integrative genomics viewer," Nat Biotechnol, 29:24-26 (2011).
Rolph et al., "Recombinant viruses as vaccines and immunological tools," Curr Opin Immunol, 9(4):517-524 (1997).
Ronchetti et al., "Frontline:GITR, a member of the TNF receptor superfamily, is costimulatory to mouse T lymphocytesubpopulations," Eur J Immunol, 34(3):613-622 (2004).
Rosenberg et al., "Adoptive cell transfer as personalized immunotherapy for human cancer," Science, 348(6230):62-68 (2015).
Rosenberg, "Raising the Bar: The Curative Potential of Human Cancer Immunotherapy," Sci Transl Med, 4(127):127ps128 (2012).
Rossi et al., "Integrated mutational and cytogenetic analysis identifies new prognostic subgroups in chronic lymphocytic leukemia," Blood, 121:1403-1412 (2013).
Rubio-Moscardo et al., "Characterization of 8p21.3 chromosomal deletions in B-cell lymphoma: TRAIL-R1 and TRAIL-R2 as candidate dosage-dependent tumor suppressor genes," Blood, 106:3214-3222 (2005).
Rupprecht et al., "Oral immunization and protection of raccoons (*Procyon lotor*) with a vaccinia-rabies glycoprotein recombinant virus vaccine," PNAS, 83:7947-7950 (1986).
Rutledge et al., "Tumor-Infiltrating Lymphocytes in Glioblastoma Are Associated with Specific Genomic Alterations and Related to Transcriptional Class," Clin Cancer Res, 19:4951-4960 (2013).
Sabado et al., "Preparation of Tumor Antigen-loaded Mature Dendritic Cells for Immunotherapy," J Vis Exp, 78:50085 (2013).
Sadelain, "Eliminating Cells Gone Astray," New Engl J Med, 365:1735-1737 (2011).
Salem et al., "Defining the Antigen-Specific T-Cell Response to Vaccination and Poly(I:C)/TLR3 Signaling: Evidence of Enhanced Primary and Memory CD8 T-Cell Responses and Antitumor Immunity." J Immunother, 28(3):220-228 (2005).
Sampson et al., "An epidermal growth factor receptor variant III-targeted vaccine is safe and immunogenic in patients with glioblastomas multiforme," Mol Cancer Ther, 8(10):2773-2779 (2009).
Sampson et al., "Greater chemotherapy-induced lymphopenia enhances tumor-specific immune responses that eliminate EGFRvIII-expressing tumor cells in patients with glioblastoma," Neuro-Oncology, 13(3):324-333 (2011).
Sampson et al., "Immunologic Escape After Prolonged Progression-Free Survival With Epidermal Growth Factor Receptor Variant III Peptide Vaccination in Patients With Newly Diagnosed Glioblastoma," J Clin Oncol, 28(31):4722-4729 (2010).
Samuels et al., "Oncogenic PI3K and its role in cancer," Curr Opin Oncol, 18:77-82n (2006).
Sancho, "The Block in Assembly of Modified Vaccinia Virus Ankara in HeLa Cells Reveals New Insights into Vaccinia Virus Morphogenesis," J Virol, 76(16):8313-8334 (2002).
Sato et al., "Discovery of Novel Targets for Aberrant Methylation in Pancreatic Carcinoma Using High-Throughput Microarrays." Cancer Res, 63(13):3735-3742 (2003).
Saturno et al., "Combining TRAIL with PI3 Kinase or HSP90 inhibitors enhances apoptosis in colorectal cancer cells via suppression of survival signaling," Oncotarget, 4(8):1185-1198 (2013).
Saunders et al., "Strelka: accurate somatic small-variant calling from sequenced tumor-normal sample pairs," Bioinformatics, 28(14):1811-1817 (2012).
Schmitt et al., "Transcriptional Profiling of Human Endogenous Retrovirus Group HERV-K(HML-2) Loci in Melanoma," Genome Biol Evol, 5(2):307-328 (2013).
Schneider et al, "Induction of CD8+ T cells using heterologous prime-boost immunisation strategies," Immunol Rev, 170(1):29-38 (1999).
Schreiber et al., "Cancer Immunoediting: Integrating Immunity's Roles in Cancer Suppression and Promotion," Science, 331(6024):1565-1570 (2011).
Schumacher et al., "Prognostic Significance of Activated CD8+ T Cell Infiltrations within Esophageal Carcinomas," Cancer Res, 61(10):3932-3936 (2001).
Schuster et al., "Vaccination With Patient-Specific Tumor-Derived Antigen in First Remission Improves Disease-Free Survival in Follicular Lymphoma," J Clin Oncol, 29(20):2787-2794 (2011).
Scriba et al., "Modified vaccinia Ankara expressing Ag85A, a novel tuberculosis vaccine, is safe in adolescents and children, and induces polyfunctional CD4+ T cells," Eur J Immunol, 40(1):279-290 (2010).
Seberg et al., "How Many Loci Does it Take to DNA Barcode a Crocus?," PLoS One 4(2):e4598 (2009).
Secchiero et al., "Aberrant expression of TRAIL in B chronic lymphocytic leukemia (B-CLL) cells," J Cell Physiol, 205(2):246-252 (2005).
Sedegah et al., "Protection against malaria by immunization with plasmid DNA encoding circumsporozoite protein," PNAS, 91(21):9866-9870 (1994).
Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell, 2(2):117-125 (2002).
Shalek et al., "Single-cell RNA-seq reveals dynamic paracrine control of cellular variation," Nature, 510(7505):363-369 (2014).
Shannon, "A Mathematical Theory of Communication," Bell System Technical Journal, 27(3):379-423 (1948).
Shao et al., "Clonally related histiocytic/dendritic cell sarcoma and chronic lymphocytic leukemia/small lymphocytic lymphoma: a study of seven cases," Mod Pathol, 24:1421-1432 (2011).
Sharei et al., "Ex Vivo Cytosolic Delivery of Functional Macromolecules to Immune Cells," PLOS ONE, 10(4):e0118803 (2015).
Shida, "Effects and virulences of recombinant vaccinia viruses derived from attenuated strains that express the human T-cell leukemia virus type I envelope gene," J Virol, 62(12):4474-4480 (1988).
Shipony et al., "Dynamic and static maintenance of epigenetic memory in pluripotent and somatic cells," Nature, 513:115-119 (2014).
Sidney et al., "HLA class I supertypes: a revised and updated classification," BMC Immunol, 9:1 (2008).
Siegel et al., "Cancer statistics, 2013," CA, 63(1):11-30 (2013).
Simmons et al., "Local secretion of anti-CTLA-4 enhances the therapeutic efficacy of a cancer immunotherapy with reduced evidence of systemic autoimmunity," Cancer Immunol Immunother, 57(8):1263-1270 (2008).
Simpson et al., "Cancer/testis antigens, gametogenesis and cancer," Nat Rev Cancer, 5:615-625 (2005).
Simpson et al., "Fc-dependent depletion of tumor-infiltrating regulatory T cells co-defines the efficacy of anti-CTLA-4 therapy against melanoma," J Exp Med, 210(9):1695-1710 (2013).
Sizemore, "Attenuated Shigella as a DNA Delivery Vehicle for DNA-Mediated Immunization," Science, 270(5234):299-303 (1995).
Slingluff et al., "Immunologic and Clinical Outcomes of a Randomized Phase II Trial of Two Multipeptide Vaccines for Melanoma in the Adjuvant Setting," Clin Cancer Res, 13(21):6386-6395 (2007).
Slingluff et al., "Randomized Multicenter Trial of the Effects of Melanoma-Associated Helper Peptides and Cyclophosphamide on the Immunogenicity of a Multipeptide Melanoma Vaccine," J Clin Oncol, 29(21):2924-2932 (2011).
Smith et al., "Comparison of biosequences," Adv Appl Math, 2(4):482-489 (1981).

(56) References Cited

OTHER PUBLICATIONS

Smith et al., "Construction and characterization of an infectious vaccinia virus recombinant that expresses the influenza hemagglutinin gene and induces resistance to influenza virus infection in hamsters," PNAS, 80(23):7155-7159 (1983).
Smith et al., "Infectious vaccinia virus recombinants that express hepatitis B virus surface antigen," Nature, 302:490-495 (1983).
Smoley et al., "Standardization of fluorescence in situ hybridization studies on chronic lymphocytic leukemia (CLL) blood and marrow cells by the CLL Research Consortium," Cancer Genet Cytogenet, 203(2):141-148 (2010).
Soares et al. "A subset of dendritic cells induces CD4+ T cells to produce IFN-gamma by an IL-12-independent but CD70-dependent mechanism in vivo," J Exp Med, 2215(11):1095-1106 (2007).
Soininen et al., "Analysing diet of small herbivores: the efficiency of DNA barcoding coupled with high-throughput pyrosequencing for deciphering the composition of complex plant mixtures," Front Zool, 6:16 (2009).
Sommnerfeit et al., "Receptor interference groups of 20 retroviruses plating on human cells," Virol, 176:58-59 (1990).
Song et al., "c-Cbl acts as a mediator of Src-induced activation of the PI3K-Akt signal transduction pathway during TRAIL treatment," Cellular Signalling, 22(3):377-385 (2010).
Sosman et al., "A phase 2 trial of complete resection for stage IV melanoma: results of Southwest Oncology Group Clinical Trial S9430," Cancer, 117(20):4740-4706 (2011).
Speetjens et al., "Induction of p53-Specific Immunity by a p53 Synthetic Long Peptide Vaccine in Patients Treated for Metastatic Colorectal Cancer," Clin Cancer Res, 15(3):1086-1095 (2009).
Speiser et al., "Molecularly defined vaccines for cancer immunotherapy, and protective T cell immunity," Semin Immunol, 22(3):144-154 (2010).
Spencer et al., "Non-genetic origins of cell-to-cell variability in TRAIL-induced apoptosis," Nature, 459:428-432 (2009).
Spranger et al., "Up-regulation of PD-LI, IDO, and Tregs in the melanoma tumor microenvironment is driven by CD8+ T cells," Sci Transl Med, 5(200):200ra116 (2013).
Staehler et al., "An open label study to evaluate the safety and immunogenicity of the peptide based cancer vaccine IMA901," ASCO meeting 2007; Abstract No. 3017.
Stahl-Hennig et al., "Synthetic double-stranded RNAs are adjuvants for the induction of T helper 1 and humoral immune responses to human papillomavirus in rhesus macaques," PLoS pathogens, 5(4):e1000373 (2009).
Stover et al., "New Use of BCG for Recombinant Vaccines," Nature, 351(6326): 456-460 (1991).
Stransky et al., "The Mutational Landscape of Head and Neck Squamous Cell Carcinoma," Science, 333:1157-1160 (2011).
Subramanian et al., "Gene set enrichment analysis: a knowledge-based approach for interpreting genome-wide expression profiles," PNAS, 102:15545-15550 (2005).
Sullivan et al., "Expression and Characterization of Herpes Simplex Virus Type 1 (HSV-1) Glycoprotein G (gG) by Recombinant Vaccinia Virus: Neutralization of HSV-1 Infectivity with Anti-gG Antibody," Gen Vir, 68:2587-2598 (1987).
Suzuki et al., "A Novel Glycosylphosphatidyl Inositol-Anchored Protein on Human Leukocytes: A Possible Role for Regulation of Neutrophil Adherence and Migration," J Immunol, 162(7):4277-4284 (1999).
Sykulev et al., "Evidence that a Single Peptide-MHC Complex on a Target Cell Can Elicit a Cytolytic T Cell Response," Immunity, 4:565-571 (1996).
Tang et al., "The landscape of viral expression and host gene fusion and adaptation in human cancer," Nat Commun, 4:2513 (2013).
Tartaglia et al., "NYVAC: A highly attenuated strain of vaccinia virus," Virology, 188(1):217-232 (1992).
Ten Bosch et al., "Keeping Up With the Next Generation: Massively Parallel Sequencing in Clinical Diagnostics," J Mol Diagn, 10(6):484-492 (2008).

Teng et al., "A human TAPBP (TAPASIN)-related gene, TAPBP-R," Eur J Immunol, 32:1059-1068 (2002).
Testori et al., "Phase III comparison of vitespen, an autologous tumor-derived heat shock protein gp96 peptide complex vaccine, with physician's choice of treatment for stage IV melanoma: the C-100-21 Study Group," J Clin Oncol, 26(6):955-962 (2008).
Textor et al., "Human NK cells are alerted to induction of p53 in cancer cells by upregulation of the NKG2D ligands ULBPI and ULBP2," Cancer Res, 71:5998-6009 (2011).
Timp et al., "Cancer as a dysregulated epigenome allowing cellular growth advantage at the expense of the host," Nat Rev Cancer, 13:497-510 (2013).
Tjoa et al., "Follow-Up Evaluation of Prostate Cancer Patients Infused with Autologous Dendritic Cells Pulsed with PSMA Peptides," Prostate, 32(4): 272-278 (1997).
Topalian et al., "Survival, Durable Tumor Remission, and Long-Term Safety in Patients With Advanced Melanoma Receiving Nivolumab," J Clin Oncol, 32(10):1020-1030 (2014).
Tough et al., "Induction of bystander T cell proliferation by viruses and type I interferon in vivo," Science, 272(5270):1947-1950 (1996).
Tran et al., "Cancer Immunotherapy Based on Mutation-Specific CD4+ T Cells in a Patient with Epithelial Cancer," Science, 344(6184):641-645 (2014).
Trumpfheller et al., "Intensified and protective CD4+ T cell immunity in mice with anti-dendritic cell HIV gag fusion antibody vaccine," J Exp Med, 203(3):607-617 (2006).
Trumpfheller et al., "The microbial mimic poly IC induces durable and protective CD4+ T cell immunity together with a dendritic cell targeted vaccine," PNAS, 105(7):2574-2579 (2008).
Tucker et al., "Massively Parallel Sequencing: The Next Big Thing in Genetic Medicine," Am J Hum Genet, 85(2):142-154 (2009).
Uderhardt et al., "12/15-lipoxygenase orchestrates the clearance of apoptotic cells and maintains immunologic tolerance," Immunity, 36(5):834-846 (2012).
Ushijima et al., "Fidelity of the methylation pattern and its variation in the genome," Genome research, 13:868-874 (2005).
Uyttenhove et al., "Evidence for a tumoral immune resistance mechanism based on tryptophan degradation by indoleamine 2,3-di oxygenase," Nature medicine, 9:1269-1274 (2003).
Vaishampayan et al., "Active immunotherapy of metastatic melanoma with allogeneic melanoma lysates and interferon alpha," Clin Cancer Res, 8(12):3696-3701 (2002).
Van Elsas et al., "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," Journal of Experimental Medicine, 190(3):355-366 (1999).
Van Poelgeest et al., "HPV16 synthetic long peptide (HPV16-SLP) vaccination therapy of patients with advanced or recurrent HPV16-induced gynecological carcinoma, a phase II trial," J Transl Med, 11:88 (2013).
Van Rooij et al., "Tumor Exome Analysis Reveals Neoantigen-Specific T-Cell Reactivity in an 1pilimumab-Responsive Melanoma," Journal of Clinical Oncology, 31(32):e439-e442 (2013).
Verardi et al., "A vaccinia virus renaissance: new vaccine and immunotherapeutic uses after smallpox eradication," Human vaccines & immunotherapeutics, 8(7):961-970 (2012).
Vermeij et al., "Potentiation of a p53-SLP vaccine by cyclophosphamide in ovarian cancer: a single-arm phase II study," Int J Cancer, 131(5):E670-680 (2012).
Von Krempelhuber et al., "A randomized, double-blind, dose-finding Phase II study to evaluate immunogenicity and safety of the third generation smallpox vaccine candidate IMVAMUNE®," Vaccine, 28(5):1209-1216 (2010).
Von Mehren et al., "Pilot study of a dual gene recombinant avipox vaccine containing both carcinoembryonic antige (CEA.) and B7.1 transgenes in patients with, recurrent CEA-expressing adenocarcinomas," Clin Cancer Res, 6:2219-28 (2000).
Wahl et al., "[43] Molecular hybridization of immobilized nucleic acids: Theoretical concepts and practical considerations," Methods in enzymology, Academic Press, 152:399-407 (1987).

(56) References Cited

OTHER PUBLICATIONS

Walter et al., "Multipeptide immune response to cancer vaccine IMA901 after single-dose cyclophosphamide associates with longer patient survival," Nature medicine, 18(8):1254 (2012).
Wang et al., "Role of protein kinase CK2 in the regulation of tumor necrosis factor-related apoptosis inducing ligand-induced apoptosis in prostate cancer cells," Cancer research, 66:2242-2249 (2006).
Wang et al., "SF3B1 and other novel cancer genes in chronic lymphocytic leukemia," N Engl J Med, 365:2497-2506 (2011).
Wang et al., "Widespread plasticity in CTCF occupancy linked to DNA methylation," Genome Res, 22:1680-1688 (2012).
Watson et al., "SHP-1: the next checkpoint target for cancer immunotherapy?," Biochem Soc Trans, 44(2):356-362 (2016).
Weber et al., "Assembly of Designer TAL Effectors by Golden Gate Cloning," PLoS ONE, 6:e19722 (2001).
Webster et al., "Enhanced T cell-mediated protection against malaria in human challenges by using the recombinant poxviruses FP9 and modified vaccinia virus Ankara," Proceedings of the National Academy of Sciences, 102(13):4836-4841 (2005).
Weiner et al., "Genetic vaccines," Scientific American, 281(1):50-57 (1999).
Welters et al., "Induction of tumor-specific CD4+ and CD8+ T-cell immunity in cervical cancer patients by a human papillomavirus type 16 E6 and E7 long peptides vaccine," Clinical cancer research, 14(1):178-187 (2008).
Welters et al., "Success or failure of vaccination for HPV16-positive vulvar lesions correlates with kinetics and phenotype of induced T-cell responses," PNAS, 107(26):11895-11899 (2010).
Weyer et al., "Generation and evaluation of a recombinant modified vaccinia virus Ankara vaccine for rabies," Vaccine, 25(21):4213-4222 (2007).
Weyer et al., "Poxvirus-vectored vaccines for rabies-a review," Vaccine, 27(51):7198-7201 (2009).
Wheatley et al., "Does adjuvant interferon-alpha for high-risk melanoma provide a worthwhile benefit?A meta-analysis of the randomised trials," Cancer treatment reviews, 29(4):241-252 (2003).
Whelan et al., "Safety and immunogenicity of boosting BCG vaccinated subjects with BCG: comparison with boosting with a new TB vaccine, MVA85A," PLoS ONE, 4(6):e5934 (2009).
Widschwendter et al., "Epigenetic stem cell signature in cancer," Nat Genet, 39:157-158 (2007).
Wierda et al., "Multivariable model for time to first treatment in patients with chronic lymphocytic leukemia," J Clin Oncol, 29:4088-4095 (2011).
Wiktor et al., "Protection from rabies by a vaccinia virus recombinant containing the rabies virus glycoprotein gene," Proceedings of the National Academy of Sciences, 81(22):7194-7198 (1984).
Wilson et al., "Formation of infectious hybrid virions with gibbon ape leukemia virus and human T-cell leukemia virus retroviral envelope glycoproteins and the gag and pol proteins of Moloney murine leukemia virus," Journal of virology, 63(5):2374-2378 (1989).
Winzeler et al., "Functional characterization of the *S. cerevisiae* genome by gene deletion and parallel analysis," science, 285(5429):901-906 (1999).
Wolchok et al., "Nivolumab plus ipilimumab in advanced melanoma," N Engl J Med, 369(2):122-133 (2013).
Wolff et al., "Direct Gene Transfer into Mouse Muscice in Vivo," Science, 247(4949):1465-1468 (1990).
Wong et al., "Module map of stem cell genes guides creation of epithelial cancer stem cells," Cell Stem Cell, 2:333-344 (2008).

Woodfine et al., "Quantitative analysis of DNA methylation at all human imprinted regions reveals preservation of epigenetic stability in adult somatic tissue," Epigenetics & chromatin, 4:1 (2011).
Woyach et al., "Resistance mechanisms for the Bruton's tyrosine kinase inhibitor ibrutinib," The New England journal of medicine, 370:2286-94 (2014).
Wyatt et al., "Marker rescue of the host range restriction defects of modified vaccinia virus Ankara," Virology, 251(2):334-342 (1998).
Wyatt et al., "Multiprotein HIV type 1 clade B DNA and MVA vaccines: construction, expression, and immunogenicity in rodents of the MVA component," AIDS research and human retroviruses, 20(6):645-653 (2004).
Xi et al., "BSMAP: whole genome bisulfite sequence MAPping program," BMC bioinformatics, 10:232 (2009).
Xie et al., "Stepwise reprogramming of B cells into macrophages," Cell, 117(5):663-676 (2004).
Xu et al., "Design of 240,000 orthogonal 25mer DNA barcode probes," Proceedings of the National Academy of Sciences, pnas-0812506106 (2009).
Yan et al., "PBAF chromatin-remodeling complex requires a novel specificity subunit, BAF200, to regulate expression of selective interferon-responsive genes," Genes & development, 19(14):1662-1667 (2005).
Yang et al. "CML66, a broadly immunogenic tumor antigen, elicits a humoral immune response associated with remission of chronic myelogenous leukemia," PNAS, 98(13):7492-7497 (2001).
Yilma, "Prospects for the total eradication of rinderpest," Vaccine, 7(6):484-485 (1989).
Yoshihara et al., Inferring tumour purity and stromal and immune cell admixture from expression data,: Nature communications 4:2612 (2013).
Young et al., "Resurrection of endogenous retroviruses in antibody-deficient mice," Nature, 491(7426):774 (2012).
Yu et al., "Nucleic acid-sensing Toll-like receptors are essential for the control of endogenous retrovirus viremia and ERV-induced tumors," Immunity, 37(5):867-879 (2012).
Yuille et al., "TCL1 is activated by chromosomal rearrangement or by hypomethylation," Genes, Chromosomes and Cancer, 30(4):336-341 (2001).
Zeestraten et al., "Addition of interferon-alpha to the p53-SLP(R) vaccine results in increased production of interferon-gamma in vaccinated colorectal cancer patients: a phase I/11 clinical trial," Int J Cancer, 132(7):1581-1591 (2013).
Zhang et al., "Machine learning competition in immunology-prediction of HLA class I binding peptides," J Immunol Methods 374:1-4 (2009).
Zhou et al., "A hypermorphic missense mutation in PLCG2, encoding phospholipase Cgamma2, causes a dominantly inherited autoinflammatory disease with immunodeficiency," Am J Hum Genet, 91:713-20 (2012).
Zhou et al., "Long-term outcome after haploidentical stem cell transplant and infusion of T cells expressing the inducible caspase 9 safety transgene," Blood, 123(25):3895-3905 (2014).
Zhu et al., "Toll like receptor-3 ligand poly-ICLC promotes the efficacy of peripheral vaccinations with tumor antigen-derived peptide epitopes in murine CNS tumor models," Journal of translational medicine, 5:10 (2007).
Ziller et al., "Charting a dynamic DNA methylation landscape of the human genome," Nature, 500:477-481 (2013).
Zitvogel et al., "Immunological aspects of cancer chemotherapy," Nature reviews immunology, 8:59 (2008).
Zorn et al., "A natural cytotoxic T cell response in a spontaneously regressing human melanoma targets a neoantigen resulting from a somatic point mutation," Eur J Immunol, 29(2):592-601 (1999).
Zwaveling et al., "Established human papillomavirus type 16-expressing tumors are effectively eradicated following vaccination with long peptides," J Immunol, 169(1):350-358 (2002).

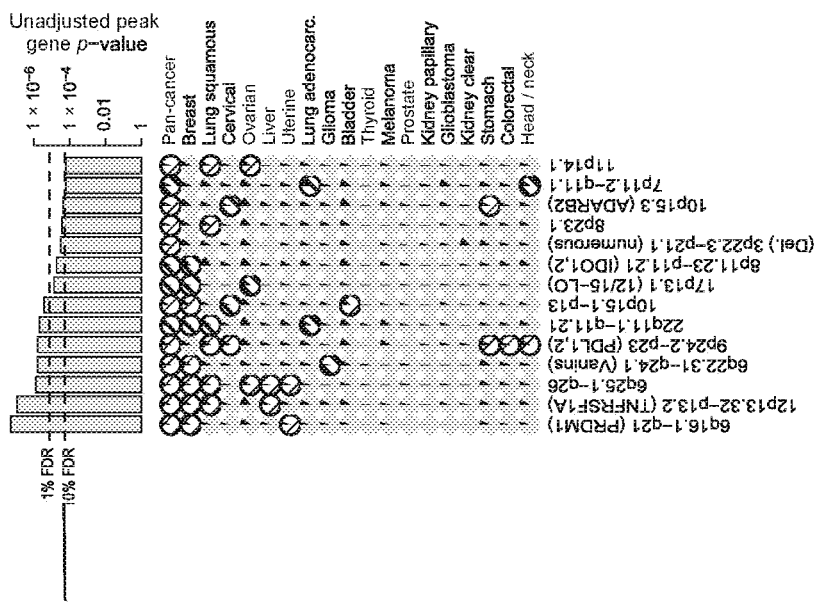
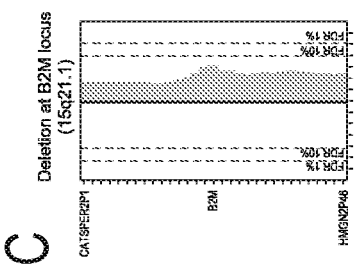
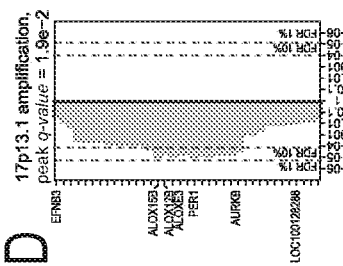
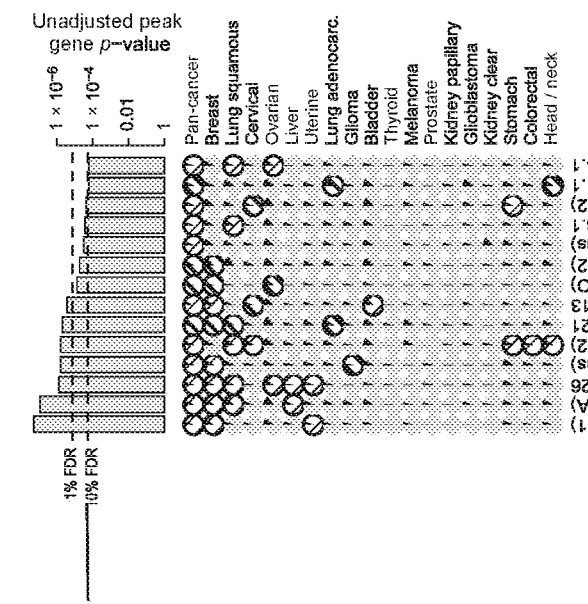
FIG. 6A  FIG. 6B  FIG. 6C  FIG. 6D  FIG. 6E

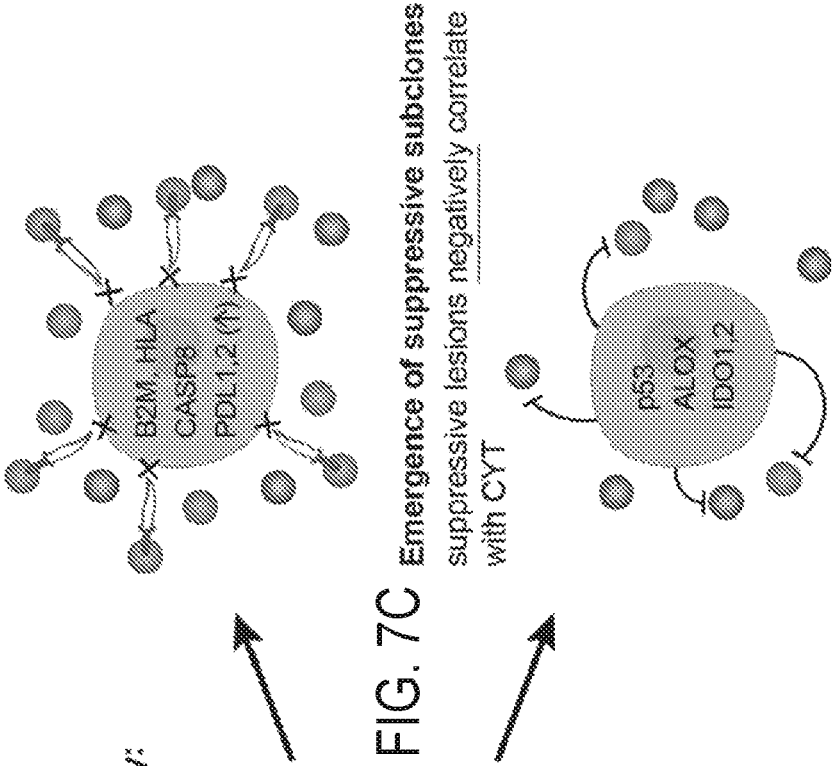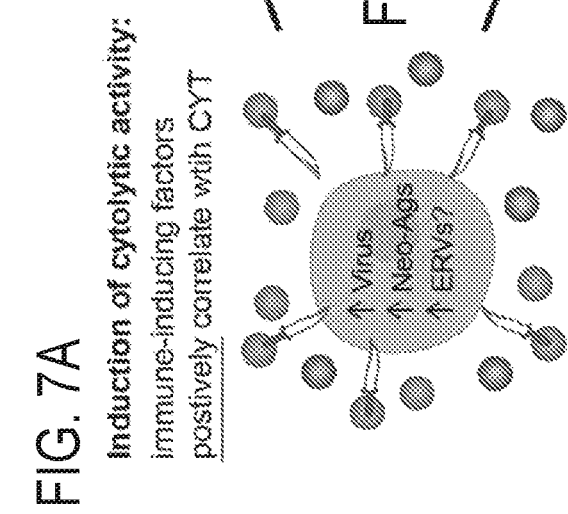

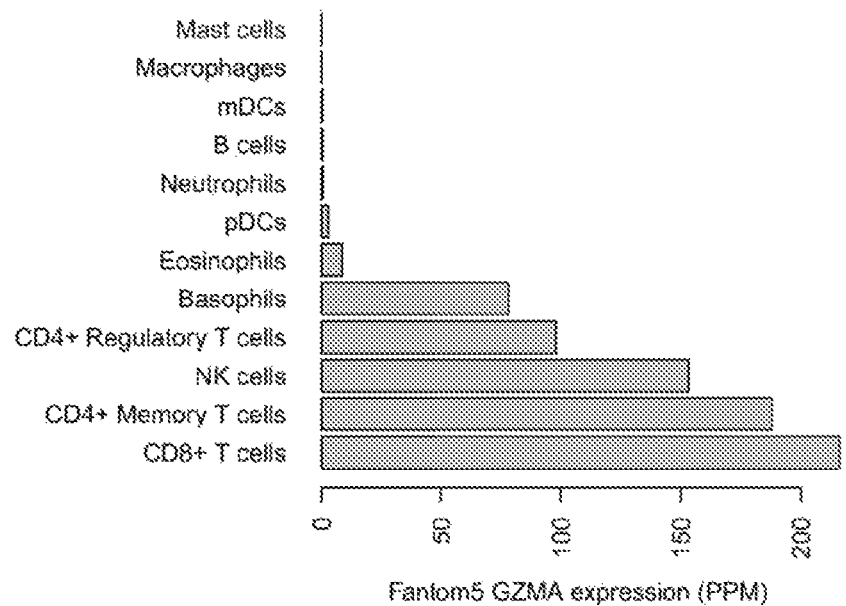
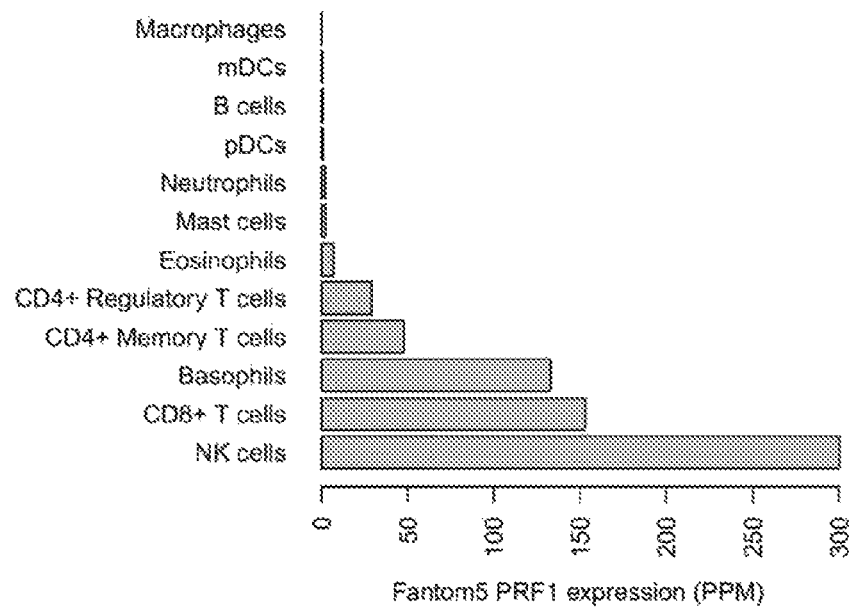
FIG. 8D

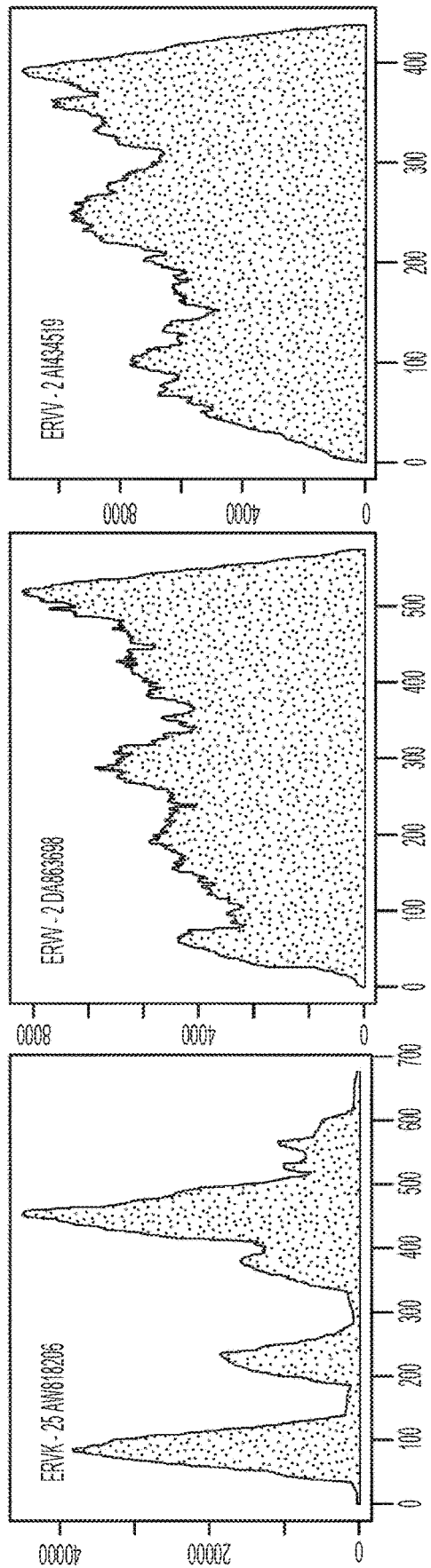
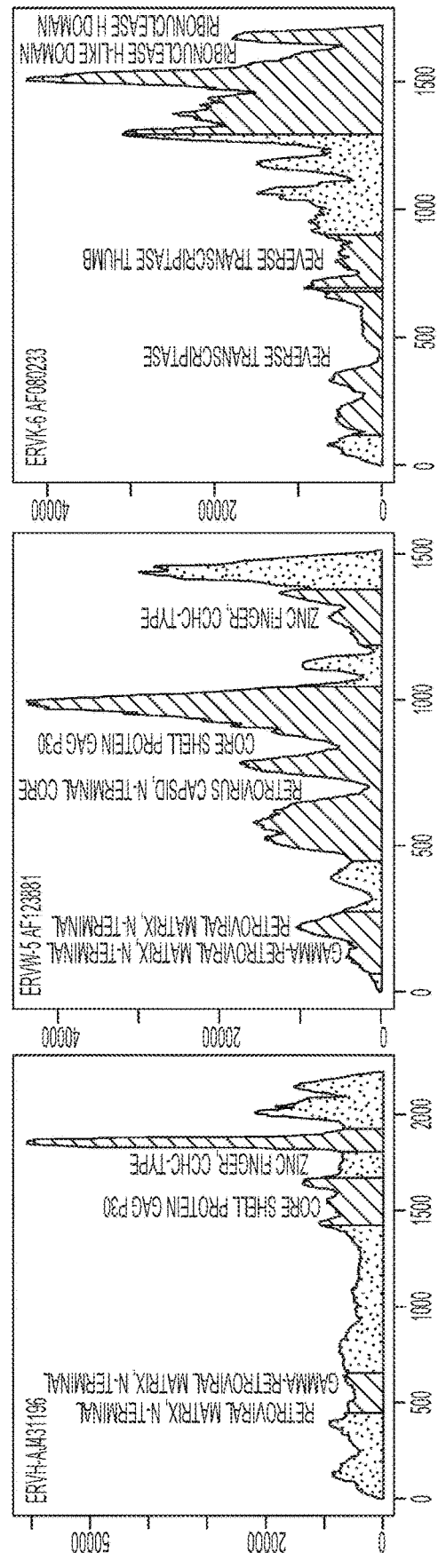
FIG. 11F
CONTINUED

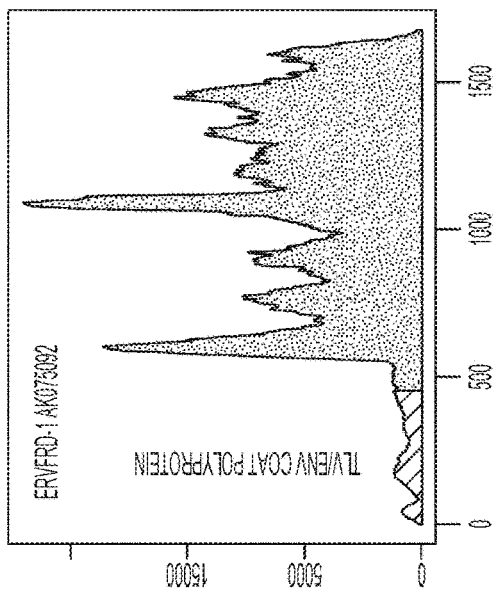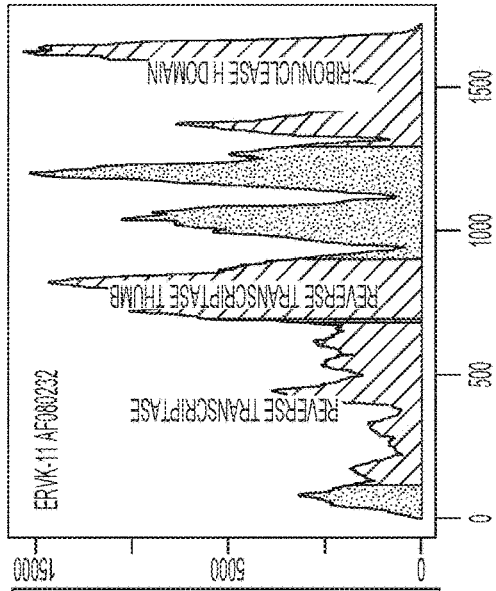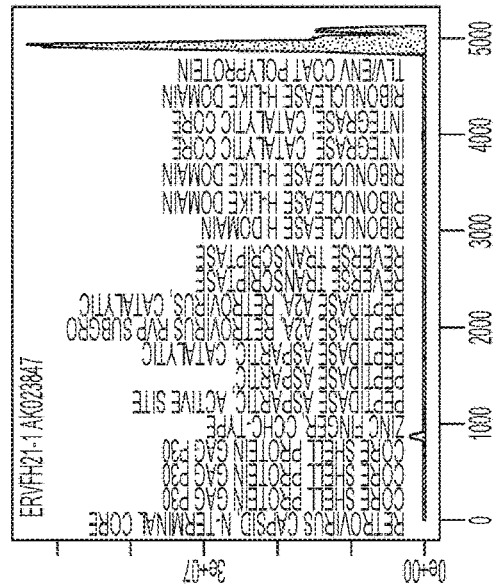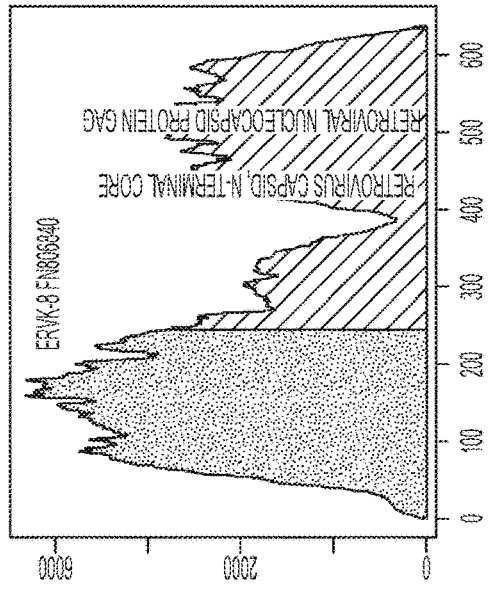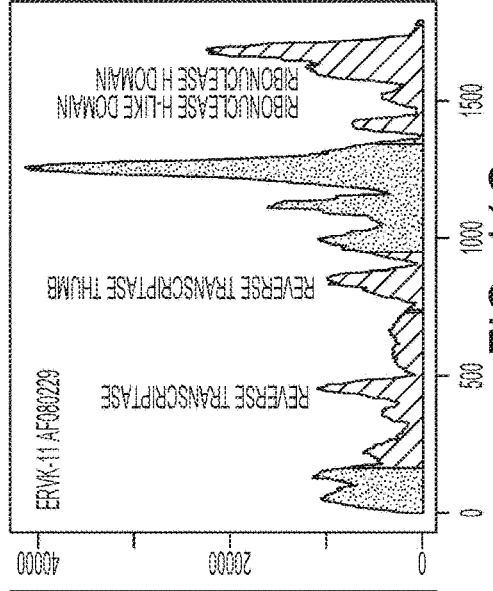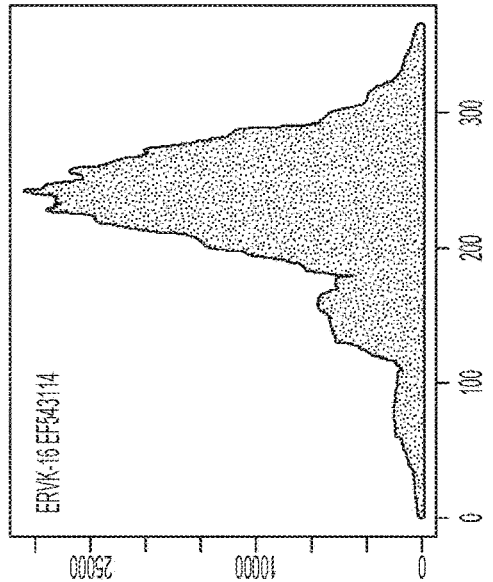
FIG. 11G CONTINUED

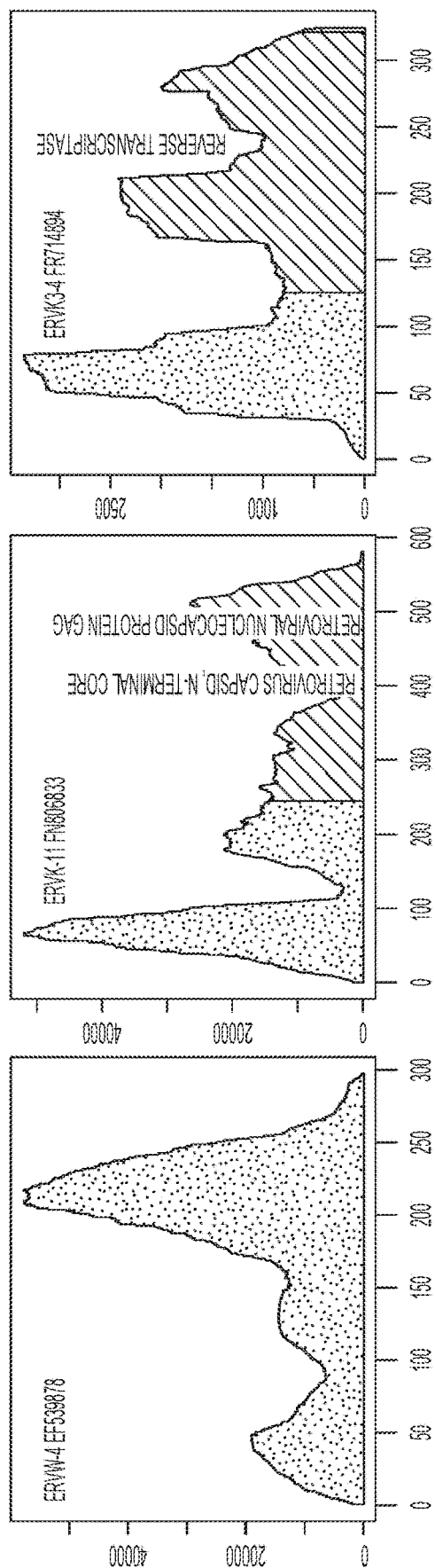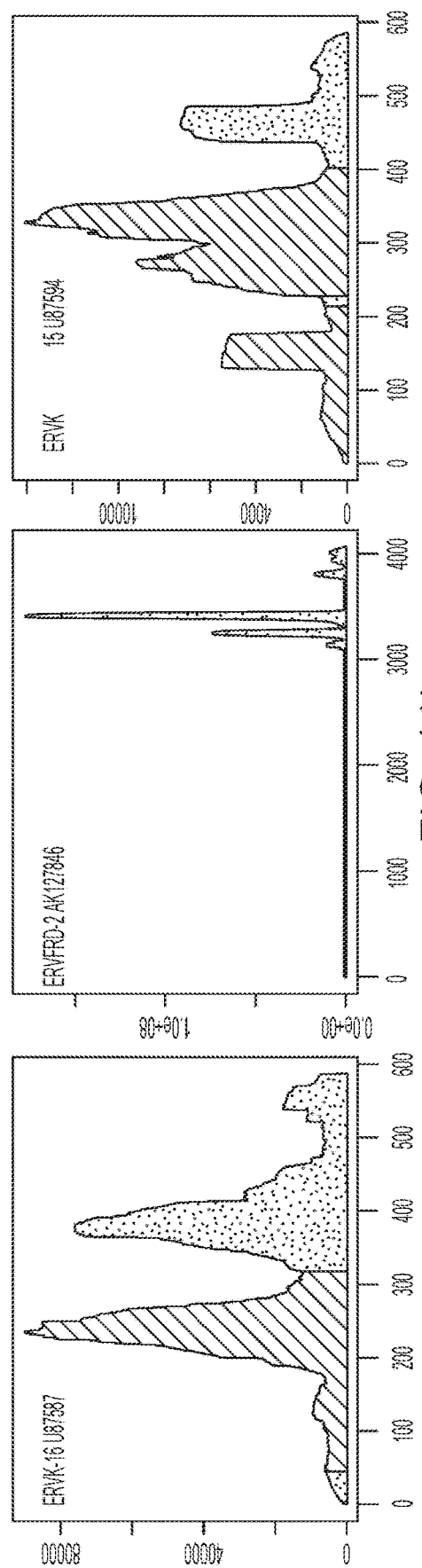
FIG. 11I

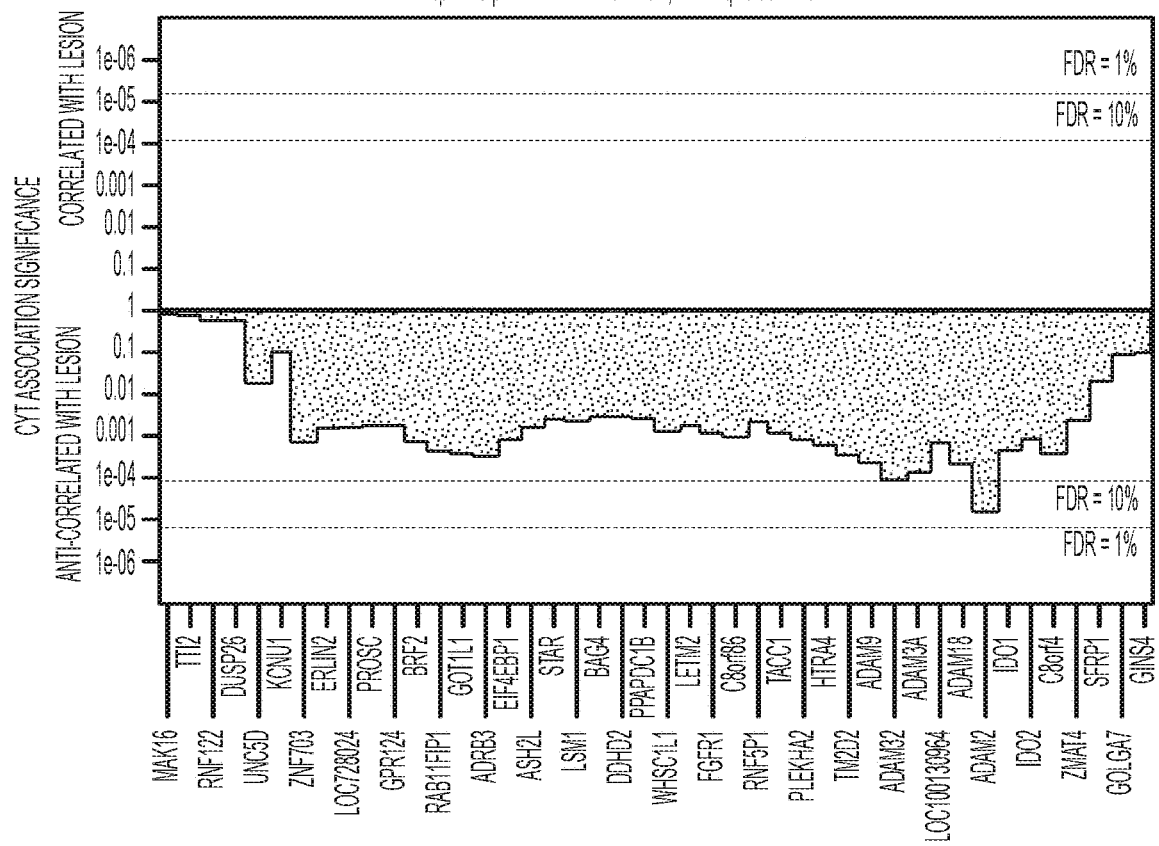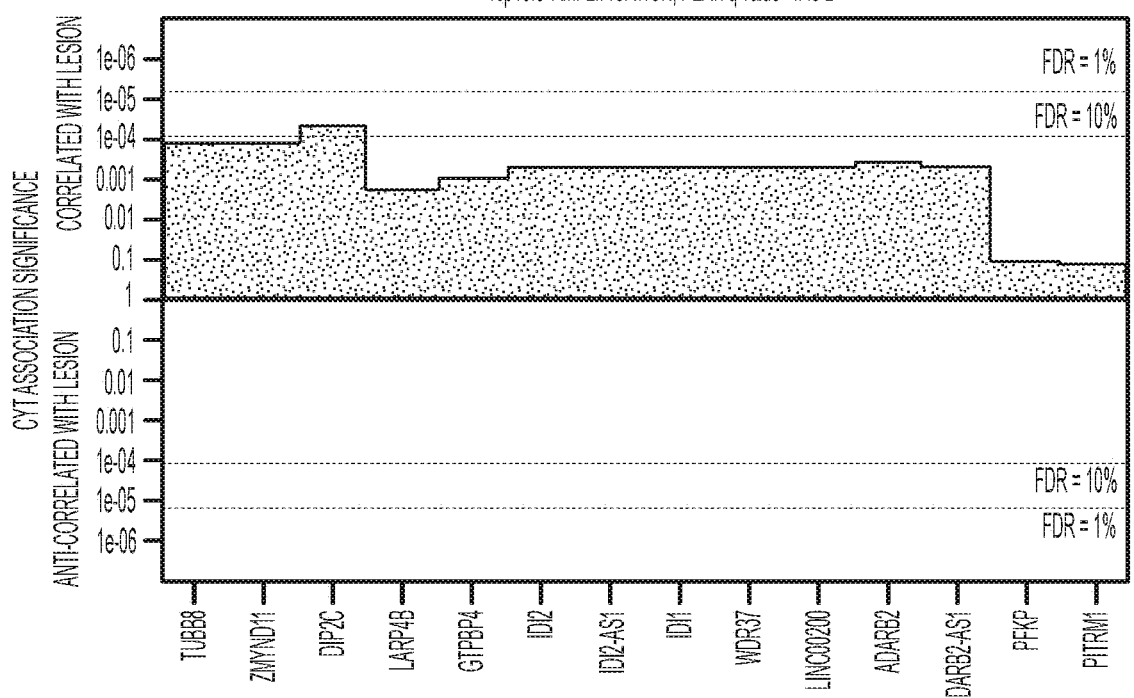
FIG. 13A
CONTINUED

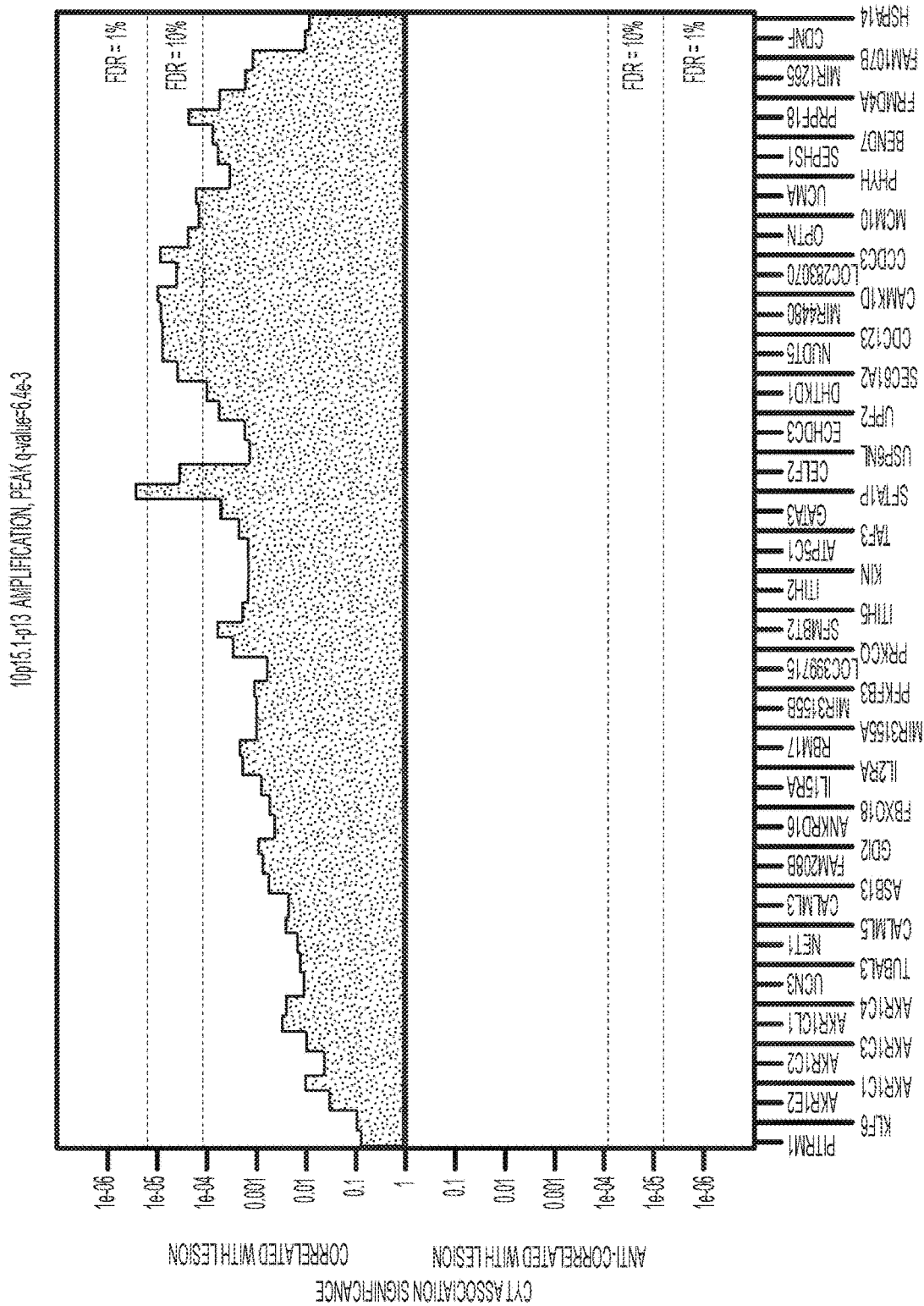

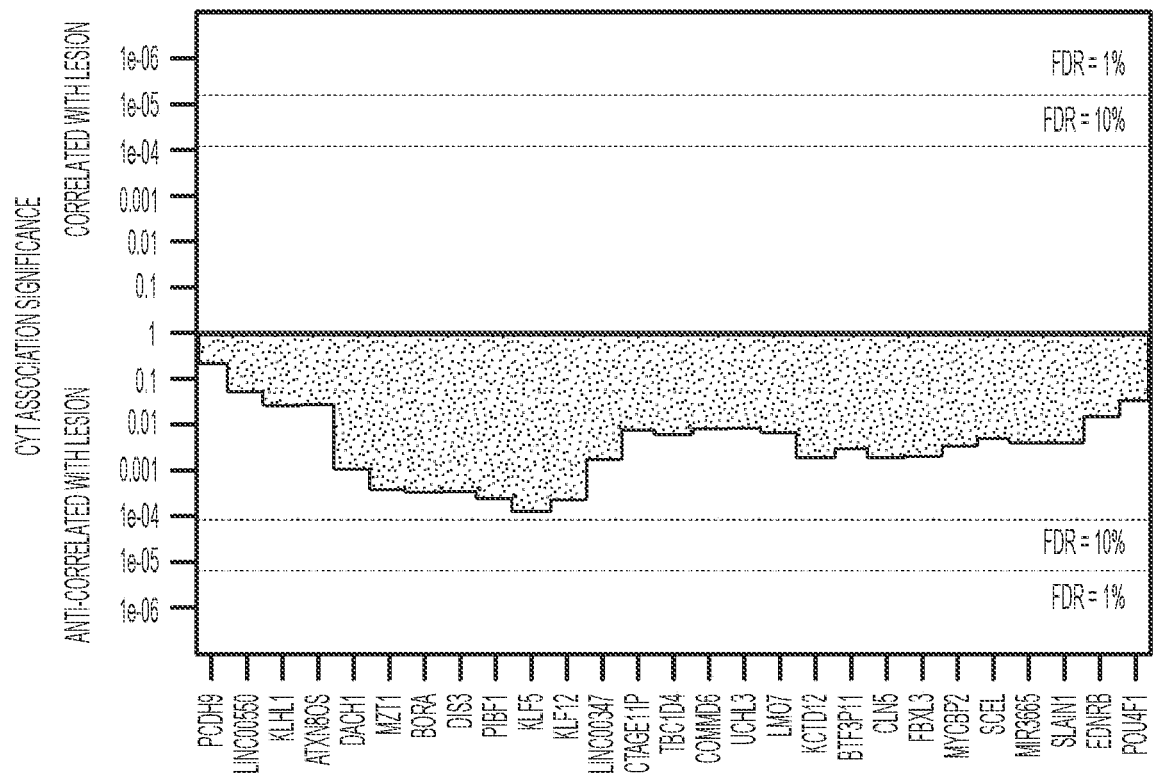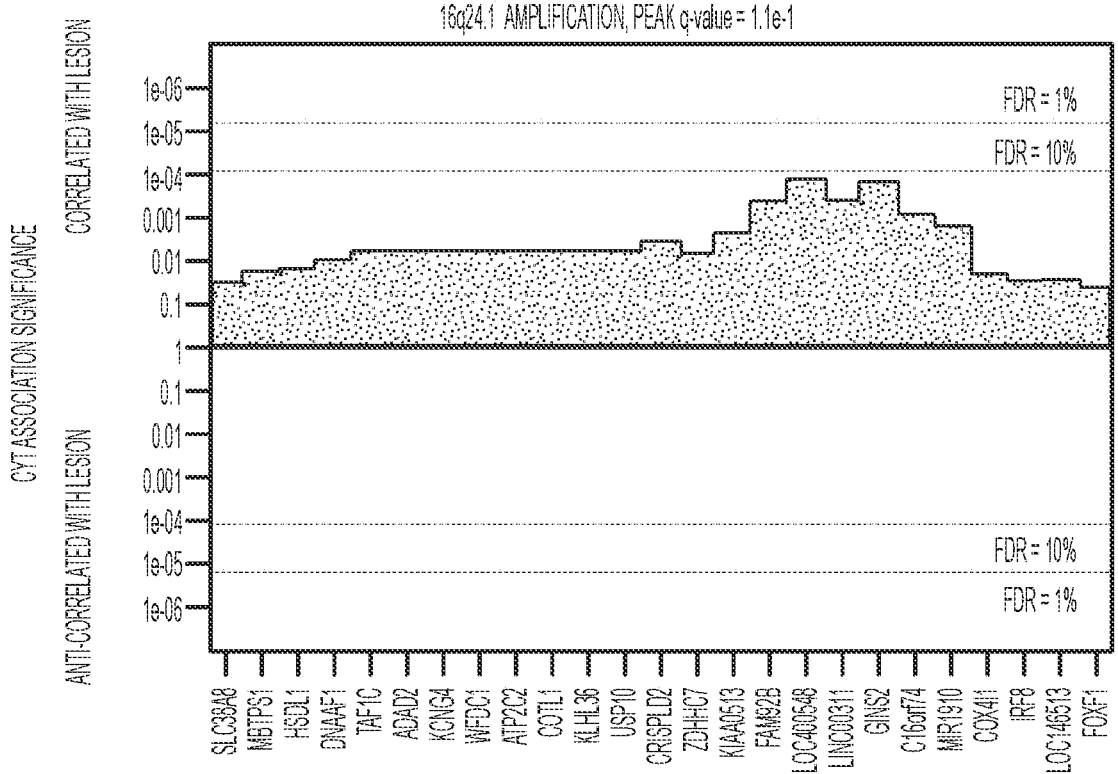
FIG. 13B
CONTINUED

FIG. 13B CONTINUED

MOLECULAR BIOMARKERS FOR CANCER IMMUNOTHERAPY

RELATED APPLICATIONS AND INCORPORATION BY REFERENCE

This application is divisional of U.S. application Ser. No. 15/537,839, which is a national stage filing under 35 U.S.C. § 371 of PCT International Application No. PCT/US2015/067143, filed Dec. 21, 2015, which claims benefit of and priority to U.S. provisional patent application Ser. No. 62/124,473, filed Dec. 19, 2014. The entire contents of these applications are incorporated herein by reference in their entirety.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under Grant No. T32 HG002295 awarded by the National Institutes of Health. The government has certain rights in the invention.

FIELD OF THE INVENTION

The present invention relates to methods for the diagnosis and treatment of neoplasia, e.g. tumors, and in particular for identifying and treating subjects who are responsive to immunotherapy.

BACKGROUND OF THE INVENTION

With the recent success of checkpoint blockades (against CTLA4 or PD1/PDL1) and adoptive T cell therapy in durable reduction of tumor burden in humans (1, 2), there is an increasingly urgent need to improve the efficacy of these therapies as well as develop new therapies for non-responding or resistant tumors. While mouse modeling has been very fruitful in this area, little is known about the tumor-immune interactions occurring in human tumors.

High-dimensional datasets—such as The Cancer Genome Atlas (TCGA) that include genome-wide DNA sequencing, RNA sequencing and copy number profiles—have made it possible to dissect the factors driving malignancy with unprecedented depth (3-8). Nonetheless, the intersection between the genomic landscape of cancer and anti-tumor immunity has not been systematically surveyed. While no direct in vivo quantification of tumor cell killing is currently available in humans, much can be inferred from expression data in biopsies because they contain the tumor with its microenvironment. This provides an opportunity to integrate immune phenotype and tumor genomics on an unprecedented scale and to generate new therapeutic and diagnostic methods.

Citation or identification of any document in this application is not an admission that such document is available as prior art to the present invention.

SUMMARY OF THE INVENTION

In one aspect the invention provides a personalized treatment for a patient in need thereof comprising (a) (i) determining cytolytic activity in a tumor from the subject; and/or (ii) determining genetic alterations associated with cytolytic activity in the tumor; and (b) administering an immunotherapeutic agent to the subject if (i) cytolytic activity is detected in the tumor and/or (ii) genetic alterations that are associated with induction or suppression to cytolytic activity are found in the tumor.

In one embodiment, the cytolytic activity is determined by assaying the expression of granzyme A (GZMA) and perforin (PRF1). For instance, the cytolytic activity may be determined by (a) sequencing RNA expressed in the tumour sample, (b) calculating the log-average of the transcript levels of granzyme A (GZMA) and perforin (PRF1), and (c) assigning a cytolytic activity (CYT) score to the tumour based on the log average calculated in (b).

In some embodiments, the genetic alteration is a mutation in a gene selected from the group consisting of CASP8, B2M, PIK3CA, SMC1A, ARID5B, TET2, ALPK2, COL5A1, TP53, DNER, NCOR1, MORC4, CIC, IRF6, MYOCD, ANKLE1, CNKSR1, NF1, SOS1, ARID2, CUL4B, DDX3X, FUBP1, TCP11L2, HLA-A, B or C, CSNK2A1, MET and ASXL1.

In one embodiment, the genetic alteration is the copy number gain, excluding whole-chromosome events, of any of the following chromosomal bands: 6q16.1-q21, 6q22.31-q24.1, 6q25.1-q26, 7p11.2-q11.1, 8p23.1, 8p11.23-p11.21 (containing IDO1, IDO2), 9p24.2-p23 (containing PDL1, PDL2), 10p15.3, 10p15.1-p13, 11p14.1, 12p13.32-p13.2, 17p13.1 (containing ALOX12B, ALOX15B), and 22q11.1-q11.21.

In some embodiments, wherein the tumor is head and neck cancer, colon cancer, stomach cancer, lung adenocarcinoma, lung squamous cell carcinoma, uterine cancer, glioma, cervical cancer, breast cancer or bladder cancer.

In one embodiment, wherein the genetic alteration is a mutation in CASP8. In this embodiment, the tumor is preferably selected from the group consisting of head and neck cancer, colorectal cancer, lung squamous cell carcinoma and uterine cancer.

In another embodiment, wherein the genetic alteration is a mutation in PIK3CA. In this embodiment, the tumor is preferably stomach cancer.

In another embodiment, the genetic alteration is a mutation in B2M. In this embodiment, the tumor is preferably uterine cancer, breast cancer, colorectal cancer or stomach cancer.

In another embodiment, the genetic alteration is a mutation in HLA-A, B or C. In this embodiment, the tumor is preferably colorectal cancer, head and neck cancer, uterine cancer, stomach cancer or cervical cancer.

In another embodiment, wherein the genetic alteration is a mutation in CNKSR1, MET or CSNK2A1.

In one embodiment, wherein the genetic alteration is a copy number alteration. For instance, the genetic alternation may be an amplification of a gene selected from PDL-1 and PDL-2. In this embodiment, the tumor is preferably lung squamous cell carcinoma, head and neck cancer or colorectal cancer.

In another embodiment, the genetic alteration is an amplification of a gene selected from IDO1, IDO2, ALOX12B and ALOX15B. In this embodiment, the tumor is preferably breast cancer or ovarian cancer.

In one embodiment, the genetic alteration is the copy number gain, excluding whole-chromosome events, of any of the following chromosomal bands: 6q16.1-q21, 6q22.31-q24.1, 6q25.1-q26, 7p11.2-q11.1, 8p23.1, 8p11.23-p11.21 (containing IDO1, IDO2), 9p24.2-p23 (containing PDL1, PDL2), 10p15.3, 10p15.1-p13, 11p14.1, 12p13.32-p13.2, 17p13.1 (containing ALOX12B, ALOX15B), and 22q11.1-q11.21.

In further embodiments, the genetic alterations permit cytolytic cell death and antigen presentation.

In another embodiment, the genetic alteration comprises a plurality of neoantigen mutations. For instance, at least 2, 3, 4, 5, 6, 7, 8, 9, 10, 15 or 20 neoantigen mutations may be present in the tumor. Preferably, the patient in need thereof has at least 10 neoantigen mutations. In this embodiment, the tumor is preferably selected from the group consisting of uterine cancer, breast cancer, stomach cancer, cervical cancer, colorectal cancer and lung adenocarcinoma.

In another embodiment, wherein cytolytic activity in the tumor is associated with virus infection. In one such embodiment, the virus is HPV. In this embodiment, the tumor is preferably cervical cancer, head and neck cancer, bladder cancer, kidney clear cell cancer, colorectal cancer, glioma, lung squamous cell cancer or uterine cancer. In another embodiment, the virus is EBV. In this embodiment, the tumor is preferably stomach cancer. In another embodiment, cytolytic activity in the tumor is associated with expression of one or more endogenous retrovirus genes.

In one embodiment, the immunotherapeutic agent comprises an agent that stimulates the patients preexisting immune response.

In one embodiment, the immunotherapeutic agent comprises a neoplasia vaccine or immunogenic composition. For instance, the immunotherapeutic agent may comprise at least two, at least three, at least four or at least five neoantigenic peptides.

In another embodiment, the immunotherapeutic agent comprises at least one checkpoint inhibitor. For instance, the checkpoint inhibitor may be an inhibitor of the programmed death-1 (PD-1) pathway, e.g. an anti-PD1 antibody such as nivolumab. In another embodiment, the checkpoint inhibitor is an anti-cytotoxic T-lymphocyte-associated antigen 4 (CTLA4) antibody, e.g. ipilimumab or tremelimumab.

In another aspect, the invention provides a method for selecting subjects suffering from cancer for immunotherapy, comprising: (a) (i) determining cytolytic activity in a tumor from the subject; and/or (ii) determining genetic alterations associated with cytolytic activity in the tumor; and (b) selecting a subject for immunotherapy if (i) cytolytic activity is detected in the tumor and/or (ii) a genetic alteration associated with induction of cytolytic activity, tumor resistance to cytolytic activity and/or suppression of cytolytic activity is detected in the tumor.

In one embodiment, the immunotherapy comprises administration of an immunotherapeutic agent selected from a neoplasia vaccine or immunogenic composition and a checkpoint inhibitor. For instance, the immunotherapeutic agent may comprise at least two, at least three, at least four or at least five neoantigenic peptides.

In some embodiments, the genetic alteration is a mutation in a gene selected from the group consisting of CASP8, B2M, PIK3CA, SMC1A, ARID5B, TET2, ALPK2, COL5A1, TP53, DNER, NCOR1, MORC4, CIC, IRF6, MYOCD, ANKLE1, CNKSR1, NF1, SOS1, ARID2, CUL4B, DDX3X, FUBP1, TCP11L2, HLA-A, B or C, CSNK2A1, MET and ASXL1.

In another embodiment, the genetic alteration is the copy number gain, excluding whole-chromosome events, of any of the following chromosomal bands: 6q16.1-q21, 6q22.31-q24.1, 6q25.1-q26, 7p11.2-q11.1, 8p23.1, 8p11.23-p11.21 (containing IDO1, IDO2), 9p24.2-p23 (containing PDL1, PDL2), 10p15.3, 10p15.1-p13, 11p14.1, 12p13.32-p13.2, 17p13.1 (containing ALOX12B, ALOX15B), and 22q11.1-q11.21.

In some embodiments, the tumor is head and neck cancer, colon cancer, stomach cancer, lung adenocarcinoma, lung squamous cell carcinoma, uterine cancer, glioma, cervical cancer, breast cancer or bladder cancer.

In a further aspect, the invention provides a method for determining cytolytic activity in a tumor, comprising (a) measuring expression levels of granzyme A (GZMA) and perforin (PRF1) in a sample from the tumor, and (b) assigning a cytolytic activity (CYT) score to the tumor based on the expression levels obtained in (a).

In one embodiment, step (a) comprises sequencing RNA expressed in the tumor sample. In another embodiment, step (b) comprises (i) calculating the log-average of the transcript levels of granzyme A (GZMA) and perforin (PRF1), and (ii) assigning a cytolytic activity (CYT) score to the tumor based on the log average calculated in (i). In a preferred embodiment cytolytic activity is expressed as transcripts per million (TPM).

In one embodiment subjects suffering from cancer are selected for immunotherapy by comparing TPM to a median value for the tumor. Subjects in need thereof may be selected if a TPM value is determined to be at least fifty-fold, or twenty-fold, or ten-fold, or five-fold greater than the median value observed among patients diagnosed with the same histological cancer type, preferably at least two fold. In one embodiment median values for cytolytic activity for different patient populations may be: 28.0 TPM, kidney clear cell cancer; 5.9 TPM, kidney papillary cell cancer; 14.7 TPM, lung adenocarcinoma; 13.6 TPM, lung squamous cell carcinoma; 13.6 TPM, cervical cancer; 6.3 TPM, colorectal cancer; 11.5 TPM; stomach cancer; 11.0 TPM, head and neck cancer; 6.9 TPM, uterine cancer; 5.1 TPM, bladder cancer; 5.7 TPM, breast cancer; 5.6 TPM, melanoma; 4.3 TPM, thyroid cancer; 4.0 TPM, ovarian cancer, 3.3 TPM, prostate cancer, 3.5 TPM, glioblastoma, and 0.7 TPM, low grade glioma.

In another aspect the invention provides a personalized cancer treatment for a patient in need thereof comprising: (a) (i) determining neoantigen mutations in tumor, which are not present in non-tumor tissue from the patient; and/or (ii) detecting genetic alterations associated with cytolytic activity in the tumor; and administering an immunotherapy if (i) neoantigen mutations detected in the tumor are greater than a threshold value (ii) a genetic alteration associated with induction of cytolytic activity, tumor resistance to cytolytic activity and/or suppression of cytolytic activity is detected in the tumor.

In one embodiment, the threshold value for neoantigen mutations may be at least 2, 3, 4, 5, 6, 7, 8, 9, 10, 15, 20, or 50 neoantigen mutations. Preferably, the patient in need thereof has greater than at least 10 neoantigen mutations.

In another aspect the invention provides a personalized cancer treatment for a patient in need thereof comprising: (a) (i) determining tumor specific DNA/RNA sequence variants in tumor tissue, which are not present in non-tumor tissue from the patient; and/or (ii) detecting genetic alterations associated with cytolytic activity in the tumor; and administering an immunotherapy if (i) tumor specific DNA/RNA sequence variants detected in the tumor are greater than a threshold value and/or (ii) a genetic alteration associated with induction of cytolytic activity, tumor resistance to cytolytic activity and/or suppression of cytolytic activity is detected in the tumor.

Tumor specific DNA/RNA sequence variants may be defined as 1-3 nucleotide tumor-specific DNA sequence variants as described herein. These tumor specific DNA/RNA sequence variants may be defined as non-silent mutations. These sequence variants may be quantified by sequencing tumor and normal samples from the same patient. The non-silent mutations may be sequence variants that are not known population variants from the 1000 Genomes Project. The non-silent mutations may be sequence variants that are not variants predicted to have no effect on protein sequence. The non-silent mutations may be sequence variants that are not known population variants from the 1000 Genomes Project and that are not variants predicted to have no effect on protein sequence. In an embodiment the number of tumor-specific DNA sequence variants exceeds a threshold of 50, of 100, preferably of 200.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

(B) Spearman-rank correlations between CYT and ERV expression. Grey squares indicate non-significant association (unadjusted p>0.05) and blank squares indicate no over-expression of the given ERV in the given tumor type (expression strictly below the normal tissue maximum).

Figure 5A:
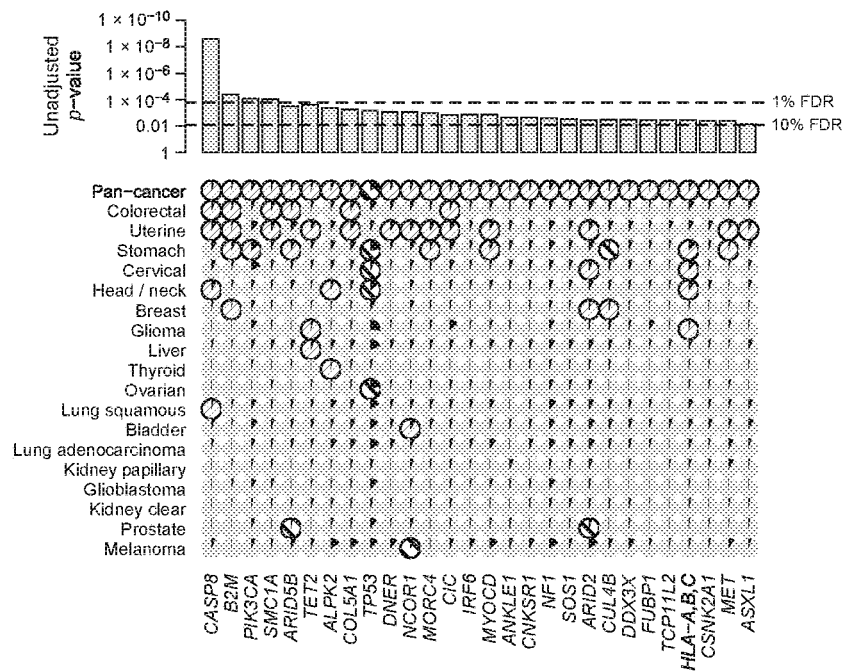
Figure 5B:
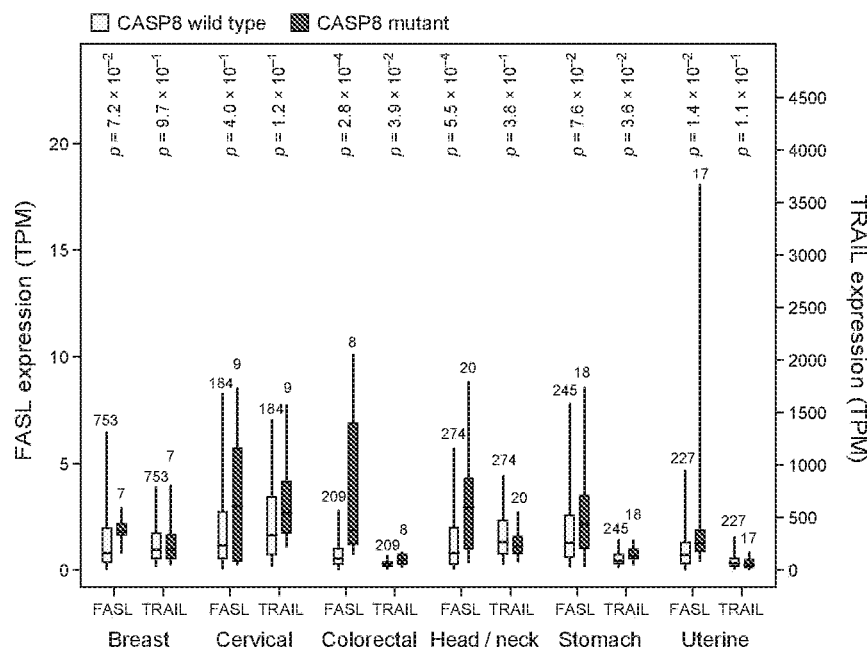

FIG. 5A-5B Gene mutations associated with high or low immune cytolytic activity. (A) Only genes showing pan-cancer significance (adj. p<0.1, red for positive, blue for negative and grey for non-significant association) for non-silent mutation association with CYT are shown in top row. Additional rows, clustered by similarity, show independent significant (unadjusted p<0.05) enrichment upon sub-analysis. The black wedges represent the share of samples exhibiting mutation. Bar plot indicates unadjusted pan-cancer p-values for mutational association with CYT, dashed lines indicating thresholds yielding 1% and 10% FDRs. (B) Association between CASP8 mutational status and FASLG (left axis) and TRAIL (right axis) gene expression (TPM) for tumor types demonstrating at least 5 instances of nonsynonymous CASP8 mutation. Light and dark bars correspond to wild type and (nonsynonymous) mutant samples, respectively. Box plots as in FIG. 1. P-values are calculated by Wilcoxon rank-sum test.

FIG. 6A-6E Amplifications and deletions are associated with cytolytic activity in tumors. (A) The significance of association between CYT and amplification (orange) and between CYT and deletion (green) for all genic loci. Upward lines show unadjusted p-values for instances in which the lesion was positively associated with CYT, and downward lines show unadjusted p-values for instances in which the lesion was negatively associated with CYT. Dotted lines represent the significance cutoff yielding 1% and 10% FDRs (and also appear in parts B-E). Labels on the right side mark events significant at the 10% FDR, plus B2M. Potential driver genes appear in parentheses. (B) Locus zoom on the 9p24.2-p23 amplification, each bar corresponding to a single gene. Labeled genes include those with driver potential or those on the locus boundary. (C) Locus zoom on the region containing B2M, which was not genome-wide significant. (D) Locus zoom on the 17p13.1 amplification. (E) Significant associations between CNAs and CYT on the pan-cancer and cancer-specific level (as in FIG. 5). Pan-cancer significance was defined at a 10% FDR, and significance for individual tumor types was defined at unadjusted p<0.05. Positive association is indicated with red circles, negative with blue circles, and non-association with gray circles. Black wedges indicate the share of samples exhibiting the event (ie. non-zero GISTIC score at the locus). Bar plot indicates unadjusted pan-cancer p-values for CNAs, sorted by significance, with dashed lines indicating thresholds yielding 1% and 10% FDRs.

FIG. 7A-7C Proposed model for evolution of tumor-immune interactions. (A) As the tumor develops, Applicants propose that intrinsic tumor factors—such as mutated neoantigens or viruses—induce local immune infiltrates (blue circles) that include cytolytic effector cells (expressing GZMA/PRF1; red circles) that kill tumors (daggers). These factors are expected to be positively correlated with CYT across tumors. (B,C) Under pressure from cytolytic immune cells, subclones with resistance mutations will grow out over time. (B) One subset of these mutations would enable tumors to evade killing, but does not impact the infiltrate, and are positively correlated with CYT (i.e. higher infiltrate samples are enriched for these mutations). (C) Another subset suppresses the immune infiltrate (i.e. lower infiltrate samples are enriched for these mutations), and is negatively correlated with CYT. Notably, p53 mutations and ALOX amplifications were also significantly negatively associated with CD8A, suggesting a reduction in cell numbers and not just activity.

FIG. 8A-8J Cytolytic activity and its expression correlates. (A) GZMA vs. PRF1 expression across TCGA tumor biopsies. Points are colored according to cancer type using the same color-coding employed in FIG. 8B. Pan-cancer, a spearman rank correlation (r) of 0.88 waJs observed. (B) GZMA and PRF1 expression across TCGA tumor biopsies. Solid bodies represent interquartile ranges and are notched by the median; vertical lines demarcate the $5^{th}$ to $95^{th}$ percentile range. (C) GZMA and PRF1 expression in Cancer Cell Line Encyclopedia (CCLE) cancer cell lines. Log 2 (Affymetrix U133) array expression for ~1000 cancer cell lines grouped by cell lineage. Probes 205488_at and 1553681_a_at were used to represent GZMA and PRF1, respectively. Hematopoietic cell lines were further subdivided as T lymphocytic, B lymphocytic, or myeloid. Solid bodies represent interquartile ranges and are notched by the median; vertical lines demarcate the $5^{th}$ to $95^{th}$ percentile range. (D) Fantom5 CAGE expression (parts per million) of GZMA and PRF1 in 12 immune cell types. (E) CYT in normal colon and in colorectal cancer by microsatellite instability status (stable, low MSI, high MIS). Quantiles are represented as in part b. P-values correspond to comparison to stable tumors by Wilcoxon rank-sum test. (F) Cell type marker enrichments vs. Cytolytic Activity (all calculated by ssGSEA). Each panel represents a scatter plot of z-scored enrichment scores with CYT on the x-axis and the relevant cell type on the y-axis. Background color of each scatter corresponds to the Spearman rank correlation, the color mapping indicated in the legend. Applicants note that there are limitations to the precision of our markers genes; for example, Applicants could not identify markers for NK cells that are not expressed (to some level) in activated CTLs. (G) Tumor-normal expression differences of z-scored cell type marker enrichments (all by ssGSEA, including CYT). Thin lines span the $5^{th}$ to $95^{th}$ percentile range and thick lines span the interquartile range. Colors correspond to cell type as indicated in the figure; gray bars represent the enrichment of the adjacent cell type in normal control tissues (from TCGA and GTEx) (H) CYT (geometric mean) by tumor stage. Stages are shown with at least 30 corresponding samples. Each gray dot represents a sample, and black lines mark the medians. P-values (upper right of each plot) correspond to Pearson correlation between log CYT and rank stage (i.e. "stage 1A"=1, "stage 1B"=2, etc.). (I) Heatmap indicating the association between rank stage and z-scored marker gene enrichment in each tumor type. Colors represent the magnitude and direction of the correlation as indicated in the legend. Cell borders indicate significance levels (thin black lines, p<0.05; thick black lines, p<0.0005). (J) Survival curves based on cytolytic activity and other cell type markers. In each survival analysis, patients were segregated into "high" (black line) and "low" (gray line) cohorts, each with an identical admixture of tumor histological type and stage (Methods). In the leftmost column, "high" and "low" were based on metagene expression. In other panels, "high" and "low" were based on expression ratios, as indicated. P-values were assigned based on Cox proportional hazards models. Panels are highlighted in green when the "high" group had a advantage and in orange when the "low" group had a survival advantage (using a nominal significance cutoff of p<0.05). Darker orange and green correspond to stronger unadjusted p-values (p<0.0005).

Figure 9A:
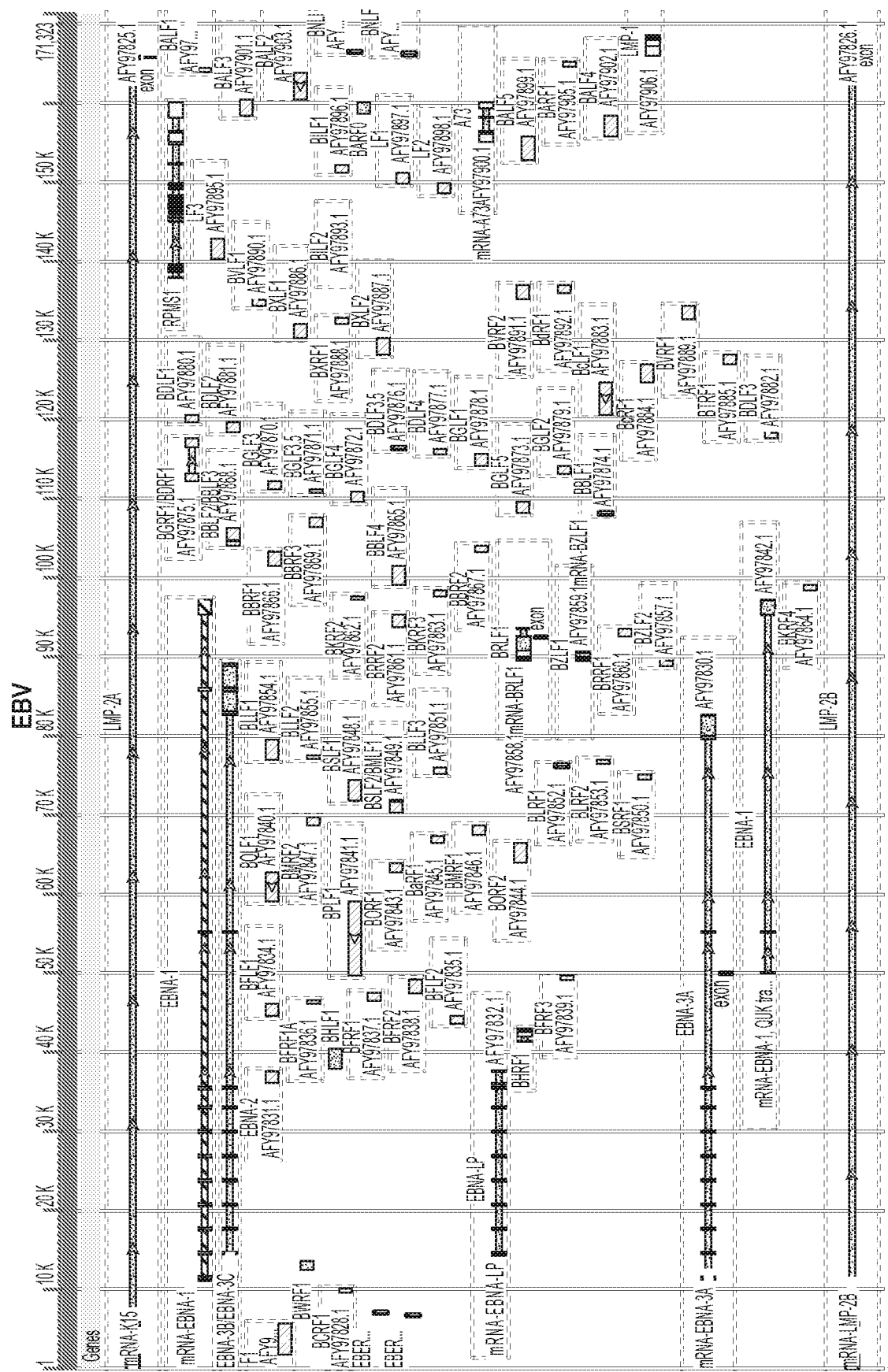
Figure 9A:
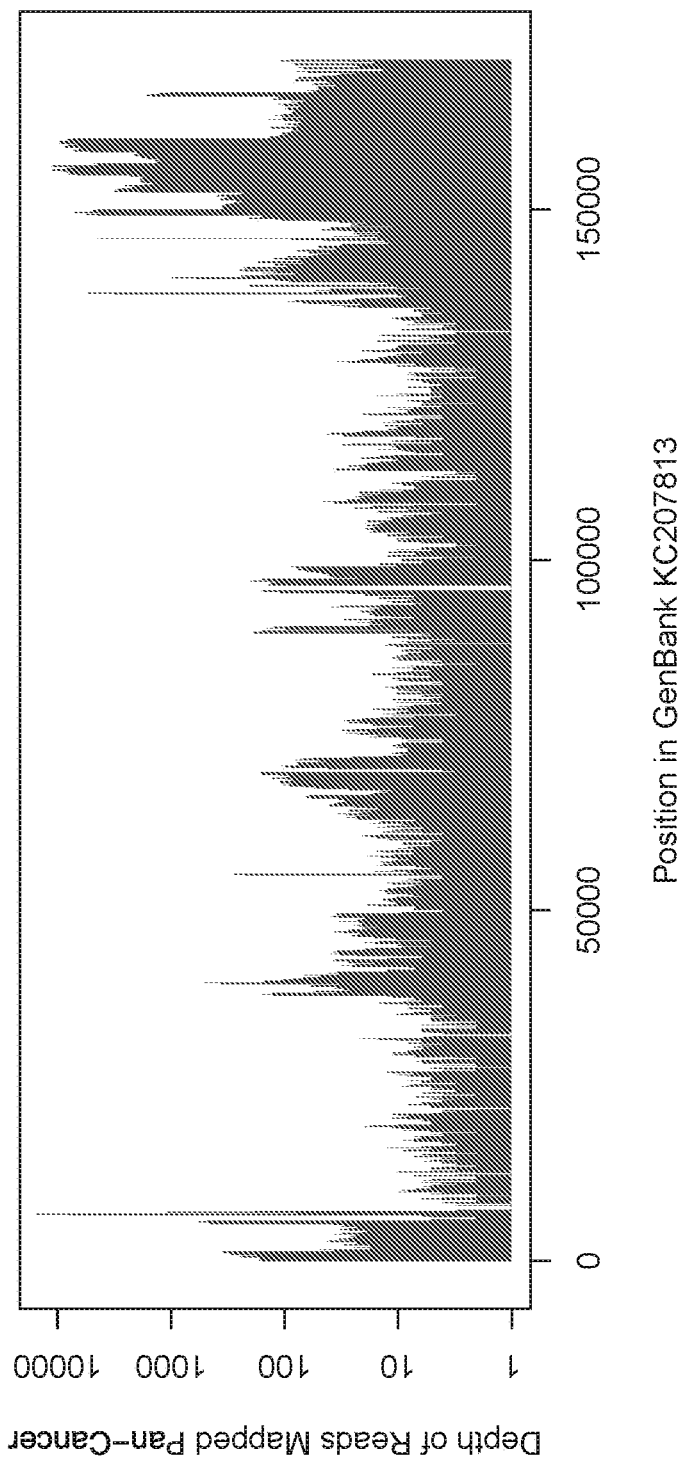
Figure 9B:
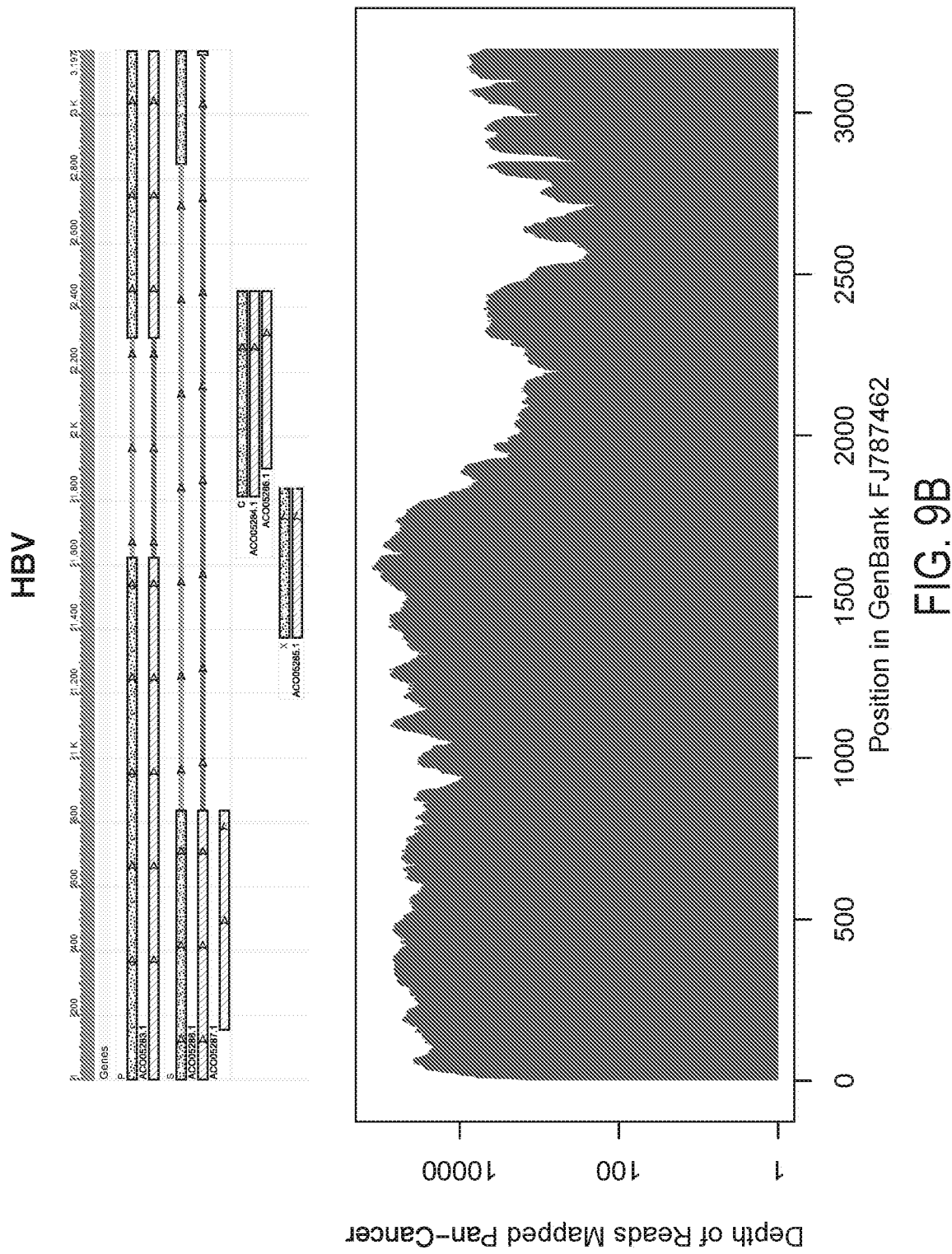
Figure 9C:
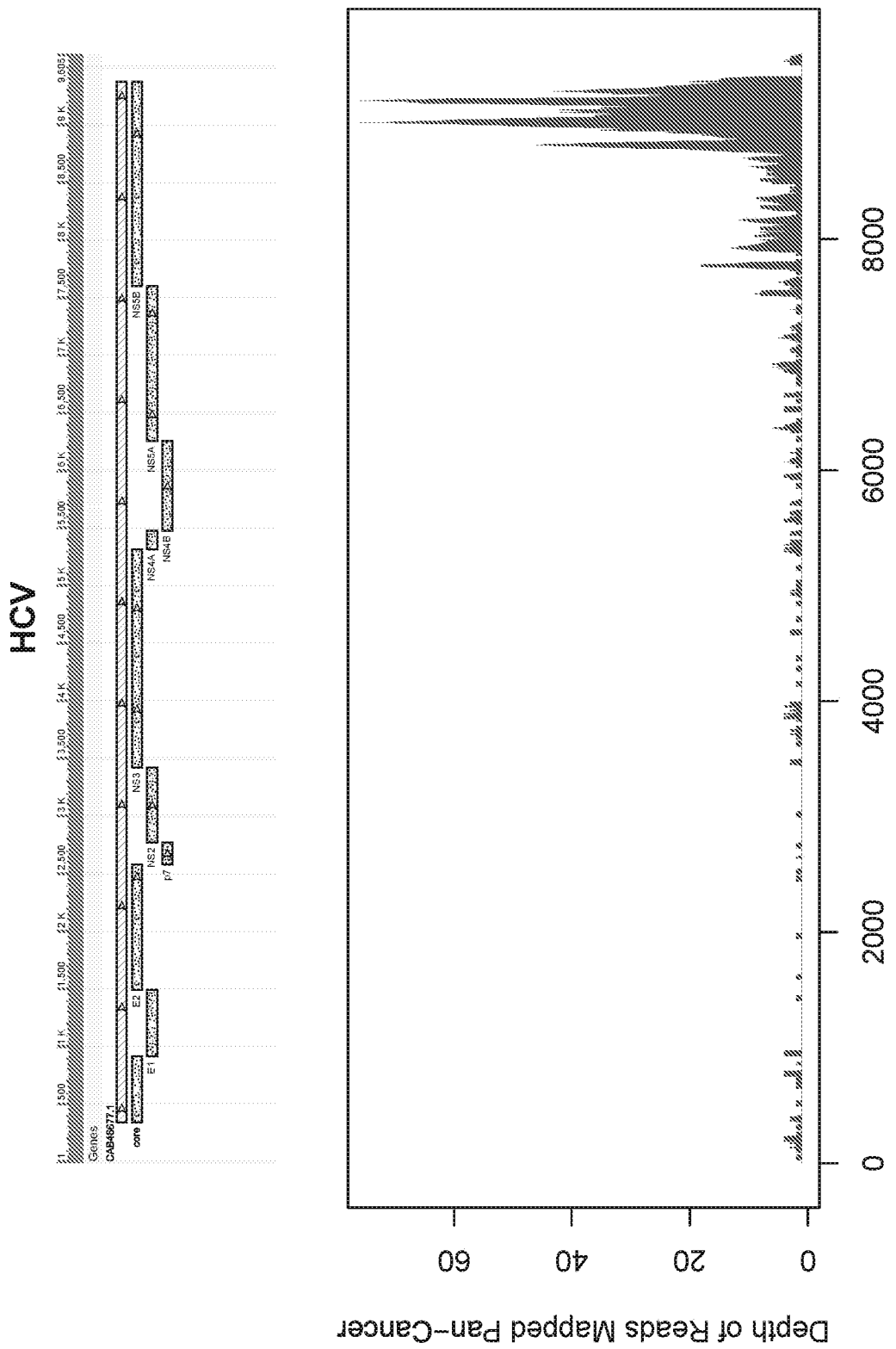
Figure 9D:
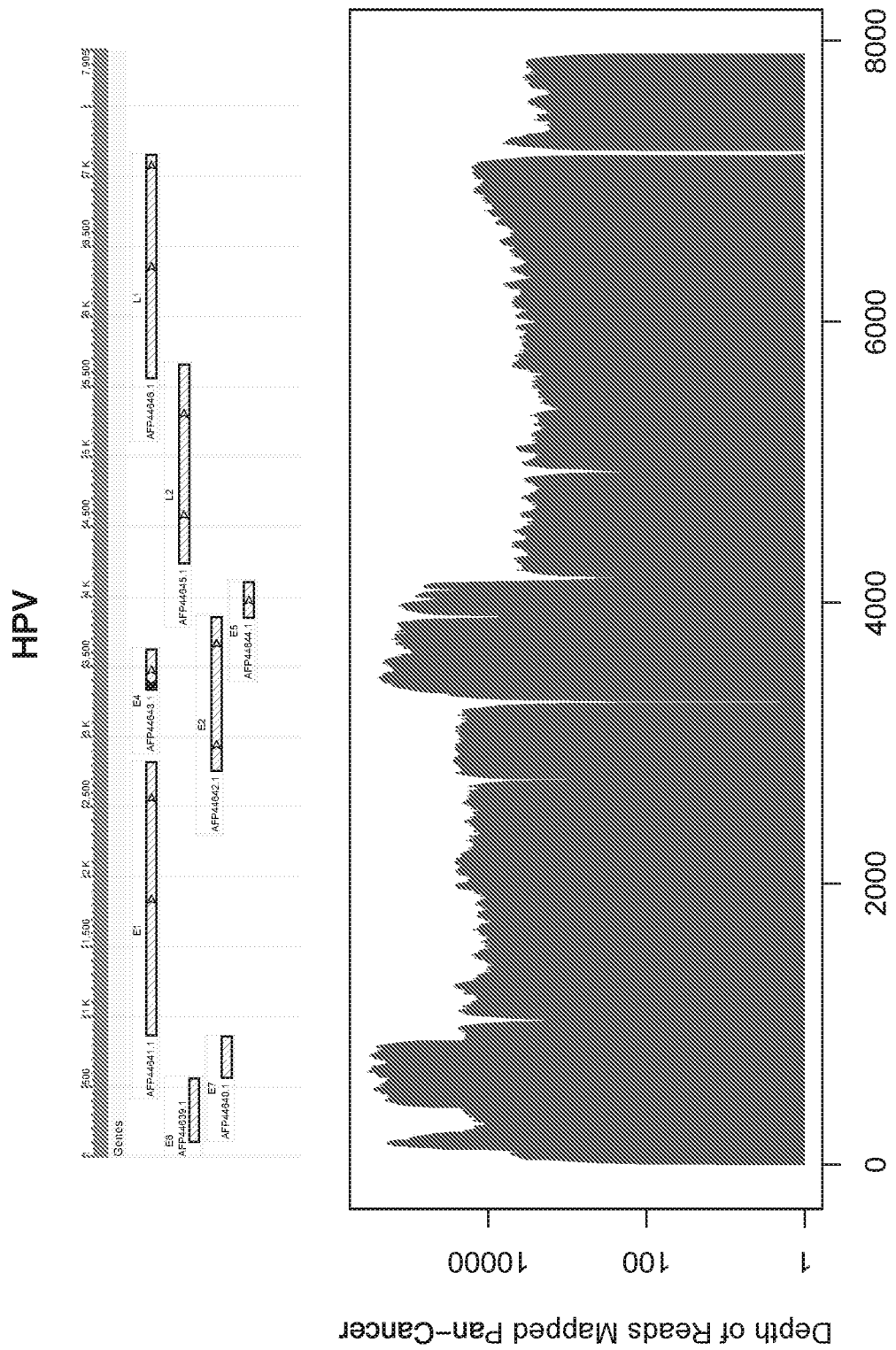
Figure 9E:
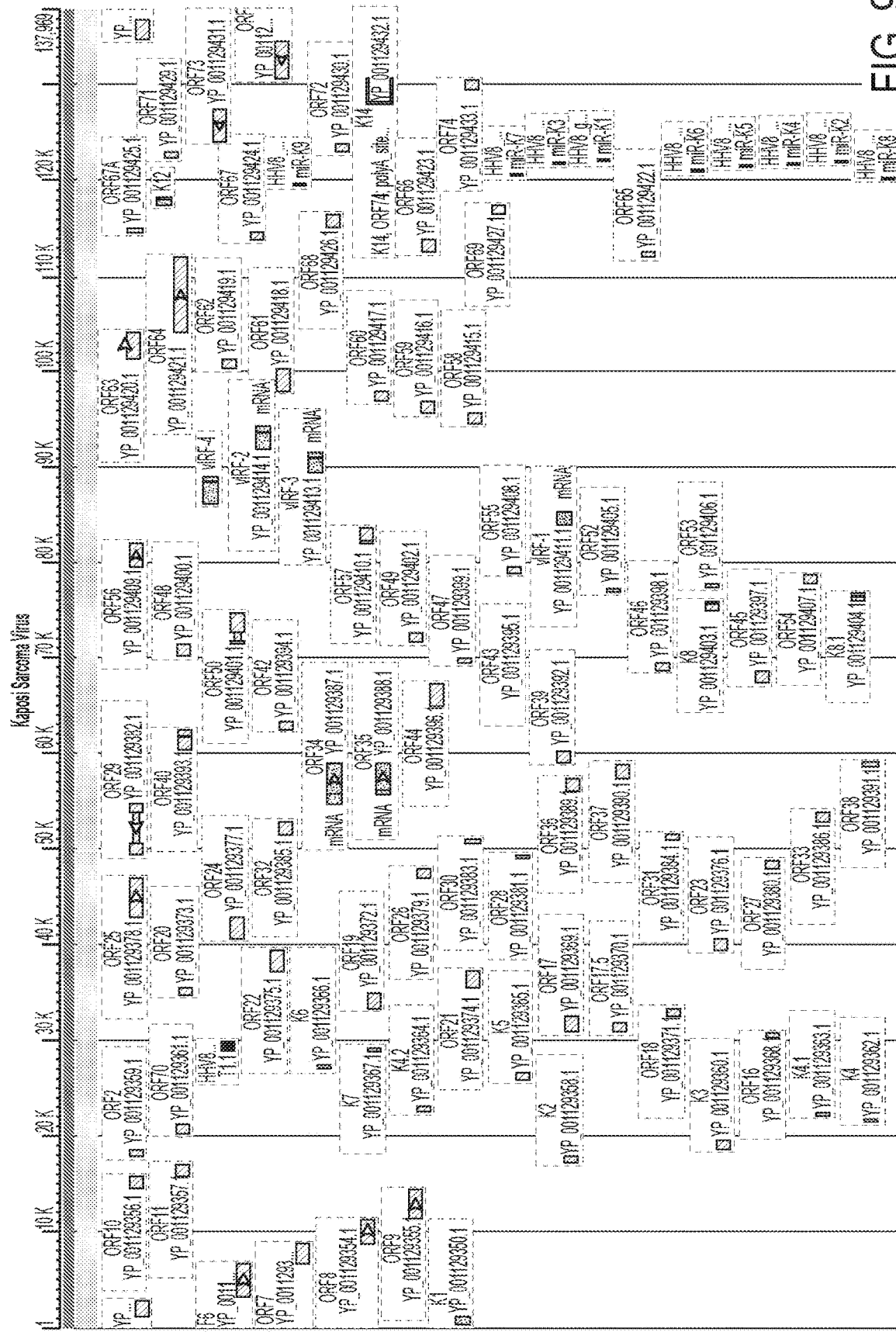
Figure 9E:
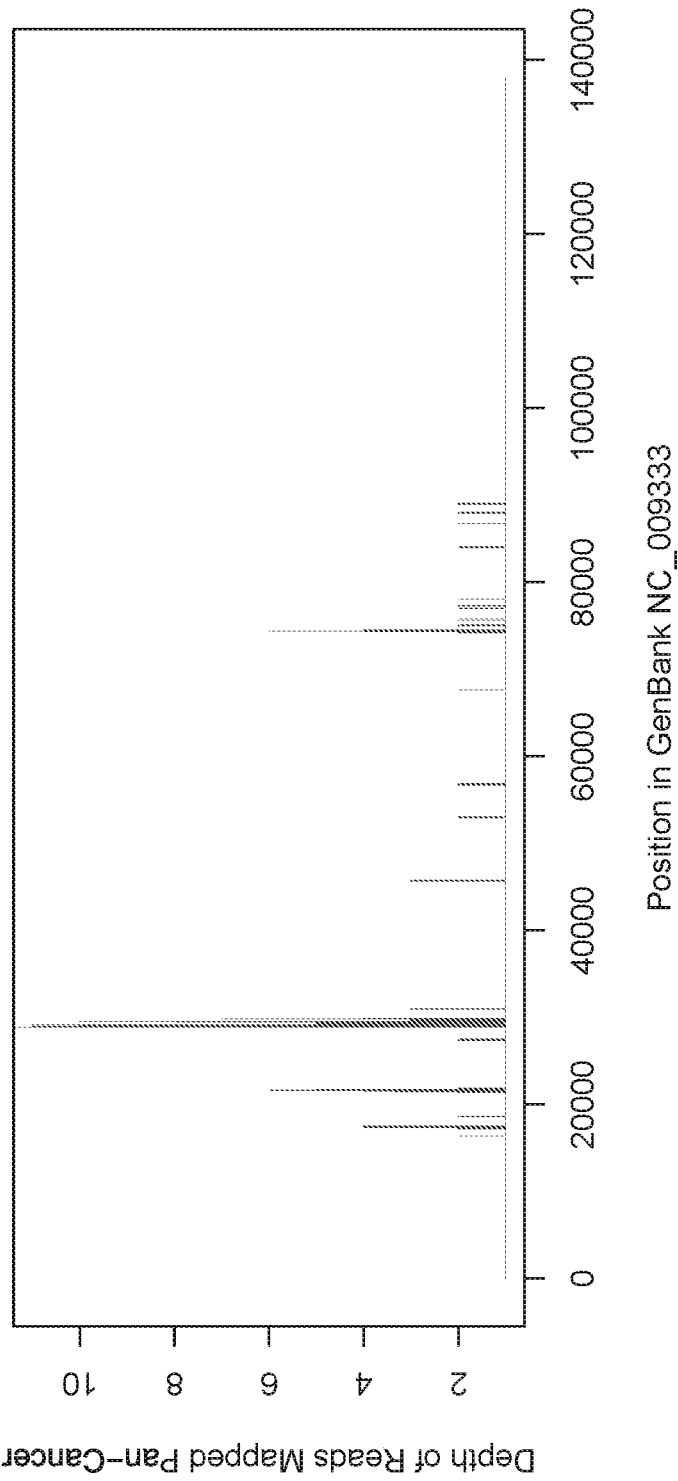
Figure 9F:
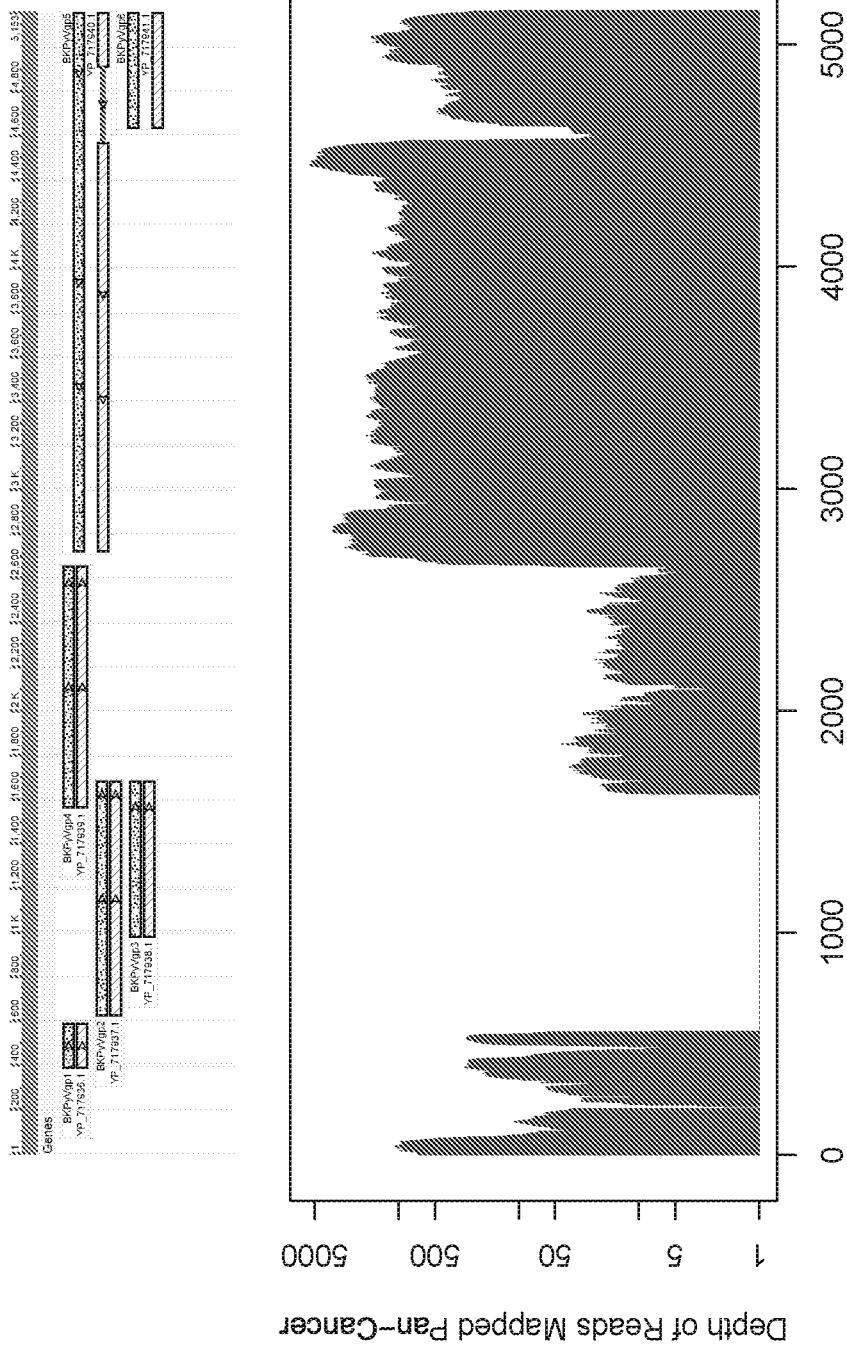
Figure 9G:
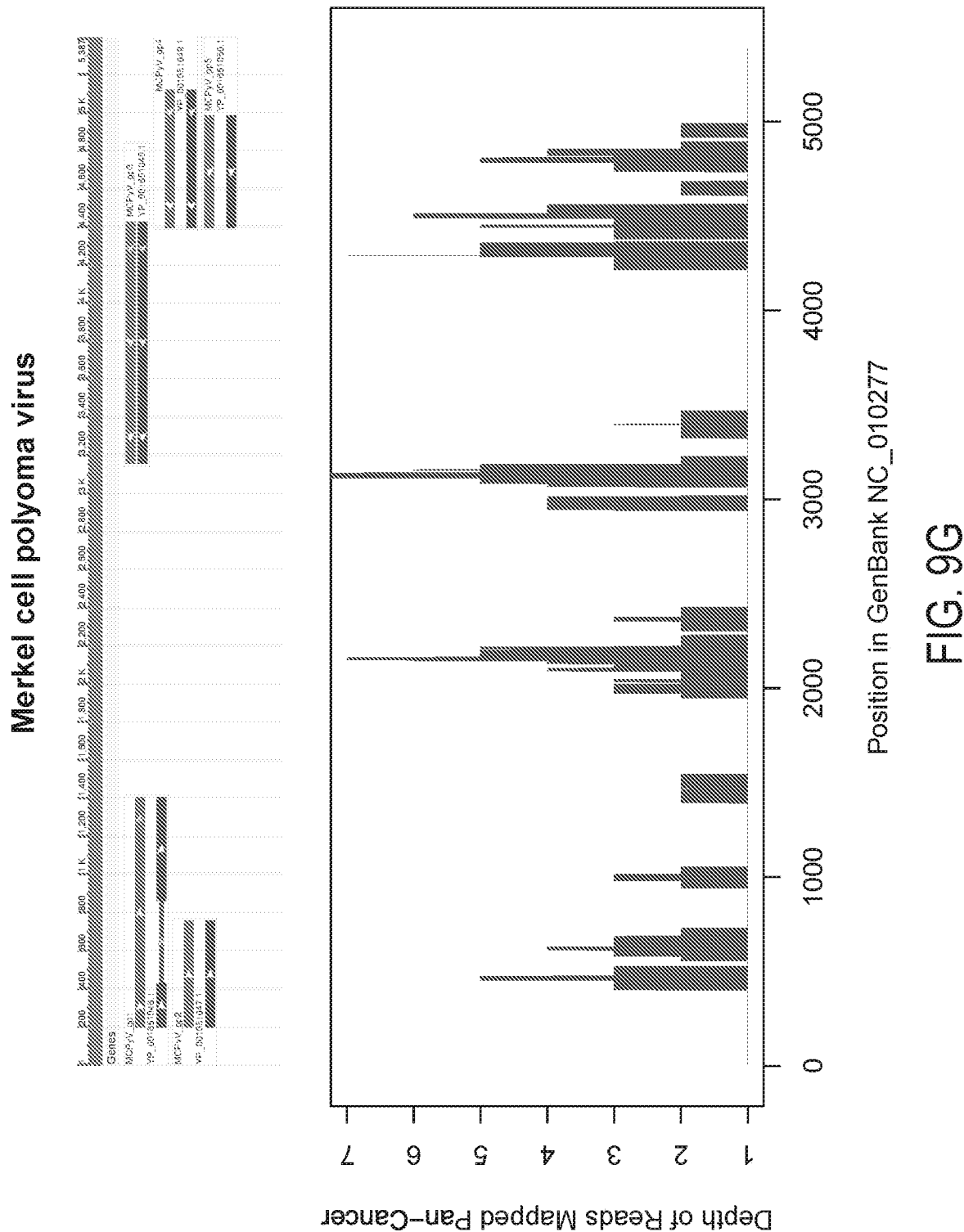
Figure 9H:
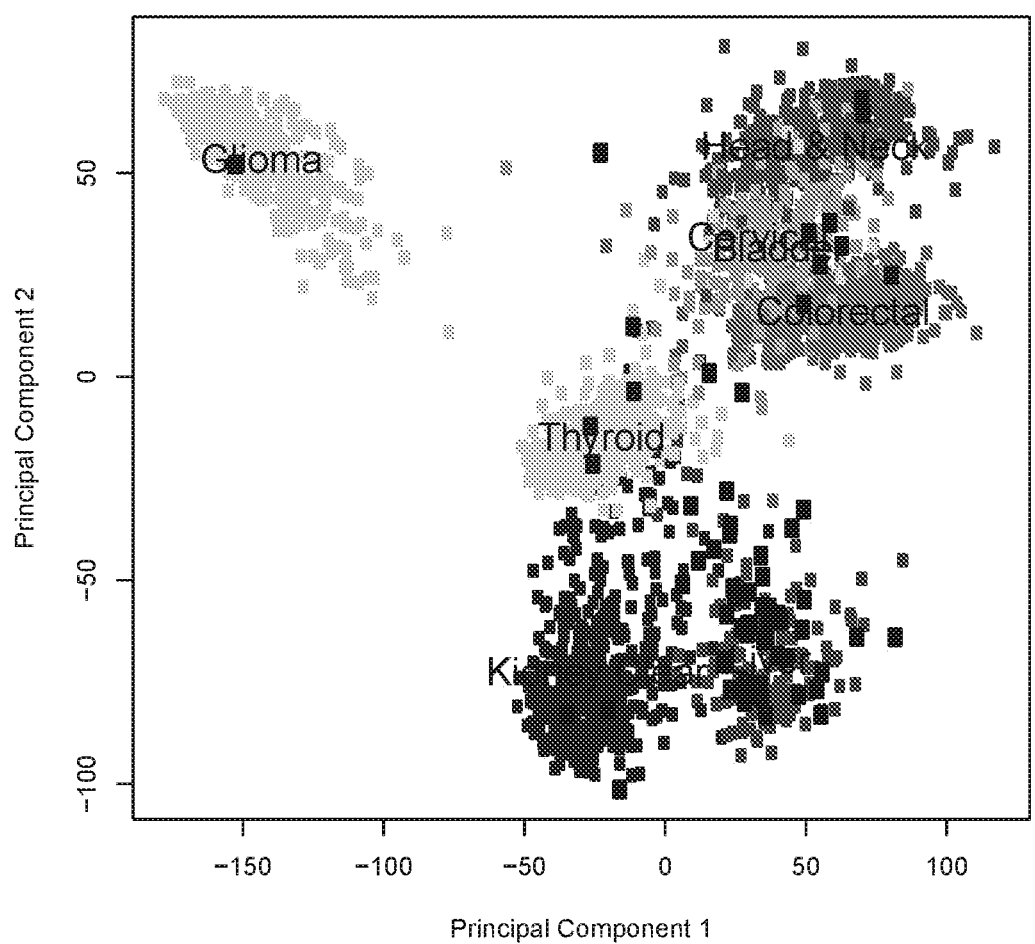
Figure 9I:
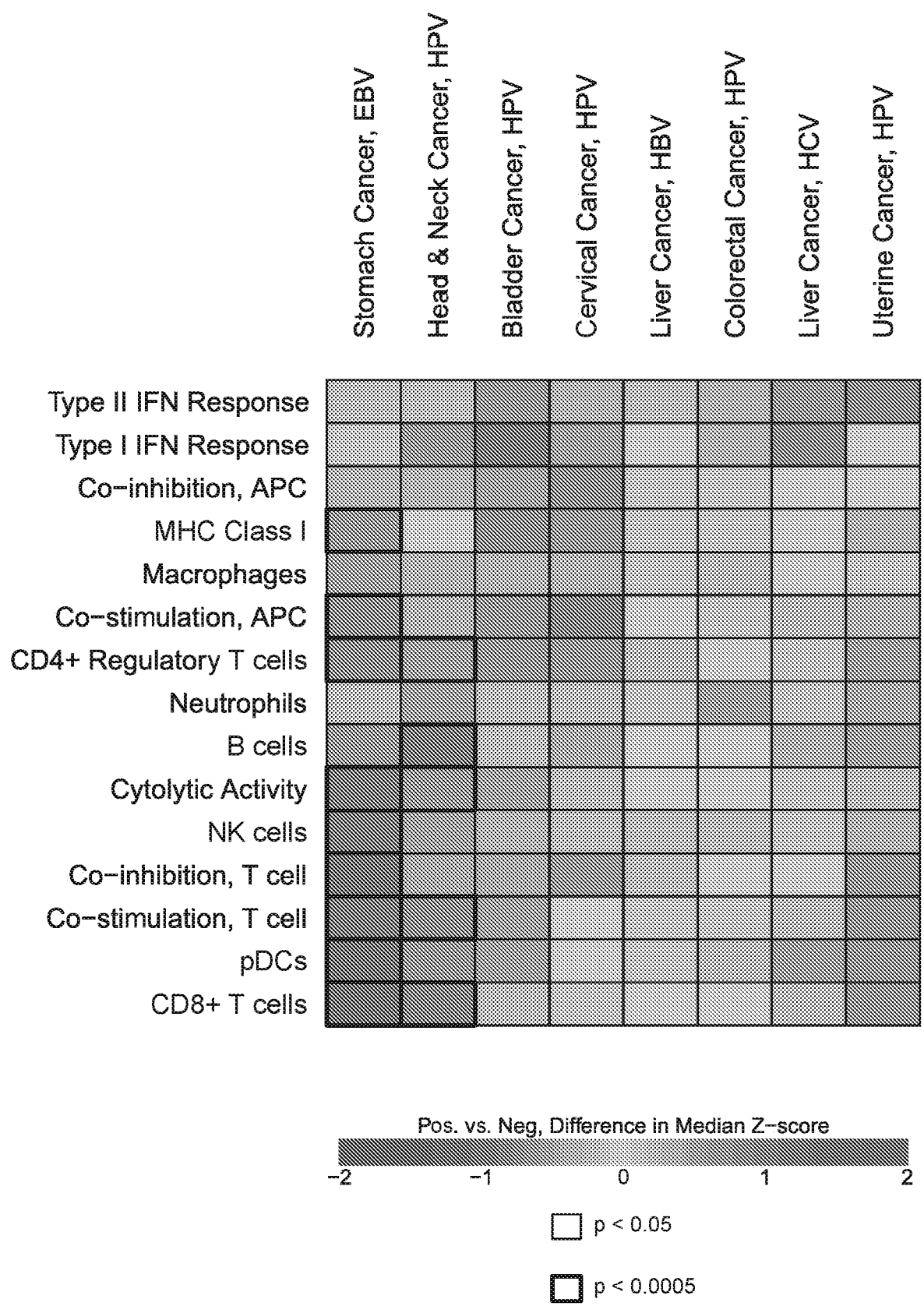
Figure 9J:
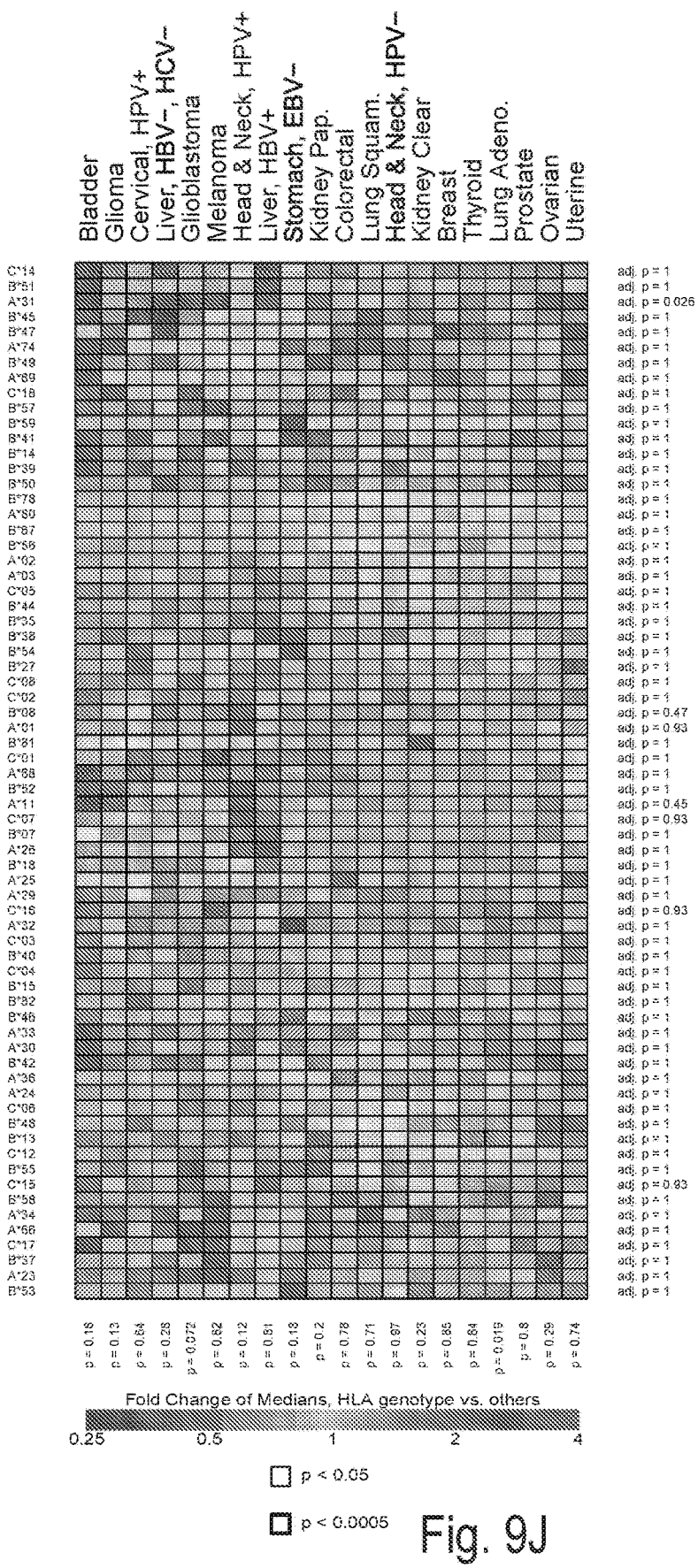
Figure 9K:
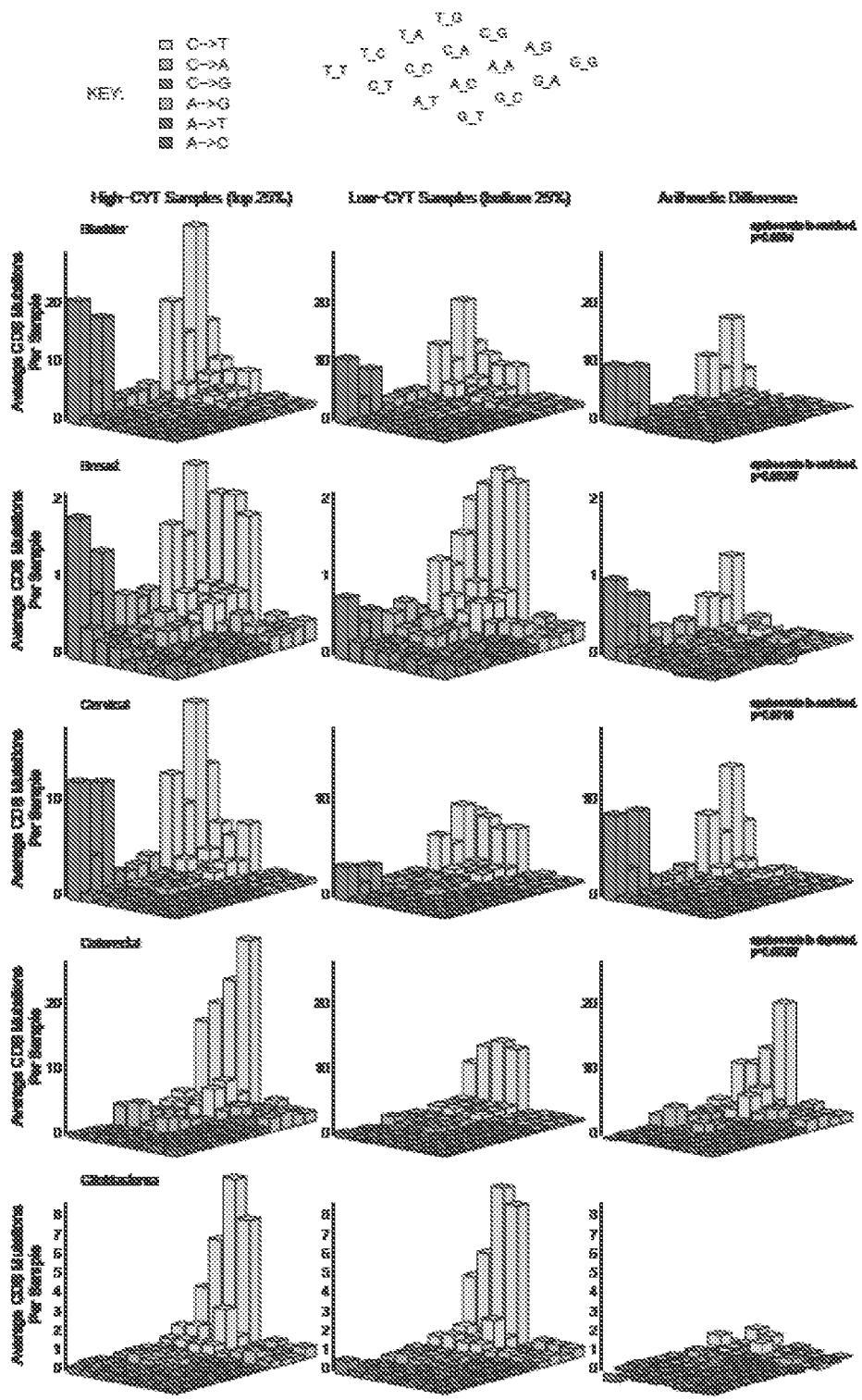
Figure 9L:
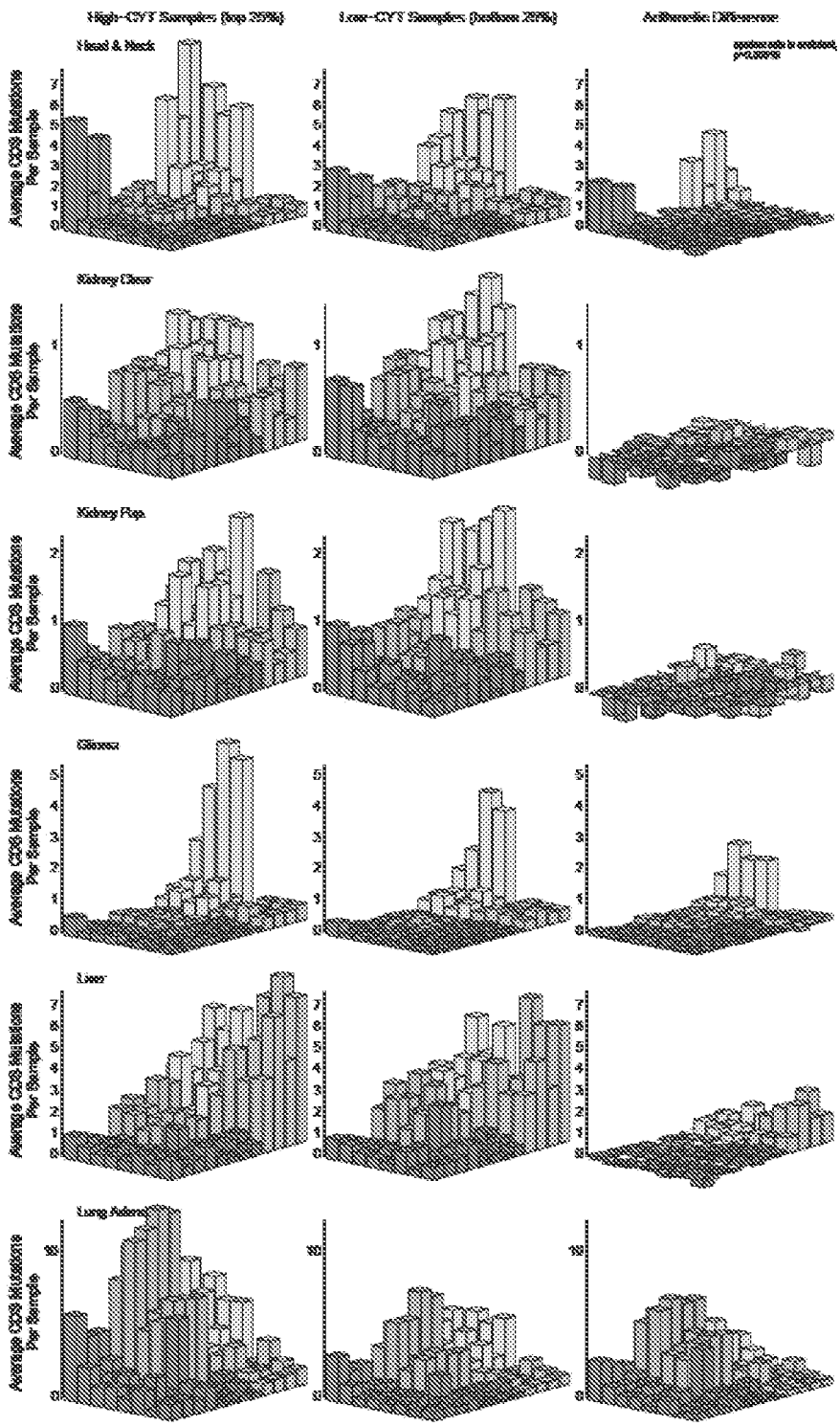
Figure 9M:
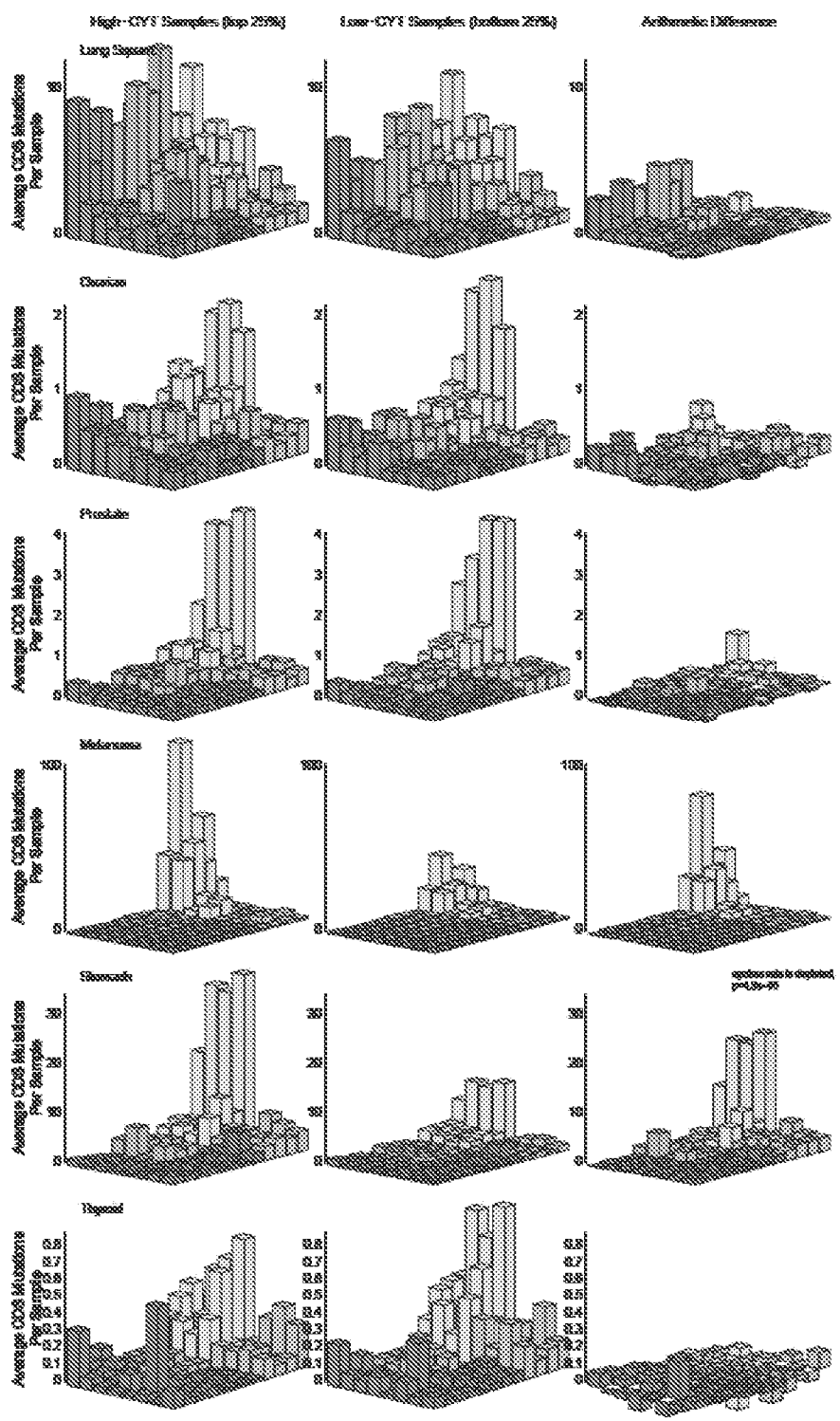
Figure 9N:
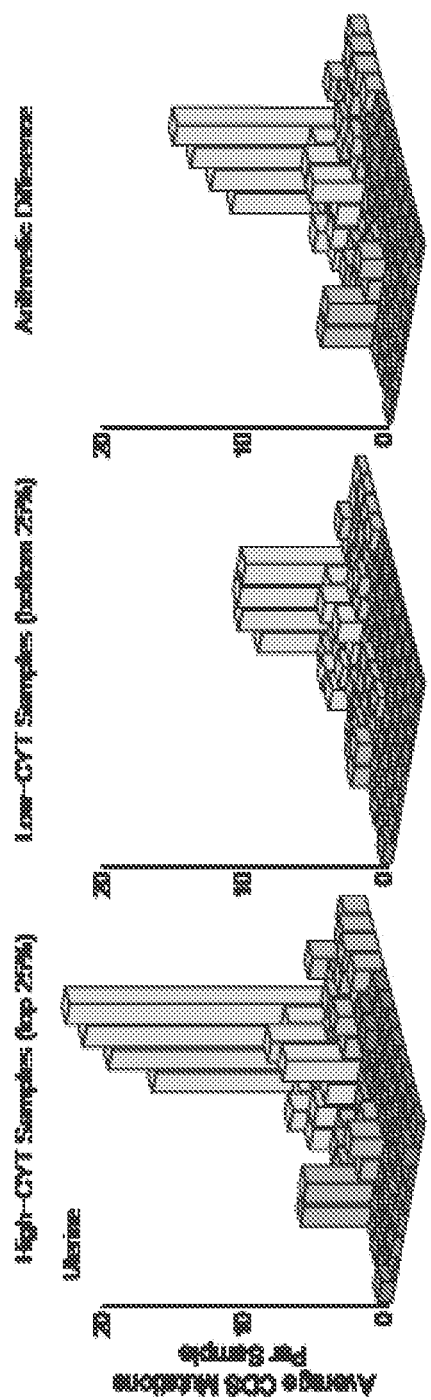

FIG. 9A-9N Viral gene expression and cell type correlates. (A-G) Read depths are presented on log-scale for viruses with depths exceeding 100 and on linear scale otherwise. GenBank annotations of known viral elements are presented above. (H) Tumor samples plotted according to the first two principal components log-transformed gene expression (for tumor types with ≥1 HBV+case). Color coding corresponds to that used in FIG. 1. HBV-infected samples are represented by larger, black-outlined points. (I) Heatmap showing association between viral infection status and the enrichment of cell type markers. Colors correspond to the difference in z-scored enrichment between infected and non-infected samples. Cell borders indicate the unadjusted significance of the association according to Wilcoxon rank-sum test. (J) Heatmap showing associations between HLA type and CYT. Colors correspond to the fold change between median expression in infected and non-infected samples. Cell borders indicate the significance of the association according to Wilcoxon rank sum test. Marginal HLA type significances are based on combination of each row's p-values by Fisher's method and are adjusted by BH method. Marginal tumor type significances are based on rank-CYT ANOVA and are presented without multiple comparisons correction. (K-N) Single-nucleotide variant spectra for high-vs. low-CYT tumors. Mutational spectra are defined by the base change and the sequence context one base upstream and one base downstream. T→X and G→X mutations are considered from the perspective of the opposite strand such that all mutations are A→X or C→X. The average rate of each mutation per sample (counting mutations in coding sequence only) is represented in an 8×12 grid according to the provided legends. The first plot in each row represents mutation rate averages for high-CYT tumors (top 25% for that tumor type). The middle plot represents mutation rate averages for low-CYT tumors (bottom 25% for that tumor type). The third plot represents the arithmetic difference. In each plot, the back left row of bars corresponds to Apobec-characteristic tCx→tXx mutations. To assess Apobec enrichment for a tumor type, the Spearman rank correlation between CYT and the Apobec/non-Apobec mutation ratio was calculated across all samples.

FIG. 10A-10I Mutations, Neo-epitopes and their correlates. (A) Boxplots indicate typical rates of mutation (coding sequence events only) in each tumor type. Solid bodies represent interquartile ranges and are notched by the median; lines demarcate the $5^{th}$ to $95^{th}$ percentile range. (B) Analogous to (A) but presenting the rate of mutations expected to yield an epitope with strong predicted binding to patient-matched HLA and moderate-to-high expression (median expression≥10 TPM within the given tumor type). (C-E) Relationship between smoking and cytolytic activity in lung and head and neck tumors. Cytolytic activity for smokers and those reformed for less than 15 years verses never-smokers in lung squamous cell carcinoma, lung adenocarcinoma, and head and neck cancer. Solid bodies represent interquartile ranges and are notched by the median; vertical lines demarcate the $5^{th}$ to $95^{th}$ percentile range. P-values reflect Wilcoxon rank-sum tests. (F) Heatmap showing association between total count of mutations and cell type marker gene enrichment. Colors correspond to Spearman correlation, and borders indicate unadjusted p-value. (G) Analogous to (F) but presenting association for neo-epitope counts shown in (B). (H) Scatter plot showing correlation of total mutations and the count of predicted expressed neo-epitopes. (I) Analogous to FIG. 3C, but using neo-epitope prediction based on randomly re-permuted HLA genotype assignments.

Figure 11A:
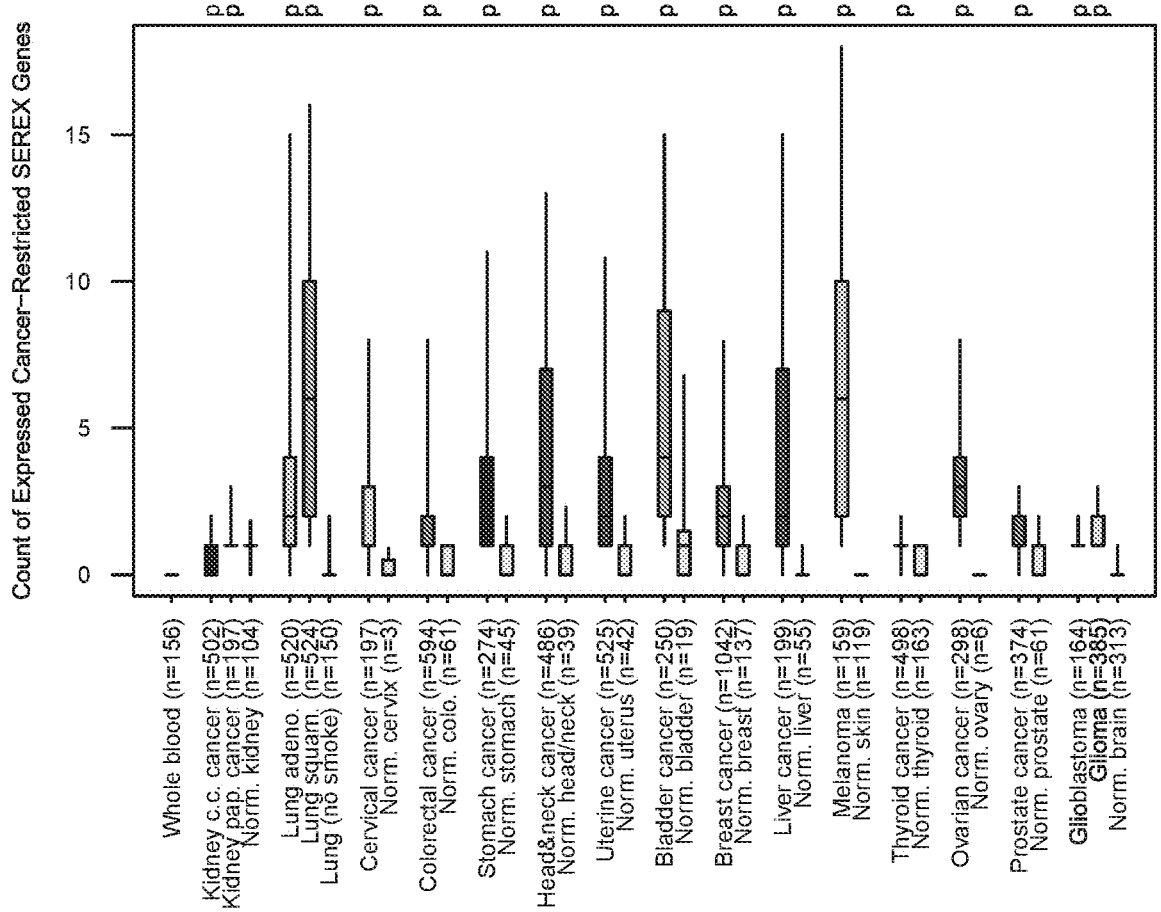
Figure 11B:
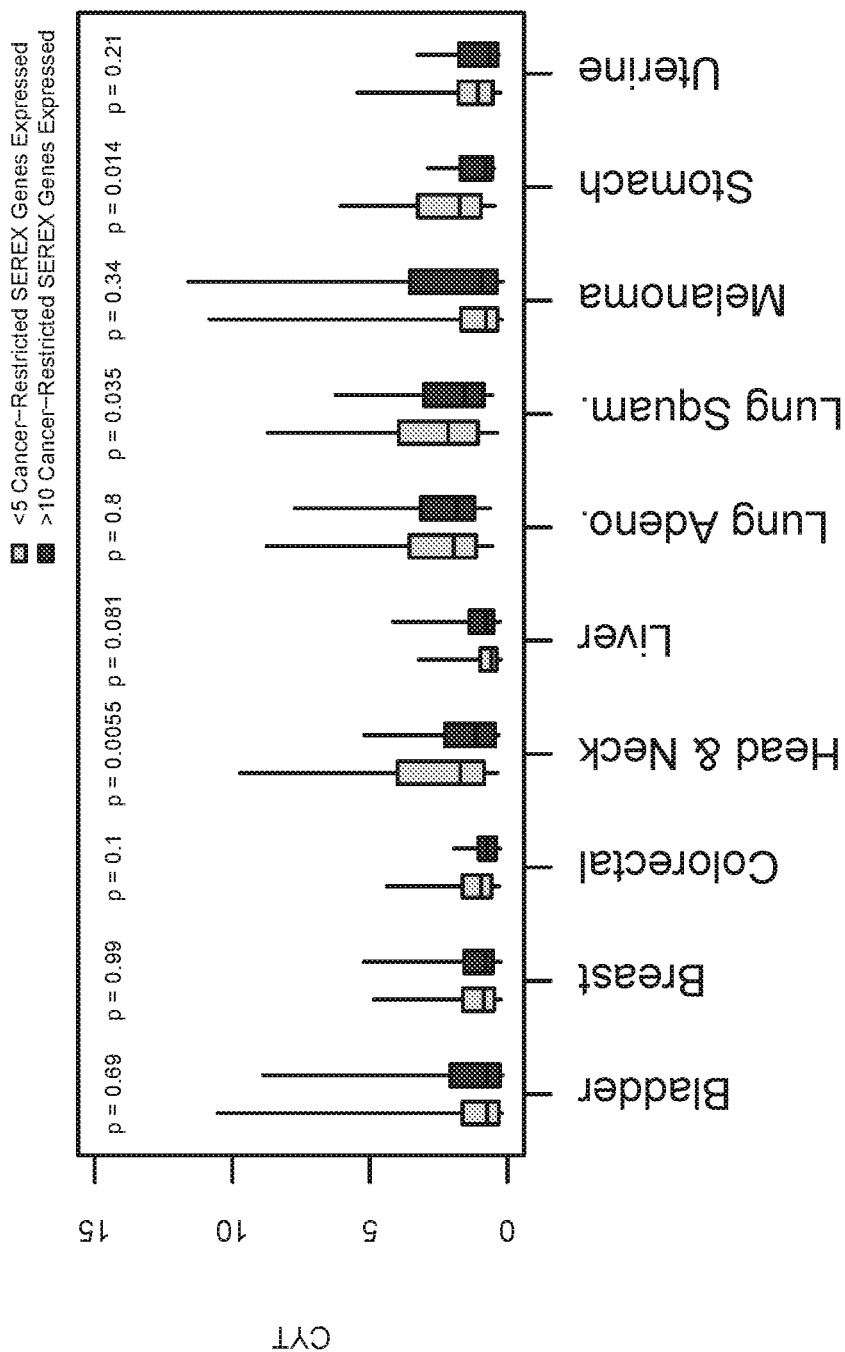
Figure 11C:
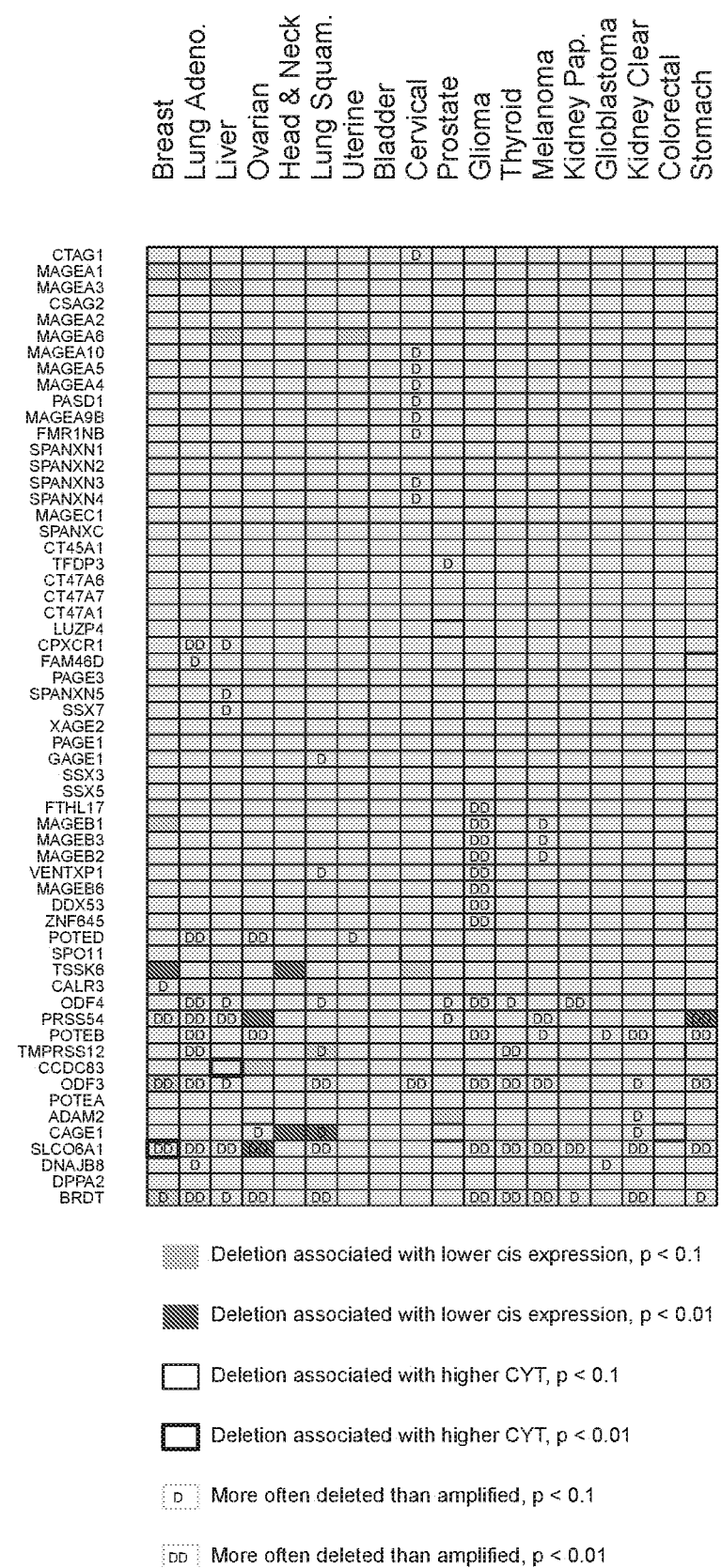
Figure 11D:
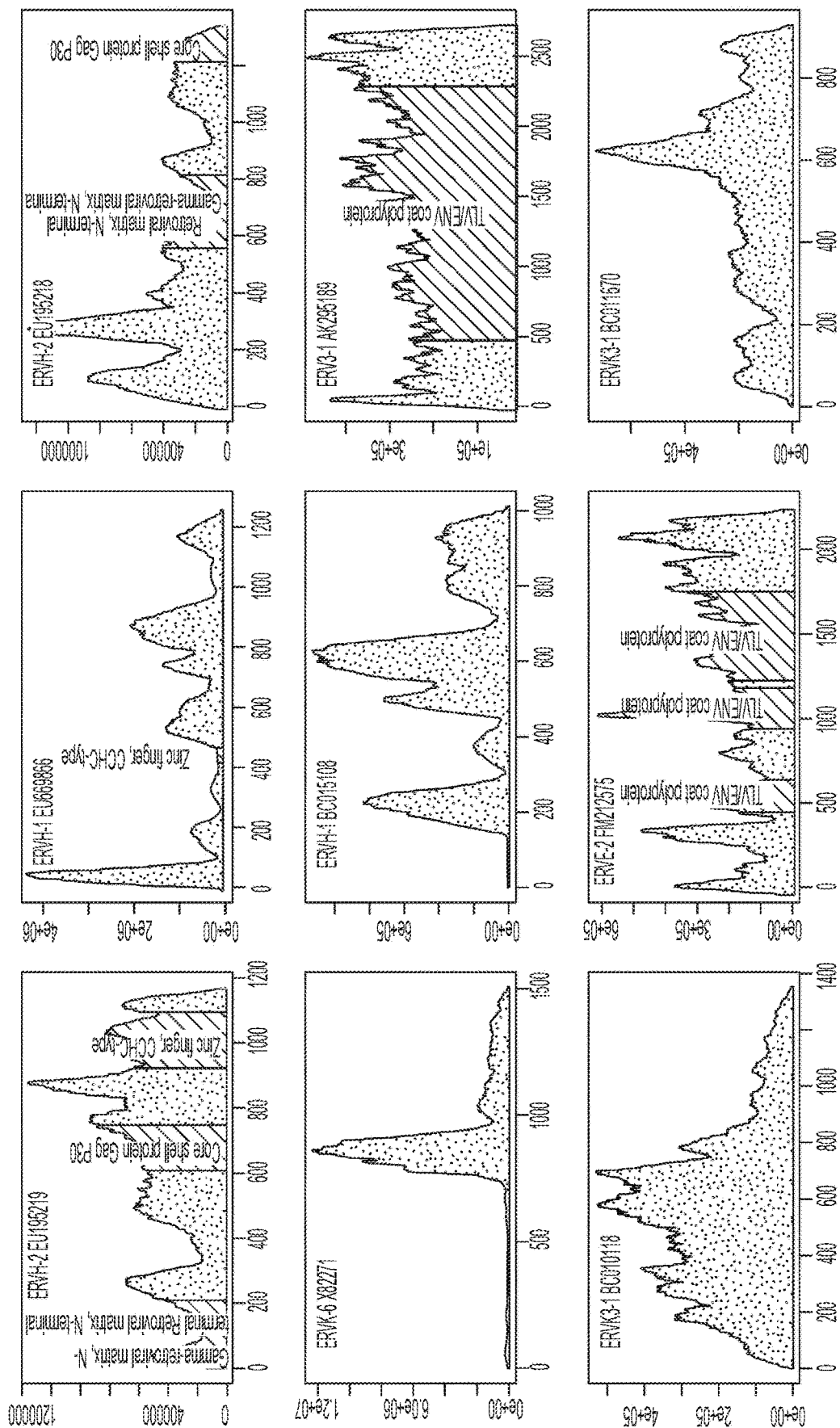
Figure 11D:
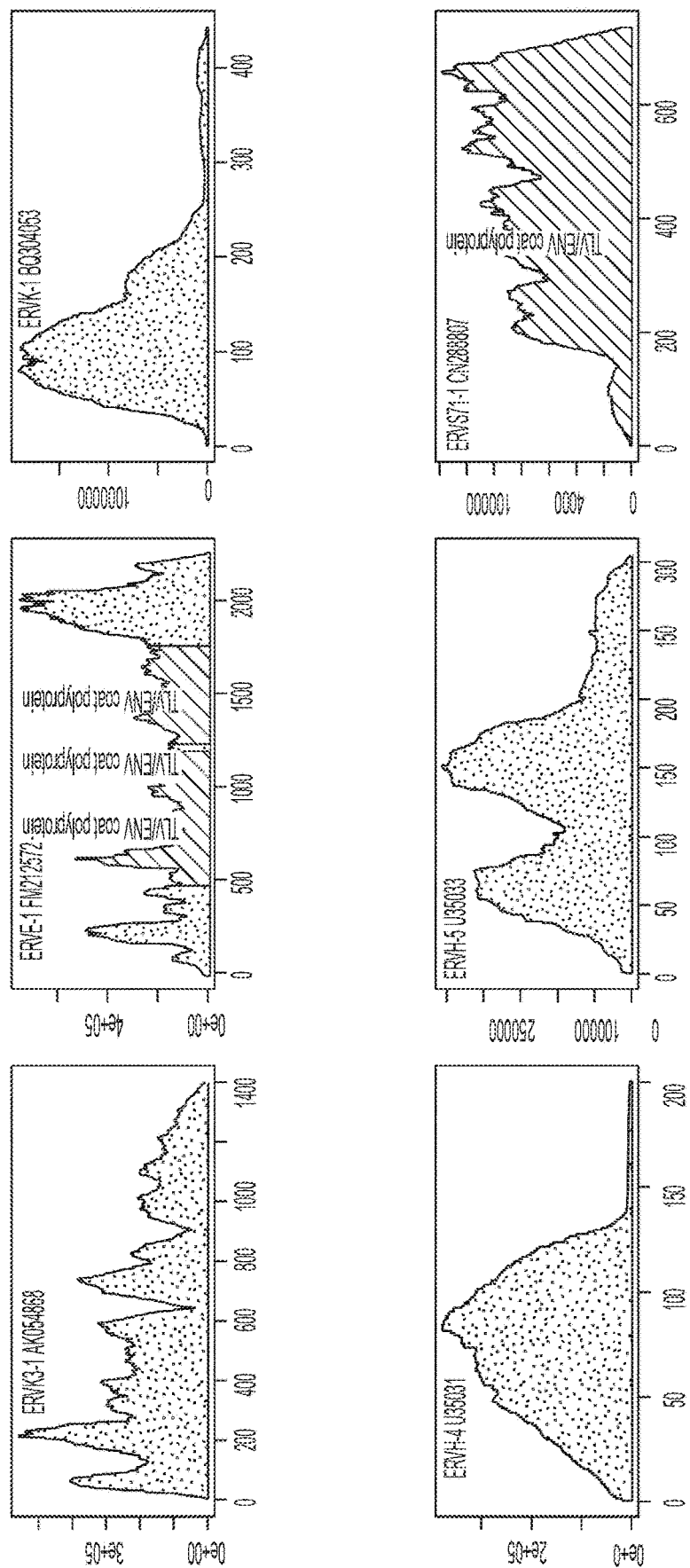
Figure 11D:
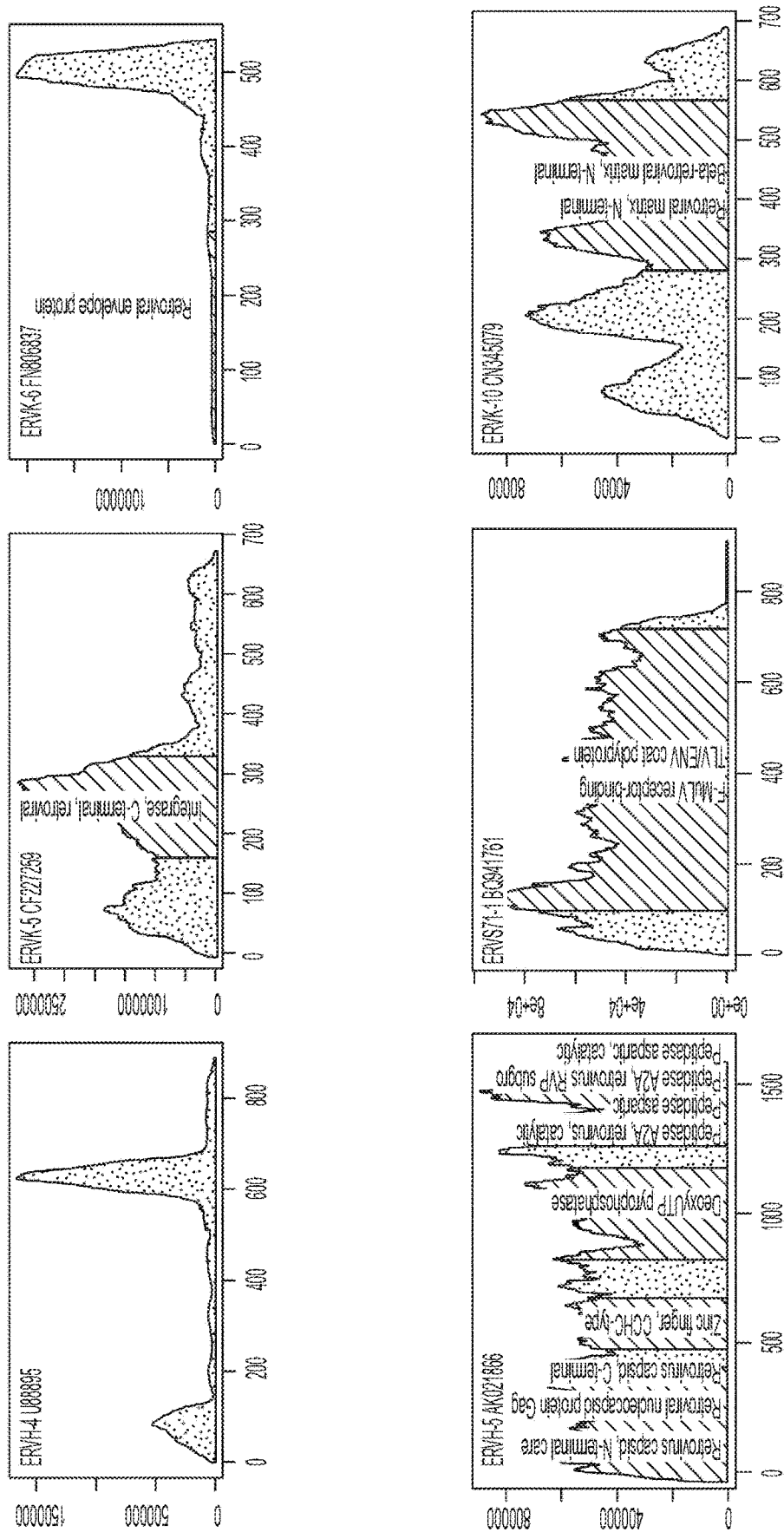
Figure 11E:
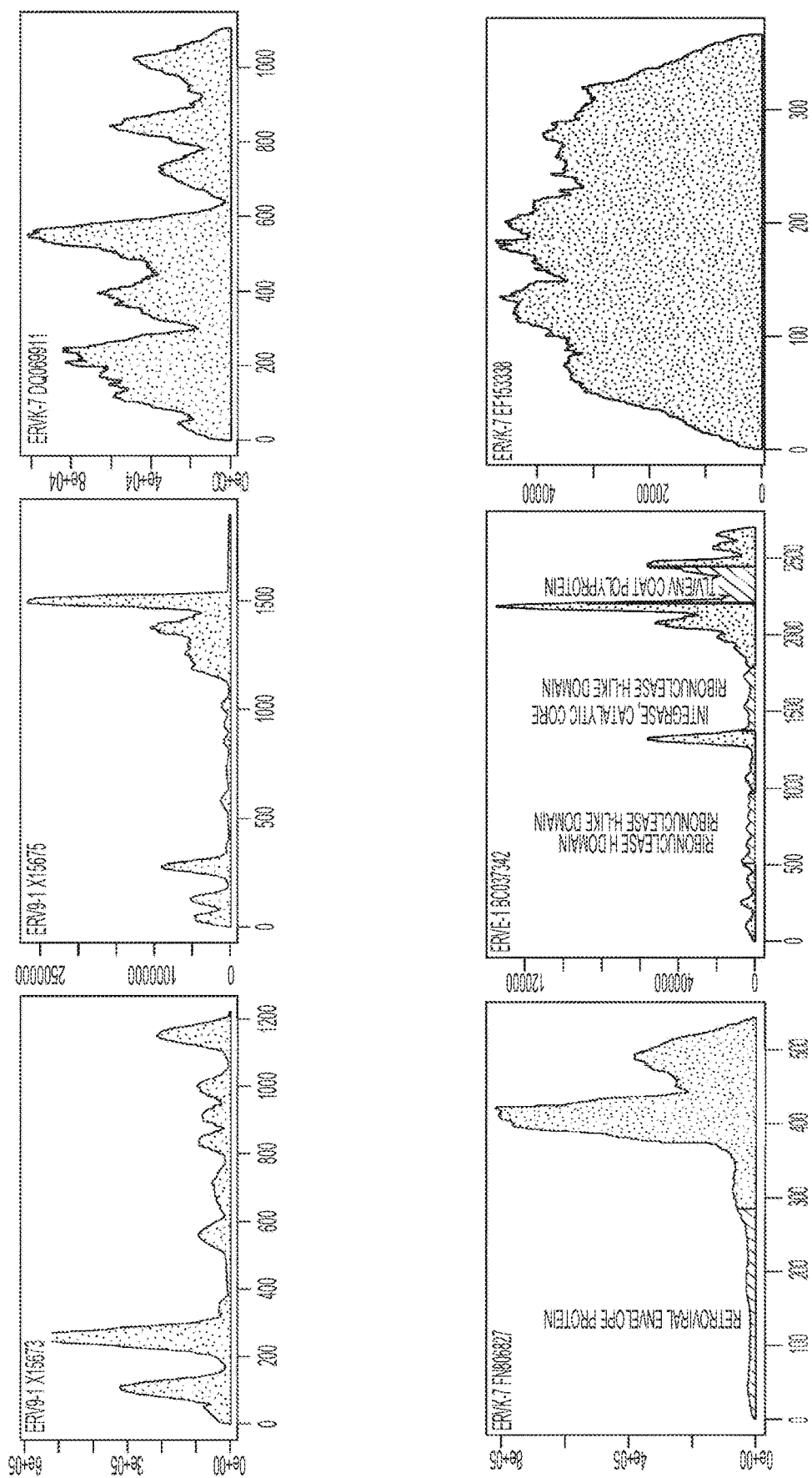
Figure 11E:
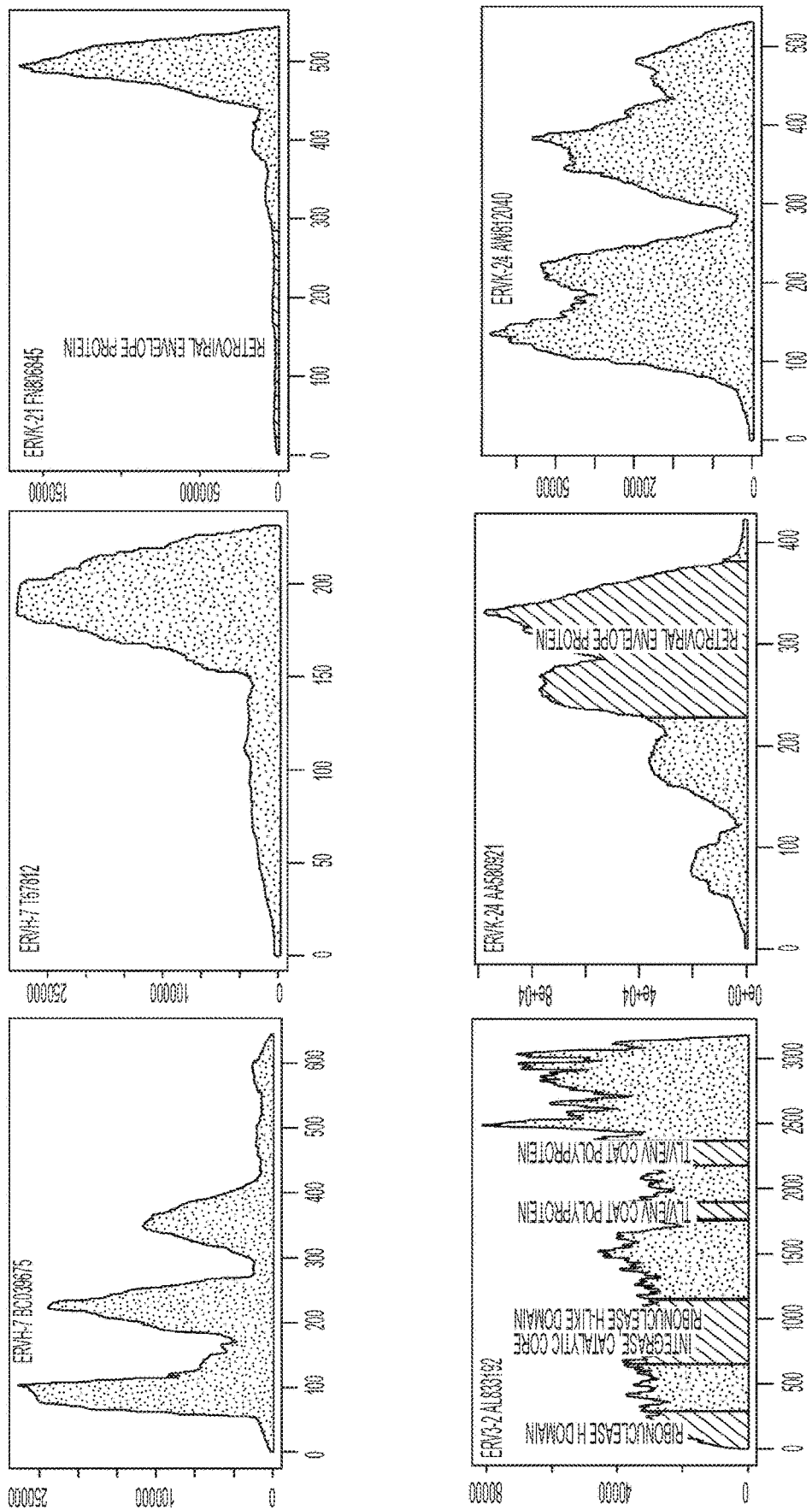
Figure 11E:
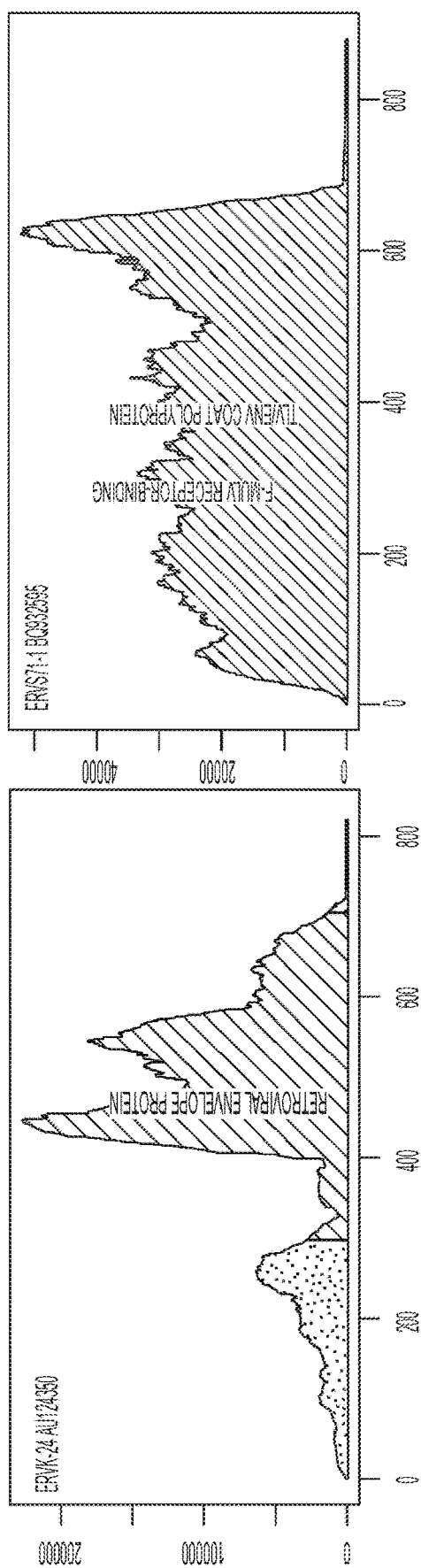
Figure 11E:
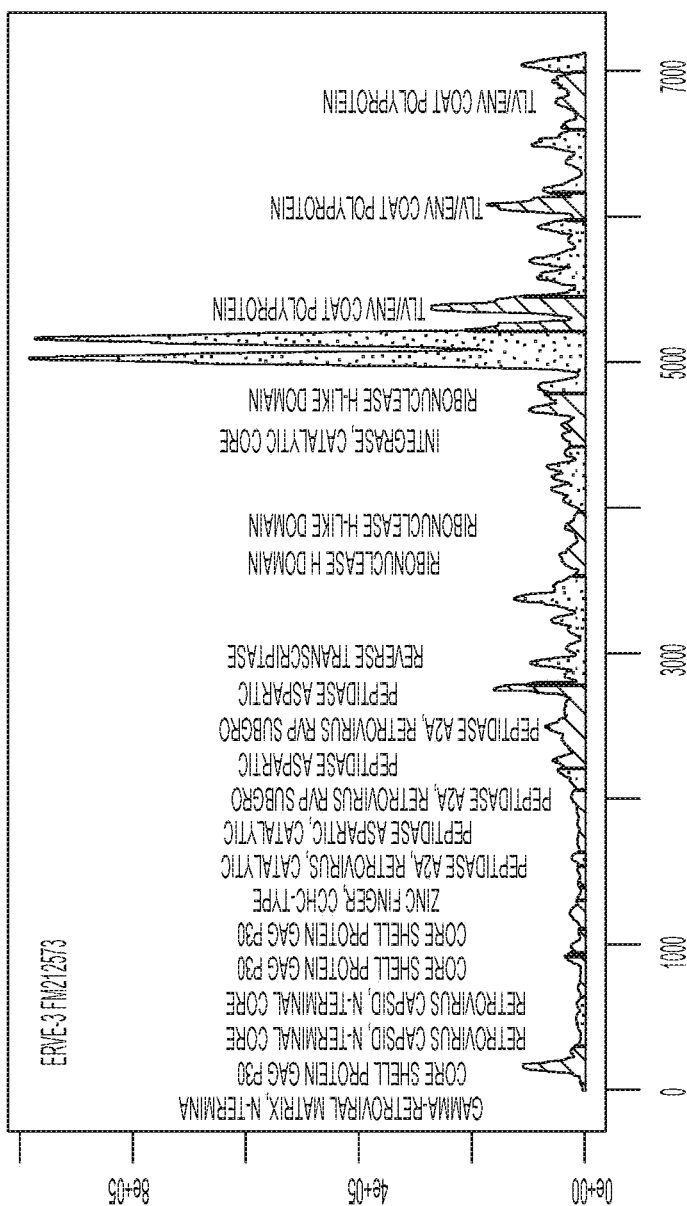
Figure 11E:
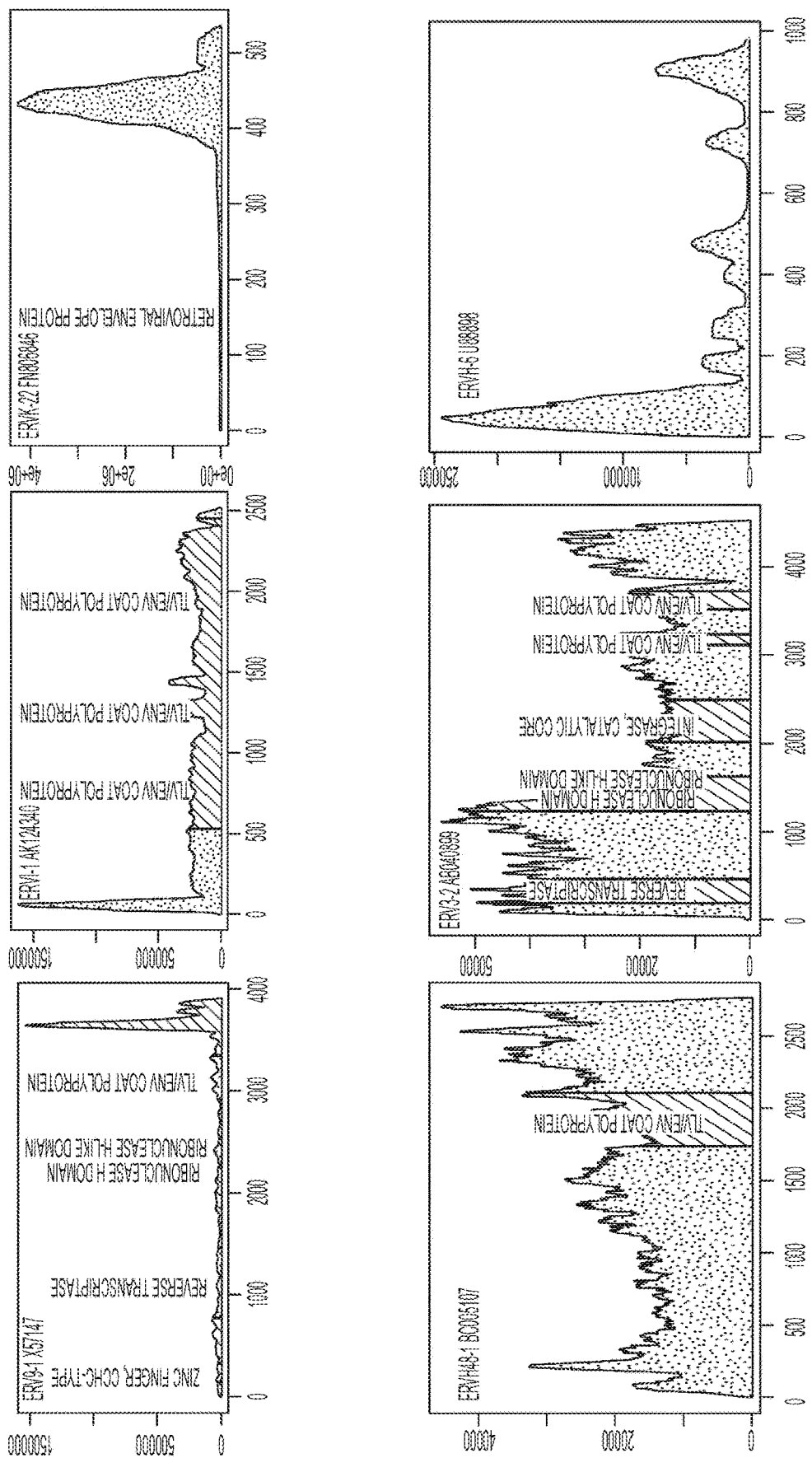
Figure 11F:
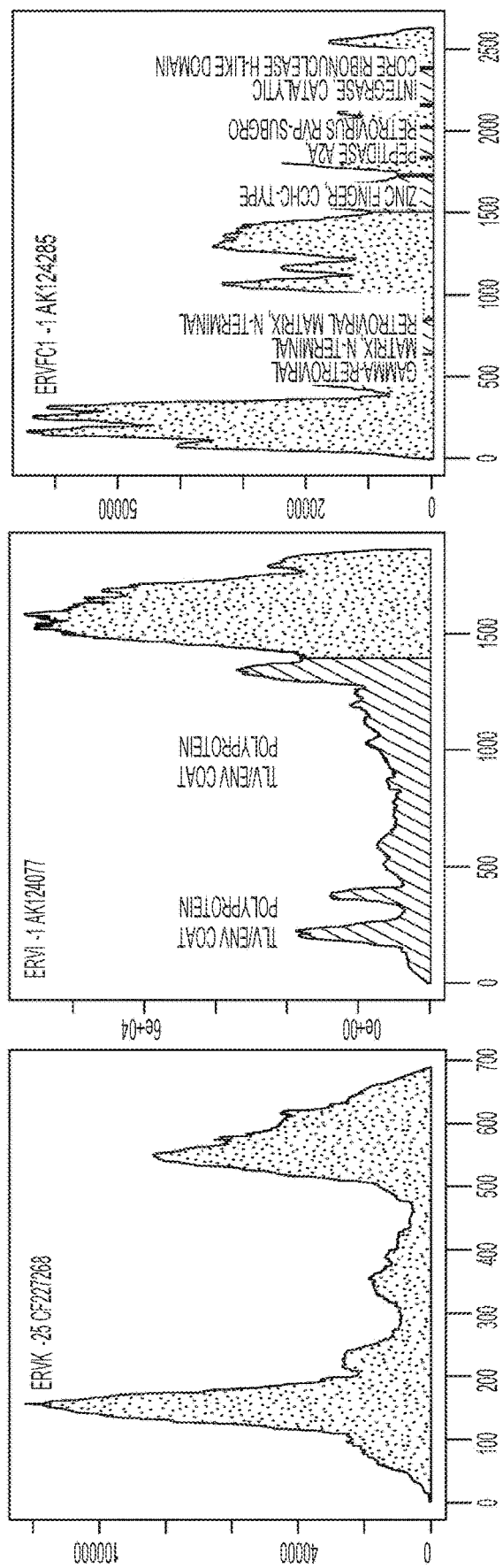
Figure 11F:
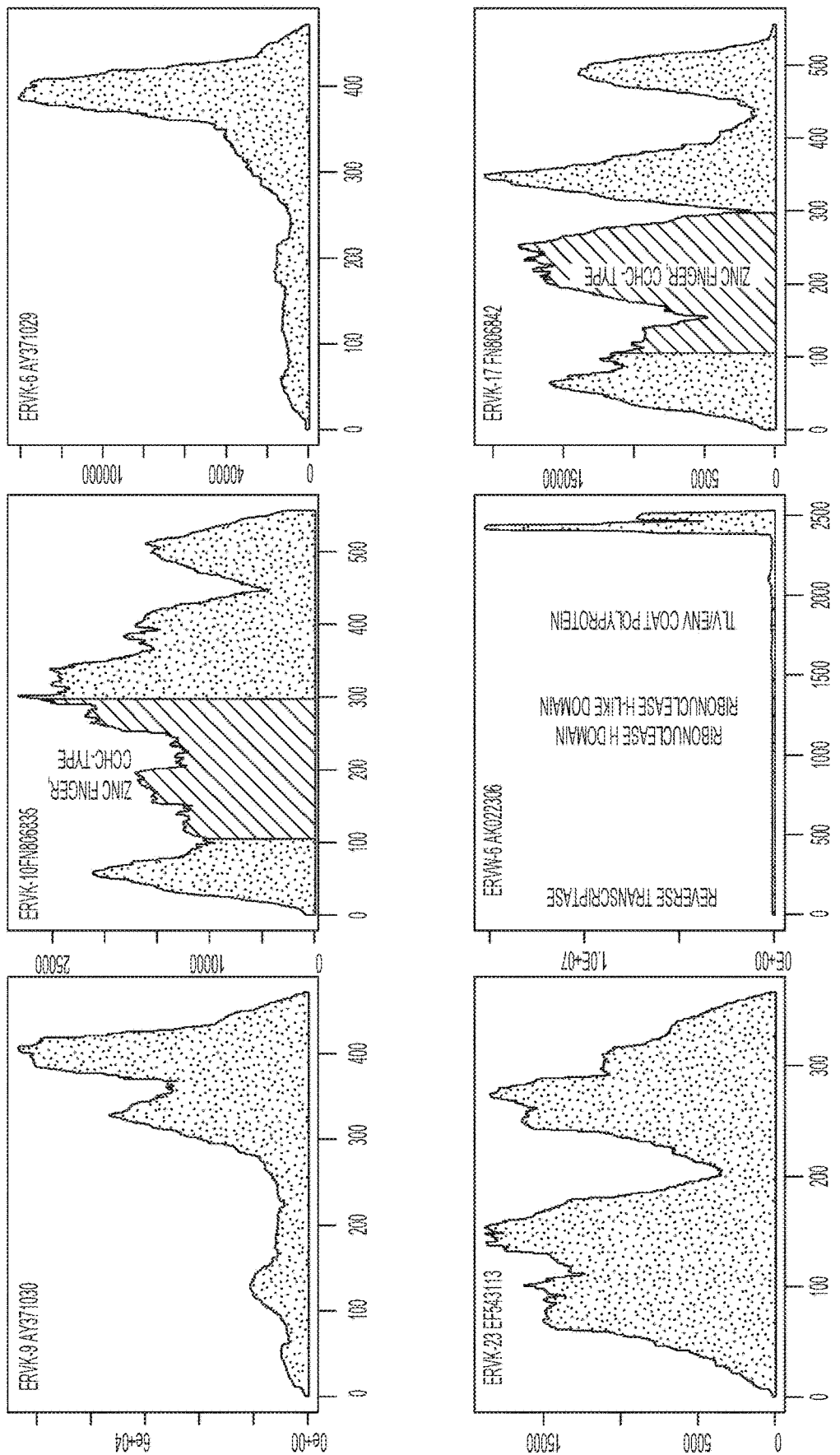
Figure 11F:
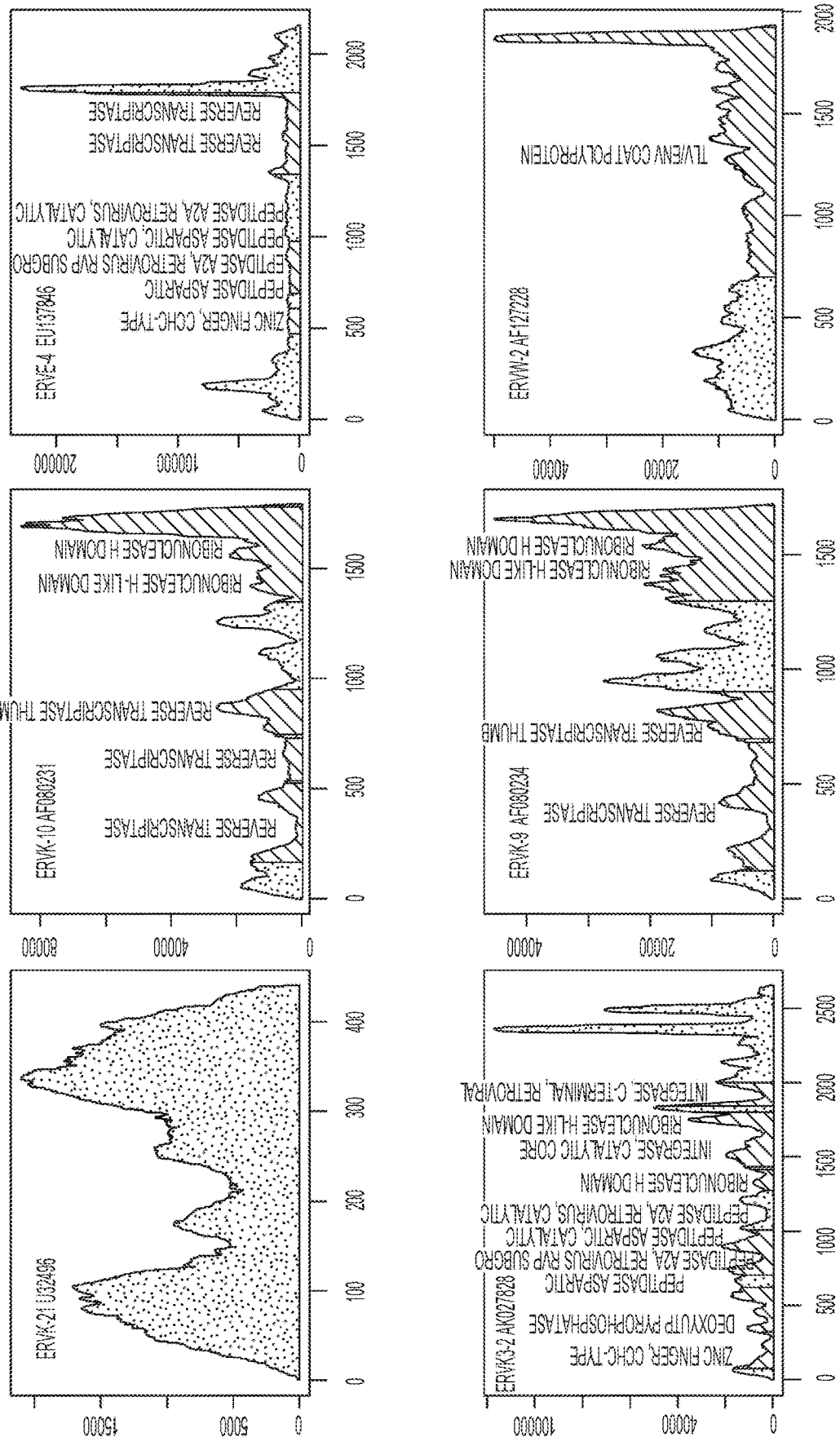
Figure 11G:
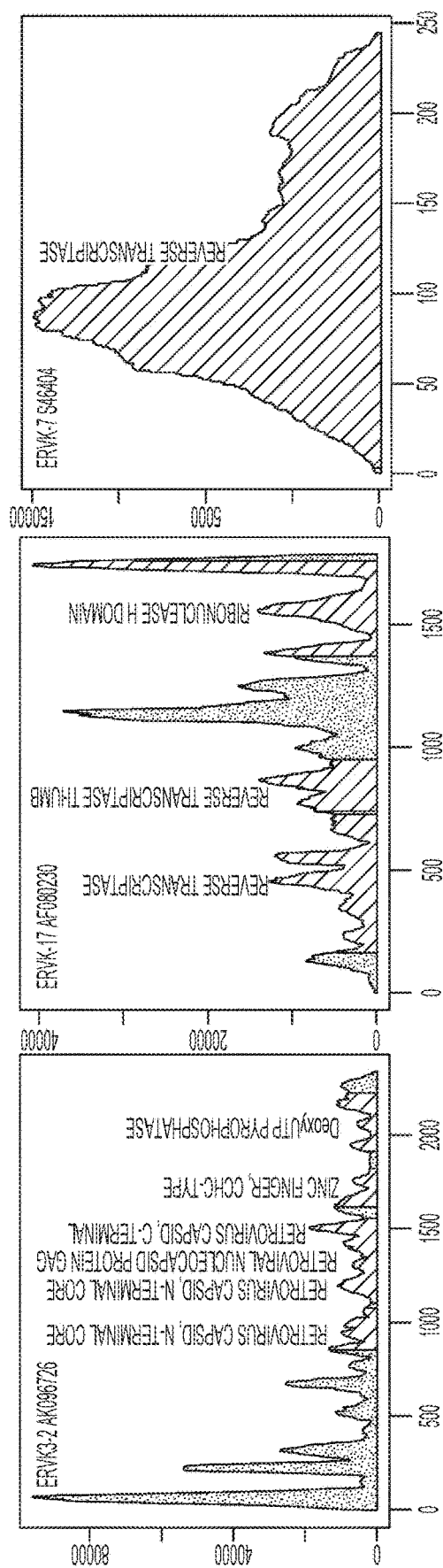
Figure 11G:
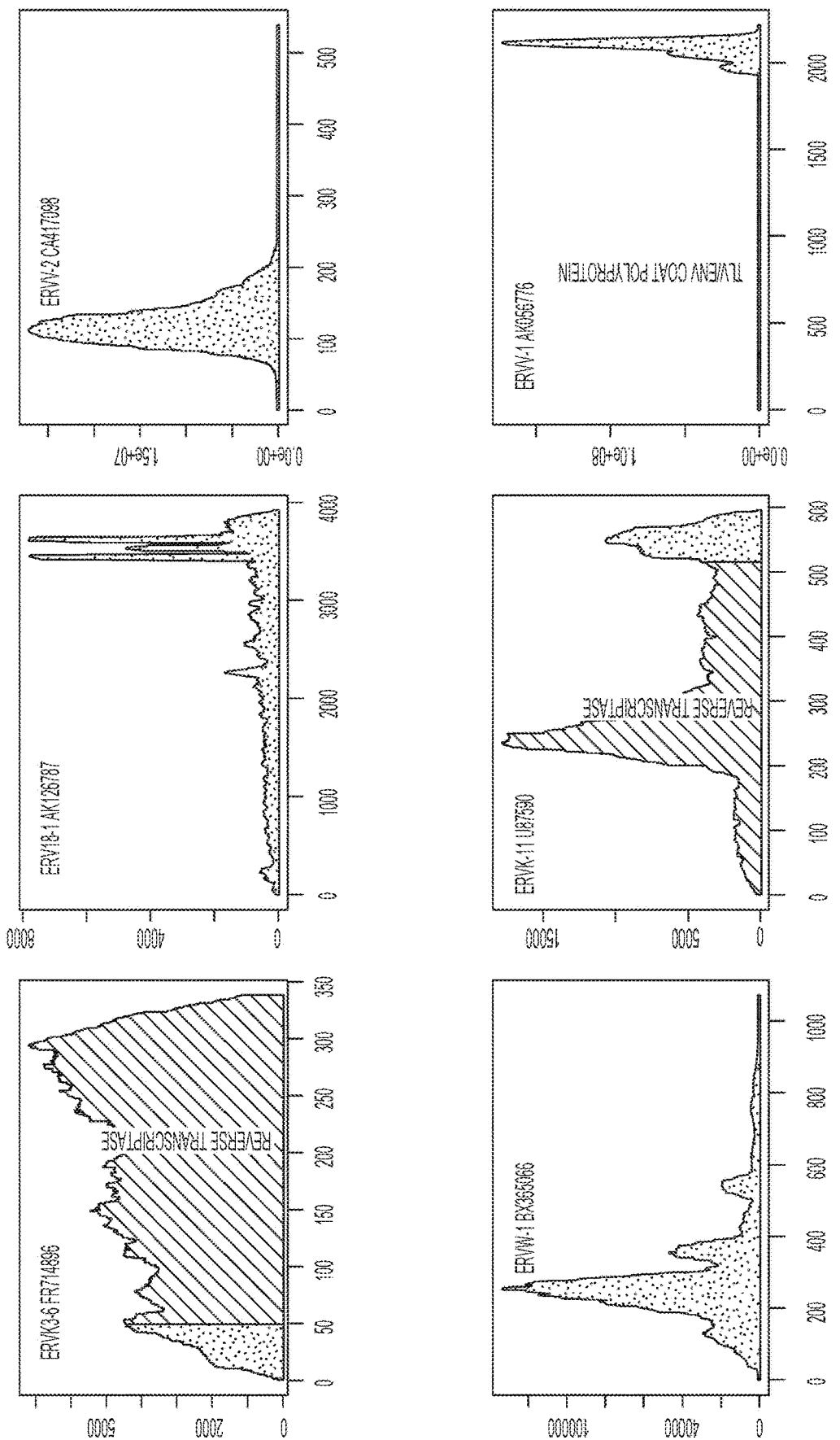
Figure 11G:
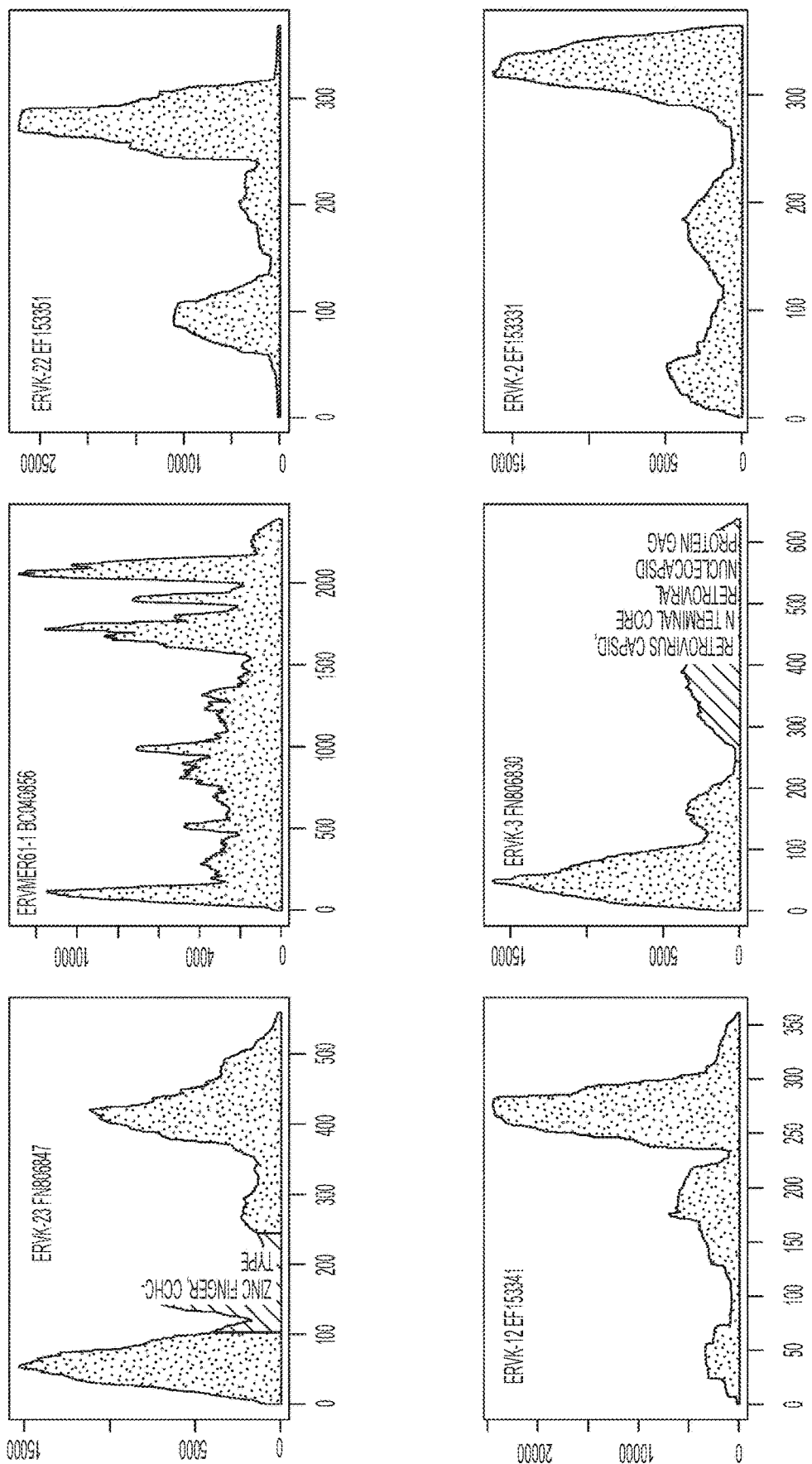
Figure 11H:
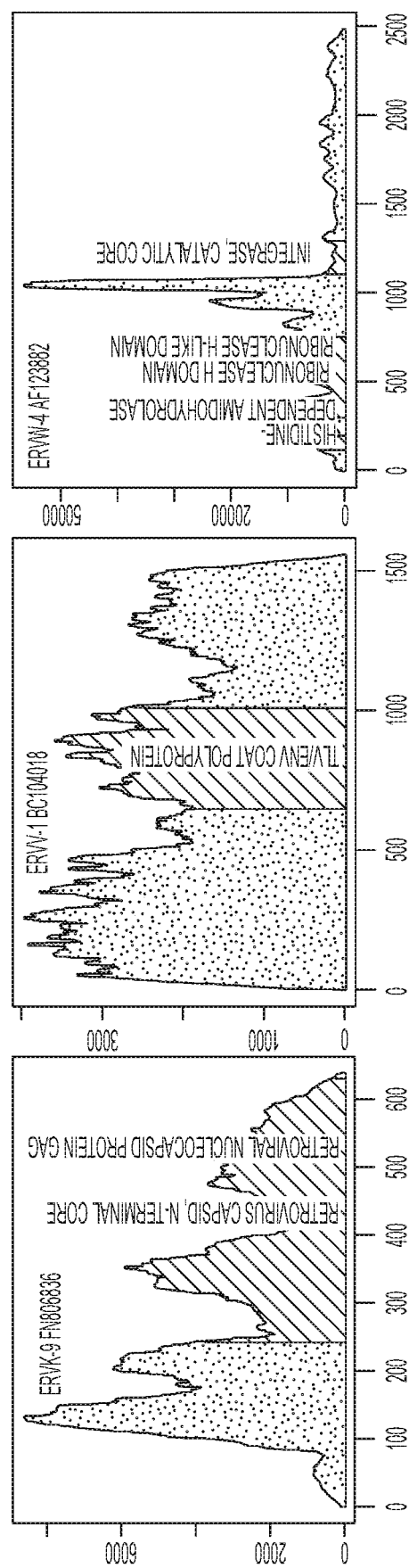
Figure 11H:
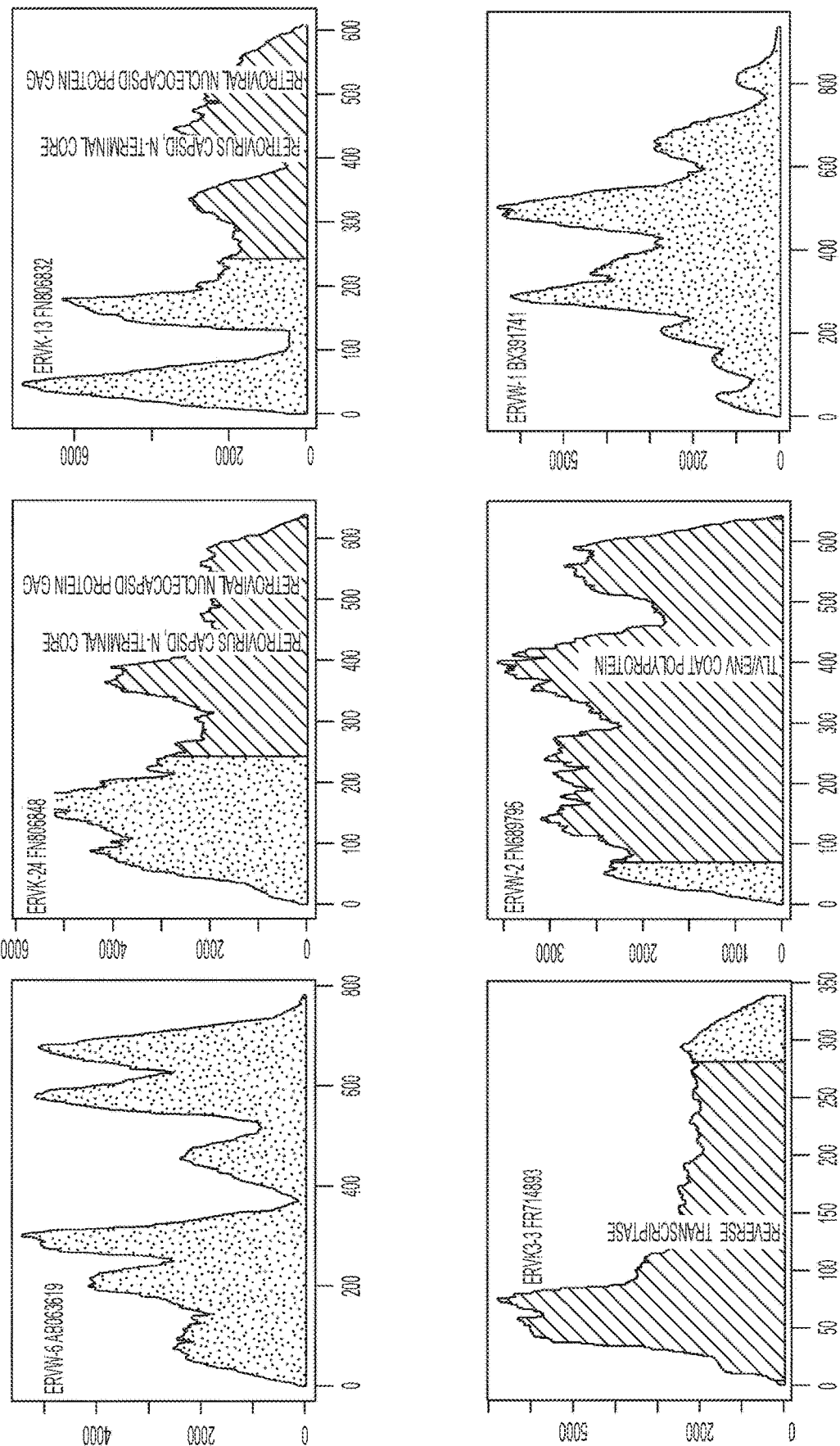
Figure 11H:
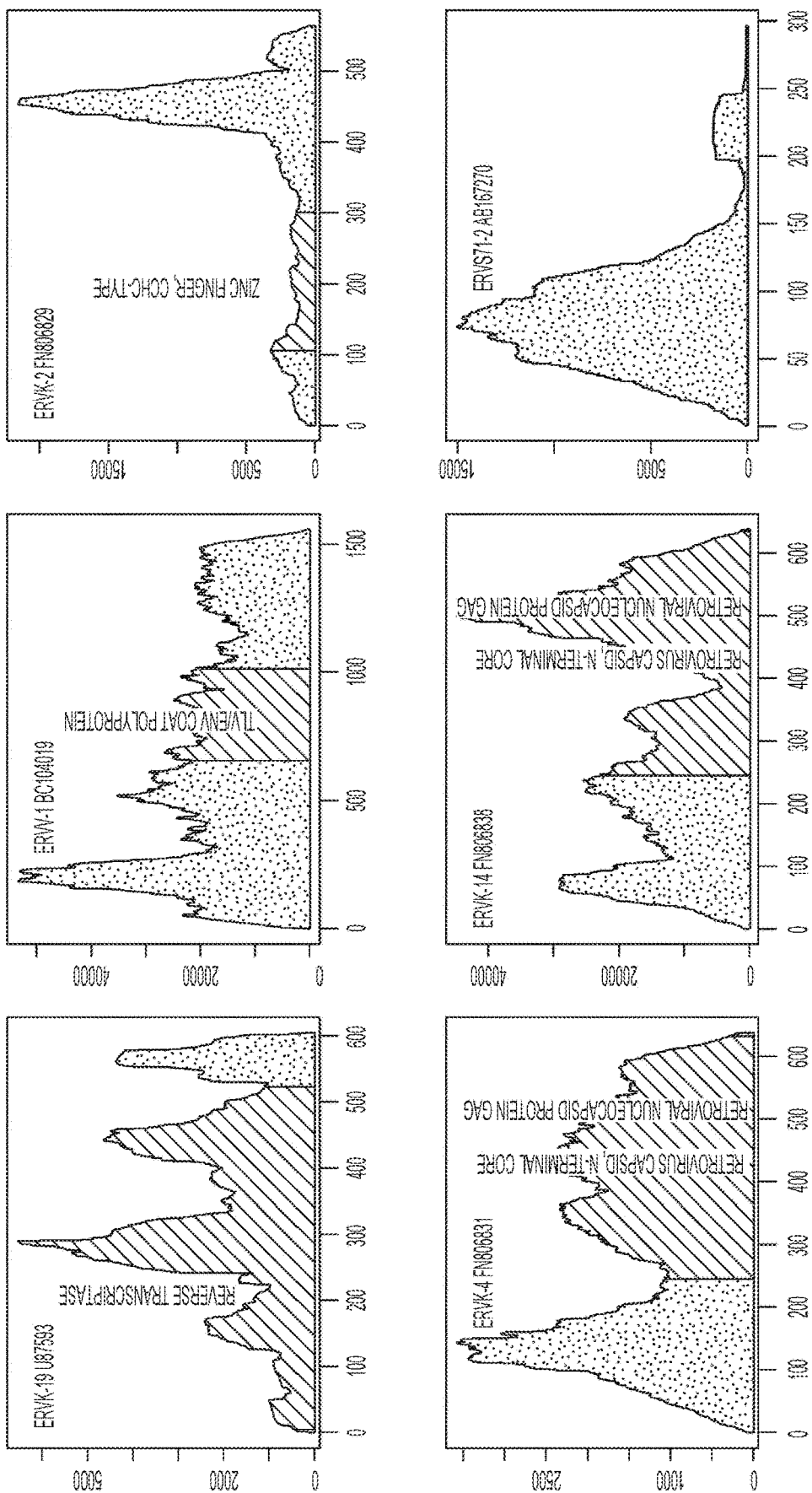
Figure 11H:
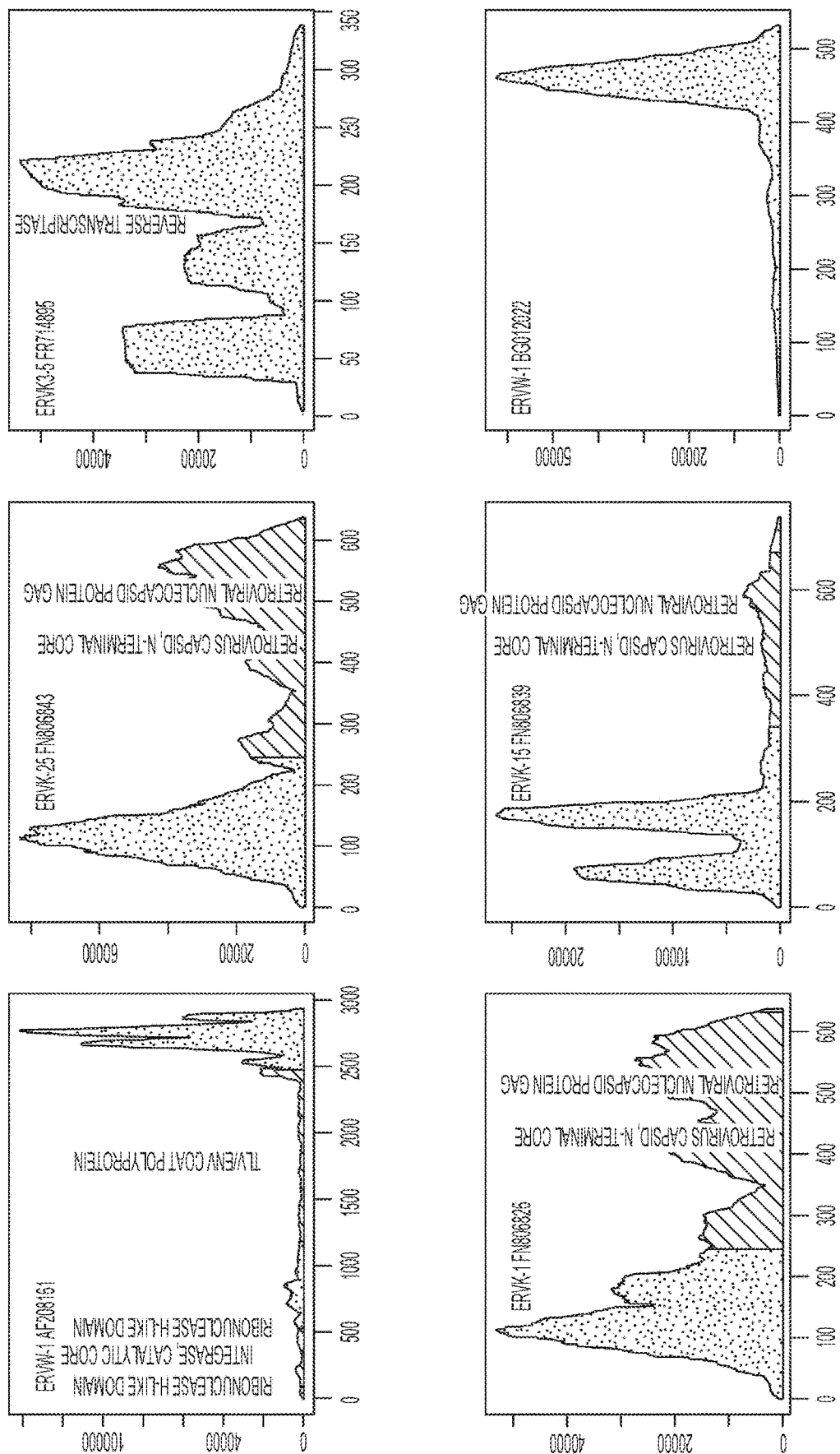
Figure 11I:
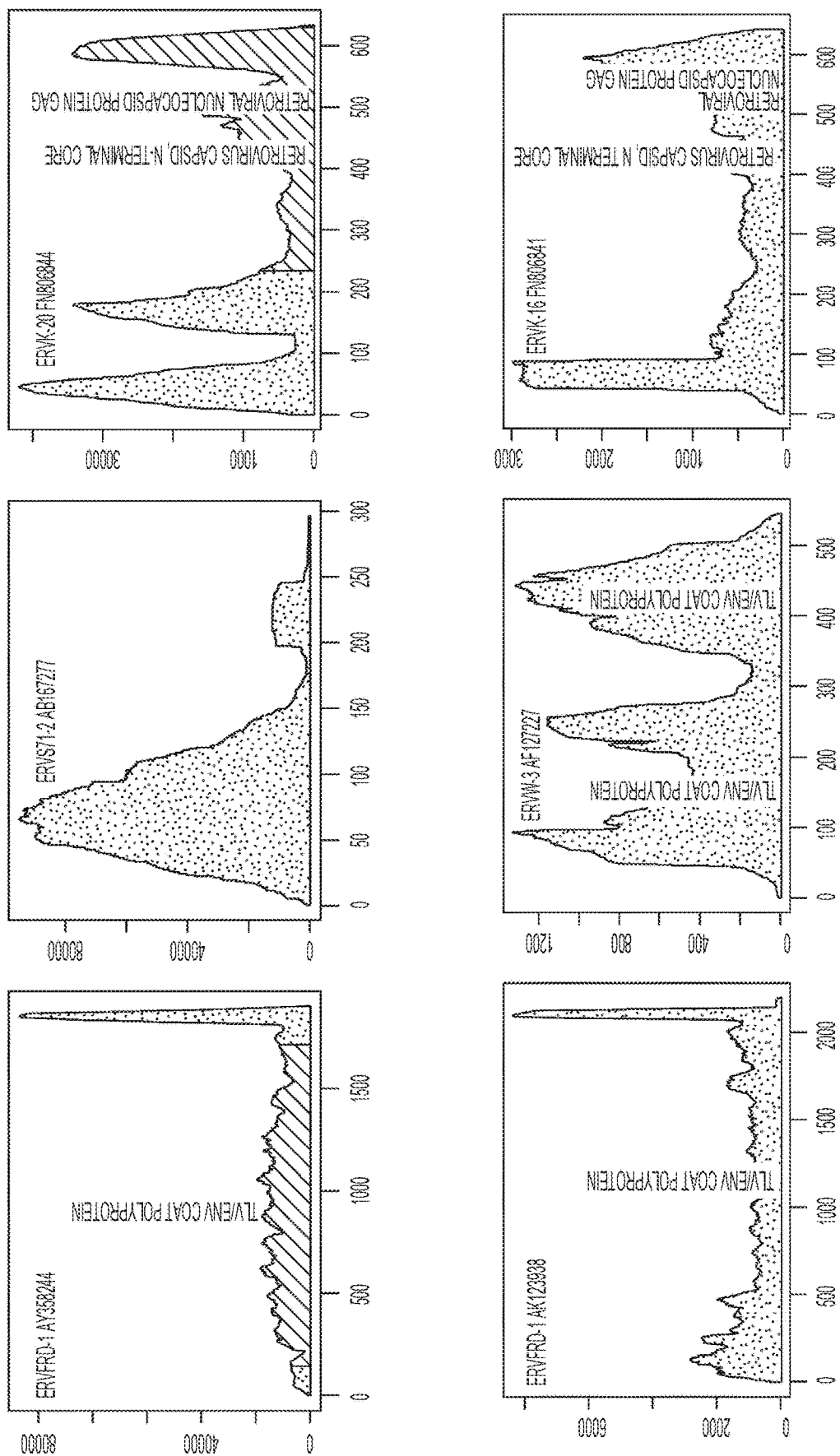
Figure 11I:
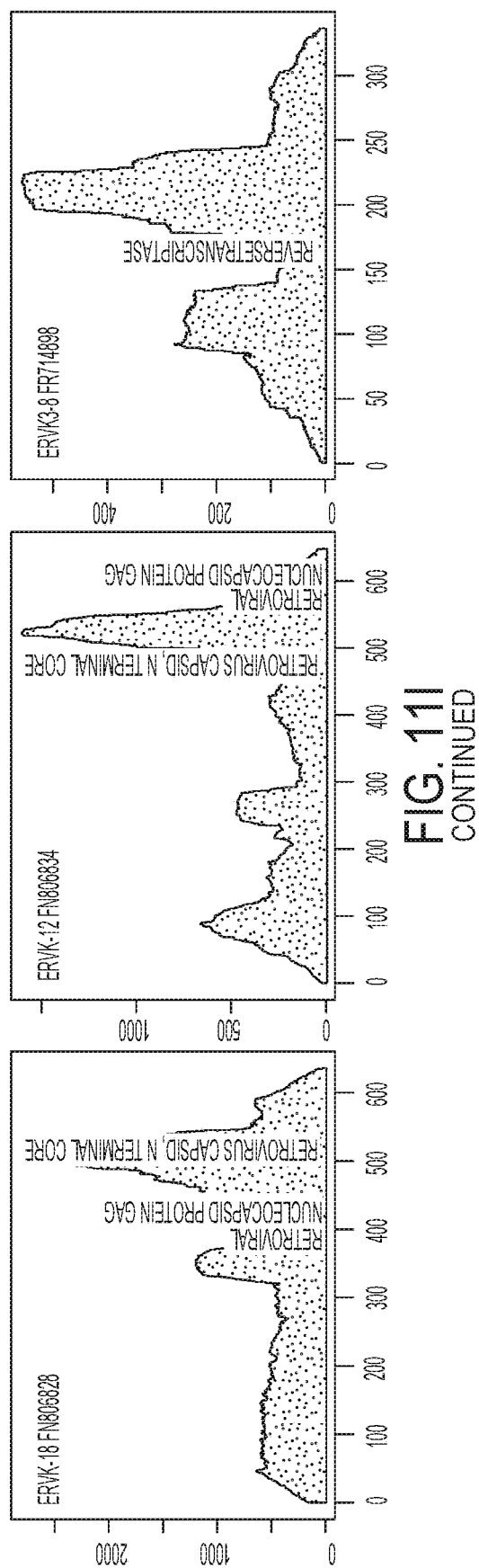
Figure 11I:
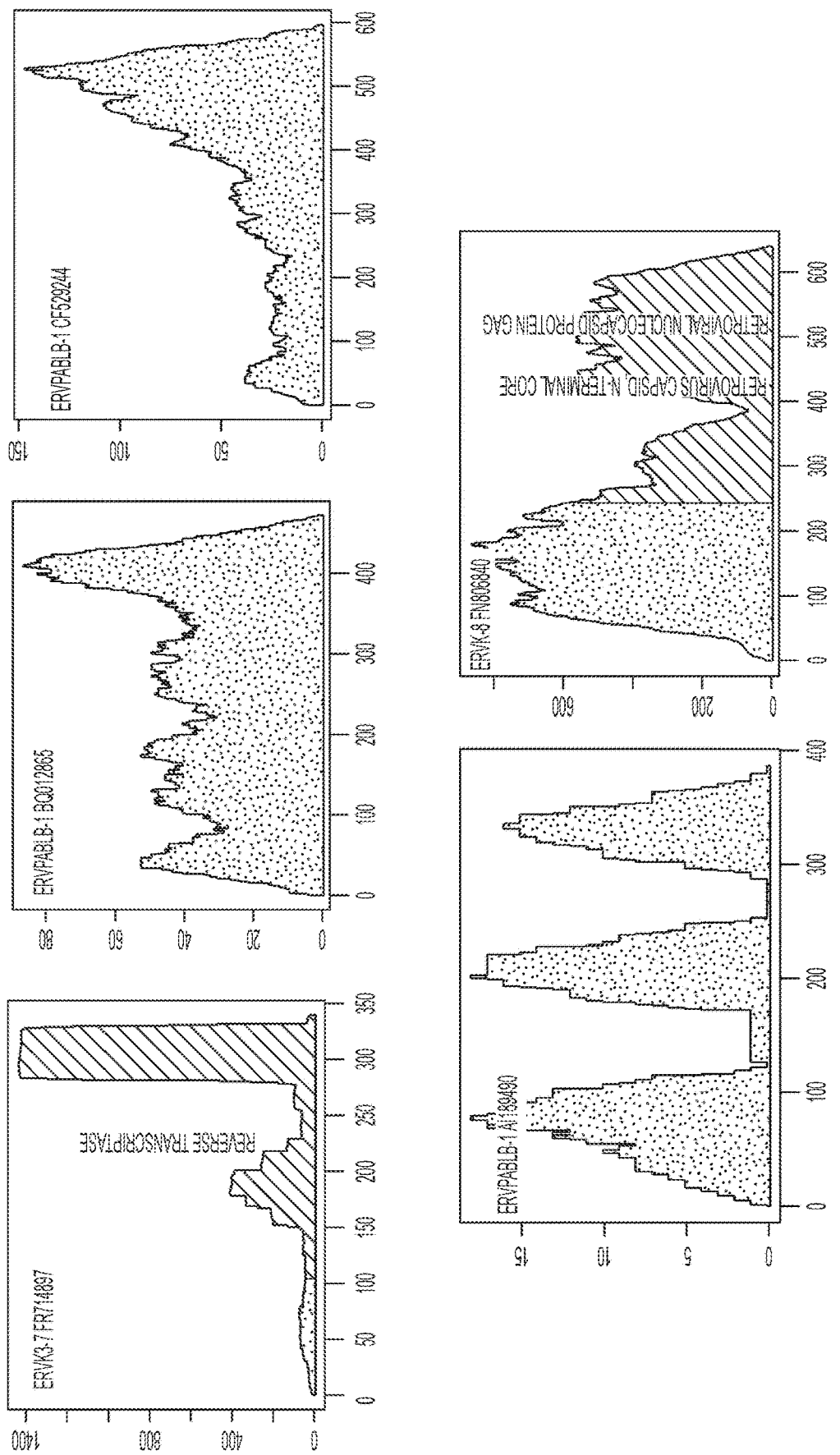
Figure 11J:
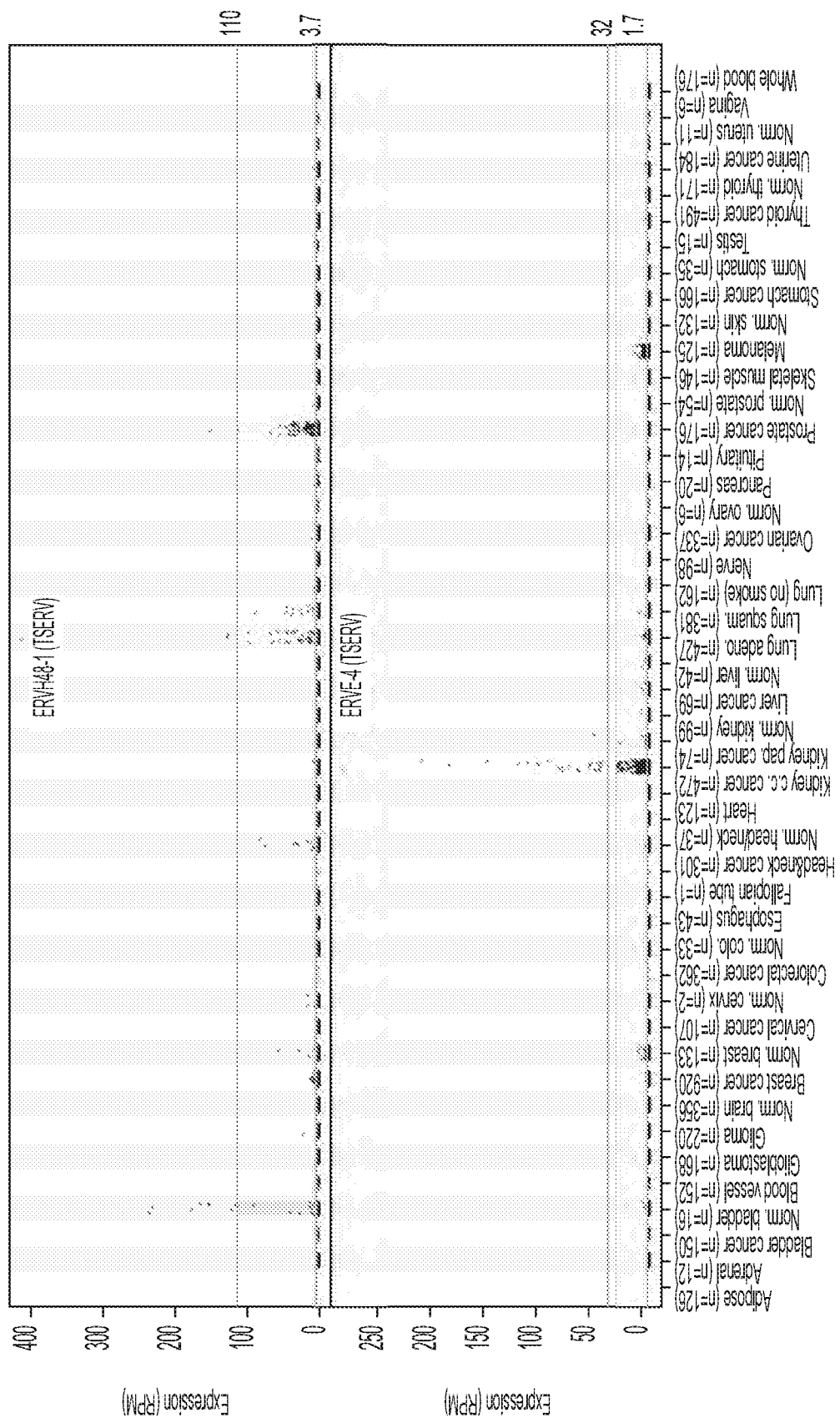
Figure 11J:
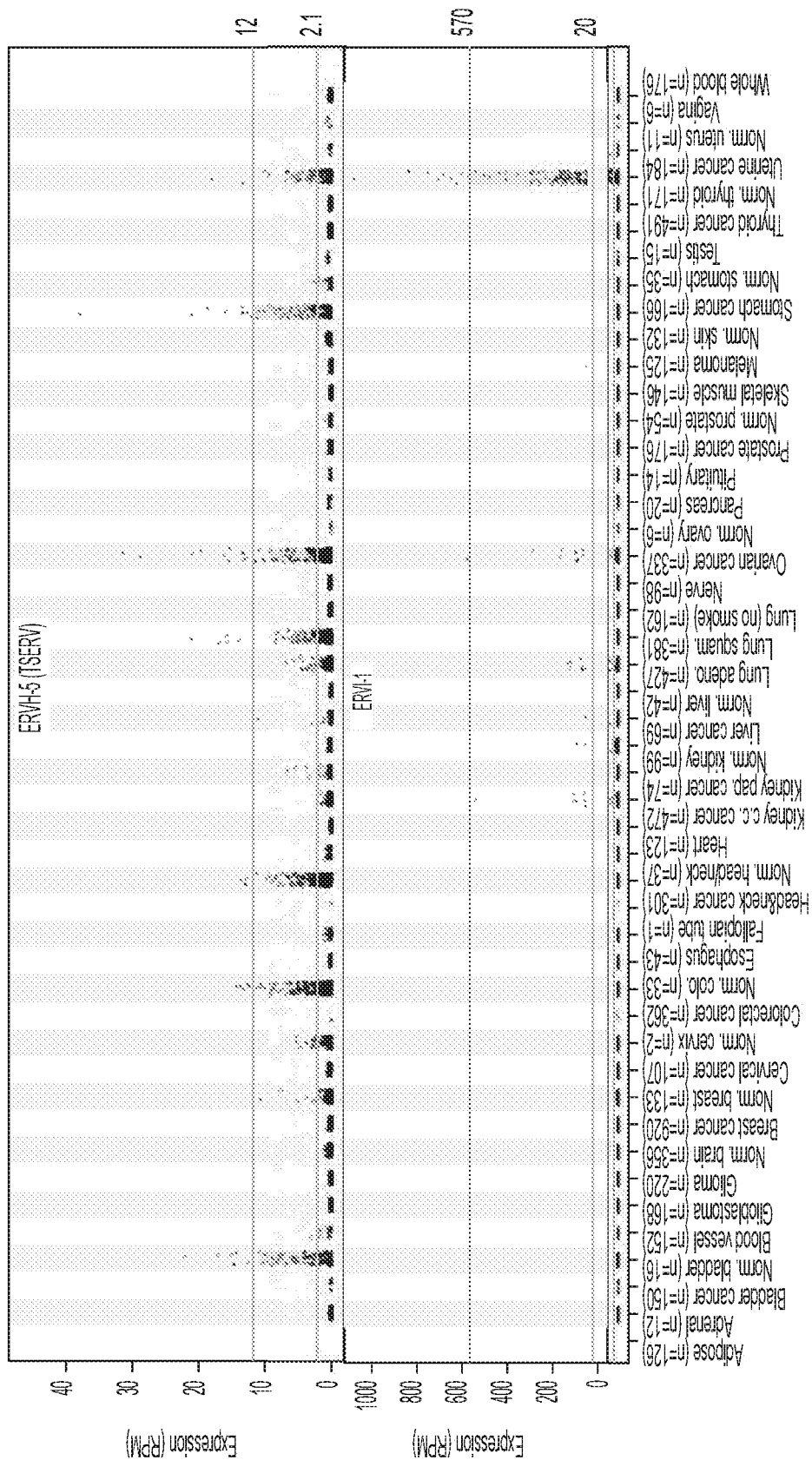
Figure 11J:
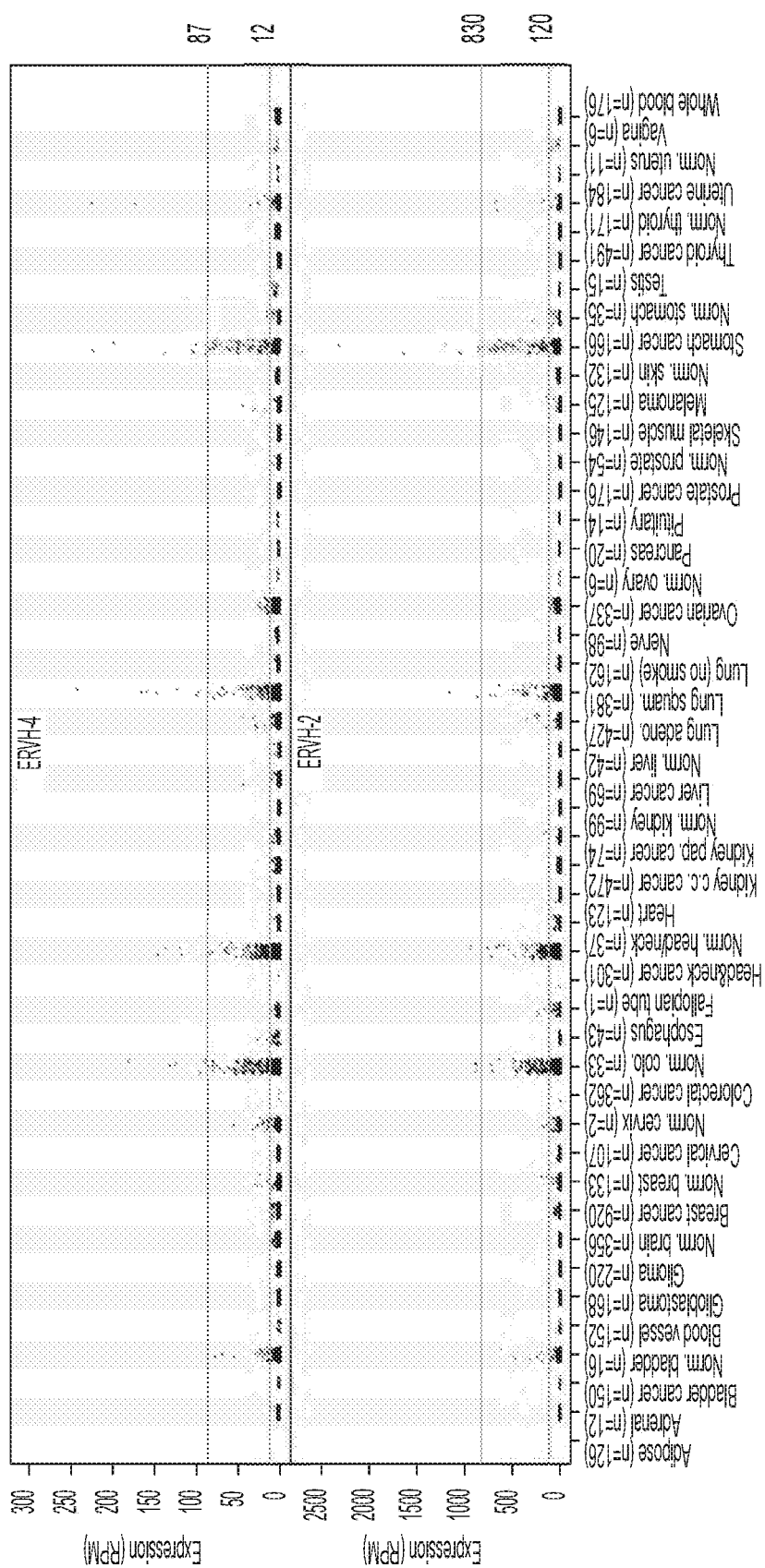
Figure 11K:
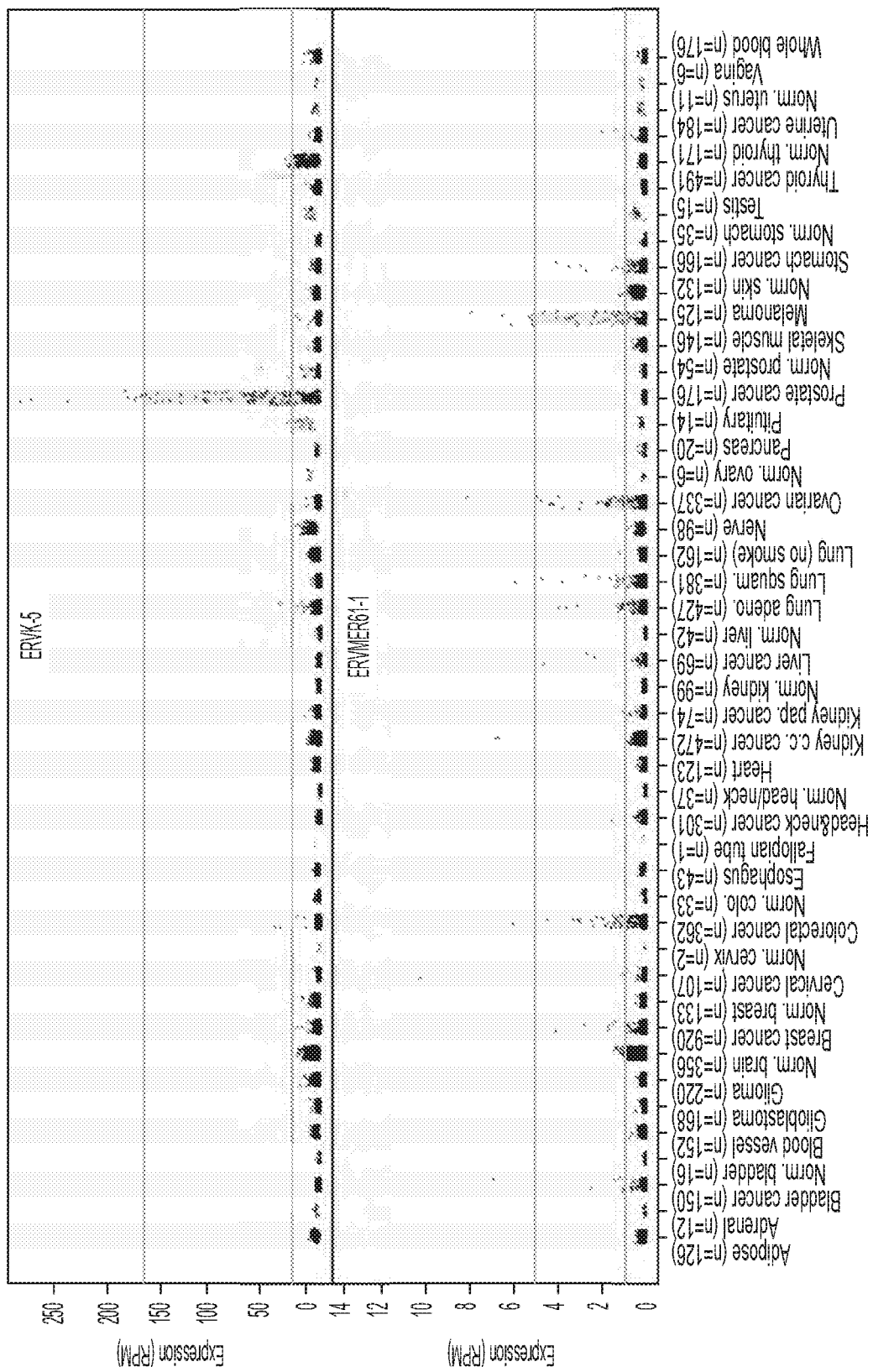
Figure 11K:
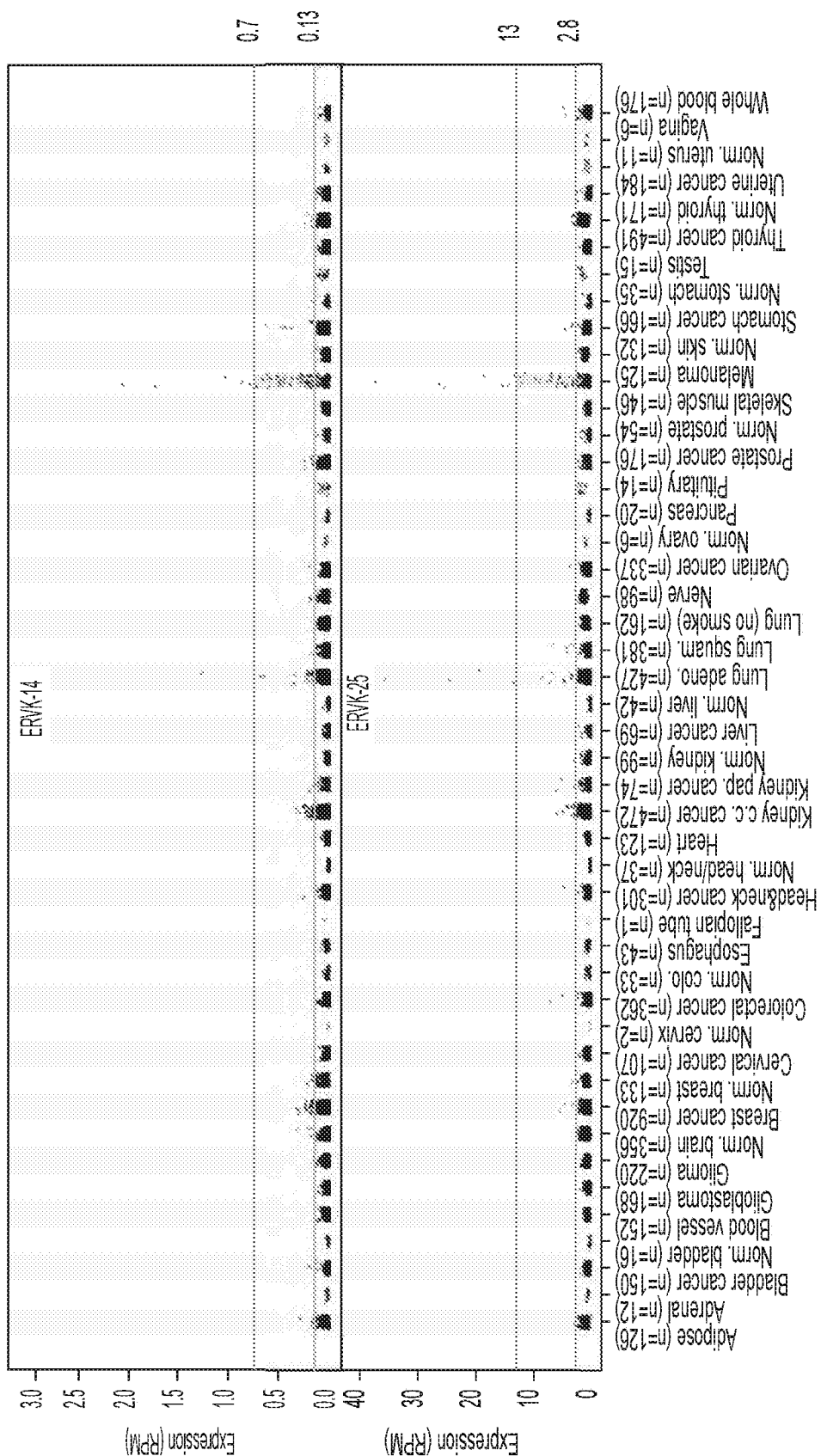
Figure 11K:
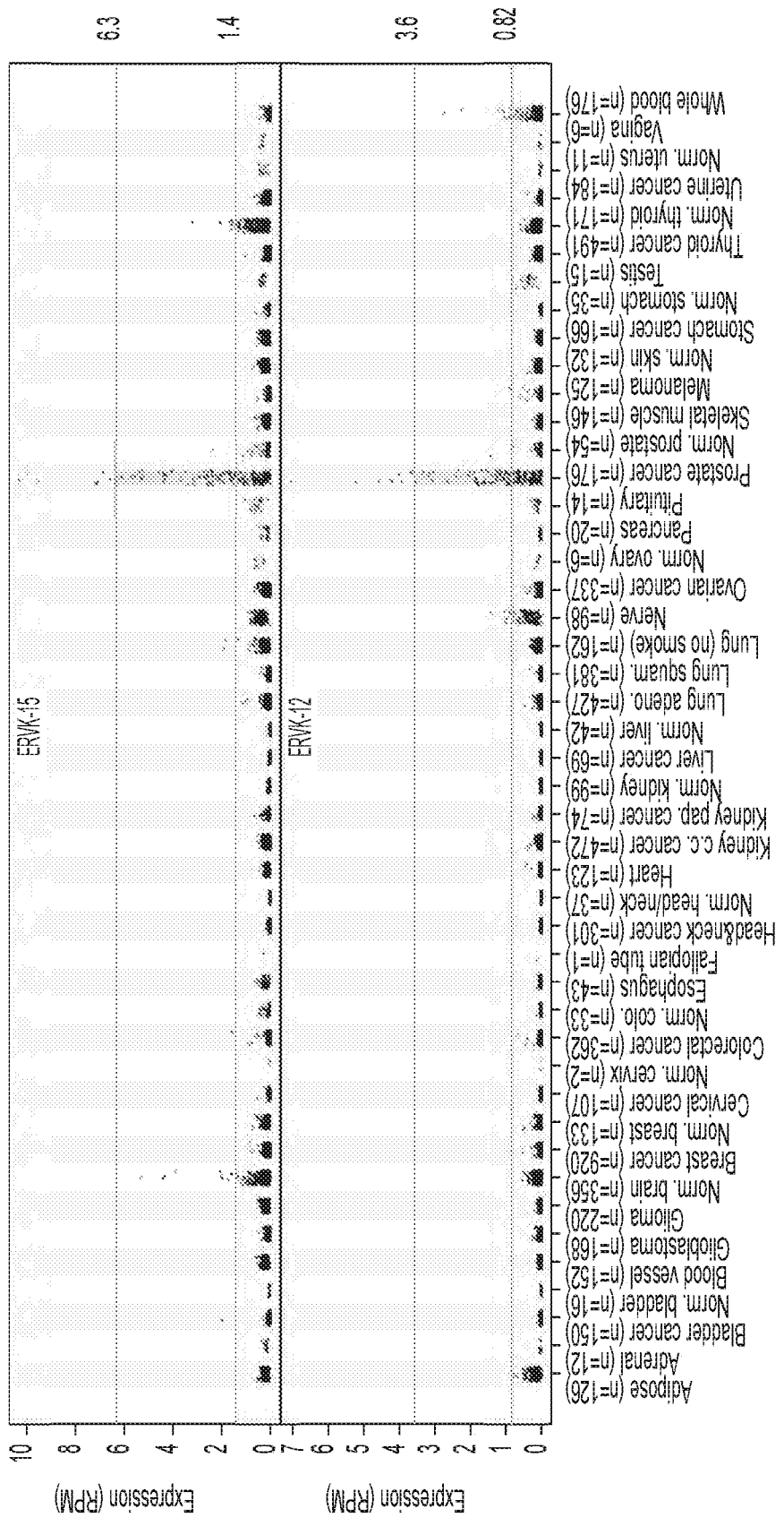
Figure 11L:
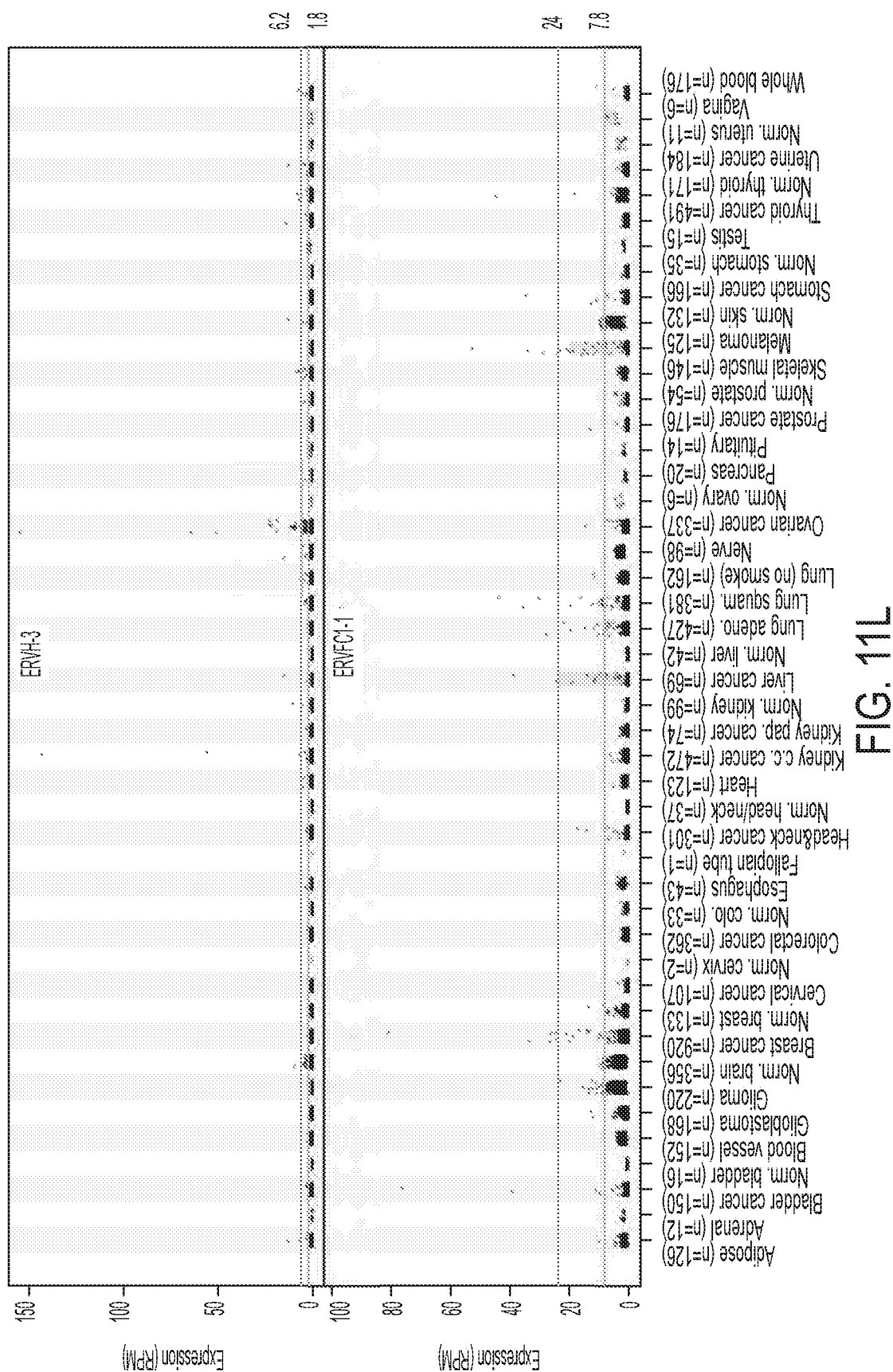
Figure 11L:
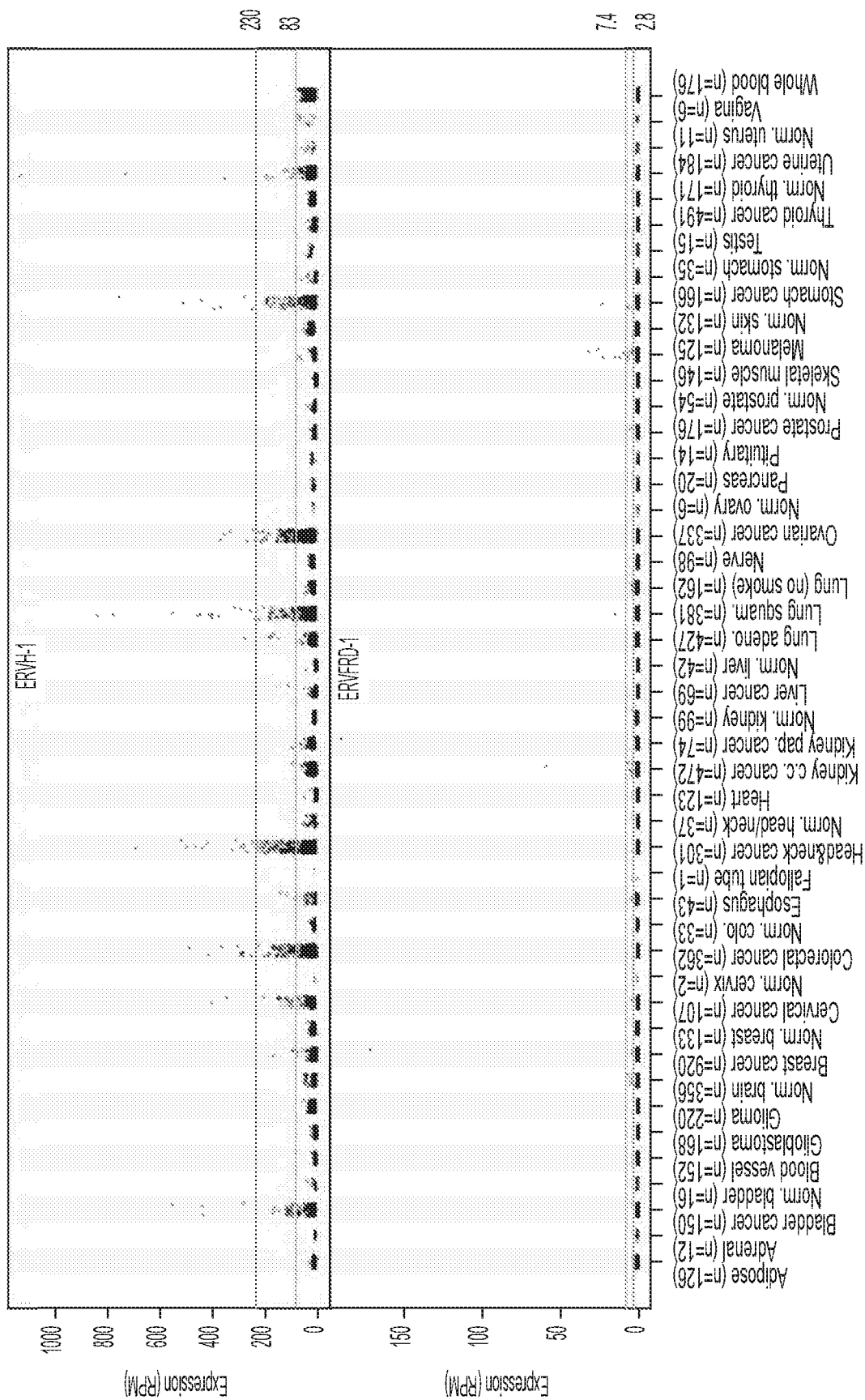
Figure 11L:
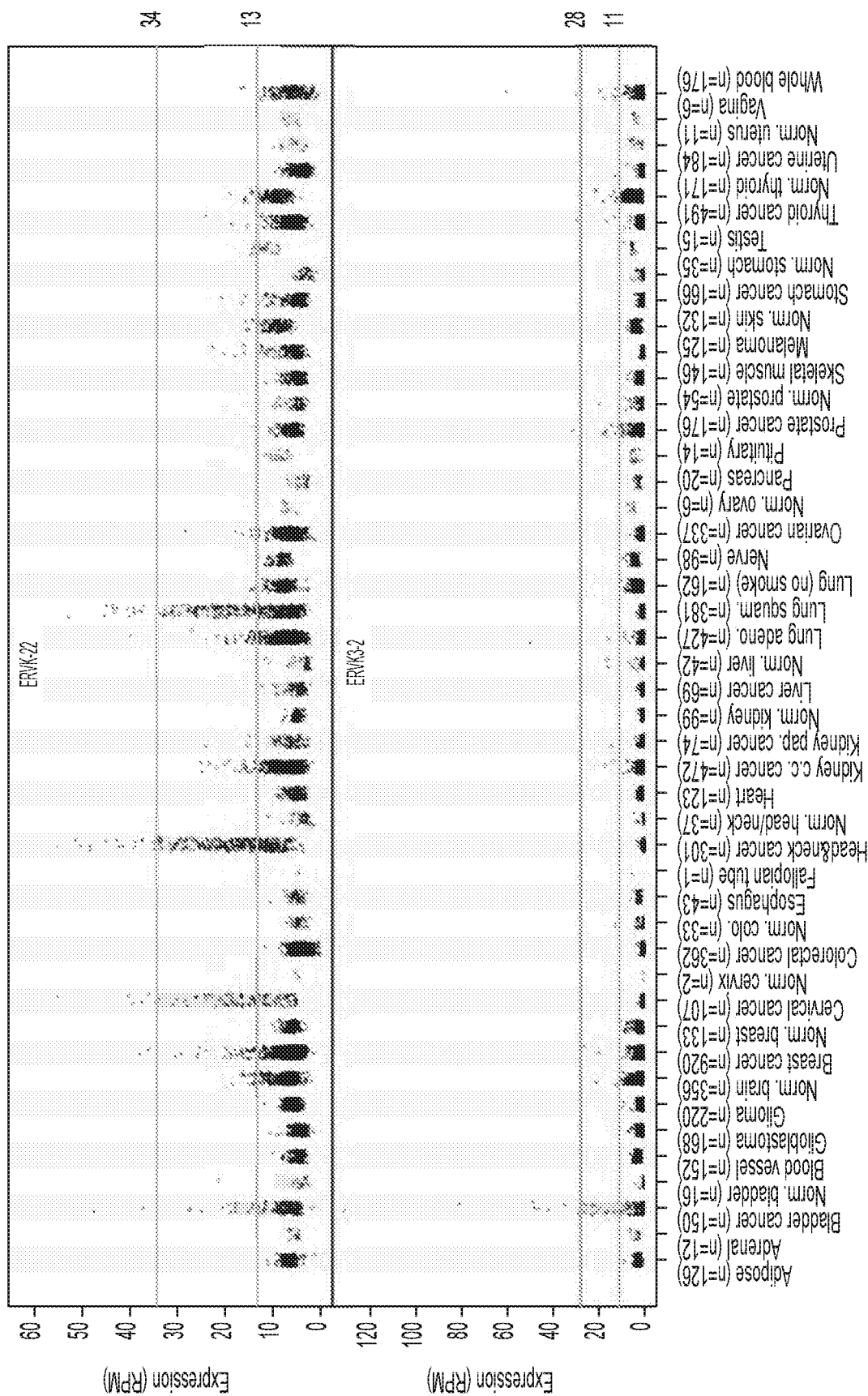
Figure 11M:
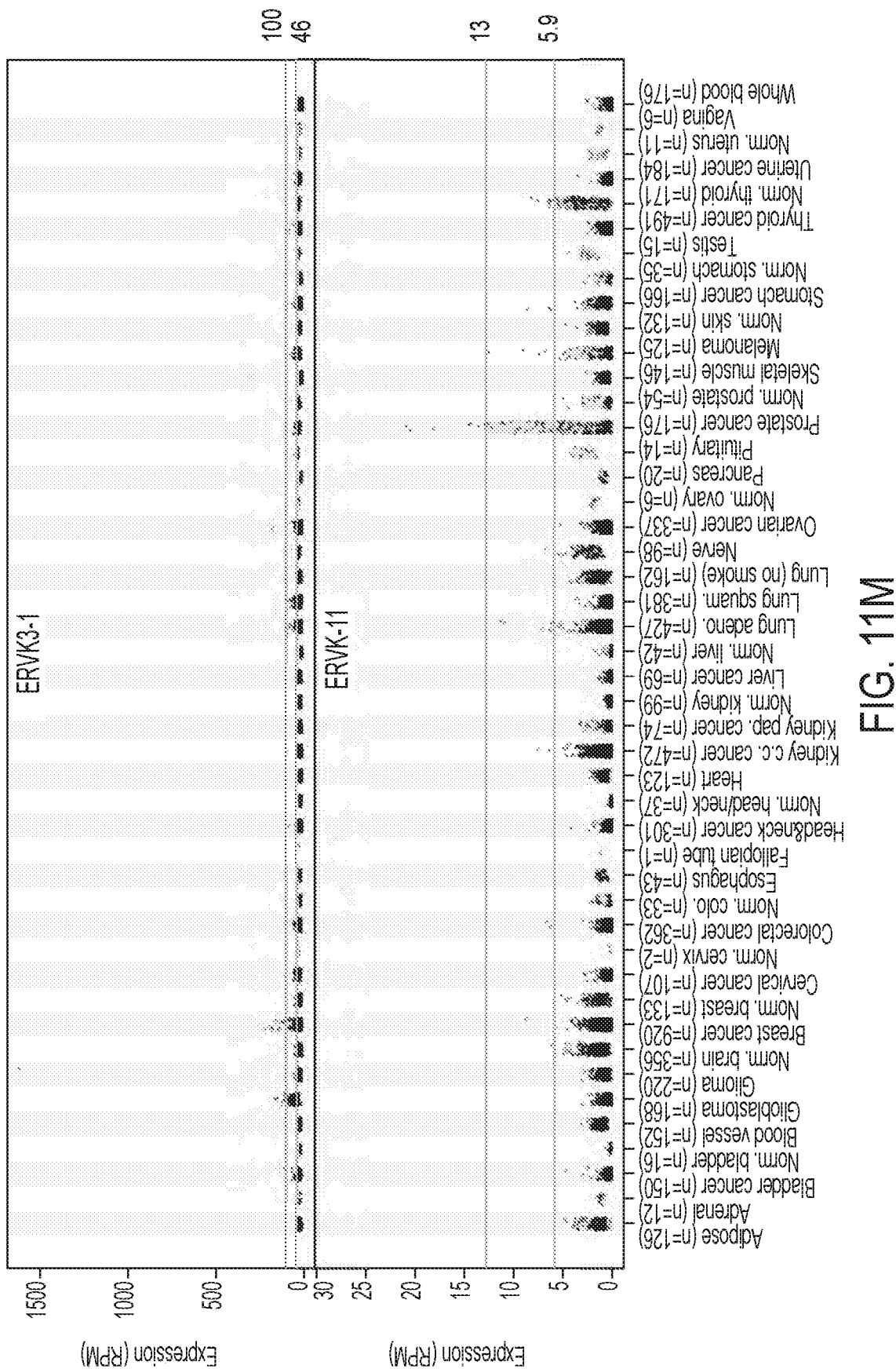
Figure 11M:
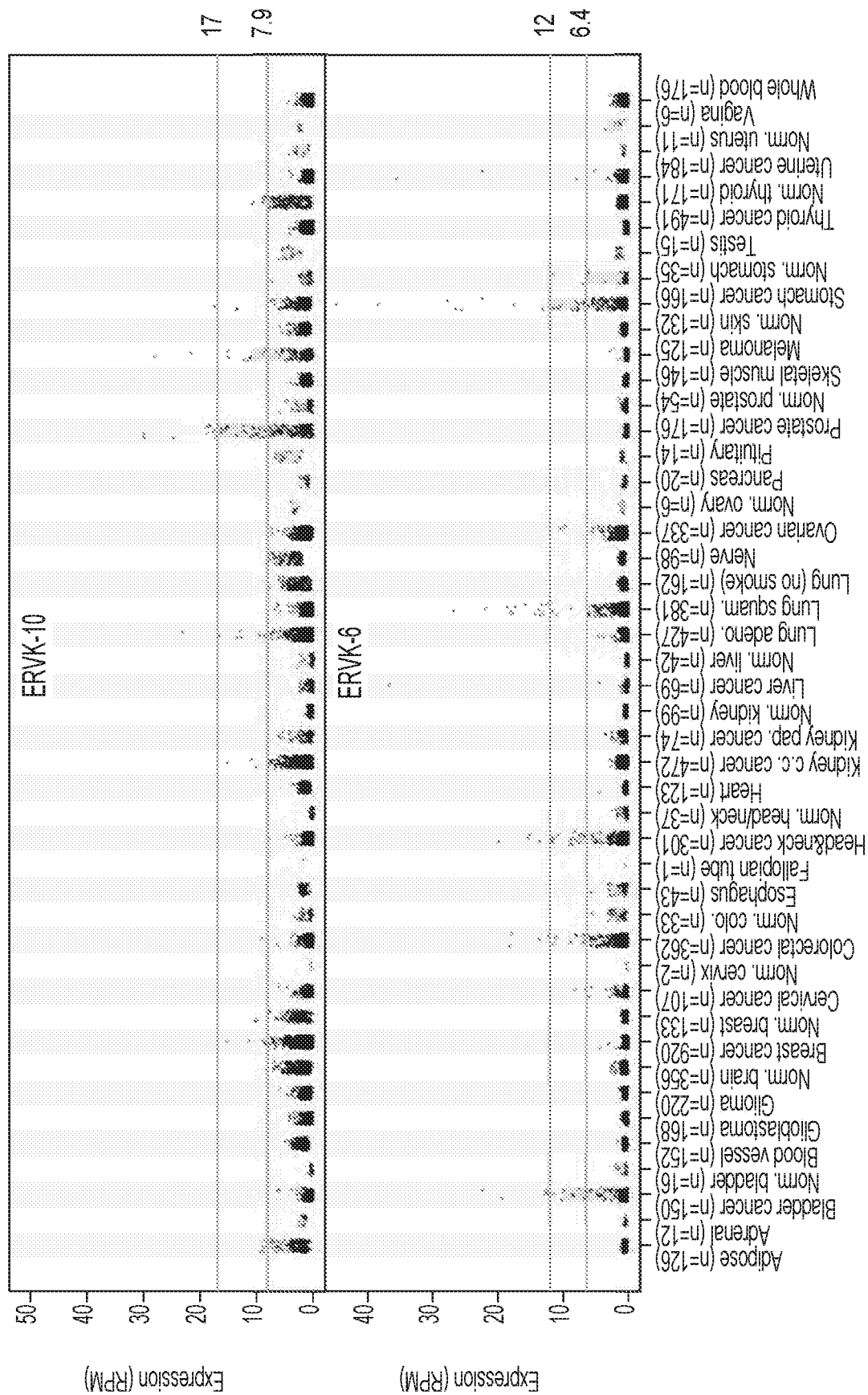
Figure 11M:
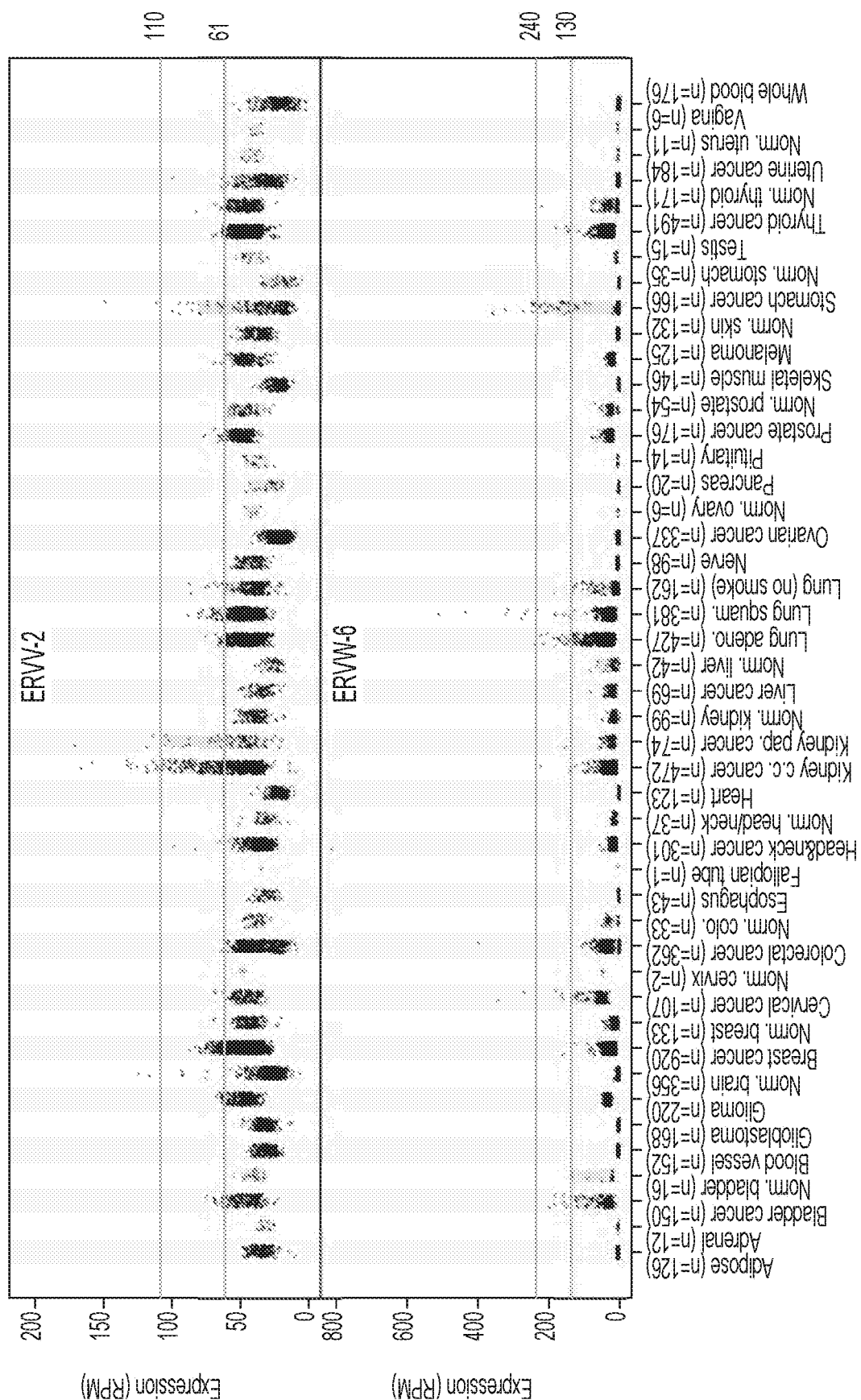
Figure 11N:
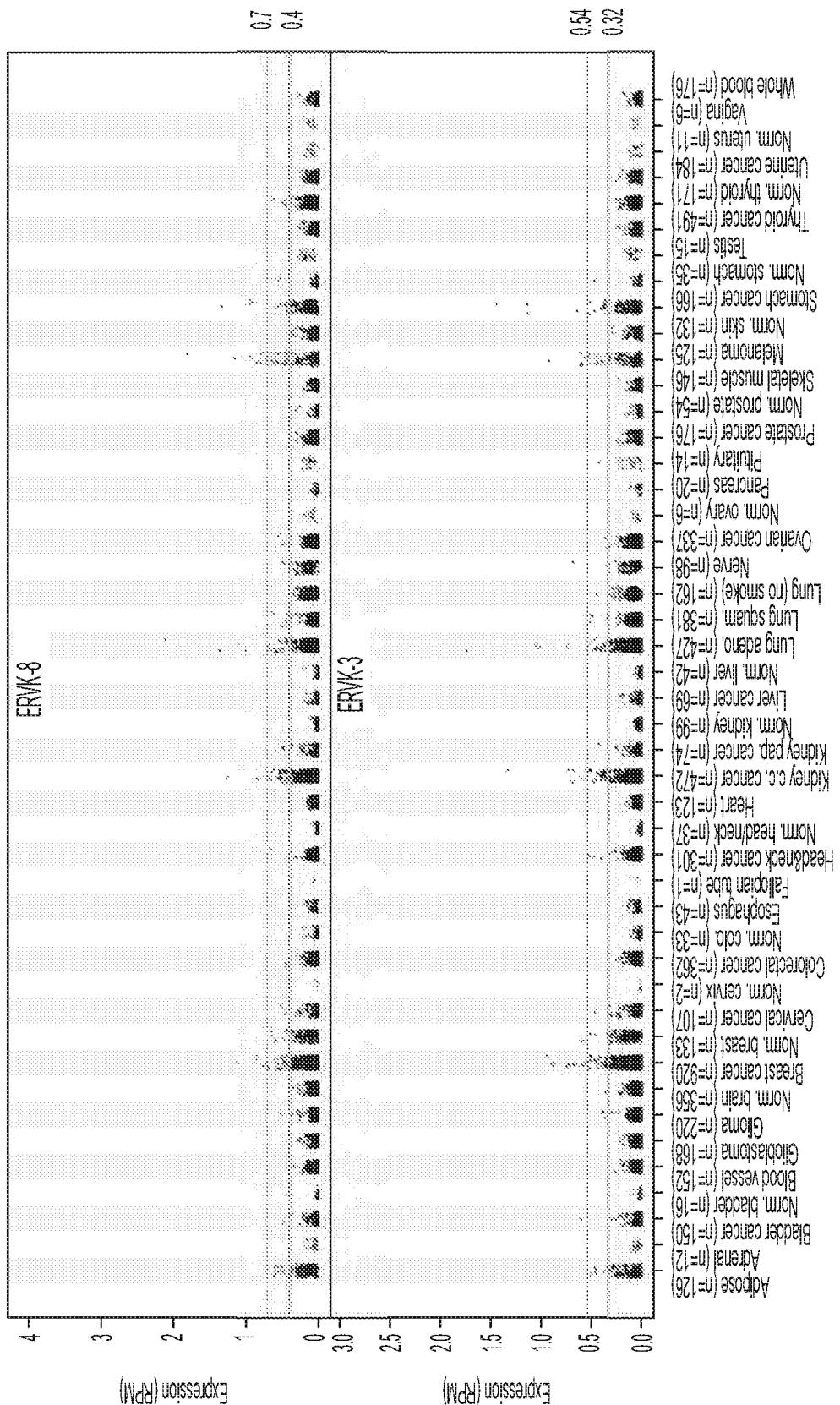
Figure 11N:
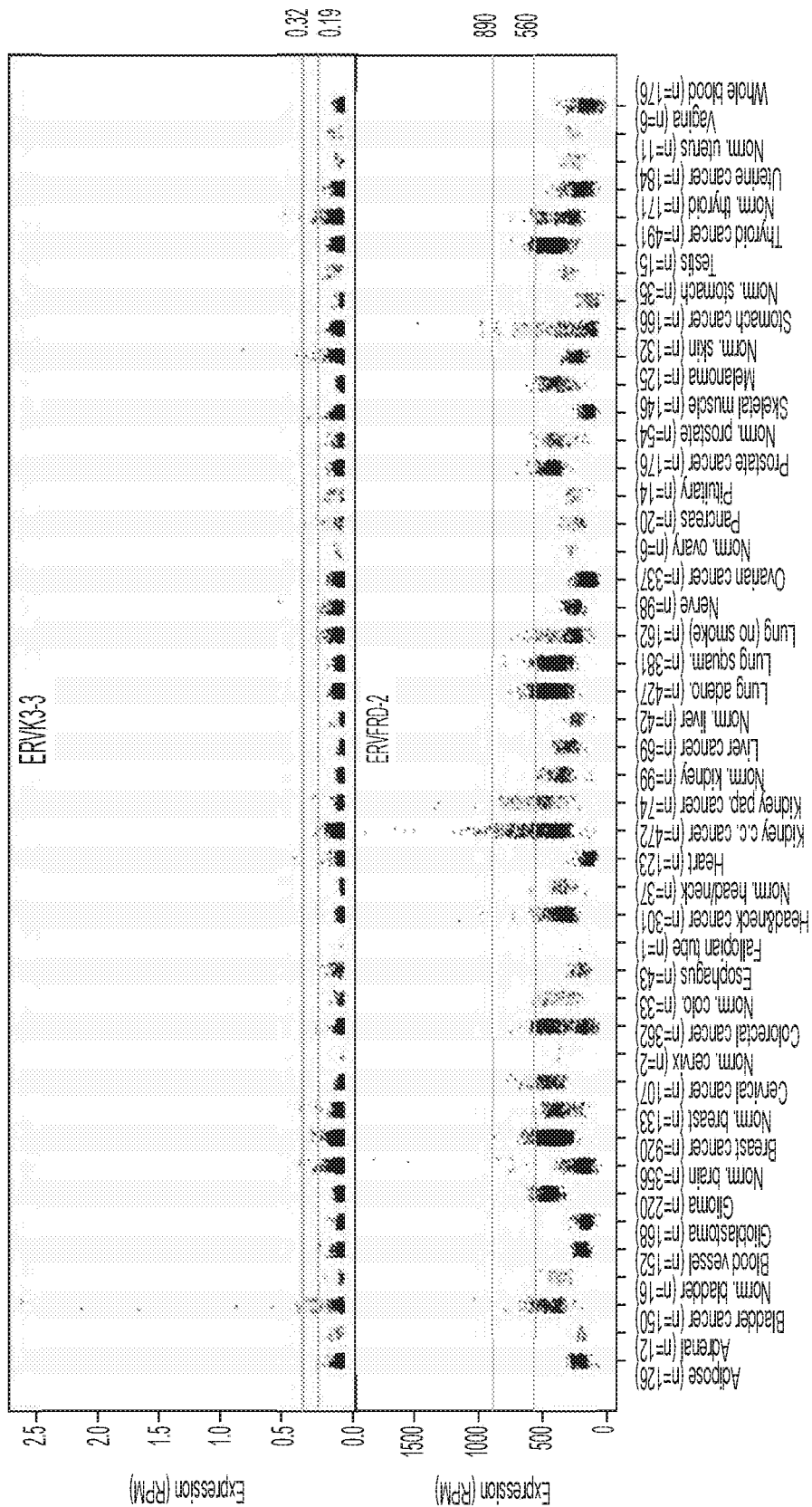
Figure 11N:
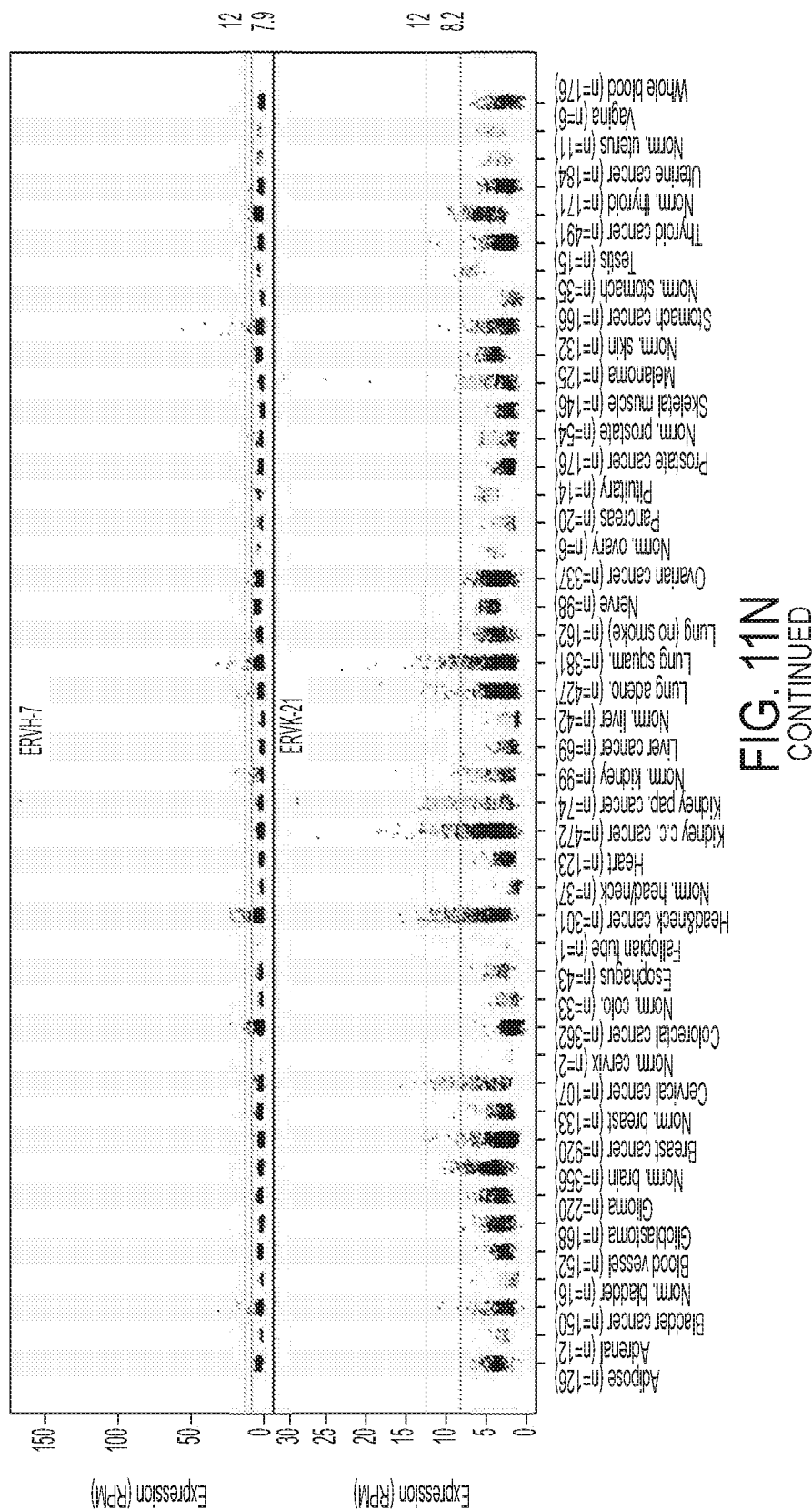
Figure 110:
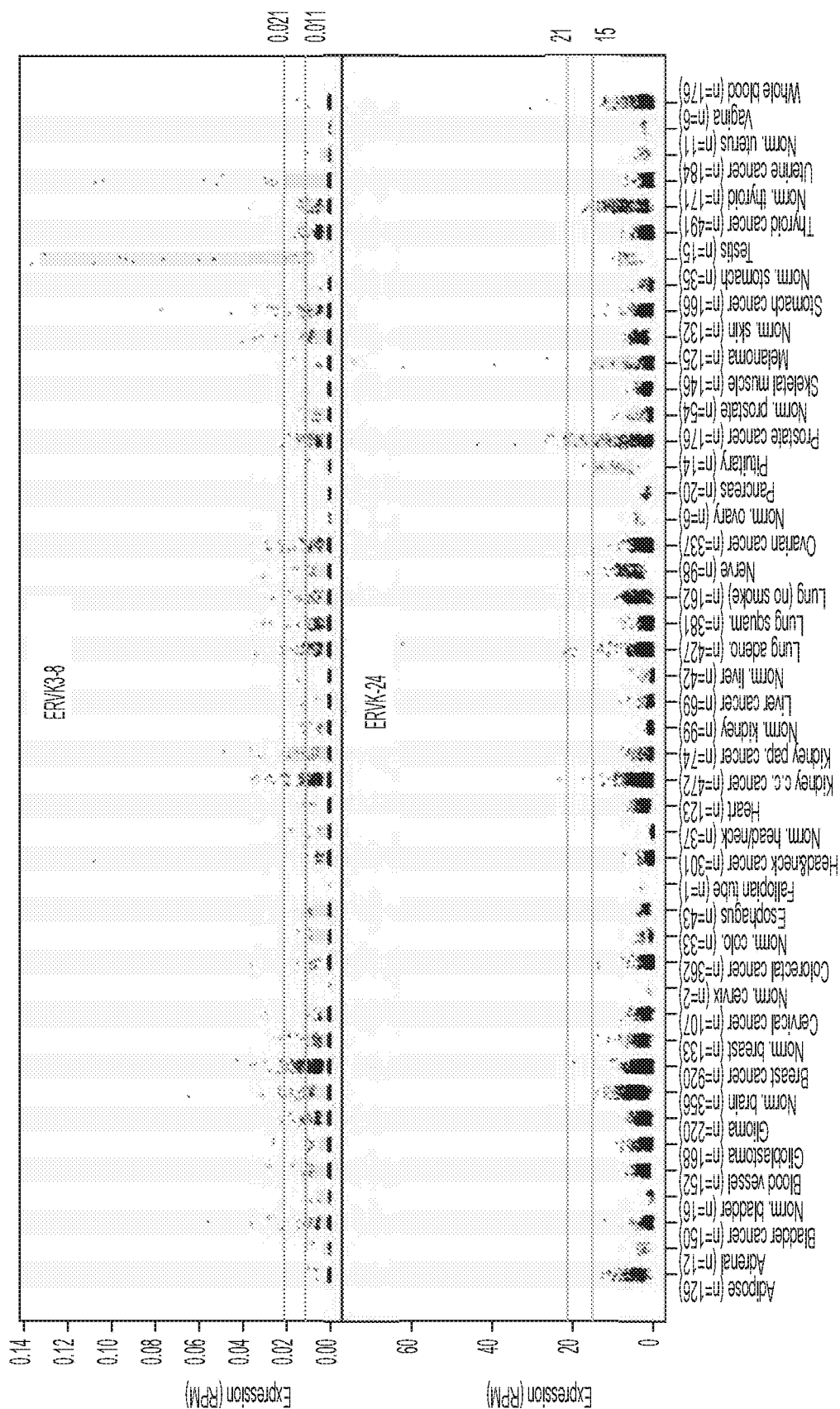
Figure 110:
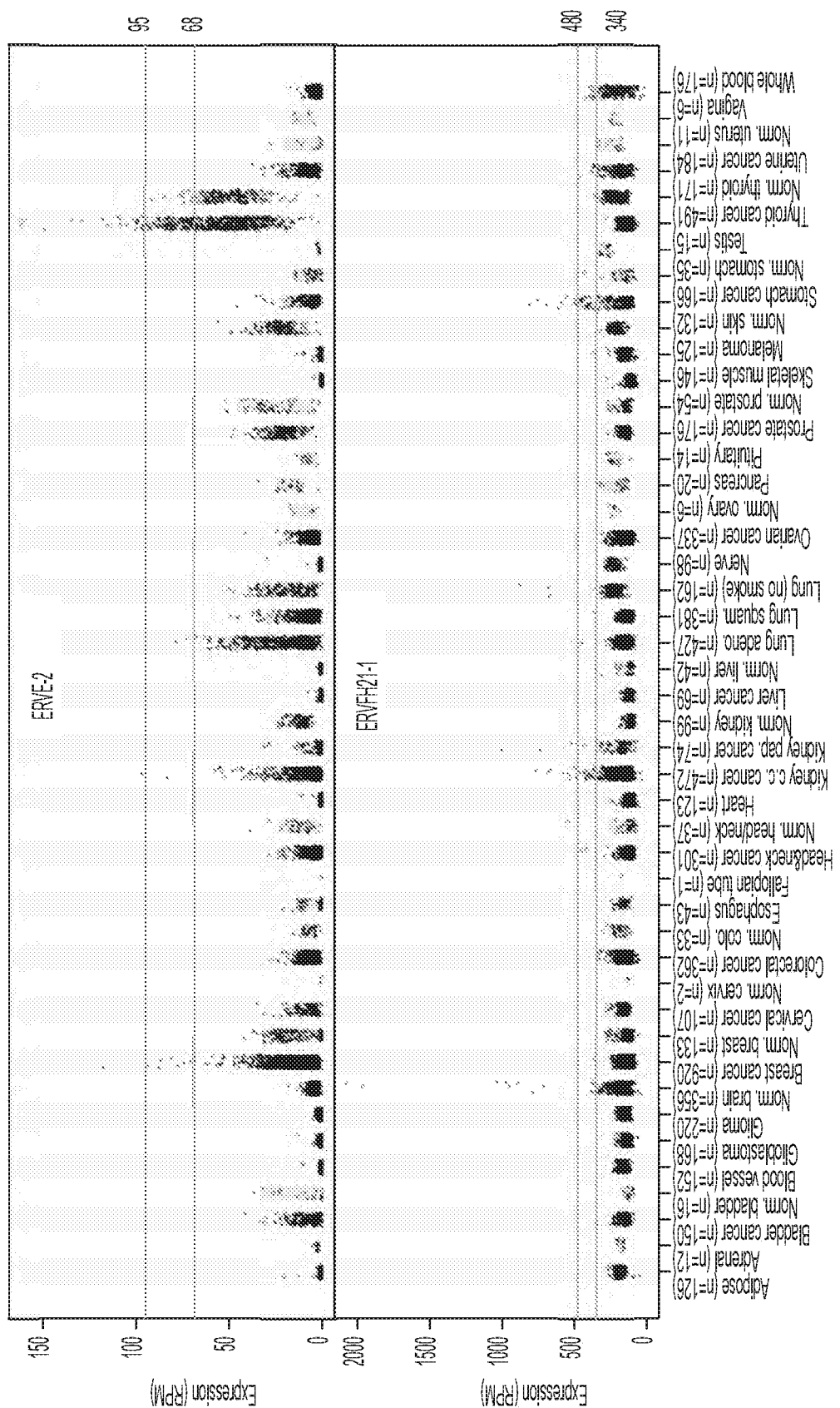
Figure 110:
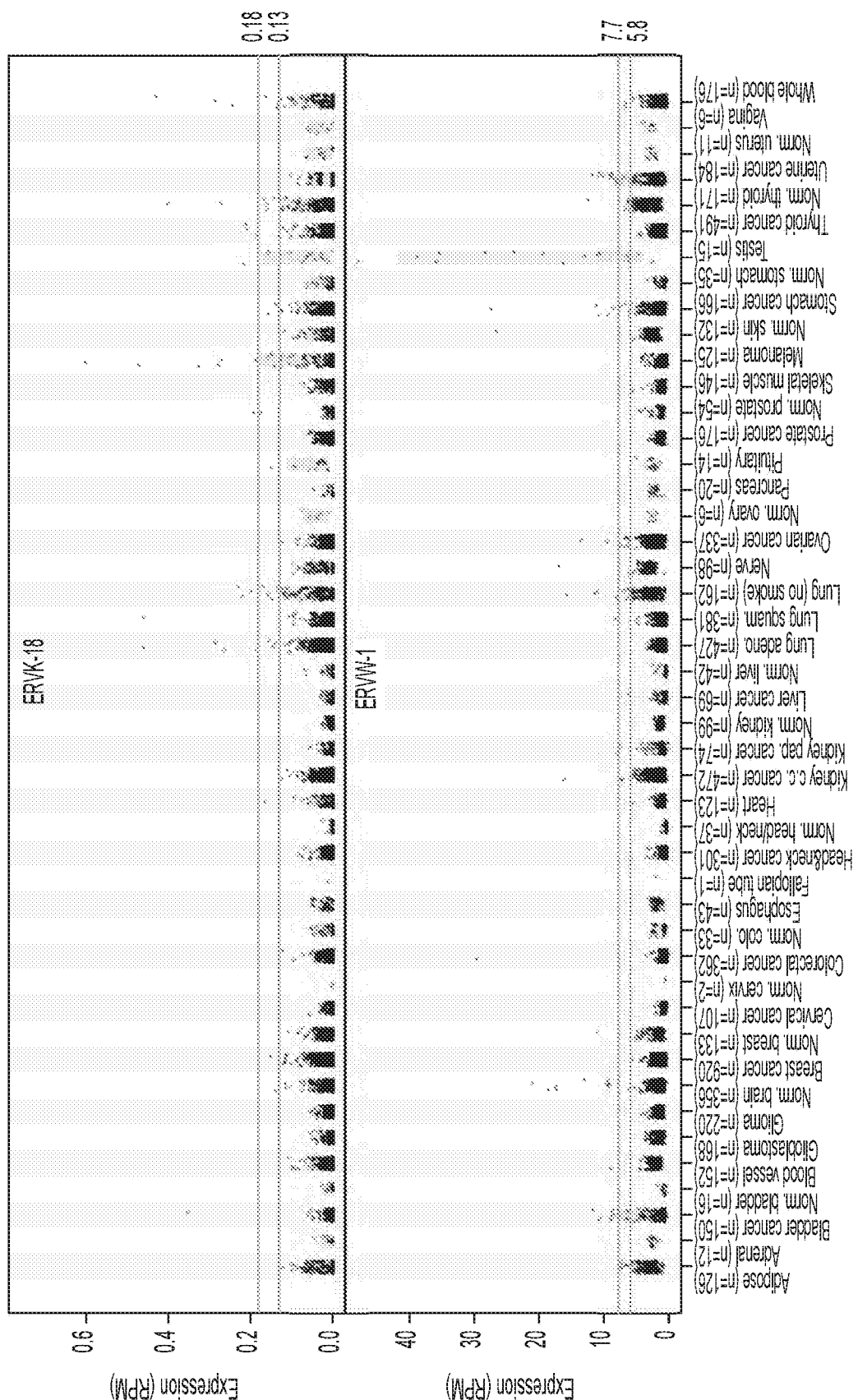
Figure 11P:
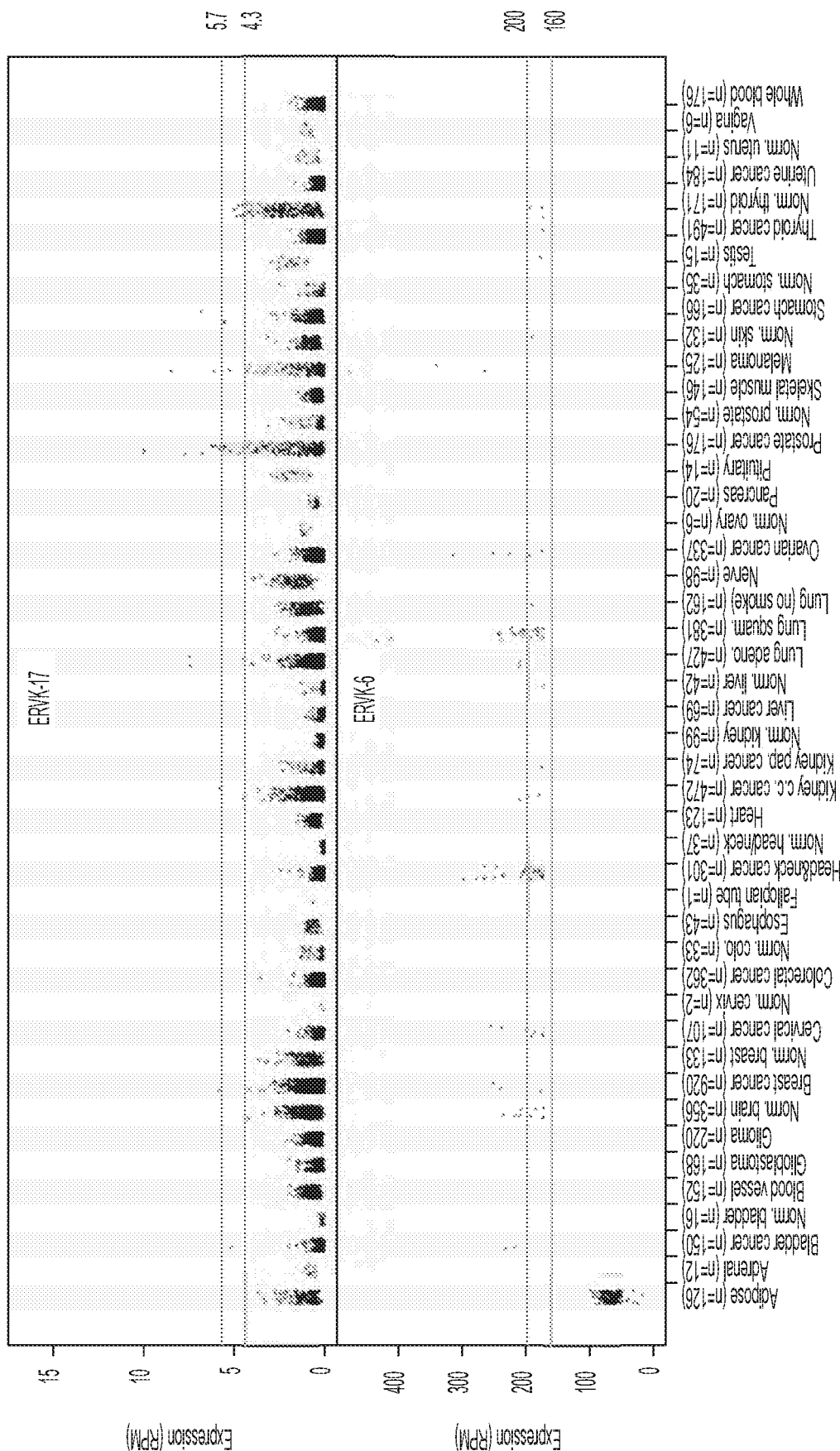
Figure 11P:
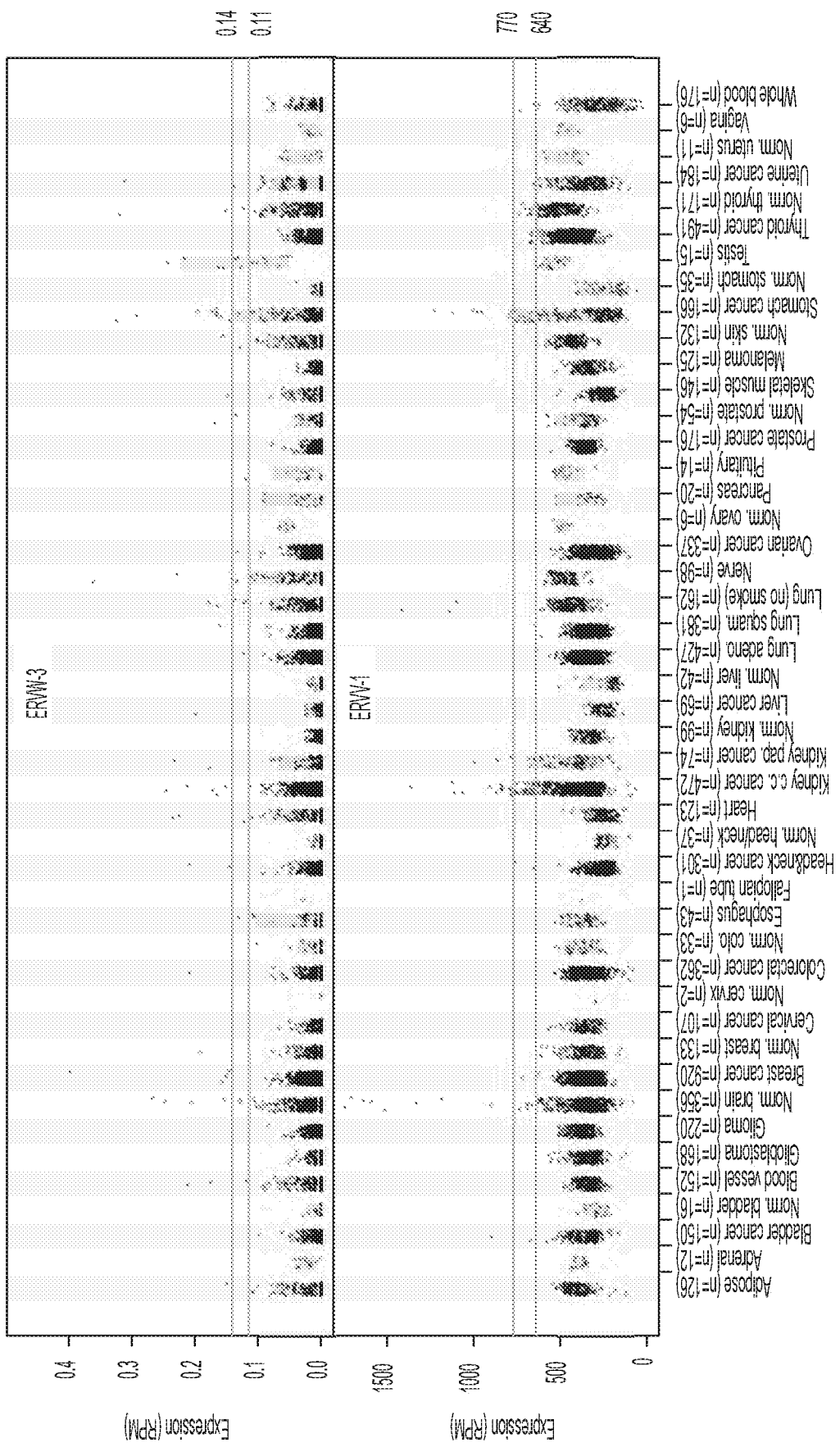
Figure 11P:
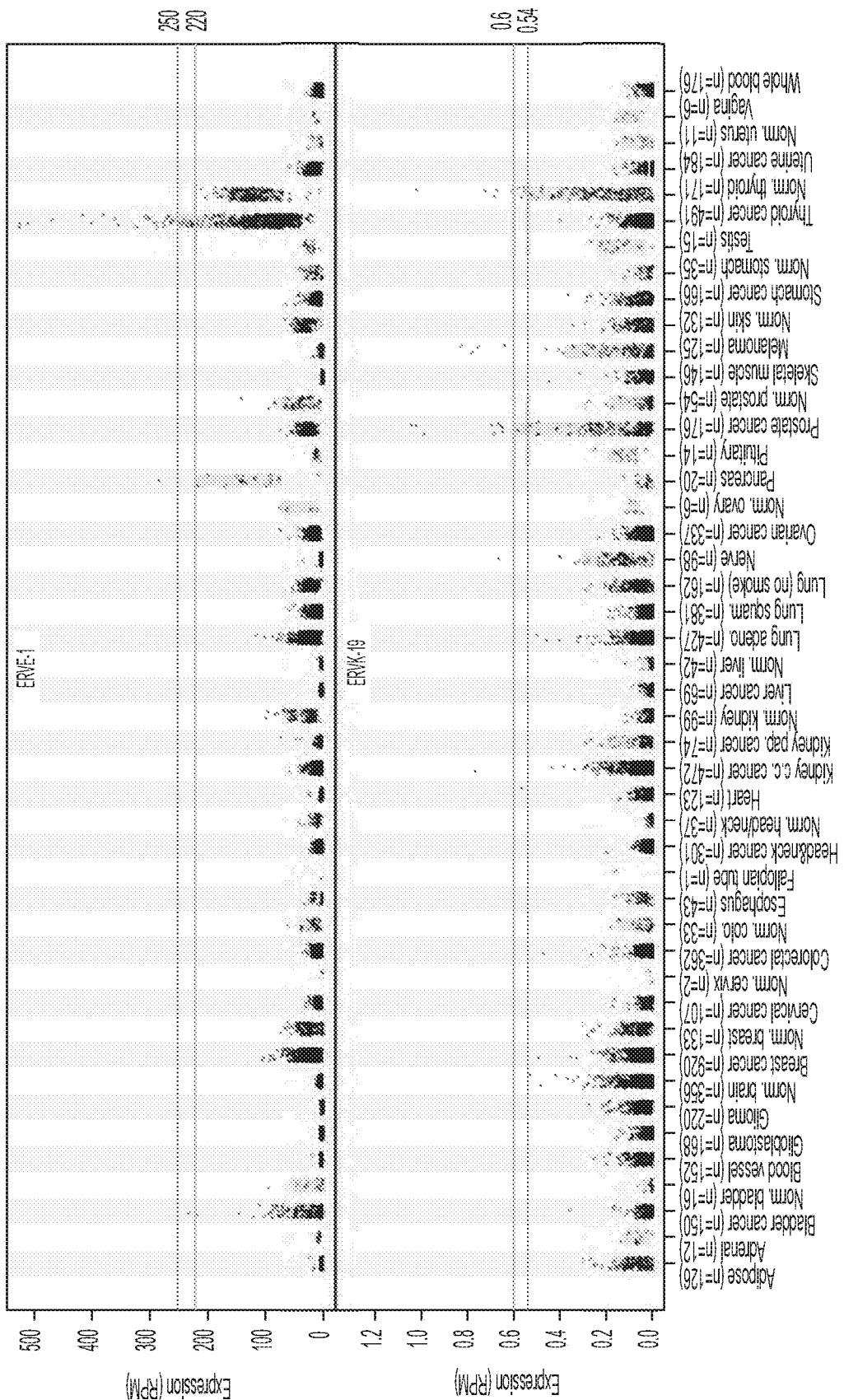
Figure 11Q:
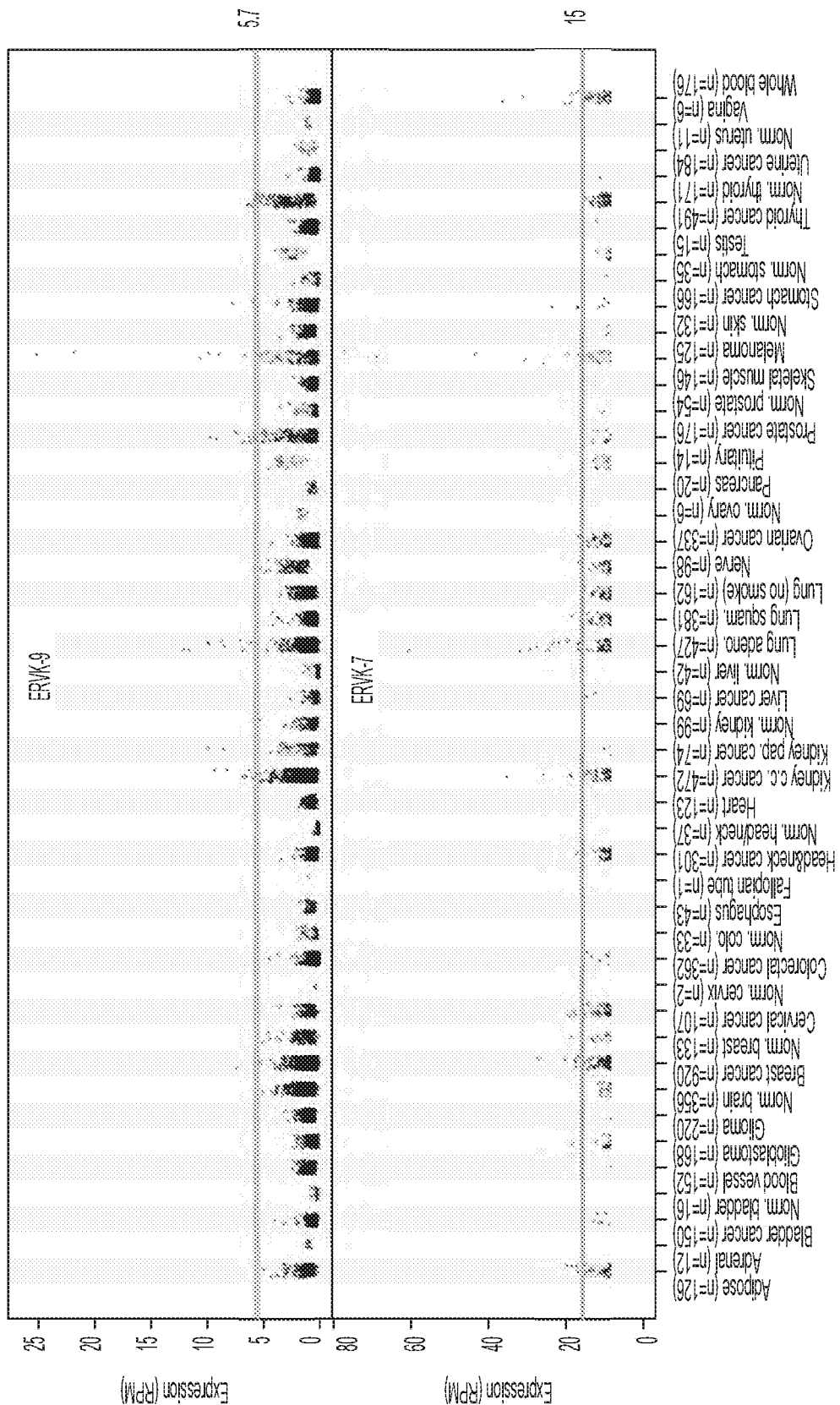
Figure 11Q:
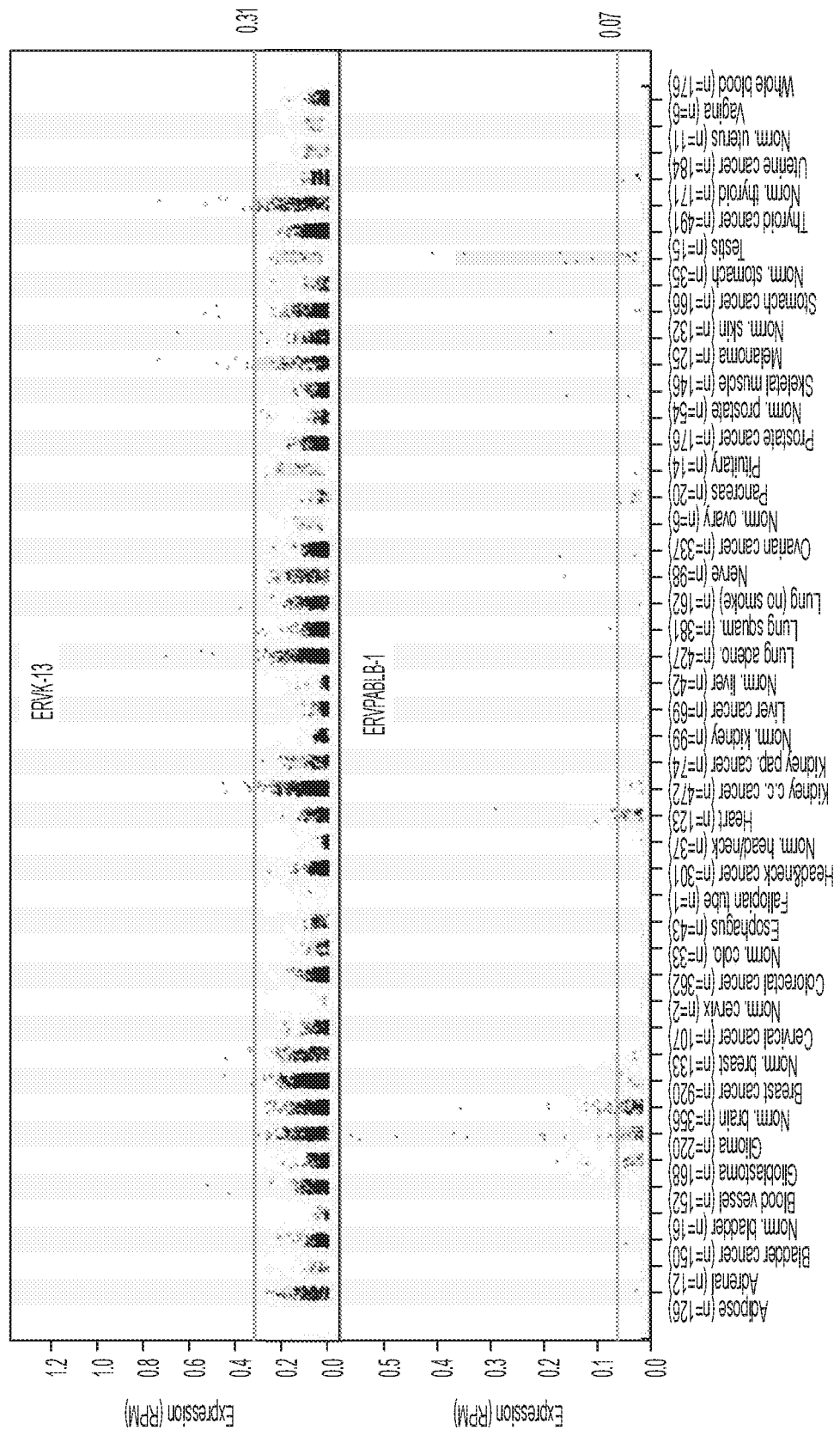
Figure 11Q:
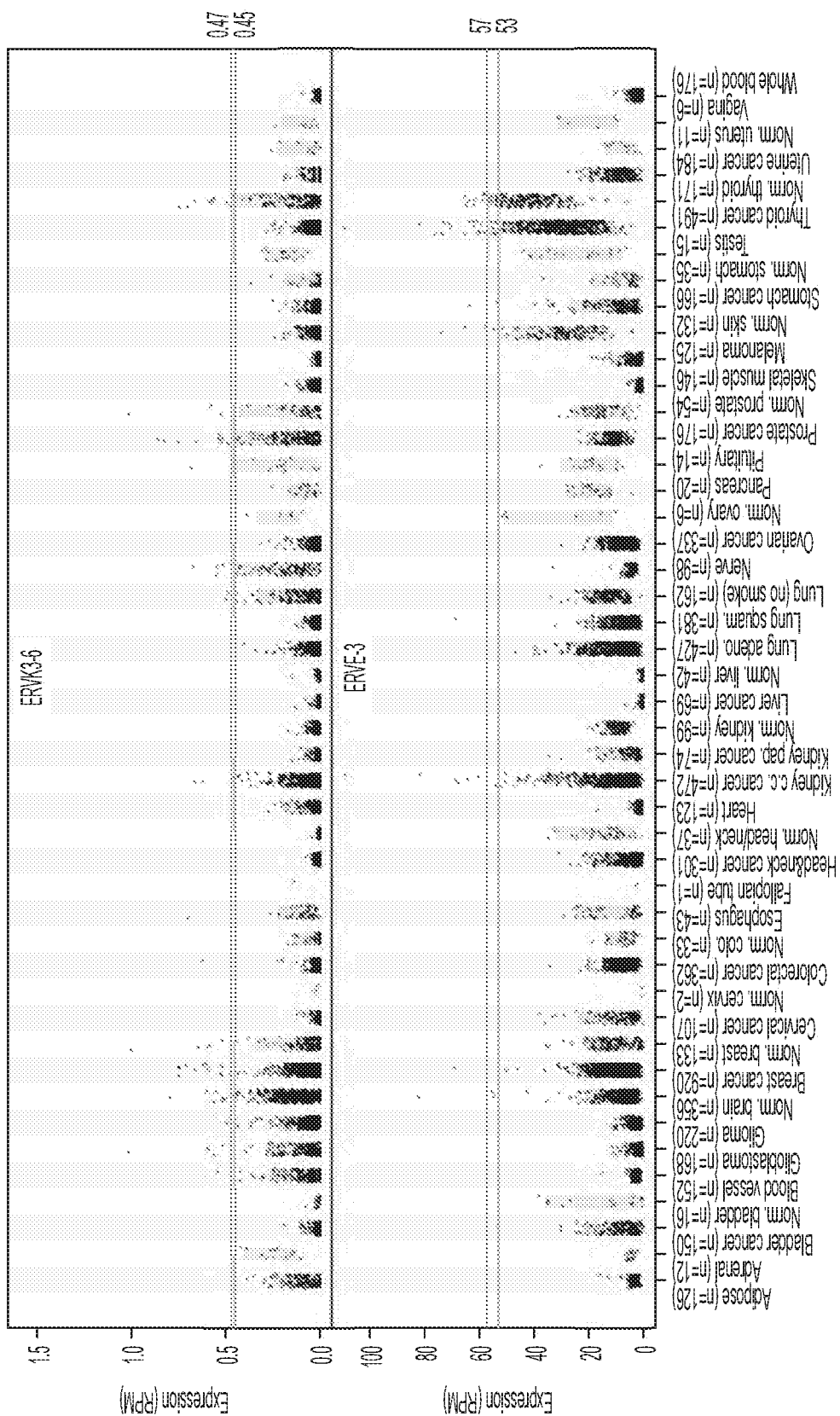
Figure 11R:
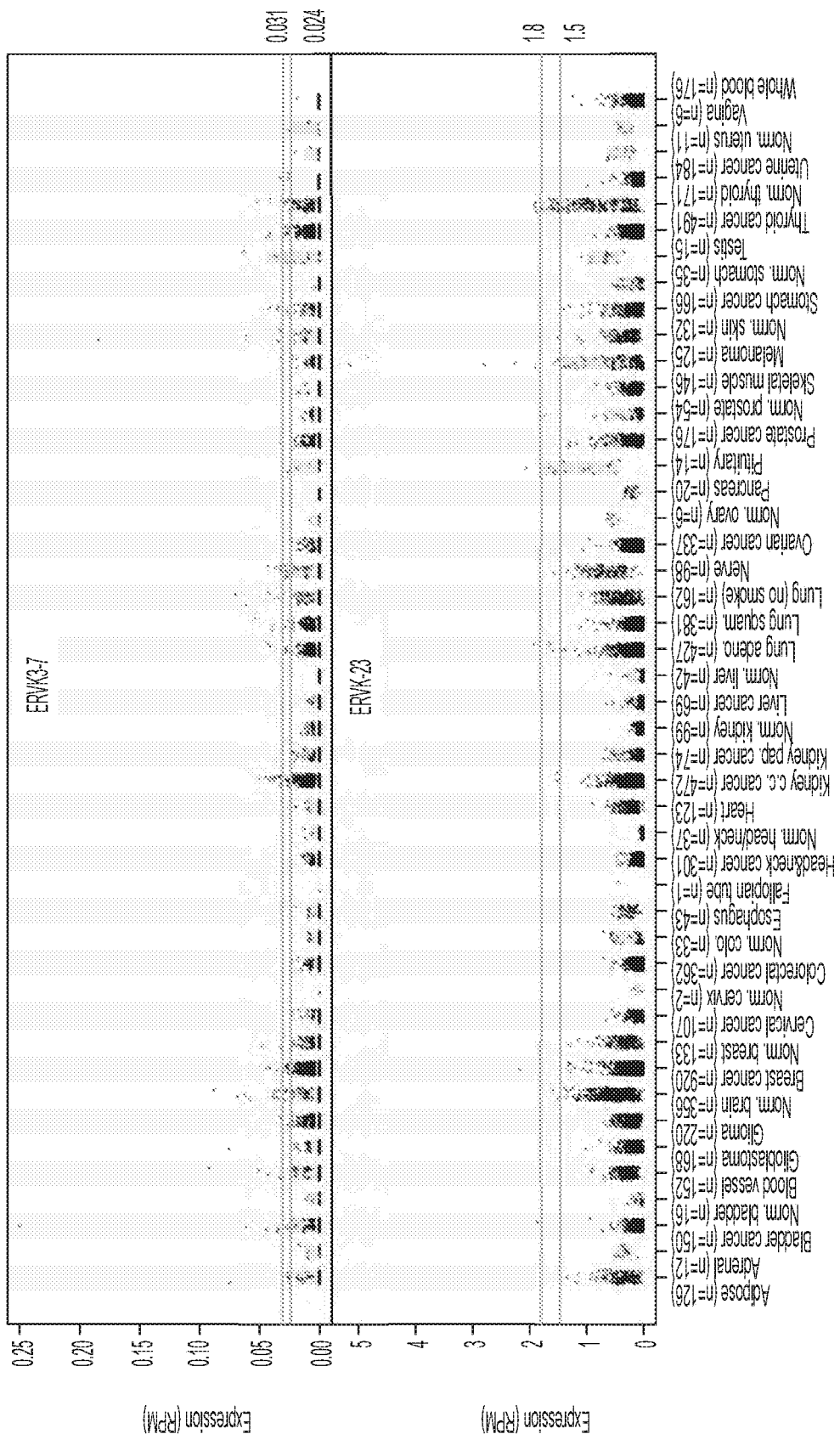
Figure 11R:
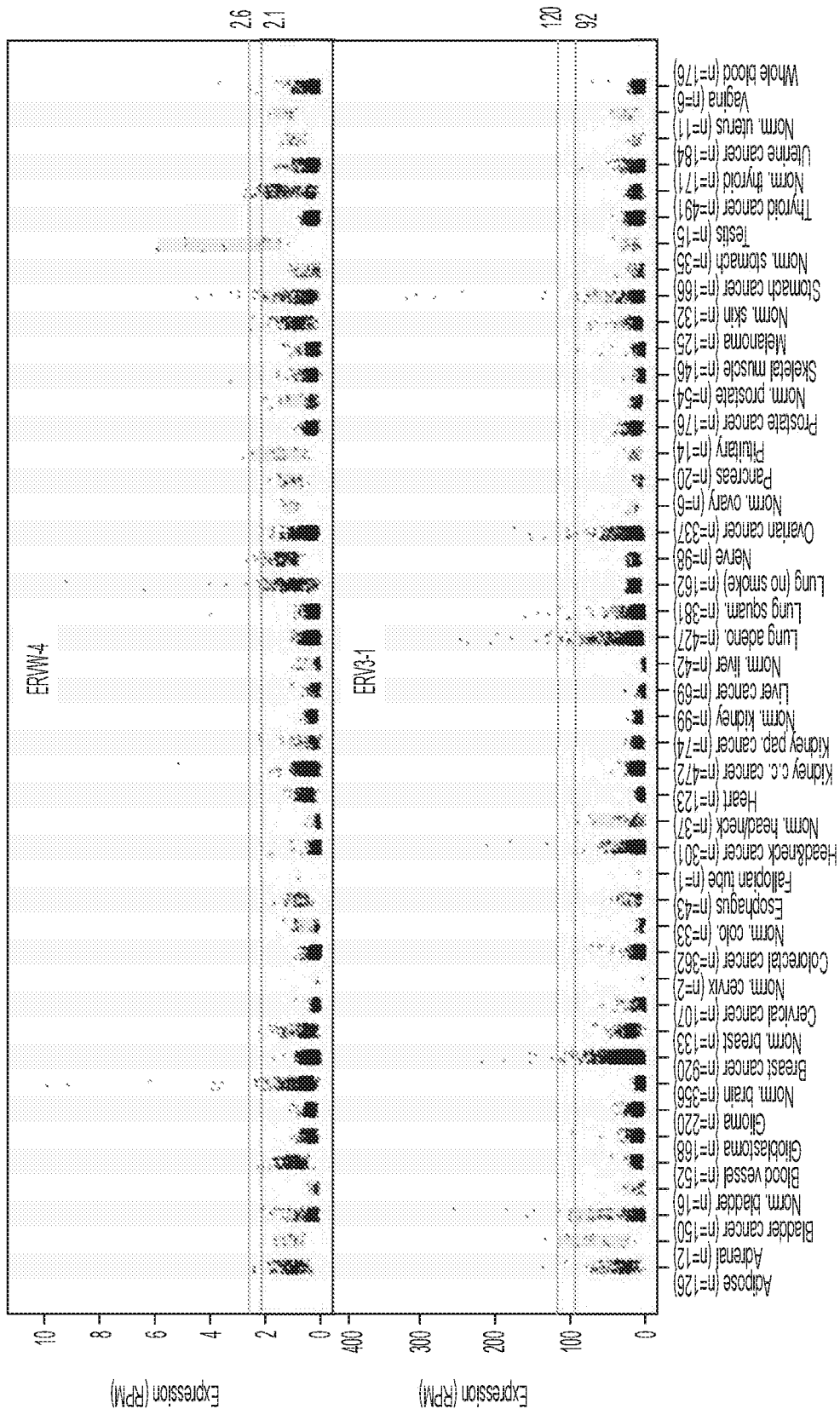
Figure 11R:
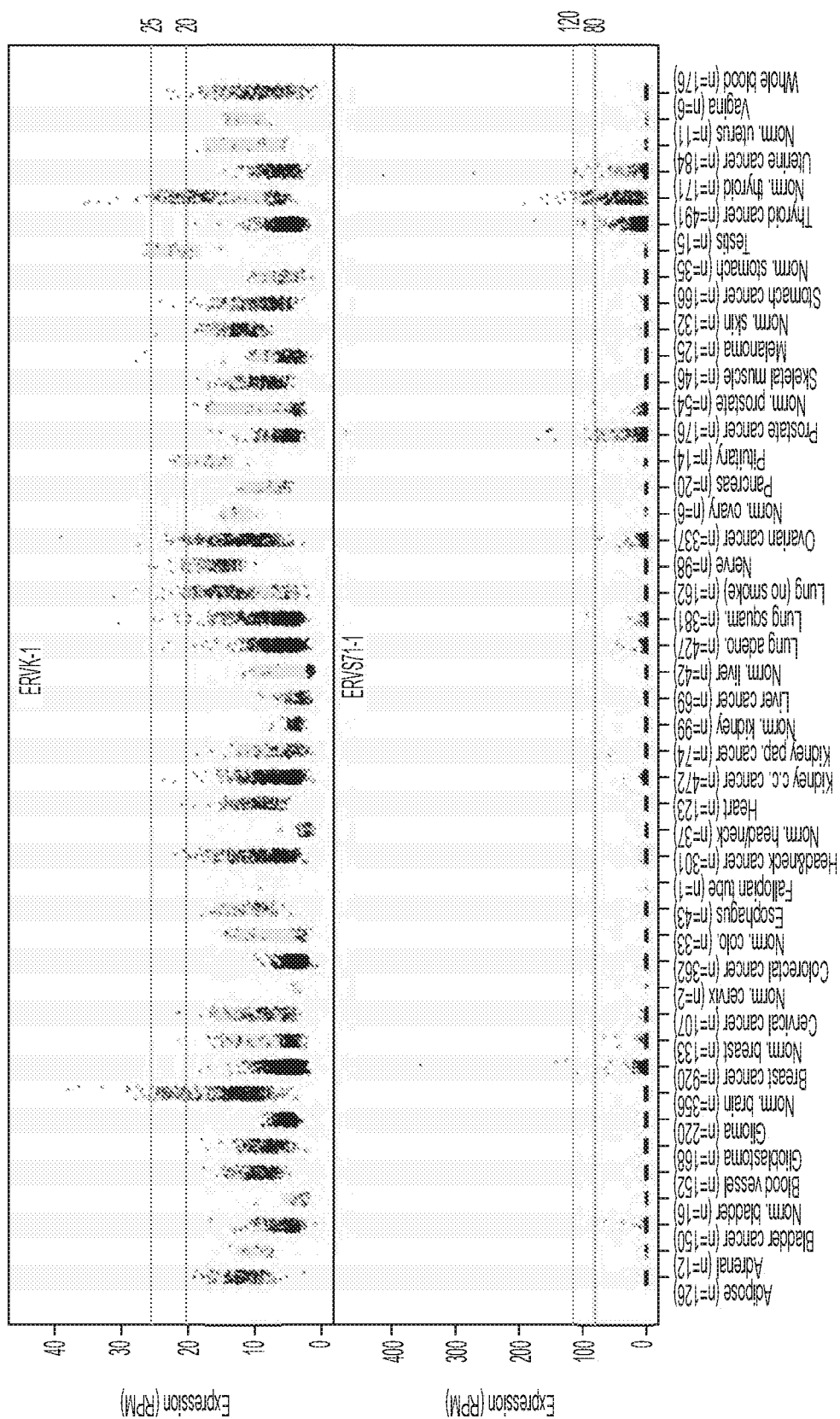
Figure 11S:
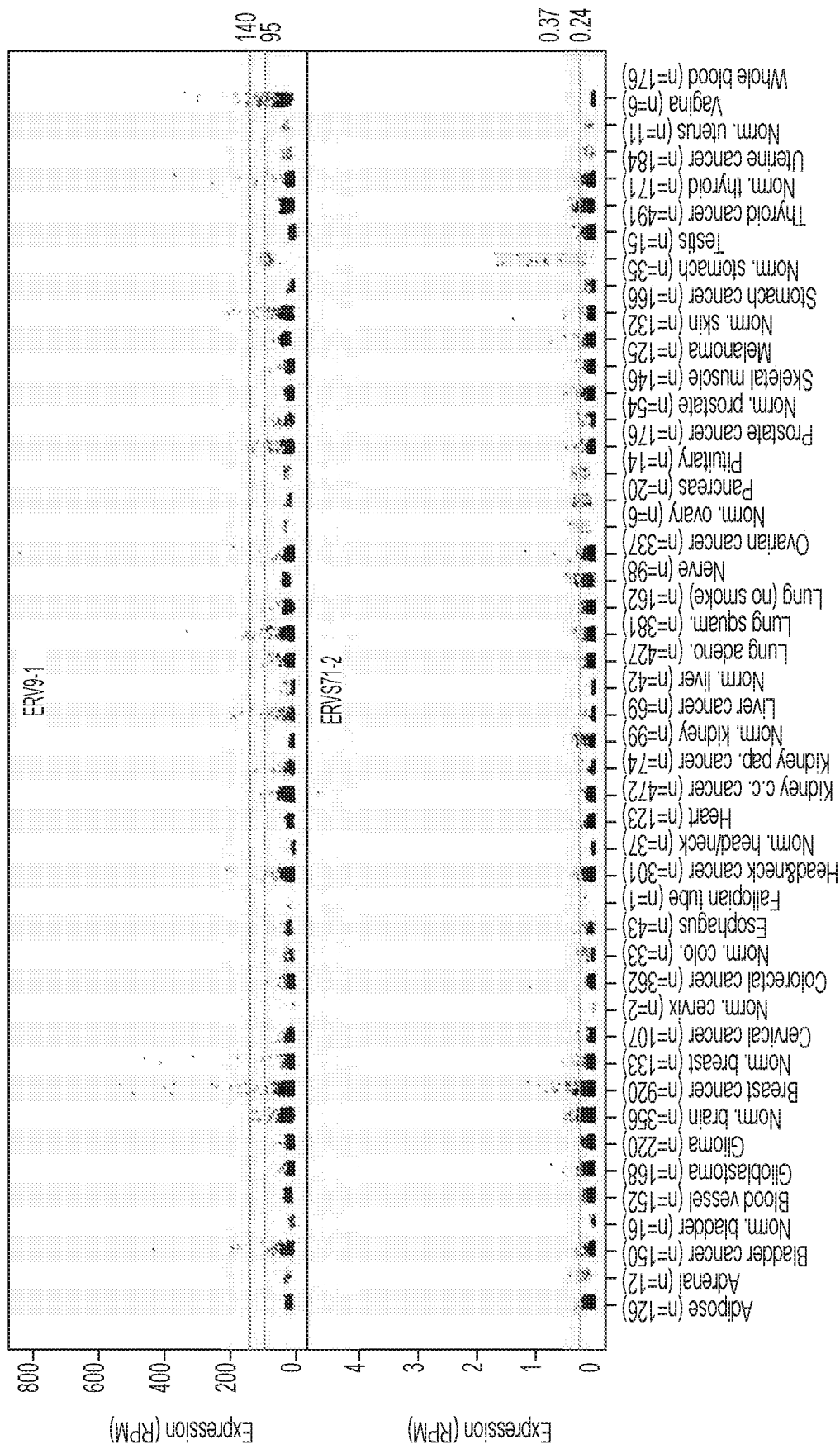
Figure 11S:
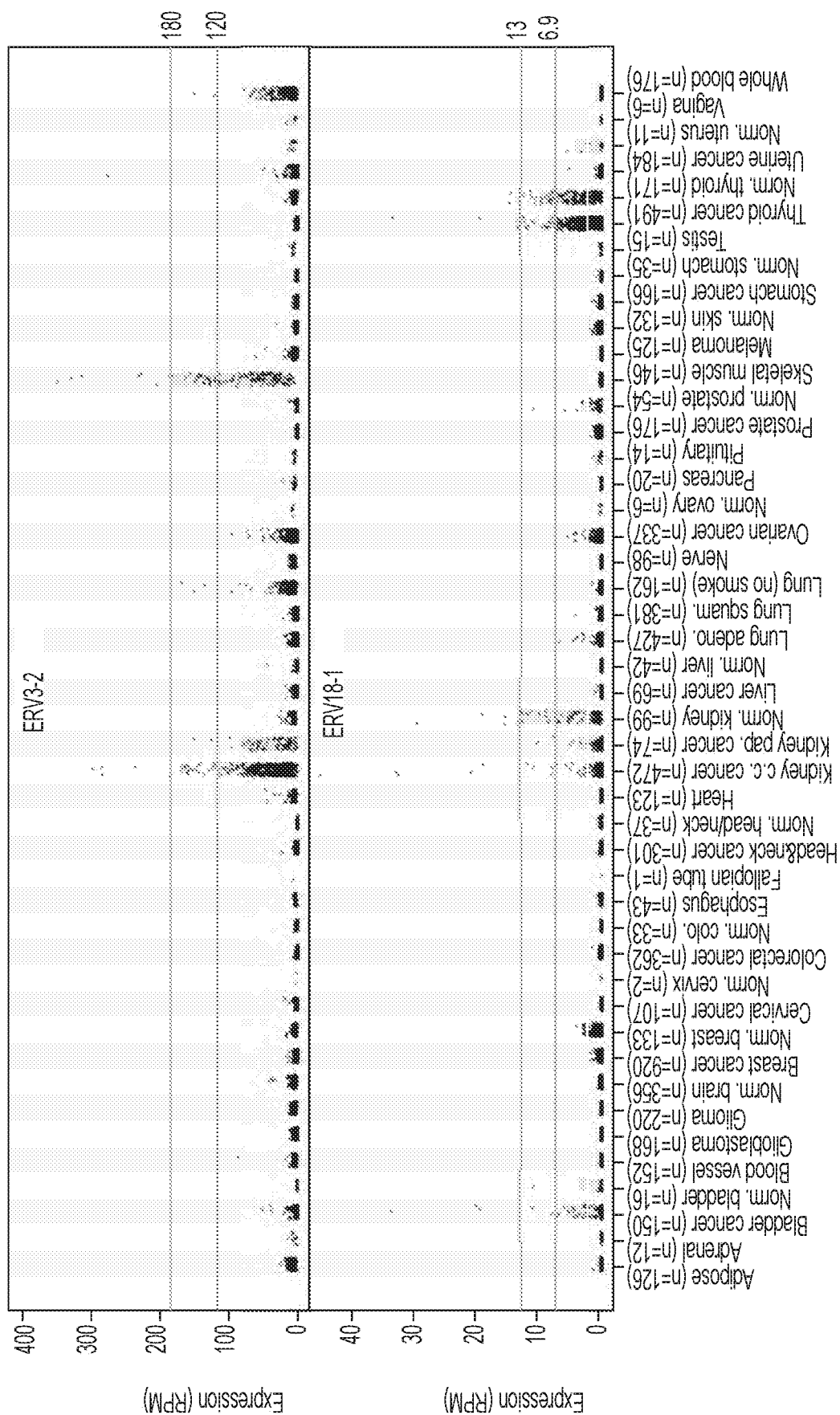
Figure 11S:
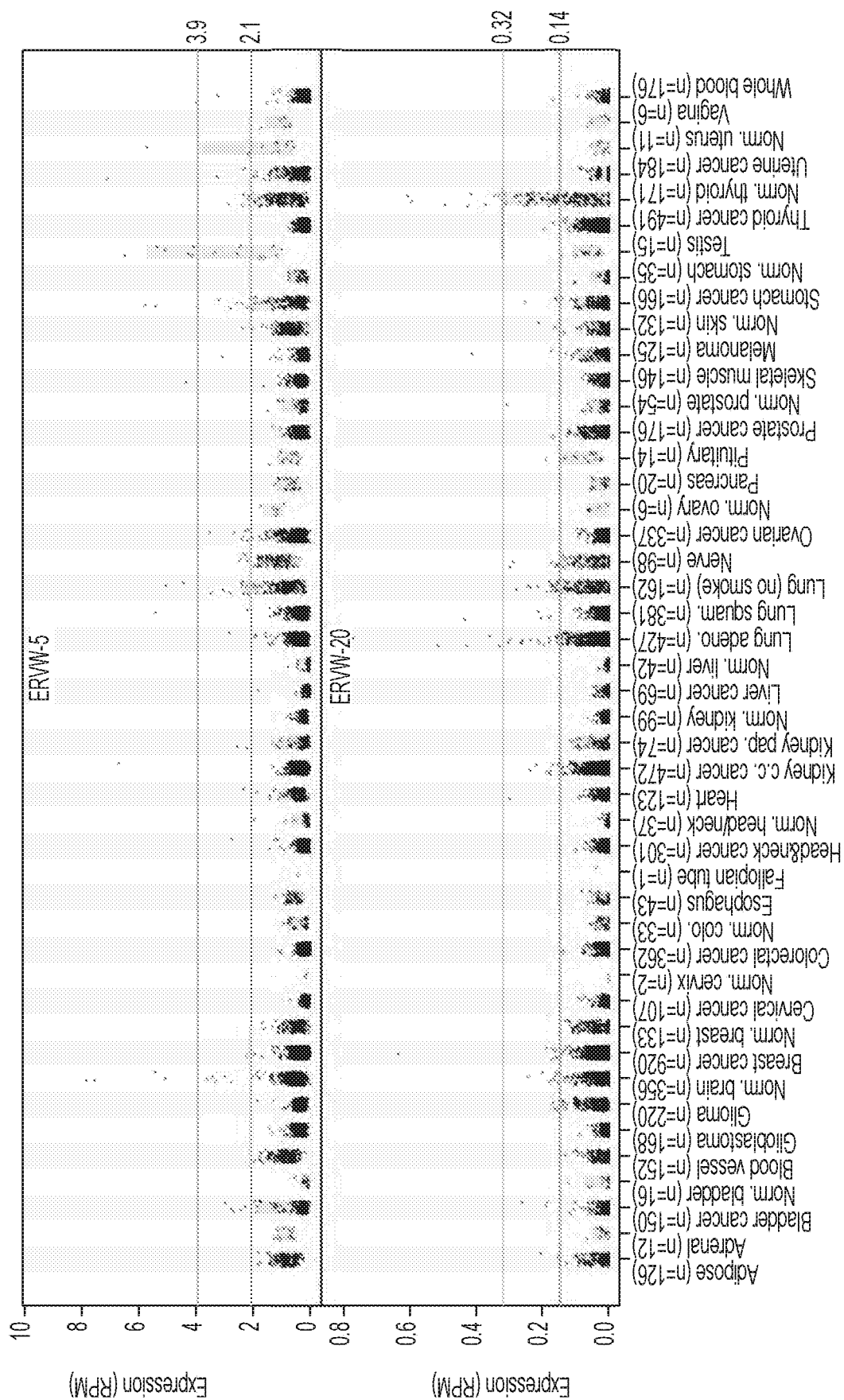
Figure 11T:
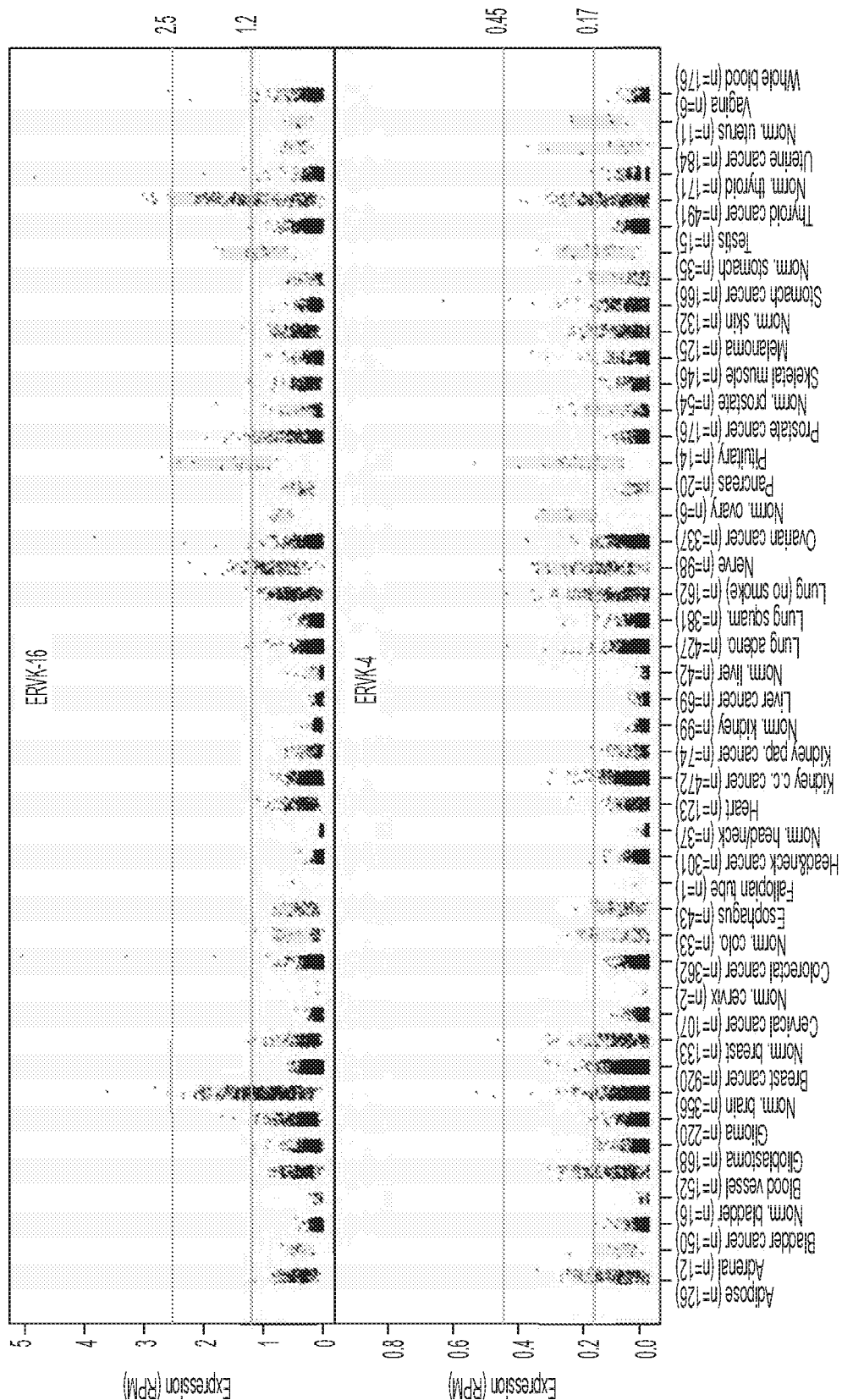
Figure 11T:
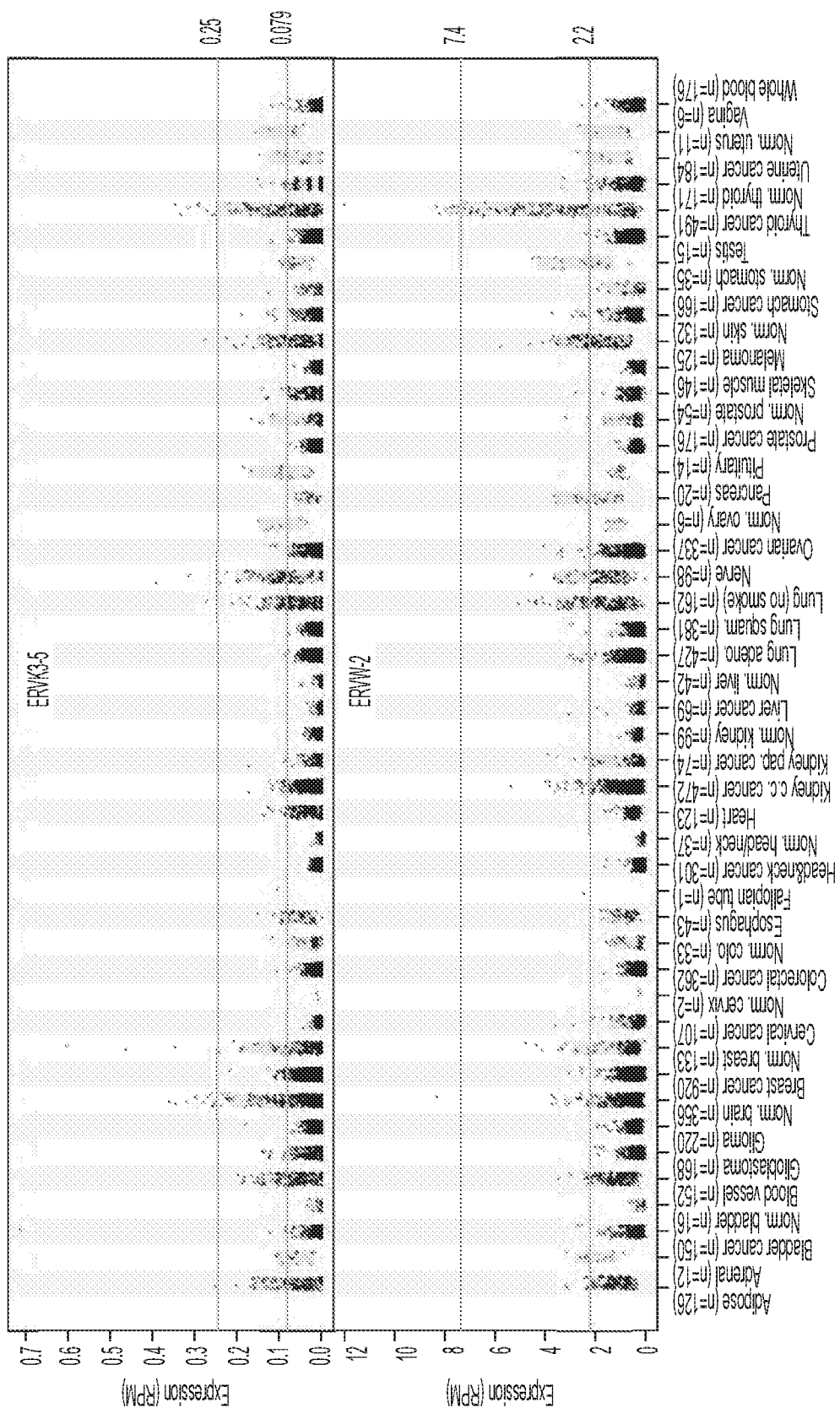
Figure 11T:
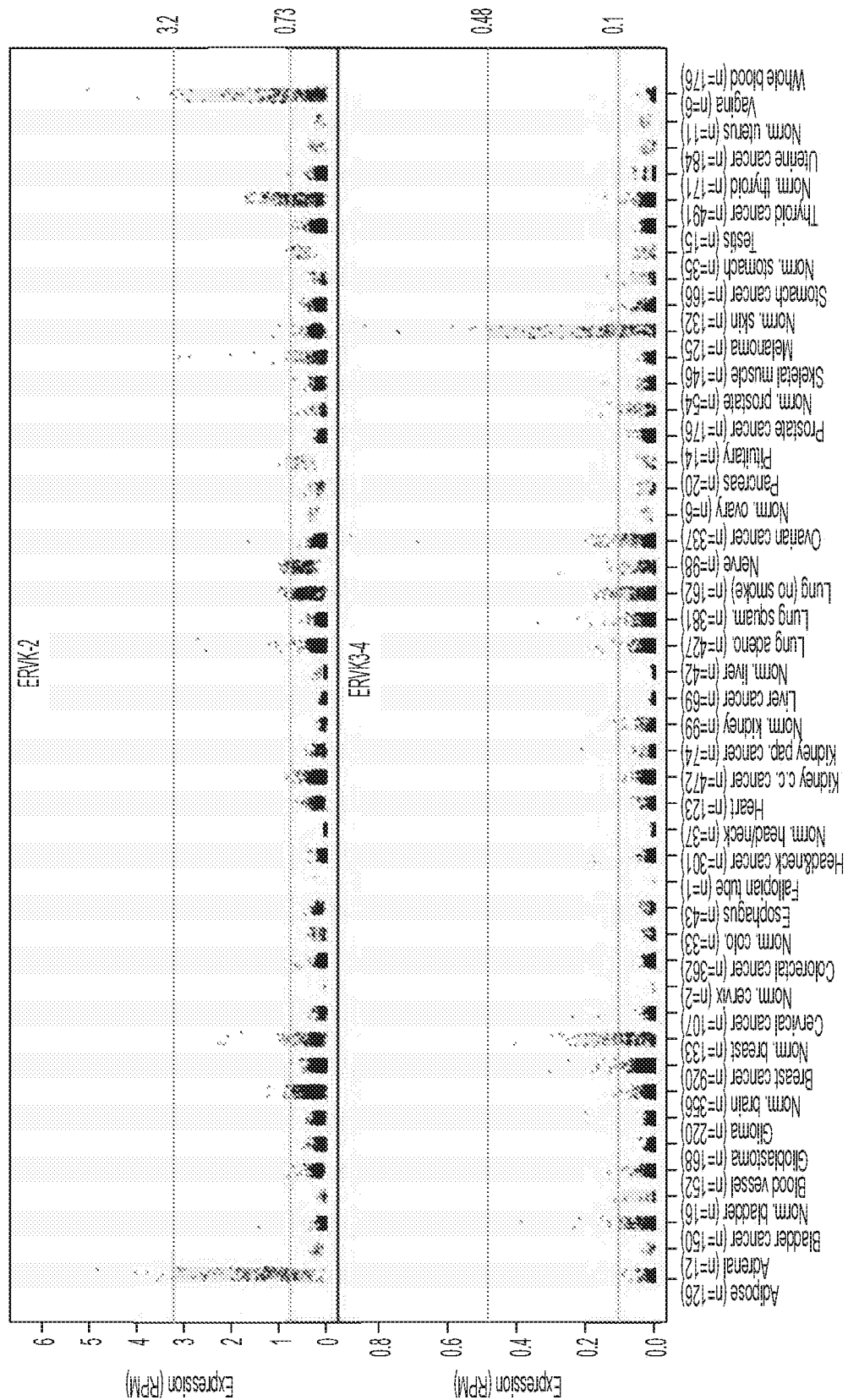
Figure 11U:
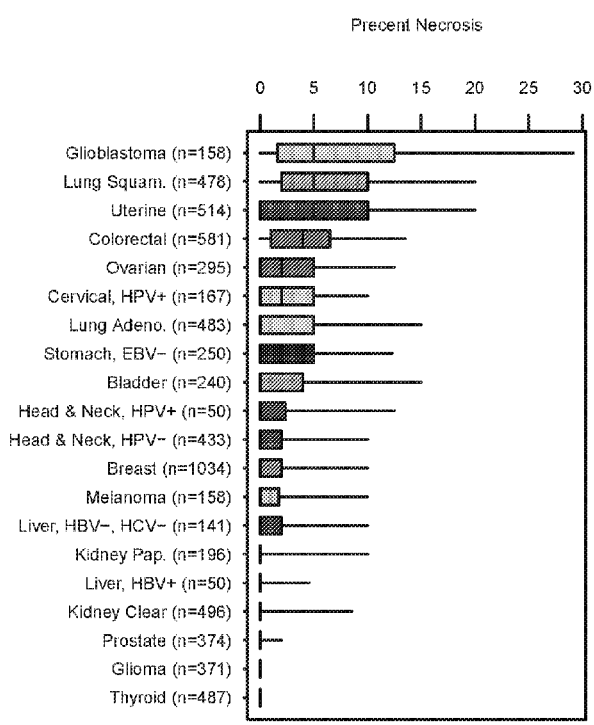
Figure 11V:
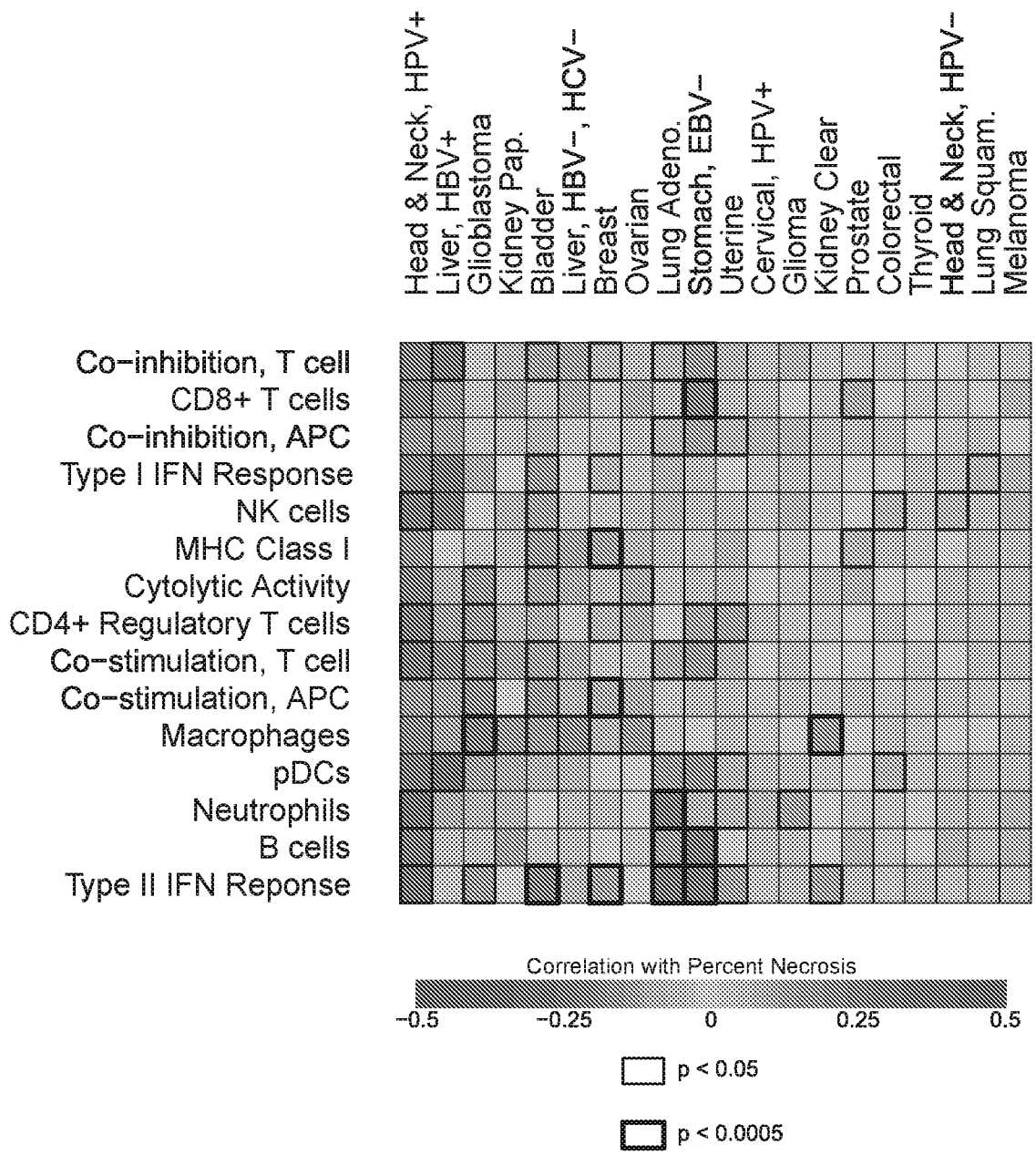

FIG. 11A-11V Ectopic Gene expression and its correlates; Necrosis. (A) Tumor-normal differences in the expression of cancer testis genes not expressed in GTEx normals. The count of select cancer testis genes (60 total; see Methods) expressed >1 TPM was calculated per sample and the distributions characterized in TCGA tumor samples verses normal samples from TCGA and GTEx. Solid bodies represent interquartile ranges and are notched by the median; vertical lines demarcate the $5^{th}$ to $95^{th}$ percentile range. (B) Distributions of cytolytic activity in low- and high-CT antigen tumors (low: fewer than five CT antigens at >1 TPM; high: greater than 10 CT antigens at >1 TPM). Solid bodies represent interquartile ranges and are notched by the median; vertical lines demarcate the $5^{th}$ to $95^{th}$ percentile range. P-values correspond to Wilcoxon rank-sum test. Only tumor types with at least 10 high-CT samples are presented. (C) Heatmap exploring chromosomal deletions targeting cancer testis genes. The color of each box indicates whether the given gene had lower expression when its locus was deleted. The outline indicates whether high CYT was positively associated with deletion status. The text (blank/"D"/"DD") indicates whether the locus was more likely to be deleted than amplified (with respect to average rate across genes in the tumor type). Thresholds reflect liberal nominal p-values, p<0.1 and p<0.01. (D-I) Coverage depth of ERV of reference sequence with reads from TCGA tumor samples. Each plot represents the depth of reads mapping to a given ERV reference sequence. Some ERVs are represented by multiple sequences. ORFs of length greater than 75 nt that scored for InterProScan motifs are highlighted in green along with the name of the motif for which they scored. (J-T) ERV expression ranges for tumor vs. normal samples, all ERVs. Semi-transparent left-right jittered points represent the expression values observed in a compendium of tissues. The $5^{th}$ to $95^{th}$ percentile range is highlighted in orange for tumor tissues and in green for normal tissues. The maximum $95^{th}$ percentile value observed in tumors is marked with an orange horizontal line, and the corresponding maximum for normal tissues is marked with a green horizontal line. These values (marked on the right axis) were the basis for determining tumor-specific expression. ERVs designated as TSERVs are marked as such. Many ERVs, while not specific to tumors, were elevated in tumors. (U) Percent necrosis by tumor type. Solid bodies represent interquartile ranges and are notched by the median; lines demarcate the $5^{th}$ to $95^{th}$ percentile range. (V) Heatmap indicating association between percent necrosis and ssGSEA enrichments for markers for various immune cell types, by cancer. Colors correspond to Spearman correlations, and cell borders correspond to association p-values, as indicated in the legend.

FIG. 12A-12F Genes with enriched point mutation in high- and low-CYT tumors. (A) Non-silent mutation counts for significant genes in high- and low-CYT tumors. High- and low-CYT tumors were defined as the top and bottom CYT quartile, respectively, per tumor type. Mutation counts in high-CYT samples point upward from the x-axis, mutation counts in low-CYT samples point downward from the x-axis. Bars are color-coded according to tumor type using the color code indicated in the legend and used elsewhere. For a given gene, tumor types exhibiting no mutations among the high-CYT or low-CYT samples are not depicted. Gene names and pan-cancer adjusted p-values (BH method) appear at the top of the figure. (B) Heatmap representing pan-cancer enrichments identified for other cell type signatures. Color corresponds to the effect size of non-silent mutation on rank-transformed signature expression; cell borders represent the adjusted p-value for association. (C-F) Positions of point mutation in CYT-associated genes. Mutated positions and their functional classifications are reported for each gene. Colors indicate mutation severity (synonymous, nonsynonymous, or probable loss of function), and vertical height represents event frequency. Total counts of each class of mutation appear in the upper left corner. Light blue peaks represent the relative local density of events as estimated using a smoothing bandwidth of 30 nucleotides. Sequence domains, as scored by Interpro, are represented by widened regions. Distinct exons are demarcated by alternating domains of gray and light gray.

Figure 13A:
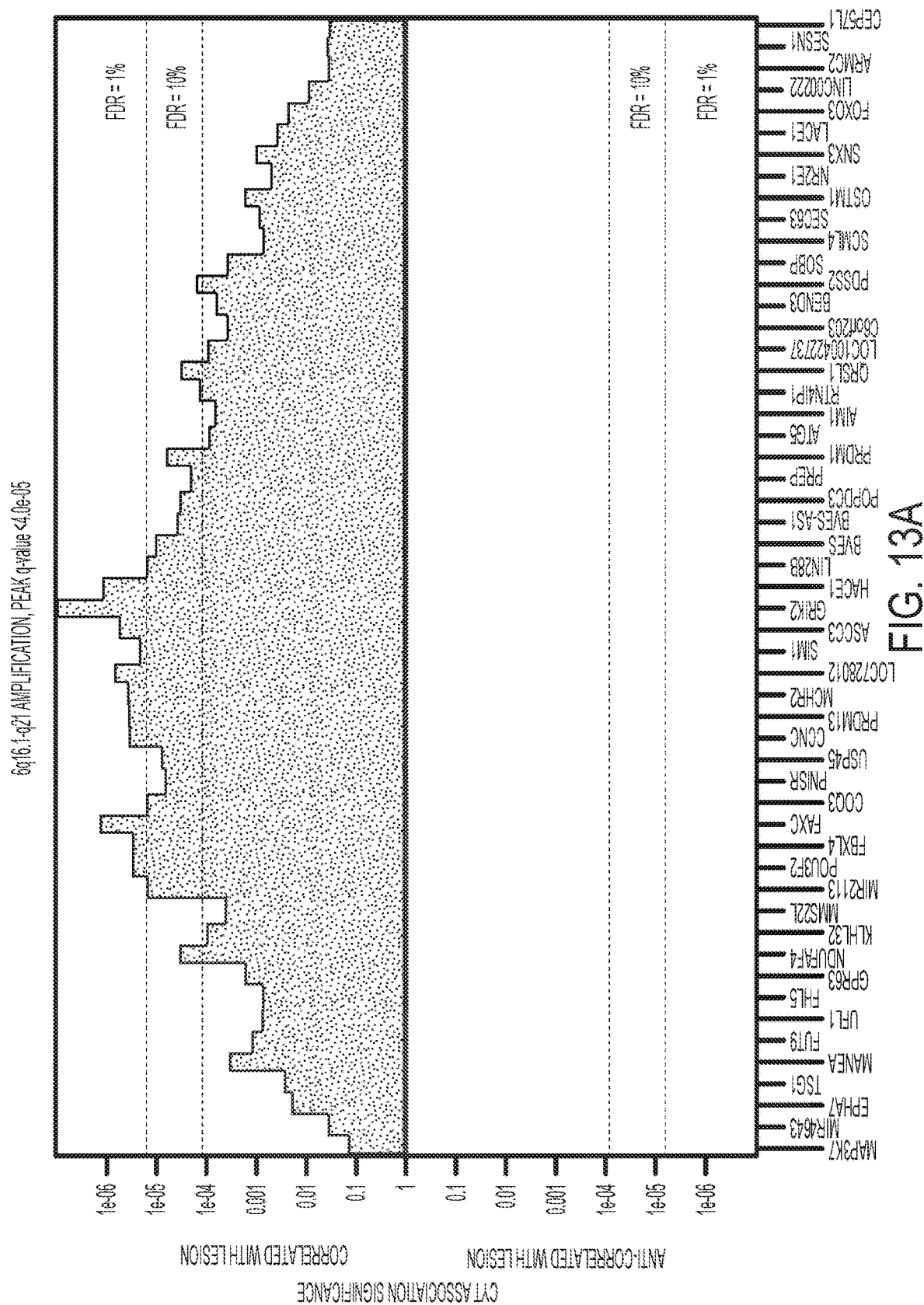
Figure 13A:
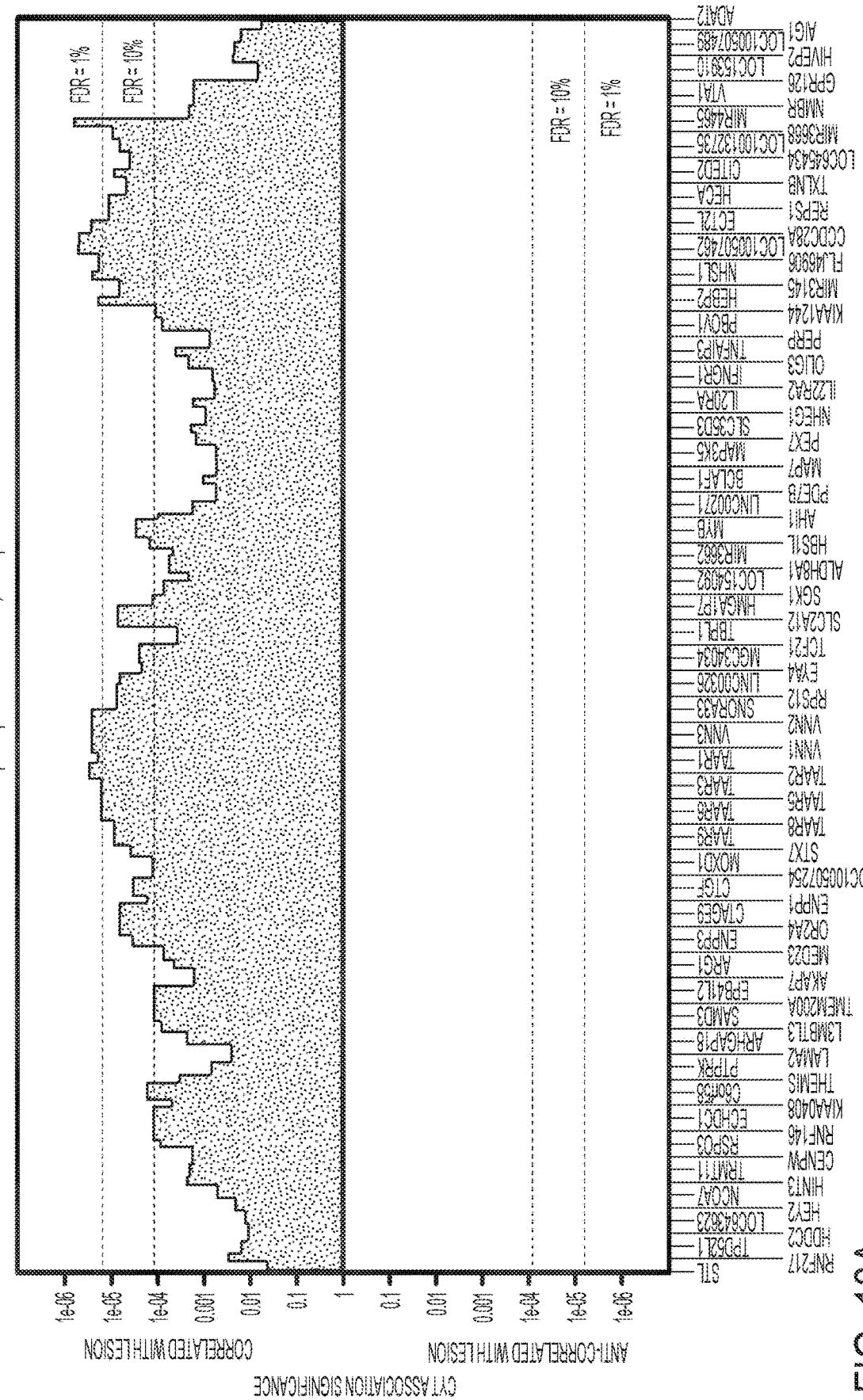
Figure 13A:
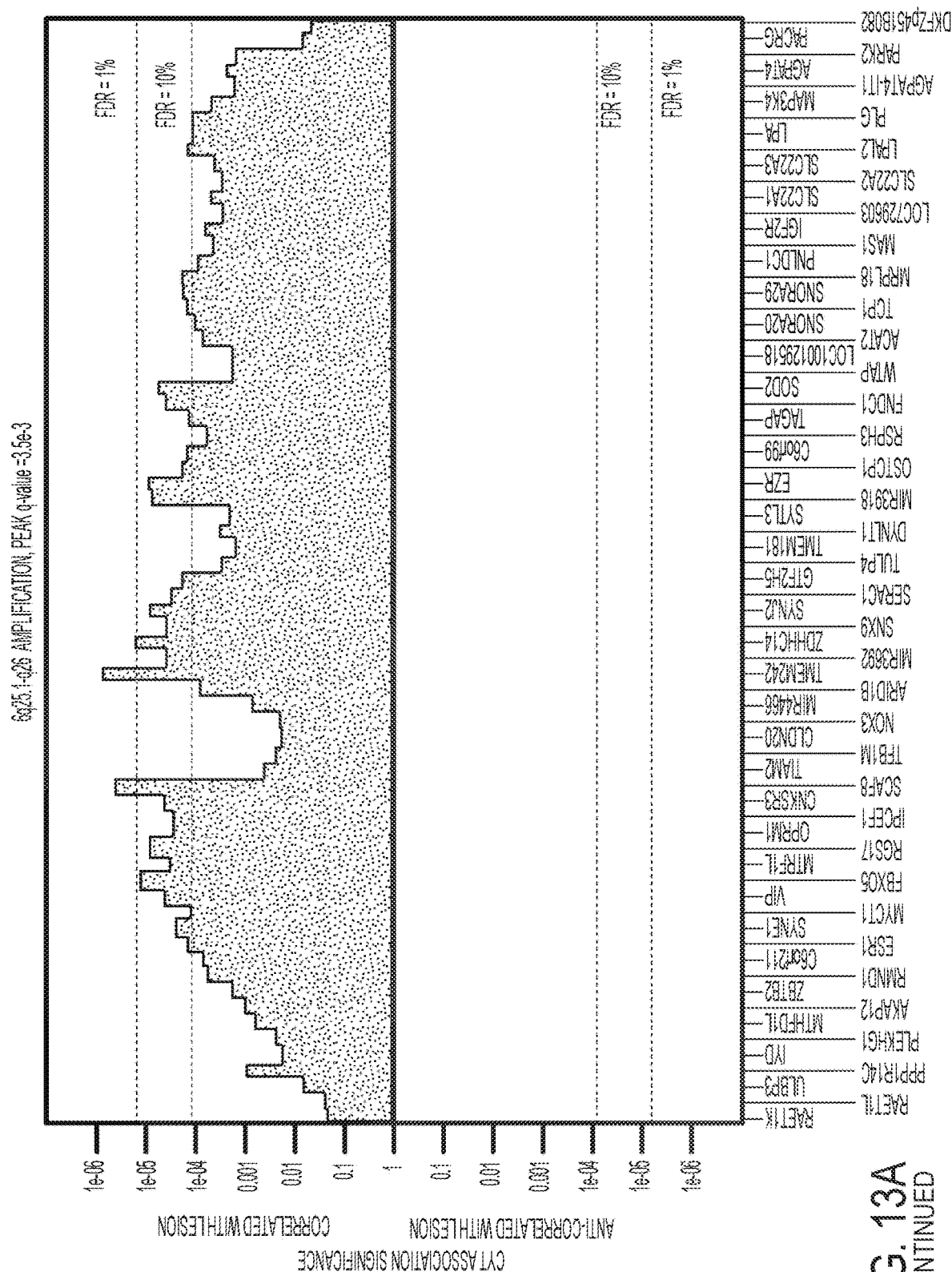
Figure 13A:
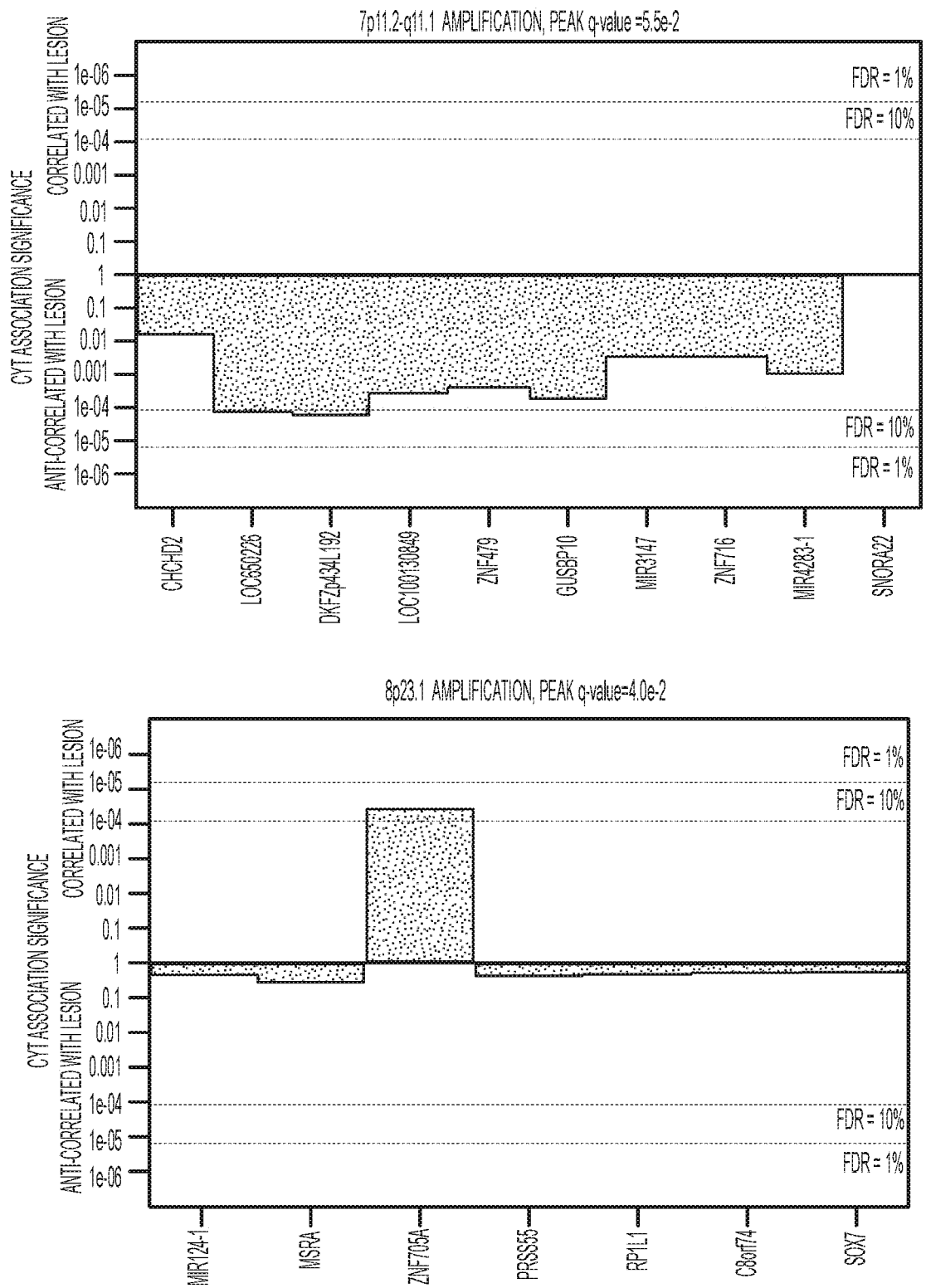
Figure 13B:
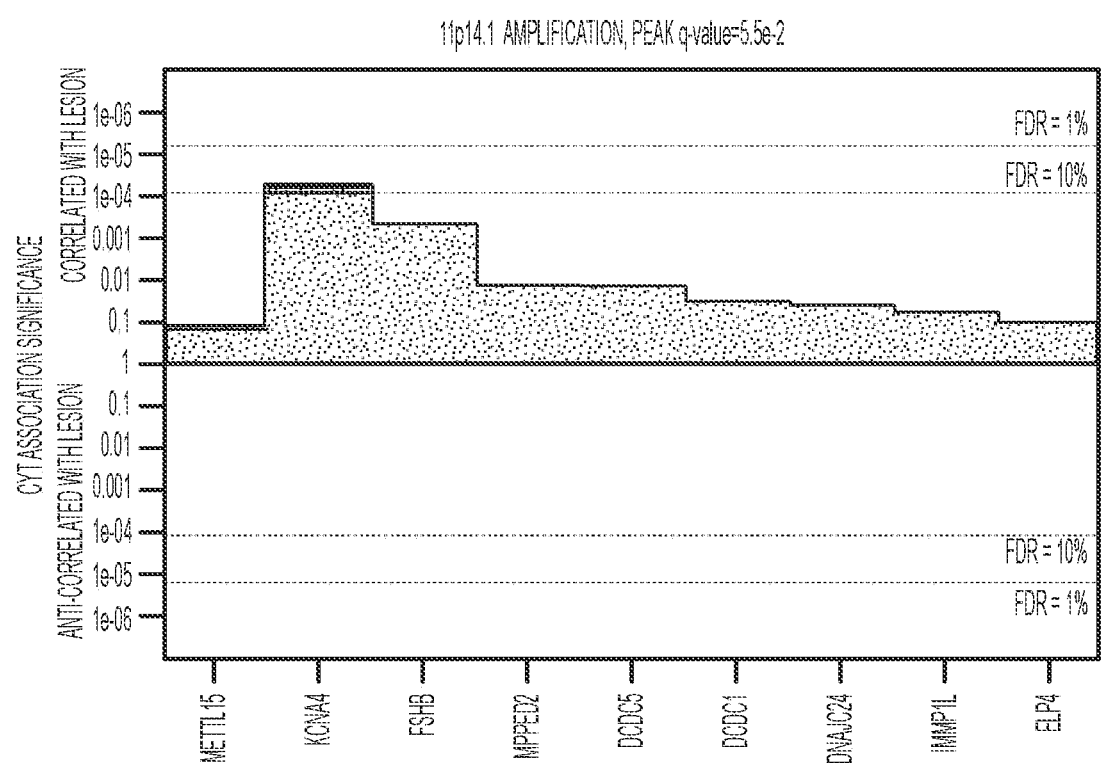
Figure 13B:
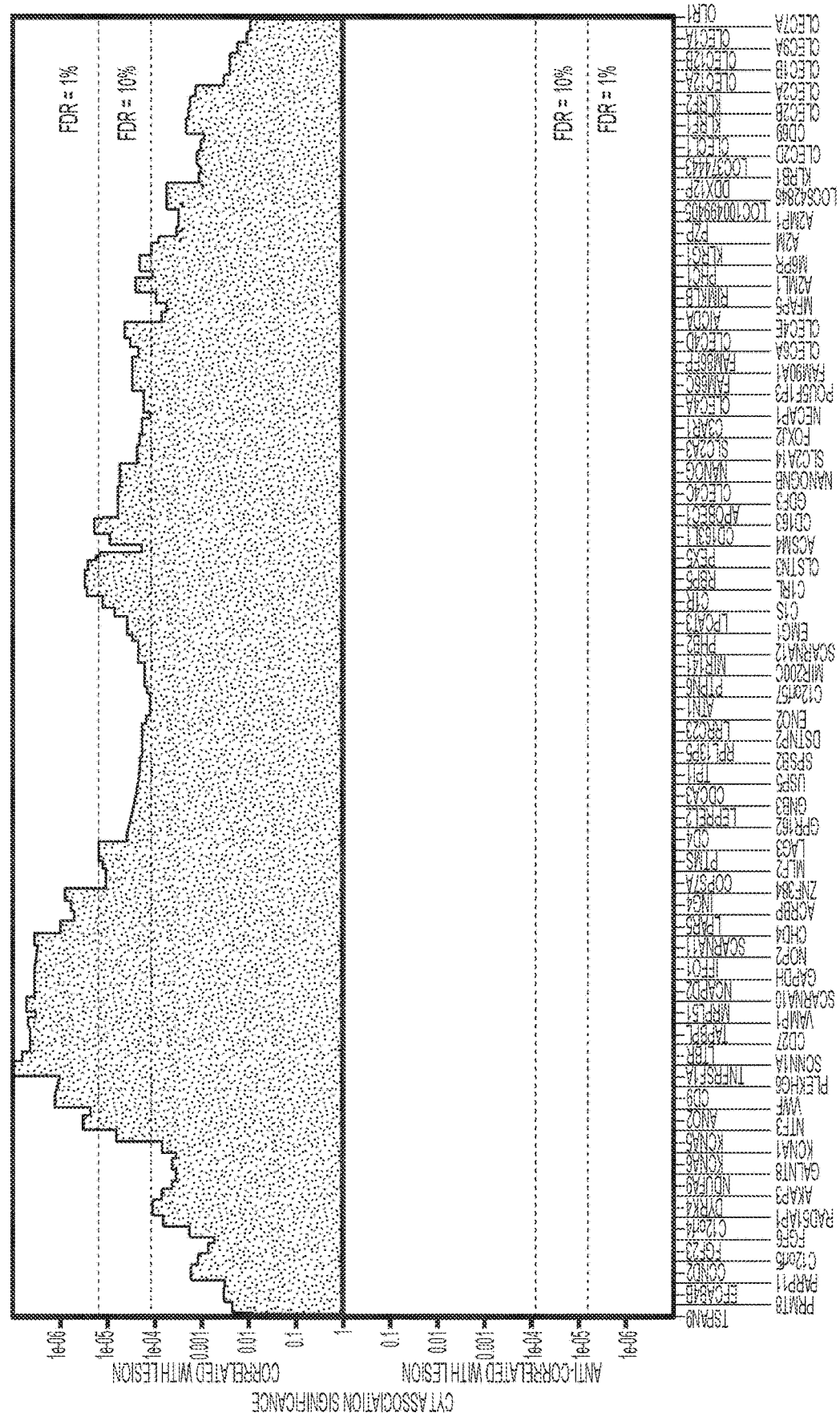
Figure 13B:
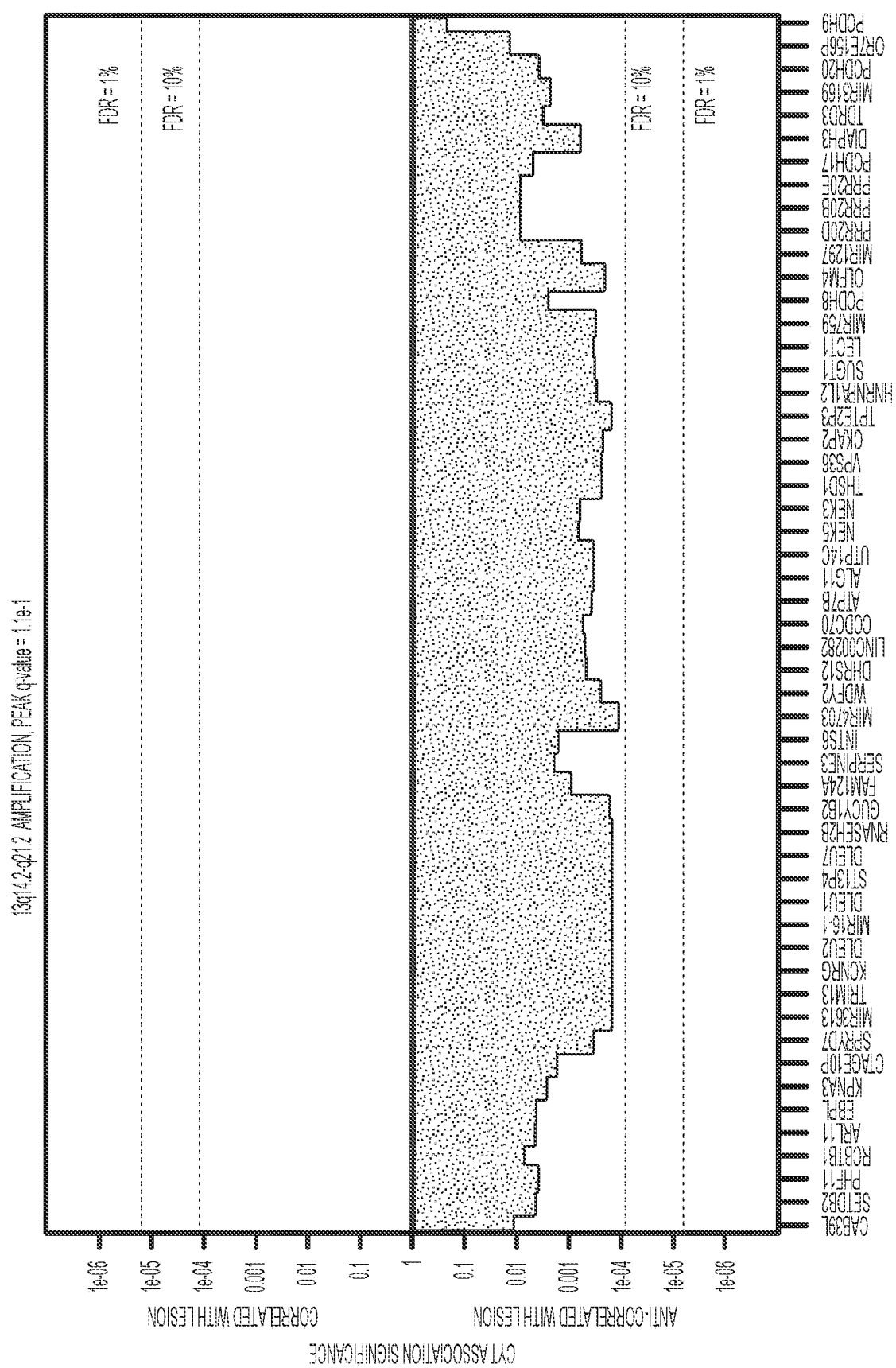
Figure 13B:
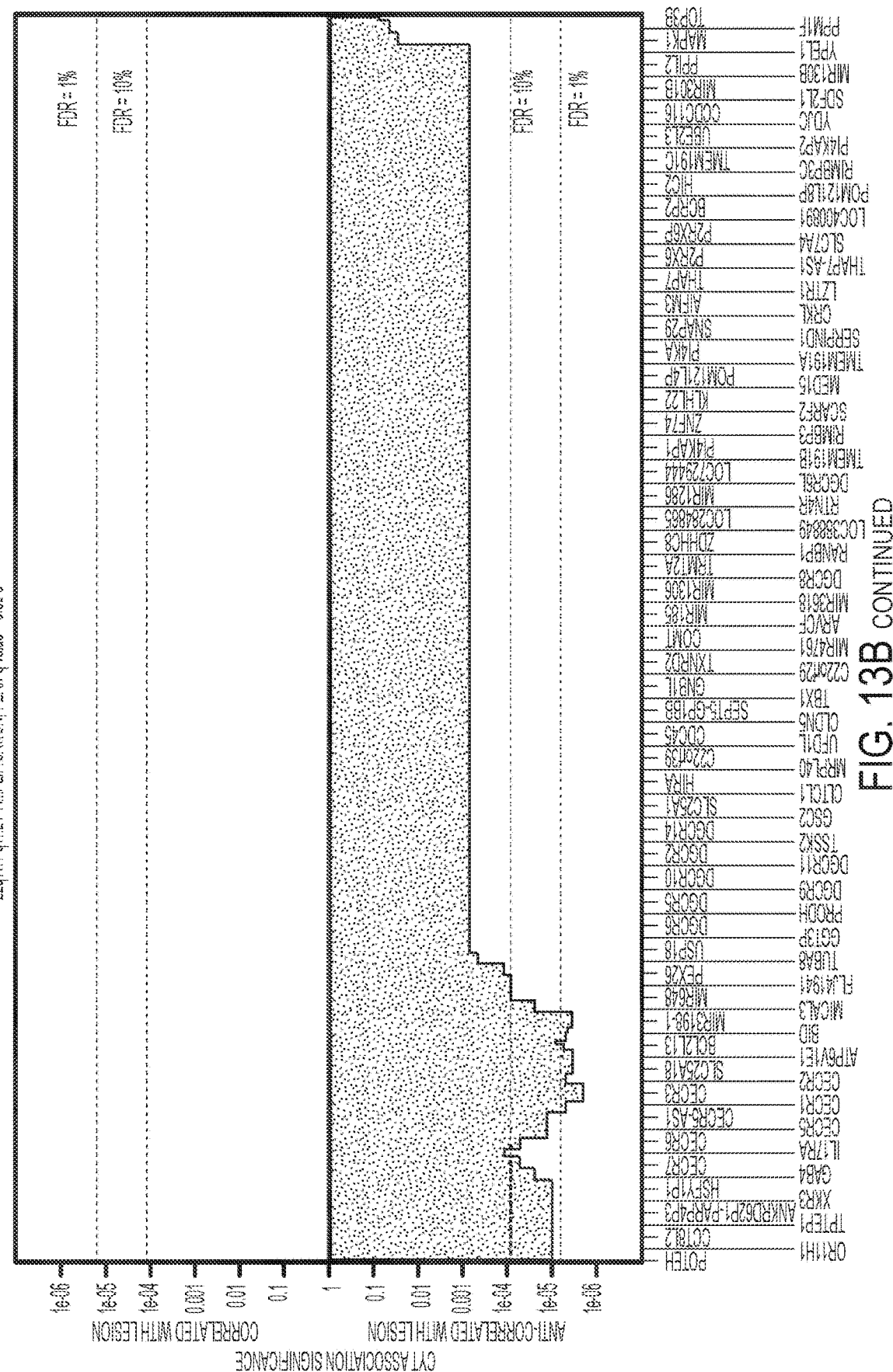
Figure 13B:
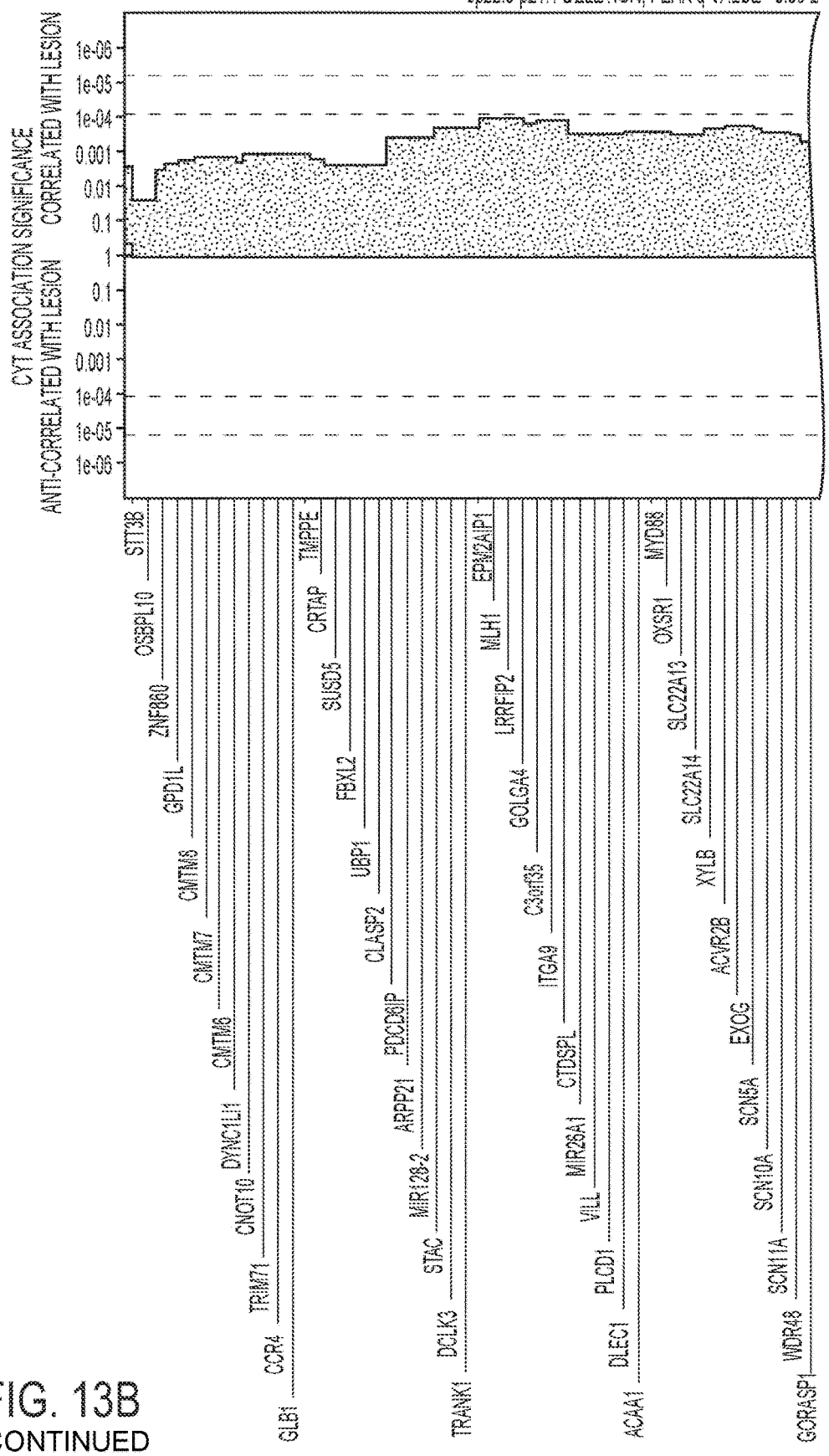
Figure 13B:
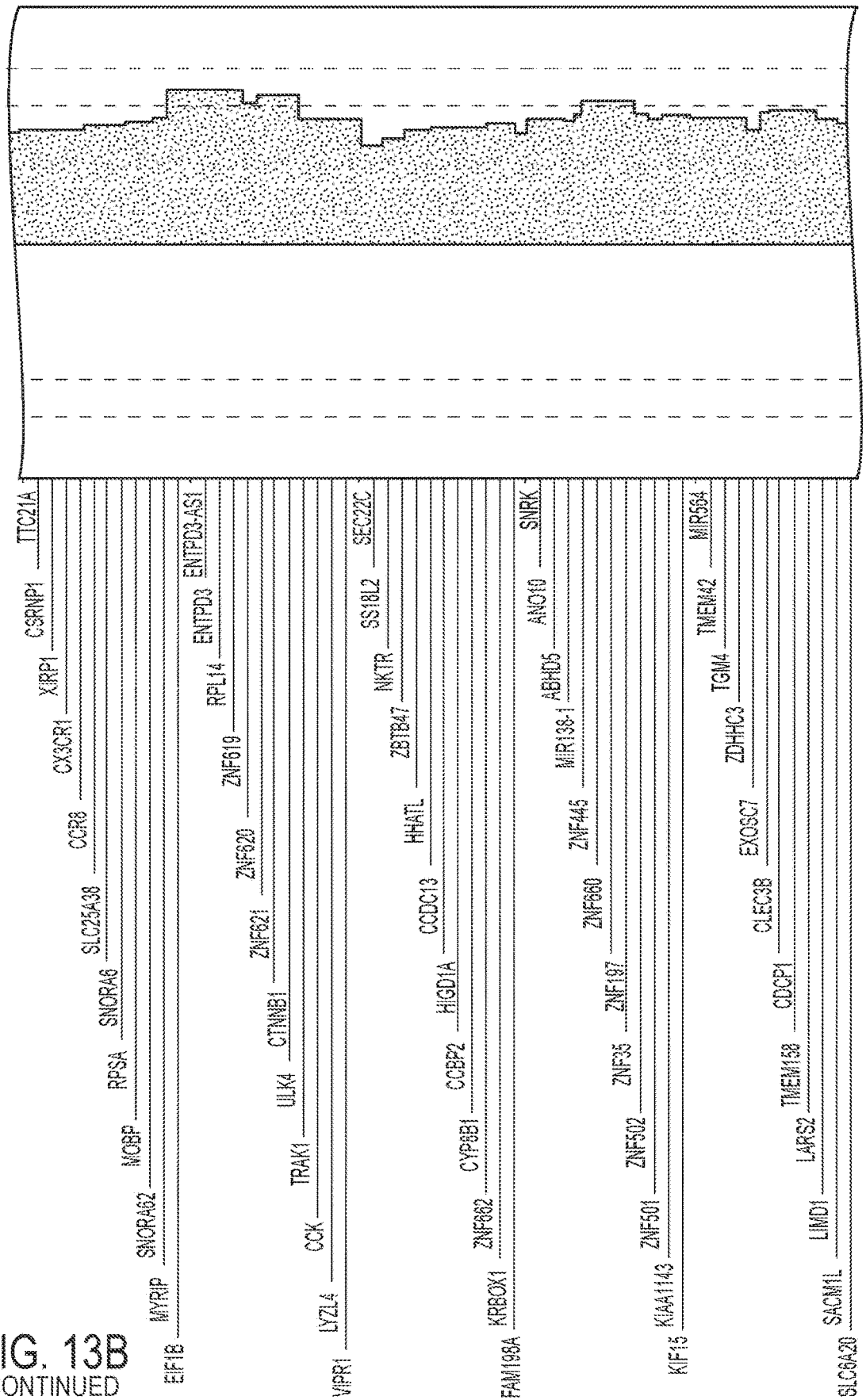
Figure 13B:
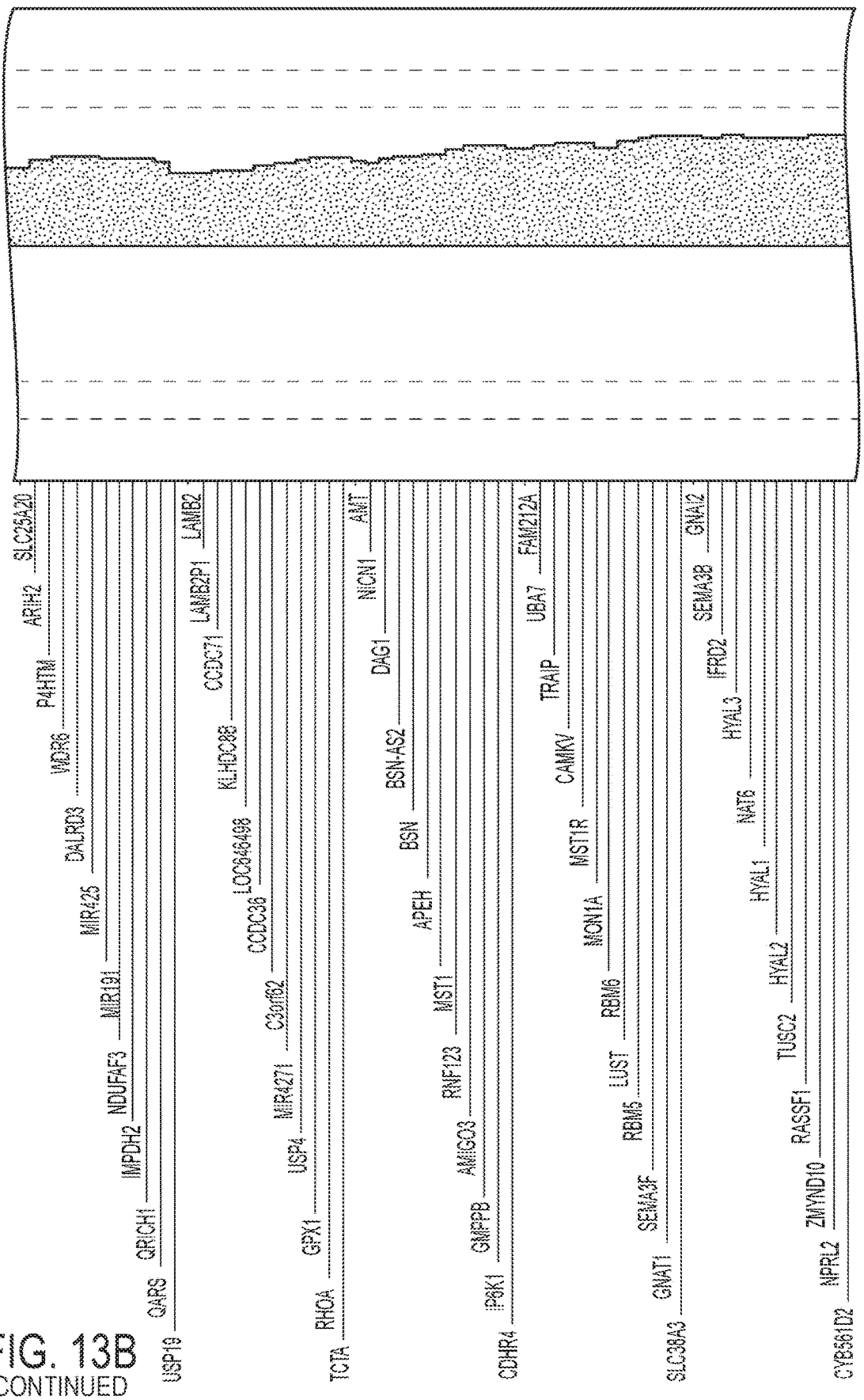
Figure 13B:
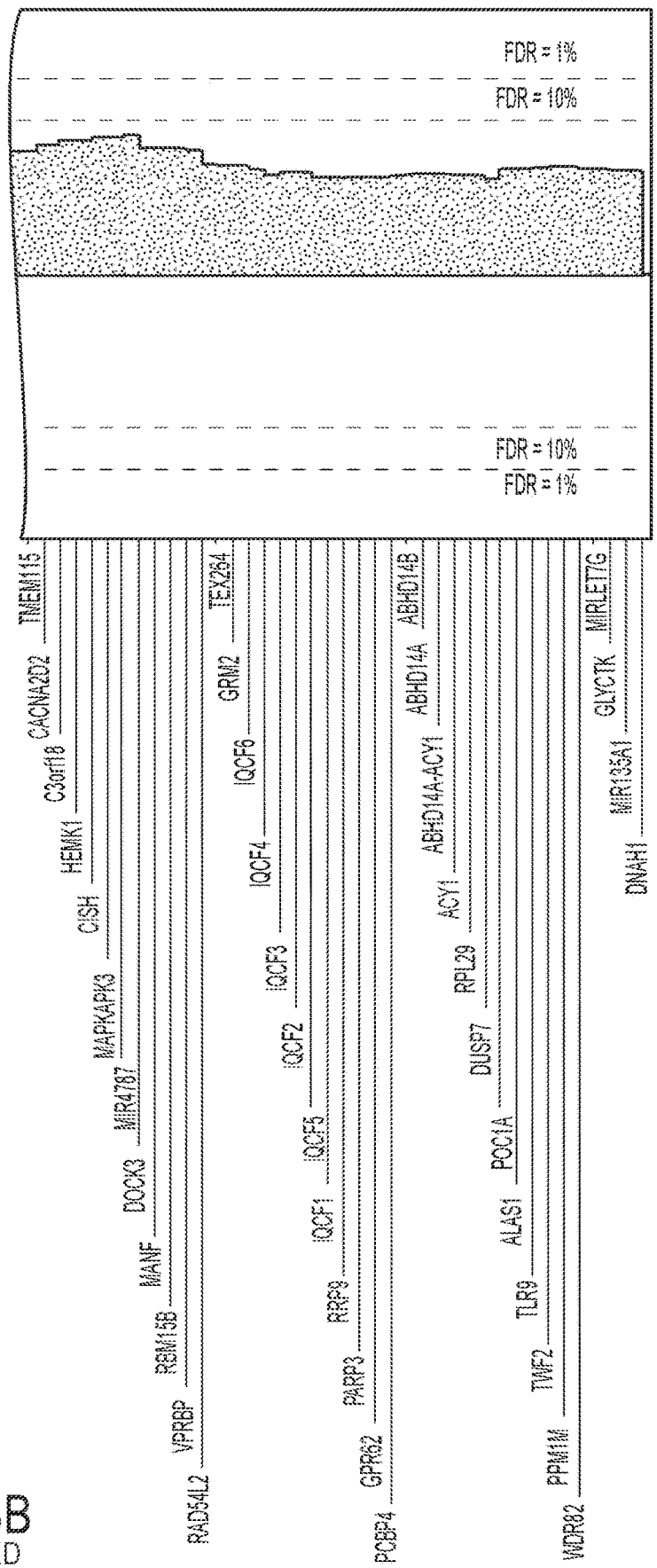
Figure 13C:
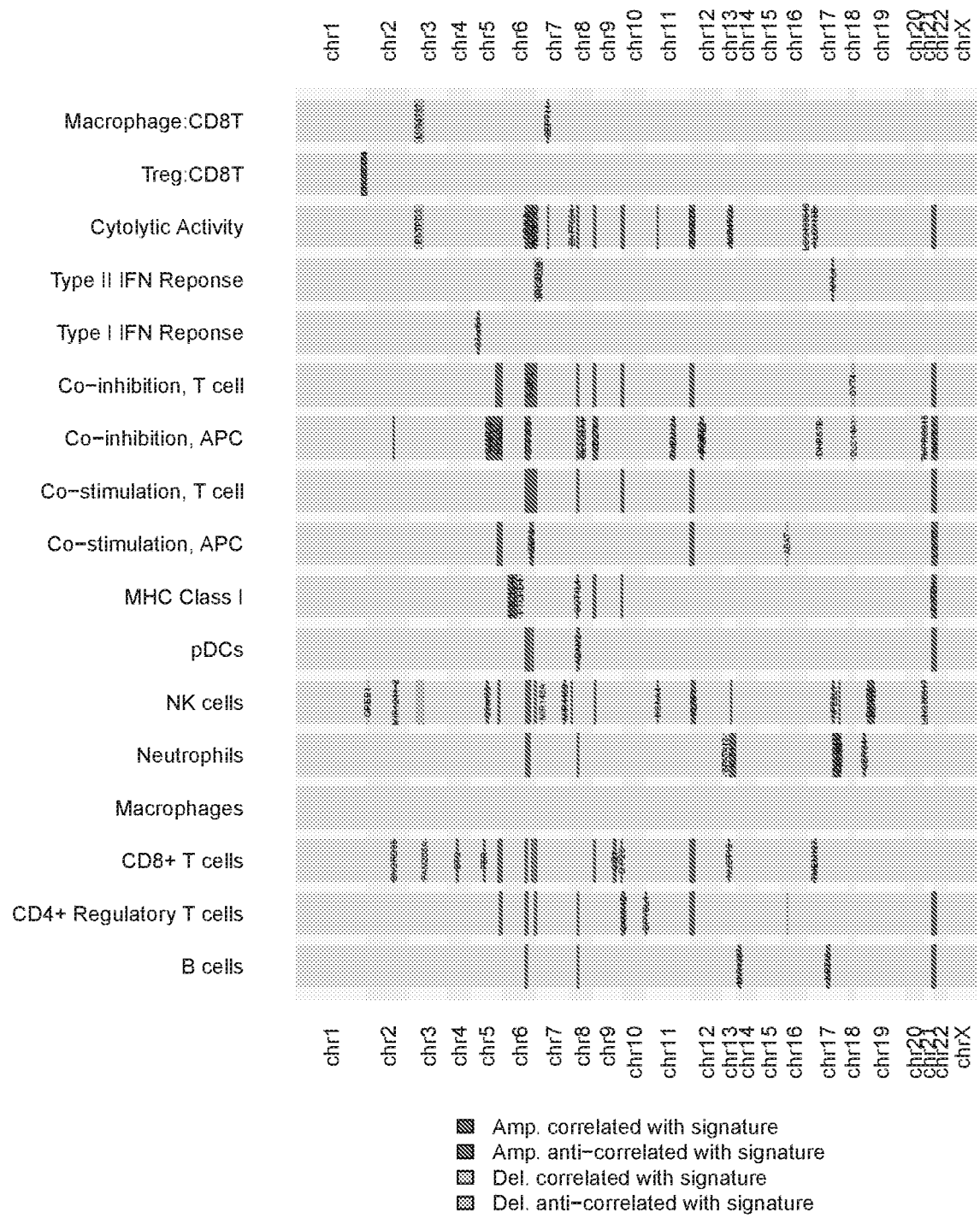

FIG. 13A-13C Significant copy number alterations. (A-B) Locus zooms for copy number alterations with uncorrected p<0.05. Plots indicate CYT association for amplifications (orange) and deletions (green) in significant and near-significant regions. Upward/downward direction indicates positive/negative association of lesion with CYT. One bar is presented for each gene in the region. Dotted lines indicate the uncorrected p-values at which a 1% and 10% FDRs are established. (C) CNA associations with enrichments of other cell type markers. Significant regions are highlighted according to the class of lesion (amplification or deletion) and the direction of the association. Many loci were significantly associated with multiple cell type markers. For the analysis yielding the strongest signal for a locus, the unbiased peak gene is labeled.

Figures 14A, 14B, 14C:
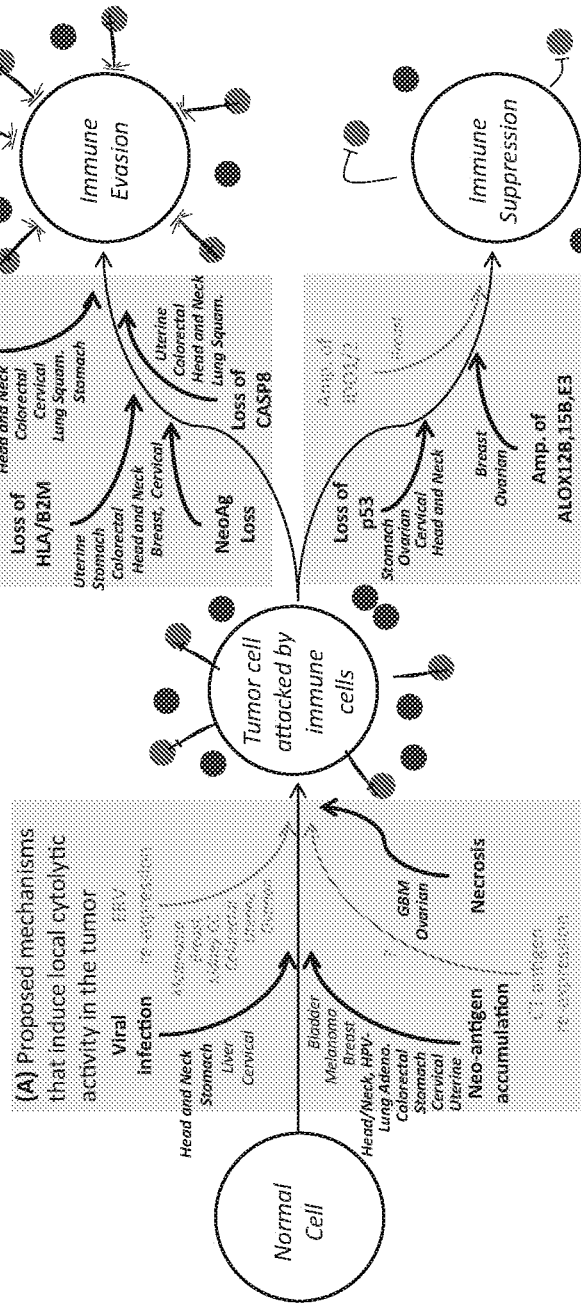

FIG. 14A-14C Classifying tumors by their immunological properties. A more elaborate version of FIG. 7 showing the specific tumor types and mechanisms implicated in (A) immune provocation (B) intrinsic immune escape and (C) extrinsic immune escape. Red cells represent cytolytic effectors (with spears) and blue cells represent other immune infiltrates. Large green cell represents tissue pre-transformation, and brown cells represent the tumor in various stages of immune interaction. In (B), "ricochet" lines indicate resistance to cytolytic action; whereas in (C), flat-capped arrows indicate suppression/removal/exclusion of cytolytic effector cells.

DETAILED DESCRIPTION OF THE INVENTION

Definitions

To facilitate an understanding of the present invention, a number of terms and phrases are defined herein:

Unless specifically stated or obvious from context, as used herein, the term "about" is understood as within a range of normal tolerance in the art, for example within 2 standard deviations of the mean. About can be understood as within 50%, 45%, 40%, 35%, 30%, 25%, 20%, 15%, 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Unless specifically stated or obvious from context, as used herein, the term "or" is understood to be inclusive. Unless specifically stated or obvious from context, as used herein, the terms "a," "an," and "the" are understood to be singular or plural.

By "agent" is meant any small molecule chemical compound, antibody, nucleic acid molecule, or polypeptide, or fragments thereof.

The term "immunotherapeutic agent" refers in general to any agent which produces a therapeutic effect by targeting the immune system or a component thereof. As used herein, the immunotherapeutic agent typically promotes an immune response, e.g. the agent may be an immunostimulatory agent or an inhibitor of an immunosuppressive agent (i.e. an anti-immunosuppressive agent). The term thus includes immunogenic compositions and vaccines, e.g. neoplasia vaccines comprising neoantigenic peptides. Immunotherapeutic agents can also include checkpoint blockers or inhibitors, chimeric antigen receptors (CARs), and adoptive T-cell therapy.

Immune checkpoints are inhibitory pathways that slow down or stop immune reactions and prevent excessive tissue damage from uncontrolled activity of immune cells. By "checkpoint inhibitor" is meant to refer to any small molecule chemical compound, antibody, nucleic acid molecule, or polypeptide, or fragment thereof, that inhibits the inhibitory pathways, allowing more extensive immune activity. A "checkpoint inhibitor" can also be an agent that stimulates a preexisting immune response. In certain embodiments, the checkpoint inhibitor is an inhibitor of the programmed death-1 (PD-1) pathway, for example an anti-PD1 antibody, such as, but not limited to Nivolumab. In other embodiments, the checkpoint inhibitor is an anti-cytotoxic T-lymphocyte-associated antigen (CTLA-4) antibody. In additional embodiments, the checkpoint inhibitor is targeted at another member of the CD28CTLA4 Ig superfamily such as BTLA, LAG3, ICOS, PDL1 or KIR Page et al., Annual Review of Medicine 65:27 (2014)). In further additional embodiments, the checkpoint inhibitor is targeted at a member of the TNFR superfamily such as CD40, OX40, CD137, GITR, CD27 or TIM-3. In some cases targeting a checkpoint inhibitor is accomplished with an inhibitory antibody or similar molecule. In other cases, it is accomplished with an agonist for the target; examples of this class include the stimulatory targets OX40 and GITR.

The term "combination" embraces the administration of a neoplasia vaccine or immunogenic composition (e.g. a pooled sample of neoplasia/tumor specific neoantigens) and one or more checkpoint inhibitors, as part of a treatment regimen intended to provide a beneficial (additive or synergistic) effect from the co-action of one or more of these therapeutic agents. The combination may also include one or more additional agents, for example, but not limited to, chemotherapeutic agents, anti-angiogenesis agents and agents that reduce immune-suppression. The beneficial effect of the combination includes, but is not limited to, pharmacokinetic or pharmacodynamic co-action resulting from the combination of therapeutic agents. Administration of these therapeutic agents in combination typically is carried out over a defined time period (for example, minutes, hours, days, or weeks depending upon the combination selected).

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. For example, one combination of the present invention may comprise a pooled sample of tumor specific neoantigens and a checkpoint inhibitor administered at the same or different times, or they can be formulated as a single, co-formulated pharmaceutical composition comprising the two compounds. As another example, a combination of the present invention (e.g., a pooled sample of tumor specific neoantigens and a checkpoint inhibitor and/or an anti-CTLA4 antibody) may be formulated as separate pharmaceutical compositions that can be administered at the same or different time. As used herein, the term "simultaneously" is meant to refer to administration of one or more agents at the same time. For example, in certain embodiments, a neoplasia vaccine or immunogenic composition and a checkpoint inhibitor are administered simultaneously. Simultaneously includes administration contemporaneously, that is during the same period of time. In certain embodiments, the one or more agents are administered simultaneously in the same hour, or simultaneously in the same day. Sequential or substantially simultaneous administration of each therapeutic agent can be effected by any appropriate route including, but not limited to, oral routes, intravenous routes, sub-cutaneous routes, intramuscular routes, direct absorption through mucous membrane tissues (e.g., nasal, mouth, vaginal, and rectal), and ocular routes (e.g., intravitreal, intraocular, etc.). The therapeutic agents can be administered by the same route or by different routes. For example, one component of a particular combination may be administered by intravenous injection while the other component(s) of the combination may be administered orally. The components may be administered in any therapeutically effective sequence. The phrase "combination" embraces groups of compounds or non-drug therapies useful as part of a combination therapy.

The term "neoantigen" or "neoantigenic" means a class of tumor antigens that arises from a tumor-specific mutation(s) which alters the amino acid sequence of genome encoded proteins.

By "neoplasia" is meant any disease that is caused by or results in inappropriately high levels of cell division, inappropriately low levels of apoptosis, or both. For example, cancer is an example of a neoplasia. Examples of cancers include, without limitation, leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

The term "neoplasia vaccine" is meant to refer to a pooled sample of neoplasia/tumor specific neoantigens, for example at least two, at least three, at least four, at least five, or more neoantigenic peptides. A "vaccine" is to be understood as meaning a composition for generating immunity for the prophylaxis and/or treatment of diseases (e.g., neoplasia/tumor). Accordingly, vaccines are medicaments which comprise antigens and are intended to be used in humans or animals for generating specific defense and protective substance by vaccination. A "neoplasia vaccine composition" can include a pharmaceutically acceptable excipient, carrier or diluent.

The term "pharmaceutically acceptable" refers to approved or approvable by a regulatory agency of the Federal or a state government or listed in the U.S. Pharmacopeia or other generally recognized pharmacopeia for use in animals, including humans.

A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" of pooled tumor specific neoantigens as recited herein may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts for the pooled tumor specific neoantigens provided herein, including those listed by Remington's Pharmaceutical Sciences, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

By a "polypeptide" or "peptide" is meant a polypeptide that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide. An isolated polypeptide may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

As used herein, the terms "prevent," "preventing," "prevention," "prophylactic treatment," and the like, refer to reducing the probability of developing a disease or condition in a subject, who does not have, but is at risk of or susceptible to developing a disease or condition.

The term "prime/boost" or "prime/boost dosing regimen" is meant to refer to the successive administrations of a vaccine or immunogenic or immunological compositions. The priming administration (priming) is the administration of a first vaccine or immunogenic or immunological composition type and may comprise one, two or more administrations. The boost administration is the second administration of a vaccine or immunogenic or immunological composition type and may comprise one, two or more administrations, and, for instance, may comprise or consist essentially of annual administrations. In certain embodiments, administration of the neoplasia vaccine or immunogenic composition is in a prime/boost dosing regimen.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "cytolytic activity" refers in general to the capacity of the immune system in a tissue to provide cytolysis, e.g. to mediate the targeted destruction of cells. In the context of the present invention, the term typically refers to the capacity to kill tumor cells, e.g. via cytotoxic T cell or natural killer cell activity. Cytolytic activity in a tissue may reflect the number and/or activity of immune system cells (e.g. cytotoxic T cell or natural killer cells) infiltrated into the tissue. For instance, in some embodiments cytolytic activity may be determined by measuring the expression of one or more markers which mediate cytolysis, e.g. granzyme A and/or perforin. As described hereinafter, in many cases tumors appear to be resistant to a greater or lesser extent to cytolytic activity, e.g. high cytolytic activity may be present in a tumor tissue in the apparent absence of significant tumor cell death. Thus as used herein, the term "cytolytic activity" typically refers to the capacity or potential of a tissue to exert a tumor cytolytic effect (e.g. based on numbers and/or activity of cytotoxic T cells and/or natural killer cells or expression of markers thereof) rather than being a measure of actual tumor cell death.

A "receptor" is to be understood as meaning a biological molecule or a molecule grouping capable of binding a ligand. A receptor may serve, to transmit information in a cell, a cell formation or an organism. The receptor comprises at least one receptor unit and frequently contains two or more receptor units, where each receptor unit may consist of a protein molecule, in particular a glycoprotein molecule. The receptor has a structure that complements the structure of a ligand and may complex the ligand as a binding partner. Signaling information may be transmitted by conformational changes of the receptor following binding with the ligand on the surface of a cell. According to the invention, a receptor may refer to particular proteins of MHC classes I and II capable of forming a receptor/ligand complex with a ligand, in particular a peptide or peptide fragment of suitable length.

The term "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

The terms "treat," "treated," "treating," "treatment," and the like are meant to refer to reducing or ameliorating a disorder and/or symptoms associated therewith (e.g., a neoplasia or tumor). "Treating" may refer to administration of the combination therapy to a subject after the onset, or suspected onset, of a cancer. "Treating" includes the concepts of "alleviating", which refers to lessening the frequency of occurrence or recurrence, or the severity, of any symptoms or other ill effects related to a cancer and/or the side effects associated with cancer therapy. The term "treating" also encompasses the concept of "managing" which refers to reducing the severity of a particular disease or disorder in a patient or delaying its recurrence, e.g., lengthening the period of remission in a patient who had suffered from the disease. It is appreciated that, although not precluded, treating a disorder or condition does not require that the disorder, condition, or symptoms associated therewith be completely eliminated.

The term "therapeutic effect" refers to some extent of relief of one or more of the symptoms of a disorder (e.g., a neoplasia or tumor) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required. For example, the physician or veterinarian could start doses of the compounds of the invention employed in a pharmaceutical composition at levels lower than that required in order to achieve the desired therapeutic effect and gradually increase the dosage until the desired effect is achieved.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

In embodiments of the present invention, cytolytic activity of a tumor is monitored in order to determine susceptibility of the tumor to immunotherapy. In particular, high cytolytic activity in the tumor may be indicative of cytotoxic T cell and/or natural killer cell infiltration into the tumor, and therefore the potential for the immune system to specifically target tumor cells and thereby exert a therapeutic effect. However, in many cases mutations in tumor cells may lead to tumor resistance to cytolytic activity. In such cases, despite a high level of cytotoxic activity in the tumor, tumor cells may evade immune system attack by mutations involved in, for example, cytolytic cell death and/or antigen presentation. In embodiments of the present invention, tumor resistance to cytolytic activity may be overcome by targeting an immunotherapy at subjects whose tumors are vulnerable to immune system attack, but which have avoided destruction by cytotoxic T cells and/or natural killer cells through immunosuppressive mutations. By boosting the immune response in such subjects, tumor evasion of cytolytic activity can be overcome leading to an enhanced therapeutic effect. In a similar manner, in further embodiments of the invention where tumor mutations result in suppression of cytolytic activity, immunotherapy may be used to overcome such suppression and lead to cytolytic destruction of tumor cells.

Thus in one embodiment, a tumor is assessed for its ability to mount an immunological response or tumor immunity. Tumor immunity is based on the factors described herein.

In another embodiment, the invention provides a method for selecting patients most likely to benefit from an immunotherapy, e.g. a combination therapy as described therein. In one embodiment patients are selected based on the notion that effective natural anti-tumor immunity requires a cytolytic immune response (CYT). In another embodiment patients are selected based on the need for additional activation of the immune system. In another embodiment patients are selected based on the need for derepression of the immune system. In another embodiment patients are selected based on the ability to present tumor neoantigens to the immune system. In one embodiment patients are selected based on the ability to produce a cytolytic response and the ability to present tumor neoantigens to the immune system. In another embodiment patients are selected based on the ability to produce a cytolytic response, the ability to present tumor neoantigens to the immune system, and the need for additional immune stimulation. In another embodiment patients are selected that have tumors with mutations encoding neoantigens. In one embodiment patients are selected that have cytolytic activity, neoantigens expressed in their tumors, and that do not have mutations that prevent the presentation of antigens or prevent cytolytic killing by T-cells.

Determining Cytolytic Activity in a Tumor

In one embodiment the cytolytic immune response is determined by observing the number of activated T-cells and natural killer cells. This can be done by assaying for markers of cytolytic T-cells or NK cells. Markers can include cell surface markers or release of cytokines. Cytokines may include Interferon-γ or interleukin-2. Additionally, the expression of cell specific genes can be determined. In one embodiment CD8 expression is determined. In another embodiment the cytolytic immune response is determined by observing tumor cell infiltration by T-cells.

In another embodiment cytolytic immune response is quantified using a metric based on the key effector molecules that mediate cytolysis. In one embodiment the key effector molecules are granzyme A (GZMA) and perforin (PRF1). In a preferred embodiment gene expression analysis of granzyme A (GZMA) and perforin (PRF1) are used. For instance, cytolytic activity may be determined by (a) sequencing RNA expressed in a tumor sample, (b) calculating the log-average of the transcript levels of GZMA and PRF1 and (c) assigning a cytolytic activity (CYT) score to the tumor based on the log average calculated in (b).

Determining Genetic Alterations Associated with Cytolytic Activity in a Tumor

In one embodiment, the method comprises a step of determining genetic alterations associated with cytolytic activity in the tumor. In one embodiment, such genetic alterations may be mutations associated with induction of cytolytic activity. In another embodiment, the genetic alterations may be associated with tumor resistance to cytolytic activity. In a further embodiment, the genetic alterations may be associated with suppression of cytolytic activity. Typically the genetic alterations are mutations which are commonly found in tumors which show high cytolytic activity (e.g. high infiltration of cytotoxic T cells and/or natural killer cells), but which nevertheless evade immune-mediated destruction. However in an alternative embodiment, the genetic alteration may be found in tumors showing a low level of cytolytic activity. Thus embodiments of the present invention may comprise a step of detecting enrichment of somatic genetic alterations or mutations in tumors. In preferred embodiments, the tumor is uterine, stomach or colorectal cancer.

In general, mutations in the following genes may be determined in the present method:

| Gene | Full name | Entrez gene ID no. |
|---|---|---|
| CASP8 | caspase-8 | 841 |
| B2M | beta-2-microglobulin | 567 |
| PIK3CA | Phosphatidylinositol-4,5-Bisphosphate 3-Kinase, Catalytic Subunit Alpha | 5290 |
| SMC1A | Structural Maintenance Of Chromosomes 1A | 8243 |
| ARID5B | AT Rich Interactive Domain 5B (MRF1-Like) | 84159 |
| TET2 | Tet Methylcytosine Dioxygenase 21 | 54790 |
| ALPK2 | Alpha-Kinase 2 | 115701 |
| COL5A1 | Collagen, Type V, Alpha 1 | 1289 |
| TP53 | Tumor Protein P53 | 7157 |
| DNER | Delta/Notch-Like EGF Repeat Containing | 92737 |
| NCOR1 | Nuclear Receptor Corepressor 1 | 9611 |
| MORC4 | MORC Family CW-Type Zinc Finger 4 | 79710 |
| CIC | Capicua Transcriptional Repressor | 23152 |
| IRF6 | Interferon Regulatory Factor 6 | 3664 |
| MYOCD | myocardin | 93649 |
| ANKLE1 | Ankyrin Repeat And LEM Domain Containing 1 | 126549 |
| CNKSR1 | Connector Enhancer Of Kinase Suppressor Of Ras 1 | 10256 |
| NF1 | Neurofibromin 1 | 4763 |
| SOS1 | Son Of Sevenless Homolog 1 | 6654 |
| ARID2 | AT Rich Interactive Domain 2 (ARID, RFX-Like) | 196528 |
| CUL4B | Cullin 4B | 8450 |
| DDX3X | DEAD (Asp-Glu-Ala-Asp) Box Helicase 3, X-Linked | 1654 |
| FUBP1 | Far Upstream Element (FUSE) Binding Protein 1 | 8880 |
| TCP11L2 | T-Complex 11, Testis-Specific-Like 2 | 255394 |
| HLA-A | Human Leukocyte Antigen, Class I-A | 3105 |
| HLA-B | Human Leukocyte Antigen, Class I-B | 3106 |
| HLA-C | Human Leukocyte Antigen, Class I-C | 3107 |
| CSNK2A1 | Casein Kinase 2, Alpha 1 Polypeptide | 1457 |
| MET | Met Proto-Oncogene | 4233 |
| ASXL1 | Additional Sex Combs Like 1 | 171023 |
| PD-1 | Programmed Cell Death 1 | 5133 |
| PD-L1 | Programmed Death Ligand 1 (CD274) | 29126 |
| PD-L2 | Programmed Cell Death 1 Ligand 2 (CD273) | 80380 |
| IDO1 | Indoleamine 2,3-Dioxygenase 1 | 3620 |
| IDO2 | Indoleamine 2,3-Dioxygenase 2 | 169355 |
| ALOX12B | Arachidonate 12-Lipoxygenase, 12R Type | 242 |
| ALOX15B | Arachidonate 15-Lipoxygenase, Type B | 247 |

Nucleotide and amino acid sequences for the above genes in humans and other species are accessible from publicly available databases, e.g. via the NCBI Entrez database accession nos. shown above.

The genetic alterations determined according to the present method are typically mutations affecting an immune response. In some embodiments, the genetic alteration associated with tumor resistance to cytolytic activity is a mutation in a gene associated with immunosuppression, e.g. a gene which codes for a polypeptide having immunosuppressant properties. In this embodiment, the mutation may, for example, be a copy number alteration (e.g. a gene amplification) or a gain-of-function (e.g. an activating or activity-enhancing) mutation. Typically mutations which enhance immunosuppressive effects may be associated with tumor resistance to cytolytic activity, for instance by inhibiting destruction of tumor cells by activated cytotoxic T cells and/or natural killer cells. In some embodiments, the mutated gene is PD-1, PD-L1 or PD-L2. In such cases, the genetic alteration is typically a gene amplification. Typically mutations in such genes are associated with a high level of cytolytic activity in the tumor, i.e. cytolytic activity is induced but does not result in immune-mediated tumor cell death. In some such embodiments, the tumor is selected from lung squamous cell carcinoma, head and neck cancer, cervical cancer and colorectal cancer.

In other embodiments, the genetic alteration is in a gene associated with immunosuppression, but which is associated with a reduced level of cytolytic activity in the tumor. The mutation may, for example, be a copy number alteration (e.g. a gene amplification) or a gain-of-function (e.g. an activating or activity-enhancing) mutation. Such mutations may suppress cytolytic activity and thereby inhibit immune-mediated tumor cell death. For instance, the mutation may be in a gene selected from IDO1, IDO2, ALOX12B and ALOX15B. In such cases, the genetic alteration is typically a gene amplification. In some such embodiments, the tumor is selected from breast cancer and ovarian cancer.

In another embodiment, the genetic alteration associated with tumor resistance to cytolytic activity is a mutation in a gene which promotes immune responses or immune-mediated cytotoxicity, e.g. a gene which codes for a polypeptide having immunostimulatory properties or a polypeptide involved in a cell death pathway. In this embodiment, the mutation may be, for example, a loss-of-function mutation, e.g. a point mutation, splice-site mutation, frameshift mutation, deletion or truncation mutation which decreases or eliminates expression or activity of the encoded polypeptide. In some embodiments, the mutation may be in a gene associated with cytotoxic cell death or antigen presentation.

For instance, in one embodiment the mutation is in a gene associated with the MHC Class I complex, e.g. B2M (which encodes the invariant chain of MHC Class I) or HLA-A, HLA-B or HLA-C. In another embodiment, the mutation is in a gene associated with an apoptosis pathway, e.g. a gene required for FasL-Fas-mediated cytotoxicity. For instance, the mutation may be in a gene selected from CASP8, CNLSR1, MET, CSNK2A1 and PIK3CA. Typically such mutations may be associated with tumor resistance to cytotoxic activity in the presence of a high level of cytotoxic activity in the tumor tissue, for instance by inhibiting antigen-specific recognition of tumor cells by cytotoxic T cells and/or immune-mediated tumor cell death. In one embodiment, the gene is CASP8 and the tumor is selected from head and neck cancer, colorectal cancer, lung squamous cell carcinoma and uterine cancer. In another embodiment, the gene is PIK3CA and the tumor is stomach cancer. In another embodiment, the gene is B2M and the tumor is selected from uterine, breast, colorectal and stomach cancer. In another embodiment, the gene is HLA-A, HLA-B or HLA-C and the tumor is selected from colorectal, head and neck, uterine, stomach and cervical cancer.

In a further embodiment, the mutations are associated with induction of cytolytic activity. In general, increased cytolytic activity in a tumor is considered to be indicative of a potential for the tumor to respond to immunotherapy, since the tumor is likely to already be infiltrated with e.g. cytotoxic T cells and/or natural killer cells. Regardless of the mechanism by which such tumors evade natural immune-mediated tumor destruction, immunotherapy may be more likely to boost immune responses in the subject and overcome tumor resistance to cytolytic activity. Thus biomarkers indicative of the induction of cytolytic activity may be used to identify subjects likely to respond to immunotherapy.

In one embodiment, the genetic alteration associated with induction of cytolytic activity comprises a plurality of neoantigen mutations. Thus in embodiments of the present invention, neoantigen load may be used to assess the ability to present tumor neoantigens to the immune system. Neoantigen load refers to the number of neoantigens that will bind a subject's HLA proteins present in a tumor. In one embodiment at least 2 neoantigens are present. In a preferred embodiment greater than 10 neoantigens are present. More preferably more than 20 neoantigens are present. In another preferred embodiment 20-30 neoantigens are present. In another embodiment total mutation count in a tumor is used. In such embodiments, the tumor is preferably selected from uterine cancer, breast cancer, stomach cancer, cervical cancer, colorectal cancer and lung adenocarcinoma.

In further embodiments, the induction of cytolytic activity in the tumor may be associated with a viral infection, e.g. human papilloma virus (HPV) or Epstein Barr virus (EBV). In one embodiment, the virus is HPV and the tumor is selected from cervical cancer, head and neck cancer, bladder cancer, colorectal cancer, kidney clear cell, glioma, lung squamous cell carcinoma and uterine cancer, preferably cervical cancer. In another embodiment, the virus is EBV and the tumor is stomach cancer. In a further embodiment, the virus is hepatitis B or C (HBV or HCV) and the tumor is liver cancer. Tumor cytolytic activity may alternatively be associated with expression of one or more endogenous retroviral genes.

In one embodiment mutations are determined by sequencing the genomes or exomes of tumors as described herein. In one embodiment the amplifications and/or deletions at genomic loci are determined. In another embodiment mutations in specific genes are determined.

Selecting Subjects for Immunotherapy

In embodiments of the present invention, subjects may be treated by immunotherapy based on the results of the above steps, e.g. based on a level of cytolytic activity in the tumor or the presence of genetic alterations associated with cytolytic activity. Thus the method may comprise treating a sub-population of subjects with cancer, the sub-population being identified as susceptible to (i.e. likely to respond to) immunotherapy. In one aspect the invention provides a method for selecting a patient population based on the above detection steps.

In one embodiment, the subject is selected for immunotherapy if cytolytic activity is detected in the tumor. In a preferred embodiment, the subject is selected if cytolytic activity is elevated in a tumor sample compared to a control sample. The control sample may be from the same individual subject or a different (control) subject. For example, the control sample may comprise a sample of non-cancerous tissue from the same subject, or be derived from the same tissue type from a normal subject (e.g. a subject not suffering from cancer). Preferably cytolytic activity is elevated in the tumor sample by at least 5%, at least 10%, at least 20%, at least 50% or at least 100% compared to the control sample.

In another embodiment, the subject is selected for immunotherapy if a genetic alteration associated with induction of cytolytic activity is detected in the tumor. For instance, the subject may be selected for immunotherapy if the tumor comprises a plurality of neoantigen mutations, e.g. a high neoantigen load.

In another embodiment, the subject is selected for immunotherapy if a genetic alteration associated with tumor resistance to cytolytic activity is detected in the tumor. For instance, the subject may be selected for immunotherapy if the tumor comprises a mutation in a gene associated with immunosuppression, e.g. an amplification in a gene such as PD-1, PDL-1 or PDL-2.

In another embodiment, the subject is selected for immunotherapy if a genetic alteration associated with suppression of cytolytic activity is detected in the tumor. In such embodiments, the subject may be selected for immunotherapy even if cytolytic activity in the tumor is low.

In another embodiment, the subject may be selected for immunotherapy if the tumor comprises a mutation in a gene which promotes immune responses or immune-mediated cytotoxicity, e.g. a loss-of-function mutation in a gene associated with antigen presentation or an apoptosis pathway. In these embodiments, it is preferred that the subject has at least one non-mutated allele in such genes. Without being bound by theory, mutations in a single allele of such genes may reduce anti-tumor immune responses, but immunotherapy may boost the immune system and thereby restore effective immune-mediated tumor destruction. In contrast, loss-of-function mutations in both alleles of e.g. a gene encoding an antigen presentation molecule (e.g. B2M or HLA-A, B or C) or a gene involved in apoptosis (e.g CASP8) may indicate that the subject is unlikely to respond to immunotherapy, because tumor cells are incapable of presenting tumor antigens to cytotoxic T cells.

Thus in one embodiment patients are selected for immunotherapy if they have at least one non-mutated allele in a gene encoding a component of the antigen presentation machinery. In one embodiment patients are selected if they have at least one non-mutated allele in a gene required for cytolytic cells to kill tumors via FasL-Fas interactions. In one embodiment these genes include HLA and B2M, as well as extrinsic apoptosis genes, such as CASP8, that would prevent cytolytic cells from killing tumors via FasL-Fas interactions. In another embodiment the patient is selected based on genetic alterations or mutations associated with genes that function in immunosuppression, such as PDL1, PDL2. In one embodiment amplification of genomic regions encoding these genes is found. In another embodiment mutations that correlated negatively with cytolytic activity are determined. In one embodiment these mutations represent non-autonomous mechanisms of suppressing immunity, and include IDO1 and IDO2, p53 and the ALOX locus. These patients are selected even though they have a low cytolytic activity because the immunotherapy described herein can induce an immune response greater than a natural response.

Subjects may be selected for immunotherapy based on a combination of factors as described herein, e.g. cytolytic activity in the tumor and the presence of genetic alterations associated with cytolytic activity. Thus in one embodiment the invention involves selecting subjects most likely to benefit from immunotherapy, based on a combination of factors related to cytolytic activity in the tumor. For instance, in one embodiment subjects are selected for immunotherapy if they have elevated cytolytic activity, a mutation associated with induction of cytolytic activity and a mutation associated with tumor resistance to cytolytic activity. In one embodiment patients with the greatest potential benefit from immunotherapy are identified by determining neoantigen load, cytolytic T-cell activity, as well as immunosuppressive mutations. In one embodiment, patients are treated based on this analysis.

In one embodiment patients are selected based on a cytolytic immune response (CYT). In another embodiment patients are selected based on the need for additional activation of the immune system. In another embodiment patients are selected based on the ability to present tumor neoantigens to the immune system. In a preferred embodiment patients are selected based on the ability to have a cytolytic response and the ability to present tumor neoantigens to the immune system. In another preferred embodiment patients are selected based on the ability to produce a cytolytic response, the ability to present tumor neoantigens to the immune system, and the need for additional immune stimulation. In one embodiment patients are selected that have cytolytic activity, neoantigens expressed in their tumors, and do not have mutations that prevent the presentation of antigens or prevent cytolytic killing by T-cells.

Without being bound by theory, patients that have high cytolytic activity, a plurality of neoantigen mutations, and mutations (esp. amplifications) in genes that function in immunosuppression, while not having mutations that eliminate all alleles required for antigen presentation and cytotoxic T-cell killing, are ideal candidates for the immunotherapy described herein. For instance, treatment with a checkpoint inhibitor may allow the immunosuppression to be reversed allowing the neoantigens to be presented to T-cells that would then kill the tumors.

In an alternative embodiment, subjects with low cytolytic activity associated with a mutation (e.g. amplification) in an immunosuppressive gene, but that express a plurality of neoantigens, may be treated with immunotherapy. Treatment with immunotherapy (e.g. a combination therapy as described herein) may activate the T-cell activity. Without being bound by theory, subjects that have mutations that do not allow any expression of HLA and/or B2M, and thus which are incapable of presenting neoantigens to T cells, may be eliminated from the group of patients selected for the immunotherapy. In another embodiment, subjects that have inactivating mutations that do not allow any expression of functional genes required for cytolytic killing by T-cells (e.g. CASP8) may also be eliminated from the group of patients selected for the combination therapy.

Immunotherapy

If a subject is selected as suitable according to the methods described above, the method may further comprise administering an immunotherapeutic agent to the subject. In one embodiment, the immunotherapeutic agent comprises a neoplasia vaccine or immunogenic composition. In another embodiment, the immunotherapeutic agent comprises an immune checkpoint inhibitor. In a preferred embodiment, a combination therapy comprising a neoplasia vaccine or immunogenic composition and a checkpoint inhibitor is administered to the subject.

The therapy disclosed herein constitutes a new method for treating various types of cancer. The therapy described herein also provides a method for achieving clinical benefit without an unacceptable level of side effects.

In one embodiment, a neoplasia vaccine or immunogenic composition comprising a plurality of neoplasia/tumor specific neoantigens is administered to the subject. As described in more detail herein, whole genome/exome sequencing may be used to identify all, or nearly all, mutated neoantigens that are uniquely present in a neoplasia/tumor of an individual patient, and that this collection of mutated neoantigens may be analyzed to identify a specific, optimized subset of neoantigens for use as a personalized cancer vaccine or immunogenic composition for treatment of the patient's neoplasia/tumor. For example, a population of neoplasia/tumor specific neoantigens may be identified by sequencing the neoplasia/tumor and normal DNA of each patient to identify tumor-specific mutations, and the patient's HLA allotype can be identified. The population of neoplasia/tumor specific neoantigens and their cognate native antigens may then be subject to bioinformatic analysis using validated algorithms to predict which tumor-specific mutations create epitopes that could bind to the patient's HLA allotype. Based on this analysis, a plurality of peptides corresponding to a subset of these mutations may be designed and synthesized for each patient, and pooled together for use as a cancer vaccine or immunogenic composition in immunizing the patient.

The immune system can be classified into two functional subsystems: the innate and the acquired immune system. The innate immune system is the first line of defense against infections, and most potential pathogens are rapidly neutralized by this system before they can cause, for example, a noticeable infection. The acquired immune system reacts to molecular structures, referred to as antigens, of the intruding organism. There are two types of acquired immune reactions, which include the humoral immune reaction and the cell-mediated immune reaction. In the humoral immune reaction, antibodies secreted by B cells into bodily fluids bind to pathogen-derived antigens, leading to the elimination of the pathogen through a variety of mechanisms, e.g. complement-mediated lysis. In the cell-mediated immune reaction, T-cells capable of destroying other cells are activated. For example, if proteins associated with a disease are present in a cell, they are fragmented proteolytically to peptides within the cell. Specific cell proteins then attach themselves to the antigen or peptide formed in this manner and transport them to the surface of the cell, where they are presented to the molecular defense mechanisms, in particular T-cells, of the body. Cytotoxic T cells recognize these antigens and kill the cells that harbor the antigens.

The molecules that transport and present peptides on the cell surface are referred to as proteins of the major histocompatibility complex (MHC). MHC proteins are classified into two types, referred to as MHC class I and MHC class II. The structures of the proteins of the two MHC classes are very similar; however, they have very different functions. Proteins of MHC class I are present on the surface of almost all cells of the body, including most tumor cells. MHC class I proteins are loaded with antigens that usually originate from endogenous proteins or from pathogens present inside cells, and are then presented to naïve or cytotoxic T-lymphocytes (CTLs). MHC class II proteins are present on dendritic cells, B-lymphocytes, macrophages and other antigen-presenting cells. They mainly present peptides, which are processed from external antigen sources, i.e. outside of the cells, to T-helper (Th) cells. Most of the peptides bound by the MHC class I proteins originate from cytoplasmic proteins produced in the healthy host cells of an organism itself, and do not normally stimulate an immune reaction. Accordingly, cytotoxic T-lymphocytes that recognize such self-peptide-presenting MHC molecules of class I are deleted in the thymus (central tolerance) or, after their release from the thymus, are deleted or inactivated, i.e. tolerized (peripheral tolerance). MHC molecules are capable of stimulating an immune reaction when they present peptides to non-tolerized T-lymphocytes. Cytotoxic T-lymphocytes have both T-cell receptors (TCR) and CD8 molecules on their surface. T-Cell receptors are capable of recognizing and binding peptides complexed with the molecules of MHC class I. Each cytotoxic T-lymphocyte expresses a unique T-cell receptor which is capable of binding specific MHC/peptide complexes.

The peptide antigens attach themselves to the molecules of MHC class I by competitive affinity binding within the endoplasmic reticulum, before they are presented on the cell surface. Here, the affinity of an individual peptide antigen is directly linked to its amino acid sequence and the presence of specific binding motifs in defined positions within the amino acid sequence. If the sequence of such a peptide is known, it is possible to manipulate the immune system against diseased cells using, for example, peptide vaccines.

One of the critical barriers to developing curative and tumor-specific immunotherapy is the identification and selection of highly specific and restricted tumor antigens to avoid autoimmunity. Tumor neoantigens, which arise as a result of genetic change (e.g., inversions, translocations, deletions, missense mutations, splice site mutations, etc.) within malignant cells, represent the most tumor-specific class of antigens. Neoantigens have rarely been used in cancer vaccine or immunogenic compositions due to technical difficulties in identifying them, selecting optimized neoantigens, and producing neoantigens for use in a vaccine or immunogenic composition. These problems may be addressed by:

- identifying all, or nearly all, mutations in the neoplasia/tumor at the DNA level using whole genome, whole exome (e.g., only captured exons), or RNA sequencing of tumor versus matched germline samples from each patient;
- analyzing the identified mutations with one or more peptide-MHC binding prediction algorithms to generate a plurality of candidate neoantigen T cell epitopes that are expressed within the neoplasia/tumor and may bind patient HLA alleles; and
- synthesizing the plurality of candidate neoantigen peptides selected from the sets of all neoORF peptides and predicted binding peptides for use in a cancer vaccine or immunogenic composition.

As described herein, there is a large body of evidence in both animals and humans that mutated epitopes are effective in inducing an immune response and that cases of spontaneous tumor regression or long term survival correlate with CD8+ T-cell responses to mutated epitopes (Buckwalter and Srivastava P K. "It is the antigen(s), stupid" and other lessons from over a decade of vaccitherapy of human cancer. Seminars in immunology 20:296-300 (2008); Karanikas et al, High frequency of cytolytic T lymphocytes directed against a tumor-specific mutated antigen detectable with HLA tetramers in the blood of a lung carcinoma patient with long survival. Cancer Res. 61:3718-3724 (2001); Lennerz et al, The response of autologous T cells to a human melanoma is dominated by mutated neoantigens. Proc Natl Acad Sci USA. 102:16013 (2005)) and that "immunoediting" can be tracked to alterations in expression of dominant mutated antigens in mice and man (Matsushita et al, Cancer exome analysis reveals a T-cell-dependent mechanism of cancer immunoediting Nature 482:400 (2012); DuPage et al, Expression of tumor-specific antigens underlies cancer immunoediting Nature 482:405 (2012); and Sampson et al, Immunologic escape after prolonged progression-free survival with epidermal growth factor receptor variant III peptide vaccination in patients with newly diagnosed glioblastoma J Clin Oncol. 28:4722-4729 (2010)). In one embodiment, the mutated epitopes of a cancer patient are determined.

In one embodiment mutated epitopes are determined by sequencing the genome and/or exome of tumor tissue and healthy tissue from a cancer patient using next generation sequencing technologies. In another embodiment genes that are selected based on their frequency of mutation and ability to act as a neoantigen are sequenced using next generation sequencing technology. Next-generation sequencing applies to genome sequencing, genome resequencing, transcriptome profiling (RNA-Seq), DNA-protein interactions (ChIP-sequencing), and epigenome characterization (de Magalhaes J P, Finch C E, Janssens G (2010). "Next-generation sequencing in aging research: emerging applications, problems, pitfalls and possible solutions". Ageing Research Reviews 9 (3): 315-323; Hall N (May 2007). "Advanced sequencing technologies and their wider impact in microbiology". J. Exp. Biol. 209 (Pt 9): 1518-1525; Church G M (January 2006). "Genomes for all". Sci. Am. 294 (1): 46-54; ten Bosch J R, Grody W W (2008). "Keeping Up with the Next Generation". The Journal of Molecular Diagnostics 10 (6): 484-492; Tucker T, Marra M, Friedman J M (2009). "Massively Parallel Sequencing: The Next Big Thing in Genetic Medicine". The American Journal of Human Genetics 85 (2): 142-154). Next-generation sequencing can now rapidly reveal the presence of discrete mutations such as coding mutations in individual tumors, most commonly single amino acid changes (e.g., missense mutations) and less frequently novel stretches of amino acids generated by frame-shift insertions/deletions/gene fusions, read-through mutations in stop codons, and translation of improperly spliced introns (e.g., neoORFs). NeoORFs are particularly valuable as immunogens because the entirety of their sequence is completely novel to the immune system and so are analogous to a viral or bacterial foreign antigen. Thus, neoORFs: (1) are highly specific to the tumor (i.e. there is no expression in any normal cells); (2) can bypass central tolerance, thereby increasing the precursor frequency of neoantigen-specific CTLs. For example, the power of utilizing analogous foreign sequences in a therapeutic anti-cancer vaccine or immunogenic composition was recently demonstrated with peptides derived from human papilloma virus (HPV). ~50% of the 19 patients with pre-neoplastic, viral-induced disease who received 3-4 vaccinations of a mix of HPV peptides derived from the viral oncogenes E6 and E7 maintained a complete response for ≥24 months (Kenter et a, Vaccination against HPV-16 Oncoproteins for Vulvar Intraepithelial Neoplasia NEJM 361:1838 (2009)).

Sequencing technology has revealed that each tumor contains multiple, patient-specific mutations that alter the protein coding content of a gene. Such mutations create altered proteins, ranging from single amino acid changes (caused by missense mutations) to addition of long regions of novel amino acid sequence due to frame shifts, read-through of termination codons or translation of intron regions (novel open reading frame mutations; neoORFs). These mutated proteins are valuable targets for the host's immune response to the tumor as, unlike native proteins, they are not subject to the immune-dampening effects of self-tolerance. Therefore, mutated proteins are more likely to be immunogenic and are also more specific for the tumor cells compared to normal cells of the patient.

An alternative method for identifying tumor specific neoantigens is direct protein sequencing. Protein sequencing of enzymatic digests using multidimensional MS techniques (MSn) including tandem mass spectrometry (MS/MS)) can also be used to identify neoantigens of the invention. Such proteomic approaches permit rapid, highly automated analysis (see, e.g., K. Gevaert and J. Vandekerckhove, Electrophoresis 21:1145-1154 (2000)). It is further contemplated within the scope of the invention that high-throughput methods for de novo sequencing of unknown proteins may be used to analyze the proteome of a patient's tumor to identify expressed neoantigens. For example, meta shotgun protein sequencing may be used to identify expressed neoantigens (see e.g., Guthals et al. (2012) Shotgun Protein Sequencing with Meta-contig Assembly, Molecular and Cellular Proteomics 11(10):1084-96).

Tumor specific neoantigens may also be identified using MHC multimers to identify neoantigen-specific T-cell responses. For example, high-throughput analysis of neoantigen-specific T-cell responses in patient samples may be performed using MHC tetramer-based screening techniques (see e.g., Hombrink et al. (2011) High-Throughput Identification of Potential Minor Histocompatibility Antigens by MHC Tetramer-Based Screening: Feasibility and Limitations 6(8):1-11; Hadrup et al. (2009) Parallel detection of antigen-specific T-cell responses by multidimensional encoding of MHC multimers, Nature Methods, 6(7):520-26; van Rooij et al. (2013) Tumor exome analysis reveals neoantigen-specific T-cell reactivity in an Ipilimumab-responsive melanoma, Journal of Clinical Oncology, 31:1-4; and Heemskerk et al. (2013) The cancer antigenome, EMBO Journal, 32(2):194-203). Such tetramer-based screening techniques may be used for the initial identification of tumor specific neoantigens, or alternatively as a secondary screening protocol to assess what neoantigens a patient may have already been exposed to, thereby facilitating the selection of candidate neoantigens for the invention.

In one embodiment the sequencing data derived from determining the presence of mutations in a cancer patient is analysed to predict personal mutated peptides that can bind to HLA molecules of the individual. In one embodiment the data is analysed using a computer. In another embodiment the sequence data is analysed for the presence of neoantigens. In one embodiment neoantigens are determined by their affinity to MHC molecules. Efficiently choosing which particular mutations to utilize as immunogen requires identification of the patient HLA type and the ability to predict which mutated peptides would efficiently bind to the patient's HLA alleles. Recently, neural network based learning approaches with validated binding and non-binding peptides have advanced the accuracy of prediction algorithms for the major HLA-A and -B alleles. Utilizing the recently improved algorithms for predicting which missense mutations create strong binding peptides to the patient's cognate MHC molecules, a set of peptides representative of optimal mutated epitopes (both neoORF and mis sense) for each patient may be identified and prioritized (Zhang et al, Machine learning competition in immunology—Prediction of HLA class I binding peptides J Immunol Methods 374:1 (2011); Lundegaard et al Prediction of epitopes using neural network based methods J Immunol Methods 374:26 (2011)).

Targeting as many mutated epitopes as practically possible takes advantage of the enormous capacity of the immune system, prevents the opportunity for immunological escape by down-modulation of a particular immune targeted gene product, and compensates for the known inaccuracy of epitope prediction approaches. Synthetic peptides provide a particularly useful means to prepare multiple immunogens efficiently and to rapidly translate identification of mutant epitopes to an effective vaccine or immunogenic composition. Peptides can be readily synthesized chemically and easily purified utilizing reagents free of contaminating bacteria or animal substances. The small size allows a clear focus on the mutated region of the protein and also reduces irrelevant antigenic competition from other components (unmutated protein or viral vector antigens).

In one embodiment the drug formulation is a multi-epitope vaccine or immunogenic composition of long peptides. Such "long" peptides undergo efficient internalization, processing and cross-presentation in professional antigen-presenting cells such as dendritic cells, and have been shown to induce CTLs in humans (Melief and van der Burg, Immunotherapy of established (pre) malignant disease by synthetic long peptide vaccines Nature Rev Cancer 8:351 (2008)). In one embodiment at least 1 peptide is prepared for immunization. In a preferred embodiment 20 or more peptides are prepared for immunization. In one embodiment the neoantigenic peptide ranges from about 5 to about 50 amino acids in length. In another embodiment peptides from about 15 to about 35 amino acids in length is synthesized. In preferred embodiment the neoantigenic peptide ranges from about 20 to about 35 amino acids in length.

Production of Tumor Specific Neoantigens

The present invention is based, at least in part, on the ability to present the immune system of the patient with a pool of tumor specific neoantigens. One of skill in the art from this disclosure and the knowledge in the art will appreciate that there are a variety of ways in which to produce such tumor specific neoantigens. In general, such tumor specific neoantigens may be produced either in vitro or in vivo. Tumor specific neoantigens may be produced in vitro as peptides or polypeptides, which may then be formulated into a personalized neoplasia vaccine or immunogenic composition and administered to a subject. As described in further detail herein, such in vitro production may occur by a variety of methods known to one of skill in the art such as, for example, peptide synthesis or expression of a peptide/polypeptide from a DNA or RNA molecule in any of a variety of bacterial, eukaryotic, or viral recombinant expression systems, followed by purification of the expressed peptide/polypeptide. Alternatively, tumor specific neoantigens may be produced in vivo by introducing molecules (e.g., DNA, RNA, viral expression systems, and the like) that encode tumor specific neoantigens into a subject, whereupon the encoded tumor specific neoantigens are expressed. The methods of in vitro and in vivo production of neoantigens is also further described herein as it relates to pharmaceutical compositions and methods of delivery of the therapy.

In Vitro Peptide/Polypeptide Synthesis

Proteins or peptides may be made by any technique known to those of skill in the art, including the expression of proteins, polypeptides or peptides through standard molecular biological techniques, the isolation of proteins or peptides from natural sources, in vitro translation, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases located at the National Institutes of Health website. The coding regions for known genes may be amplified and/or expressed using the techniques disclosed herein or as would be known to those of ordinary skill in the art. Alternatively, various commercial preparations of proteins, polypeptides and peptides are known to those of skill in the art.

Peptides can be readily synthesized chemically utilizing reagents that are free of contaminating bacterial or animal substances (Merrifield R B: Solid phase peptide synthesis. I. The synthesis of a tetrapeptide. J. Am. Chem. Soc. 85:2149-54, 1963). In certain embodiments, neoantigenic peptides are prepared by (1) parallel solid-phase synthesis on multi-channel instruments using uniform synthesis and cleavage conditions; (2) purification over a RP-HPLC column with column stripping; and re-washing, but not replacement, between peptides; followed by (3) analysis with a limited set of the most informative assays. The Good Manufacturing Practices (GMP) footprint can be defined around the set of peptides for an individual patient, thus requiring suite changeover procedures only between syntheses of peptides for different patients.

Alternatively, a nucleic acid (e.g., a polynucleotide) encoding a neoantigenic peptide of the invention may be used to produce the neoantigenic peptide in vitro. The polynucleotide may be, e.g., DNA, cDNA, PNA, CNA, RNA, either single- and/or double-stranded, or native or stabilized forms of polynucleotides, such as e.g. polynucleotides with a phosphorothiate backbone, or combinations thereof and it may or may not contain introns so long as it codes for the peptide. In one embodiment in vitro translation is used to produce the peptide. Many exemplary systems exist that one skilled in the art could utilize (e.g., Retic Lysate IVT Kit, Life Technologies, Waltham, Mass.).

An expression vector capable of expressing a polypeptide can also be prepared. Expression vectors for different cell types are well known in the art and can be selected without undue experimentation. Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host (e.g., bacteria), although such controls are generally available in the expression vector. The vector is then introduced into the host bacteria for cloning using standard techniques (see, e.g., Sambrook et al. (1989) Molecular Cloning, A Laboratory Manual, Cold Spring Harbor Laboratory, Cold Spring Harbor, N.Y.).

Expression vectors comprising the isolated polynucleotides, as well as host cells containing the expression vectors, are also contemplated. The neoantigenic peptides may be provided in the form of RNA or cDNA molecules encoding the desired neoantigenic peptides. One or more neoantigenic peptides of the invention may be encoded by a single expression vector.

The term "polynucleotide encoding a polypeptide" encompasses a polynucleotide which includes only coding sequences for the polypeptide as well as a polynucleotide which includes additional coding and/or non-coding sequences. Polynucleotides can be in the form of RNA or in the form of DNA. DNA includes cDNA, genomic DNA, and synthetic DNA; and can be double-stranded or single-stranded, and if single stranded can be the coding strand or non-coding (anti-sense) strand.

In embodiments, the polynucleotides may comprise the coding sequence for the tumor specific neoantigenic peptide fused in the same reading frame to a polynucleotide which aids, for example, in expression and/or secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide.

In embodiments, the polynucleotides can comprise the coding sequence for the tumor specific neoantigenic peptide fused in the same reading frame to a marker sequence that allows, for example, for purification of the encoded polypeptide, which may then be incorporated into the personalized neoplasia vaccine or immunogenic composition. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. Additional tags include, but are not limited to, Calmodulin tags, FLAG tags, Myc tags, S tags, SBP tags, Softag 1, Softag 3, V5 tag, Xpress tag, Isopeptag, SpyTag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, and the like.

In embodiments, the polynucleotides may comprise the coding sequence for one or more of the tumor specific neoantigenic peptides fused in the same reading frame to create a single concatamerized neoantigenic peptide construct capable of producing multiple neoantigenic peptides.

In certain embodiments, isolated nucleic acid molecules having a nucleotide sequence at least 60% identical, at least 65% identical, at least 70% identical, at least 75% identical, at least 80% identical, at least 85% identical, at least 90% identical, at least 95% identical, or at least 96%, 97%, 98% or 99% identical to a polynucleotide encoding a tumor specific neoantigenic peptide of the present invention, can be provided.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The isolated tumor specific neoantigenic peptides described herein can be produced in vitro (e.g., in the laboratory) by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest is produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (e.g., by synthesis, site-directed mutagenesis, or another method), the polynucleotide sequences encoding a particular isolated polypeptide of interest is inserted into an expression vector and optionally operatively linked to an expression control sequence appropriate for expression of the protein in a desired host. Proper assembly can be confirmed by nucleotide sequencing, restriction mapping, and expression of a biologically active polypeptide in a suitable host. As well known in the art, in order to obtain high expression levels of a transfected gene in a host, the gene can be operatively linked to transcriptional and translational expression control sequences that are functional in the chosen expression host.

Recombinant expression vectors may be used to amplify and express DNA encoding the tumor specific neoantigenic peptides. Recombinant expression vectors are replicable DNA constructs which have synthetic or cDNA-derived DNA fragments encoding a tumor specific neoantigenic peptide or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail herein. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous, and in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

Useful expression vectors for eukaryotic hosts, especially mammals or humans include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a polypeptide include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are well known in the art (see Pouwels et al., Cloning Vectors: A Laboratory Manual, Elsevier, N.Y., 1985).

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), 293, HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography, and the like), centrifugation, differential solubility, or by any other standard technique for protein purification. Affinity tags such as hexahistidine, maltose binding domain, influenza coat sequence, glutathione-S-transferase, and the like can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

In Vivo Peptide/Polypeptide Synthesis

The present invention also contemplates the use of nucleic acid molecules as vehicles for delivering neoantigenic peptides/polypeptides to the subject in need thereof, in vivo, in the form of, e.g., DNA/RNA vaccines (see, e.g., WO2012/159643, and WO2012/159754, hereby incorporated by reference in their entirety).

In one embodiment neoantigens may be administered to a patient in need thereof by use of a plasmid. These are plasmids which usually consist of a strong viral promoter to drive the in vivo transcription and translation of the gene (or complementary DNA) of interest (Mor, et al., (1995). The Journal of Immunology 155 (4): 2039-2046). Intron A may sometimes be included to improve mRNA stability and hence increase protein expression (Leitner et al. (1997). The Journal of Immunology 159 (12): 6112-6119). Plasmids also include a strong polyadenylation/transcriptional termination signal, such as bovine growth hormone or rabbit beta-globulin polyadenylation sequences (Alarcon et al., (1999). Adv. Parasitol. Advances in Parasitology 42: 343-410; Robinson et al., (2000). Adv. Virus Res. Advances in Virus Research 55: 1-74; Bohm et al., (1996). Journal of Immunological Methods 193 (1): 29-40). Multicistronic vectors are sometimes constructed to express more than one immunogen, or to express an immunogen and an immunostimulatory protein (Lewis et al., (1999). Advances in Virus Research (Academic Press) 54: 129-88).

Because the plasmid is the "vehicle" from which the immunogen is expressed, optimising vector design for maximal protein expression is essential (Lewis et al., (1999). Advances in Virus Research (Academic Press) 54: 129-88). One way of enhancing protein expression is by optimising the codon usage of pathogenic mRNAs for eukaryotic cells.

Another consideration is the choice of promoter. Such promoters may be the SV40 promoter or Rous Sarcoma Virus (RSV).

Plasmids may be introduced into animal tissues by a number of different methods. The two most popular approaches are injection of DNA in saline, using a standard hypodermic needle, and gene gun delivery. A schematic outline of the construction of a DNA vaccine plasmid and its subsequent delivery by these two methods into a host is illustrated at Scientific American (Weiner et al., (1999) Scientific American 281 (1): 34-41). Injection in saline is normally conducted intramuscularly (IM) in skeletal muscle, or intradermally (ID), with DNA being delivered to the extracellular spaces. This can be assisted by electroporation by temporarily damaging muscle fibres with myotoxins such as bupivacaine; or by using hypertonic solutions of saline or sucrose (Alarcon et al., (1999). Adv. Parasitol. Advances in Parasitology 42: 343-410). Immune responses to this method of delivery can be affected by many factors, including needle type, needle alignment, speed of injection, volume of injection, muscle type, and age, sex and physiological condition of the animal being injected (Alarcon et al., (1999). Adv. Parasitol. Advances in Parasitology 42: 343-410).

Gene gun delivery, the other commonly used method of delivery, ballistically accelerates plasmid DNA (pDNA) that has been adsorbed onto gold or tungsten microparticles into the target cells, using compressed helium as an accelerant (Alarcon et al., (1999). Adv. Parasitol. Advances in Parasitology 42: 343-410; Lewis et al., (1999). Advances in Virus Research (Academic Press) 54: 129-88).

Alternative delivery methods may include aerosol instillation of naked DNA on mucosal surfaces, such as the nasal and lung mucosa, (Lewis et al., (1999). Advances in Virus Research (Academic Press) 54: 129-88) and topical administration of pDNA to the eye and vaginal mucosa (Lewis et al., (1999) Advances in Virus Research (Academic Press) 54: 129-88). Mucosal surface delivery has also been achieved using cationic liposome-DNA preparations, biodegradable microspheres, attenuated *Shigella* or *Listeria* vectors for oral administration to the intestinal mucosa, and recombinant adenovirus vectors.

The method of delivery determines the dose of DNA required to raise an effective immune response. Saline injections require variable amounts of DNA, from 10 µg-1 mg, whereas gene gun deliveries require 100 to 1000 times less DNA than intramuscular saline injection to raise an effective immune response. Generally, 0.2 µg-20 µg are required, although quantities as low as 16 ng have been reported. These quantities vary from species to species, with mice, for example, requiring approximately 10 times less DNA than primates. Saline injections require more DNA because the DNA is delivered to the extracellular spaces of the target tissue (normally muscle), where it has to overcome physical barriers (such as the basal lamina and large amounts of connective tissue, to mention a few) before it is taken up by the cells, while gene gun deliveries bombard DNA directly into the cells, resulting in less "wastage" (See e.g., Sedegah et al., (1994). Proceedings of the National Academy of Sciences of the United States of America 91 (21): 9866-9870; Daheshia et al., (1997). The Journal of Immunology 159 (4): 1945-1952; Chen et al., (1998). The Journal of Immunology 160 (5): 2425-2432; Sizemore (1995) Science 270 (5234): 299-302; Fynan et al., (1993) Proc. Natl. Acad. Sci. U.S.A. 90 (24): 11478-82).

In one embodiment, a neoplasia vaccine or immunogenic composition may include separate DNA plasmids encoding, for example, one or more neoantigenic peptides/polypeptides as identified in according to the invention. As discussed herein, the exact choice of expression vectors can depend upon the peptide/polypeptides to be expressed, and is well within the skill of the ordinary artisan. The expected persistence of the DNA constructs (e.g., in an episomal, non-replicating, non-integrated form in the muscle cells) is expected to provide an increased duration of protection.

One or more neoantigenic peptides of the invention may be encoded and expressed in vivo using a viral based system (e.g., an adenovirus system, an adeno associated virus (AAV) vector, a poxvirus, or a lentivirus). In one embodiment, the neoplasia vaccine or immunogenic composition may include a viral based vector for use in a human patient in need thereof, such as, for example, an adenovirus (see, e.g., Baden et al. First-in-human evaluation of the safety and immunogenicity of a recombinant adenovirus serotype 26 HIV-1 Env vaccine (IPCAVD 001). J Infect Dis. 2013 Jan. 15; 207(2):240-7, hereby incorporated by reference in its entirety). Plasmids that can be used for adeno associated virus, adenovirus, and lentivirus delivery have been described previously (see e.g., U.S. Pat. Nos. 6,955,808 and 6,943,019, and U.S. Patent application No. 20080254008, hereby incorporated by reference).

Among vectors that may be used in the practice of the invention, integration in the host genome of a cell is possible with retrovirus gene transfer methods, often resulting in long term expression of the inserted transgene. In a preferred embodiment the retrovirus is a lentivirus. Additionally, high transduction efficiencies have been observed in many different cell types and target tissues. The tropism of a retrovirus can be altered by incorporating foreign envelope proteins, expanding the potential target population of target cells. A retrovirus can also be engineered to allow for conditional expression of the inserted transgene, such that only certain cell types are infected by the lentivirus. Cell type specific promoters can be used to target expression in specific cell types. Lentiviral vectors are retroviral vectors (and hence both lentiviral and retroviral vectors may be used in the practice of the invention). Moreover, lentiviral vectors are preferred as they are able to transduce or infect non-dividing cells and typically produce high viral titers. Selection of a retroviral gene transfer system may therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the desired nucleic acid into the target cell to provide permanent expression. Widely used retroviral vectors that may be used in the practice of the invention include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., (1992) J. Virol. 66:2731-2739; Johann et al., (1992) J. Virol. 66:1635-1640; Sommnerfelt et al., (1990) Virol. 176:58-59; Wilson et al., (1998) J. Virol. 63:2374-2378; Miller et al., (1991) J. Virol. 65:2220-2224; PCT/US94/05700). Zou et al. administered about 10 µl of a recombinant lentivirus having a titer of $1\times10^9$ transducing units (TU)/ml by an intrathecal catheter. These sort of dosages can be adapted or extrapolated to use of a retroviral or lentiviral vector in the present invention.

Also useful in the practice of the invention is a minimal non-primate lentiviral vector, such as a lentiviral vector based on the equine infectious anemia virus (EIAV) (see, e.g., Balagaan, (2006) J Gene Med; 8: 275-285, Published online 21 Nov. 2005 in Wiley InterScience (www.interscience.wiley.com). DOI: 10.1002/jgm.845). The vectors may have cytomegalovirus (CMV) promoter driving expression of the target gene. Accordingly, the invention contemplates amongst vector(s) useful in the practice of the invention: viral vectors, including retroviral vectors and lentiviral vectors.

Also useful in the practice of the invention is an adenovirus vector. One advantage is the ability of recombinant adenoviruses to efficiently transfer and express recombinant genes in a variety of mammalian cells and tissues in vitro and in vivo, resulting in the high expression of the transferred nucleic acids. Further, the ability to productively infect quiescent cells, expands the utility of recombinant adenoviral vectors. In addition, high expression levels ensure that the products of the nucleic acids will be expressed to sufficient levels to generate an immune response (see e.g., U.S. Pat. No. 7,029,848, hereby incorporated by reference).

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6$-$1 \times 10^{12}$ particles), more preferably at least about $1 \times 10^7$ particles, more preferably at least about $1 \times 10^8$ particles (e.g., about $1 \times 10^8$-$1 \times 10^{11}$ particles or about $1 \times 10^8$-$1 \times 10^{12}$ particles), and most preferably at least about $1 \times 10^9$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In terms of in vivo delivery, AAV is advantageous over other viral vectors due to low toxicity and low probability of causing insertional mutagenesis because it doesn't integrate into the host genome. AAV has a packaging limit of 4.5 or 4.75 Kb. Constructs larger than 4.5 or 4.75 Kb result in significantly reduced virus production. There are many promoters that can be used to drive nucleic acid molecule expression. AAV ITR can serve as a promoter and is advantageous for eliminating the need for an additional promoter element. For ubiquitous expression, the following promoters can be used: CMV, CAG, CBh, PGK, SV40, Ferritin heavy or light chains, etc. For brain expression, the following promoters can be used: SynapsinI for all neurons, CaMKIIalpha for excitatory neurons, GAD67 or GAD65 or VGAT for GABAergic neurons, etc. Promoters used to drive RNA synthesis can include: Pol III promoters such as U6 or H1. The use of a Pol II promoter and intronic cassettes can be used to express guide RNA (gRNA).

As to AAV, the AAV can be AAV1, AAV2, AAV5 or any combination thereof. One can select the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The above promoters and vectors are preferred individually.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{50}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. In a preferred embodiment, AAV is used with a titer of about $2 \times 10^{13}$ viral genomes/milliliter, and each of the striatal hemispheres of a mouse receives one 500 nanoliter injection. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In another embodiment effectively activating a cellular immune response for a neoplasia vaccine or immunogenic composition can be achieved by expressing the relevant neoantigens in a vaccine or immunogenic composition in a non-pathogenic microorganism. Well-known examples of such microorganisms are *Mycobacterium bovis* BCG, *Salmonella* and *Pseudomona* (See, U.S. Pat. No. 6,991,797, hereby incorporated by reference in its entirety).

In another embodiment a Poxvirus is used in the neoplasia vaccine or immunogenic composition. These include orthopoxvirus, avipox, vaccinia, MVA, NYVAC, canarypox, ALVAC, fowlpox, TROVAC, etc. (see e.g., Verardi et al., Hum Vaccin Immunother. 2012 July; 8(7):961-70; and Moss, Vaccine. 2013; 31(39): 4220-4222). Poxvirus expression vectors were described in 1982 and quickly became widely used for vaccine development as well as research in numerous fields. Advantages of the vectors include simple construction, ability to accommodate large amounts of foreign DNA and high expression levels.

In another embodiment the vaccinia virus is used in the neoplasia vaccine or immunogenic composition to express a neoantigen. (Rolph et al., Recombinant viruses as vaccines and immunological tools. Curr Opin Immunol 9:517-524, 1997). The recombinant vaccinia virus is able to replicate within the cytoplasm of the infected host cell and the polypeptide of interest can therefore induce an immune response. Moreover, Poxviruses have been widely used as vaccine or immunogenic composition vectors because of their ability to target encoded antigens for processing by the major histocompatibility complex class I pathway by directly infecting immune cells, in particular antigen-presenting cells, but also due to their ability to self-adjuvant.

In another embodiment ALVAC is used as a vector in a neoplasia vaccine or immunogenic composition. ALVAC is a canarypox virus that can be modified to express foreign transgenes and has been used as a method for vaccination against both prokaryotic and eukaryotic antigens (Honig H, Lee D S, Conkright W, et al. Phase I clinical trial of a recombinant canarypoxvirus (ALVAC) vaccine expressing human carcinoembryonic antigen and the B7.1 co-stimulatory molecule. Cancer Immunol Immunother 2000; 49:504-14; von Mehren M, Arlen P, Tsang K Y, et al. Pilot study of a dual gene recombinant avipox vaccine containing both carcinoembryonic antigen (CEA) and B7.1 transgenes in patients with recurrent CEA-expressing adenocarcinomas. Clin Cancer Res 2000; 6:2219-28; Musey L, Ding Y, Elizaga M, et al. HIV-1 vaccination administered intramuscularly can induce both systemic and mucosal T cell immunity in HIV-1-uninfected individuals. J Immunol 2003; 171:1094-101; Paoletti E. Applications of pox virus vectors to vaccination: an update. Proc Natl Acad Sci USA 1996; 93:11349-53; U.S. Pat. No. 7,255,862). In a phase I clinical trial, an ALVAC virus expressing the tumor antigen CEA showed an excellent safety profile and resulted in increased CEA-specific T-cell responses in selected patients; objective clinical responses, however, were not observed (Marshall J L, Hawkins M J, Tsang K Y, et al. Phase I study in cancer patients of a replication-defective avipox recombinant vaccine that expresses human carcinoembryonic antigen. J Clin Oncol 1999; 17:332-7).

In another embodiment a Modified Vaccinia Ankara (MVA) virus may be used as a viral vector for a neoantigen vaccine or immunogenic composition. MVA is a member of the Orthopoxvirus family and has been generated by about 570 serial passages on chicken embryo fibroblasts of the Ankara strain of Vaccinia virus (CVA) (for review see Mayr, A., et al., Infection 3, 6-14, 1975). As a consequence of these passages, the resulting MVA virus contains 31 kilobases less genomic information compared to CVA, and is highly host-cell restricted (Meyer, H. et al., J. Gen. Virol. 72, 1031-1038, 1991). MVA is characterized by its extreme attenuation, namely, by a diminished virulence or infectious ability, but still holds an excellent immunogenicity. When tested in a variety of animal models, MVA was proven to be avirulent, even in immuno-suppressed individuals. Moreover, MVA-BN®-HER2 is a candidate immunotherapy designed for the treatment of HER-2-positive breast cancer and is currently in clinical trials. (Mandl et al., Cancer Immunol Immunother. January 2012; 61(1): 19-29). Methods to make and use recombinant MVA has been described (e.g., see U.S. Pat. Nos. 8,309,098 and 5,185,146 hereby incorporated in its entirety).

In another embodiment the modified Copenhagen strain of vaccinia virus, NYVAC and NYVAC variations are used as a vector (see U.S. Pat. No. 7,255,862; PCT WO 95/30018; U.S. Pat. Nos. 5,364,773 and 5,494,807, hereby incorporated by reference in its entirety).

In one embodiment recombinant viral particles of the vaccine or immunogenic composition are administered to patients in need thereof. Dosages of expressed neoantigen can range from a few to a few hundred micrograms, e.g., 5 to 500 .mu.g. The vaccine or immunogenic composition can be administered in any suitable amount to achieve expression at these dosage levels. The viral particles can be administered to a patient in need thereof or transfected into cells in an amount of about at least $10^{35}$ pfu; thus, the viral particles are preferably administered to a patient in need thereof or infected or transfected into cells in at least about $10^4$ pfu to about $10^6$ pfu; however, a patient in need thereof can be administered at least about $10^8$ pfu such that a more preferred amount for administration can be at least about $10^7$ pfu to about $10^9$ pfu. Doses as to NYVAC are applicable as to ALVAC, MVA, MVA-BN, and avipoxes, such as canarypox and fowlpox.

Vaccine or Immunogenic Composition Adjuvant

Effective vaccine or immunogenic compositions advantageously include a strong adjuvant to initiate an immune response. As described herein, poly-ICLC, an agonist of TLR3 and the RNA helicase-domains of MDA5 and RIGS, has shown several desirable properties for a vaccine or immunogenic composition adjuvant. These properties include the induction of local and systemic activation of immune cells in vivo, production of stimulatory chemokines and cytokines, and stimulation of antigen-presentation by DCs. Furthermore, poly-ICLC can induce durable CD4+ and CD8+ responses in humans. Importantly, striking similarities in the upregulation of transcriptional and signal transduction pathways were seen in subjects vaccinated with poly-ICLC and in volunteers who had received the highly effective, replication-competent yellow fever vaccine. Furthermore, >90% of ovarian carcinoma patients immunized with poly-ICLC in combination with a NY-ESO-1 peptide vaccine (in addition to Montanide) showed induction of CD4+ and CD8+ T cell, as well as antibody responses to the peptide in a recent phase 1 study. At the same time, poly-ICLC has been extensively tested in more than 25 clinical trials to date and exhibited a relatively benign toxicity profile. In addition to a powerful and specific immunogen the neoantigen peptides may be combined with an adjuvant (e.g., poly-ICLC) or another anti-neoplastic agent. Without being bound by theory, these neoantigens are expected to bypass central thymic tolerance (thus allowing stronger anti-tumor T cell response), while reducing the potential for autoimmunity (e.g., by avoiding targeting of normal self-antigens). An effective immune response advantageously includes a strong adjuvant to activate the immune system (Speiser and Romero, Molecularly defined vaccines for cancer immunotherapy, and protective T cell immunity Seminars in Immunol 22:144 (2010)). For example, Toll-like receptors (TLRs) have emerged as powerful sensors of microbial and viral pathogen "danger signals", effectively inducing the innate immune system, and in turn, the adaptive immune system (Bhardwaj and Gnjatic, TLR AGONISTS: Are They Good Adjuvants? Cancer J. 16:382-391 (2010)). Among the TLR agonists, poly-ICLC (a synthetic double-stranded RNA mimic) is one of the most potent activators of myeloid-derived dendritic cells. In a human volunteer study, poly-ICLC has been shown to be safe and to induce a gene expression profile in peripheral blood cells comparable to that induced by one of the most potent live attenuated viral vaccines, the yellow fever vaccine YF-17D (Caskey et al, Synthetic double-stranded RNA induces innate immune responses similar to a live viral vaccine in humans J Exp Med 208:2357 (2011)). In a preferred embodiment Hiltonol®, a GMP preparation of poly-ICLC prepared by Oncovir, Inc, is utilized as the adjuvant. In other embodiments, other adjuvants described herein are envisioned. For instance oil-in-water, water-in-oil or multiphasic W/O/W; see, e.g., U.S. Pat. No. 7,608,279 and Aucouturier et al, Vaccine 19 (2001), 2666-2672, and documents cited therein.

Checkpoint Inhibitors

In further embodiments, the immunotherapeutic agent comprises one or more checkpoint inhibitors, optionally in combination with a neoplasia vaccine or immunogenic composition, as described herein. Accordingly, 1, 2, 3, 4, 5, or more checkpoint inhibitors may be administered. In certain exemplary embodiments, one checkpoint inhibitor is administered. In other exemplary embodiments, 2 checkpoint inhibitors are administered.

Page et al. (Annu. Rev. Med. 2014.65) summarizes published trials investigating checkpoint modulators in solid tumors. Mullard, A. (Nature Reviews, Drug Discovery. Vol. 12, July 2013) provides a review of checkpoint inhibitors. A summary table of exemplary checkpoint inhibitors is provided herein.

| Drug | Lead company | Most advanced indications | Phase |
|---|---|---|---|
| Anti-PD1 | | | |
| Nivolumab | Bristol-Myers Squibb | Renal cell cancer, melanoma, NSCLC | III |
| Lambrolizumab | Merck & Co. | Melanoma | II |
| Pidilizumab | CureTech | Colorectal cancer, melanoma, DLBCL | II |
| AMP-224 | GlaxoSmithKline | Solid tumors | I |
| Anti-PDL1 | | | |
| MEDI-4736 | AstraZeneca | Solid tumors | I |
| MPDL3280A | Roche | Melanoma, solid tumors | I |

Anti-CTLA4 Antibodies

In one embodiment, the immunotherapeutic agent is an anti-CTLA4 antibody. Cytotoxic T-lymphocyte-associated antigen (CTLA-4), also known as CD152, is a co-inhibitory molecule that functions to regulate T-cell activation.

CTLA4 was initially identified as negative regulator on the surface of T-cells that was upregulated shortly after initiation of a de novo immune response or stimulation of an existing response in order to dampen the subsequent immune T-cell response and prevent auto-immunity or uncontrolled inflammation. Thus, the magnitude of the developing immune response has been closely tied to CTLA4 action. In certain embodiments, the anti-CTLA4 antibody is Ipilumumab or Tremelimumab.

Checkpoint inhibitors function by modulating the immune system's endogenous mechanisms of T cell regulation. Ipilimumab (YERVOY, Bristol-Meyers Squibb, New York, N.Y.)—is a monoclonal antibody and is the first such checkpoint inhibitor to be approved by the US Food and Drug Administration (FDA)—has become standard treatment for metastatic melanoma (Hodi et al., N. Engl. J. Med. 363:711-23. 2010; Robert et al., N. Engl. J. Med. 364:2517-26. 2011). Ipilimumab binds and blocks inhibitory signaling mediated by the T cell surface co-inhibitory molecule cytotoxic T lymphocyte antigen 4 (CTLA-4). Because the mechanism of action is not specific to one tumor type, and because a wealth of preclinical data supports the role of tumor immune surveillance across multiple malignancies (Andre et al., Clin. Cancer Res. 19:28-33. 2013; May et al. Clin. Cancer Res. 17:5233-38. 2011), Ipilumumab is being investigated as a treatment for patients with prostate, lung, renal, and breast cancer, among other tumor types. Ipilimumab works by activating the immune system by targeting CTLA-4.

Another CTLA-4-blocking antibody, Tremelimumab, continues to be investigated in clinical trials and has also demonstrated durable responses in patients with melanoma (Kirkwood et al., Clin. Cancer Res. 16:1042-48. 2010; Ribas et al. J. Clin. Oncol. 31:616-22, 2013).

Accordingly, in some embodiments, the immunotherapeutic agent comprises a combination of a neoplasia vaccine or immunogenic composition and one or more anti-CTLA4 antibodies, e.g. Ipilimumab.

Inhibitors of Programmed Cell Death-1 Pathway

Whereas CTLA-4 serves to regulate early T cell activation, Programmed Death-1 (PD-1) signaling functions in part to regulate T cell activation in peripheral tissues. The PD-1 receptor refers to an immunoinhibitory receptor belonging to the CD28 family. PD-1 is expressed on a number of cell types including T regs, activated B cells, and natural killer (NK) cells, and is expressed predominantly on previously activated T cells in vivo, and binds to two ligands, PD-L1 and PD-L2. PD1's endogenous ligands, PD-L1 and PD-L2, are expressed in activated immune cells as well as nonhematopoietic cells, including tumor cells. PD-1 as used herein is meant to include human PD-1 (hPD-1), variants, isoforms, and species homologs of hPD-1, and analogs having at least one common epitope with hPD-1. The complete hPD-1 sequence can be found under GENBANK Accession No. U64863. Programmed Death Ligand-1 (PD-L1" is one of two cell surface glycoprotein ligands for PD-1 (the other being PD-L2) that downregulate T cell activation and cytokine secretion upon binding to PD-1. PD-L1 as used herein includes human PD-L1 (hPD-L1), variants, isoforms, and species homologs of hPD-L1, and analogs having at least one common epitope with hPD-L1. The complete hPD-L1 sequence can be found under GENBANK Accession No. Q9NZQ7. Tumors have been demonstrated to escape immune surveillance by expressing PD-L1/L2, thereby suppressing tumor-infiltrating lymphocytes via PD-1/PD-L1,2 interactions (Dong et al. Nat. Med. 8:793-800. 2002). Inhibition of these interactions with therapeutic antibodies has been shown to enhance T cell response and stimulate antitumor activity (Freeman et al. J. Exp. Med. 192:1027-34.2000).

The Abs of the invention include, but are not limited to, all of the anti-PD-1 and anti-PD-L1 Abs disclosed in U.S. Pat. Nos. 8,008,449 and 7,943,743, respectively. Other anti-PD-1 mAbs have been described in, for example, U.S. Pat. Nos. 7,488,802 and 8,168,757, and anti-PD-L1 mAbs have been described in, for example, U.S. Pat. Nos. 7,635,757 and 8,217,149, and U.S. Publication No. 2009/0317368. U.S. Pat. No. 8,008,449 exemplifies seven anti-PD-1 HuMAbs: 17D8, 2D3, 4H1, 5C4 (also referred to herein as nivolumab or BMS-936558), 4A11, 7D3 and 5F4.

In some embodiments, the anti-PD-1 antibody is nivolumab. Alternative names for Nivolumab include MDX-1 106, MDX-1 106-04, ONO-4538, BMS-936558. In some embodiments, the anti-PD-1 antibody is Nivolumab (CAS Registry Number: 946414-94-4).

Nivolumab is a fully human IgG4 blocking monoclonal antibody against PD-1 (Topaliam et al., N. Engl. J. Med. 366:2443-54. 2012). Nivolumab specifically blocks PD-1, which can overcome immune resistance. The ligands for PD-1 have been identified as PD-L1 (B7-H1), which is expressed on all hemopoietic cells and many nonhemopoietic tissues, and PD-L2 (B7-DC), whose expression is restricted primarily to dendritic cells and macrophages (Dong, H. et al. 1999. Nat. Med. 5:1365; Freeman, G. J. et al. 2000. J. Exp. Med. 192:1027; Latchman, Y. et al. 2001. Nat. Immunol. 2:261; Tseng, S. Y. et al. 2001. J. Exp. Med. 193:839). PD-L1 is overexpressed in many cancers and is often associated with poor prognosis (Okazaki T et al., Intern. Immun. 2007 19(7):813) (Thompson R H et al., Cancer Res 2006, 66(7):3381). Interestingly, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 1 14(8):

1537). Specifically, since tumor cells express PD-L1, an immunosuppressive PD-1 ligand, inhibition of the interaction between PD-1 and PD-L1 can enhance T-cell responses in vitro and mediate preclinical antitumor activity.

A number of clinical trials (Phase I, II and III) involving Nivolumab have been conducted or are on-going (see clinicaltrials.gov/ct2/results?term=nivolumab&pg=1, accessed on Dec. 20, 2013). For example, in a phase I dose escalation trial, nivolumab was safe, and objective responses were 16-31% across tumor types, with most responses being durable for >1 year (Topaliam et al., Presented at Annu. Meet. Am. Soc. Clin. Oncol., Chicago, May 31-Jun. 4, 2013). In another study, the safety and clinical activity of nivolumab (anti-PD-1, BMS-936558, ONO-4538) in combination with ipilimumab in patients with advanced melanoma was investigated (Wolchok, J Clin Oncol 31, 2013 (suppl; abstr 9012 2013 ASCO Annual Meeting).

Two anti-PD-L1 inhibitory antibodies, MPDL3280A (Genentech, South San Francisco, Calif.) and BMS-936559 (Bristol Meyers Squibb, New York, N.Y.), have undergone clinical investigation. Like nivolumab and MK-3475, these antibodies are thought to function principally by blocking PD-1/PD-L1 signaling. Unlike PD-1 antibodies, PD-L1 antibodies spare potential interactions between PD-L2 and PD-1, but additionally block interactions between PD-L1 and CD80 (Park et al., 2010. Blood 116:1291-98). MPDL3280A has been evaluated in multiple tumor types, with safety and preliminary efficacy identified in melanoma; renal cell carcinoma; non-small cell lung carcinoma (NSCLC); and colorectal, gastric, and head/neck squamous cell carcinoma (Herbst et al. presented at Annu. Meet. Am. Soc. Clin. Oncol., Chicago, May 31-Jun. 4, 2013). Similarly, BMS-936559 was shown to be safe and clinically active across multiple tumor types in a phase I trial. MEDI-4736 is another PD-L1-blocking antibody currently in clinical development (NCT01693562).

In addition to CTLA-4 and PD-1/PD-L1, numerous other immunomodulatory targets have been identified preclinically, many with corresponding therapeutic antibodies that are being investigated in clinical trials. Page et al. (Annu. Rev. Med. 2014.65) details targets of antibody immune modulators in FIG. 1, incorporated by reference herein.

In some embodiments, the immunotherapeutic agent comprises a combination of a neoplasia vaccine or immunogenic composition and one or more inhibitors of the PD-1 pathway. In preferred embodiments, the inhibitor of the PD-1 pathway is an anti-PD1 antibody, for example Nivolumab. In another embodiment, the immunotherapeutic agent comprises a combination of a neoplasia vaccine or immunogenic composition and Nivolumab and/or one or more anti-CTLA4 antibodies.

Other Immunotherapeutic Agents

In certain embodiments, the immunotherapeutic agent is an anti-glucocorticoid-induced tumor necrosis factor family receptor (GITR) agonistic antibody. GITR is a costimulatory molecule for T lymphocytes, modulates innate and adaptive immune system and has been found to participate in a variety of immune responses and inflammatory processes. GITR was originally described by Nocentini et al. after being cloned from dexamethasone-treated murine T cell hybridomas (Nocentini et al. Proc Natl Acad Sci USA 94:6216-6221.1997). Unlike CD28 and CTLA-4, GITR has a very low basal expression on naive CD4+ and CD8+ T cells (Ronchetti et al. Eur J Immunol 34:613-622. 2004). The observation that GITR stimulation has immunostimulatory effects in vitro and induced autoimmunity in vivo prompted the investigation of the antitumor potency of triggering this pathway. A review of Modulation Of Ctla 4 And Gitr For Cancer Immunotherapy can be found in Cancer Immunology and Immunotherapy (Avogadri et al. Current Topics in Microbiology and Immunology 344. 2011). Other agents that can contribute to relief of immune suppression include checkpoint inhibitors targeted at another member of the CD28/CTLA4 Ig superfamily such as BTLA, LAGS, ICOS, PDL1 or KIR (Page et a, Annual Review of Medicine 65:27 (2014)). In further additional embodiments, the checkpoint inhibitor is targeted at a member of the TNFR superfamily such as CD40, OX40, CD137, GITR, CD27 or TIM-3. In some cases targeting a checkpoint inhibitor is accomplished with an inhibitory antibody or similar molecule. In other cases, it is accomplished with an agonist for the target; examples of this class include the stimulatory targets OX40 and GITR.

Indications

Examples of cancers and cancer conditions that can be treated with immunotherapeutic agent include, but are not limited to a patient in need thereof that has been diagnosed as having cancer, or at risk of developing cancer. The subject may have a solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas, tumors of the brain and central nervous system (e.g., tumors of the meninges, brain, spinal cord, cranial nerves and other parts of the CNS, such as glioblastomas or medulla blastomas); head and/or neck cancer, breast tumors, tumors of the circulatory system (e.g., heart, mediastinum and pleura, and other intrathoracic organs, vascular tumors, and tumor-associated vascular tissue); tumors of the blood and lymphatic system (e.g., Hodgkin's disease, Non-Hodgkin's disease lymphoma, Burkitt's lymphoma, AIDS-related lymphomas, malignant immunoproliferative diseases, multiple myeloma, and malignant plasma cell neoplasms, lymphoid leukemia, myeloid leukemia, acute or chronic lymphocytic leukemia, monocytic leukemia, other leukemias of specific cell type, leukemia of unspecified cell type, unspecified malignant neoplasms of lymphoid, hematopoietic and related tissues, such as diffuse large cell lymphoma, T-cell lymphoma or cutaneous T-cell lymphoma); tumors of the excretory system (e.g., kidney, renal pelvis, ureter, bladder, and other urinary organs); tumors of the gastrointestinal tract (e.g., esophagus, stomach, small intestine, colon, colorectal, rectosigmoid junction, rectum, anus, and anal canal); tumors involving the liver and intrahepatic bile ducts, gall bladder, and other parts of the biliary tract, pancreas, and other digestive organs; tumors of the oral cavity (e.g., lip, tongue, gum, floor of mouth, palate, parotid gland, salivary glands, tonsil, oropharynx, nasopharynx, puriform sinus, hypopharynx, and other sites of the oral cavity); tumors of the reproductive system (e.g., vulva, vagina, Cervix uteri, uterus, ovary, and other sites associated with female genital organs, placenta, penis, prostate, testis, and other sites associated with male genital organs); tumors of the respiratory tract (e.g., nasal cavity, middle ear, accessory sinuses, larynx, trachea, bronchus and lung, such as small cell lung cancer and non-small cell lung cancer); tumors of the skeletal system (e.g., bone and articular cartilage of limbs, bone articular cartilage and other sites); tumors of the skin (e.g., malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneoum and peritoneum, eye, thyroid, adrenal gland, and other endocrine glands and related structures, secondary and unspecified malignant neoplasms of lymph nodes, secondary malignant neoplasm of respiratory and digestive systems and secondary malignant neoplasm of other sites.

Of special interest is the treatment of Non-Hodgkin's Lymphoma (NHL), clear cell Renal Cell Carcinoma (ccRCC), metastatic melanoma, sarcoma, leukemia or a cancer of the bladder, colon, brain, breast, head and neck, endometrium, lung, ovary, pancreas or prostate. In certain embodiments, the melanoma is high risk melanoma.

Cancers that can be treated using the immunotherapeutic agent may include among others cases which are refractory to treatment with other chemotherapeutics. The term "refractory, as used herein refers to a cancer (and/or metastases thereof), which shows no or only weak antiproliferative response (e.g., no or only weak inhibition of tumor growth) after treatment with another chemotherapeutic agent. These are cancers that cannot be treated satisfactorily with other chemotherapeutics. Refractory cancers encompass not only (i) cancers where one or more chemotherapeutics have already failed during treatment of a patient, but also (ii) cancers that can be shown to be refractory by other means, e.g., biopsy and culture in the presence of chemotherapeutics.

The immunotherapeutic agent is also applicable to the treatment of patients who have not been previously treated. The immunotherapeutic agent is also applicable where the subject has no detectable neoplasia but is at high risk for disease recurrence.

Also of special interest is the treatment of patients who have undergone Autologous Hematopoietic Stem Cell Transplant (AHSCT), and in particular patients who demonstrate residual disease after undergoing AHSCT. The post-AHSCT setting is characterized by a low volume of residual disease, the infusion of immune cells to a situation of homeostatic expansion, and the absence of any standard relapse-delaying therapy. These features provide a unique opportunity to use the immunotherapeutic agent to delay disease relapse.

In some embodiments, specific genetic alternations associated with cytolytic activity in an individual cancer or tumor type are analysed. Preferred tumor types and their associated mutations are discussed above in relation to the step of determining genetic alterations associated with cytolytic activity in a tumor.

Pharmaceutical Compositions/Methods of Delivery

Also disclosed herein are pharmaceutical compositions comprising an effective amount of an immunotherapeutic agent (including a pharmaceutically acceptable salt, thereof), optionally in combination with a pharmaceutically acceptable carrier, excipient or additive.

When administered as a combination, the immunotherapeutic agents (e.g. a neoplasia vaccine or immunogenic composition and one or more checkpoint inhibitors) can be formulated as separate compositions that are given at the same time or different times, or the therapeutic agents can be given as a single composition.

The compositions may be administered once daily, twice daily, once every two days, once every three days, once every four days, once every five days, once every six days, once every seven days, once every two weeks, once every three weeks, once every four weeks, once every two months, once every six months, or once per year. The dosing interval can be adjusted according to the needs of individual patients. For longer intervals of administration, extended release or depot formulations can be used.

The compositions disclosed herein can be used to treat diseases and disease conditions that are acute, and may also be used for treatment of chronic conditions. In particular, the compositions of the invention are used in methods to treat or prevent a neoplasia.

In certain embodiments, the compositions are administered for time periods exceeding two weeks, three weeks, one month, two months, three months, four months, five months, six months, one year, two years, three years, four years, or five years, ten years, or fifteen years; or for example, any time period range in days, months or years in which the low end of the range is any time period between 14 days and 15 years and the upper end of the range is between 15 days and 20 years (e.g., 4 weeks and 15 years, 6 months and 20 years). In some cases, it may be advantageous for the compositions to be administered for the remainder of the patient's life. In preferred embodiments, the patient is monitored to check the progression of the disease or disorder, and the dose is adjusted accordingly. In preferred embodiments, treatment according to the invention is effective for at least two weeks, three weeks, one month, two months, three months, four months, five months, six months, one year, two years, three years, four years, or five years, ten years, fifteen years, twenty years, or for the remainder of the subject's life.

As described herein, in certain embodiments, administration of a checkpoint inhibitor is initiated before initiation of administration of a neoplasia vaccine or immunogenic composition. In other embodiments, administration of a checkpoint inhibitor is initiated after initiation of administration of a neoplasia vaccine or immunogenic composition. In still other embodiments, administration of a checkpoint inhibitor is initiated simultaneously with the initiation of administration of a neoplasia vaccine or immunogenic composition.

Administration of an immunotherapeutic agent (e.g. checkpoint inhibitor) may continue every 2, 3, 4, 5, 6, 7, 8 or more weeks after the first administration of the immunotherapeutic agent (e.g. checkpoint inhibitor). It is understood that week 1 is meant to include days 1-7, week 2 is meant to include days 8-14, week 3 is meant to include days 15-21 and week 4 is meant to include days 22-28. When dosing is described as being on weekly intervals it means approximately 7 days apart although in any given week the day can be one or more days before or after the scheduled day.

Surgical resection uses surgery to remove abnormal tissue in cancer, such as mediastinal, neurogenic, or germ cell tumors, or thymoma. In certain embodiments, administration of the immunotherapeutic agent is initiated following tumor resection. In other embodiments, administration of the immunotherapeutic agent is initiated 1, 2, 3, 4, 5, 6, 7, 8, 9, 10, 11, 12, 13, 14, 15 or more weeks after tumor resection, e.g. 4 to 12 weeks after tumor resection.

Prime/boost regimens refer to the successive administrations of a vaccine or immunogenic or immunological compositions. In certain embodiments, administration of a neoplasia vaccine or immunogenic composition is in a prime/boost dosing regimen, for example administration of the neoplasia vaccine or immunogenic composition at weeks 1, 2, 3 or 4 as a prime and administration of the neoplasia vaccine or immunogenic composition is at months 2, 3 or 4 as a boost. In another embodiment heterologous prime-boost strategies are used to ellicit a greater cytotoxic T-cell response (see Schneider et al., Induction of CD8+ T cells using heterologous prime-boost immunisation strategies, Immunological Reviews Volume 170, Issue 1, pages 29-38, August 1999). In another embodiment DNA encoding neoantigens is used to prime followed by a protein boost. In another embodiment protein is used to prime followed by boosting with a virus encoding the neoantigen. In another embodiment a virus encoding the neoantigen is used to prime and another virus is used to boost. In another embodiment protein is used to prime and DNA is used to boost. In a preferred embodiment a DNA vaccine or immunogenic composition is used to prime a T-cell response and a recombinant viral vaccine or immunogenic composition is used to boost the response. In another preferred embodiment a viral vaccine or immunogenic composition is coadministered with a protein or DNA vaccine or immunogenic composition to act as an adjuvant for the protein or DNA vaccine or immunogenic composition. The patient can then be boosted with either the viral vaccine or immunogenic composition, protein, or DNA vaccine or immunogenic composition (see Hutchings et al., Combination of protein and viral vaccines induces potent cellular and humoral immune responses and enhanced protection from murine malaria challenge. Infect Immun. 2007 December; 75(12): 5819-26. Epub 2007 Oct. 1).

The pharmaceutical compositions can be processed in accordance with conventional methods of pharmacy to produce medicinal agents for administration to patients in need thereof, including humans and other mammals.

Modifications of the neoantigenic peptides can affect the solubility, bioavailability and rate of metabolism of the peptides, thus providing control over the delivery of the active species. Solubility can be assessed by preparing the neoantigenic peptide and testing according to known methods well within the routine practitioner's skill in the art.

It has been found that a pharmaceutical composition comprising succinic acid or a pharmaceutically acceptable salt thereof (succinate) can provide improved solubility for the neoantigenic peptides. Thus, in one aspect, the pharmaceutical composition comprises: at least one neoantigenic peptide or a pharmaceutically acceptable salt thereof; a pH modifier (such as a base, such as a dicarboxylate or tricarboxylate salt, for example, a pharmaceutically acceptable salt of succinic acid or citric acid); and a pharmaceutically acceptable carrier. Such pharmaceutical compositions can be prepared by combining a solution comprising at least one neoantigenic peptide with a base, such as a dicarboxylate or tricarboxylate salt, such as a pharmaceutically acceptable salt of succinic acid or citric acid (such as sodium succinate), or by combining a solution comprising at least one neoantigenic peptide with a solution comprising a base, such as a dicarboxylate or tricarboxylate salt, such as a pharmaceutically acceptable salt of succinic acid or citric acid (including, e.g., a succinate buffer solution). In certain embodiments, the pharmaceutical composition comprises sodium succinate. In certain embodiments, the pH modifier (such as citrate or succinate) is present in the composition at a concentration from about 1 mM to about 10 mM, and, in certain embodiments, at a concentration from about 1.5 mM to about 7.5 mM, or about 2.0 to about 6.0 mM, or about 3.75 to about 5.0 mM.

In certain embodiments, the pharmaceutically acceptable carrier comprises water. In certain embodiments, the pharmaceutically acceptable carrier further comprises dextrose. In certain embodiments, the pharmaceutically acceptable carrier further comprises dimethylsulfoxide. In certain embodiments, the pharmaceutical composition further comprises an immunomodulator or adjuvant. In certain embodiments, the immunomodulator or adjuvant is selected from the group consisting of poly-ICLC, 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, SRL172, Virosomes and other Virus-like particles, YF-17D, VEGF trap, R848, beta-glucan, Pam3Cys, and Aquila's QS21 stimulon. In certain embodiments, the immunomodulator or adjuvant comprises poly-ICLC.

Xanthenone derivatives such as, for example, Vadimezan or AsA404 (also known as 5,6-dimethylaxanthenone-4-acetic acid (DMXAA)), may also be used as adjuvants according to embodiments of the invention. Alternatively, such derivatives may also be administered in parallel to the vaccine or immunogenic composition of the invention, for example via systemic or intratumoral delivery, to stimulate immunity at the tumor site. Without being bound by theory, it is believed that such xanthenone derivatives act by stimulating interferon (IFN) production via the stimulator of IFN gene ISTING) receptor (see e.g., Conlon et al. (2013) Mouse, but not Human STING, Binds and Signals in Response to the Vascular Disrupting Agent 5,6-Dimethylxanthenone-4-Acetic Acid, Journal of Immunology, 190: 5216-25 and Kim et al. (2013) Anticancer Flavonoids are Mouse-Selective STING Agonists, 8:1396-1401).

The vaccine or immunological composition may also include an adjuvant compound chosen from the acrylic or methacrylic polymers and the copolymers of maleic anhydride and an alkenyl derivative. It is in particular a polymer of acrylic or methacrylic acid cross-linked with a polyalkenyl ether of a sugar or polyalcohol (carbomer), in particular cross-linked with an allyl sucrose or with allylpentaerythritol. It may also be a copolymer of maleic anhydride and ethylene cross-linked, for example, with divinyl ether (see U.S. Pat. No. 6,713,068 hereby incorporated by reference in its entirety).

In certain embodiments, the pH modifier can stabilize the adjuvant or immunomodulator as described herein.

In certain embodiments, a pharmaceutical composition comprises: one to five peptides, dimethylsulfoxide (DMSO), dextrose, water, succinate, poly I: poly C, poly-L-lysine, carboxymethylcellulose, and chloride. In certain embodiments, each of the one to five peptides is present at a concentration of 300 µg/ml. In certain embodiments, the pharmaceutical composition comprises ≤3% DMSO by volume. In certain embodiments, the pharmaceutical composition comprises 3.6-3.7% dextrose in water. In certain embodiments, the pharmaceutical composition comprises 3.6-3.7 mM succinate (e.g., as sodium succinate). In certain embodiments, the pharmaceutical composition comprises 0.5 mg/ml poly I: poly C. In certain embodiments, the pharmaceutical composition comprises 0.375 mg/ml poly-L-Lysine. In certain embodiments, the pharmaceutical composition comprises 1.25 mg/ml sodium carboxymethylcellulose. In certain embodiments, the pharmaceutical composition comprises 0.225% sodium chloride.

Pharmaceutical compositions comprise the herein-described tumor specific neoantigenic peptides in a therapeutically effective amount for treating diseases and conditions (e.g., a neoplasia/tumor), which have been described herein, optionally in combination with a pharmaceutically acceptable additive, carrier and/or excipient. One of ordinary skill in the art from this disclosure and the knowledge in the art will recognize that a therapeutically effective amount of one of more compounds according to the present invention may vary with the condition to be treated, its severity, the treatment regimen to be employed, the pharmacokinetics of the agent used, as well as the patient (animal or human) treated.

To prepare the pharmaceutical compositions, a therapeutically effective amount of one or more of the compounds described herein is preferably intimately admixed with a pharmaceutically acceptable carrier according to conventional pharmaceutical compounding techniques to produce a dose. A carrier may take a wide variety of forms depending on the form of preparation desired for administration, e.g., ocular, oral, topical or parenteral, including gels, creams ointments, lotions and time released implantable preparations, among numerous others. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

The active compound is included in the pharmaceutically acceptable carrier or diluent in an amount sufficient to deliver to a patient a therapeutically effective amount for the desired indication, without causing serious toxic effects in the patient treated.

Oral compositions generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material herein discussed, a liquid carrier such as a fatty oil. In addition, dosage unit forms can contain various other materials which modify the physical form of the dosage unit, for example, coatings of sugar, shellac, or enteric agents.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Methods of formulating such slow or controlled release compositions of pharmaceutically active ingredients, are known in the art and described in several issued US Patents, some of which include, but are not limited to, U.S. Pat. Nos. 3,870,790; 4,226,859; 4,369,172; 4,842,866 and 5,705,190, the disclosures of which are incorporated herein by reference in their entireties. Coatings can be used for delivery of compounds to the intestine (see, e.g., U.S. Pat. Nos. 6,638,534, 5,541,171, 5,217,720, and 6,569,457, and references cited therein).

The active compound or pharmaceutically acceptable salt thereof may also be administered as a component of an elixir, suspension, syrup, wafer, chewing gum or the like. A syrup may contain, in addition to the active compounds, sucrose or fructose as a sweetening agent and certain preservatives, dyes and colorings and flavors.

Solutions or suspensions used for ocular, parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose.

In certain embodiments, the pharmaceutically acceptable carrier is an aqueous solvent, i.e., a solvent comprising water, optionally with additional co-solvents. Exemplary pharmaceutically acceptable carriers include water, buffer solutions in water (such as phosphate-buffered saline (PBS), and 5% dextrose in water (D5W). In certain embodiments, the aqueous solvent further comprises dimethyl sulfoxide (DMSO), e.g., in an amount of about 1-4%, or 1-3%. In certain embodiments, the pharmaceutically acceptable carrier is isotonic (i.e., has substantially the same osmotic pressure as a body fluid such as plasma).

In one embodiment, the active compounds are prepared with carriers that protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid, and polylactic-co-glycolic acid (PLGA). Methods for preparation of such formulations are within the ambit of the skilled artisan in view of this disclosure and the knowledge in the art.

A skilled artisan from this disclosure and the knowledge in the art recognizes that in addition to tablets, other dosage forms can be formulated to provide slow or controlled release of the active ingredient. Such dosage forms include, but are not limited to, capsules, granulations and gel-caps.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations and compositions suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

The parenteral preparation can be enclosed in ampoules, disposable syringes or multiple dose vials made of glass or plastic. If administered intravenously, preferred carriers include, for example, physiological saline or phosphate buffered saline (PBS).

For parenteral formulations, the carrier usually comprises sterile water or aqueous sodium chloride solution, though other ingredients including those which aid dispersion may be included. Of course, where sterile water is to be used and maintained as sterile, the compositions and carriers are also sterilized. Injectable suspensions may also be prepared, in which case appropriate liquid carriers, suspending agents and the like may be employed.

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Administration of the active compound may range from continuous (intravenous drip) to several oral administrations per day (for example, Q.I.D.) and may include oral, topical, eye or ocular, parenteral, intramuscular, intravenous, subcutaneous, transdermal (which may include a penetration enhancement agent), buccal and suppository administration, among other routes of administration, including through an eye or ocular route.

The immunotherapeutic agent, and any additional agents, may be administered by injection, orally, parenterally, by inhalation spray, rectally, vaginally, or topically in dosage unit formulations containing conventional pharmaceutically acceptable carriers, adjuvants, and vehicles. The term parenteral as used herein includes, into a lymph node or nodes, subcutaneous, intravenous, intramuscular, intrasternal, infusion techniques, intraperitoneally, eye or ocular, intravitreal, intrabuccal, transdermal, intranasal, into the brain, including intracranial and intradural, into the joints, including ankles, knees, hips, shoulders, elbows, wrists, directly into tumors, and the like, and in suppository form. In certain embodiments, the immunotherapeutic agent is administered intravenously or subcutaneously.

Application of the immunotherapeutic agent may be local, so as to be administered at the site of interest. In certain embodiments involving a combination therapy, a checkpoint inhibitor is administered subcutaneously near the site of administration of a neoplasia vaccine or immunogenic composition, for example within about 1, 2, 3, 4, 5, 6, 7, 8, 9, 10 cm of the site of vaccine or immunogenic composition administration, and preferably within 5 cm of the site of administration of the neoplasia vaccine or immunogenic composition. It is to be understood by one skilled in the art administering the compositions that the concentration of the checkpoint inhibitor administered to the subject may be changed based on the location of administration. For example, if the checkpoint inhibitor is administered near the site of administration of the neoplasia vaccine or immunogenic composition, then the concentration of the checkpoint inhibitor may be decreased.

Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way.

The immunotherapeutic agent may be administered through a device suitable for the controlled and sustained release of a composition effective in obtaining a desired local or systemic physiological or pharmacological effect. The method includes positioning the sustained released drug delivery system at an area wherein release of the agent is desired and allowing the agent to pass through the device to the desired area of treatment.

The immunotherapeutic agent may be utilized in combination with at least one known other therapeutic agent, or a pharmaceutically acceptable salt of said agent. Examples of known therapeutic agents which can be used for combination therapy include, but are not limited to, corticosteroids (e.g., cortisone, prednisone, dexamethasone), non-steroidal anti-inflammatory drugs (NSAIDS) (e.g., ibuprofen, celecoxib, aspirin, indomethicin, naproxen), alkylating agents such as busulfan, cis-platin, mitomycin C, and carboplatin; antimitotic agents such as colchicine, vinblastine, paclitaxel, and docetaxel; topo I inhibitors such as camptothecin and topotecan; topo II inhibitors such as doxorubicin and etoposide; and/or RNA/DNA antimetabolites such as 5-azacytidine, 5-fluorouracil and methotrexate; DNA antimetabolites such as 5-fluoro-2'-deoxyuridine, ara-C, hydroxyurea and thioguanine; antibodies such as HERCEPTIN and RITUXAN.

It should be understood that in addition to the ingredients particularly mentioned herein, the formulations of the present invention may include other agents conventional in the art having regard to the type of formulation in question, for example, those suitable for oral administration may include flavoring agents.

Pharmaceutically acceptable salt forms may be the preferred chemical form of compounds according to the present invention for inclusion in pharmaceutical compositions according to the present invention.

The present compounds or their derivatives, including prodrug forms of these agents, can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others; (b) base addition salts formed with metal cations such as zinc, calcium, sodium, potassium, and the like, among numerous others.

The compounds herein are commercially available or can be synthesized. As can be appreciated by the skilled artisan, further methods of synthesizing the compounds of the formulae herein is evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, 2nd. Ed., Wiley-VCH Publishers (1999); T. W. Greene and P.G.M. Wuts, Protective Groups in Organic Synthesis, 3rd. Ed., John Wiley and Sons (1999); L. Fieser and M. Fieser, Fieser and Fieser's Reagents for Organic Synthesis, John Wiley and Sons (1999); and L. Paquette, ed., Encyclopedia of Reagents for Organic Synthesis, John Wiley and Sons (1995), and subsequent editions thereof.

Dosage

When the agents described herein are administered as pharmaceuticals to humans or animals, they can be given per se or as a pharmaceutical composition containing active ingredient in combination with a pharmaceutically acceptable carrier, excipient, or diluent.

Actual dosage levels and time course of administration of the active ingredients in the pharmaceutical compositions of the invention can be varied so as to obtain an amount of the active ingredient which is effective to achieve the desired therapeutic response for a particular patient, composition, and mode of administration, without being toxic to the patient. Generally, agents or pharmaceutical compositions of the invention are administered in an amount sufficient to reduce or eliminate symptoms associated with viral infection and/or autoimmune disease.

A preferred dose of an agent is the maximum that a patient can tolerate and not develop serious or unacceptable side effects.

Determination of an effective amount is well within the capability of those skilled in the art, especially in light of the detailed disclosure provided herein. Generally, an efficacious or effective amount of an agent is determined by first administering a low dose of the agent(s) and then incrementally increasing the administered dose or dosages until a desired effect (e.g., reduce or eliminate symptoms associated with cancer) is observed in the treated subject, with minimal or acceptable toxic side effects. Applicable methods for determining an appropriate dose and dosing schedule for administration of a pharmaceutical composition of the present invention are described, for example, in Goodman and Gilman's The Pharmacological Basis of Therapeutics, Goodman et al., eds., 11th Edition, McGraw-Hill 2005, and Remington: The Science and Practice of Pharmacy, 20th and 21st Editions, Gennaro and University of the Sciences in Philadelphia, Eds., Lippencott Williams & Wilkins (2003 and 2005), each of which is hereby incorporated by reference.

Preferred unit dosage formulations are those containing a daily dose or unit, daily sub-dose, as herein discussed, or an appropriate fraction thereof, of the administered ingredient.

The dosage regimen for treating a disorder or a disease with the immunotherapeutic agent is based on a variety of factors, including the type of tumor, the age, weight, sex, medical condition of the patient, the severity of the condition, the route of administration, and the particular compound employed. Thus, the dosage regimen may vary widely, but can be determined routinely using standard methods.

The amount of compound included within therapeutically active formulations according to the present invention is an effective amount for treating the disease or condition.

In general, a therapeutically effective amount of the present preferred compound in dosage form usually ranges from slightly less than about 0.025 mg/kg/day to about 2.5 g/kg/day, preferably about 0.1 mg/kg/day to about 100 mg/kg/day of the patient or considerably more, depending upon the compound used, the condition or infection treated and the route of administration, although exceptions to this dosage range may be contemplated by the present invention. In its most preferred form, the immunotherapeutic agent is administered in amounts ranging from about 1 mg/kg/day to about 100 mg/kg/day. The dosage of the compound can depend on the condition being treated, the particular compound, and other clinical factors such as weight and condition of the patient and the route of administration of the compound. It is to be understood that the present invention has application for both human and veterinary use.

According to certain exemplary embodiments, a vaccine or immunogenic composition is administered at a dose of about 10 µg-1 mg per neoantigenic peptide. According to certain exemplary embodiments, the vaccine or immunogenic composition is administered at an average weekly dose level of about 10 µg-2000 µg per neoantigenic peptide. According to certain exemplary embodiments, the checkpoint inhibitor is administered at a dose of about 0.1-10 mg/kg. According to certain exemplary embodiments, the anti-CTLA4 antibody is administered at a dose of about 1 mg/kg-3 mg/kg. For example, in certain exemplary embodiments, Nivolumab is dosed at the standard single agent dosing level of 3 mg/kg. When one or more checkpoint inhibitors are administered at the site of administration of the vaccine or immunogenic composition, the inhibitor is preferably administered at a dose of about 0.1-1 mg per site of administration of the neoplasia vaccine or immunogenic composition.

Preferred embodiments use the concentrations and timings used in clinical trials for the immunotherapeutic agents, e.g. checkpoint inhibitors, alone or in combination with a neoantigen vaccine or immunogenic composition. Topalian, et al. N Engl J Med 2012; 366:2443-2454 describes a phase 1 study that assessed the safety, antitumor activity, and pharmacokinetics of BMS-936558, a fully human IgG4-blocking monoclonal antibody directed against PD-1, in patients in need thereof with selected advanced solid tumors. The antibody was administered as an intravenous infusion every 2 weeks of each 8-week treatment cycle. Response was assessed after each treatment cycle. Patients received treatment for up to 2 years (12 cycles). Patients with advanced melanoma, non-small-cell lung cancer, renal-cell cancer, castration-resistant prostate cancer, or colorectal cancer were enrolled. Cohorts of three to six patients per dose level were enrolled sequentially at doses of 1.0, 3.0, or 10.0 mg per kilogram of body weight. Initially, five expansion cohorts of approximately 16 patients each were enrolled at doses of 10.0 mg per kilogram for melanoma, non-small-cell lung cancer, renal-cell cancer, castration-resistant prostate cancer, and colorectal cancer. On the basis of initial signals of activity, additional expansion cohorts of approximately 16 patients each were enrolled for melanoma (at a dose of 1.0 or 3.0 mg per kilogram, followed by cohorts randomly assigned to 0.1, 0.3, or 1.0 mg per kilogram), lung cancer (patients with the squamous or nonsquamous subtype, randomly assigned to a dose of 1.0, 3.0, or 10.0 mg per kilogram), and renal-cell cancer (at a dose of 1.0 mg per kilogram).

Wolchok, et al. N Engl J Med 2013; 369:122-133, describes a clinical trial using Nivolumab plus Ipilimumab in advanced melanoma. In the study patients were administered intravenous doses of nivolumab and ipilimumab every 3 weeks for 4 doses, followed by nivolumab alone every 3 weeks for 4 doses. The combined treatment was subsequently administered every 12 weeks for up to 8 doses. In a sequenced regimen, patients previously treated with ipilimumab received nivolumab every 2 weeks for up to 48 doses. The maximum doses that were associated with an acceptable level of adverse events were nivolumab at a dose of 1 mg per kilogram of body weight and ipilimumab at a dose of 3 mg per kilogram.

Wolchok et al., Clin. Cancer Res. 15, 7412; 2009 describes a phase II clinical trial program with ipilimumab. Patients were treated with induction therapy (ipilimumab 10 mg/kg every 3 wk×4) followed by maintenance therapy in eligible patients (ipilimumab 10 mg/kg every 12 wk, beginning at week 24).

Hamid et al., N Engl J Med 2013; 369:134-144, describes safety and tumor responses with Lambrolizumab (Anti-PD-1) in melanoma. Patients with advanced melanoma were administered lambrolizumab intravenously at a dose of 10 mg per kilogram of body weight every 2 or 3 weeks or 2 mg per kilogram every 3 weeks. Patients included both those who had received prior treatment with the immune checkpoint inhibitor ipilimumab and those who had not.

Spigel et al., J Clin Oncol 31, 2013 (suppl; abstr 8008) describe a phase I trial for MPDL3280A, a human monoclonal Ab containing an engineered Fc-domain designed to optimize efficacy and safety, targeting PD-L1. Patients with squamous or nonsquamous NSCLC received MPDL3280A by IV at doses between 1-20 mg/kg for up to 1 y.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Described herein are pharmaceutical compositions containing at least one immunotherapeutic agent. In embodiments, the pharmaceutical compositions contain a pharmaceutically acceptable carrier, excipient, or diluent, which includes any pharmaceutical agent that does not itself induce the production of an immune response harmful to a subject receiving the composition, and which may be administered without undue toxicity. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful for treating and/or preventing cancer.

A thorough discussion of pharmaceutically acceptable carriers, diluents, and other excipients is presented in Remington's Pharmaceutical Sciences (17th ed., Mack Publishing Company) and Remington: The Science and Practice of Pharmacy (21st ed., Lippincott Williams & Wilkins), which are hereby incorporated by reference. The formulation of the pharmaceutical composition should suit the mode of administration. In embodiments, the pharmaceutical composition is suitable for administration to humans, and can be sterile, non-particulate and/or non-pyrogenic.

Pharmaceutically acceptable carriers, excipients, or diluents include, but are not limited, to saline, buffered saline, dextrose, water, glycerol, ethanol, sterile isotonic aqueous buffer, and combinations thereof.

Wetting agents, emulsifiers and lubricants, such as sodium lauryl sulfate and magnesium stearate, as well as coloring agents, release agents, coating agents, sweetening, flavoring and perfuming agents, preservatives, and antioxidants can also be present in the compositions.

Examples of pharmaceutically-acceptable antioxidants include, but are not limited to: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In embodiments, the pharmaceutical composition is provided in a solid form, such as a lyophilized powder suitable for reconstitution, a liquid solution, suspension, emulsion, tablet, pill, capsule, sustained release formulation, or powder.

In embodiments, the pharmaceutical composition is supplied in liquid form, for example, in a sealed container indicating the quantity and concentration of the active ingredient in the pharmaceutical composition. In related embodiments, the liquid form of the pharmaceutical composition is supplied in a hermetically sealed container.

Methods for formulating the pharmaceutical compositions of the present invention are conventional and well known in the art (see Remington and Remington's). One of skill in the art can readily formulate a pharmaceutical composition having the desired characteristics (e.g., route of administration, biosafety, and release profile).

Methods for preparing the pharmaceutical compositions include the step of bringing into association the active ingredient with a pharmaceutically acceptable carrier and, optionally, one or more accessory ingredients. The pharmaceutical compositions can be prepared by uniformly and intimately bringing into association the active ingredient with liquid carriers, or finely divided solid carriers, or both, and then, if necessary, shaping the product. Additional methodology for preparing the pharmaceutical compositions, including the preparation of multilayer dosage forms, are described in Ansel's Pharmaceutical Dosage Forms and Drug Delivery Systems (9th ed., Lippincott Williams & Wilkins), which is hereby incorporated by reference.

Pharmaceutical compositions suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound(s) described herein, a derivative thereof, or a pharmaceutically acceptable salt or prodrug thereof as the active ingredient(s). The active ingredient can also be administered as a bolus, electuary, or paste.

In solid dosage forms for oral administration (e.g., capsules, tablets, pills, dragees, powders, granules and the like), the active ingredient is mixed with one or more pharmaceutically acceptable carriers, excipients, or diluents, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions can also comprise buffering agents. Solid compositions of a similar type can also be prepared using fillers in soft and hard-filled gelatin capsules, and excipients such as lactose or milk sugars, as well as high molecular weight polyethylene glycols and the like.

A tablet can be made by compression or molding, optionally with one or more accessory ingredients. Compressed tablets can be prepared using binders (for example, gelatin or hydroxypropylmethyl cellulose), lubricants, inert diluents, preservatives, disintegrants (for example, sodium starch glycolate or cross-linked sodium carboxymethyl cellulose), surface-actives, and/or dispersing agents. Molded tablets can be made by molding in a suitable machine a mixture of the powdered active ingredient moistened with an inert liquid diluent.

The tablets and other solid dosage forms, such as dragees, capsules, pills, and granules, can optionally be scored or prepared with coatings and shells, such as enteric coatings and other coatings well known in the art.

In some embodiments, in order to prolong the effect of an active ingredient, it is desirable to slow the absorption of the compound from subcutaneous or intramuscular injection. This can be accomplished by the use of a liquid suspension of crystalline or amorphous material having poor water solubility. The rate of absorption of the active ingredient then depends upon its rate of dissolution which, in turn, can depend upon crystal size and crystalline form. Alternatively, delayed absorption of a parenterally-administered active ingredient is accomplished by dissolving or suspending the compound in an oil vehicle. In addition, prolonged absorption of the injectable pharmaceutical form can be brought about by the inclusion of agents that delay absorption such as aluminum monostearate and gelatin.

Controlled release parenteral compositions can be in form of aqueous suspensions, microspheres, microcapsules, magnetic microspheres, oil solutions, oil suspensions, emulsions, or the active ingredient can be incorporated in biocompatible carrier(s), liposomes, nanoparticles, implants or infusion devices.

Materials for use in the preparation of microspheres and/or microcapsules include biodegradable/bioerodible polymers such as polyglactin, poly-(isobutyl cyanoacrylate), poly(2-hydroxyethyl-L-glutamine) and poly(lactic acid).

Biocompatible carriers which can be used when formulating a controlled release parenteral formulation include carbohydrates such as dextrans, proteins such as albumin, lipoproteins or antibodies.

Materials for use in implants can be non-biodegradable, e.g., polydimethylsiloxane, or biodegradable such as, e.g., poly(caprolactone), poly(lactic acid), poly(glycolic acid) or poly(ortho esters).

In embodiments, the active ingredient(s) are administered by aerosol. This is accomplished by preparing an aqueous aerosol, liposomal preparation, or solid particles containing the compound. A nonaqueous (e.g., fluorocarbon propellant) suspension can be used. The pharmaceutical composition can also be administered using a sonic nebulizer, which would minimize exposing the agent to shear, which can result in degradation of the compound.

Ordinarily, an aqueous aerosol is made by formulating an aqueous solution or suspension of the active ingredient(s) together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Dosage forms for topical or transdermal administration of an active ingredient(s) includes powders, sprays, ointments, pastes, creams, lotions, gels, solutions, patches and inhalants. The active ingredient(s) can be mixed under sterile conditions with a pharmaceutically acceptable carrier, and with any preservatives, buffers, or propellants as appropriate.

Transdermal patches suitable for use in the present invention are disclosed in Transdermal Drug Delivery: Developmental Issues and Research Initiatives (Marcel Dekker Inc., 1989) and U.S. Pat. Nos. 4,743,249, 4,906,169, 5,198,223, 4,816,540, 5,422,119, 5,023,084, which are hereby incorporated by reference. The transdermal patch can also be any transdermal patch well known in the art, including transscrotal patches. Pharmaceutical compositions in such transdermal patches can contain one or more absorption enhancers or skin permeation enhancers well known in the art (see, e.g., U.S. Pat. Nos. 4,379,454 and 4,973,468, which are hereby incorporated by reference). Transdermal therapeutic systems for use in the present invention can be based on iontophoresis, diffusion, or a combination of these two effects.

Transdermal patches have the added advantage of providing controlled delivery of active ingredient(s) to the body. Such dosage forms can be made by dissolving or dispersing the active ingredient(s) in a proper medium. Absorption enhancers can also be used to increase the flux of the active ingredient across the skin. The rate of such flux can be controlled by either providing a rate controlling membrane or dispersing the active ingredient(s) in a polymer matrix or gel.

Such pharmaceutical compositions can be in the form of creams, ointments, lotions, liniments, gels, hydrogels, solutions, suspensions, sticks, sprays, pastes, plasters and other kinds of transdermal drug delivery systems. The compositions can also include pharmaceutically acceptable carriers or excipients such as emulsifying agents, antioxidants, buffering agents, preservatives, humectants, penetration enhancers, chelating agents, gel-forming agents, ointment bases, perfumes, and skin protective agents.

Examples of emulsifying agents include, but are not limited to, naturally occurring gums, e.g. gum acacia or gum tragacanth, naturally occurring phosphatides, e.g. soybean lecithin and sorbitan monooleate derivatives.

Examples of antioxidants include, but are not limited to, butylated hydroxy anisole (BHA), ascorbic acid and derivatives thereof, tocopherol and derivatives thereof, and cysteine.

Examples of preservatives include, but are not limited to, parabens, such as methyl or propyl p-hydroxybenzoate and benzalkonium chloride.

Examples of humectants include, but are not limited to, glycerin, propylene glycol, sorbitol and urea.

Examples of penetration enhancers include, but are not limited to, propylene glycol, DMSO, triethanolamine, N,N-dimethylacetamide, N,N-dimethylformamide, 2-pyrrolidone and derivatives thereof, tetrahydrofurfuryl alcohol, propylene glycol, diethylene glycol monoethyl or monomethyl ether with propylene glycol monolaurate or methyl laurate, eucalyptol, lecithin, TRANSCUTOL, and AZONE.

Examples of chelating agents include, but are not limited to, sodium EDTA, citric acid and phosphoric acid.

Examples of gel forming agents include, but are not limited to, Carbopol, cellulose derivatives, bentonite, alginates, gelatin and polyvinylpyrrolidone.

In addition to the active ingredient(s), the ointments, pastes, creams, and gels of the present invention can contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons, and volatile unsubstituted hydrocarbons, such as butane and propane.

Injectable depot forms are made by forming microencapsule matrices of compound(s) of the invention in biodegradable polymers such as polylactide-polyglycolide. Depending on the ratio of compound to polymer, and the nature of the particular polymer employed, the rate of compound release can be controlled. Examples of other biodegradable polymers include poly(orthoesters) and poly(anhydrides). Depot injectable formulations are also prepared by entrapping the drug in liposomes or microemulsions which are compatible with body tissue.

Subcutaneous implants are well known in the art and are suitable for use in the present invention. Subcutaneous implantation methods are preferably non-irritating and mechanically resilient. The implants can be of matrix type, of reservoir type, or hybrids thereof. In matrix type devices, the carrier material can be porous or non-porous, solid or semi-solid, and permeable or impermeable to the active compound or compounds. The carrier material can be biodegradable or may slowly erode after administration. In some instances, the matrix is non-degradable but instead relies on the diffusion of the active compound through the matrix for the carrier material to degrade. Alternative subcutaneous implant methods utilize reservoir devices where the active compound or compounds are surrounded by a rate controlling membrane, e.g., a membrane independent of component concentration (possessing zero-order kinetics). Devices consisting of a matrix surrounded by a rate controlling membrane also suitable for use.

Both reservoir and matrix type devices can contain materials such as polydimethylsiloxane, such as SILASTIC, or other silicone rubbers. Matrix materials can be insoluble polypropylene, polyethylene, polyvinyl chloride, ethylvinyl acetate, polystyrene and polymethacrylate, as well as glycerol esters of the glycerol palmitostearate, glycerol stearate, and glycerol behenate type. Materials can be hydrophobic or hydrophilic polymers and optionally contain solubilizing agents.

Subcutaneous implant devices can be slow-release capsules made with any suitable polymer, e.g., as described in U.S. Pat. Nos. 5,035,891 and 4,210,644, which are hereby incorporated by reference.

In general, at least four different approaches are applicable in order to provide rate control over the release and transdermal permeation of a drug compound. These approaches are: membrane-moderated systems, adhesive diffusion-controlled systems, matrix dispersion-type systems and microreservoir systems. It is appreciated that a controlled release percutaneous and/or topical composition can be obtained by using a suitable mixture of these approaches.

In a membrane-moderated system, the active ingredient is present in a reservoir which is totally encapsulated in a shallow compartment molded from a drug-impermeable laminate, such as a metallic plastic laminate, and a rate-controlling polymeric membrane such as a microporous or a non-porous polymeric membrane, e.g., ethylene-vinyl acetate copolymer. The active ingredient is released through the rate controlling polymeric membrane. In the drug reservoir, the active ingredient can either be dispersed in a solid polymer matrix or suspended in an unleachable, viscous liquid medium such as silicone fluid. On the external surface of the polymeric membrane, a thin layer of an adhesive polymer is applied to achieve an intimate contact of the transdermal system with the skin surface. The adhesive polymer is preferably a polymer which is hypoallergenic and compatible with the active drug substance.

In an adhesive diffusion-controlled system, a reservoir of the active ingredient is formed by directly dispersing the active ingredient in an adhesive polymer and then by, e.g., solvent casting, spreading the adhesive containing the active ingredient onto a flat sheet of substantially drug-impermeable metallic plastic backing to form a thin drug reservoir layer.

A matrix dispersion-type system is characterized in that a reservoir of the active ingredient is formed by substantially homogeneously dispersing the active ingredient in a hydrophilic or lipophilic polymer matrix. The drug-containing polymer is then molded into disc with a substantially well-defined surface area and controlled thickness. The adhesive polymer is spread along the circumference to form a strip of adhesive around the disc.

A microreservoir system can be considered as a combination of the reservoir and matrix dispersion type systems. In this case, the reservoir of the active substance is formed by first suspending the drug solids in an aqueous solution of water-soluble polymer and then dispersing the drug suspension in a lipophilic polymer to form a multiplicity of unleachable, microscopic spheres of drug reservoirs.

Any of the herein-described controlled release, extended release, and sustained release compositions can be formulated to release the active ingredient in about 30 minutes to about 1 week, in about 30 minutes to about 72 hours, in about 30 minutes to 24 hours, in about 30 minutes to 12 hours, in about 30 minutes to 6 hours, in about 30 minutes to 4 hours, and in about 3 hours to 10 hours. In embodiments, an effective concentration of the active ingredient(s) is sustained in a subject for 4 hours, 6 hours, 8 hours, 10 hours, 12 hours, 16 hours, 24 hours, 48 hours, 72 hours, or more after administration of the pharmaceutical compositions to the subject.

Vaccine or Immunogenic Compositions

In one embodiment, the immunotherapeutic agent comprises at least an immunogenic composition, e.g., a neoplasia vaccine or immunogenic composition capable of raising a specific T-cell response. The neoplasia vaccine or immunogenic composition preferably comprises neoantigenic peptides and/or neoantigenic polypeptides corresponding to tumor specific neoantigens identified by the methods described herein. A suitable neoplasia vaccine or immunogenic composition can preferably contain a plurality of tumor specific neoantigenic peptides. In an embodiment, the vaccine or immunogenic composition can include between 1 and 100 sets of peptides, more preferably between 1 and 50 such peptides, even more preferably between 10 and 30 sets peptides, even more preferably between 15 and 25 peptides. According to another preferred embodiment, the vaccine or immunogenic composition can include at least one peptides, more preferably 2, 3, 4, or 5 peptides. In certain embodiments, the vaccine or immunogenic composition can comprise 5, 6, 7, 8, 9, 10, 11, 12, 13, 14, 15, 16, 17, 18, 19, 20, 21, 22, 23, 24, 25, 26, 27, 28, 29, or 30 different peptides.

The optimum amount of each peptide to be included in the vaccine or immunogenic composition and the optimum dosing regimen can be determined by one skilled in the art without undue experimentation. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c, i.d., i.p., i.m., and i.v. Preferred methods of DNA injection include i.d., i.m., s.c, i.p. and i.v. For example, doses of between 1 and 500 mg 50 µg and 1.5 mg, preferably 10 µg to 500 µg, of peptide or DNA may be given and can depend from the respective peptide or DNA. Doses of this range were successfully used in previous trials (Brunsvig P F, et al., Cancer Immunol Immunother. 2006; 55(12): 1553-1564; M. Staehler, et al., ASCO meeting 2007; Abstract No 3017). Other methods of administration of the vaccine or immunogenic composition are known to those skilled in the art.

In one embodiment of the present invention the different tumor specific neoantigenic peptides and/or polypeptides are selected for use in the neoplasia vaccine or immunogenic composition so as to maximize the likelihood of generating an immune attack against the neoplasia/tumor of the patient. Without being bound by theory, it is believed that the inclusion of a diversity of tumor specific neoantigenic peptides can generate a broad scale immune attack against a neoplasia/tumor. In one embodiment, the selected tumor specific neoantigenic peptides/polypeptides are encoded by missense mutations. In a second embodiment, the selected tumor specific neoantigenic peptides/polypeptides are encoded by a combination of missense mutations and neoORF mutations. In a third embodiment, the selected tumor specific neoantigenic peptides/polypeptides are encoded by neoORF mutations.

In one embodiment in which the selected tumor specific neoantigenic peptides/polypeptides are encoded by missense mutations, the peptides and/or polypeptides are chosen based on their capability to associate with the particular MHC molecules of the patient. Peptides/polypeptides derived from neoORF mutations can also be selected on the basis of their capability to associate with the particular MHC molecules of the patient, but can also be selected even if not predicted to associate with the particular MHC molecules of the patient.

The vaccine or immunogenic composition is capable of raising a specific cytotoxic T-cells response and/or a specific helper T-cell response.

The vaccine or immunogenic composition can further comprise an adjuvant and/or a carrier. Examples of useful adjuvants and carriers are given herein. The peptides and/or polypeptides in the composition can be associated with a carrier such as, e.g., a protein or an antigen-presenting cell such as e.g. a dendritic cell (DC) capable of presenting the peptide to a T-cell.

Adjuvants are any substance whose admixture into the vaccine or immunogenic composition increases or otherwise modifies the immune response to the mutant peptide. Carriers are scaffold structures, for example a polypeptide or a polysaccharide, to which the neoantigenic peptides, is capable of being associated. Optionally, adjuvants are conjugated covalently or non-covalently to the peptides or polypeptides of the invention.

The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th2 response into a primarily cellular, or Th1 response.

Suitable adjuvants include, but are not limited to 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PEPTEL. vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Several immunological adjuvants (e.g., MF59) specific for dendritic cells and their preparation have been described previously (Dupuis M, et al., Cell Immunol. 1998; 186(1): 18-27; Allison A C; Dev Biol Stand. 1998; 92:3-11). Also cytokines may be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

Toll like receptors (TLRs) may also be used as adjuvants, and are important members of the family of pattern recognition receptors (PRRs) which recognize conserved motifs shared by many micro-organisms, termed "pathogen-associated molecular patterns" (PAMPS). Recognition of these "danger signals" activates multiple elements of the innate and adaptive immune system. TLRs are expressed by cells of the innate and adaptive immune systems such as dendritic cells (DCs), macrophages, T and B cells, mast cells, and granulocytes and are localized in different cellular compartments, such as the plasma membrane, lysosomes, endosomes, and endolysosomes. Different TLRs recognize distinct PAMPS. For example, TLR4 is activated by LPS contained in bacterial cell walls, TLR9 is activated by unmethylated bacterial or viral CpG DNA, and TLR3 is activated by double stranded RNA. TLR ligand binding leads to the activation of one or more intracellular signaling pathways, ultimately resulting in the production of many key molecules associated with inflammation and immunity (particularly the transcription factor NF-κB and the Type-I interferons). TLR mediated DC activation leads to enhanced DC activation, phagocytosis, upregulation of activation and co-stimulation markers such as CD80, CD83, and CD86, expression of CCR7 allowing migration of DC to draining lymph nodes and facilitating antigen presentation to T cells, as well as increased secretion of cytokines such as type I interferons, IL-12, and IL-6. All of these downstream events are critical for the induction of an adaptive immune response.

Among the most promising cancer vaccine or immunogenic composition adjuvants currently in clinical development are the TLR9 agonist CpG and the synthetic double-stranded RNA (dsRNA) TLR3 ligand poly-ICLC. In preclinical studies poly-ICLC appears to be the most potent TLR adjuvant when compared to LPS and CpG due to its induction of pro-inflammatory cytokines and lack of stimulation of IL-10, as well as maintenance of high levels of co-stimulatory molecules in DCs1. Furthermore, poly-ICLC was recently directly compared to CpG in non-human primates (rhesus macaques) as adjuvant for a protein vaccine or immunogenic composition consisting of human papillomavirus (HPV)16 capsomers (Stahl-Hennig C, Eisenblatter M, Jasny E, et al. Synthetic double-stranded RNAs are adjuvants for the induction of T helper 1 and humoral immune responses to human papillomavirus in rhesus macaques. PLoS pathogens. April 2009; 5(4)).

CpG immuno stimulatory oligonucleotides have also been reported to enhance the effects of adjuvants in a vaccine or immunogenic composition setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly, it enhances dendritic cell maturation and differentiation, resulting in enhanced activation of Th1 cells and strong cytotoxic T-lymphocyte (CTL) generation, even in the absence of CD4 T-cell help. The Th1 bias induced by TLR9 stimulation is maintained even in the presence of vaccine adjuvants such as alum or incomplete Freund's adjuvant (IFA) that normally promote a Th2 bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Arthur M. Krieg, Nature Reviews, Drug Discovery, 5, Jun. 2006, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, GERMANY), which is a preferred component of the pharmaceutical composition of the present invention. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly(I:C)(e.g. polyi:Cl2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim).

Poly-ICLC is a synthetically prepared double-stranded RNA consisting of polyI and polyC strands of average length of about 5000 nucleotides, which has been stabilized to thermal denaturation and hydrolysis by serum nucleases by the addition of polylysine and carboxymethylcellulose. The compound activates TLR3 and the RNA helicase-domain of MDA5, both members of the PAMP family, leading to DC and natural killer (NK) cell activation and production of a "natural mix" of type I interferons, cytokines, and chemokines. Furthermore, poly-ICLC exerts a more direct, broad host-targeted anti-infectious and possibly antitumor effect mediated by the two IFN-inducible nuclear enzyme systems, the 2'5'-OAS and the P1/eIF2a kinase, also known as the PKR (4-6), as well as RIG-I helicase and MDA5.

In rodents and non-human primates, poly-ICLC was shown to enhance T cell responses to viral antigens, cross-priming, and the induction of tumor-, virus-, and autoantigen-specific CD8+ T-cells. In a recent study in non-human primates, poly-ICLC was found to be essential for the generation of antibody responses and T-cell immunity to DC targeted or non-targeted HIV Gag p24 protein, emphasizing its effectiveness as a vaccine adjuvant.

In human subjects, transcriptional analysis of serial whole blood samples revealed similar gene expression profiles among the 8 healthy human volunteers receiving one single s.c. administration of poly-ICLC and differential expression of up to 212 genes between these 8 subjects versus 4 subjects receiving placebo. Remarkably, comparison of the poly-ICLC gene expression data to previous data from volunteers immunized with the highly effective yellow fever vaccine YF17D showed that a large number of transcriptional and signal transduction canonical pathways, including those of the innate immune system, were similarly upregulated at peak time points.

More recently, an immunologic analysis was reported on patients with ovarian, fallopian tube, and primary peritoneal cancer in second or third complete clinical remission who were treated on a phase 1 study of subcutaneous vaccination with synthetic overlapping long peptides (OLP) from the cancer testis antigen NY-ESO-1 alone or with Montanide-ISA-51, or with 1.4 mg poly-ICLC and Montanide. The generation of NY-ESO-1-specific CD4+ and CD8+ T-cell and antibody responses were markedly enhanced with the addition of poly-ICLC and Montanide compared to OLP alone or OLP and Montanide.

A vaccine or immunogenic composition used herein may comprise more than one different adjuvant. Furthermore, the invention encompasses a therapeutic composition comprising any adjuvant substance including any of those herein discussed. It is also contemplated that the peptide or polypeptide, and the adjuvant can be administered separately in any appropriate sequence.

A carrier may be present independently of an adjuvant. The carrier may be covalently linked to the antigen. A carrier can also be added to the antigen by inserting DNA encoding the carrier in frame with DNA encoding the antigen. The function of a carrier can for example be to confer stability, to increase the biological activity, or to increase serum half-life. Extension of the half-life can help to reduce the number of applications and to lower doses, thus are beneficial for therapeutic but also economic reasons. Furthermore, a carrier may aid presenting peptides to T-cells. The carrier may be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier may be a physiologically acceptable carrier acceptable to humans and safe. However, tetanus toxoid and/or diptheria toxoid are suitable carriers in one embodiment of the invention. Alternatively, the carrier may be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is only possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments the immunotherapeutic agent additionally contains at least one antigen presenting cell.

The antigen-presenting cell (or stimulator cell) typically has an MHC class I or II molecule on its surface, and in one embodiment is substantially incapable of itself loading the MHC class I or II molecule with the selected antigen. As is described in more detail herein, the MHC class I or II molecule may readily be loaded with the selected antigen in vitro.

CD8+ cell activity may be augmented through the use of CD4+ cells. The identification of CD4 T+ cell epitopes for tumor antigens has attracted interest because many immune based therapies against cancer may be more effective if both CD8+ and CD4+T lymphocytes are used to target a patient's tumor. CD4+ cells are capable of enhancing CD8 T cell responses. Many studies in animal models have clearly demonstrated better results when both CD4+ and CD8+ T cells participate in anti-tumor responses (see e.g., Nishimura et al. (1999) Distinct role of antigen-specific T helper type 1 (TH1) and Th2 cells in tumor eradication in vivo. J Ex Med 190:617-27). Universal CD4+ T cell epitopes have been identified that are applicable to developing therapies against different types of cancer (see e.g., Kobayashi et al. (2008) Current Opinion in Immunology 20:221-27). For example, an HLA-DR restricted helper peptide from tetanus toxoid was used in melanoma vaccines to activate CD4+ T cells non-specifically (see e.g., Slingluff et al. (2007) Immunologic and Clinical Outcomes of a Randomized Phase II Trial of Two Multipeptide Vaccines for Melanoma in the Adjuvant Setting, Clinical Cancer Research 13(21):6386-95). It is contemplated within the scope of the invention that such CD4+ cells may be applicable at three levels that vary in their tumor specificity: 1) a broad level in which universal CD4+ epitopes (e.g., tetanus toxoid) may be used to augment CD8+ cells; 2) an intermediate level in which native, tumor-associated CD4+ epitopes may be used to augment CD8+ cells; and 3) a patient specific level in which neoantigen CD4+ epitopes may be used to augment CD8+ cells in a patient specific manner.

CD8+ cell immunity may also be generated with neoantigen loaded dendritic cell (DC) vaccine. DCs are potent antigen-presenting cells that initiate T cell immunity and can be used as cancer vaccines when loaded with one or more peptides of interest, for example, by direct peptide injection. For example, patients that were newly diagnosed with metastatic melanoma were shown to be immunized against 3 HLA-A*0201-restricted gp100 melanoma antigen-derived peptides with autologous peptide pulsed CD40L/IFN-g-activated mature DCs via an IL-12p70-producing patient DC vaccine (see e.g., Carreno et al (2013) L-12p70-producing patient DC vaccine elicits Tc1-polarized immunity, Journal of Clinical Investigation, 123(8):3383-94 and Ali et al. (2009) In situ regulation of DC subsets and T cells mediates tumor regression in mice, Cancer Immunotherapy, 1(8):1-

10). It is contemplated within the scope of the invention that neoantigen loaded DCs may be prepared using the synthetic TLR 3 agonist Polyinosinic-Polycytidylic Acid-poly-L-lysine Carboxymethylcellulose (Poly-ICLC) to stimulate the DCs. Poly-ICLC is a potent individual maturation stimulus for human DCs as assessed by an upregulation of CD83 and CD86, induction of interleukin-12 (IL-12), tumor necrosis factor (TNF), interferon gamma-induced protein 10 (IP-10), interleukin 1 (IL-1), and type I interferons (IFN), and minimal interleukin 10 (IL-10) production. DCs may be differentiated from frozen peripheral blood mononuclear cells (PBMCs) obtained by leukapheresis, while PBMCs may be isolated by Ficoll gradient centrifugation and frozen in aliquots.

Illustratively, the following 7 day activation protocol may be used. Day 1—PBMCs are thawed and plated onto tissue culture flasks to select for monocytes which adhere to the plastic surface after 1-2 hr incubation at 37° C. in the tissue culture incubator. After incubation, the lymphocytes are washed off and the adherent monocytes are cultured for 5 days in the presence of interleukin-4 (IL-4) and granulocyte macrophage-colony stimulating factor (GM-CSF) to differentiate to immature DCs. On Day 6, immature DCs are pulsed with the keyhole limpet hemocyanin (KLH) protein which serves as a control for the quality of the vaccine and may boost the immunogenicity of the vaccine. The DCs are stimulated to mature, loaded with peptide antigens, and incubated overnight. On Day 7, the cells are washed, and frozen in 1 ml aliquots containing 4-20×10(6) cells using a controlled-rate freezer. Lot release testing for the batches of DCs may be performed to meet minimum specifications before the DCs are injected into patients (see e.g., Sabado et al. (2013) Preparation of tumor antigen-loaded mature dendritic cells for immunotherapy, J. Vis Exp. August 1; (78). doi: 10.3791/50085).

A DC vaccine may be incorporated into a scaffold system to facilitate delivery to a patient. Therapeutic treatment of a patients neoplasia with a DC vaccine may utilize a biomaterial system that releases factors that recruit host dendritic cells into the device, differentiates the resident, immature DCs by locally presenting adjuvants (e.g., danger signals) while releasing antigen, and promotes the release of activated, antigen loaded DCs to the lymph nodes (or desired site of action) where the DCs may interact with T cells to generate a potent cytotoxic T lymphocyte response to the cancer neoantigens. Implantable biomaterials may be used to generate a potent cytotoxic T lymphocyte response against a neoplasia in a patient specific manner. The biomaterial-resident dendritic cells may then be activated by exposing them to danger signals mimicking infection, in concert with release of antigen from the biomaterial. The activated dendritic cells then migrate from the biomaterials to lymph nodes to induce a cytotoxic T effector response. This approach has previously been demonstrated to lead to regression of established melanoma in preclinical studies using a lysate prepared from tumor biopsies (see e.g., Ali et al. (2209) In situ regulation of DC subsets and T cells mediates tumor regression in mice, Cancer Immunotherapy 1(8):1-10; Ali et al. (2009) Infection-mimicking materials to program dendritic cells in situ. Nat Mater 8:151-8), and such a vaccine is currently being tested in a Phase I clinical trial recently initiated at the Dana-Farber Cancer Institute. This approach has also been shown to lead to regression of glioblastoma, as well as the induction of a potent memory response to prevent relapse, using the C6 rat glioma model.24 in the current proposal. The ability of such an implantable, biomatrix vaccine delivery scaffold to amplify and sustain tumor specific dendritic cell activation may lead to more robust anti-tumor immunosensitization than can be achieved by traditional subcutaneous or intra-nodal vaccine administrations.

Preferably, the antigen presenting cells are dendritic cells. Suitably, the dendritic cells are autologous dendritic cells that are pulsed with the neoantigenic peptide. The peptide may be any suitable peptide that gives rise to an appropriate T-cell response. T-cell therapy using autologous dendritic cells pulsed with peptides from a tumor associated antigen is disclosed in Murphy et al. (1996) The Prostate 29, 371-380 and Tjua et al. (1997) The Prostate 32, 272-278.

Thus, in one embodiment of the present invention an immunotherapeutic agent (e.g. a vaccine or immunogenic composition) containing at least one antigen presenting cell is pulsed or loaded with one or more peptides described herein. Alternatively, peripheral blood mononuclear cells (PBMCs) isolated from a patient may be loaded with peptides ex vivo and injected back into the patient. As an alternative the antigen presenting cell comprises an expression construct encoding a peptide described herein. The polynucleotide may be any suitable polynucleotide and it is preferred that it is capable of transducing the dendritic cell, thus resulting in the presentation of a peptide and induction of immunity.

The pharmaceutical composition may be compiled so that the selection, number and/or amount of peptides present in the composition is/are tissue, cancer, and/or patient-specific. For instance, the exact selection of peptides can be guided by expression patterns of the parent proteins in a given tissue to avoid side effects. The selection may be dependent on the specific type of cancer, the status of the disease, earlier treatment regimens, the immune status of the patient, and, of course, the HLA-haplotype of the patient. Furthermore, the vaccine or immunogenic composition can contain individualized components, according to personal needs of the particular patient. Examples include varying the amounts of peptides according to the expression of the related neoantigen in the particular patient, unwanted side-effects due to personal allergies or other treatments, and adjustments for secondary treatments following a first round or scheme of treatment.

Pharmaceutical compositions comprising neoantigens may be administered to an individual already suffering from cancer. In therapeutic applications, compositions are administered to a patient in an amount sufficient to elicit an effective CTL response to the tumor antigen and to cure or at least partially arrest symptoms and/or complications. An amount adequate to accomplish this is defined as "therapeutically effective dose." Amounts effective for this use can depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 µg to about 50,000 µg of peptide for a 70 kg patient, followed by boosting dosages or from about 1.0 µg to about 10,000 µg of peptide pursuant to a boosting regimen over weeks to months depending upon the patient's response and condition and possibly by measuring specific CTL activity in the patient's blood. It should be kept in mind that the peptide and compositions described herein may generally be employed in serious disease states, that is, life-threatening or potentially life threatening situations, especially when the cancer has metastasized. For therapeutic use, administration should begin as soon as possible after the detection or surgical removal of tumors. This is followed by boosting doses until at least symptoms are substantially abated and for a period thereafter.

The pharmaceutical compositions (e.g., vaccine compositions) for therapeutic treatment are intended for parenteral, topical, nasal, oral or local administration. Preferably, the pharmaceutical compositions are administered parenterally, e.g., intravenously, subcutaneously, intradermally, or intramuscularly. The compositions may be administered at the site of surgical excision to induce a local immune response to the tumor. The invention provides compositions for parenteral administration which comprise a solution of the peptides and vaccine or immunogenic compositions are dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

A liposome suspension containing a peptide may be administered intravenously, locally, topically, etc. in a dose which varies according to, inter alia, the manner of administration, the peptide being delivered, and the stage of the disease being treated. For targeting to the immune cells, a ligand, such as, e.g., antibodies or fragments thereof specific for cell surface determinants of the desired immune system cells, can be incorporated into the liposome.

For solid compositions, conventional or nanoparticle nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more neoantigenic peptides, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant can, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included as desired, as with, e.g., lecithin for intranasal delivery.

The peptides and polypeptides described herein can be readily synthesized chemically utilizing reagents that are free of contaminating bacterial or animal substances (Merrifield R B: Solid phase peptide synthesis. I. The synthesis of a tetrapeptide. J. Am. Chem. Soc. 85:2149-54, 1963).

The peptides and polypeptides described herein can also be expressed by a vector, e.g., a nucleic acid molecule as herein-discussed, e.g., RNA or a DNA plasmid, a viral vector such as a poxvirus, e.g., orthopox virus, avipox virus, or adenovirus, AAV or lentivirus. This approach involves the use of a vector to express nucleotide sequences that encode the peptides. Upon introduction into an acutely or chronically infected host or into a noninfected host, the vector expresses the immunogenic peptide, and thereby elicits a host CTL response.

For therapeutic or immunization purposes, nucleic acids encoding the neoantigenic peptides and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. Generally, a plasmid for a vaccine or immunological composition can comprise DNA encoding an antigen (e.g., one or more neoantigens) operatively linked to regulatory sequences which control expression or expression and secretion of the antigen from a host cell, e.g., a mammalian cell; for instance, from upstream to downstream, DNA for a promoter, such as a mammalian virus promoter (e.g., a CMV promoter such as an hCMV or mCMV promoter, e.g., an early-intermediate promoter, or an SV40 promoter—see documents cited or incorporated herein for useful promoters), DNA for a eukaryotic leader peptide for secretion (e.g., tissue plasminogen activator), DNA for the neoantigen(s), and DNA encoding a terminator (e.g., the 3' UTR transcriptional terminator from the gene encoding Bovine Growth Hormone or bGH polyA). A composition can contain more than one plasmid or vector, whereby each vector contains and expresses a different neoantigen. Mention is also made of Wasmoen U.S. Pat. No. 5,849,303, and Dale U.S. Pat. No. 5,811,104, whose text may be useful. DNA or DNA plasmid formulations can be formulated with or inside cationic lipids; and, as to cationic lipids, as well as adjuvants, mention is also made of Loosmore U.S. Patent Application 2003/0104008. Also, teachings in Audonnet U.S. Pat. Nos. 6,228,846 and 6,159,477 may be relied upon for DNA plasmid teachings that can be employed in constructing and using DNA plasmids that contain and express in vivo.

The nucleic acids can also be delivered complexed to cationic compounds, such as cationic lipids. Lipid-mediated gene delivery methods are described, for instance, in WO1996/18372; WO 1993/24640; Mannino & Gould-Fogerite, BioTechniques 6(7): 682-691 (1988); U.S. Pat. No. 5,279,833; WO 1991/06309; and Feigner et al., Proc. Natl. Acad. Sci. USA 84: 7413-7414 (1987).

RNA encoding the peptide of interest (e.g., mRNA) can also be used for delivery (see, e.g., Kiken et al, 2011; Su et al, 2011; see also U.S. Pat. No. 8,278,036; Halabi et al. J Clin Oncol (2003) 21:1232-1237; Petsch et al, Nature Biotechnology 2012 Dec. 7; 30(12):1210-6).

Information concerning poxviruses that may be used in the practice of the invention, such as Chordopoxvirinae subfamily poxviruses (poxviruses of vertebrates), for instance, orthopoxviruses and avipoxviruses, e.g., vaccinia virus (e.g., Wyeth Strain, WR Strain (e.g., ATCC® VR-1354), Copenhagen Strain, NYVAC, NYVAC.1, NYVAC.2, MVA, MVA-BN), canarypox virus (e.g., Wheatley C93 Strain, ALVAC), fowlpox virus (e.g., FP9 Strain, Webster Strain, TROVAC), dovepox, pigeonpox, quailpox, and raccoon pox, inter alia, synthetic or non-naturally occurring recombinants thereof, uses thereof, and methods for making and using such recombinants may be found in scientific and patent literature, such as:

U.S. Pat. Nos. 4,603,112, 4,769,330, 5,110,587, 5,174,993, 5,364,773, 5,762,938, 5,494,807, 5,766,597, 7,767,449, 6,780,407, 6,537,594, 6,265,189, 6,214,353, 6,130,066, 6,004,777, 5,990,091, 5,942,235, 5,833,975, 5,766,597, 5,756,101, 7,045,313, 6,780,417, 8,470,598, 8,372,622, 8,268,329, 8,268,325, 8,236,560, 8,163,293, 7,964,398, 7,964,396, 7,964,395, 7,939,086, 7,923,017, 7,897,156, 7,892,533, 7,628,980, 7,459,270, 7,445,924, 7,384,644, 7,335,364, 7,189,536, 7,097,842, 6,913,752, 6,761,893, 6,682,743, 5,770,212, 5,766,882, and 5,989,562, and Panicali, D. Proc. Natl. Acad. Sci. 1982; 79; 4927-493, Panicali D. Proc. Natl. Acad. Sci. 1983; 80(17): 5364-8, Mackett, M. Proc. Natl. Acad. Sci. 1982; 79: 7415-7419, Smith G L. Proc. Natl. Acad. Sci. 1983; 80(23): 7155-9, Smith G L. Nature 1983; 302: 490-5, Sullivan V J. Gen. Vir. 1987; 68: 2587-98, Perkus M Journal of Leukocyte Biology 1995; 58:1-13, Yilma T D. Vaccine 1989; 7: 484-485, Brochier B. Nature 1991; 354: 520-22, Wiktor, T J. Proc. Natl Acd. Sci. 1984; 81: 7194-8, Rupprecht, C E. Proc. Natl Acd. Sci. 1986; 83: 7947-50, Poulet, H Vaccine 2007; 25(July): 5606-12, Weyer J. Vaccine 2009; 27(November): 7198-201, Buller, R M Nature 1985; 317(6040): 813-5, Buller R M. J. Virol. 1988; 62(3):866-74, Flexner, C. Nature 1987; 330(6145): 259-62, Shida, H. J. Virol. 1988; 62(12): 4474-80, Kotwal, G J. J. Virol. 1989; 63(2): 600-6, Child, S J. Virology 1990; 174(2): 625-9, Mayr A. Zentralbl Bakteriol 1978; 167(5,6): 375-9, Antoine G. Virology. 1998; 244(2): 365-96, Wyatt, L S. Virology 1998; 251(2): 334-42, Sancho, M C. J. Virol. 2002; 76(16); 8313-34, Gallego-Gomez, J C. J. Virol. 2003; 77(19); 10606-22), Goebel S J. Virology 1990; (a,b) 179: 247-66, Tartaglia, J. Virol. 1992; 188(1): 217-32, Najera J L. J. Virol. 2006; 80(12): 6033-47, Najera, J L. J. Virol. 2006; 80: 6033-6047, Gomez, C E. J. Gen. Virol. 2007; 88: 2473-78, Mooij, P. Jour. Of Virol. 2008; 82: 2975-2988, Gomez, C E. Curr. Gene Ther. 2011; 11: 189-217, Cox, W. Virology 1993; 195: 845-50, Perkus, M. Jour. Of Leukocyte Biology 1995; 58: 1-13, Blanchard T J. J Gen Virology 1998; 79(5): 1159-67, Amara R. Science 2001; 292: 69-74, Hel, Z., J. Immunol. 2001; 167: 7180-9, Gherardi M M. J. Virol. 2003; 77: 7048-57, Didierlaurent, A. Vaccine 2004; 22: 3395-3403, Bissht H. Proc. Nat. Aca. Sci. 2004; 101: 6641-46, McCurdy L H. Clin. Inf. Dis 2004; 38: 1749-53, Earl P L. Nature 2004; 428: 182-85, Chen Z. J. Virol. 2005; 79: 2678-2688, Najera J L. J. Virol. 2006; 80(12): 6033-47, Nam J H. Acta. Virol. 2007; 51: 125-30, Antonis A F. Vaccine 2007; 25: 4818-4827, B Weyer J. Vaccine 2007; 25: 4213-22, Ferrier-Rembert A. Vaccine 2008; 26(14): 1794-804, Corbett M. Proc. Natl. Acad. Sci. 2008; 105(6): 2046-51, Kaufman H L., J. Clin. Oncol. 2004; 22: 2122-32, Amato, R J. Clin. Cancer Res. 2008; 14(22): 7504-10, Dreicer R. Invest New Drugs 2009; 27(4): 379-86, Kantoff P W. J. Clin. Oncol. 2010, 28, 1099-1105, Amato R J. J. Clin. Can. Res. 2010; 16(22): 5539-47, Kim, D W. Hum. Vaccine. 2010; 6: 784-791, Oudard, S. Cancer Immunol. Immunother. 2011; 60: 261-71, Wyatt, L S. Aids Res. Hum. Retroviruses. 2004; 20: 645-53, Gomez, C E. Virus Research 2004; 105: 11-22, Webster, D P. Proc. Natl. Acad. Sci. 2005; 102: 4836-4, Huang, X. Vaccine 2007; 25: 8874-84, Gomez, C E. Vaccine 2007a; 25: 2863-85, Esteban M. Hum. Vaccine 2009; 5: 867-871, Gomez, C E. Curr. Gene therapy 2008; 8(2): 97-120, Whelan, K T. Plos one 2009; 4(6): 5934, Scriba, T J. Eur. Jour. Immuno. 2010; 40(1): 279-90, Corbett, M. Proc. Natl. Acad. Sci. 2008; 105: 2046-2051, Midgley, C M. J. Gen. Virol. 2008; 89: 2992-97, Von Krempelhuber, A. Vaccine 2010; 28: 1209-16, Perreau, M. J. Of Virol. 2011; October: 9854-62, Pantaleo, G. Curr Opin HIV-AIDS. 2010; 5: 391-396, each of which is incorporated herein by reference.

As to adenovirus vectors useful in the practice of the invention, mention is made of U.S. Pat. No. 6,955,808. The adenovirus vector used can be selected from the group consisting of the Ad5, Ad35, Ad11, C6, and C7 vectors. The sequence of the Adenovirus 5 ("Ad5") genome has been published. (Chroboczek, J., Bieber, F., and Jacrot, B. (1992) The Sequence of the Genome of Adenovirus Type 5 and Its Comparison with the Genome of Adenovirus Type 2, Virology 186, 280-285; the contents if which is hereby incorporated by reference). Ad35 vectors are described in U.S. Pat. Nos. 6,974,695, 6,913,922, and 6,869,794. Ad11 vectors are described in U.S. Pat. No. 6,913,922. C6 adenovirus vectors are described in U.S. Pat. Nos. 6,780,407; 6,537,594; 6,309,647; 6,265,189; 6,156,567; 6,090,393; 5,942,235 and 5,833,975. C7 vectors are described in U.S. Pat. No. 6,277,558. Adenovirus vectors that are E1-defective or deleted, E3-defective or deleted, and/or E4-defective or deleted may also be used. Certain adenoviruses having mutations in the E1 region have improved safety margin because E1-defective adenovirus mutants are replication-defective in non-permissive cells, or, at the very least, are highly attenuated. Adenoviruses having mutations in the E3 region may have enhanced the immunogenicity by disrupting the mechanism whereby adenovirus down-regulates MHC class I molecules. Adenoviruses having E4 mutations may have reduced immunogenicity of the adenovirus vector because of suppression of late gene expression. Such vectors may be particularly useful when repeated re-vaccination utilizing the same vector is desired. Adenovirus vectors that are deleted or mutated in E1, E3, E4, E1 and E3, and E1 and E4 can be used in accordance with the present invention. Furthermore, "gutless" adenovirus vectors, in which all viral genes are deleted, can also be used in accordance with the present invention. Such vectors require a helper virus for their replication and require a special human 293 cell line expressing both E1a and Cre, a condition that does not exist in natural environment. Such "gutless" vectors are non-immunogenic and thus the vectors may be inoculated multiple times for re-vaccination. The "gutless" adenovirus vectors can be used for insertion of heterologous inserts/genes such as the transgenes of the present invention, and can even be used for co-delivery of a large number of heterologous inserts/genes.

As to lentivirus vector systems useful in the practice of the invention, mention is made of U.S. Pat. Nos. 6,428,953, 6,165,782, 6,013,516, 5,994,136, 6,312,682, and 7,198,784, and documents cited therein.

With regard to AAV vectors useful in the practice of the invention, mention is made of U.S. Pat. Nos. 5,658,785, 7,115,391, 7,172,893, 6,953,690, 6,936,466, 6,924,128, 6,893,865, 6,793,926, 6,537,540, 6,475,769 and 6,258,595, and documents cited therein.

Another vector is BCG (Bacille Calmette Guerin). BCG vectors are described in Stover et al. (Nature 351:456-460 (1991)). A wide variety of other vectors useful for therapeutic administration or immunization of the peptides of the invention, e.g., *Salmonella typhi* vectors and the like, is apparent to those skilled in the art from the description herein.

Vectors can be administered so as to have in vivo expression and response akin to doses and/or responses elicited by antigen administration A preferred means of administering nucleic acids encoding the peptide of the invention uses minigene constructs encoding multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes may be improved by including synthetic (e.g. poly-alanine) or naturally-occurring flanking sequences adjacent to the CTL epitopes.

The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Standard regulatory sequences well known to those of skill in the art are included in the vector to ensure expression in the target cells. Several vector elements are required: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences can also be considered for increasing minigene expression. It has recently been proposed that immuno stimulatory sequences (ISSs or CpGs) play a role in the immunogenicity of DNA' vaccines. These sequences could be included in the vector, outside the minigene coding sequence, if found to enhance immunogenicity.

In some embodiments, a bicistronic expression vector, to allow production of the minigene-encoded epitopes and a second protein included to enhance or decrease immunogenicity can be used. Examples of proteins or polypeptides that could beneficially enhance the immune response if co-expressed include cytokines (e.g., IL2, IL12, GM-CSF), cytokine-inducing molecules (e.g. LeIF) or costimulatory molecules. Helper (HTL) epitopes could be joined to intracellular targeting signals and expressed separately from the CTL epitopes. This would allow direction of the HTL epitopes to a cell compartment different than the CTL epitopes. If required, this could facilitate more efficient entry of HTL epitopes into the MHC class II pathway, thereby improving CTL induction. In contrast to CTL induction, specifically decreasing the immune response by co-expression of immunosuppressive molecules (e.g. TGF-β) may be beneficial in certain diseases.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

Purified plasmid DNA can be prepared for injection using a variety of formulations. The simplest of these is reconstitution of lyophilized DNA in sterile phosphate-buffer saline (PBS). A variety of methods have been described, and new techniques may become available. As noted herein, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Target cell sensitization can be used as a functional assay for expression and MHC class I presentation of minigene-encoded CTL epitopes. The plasmid DNA is introduced into a mammalian cell line that is suitable as a target for standard CTL chromium release assays. The transfection method used is dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 labeled and used as target cells for epitope-specific CTL lines. Cytolysis, detected by 51 Cr release, indicates production of MHC presentation of mini gene-encoded CTL epitopes.

In vivo immunogenicity is a second approach for functional testing of minigene DNA formulations. Transgenic mice expressing appropriate human MHC molecules are immunized with the DNA product. The dose and route of administration are formulation dependent (e.g. IM for DNA in PBS, IP for lipid-complexed DNA). Twenty-one days after immunization, splenocytes are harvested and restimulated for 1 week in the presence of peptides encoding each epitope being tested. These effector cells (CTLs) are assayed for cytolysis of peptide-loaded, chromium-51 labeled target cells using standard techniques. Lysis of target cells sensitized by MHC loading of peptides corresponding to minigene-encoded epitopes demonstrates DNA vaccine function for in vivo induction of CTLs.

Peptides may be used to elicit CTL ex vivo, as well. The resulting CTL, can be used to treat chronic tumors in patients in need thereof that do not respond to other conventional forms of therapy, or does not respond to a peptide vaccine approach of therapy. Ex vivo CTL responses to a particular tumor antigen are induced by incubating in tissue culture the patient's CTL precursor cells (CTLp) together with a source of antigen-presenting cells (APC) and the appropriate peptide. After an appropriate incubation time (typically 1-4 weeks), in which the CTLp are activated and mature and expand into effector CTL, the cells are infused back into the patient, where they destroy their specific target cell (i.e., a tumor cell). In order to optimize the in vitro conditions for the generation of specific cytotoxic T cells, the culture of stimulator cells are maintained in an appropriate serum-free medium.

Prior to incubation of the stimulator cells with the cells to be activated, e.g., precursor CD8+ cells, an amount of antigenic peptide is added to the stimulator cell culture, of sufficient quantity to become loaded onto the human Class I molecules to be expressed on the surface of the stimulator cells. In the present invention, a sufficient amount of peptide is an amount that allows about 200, and preferably 200 or more, human Class I MHC molecules loaded with peptide to be expressed on the surface of each stimulator cell. Preferably, the stimulator cells are incubated with >2 μg/ml peptide. For example, the stimulator cells are incubates with >3, 4, 5, 10, 15, or more μg/ml peptide.

Resting or precursor CD8+ cells are then incubated in culture with the appropriate stimulator cells for a time period sufficient to activate the CD8+ cells. Preferably, the CD8+ cells are activated in an antigen-specific manner. The ratio of resting or precursor CD8+ (effector) cells to stimulator cells may vary from individual to individual and may further depend upon variables such as the amenability of an individual's lymphocytes to culturing conditions and the nature and severity of the disease condition or other condition for which the within-described treatment modality is used. Preferably, however, the lymphocyte:stimulator cell ratio is in the range of about 30:1 to 300:1. The effector/stimulator culture may be maintained for as long a time as is necessary to stimulate a therapeutically useable or effective number of CD8+ cells.

The induction of CTL in vitro requires the specific recognition of peptides that are bound to allele specific MHC class I molecules on APC. The number of specific MHC/peptide complexes per APC is crucial for the stimulation of CTL, particularly in primary immune responses. While small amounts of peptide/MHC complexes per cell are sufficient to render a cell susceptible to lysis by CTL, or to stimulate a secondary CTL response, the successful activation of a CTL precursor (pCTL) during primary response requires a significantly higher number of MHC/peptide complexes. Peptide loading of empty major histocompatability complex molecules on cells allows the induction of primary cytotoxic T lymphocyte responses.

Since mutant cell lines do not exist for every human MHC allele, it is advantageous to use a technique to remove endogenous MHC-associated peptides from the surface of APC, followed by loading the resulting empty MHC molecules with the immunogenic peptides of interest. The use of non-transformed (non-tumorigenic), noninfected cells, and preferably, autologous cells of patients as APC is desirable for the design of CTL induction protocols directed towards development of ex vivo CTL therapies. This application discloses methods for stripping the endogenous MHC-associated peptides from the surface of APC followed by the loading of desired peptides.

A stable MHC class I molecule is a trimeric complex formed of the following elements: 1) a peptide usually of 8-10 residues, 2) a transmembrane heavy polymorphic protein chain which bears the peptide-binding site in its a1 and a2 domains, and 3) a non-covalently associated non-polymorphic light chain, p2microglobuiin. Removing the bound peptides and/or dissociating the p2microglobulin from the complex renders the MHC class I molecules nonfunctional and unstable, resulting in rapid degradation. All MHC class I molecules isolated from PBMCs have endogenous peptides bound to them. Therefore, the first step is to remove all endogenous peptides bound to MHC class I molecules on the APC without causing their degradation before exogenous peptides can be added to them.

Two possible ways to free up MHC class I molecules of bound peptides include lowering the culture temperature from 37° C. to 26° C. overnight to destablize p2microglobulin and stripping the endogenous peptides from the cell using a mild acid treatment. The methods release previously bound peptides into the extracellular environment allowing new exogenous peptides to bind to the empty class I molecules. The cold-temperature incubation method enables exogenous peptides to bind efficiently to the MHC complex, but requires an overnight incubation at 26° C. which may slow the cell's metabolic rate. It is also likely that cells not actively synthesizing MHC molecules (e.g., resting PBMC) would not produce high amounts of empty surface MHC molecules by the cold temperature procedure.

Harsh acid stripping involves extraction of the peptides with trifluoroacetic acid, pH 2, or acid denaturation of the immunoaffinity purified class I-peptide complexes. These methods are not feasible for CTL induction, since it is important to remove the endogenous peptides while preserving APC viability and an optimal metabolic state which is critical for antigen presentation. Mild acid solutions of pH 3 such as glycine or citrate-phosphate buffers have been used to identify endogenous peptides and to identify tumor associated T cell epitopes. The treatment is especially effective, in that only the MHC class I molecules are destabilized (and associated peptides released), while other surface antigens remain intact, including MHC class II molecules. Most importantly, treatment of cells with the mild acid solutions does not affect the cell's viability or metabolic state. The mild acid treatment is rapid since the stripping of the endogenous peptides occurs in two minutes at 4° C. and the APC is ready to perform its function after the appropriate peptides are loaded. The technique is utilized herein to make peptide-specific APCs for the generation of primary antigen-specific CTL. The resulting APC are efficient in inducing peptide-specific CD8+ CTL.

Activated CD8+ cells may be effectively separated from the stimulator cells using one of a variety of known methods. For example, monoclonal antibodies specific for the stimulator cells, for the peptides loaded onto the stimulator cells, or for the CD8+ cells (or a segment thereof) may be utilized to bind their appropriate complementary ligand. Antibody-tagged molecules may then be extracted from the stimulator-effector cell admixture via appropriate means, e.g., via well-known immunoprecipitation or immunoassay methods.

Effective, cytotoxic amounts of the activated CD8+ cells can vary between in vitro and in vivo uses, as well as with the amount and type of cells that are the ultimate target of these killer cells. The amount can also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$, and even more preferably, about $1 \times 10^9$ to about $1 \times 10^{10}$ activated CD8+ cells are utilized for adult humans, compared to about $5 \times 10^6$-$5 \times 10^7$ cells used in mice.

Preferably, as discussed herein, the activated CD8+ cells are harvested from the cell culture prior to administration of the CD8+ cells to the individual being treated. It is important to note, however, that unlike other present and proposed treatment modalities, the present method uses a cell culture system that is not tumorigenic. Therefore, if complete separation of stimulator cells and activated CD8+ cells are not achieved, there is no inherent danger known to be associated with the administration of a small number of stimulator cells, whereas administration of mammalian tumor-promoting cells may be extremely hazardous.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8+ cells via intravenous infusion is appropriate.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Wei, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments are discussed in the sections that follow.

Additional Therapies

The immunotherapeutic agents described herein can also be administered in further combination with an additional therapeutic agent. In certain embodiments, the additional agents can be, but are not limited to, chemotherapeutic agents and anti-angiogenesis agents.

The immunotherapeutic agent can be administered before, during, or after administration of the additional agent. In embodiments, the immunotherapeutic agent is administered before the first administration of the additional agent. In other embodiments, the immunotherapeutic agent is administered after the first administration of the additional therapeutic agent (e.g., 1, 2, 3, 4, 5, 6, 7, 8, 9, 10, 11, 12, 13, 14 days or more). In embodiments, the immunotherapeutic agent is administered simultaneously with the first administration of the additional therapeutic agent.

The additional therapeutic agent is for example, a chemotherapeutic or biotherapeutic agent, or radiation. Any suitable therapeutic treatment for a particular cancer may be administered. Examples of chemotherapeutic and biotherapeutic agents include, but are not limited to, an angiogenesis inhibitor, such ashydroxy angiostatin K1-3, DL-α-Difluoromethyl-ornithine, endostatin, fumagillin, genistein, minocycline, staurosporine, and thalidomide; a DNA intercaltor/cross-linker, such as Bleomycin, Carboplatin, Carmustine, Chlorambucil, Cyclophosphamide, cis-Diammineplatinum (II) dichloride (Cisplatin), Melphalan, Mitoxantrone, and Oxaliplatin; a DNA synthesis inhibitor, such as (±)-Amethopterin (Methotrexate), 3-Amino-1,2,4-benzotriazine 1,4-dioxide, Aminopterin, Cytosine β-D-arabinofuranoside, 5-Fluoro-5'-deoxyuridine, 5-Fluorouracil, Ganciclovir, Hydroxyurea, and Mitomycin C; a DNA-RNA transcription regulator, such as Actinomycin D, Daunorubicin, Doxorubicin, Homoharringtonine, and Idarubicin; an enzyme inhibitor, such as S(+)-Camptothecin, Curcumin, (−)-Deguelin, 5,6-Dichlorobenzimidazole 1-β-D-ribofuranoside, Etoposide, Formestane, Fostriecin, Hispidin, 2-Imino-1-imidazoli-dineacetic acid (Cyclocreatine), Mevinolin, Trichostatin A, Tyrphostin AG 34, and Tyrphostin AG 879; a gene regulator, such as 5-Aza-2'-deoxycytidine, 5-Azacytidine, Cholecalciferol (Vitamin D3), 4-Hydroxytamoxifen, Melatonin, Mifepristone, Raloxifene, all trans-Retinal (Vitamin A aldehyde), Retinoic acid all trans (Vitamin A acid), 9-cis-Retinoic Acid, 13-cis-Retinoic acid, Retinol (Vitamin A), Tamoxifen, and Troglitazone; a microtubule inhibitor, such as Colchicine, docetaxel, Dolastatin 15, Nocodazole, Paclitaxel, Podophyllotoxin, Rhizoxin, Vinblastine, Vincristine, Vindesine, and Vinorelbine (Navelbine); and an unclassified therapeutic agent, such as 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-α, Rapamycin, Sex hormone-binding globulin, Thapsigargin, and Urinary trypsin inhibitor fragment (Bikunin). The therapeutic agent may be altretamine, amifostine, asparaginase, capecitabine, cladribine, cisapride, cytarabine, dacarbazine (DTIC), dactinomycin, dronabinol, epoetin alpha, filgrastim, fludarabine, gemcitabine, granisetron, ifosfamide, irinotecan, lansoprazole, levamisole, leucovorin, megestrol, mesna, metoclopramide, mitotane, omeprazole, ondansetron, pilocarpine, prochloroperazine, or topotecan hydrochloride. The therapeutic agent may be a monoclonal antibody such as rituximab (Rituxan®), alemtuzumab (Campath®), Bevacizumab (Avastin®), Cetuximab (Erbitux®), panitumumab (Vectibix®), and trastuzumab (Herceptin®), Vemurafenib (Zelboraf®) imatinib mesylate (Gleevec®), erlotinib (Tarceva®), gefitinib (Iressa®), Vismodegib (Erivedge™), 90Y-ibritumomab tiuxetan, 131I-tositumomab, ado-trastuzumab emtansine, lapatinib (Tykerb®), pertuzumab (Perjeta™), ado-trastuzumab emtansine (Kadcyla™), regorafenib (Stivarga®), sunitinib (Sutent®), Denosumab (Xgeva®), sorafenib (Nexavar®), pazopanib (Votrient®), axitinib (Inlyta®), dasatinib (Sprycel®), nilotinib (Tasigna®), bosutinib (Bosulif®), ofatumumab (Arzerra®), obinutuzumab (Gazyva™), ibrutinib (Imbruvica™), idelalisib (Zydelig®), crizotinib (Xalkori®), erlotinib (Tarceva®), afatinib dimaleate (Gilotrif®), ceritinib (LDK378/Zykadia), Tositumomab and 131I-tositumomab (Bexxar®), ibritumomab tiuxetan (Zevalin®), brentuximab vedotin (Adcetris®), bortezomib (Velcade®), siltuximab (Sylvant™), trametinib (Mekinist®), dabrafenib (Tafinlar®), pembrolizumab (Keytruda®), carfilzomib (Kyprolis®), Ramucirumab (Cyramza™), Cabozantinib (Cometriq™), vandetanib (Caprelsa®), Optionally, the therapeutic agent is a neoantigen. The therapeutic agent may be a cytokine such as interferons (INFs), interleukins (ILs), or hematopoietic growth factors. The therapeutic agent may be TNF-α, IL-2, Aldesleukin, IL-2, Erythropoietin, Granulocyte-macrophage colony-stimulating factor (GM-CSF) or granulocyte colony-stimulating factor. The therapeutic agent may be a targeted therapy such as toremifene (Fareston®), fulvestrant (Faslodex®), anastrozole (Arimidex®), exemestane (Aromasin®), letrozole (Femara®), ziv-aflibercept (Zaltrap®), Alitretinoin (Panretin®), temsirolimus (Torisel®), Tretinoin (Vesanoid®), denileukin diftitox (Ontak®), vorinostat (Zolinza®), romidepsin (Istodax®), bexarotene (Targretin®), pralatrexate (Folotyn®), lenaliomide (Revlimid®), belinostat (Beleodaq™), lenaliomide (Revlimid®), pomalidomide (Pomalyst®), Cabazitaxel (Jevtana®), enzalutamide (Xtandi®), abiraterone acetate (Zytiga®), radium 223 chloride (Xofigo®), or everolimus (Afinitor®). Additionally, the therapeutic agent may be an epigenetic targeted drug such as HDAC inhibitors, kinase inhibitors, DNA methyltransferase inhibitors, histone demethylase inhibitors, or histone methylation inhibitors. The epigenetic drugs may be Azacitidine (Vidaza), Decitabine (Dacogen), Vorinostat (Zolinza), Romidepsin (Istodax), or Ruxolitinib (Jakafi). For prostate cancer treatment, a preferred chemotherapeutic agent with which anti-CTLA-4 can be combined is paclitaxel (TAXOL).

In certain embodiments, the one or more additional agents are synergistic in that they increase immunogenicity after treatment. In one embodiment the additional agent allows for lower toxicity and/or lower discomfort due to lower doses of the additional therapeutic agents or any components of the immunotherapeutic agent described herein. In another embodiment the additional agent results in longer lifespan due to increased effectiveness of the immunotherapeutic agent described herein. Chemotherapeutic treatments that enhance the immunological response in a patient have been reviewed (Zitvogel et al., Immunological aspects of cancer chemotherapy. Nat Rev Immunol. 2008 January; 8(1):59-73). Additionally, chemotherapeutic agents can be administered safely with immunotherapy without inhibiting vaccine specific T-cell responses (Perez et al., A new era in anticancer peptide vaccines. Cancer May 2010). In one embodiment the additional agent is administered to increase the efficacy of the immunotherapeutic agent described herein. In one embodiment the additional agent is a chemotherapy treatment. In one embodiment low doses of chemotherapy potentiate delayed-type hypersensitivity (DTH) responses. In one embodiment the chemotherapy agent targets regulatory T-cells. In one embodiment cyclophosphamide is the therapeutic agent. In one embodiment cyclophosphamide is administered prior to vaccination. In one embodiment cyclophosphamide is administered as a single dose before vaccination (Walter et al., Multipeptide immune response to cancer vaccine IMA901 after single-dose cyclophosphamide associates with longer patient survival. Nature Medicine; 18:8 2012). In another embodiment, cyclophosphamide is administered according to a metronomic program, where a daily dose is administered for one month (Ghiringhelli et al., Metronomic cyclophosphamide regimen selectively depletes CD4+CD25+ regulatory T cells and restores T and NK effector functions in end stage cancer patients. Cancer Immunol Immunother 2007 56:641-648). In another embodiment taxanes are administered before vaccination to enhance T-cell and NK-cell functions (Zitvogel et al., 2008). In another embodiment a low dose of a chemotherapeutic agent is administered with the immunotherapeutic agent described herein. In one embodiment the chemotherapeutic agent is estramustine. In one embodiment the cancer is hormone resistant prostate cancer. A ≥50% decrease in serum prostate specific antigen (PSA) was seen in 8.7% of advanced hormone refractory prostate cancer patients by personalized vaccination alone, whereas such a decrease was seen in 54% of patients when the personalized vaccination was combined with a low dose of estramustine (Itoh et al., Personalized peptide vaccines: A new immunological modality for cancer. Cancer Sci 2006; 97: 970-976). In another embodiment glucocorticoids are not administered with or before the immunotherapeutic agent described herein (Zitvogel et al., 2008). In another embodiment glucocorticoids are administered after the immunotherapeutic agent described herein. In another embodiment Gemcitabine is administered before, simultaneously, or after the immunotherapeutic agent described herein to enhance the frequency of tumor specific CTL precursors (Zitvogel et al., 2008). In another embodiment 5-fluorouracil is administered with the immunotherapeutic agent described herein as synergistic effects were seen with a peptide based vaccine (Zitvogel et al., 2008). In another embodiment an inhibitor of Braf, such as Vemurafenib, is used as an additional agent. Braf inhibition has been shown to be associated with an increase in melanoma antigen expression and T-cell infiltrate and a decrease in immunosuppressive cytokines in tumors of treated patients (Frederick et al., BRAF inhibition is associated with enhanced melanoma antigen expression and a more favorable tumor microenvironment in patients with metastatic melanoma. Clin Cancer Res. 2013; 19:1225-1231). In another embodiment an inhibitor of tyrosine kinases is used as an additional agent. In one embodiment the tyrosine kinase inhibitor is used before vaccination with the combination therapy described herein. In one embodiment the tyrosine kinase inhibitor is used simultaneously with the combination therapy described herein. In another embodiment the tyrosine kinase inhibitor is used to create a more immune permissive environment. In another embodiment the tyrosine kinase inhibitor is sunitinib or imatinib mesylate. It has previously been shown that favorable outcomes could be achieved with sequential administration of continuous daily dosing of sunitinib and recombinant vaccine (Farsaci et al., Consequence of dose scheduling of sunitinib on host immune response elements and vaccine combination therapy. Int J Cancer; 130: 1948-1959). Sunitinib has also been shown to reverse type-1 immune suppression using a daily dose of 50 mg/day (Finke et al., Sunitinib Reverses Type-1 Immune Suppression and Decreases T-Regulatory Cells in Renal Cell Carcinoma Patients. Clin Cancer Res 2008; 14(20)). In another embodiment targeted therapies are administered in combination with the combination therapy described herein. Doses of targeted therapies has been described previously (Alvarez, Present and future evolution of advanced breast cancer therapy. Breast Cancer Research 2010, 12(Suppl 2):S1). In another embodiment temozolomide is administered with the immunotherapeutic agent described herein. In one embodiment temozolomide is administered at 200 mg/day for 5 days every fourth week of a combination therapy with the immunotherapeutic agent described herein. Results of a similar strategy have been shown to have low toxicity (Kyte et al., Telomerase Peptide Vaccination Combined with Temozolomide: A Clinical Trial in Stage IV Melanoma Patients. Clin Cancer Res; 17(13) 2011). In another embodiment the immunotherapeutic agent is administered with an additional therapeutic agent that results in lymphopenia. In one embodiment the additional agent is temozolomide. An immune response can still be induced under these conditions (Sampson et al., Greater chemotherapy-induced lymphopenia enhances tumor-specific immune responses that eliminate EGFRvIII-expressing tumor cells in patients with glioblastoma. Neuro-Oncology 13(3):324-333, 2011).

Administering an Immunotherapeutic Agent Consistent with Standard of Care

In another aspect, the immunotherapeutic agent described herein is administered in relation to and within the standard of care for the cancer being treated for a patient in need thereof. The immunotherapeutic agent can be effectively administered even within the standard of care that includes surgery, radiation, or chemotherapy. The standards of care for the most common cancers can be found on the website of National Cancer Institute (http://www.cancer.gov/cancer-topics). The standard of care is the current treatment that is accepted by medical experts as a proper treatment for a certain type of disease and that is widely used by healthcare professionals. Standard or care is also called best practice, standard medical care, and standard therapy. Standards of Care for cancer generally include surgery, lymph node removal, radiation, chemotherapy, targeted therapies and antibodies targeting the tumor. The immunotherapy described herein can be incorporated within the standard of care. The immunotherapeutic agent described herein may also be administered where the standard of care has changed due to advances in medicine.

Incorporation of the immunotherapeutic agent described herein may depend on a treatment step in the standard of care that can lead to activation of the immune system. Treatment steps that can activate and function synergistically with the immunotherapeutic agent have been described herein.

Incorporation of the immunotherapeutic agent described herein may depend on a treatment step in the standard of care that causes the immune system to be suppressed. Such treatment steps may include irradiation, high doses of alkylating agents and/or methotrexate, steroids such as glucosteroids, surgery, such as to remove the lymph nodes, imatinib mesylate, high doses of TNF, and taxanes (Zitvogel et al., 2008). The immunotherapeutic agent may be administered before such steps or may be administered after.

In one embodiment the immunotherapeutic agent may be administered after bone marrow transplants and peripheral blood stem cell transplantation. Bone marrow transplantation and peripheral blood stem cell transplantation are procedures that restore stem cells that were destroyed by high doses of chemotherapy and/or radiation therapy. After being treated with high-dose anticancer drugs and/or radiation, the patient receives harvested stem cells, which travel to the bone marrow and begin to produce new blood cells. A "mini-transplant" uses lower, less toxic doses of chemotherapy and/or radiation to prepare the patient for transplant. A "tandem transplant" involves two sequential courses of high-dose chemotherapy and stem cell transplant. In autologous transplants, patients receive their own stem cells. In syngeneic transplants, patients receive stem cells from their identical twin. In allogeneic transplants, patients receive stem cells from their brother, sister, or parent. A person who is not related to the patient (an unrelated donor) also may be used. In some types of leukemia, the graft-versus-tumor (GVT) effect that occurs after allogeneic BMT and PBSCT is crucial to the effectiveness of the treatment. GVT occurs when white blood cells from the donor (the graft) identify the cancer cells that remain in the patient's body after the chemotherapy and/or radiation therapy (the tumor) as foreign and attack them. Immunotherapy as described herein can take advantage of this by vaccinating after a transplant. Additionally, the transferred cells may be presented with neoantigens as described herein before transplantation.

In one embodiment the immunotherapeutic agent is administered to a patient in need thereof with a cancer that requires surgery. In one embodiment the immunotherapeutic agent described herein is administered to a patient in need thereof in a cancer where the standard of care is primarily surgery followed by treatment to remove possible micrometastases, such as breast cancer. Breast cancer is commonly treated by various combinations of surgery, radiation therapy, chemotherapy, and hormone therapy based on the stage and grade of the cancer. Adjuvant therapy for breast cancer is any treatment given after primary therapy to increase the chance of long-term survival. Neoadjuvant therapy is treatment given before primary therapy. Adjuvant therapy for breast cancer is any treatment given after primary therapy to increase the chance of long-term disease-free survival. Primary therapy is the main treatment used to reduce or eliminate the cancer. Primary therapy for breast cancer usually includes surgery, a mastectomy (removal of the breast) or a lumpectomy (surgery to remove the tumor and a small amount of normal tissue around it; a type of breast-conserving surgery). During either type of surgery, one or more nearby lymph nodes are also removed to see if cancer cells have spread to the lymphatic system. When a woman has breast-conserving surgery, primary therapy almost always includes radiation therapy. Even in early-stage breast cancer, cells may break away from the primary tumor and spread to other parts of the body (metastasize). Therefore, doctors give adjuvant therapy to kill any cancer cells that may have spread, even if they cannot be detected by imaging or laboratory tests.

In one embodiment the immunotherapeutic agent is administered consistent with the standard of care for Ductal carcinoma in situ (DCIS). The standard of care for this breast cancer type is:
1. Breast-conserving surgery and radiation therapy with or without tamoxifen.
2. Total mastectomy with or without tamoxifen.
3. Breast-conserving surgery without radiation therapy.

The immunotherapeutic agent may be administered before breast conserving surgery or total mastectomy to shrink the tumor before surgery. In another embodiment the immunotherapeutic agent can be administered as an adjuvant therapy to remove any remaining cancer cells.

In another embodiment patients diagnosed with stage I, II, IIIA, and Operable IIIC breast cancer are treated with the immunotherapeutic agent as described herein. The standard of care for this breast cancer type is:
1. Local-regional treatment:
    Breast-conserving therapy (lumpectomy, breast radiation, and surgical staging of the axilla).
    Modified radical mastectomy (removal of the entire breast with level I-II axillary dissection) with or without breast reconstruction.
    Sentinel node biopsy.
2. Adjuvant radiation therapy postmastectomy in axillary node-positive tumors:
    For one to three nodes: unclear role for regional radiation (infra/supraclavicular nodes, internal mammary nodes, axillary nodes, and chest wall).
    For more than four nodes or extranodal involvement: regional radiation is advised.
3. Adjuvant systemic therapy In one embodiment the immunotherapeutic agent is administered as a neoadjuvant therapy to shrink the tumor. In another embodiment the immunotherapeutic agent is administered as an adjuvant systemic therapy.

In another embodiment patients diagnosed with inoperable stage IIIB or IIIC or inflammatory breast cancer are treated with the immunotherapeutic agent as described herein. The standard of care for this breast cancer type is:
1. Multimodality therapy delivered with curative intent is the standard of care for patients with clinical stage IIIB disease.
2. Initial surgery is generally limited to biopsy to permit the determination of histology, estrogen-receptor (ER) and progesterone-receptor (PR) levels, and human epidermal growth factor receptor 2 (HER2/neu) overexpression. Initial treatment with anthracycline-based chemotherapy and/or taxane-based therapy is standard. For patients who respond to neoadjuvant chemotherapy, local therapy may consist of total mastectomy with axillary lymph node dissection followed by post-operative radiation therapy to the chest wall and regional lymphatics. Breast-conserving therapy can be considered in patients with a good partial or complete response to neoadjuvant chemotherapy. Subsequent systemic therapy may consist of further chemotherapy. Hormone therapy should be administered to patients whose tumors are ER-positive or unknown. All patients should be considered candidates for clinical trials to evaluate the most appropriate fashion in which to administer the various components of multimodality regimens.

In one embodiment the immunotherapeutic agent is administered as part of the various components of multimodality regimens. In another embodiment the immunotherapeutic agent is administered before, simultaneously with, or after the multimodality regimens. In another embodiment the immunotherapeutic agent is administered based on synergism between the modalities. In another embodiment the immunotherapeutic agent is administered after treatment with anthracycline-based chemotherapy and/or taxane-based therapy (Zitvogel et al., 2008). Treatment after administering the immunotherapeutic agent may negatively effect dividing effector T-cells. The immunotherapeutic agent may also be administered after radiation.

In another embodiment the immunotherapeutic agent described herein is used in the treatment in a cancer where the standard of care is primarily not surgery and is primarily based on systemic treatments, such as Chronic Lymphocytic Leukemia (CLL).

In another embodiment patients diagnosed with stage I, II, III, and IV Chronic Lymphocytic Leukemia are treated with the immunotherapeutic agent as described herein. The standard of care for this cancer type is:

1. Observation in asymptomatic or minimally affected patients
2. Rituximab
3. Ofatumomab
4. Oral alkylating agents with or without corticosteroids
5. Fludarabine, 2-chlorodeoxyadenosine, or pentostatin
6. Bendamustine
7. Lenalidomide
8. Combination chemotherapy.
   combination chemotherapy regimens include the following:
   Fludarabine plus cyclophosphamide plus rituximab.
   Fludarabine plus rituximab as seen in the CLB-9712 and CLB-9011 trials.
   Fludarabine plus cyclophosphamide versus fludarabine plus cyclophosphamide plus rituximab.
   Pentostatin plus cyclophosphamide plus rituximab as seen in the MAYO-MC0183 trial, for example.
   Ofatumumab plus fludarabine plus cyclophosphamide.
   CVP: cyclophosphamide plus vincristine plus prednisone.
   CHOP: cyclophosphamide plus doxorubicin plus vincristine plus prednisone.
   Fludarabine plus cyclophosphamide versus fludarabine as seen in the E2997 trial [NCT00003764] and the LRF-CLL4 trial, for example.
   Fludarabine plus chlorambucil as seen in the CLB-9011 trial, for example.
9. Involved-field radiation therapy.
10. Alemtuzumab
11. Bone marrow and peripheral stem cell transplantations are under clinical evaluation.
12. Ibrutinib In one embodiment the immunotherapeutic agent is administered before, simultaneously with or after treatment with Rituximab or Ofatumomab. As these are monoclonal antibodies that target B-cells, treatment with the immunotherapeutic agent may be synergistic. In another embodiment the immunotherapeutic agent is administered after treatment with oral alkylating agents with or without corticosteroids, and Fludarabine, 2-chlorodeoxyadenosine, or pentostatin, as these treatments may negatively effect the immune system if administered before. In one embodiment bendamustine is administered with the immunotherapeutic agent in low doses based on the results for prostate cancer described herein. In one embodiment the immunotherapeutic agent is administered after treatment with bendamustine.

Kits and Co-Packaging

In an aspect, the invention provides kits containing any one or more of the elements discussed herein to allow administration of immunotherapeutic agents. Elements may be provided individually or in combinations, and may be provided in any suitable container, such as a vial, a bottle, or a tube. In some embodiments, the kit includes instructions in one or more languages, for example in more than one language. In some embodiments, a kit comprises one or more reagents for use in a process utilizing one or more of the elements described herein. Reagents may be provided in any suitable container. For example, a kit may provide one or more delivery or storage buffers. Reagents may be provided in a form that is usable in a particular process, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more of the vectors, proteins and/or one or more of the polynucleotides described herein. The kit may advantageously allow the provision of all elements of the systems of the invention. Kits can involve vector(s) and/or particle(s) and/or nanoparticle(s) containing or encoding RNA(s) for 1-50 or more neoantigen mutations to be administered to an animal, mammal, primate, rodent, etc., with such a kit including instructions for administering to such a eukaryote; and such a kit can optionally include any of the anti-cancer agents described herein. The kit may include any of the components above (e.g. vector(s) and/or particle(s) and/or nanoparticle(s) containing or encoding RNA(s) for 1-50 or more immunotherapeutic agents, e.g. neoantigen mutations, neoantigen proteins or peptides, checkpoint inhibitors) as well as instructions for use with any of the methods of the present invention.

In one embodiment the kit contains at least one vial with an immunotherapeutic agent (e.g. immunogenic composition or vaccine) and at least one vial with an anticancer agent. In one embodiment kits may comprise ready to use components that are mixed and ready to administer. In one aspect a kit contains a ready to use immunogenic or vaccine composition and a ready to use anti-cancer agent. The ready to use immunogenic or vaccine composition may comprise separate vials containing different pools of immunogenic compositions. The immunogenic compositions may comprise one vial containing a viral vector or DNA plasmid and the other vial may comprise immunogenic protein. The ready to use anticancer agent may comprise a cocktail of anticancer agents or a single anticancer agent. Separate vials may contain different anti-cancer agents. In another embodiment a kit may contain a ready to use anti-cancer agent and an immunogenic composition or vaccine in a ready to be reconstituted form. The immunogenic or vaccine composition may be freeze dried or lyophilized. The kit may comprise a separate vial with a reconstitution buffer that can be added to the lyophilized composition so that it is ready to administer. The buffer may advantageously comprise an adjuvant or emulsion according to the present invention. In another embodiment the kit may comprise a ready to reconstitute anti-cancer agent and a ready to reconstitute immunogenic composition or vaccine. In this aspect both may be lyophilized. In this aspect separate reconstitution buffers for each may be included in the kit. The buffer may advantageously comprise an adjuvant or emulsion according to the present invention. In another embodiment the kit may comprise single vials containing a dose of immunogenic composition and anti-cancer agent that are administered together. In another aspect multiple vials are included so that one vial is administered according to a treatment timeline. One vial may only contain the anti-cancer agent for one dose of treatment, another may contain both the anti-cancer agent and immunogenic composition for another dose of treatment, and one vial may only contain the immunogenic composition for yet another dose. In a further aspect the vials are labeled for their proper administration to a patient in need thereof. The immunogen or anti-cancer agents of any embodiment may be in a lyophilized form, a dried form or in aqueous solution as described herein. The immunogen may be a live attenuated virus, protein, or nucleic acid as described herein.

In one embodiment the anticancer agent may be a further immunotherapeutic agent, e.g. a checkpoint inhibitor. In another embodiment the kit contains multiple vials of immunogenic compositions and anti-cancer agents to be administered at different time intervals along a treatment plan. In another embodiment the kit may comprise separate vials for an immunogenic composition for use in priming an immune response and another immunogenic composition to be used for boosting. In one aspect the priming immunogenic composition could be DNA or a viral vector and the boosting immunogenic composition may be protein. Either composition may be lyophilized or ready for administering. In another embodiment different cocktails of anti-cancer agents containing at least one anti-cancer agent are included in different vials for administration in a treatment plan.

Although the present invention and its advantages have been described in detail, it should be understood that various changes, substitutions and alterations can be made herein without departing from the spirit and scope of the invention as defined in the appended claims.

The present invention is further illustrated in the following Examples which are given for illustration purposes only and are not intended to limit the invention in any way.

EXAMPLES

Experimental Procedures
Tumor and Normal Samples and Datasets
Analyzed Samples Represent Untreated Primary Tumors, Except for Melanoma, which included metastases. Metastases to lymph nodes were always excluded as were patients that received neo-adjuvant therapy. Gene-level RNA-Seq expression data were accessed from GDAC Firehose (Broad Institute TCGA Genome Data Analysis Center, 2014) (tumors and normals) and from the GTEx web portal (GTEx Consortium, 2013b) (normals only). RNA-Seq-based sequence data from the corresponding projects were accessed through CGHub and the Short Read Archive (SRP012682), respectively, and used to estimate expression of endogenous and exogenous viruses. Additional gene expression data were accessed from the CCLE web portal (http://www.broadinstitute.org/ccle/home) (Barretina et al., 2012) (Affymetrix U133+2 microarrays) and Fantom5 (Fantom Consortium et al., 2014) (cap analysis gene expression) and used to evaluate gene expression markers. Whole exome sequencing-derived point mutation calls were accessed from TumorPortal (Lawrence et al., 2014), Synapse workspace syn1729383 (https://www.synapse.org/#!Synapse:syn1729383; (Kandoth et al., 2013)), TCGA Data Portal (Health), GDAC Firehose (Broad Institute TCGA Genome Data Analysis Center, 2014), and the TCGA Research Network stomach adenocarcinoma publication (Cancer Genome Atlas Research Network, 2014). Whole exome sequencing-based sequence data, used to call HLA genotypes and mutations, were accessed through CGHub. GISTIC2 (Mermel et al., 2011) gene-level, zero-centered, focal copy number calls for each patient were accessed from GDAC Firehose (Broad Institute TCGA Genome Data Analysis Center, 2014). Clinical data for each tumor type were accessed from the TCGA public access web portal. catalog the TCGA and GTEx samples included in the study.

Cytolytic Activity and Other Cell Type-Specific Signatures

Cytolytic activity (CYT) was calculated as the geometric mean of GZMA and PRF1 (as expressed in TPM, 0.01 offset). Marker genes for specific cell types were identified as those with expression at least 2 fold greater than observed in any other cell type (using Fantom5 and DMAP), and enrichment was calculated using ssGSEA (Barbie et al., 2009). CYT-dependent survival analyses via Cox proportional hazards were performed by separating patients into a high-CYT cohort and a low-CYT cohort, each with an identical admixture of histology-stage combinations.

Expression of Exogenous and Endogenous Retroviruses

Viral expression was quantified by mapping unmapped RNA-Seq reads (bowtie2 (Langmead and Salzberg, 2012)) to viral sequence variants deposited in GenBank and normalizing against the count of mapped reads. Positive identification required at least 300nt of unique sequence to map to the viral genome and expression exceeding that observed in GTEx normals. To quantify the expression of endogenous retroviruses, RNA-Seq data (from TCGA and GTEx) was re-mapped (bowtie2 (Langmead and Salzberg, 2012)) to an annotation of known expressed elements (Mayer et al., 2011). For each ERV, the $95^{th}$ percentile expression value was calculated per tissue type, and if this value was less than <10 TPM in all normal tissues, >10 TPM in a tumor type, and at least 5-fold higher than in all non-tumor tissues, then the ERV was deemed tumor-specific.

Tumor-Specific HLA Typing, HLA-Binding Neoepitope Prediction and CT Antigen Identification The 4-digit HLA type for each sample was inferred using POLYSOLVER (POLYmorphic loci reSOLVER) which uses a normal tissue .bam file as input and employs a Bayesian classifier to determine genotype (unpublished, SAS, CJW and GG). By comparing to matched tumor .bams, POLYSOLVER also identified HLA mutations. Neoepitopes were predicted for each patient by defining all novel amino acid 9 mers and 10 mers resulting from mutation in expressed genes (median >10 TPM in the tumor type) and determining whether the predicted binding affinity to the patient's germline HLA alleles was <500 nM using NetMHCpan (v2.4) (Nielsen et al., 2007; Rajasagi et al., 2014)). A set of potential cancer testis (CT) antigens was defined by finding known CT antigens (Almeida et al., 2009) with negligible expression in GTEx normal tissues ($95^{th}$ percentile value<1 TPM in all somatic tissue types).

Comparison of Expected to Observed Neoantigen Load Per Tumor

To test whether the count of neo-epitopes was different from expected (ignoring the expression-based filter and excluding indels), the rate at which each mutational spectrum produces neo-epitopes was calculated empirically pan-cancer, and the silent mutations in each patient used to infer the expected ratio of neo-epitopes per non-silent mutation. This was compared to the actual ratio observed in the patient. Random shuffling of HLA genotypes amongst patients served as a control.

Association of CYT with Point Mutations and Amplifications/Deletions

Candidate genes were tested for non-silent point mutation association with CYT using a regression-based approach with CYT (rank-transformed) as the dependent variable, mutational status of the gene in question as the independent variable, and cancer histological subtype and the background rate of non-silent point mutations as additional control variables. Hits were defined at q<0.1. Candidate genes were defined by running MutSigCV (Lawrence et al., 2013) on each tumor type separately and all the tumor types collectively (q<0.1) and merging with a previously published result set (Lawrence et al., 2014). To assess for association between CYT and copy number alterations, a regression-based approach was likewise used, using CYT (rank-transformed) as the dependent variable, amplification or deletion signal as the independent variable, and cancer histological subtype and the background rate of copy number alteration as additional control variables. "Peaks" were defined as contiguous regions with p<0.01, and permutation testing was used to determine whether the peak score (based on the most enriched gene in the region) was truly significant (adj. p<0.1).

Selection of Tumor Types

Tumor types were selected for analysis based on publication availability as determined by The Cancer Genome Atlas (TCGA) embargo dates in September 2014, excluding non-solid tumor types. The analyzed tumor types and their corresponding project codes were urothelial bladder cancer (BLCA), breast cancer (BRCA), cervical cancer (CESC), colon and rectal adenocarcinoma (COAD and READ, a.k.a. CRC), glioblastoma multiforme (GBM), head and neck squamous cell carcinoma (HNSC), clear cell kidney carcinoma (KIRC), papillary kidney carcinoma (KIRP), lower grade glioma (LGG), liver hepatocellular carcinoma (LIHC), lung adenocarcinoma (LUAD), lung squamous cell carcinoma (LUSC), ovarian serous cystadenocarcinoma (OV), prostate adenocarcinoma (PRAD), cutaneous melanoma (SKCM), stomach adenocarcinoma (STAD), papillary thyroid carcinoma (THCA), and uterine corpus endometrial carcinoma (UCEC). Clinical data for these samples were accessed through the TCGA Portal (Health) ftp on Mar. 26, 2014 (tcga-data.nci.nih.gov/tcgafiles/ftp_auth/distro_ftpusers/anonymous.tumor.<tumortype>/bcr/nationwidechildrens.org/bio/clin/ nationwidechildrens.org_<tumortype>.bio.Level_2.X.X.X/). These data included assessment of histological subtype, tumor stage, specimen characteristics (such as percent necrosis), patient survival, and smoking history. Analyzed samples represent untreated primary tumors, except for melanoma, which includes untreated metastases. Melanoma metastases to lymph nodes were excluded from all analyses. Patients that received some form of neo-adjuvant therapy were excluded.

Data Types, Sources, and Initial Processing

Different types of data were considered: gene expression (RNA-Seq and array-based), viral expression, endogenous retrovirus expression, HLA type (and mutational status), point mutation (as identified by whole exome sequencing (WES)), neopeptide HLA-binder predictions, copy number alteration (CNA) data, and reference gene expression profiles. These data were obtained from (http://cancergenome.nih.gov/), the Genotype-Tissue Expression project (GTEx) (GTEx Consortium, 2013a), Fantom5 (Fantom Consortium et al., 2014), and/or the Cancer Cell Line Encyclopedia (CCLE) (Barretina et al., 2012). Some data were accessed and used directly, and some required post-processing to generate, as described below.

Clinical Data

Clinical data for each tumor type were accessed from the TCGA public access web portal on Mar. 26, 2014. These data included assessment of histological subtype, microsatellite instability status, tumor stage, specimen characteristics (such as percent necrosis), patient survival, and smoking history.

RNA-Seq-Based Gene Expression Data

TCGA gene expression data (90% tumor biopsies, 10% solid tissue controls) were obtained through GDAC Firehose (Broad Institute TCGA Genome Data Analysis Center, 2014) and included all available "Level_3" gene-level data (a mix of Illumina HiSeq and Illumina GA data). Samples from Genotype-Tissue Expression project (GTEx) were accessed through the GTEx web portal in November 2013 (GTEx Consortium, 2013b). For both data sets, raw read counts were tallied per gene symbol and divided by the gene symbol's maximum transcript length to represent coverage depth. Transcript lengths and mappings between gene symbols and transcript IDs were obtained from UCSC Genome Browser's table "knownIsoforms" (hg19 version) (Karolchik et al., 2004). For each sample, the corresponding coverage estimates across all genes were rescaled to sum to a total depth of 1e6, such that expression estimates may be interpreted as Transcripts Per Million transcripts (TPM).

RNA-Seq-Based Sequence Data

TCGA data were accessed from CGHub and included TCGA .bam files with "RNA-Seq" indicated in the library strategy field. Because this data set was too large to store locally, analyses were conducted "on-the-fly." Therefore, analyses based on the TCGA RNA-Seq sequence data do not always comprise the same samples set (reflecting the ongoing additional of samples to CGHub). RNA-Seq .bams for GTEx were downloaded from Short Read Archive (SRP012682, corresponding to dbGap phs000424) on Jul. 1, 2014.

Microarray-Based Gene Expression Data

While RNA-Seq-based gene expression data were used for most analyses, microarray-based data were used for assessing the baseline expression of GZMA and PRF1 in cancer cell lines. Data were obtained through the CCLE web portal (www.broadinstitute.org/ccle/home; file: CCLE_Expression_2012-2009-2029.res), and probes 205488_at and 1553681_a_at were used to represent GZMA and PRF1, respectively (Affymetrix U133+2 platform; RMA processing).

CAGE Cell Type Expression Profiles

Human cell type gene expression profiles were downloaded from the Fantom5 website on Oct. 8, 2014:fantom.gsc.riken.jp/5/datafiles/latest/extra/CAGE_peaks/hg19.cage_peak_tpm_ann.osc.txt.gz Point Mutation Data When possible, data was obtained from TumorPortal (Lawrence et al., 2014), which supplies the following ".maf" (Mutation Annotation Format) file: cancergenome.broadinstitute.org/data/per_ttype_mafs/PanCan.maf. When a patient was not present in this .maf, mutation data were obtained from Cyriac Kandoth's Synapse workspace syn1729383 (https://www.synapse.org.#!Synapse:s1729383; corresponding paper (Kandoth et al., 2013)). When a patient was not available in the previous sources, data were obtained from the TCGA Data Portal (Health) from the files:

```
genome.wustl.edu_CESC.IlluminaGA_DNASeq_curated.Level_2.1.0.0
broad.mit.edu_BLCA.IlluminaGA_DNASeq_curated.Level_2.1.4.0
broad.mit.edu_PRAD.IlluminaGA_DNASeq_curated.Level_2.1.4.0
broad.mit.edu_KIRP.IlluminaGA_DNASeq_curated.Level_2.1.1.0
broad.mit.edu_LGG.IlluminaGA_DNASeq_curated.Level_2.1.2.0
```

When not available in the previous sources, data for liver cancer patients was obtained from the GDAC Firehose standard analysis pipeline (Broad Institute TCGA Genome Data Analysis Center, 2014) (accessed Aug. 8, 2014). Finally, data from the recent TCGA stomach adenocarcinoma analysis (Cancer Genome Atlas Research Network, 2014) (tcga-data.nci.nih.gov/docs/pulications/stad_2014/; file: "Public Mutations") were included and used preferentially when a patient was already in one of the above sets.

Several possible mutation-calling artifacts were identified for the genes ZNF43, XYLT2, PAX6, PAFAH1B1, ALPK2. In each case, the gene had a reported indel appearing in multiple subjects at the edge of a homopolymer stretch. These events were manually excised from the maf.

HLA Type, HLA Mutations, and Predicted Neo-Antigen Binders

Whole exome sequencing data (.bam's) were downloaded from CGHub (University of California, 2012) for all samples for which a tumor and normal sample were available for a given patient (hg19-mapped .bam's were used when available; all files included unmapped reads). The 4-digit HLA type for each sample was inferred using the POLYSOLVER (POLYmorphic loci reSOLVER) tool which uses a normal tissue .bam file as input and employs a Bayesian classifier to determine genotype (Shukla et al, manuscript in review, Nature Biotechnology). The algorithm selects and aligns putative HLA reads to an imputed library of full-length genomic HLA allele sequences. The alignments then serve as a basis for the inference step that incorporates the number and base qualities of aligned reads, the empirical library insert size distribution and population-based allele frequencies.

Because standard mutation calling algorithms are not well-equipped to deal with highly variant regions such as the MHC loci, mutations in class I HLA genes were determined using the POLYSOLVER-based mutation detection pipeline (Shukla et al, manuscript in review, Nature Biotechnology) that takes a tumor/germline exome pair as input, and first characterizes the HLA alleles in the individual by applying POLYSOLVER on the germline data. Putative HLA reads from both the tumor and germline exomes are then aligned to the inferred alleles separately and likely erroneous alignments are filtered out. Somatic changes are subsequently identified by comparative evaluation of the aligned tumor and germline files using the Mutect (Cibulskis et al., 2013) and Strelka (Saunders et al., 2012) tools. Since CGHub contains .bam files that have not yet been processed into .maf's by the TCGA Data Coordinating Center, there are more patients with HLA mutation calls than patients appearing in the general mutation .maf.

Individual-specific HLA-binding peptides were identified by a neo-antigen prediction pipeline (Rajasagi et al., 2014) that uses all detected somatic mutations for the individual (obtained from the general mutation .maf). Binding affinities of all possible 9 and 10-mer mutant peptides to the corresponding POLYSOLVER-inferred HLA alleles were predicted using NetMHCpan (v2.4) (Nielsen et al., 2007).

Viral Expression

Variant sequences for ten putative oncoviruses were accessed from NCBI Nucleotide (http://www.ncbi.nlm.nih.gov/nucleotide/) using the following search terms:

| Virus | Query | Retrieved Count |
|---|---|---|
| JC polyomavirus | JC Polyomavirus[Organism] AND "complete genome" AND 5000:5400[Sequence Length] | 564 |
| BK polyomavirus | BK Polyomavirus[Organism] AND "complete genome" AND 5000:5400[Sequence Length] | 282 |
| KI polyomavirus | KI Polyomavirus[Organism] AND "complete genome" AND 5000:5400[Sequence Length] | 10 |
| WU polyomavirus | WU Polyomavirus[Organism] AND "complete genome" AND 5000:5400[Sequence Length] | 80 |
| Merkel cell polyomavirus | Merkel cell polyomavirus[Organism] AND "complete genome" AND 5200:5700 [Sequence Length] | 42 |
| Human papillomavirus | Human papillomavirus AND "complete genome" AND 5000:10000[Sequence Length] | 741 |
| Epstein-Barr virus | Human herpesvirus 4[Organism] AND "complete genome" AND 150000:200000 [Sequence Length] | 9 |
| Kaposi sarcoma virus | Human herpesvirus 8[Organism] AND "complete genome" AND 130000:140000 [Sequence Length] | 4 |
| Hepatitis B virus | Hepatitis B virus[Organism] AND "complete genome" AND 2800:3500[Sequence Length] | 4834 |
| Hepatitis C virus | Hepatitis C virus[Organism] AND "complete genome" AND 9000:10000[Sequence Length] | 912 |

These sequences were then filtered using Tandem Repeat Finder (Benson, 1999) using options "2 7 7 80 10 24 50-m -h" to mask low-complexity sequences. These sequences, as well as a decoy fasta of homopolymer repeats, were concatenated into a single fasta and converted into a bowtie2 (Langmead and Salzberg, 2012) search index. TCGA RNA-Seq .bam files were downloaded from CGHub, and the unmapped reads were mapped using bowtie2 and search parameters "-q --end-to-end-k 1 --no-unal". Because the read mapping pipeline used to generate the .bam's hosted at CGHub does not produced files fully consistent with SAM format (Li et al., 2009), it was not possible to revert the .bam's to paired mate-1 and mate-2.fastq files. Therefore, reads were mapped in single-end mode, and it was considered after-the-fact whether reads with the same name suffix had both aligned to the same virus. For consistency, the same approach was used for mapping the GTEx RNA-Seq data. For the TCGA data, fragment ends had been sequenced to 48 or 76 bases, and each .bam contained 114,000,000-181,000,000 mapped read ends (IQR). For GTEx, fragment ends had been sequenced to 76 bases, and each .bam contained 63,000,000-110,000,000 mapped read ends (IQR). Due to lags in sample processing in TCGA and GTEx, the counts of processed RNA-Seq .bam's do not exactly match the corresponding counts of samples with full-transcriptome expression estimates (described above).

Upon pilot analysis, the requirement that both read ends successfully map appeared to be inadequately sensitive; therefore, the paired-end nature of the data was ignored for the purposes of the viral analysis. To guard against false positives caused by spurious read mapping, non-zero viral expression calls were contingent on reads mapping to multiple loci in the viral reference sequence. For a given virus, the specific operation was to 1) identify all viral reference sequence covered by at least one read and 2) determine whether the count of unique 20 mers within that sequence (as calculated using Jellyfish (Marcais and Kingsford, 2011)) is greater than 300 (it was not possible to simply measure the length of covered sequence because multiple fastas were used to represent each virus). Given successful clearance of this robustness test, viral expression was quantified by taking the count of read ends mapping to each virus (summing across the variant sequences for the virus) and dividing by the total count of human genome-mapped read ends in the original .bam. This number was multiplied by 10e6 in order to express viral titer as viral Reads Per Million reads mapped to the human genome (RPM). "Positivity" for viral infection was determined based on whether the expression exceeded the maximum observed in the GTEx normal, with the assumption that very low levels may simply reflect the trace presence of previously exposed leukocytes in the tissue sample. Applicants acknowledge that these are conservative assessments and may miss some cases of viral infection that are transcriptionally silent.

Endogenous Retrovirus (ERV) Expression

A list of GenBank accessions corresponding to transcriptionally active endogenous retroviruses was obtained (Mayer et al., 2011) and contained sequences representing 66 ERV species. These were converted into a bowtie2 index, and .bams from TCGA, GTEx, and CCLE were remapped to this index (preserving both mapped and unmapped reads) using the same bowtie2 search parameters used in the viral analysis. Paired read ends were assigned to the same ERV sequence if there was one that provided an acceptable alignment for both; otherwise, the reads ends were aligned individually. When multiple ERV sequences provided an equally good match, ties were broken at random. ERV expression was quantified in RPM in the same manner used in the viral analysis. In the case of ERV18-1, reads aligning to positions 3990-3680 were excluded from expression estimates because of sequence overlap with a non-retroviral gene.

Copy Number Events

GISTIC2 (Mermel et al., 2011) "Level 4" copy number calls for each patient were accessed from GDAC Firehose in March 2014. GISTIC2 uses data from copy number arrays (in this instance, Affymetrix Genome-Wide Human SNP 6.0 arrays) to identify regions of copy number variation across the genome. The files accessed through GDAC Firehose contained a score for each gene representing whether that gene was in a region that was focally amplified or deleted in the given tumor (larger events, such as whole genome amplifications, were ignored). Values of zero indicate that there is no evidence of copy number alteration for the given gene, whereas positive and negative values represent amplification and deletion, respectively. Even though each tumor subclone contains an integral copy number for each locus in the genome, biopsies potentially contain multiple tumor subpopulations as well as stromal tissues; therefore, the reported values in the GISTIC2 output are continuous rather than integral. Since stromal contamination (which would presumably correlate with CYT) tends to regress the signal toward zero, each sample was rescaled so that the median non-zero event amplitude was 1.

Data Analysis

Definition of Cytolytic Activity Metric "CYT"

Cytolytic Activity Metric (CYT) was obtained by calculating the geometric mean of GZMA and PRF1 expression (as measured in TPM) per sample. The geometric mean was preferred to the arithmetic mean because it is not arbitrarily affected by the expression scales of the two genes being averaged. Because the geometric mean function requires a log transformation, 0.1 was added to each expression value before transformation in order to avoid logging zero. In order to assure robust statistical results, some analyses included an additional rank-transformation (across samples) to the CYT values, which was rescaled such that the values were uniformly distributed between 0 and 100. GZMA and PRF1 were selected based on their known roles in target cell lysis in addition to corroborating expression profile-based evidence that they were specific to killer lymphocytes (a point on which GZMB and FASL, other well-known effector genes, failed). CYT estimates were not "corrected" for the presence of gene expression markers of suppressive immune cells (e.g. the expression of FOXP3, a marker for regulatory T cells) because there is insufficient evidence to support the proper scaling of this correction and because CYT would presumably already be diminished by the presence of these suppressive cells.

Definition and Analysis of Cell Type Expression Markers and Immune Meta-Genes

Cap analysis of gene expression (CAGE) data from Fantom5 were used to define a set of transcriptomic markers for immune cell subtypes of interest. Applicants note that "regulatory T cells" in Fantom5 were represented by CD4+ CD25$^{hi}$CD45ra− cells. Applicants further note that "myeloid dendritic cells" (mDCs) in Fantom5 were monocyte-derived rather than primary and were therefore not used. Data were collapsed to the gene symbol level using summation. For each gene in each cell type, a median expression level was calculated over the given replicates (an offset of 5 TPM was added to all expression values). To determine a specificity ratio for markers, the expression of each gene was compared to maximum expression of the gene in the other immune cell types (listed in Table 1; B, Treg, NK, CD8 T cell, neutrophil, macrophage, pDC) as well as all non-hematopoietic, non-cancer cell types in FANTOM5. This specificity ratio had to be at least 2 to consider a gene as a marker for a cell type, with up to 10 markers per cell type. Because the Fantom5 project did not include activated/effector CD8+ T cells, many of the genes initially identified as NK-specific within Fantom5 were actually shared between NK cells and activated CD8+ T cells when Applicants considered data from the DMAP human blood profiling project (www.broadinstitute.org/dmap) (Novershtern et al., 2011). Therefore, Applicants used data from the DMAP project to find the genes most highly expressed in NK cells (median of types "A1", "A2", "A3", and "A4") vs. activated/effector CD8 T cells (median of types "T cell 1", and "T cell3"), identified the top 20, and then obtained a revised NK marker gene list by intersecting the FANTOM NK markers with the DMAP NK markers. Applicants note, however, that even these genes exhibited a substantial degree of expression in activated CTLs, consistent with the lack of known highly-specific NK markers.

Several other meta-genes were defined. Sets of co-inhibitory and co-stimulatory receptors expressed on T cells and antigen presenting cells (APCs) were defined based on a recent review (Chen and Flies, 2013). Type I and Type II-specific interferon response genes were defined based on recent study comparing responses of macrophages to these two stimuli (Liu et al., 2012) (Supplementary Table 1 of referenced). HLA Class I genes were defined as HLA-A, B2M, and TAP1. The final set of selected markers can be found in Table 1.

The enrichment of a cell type meta-gene in a given sample was then calculated using single sample gene set enrichment analysis (ssGSEA) (Barbie et al., 2009) as used before to analyze TCGA samples for immune/stromal infiltrates and implemented in the 'GSVA' R package (Hänzelmann et al., 2013), with subsequent z-scoring across samples. Note that these enrichments should not be interpreted as deconvolutions of actual cell type proportions. In several instances in which CYT was directly compared to the ssGSEA enrichments, CYT was also calculated according to the ssGSEA approach (rather than geometric mean) in order to make a fair comparison. These include FIG. 8F (cell type enrichments vs. CYT), FIG. 8G (tumor-normal comparison of enrichments), FIG. 8J (survival analysis of enrichments). Applicants note, however, that the two CYT calculations are nearly identical (Spearman correlation 0.96).

Relationships with Tumor Stage

To test for an overall association between CYT and tumor stage, the Pearson correlation was calculated between log-CYT and stage (stage was converted to a numeric variable: "stage 1"=1, "stage 2"=2, etc.) Z-scored ssGSEA enrichments of marker genes were also compared to stage in this manner. Since gliomas are not staged, grade (G2 or G3) was analyzed in place of stage for this tumor type.

Survival Analysis

Patient samples grouped according to histological subtype (samples were excluded when histological subtype was not available) and tumor stage. Groups with fewer than 8 samples were excluded. To assess the survival effect of a continuous variable x, each group was split equally into high-x and low-x patients. High-x patients were pooled pan-cancer and low-x patients were pooled pan-cancer and analyzed as two distinct cohorts using Cox proportional hazards modeling. Note that the two cohorts have identical admixtures of tumor type and stage. In some analyses, the variable x represented the z-scored ssGSEA enrichment of a metagene (e.g. macrophage marker genes); in other analyses it was the arithmetic difference between the z-scored ssGSEA enrichments of two meta-genes (e.g. Treg marker gene enrichment minus CTL marker gene enrichment). In contrast to most other analyses, CYT was calculated according to the ssGSEA approach to enable the analysis of differential enrichment with respect to the meta-genes.

Transcriptomic Assessment of Viral Infection

Association between CYT and viral infection status was characterized using Wilcoxon rank sum tests for tumor types exhibiting at least five cases of infection with the given virus. To further characterize viral transcription, representative variants (one for which a large number of reads mapped and for which there exists good gene annotation) were selected for each of virus that was detected, and remapped reads (pooled from all TCGA cancer samples) to these variants. These read depths are presented in FIG. 9A.

In order to assess the general gene expression correlates of viral infection in a given tumor type, a Wilcoxon rank-sum test was performed for each gene to test differential expression between infected and non-infected, and a score was assigned by multiplying the sign of the association by the negative log p-value. Genes were ranked by this differential expression score and submitted in forward and reverse order to "GOrilla" gene ontology enrichment analysis and visualization tool (Eden et al., 2007; Eden et al., 2009), to assess for gene set enrichment.

To assess whether extra-hepatic cases of HBV infection were metastases originating from the liver, samples from tumor types with at least 1 HBV+cases were plotted according to the first two principal components of their global log-transformed gene expression. The clustering of HBV+ samples (with liver or with the uninfected samples of the corresponding tumor type) was assessed visually.

Association Between HLA Type and Cytolytic Activity

HLA types (at two-digit granularity) were assessed for association for cytolytic activity in each tumor type using Wilcoxon rank sum tests. The overall significance of an HLA type pan-cancer was assessed using Fisher's method to combine the p-values of the individual tumor type Wilcoxon rank sum test p-values. The overall significance of a tumor type for HLA-CYT association was assessed using an F test of a linear regression modeling rank-scaled CYT in that tumor type as a function of HLA type.

Characterization of Mutational Spectra

Using the general-analysis .maf (which contains only coding region mutations), single-nucleotide variants were identified and characterized as C→A, C→G, C→T, A→C, A→G, or A→T (if the reference allele was T or G, the event was analyzed from the perspective of the opposite strand). In addition, the identities of the upstream and downstream reference bases were used to further categorize the mutational events. FIG. 9E depicts the rate of each mutation type, per sample, for high-CYT tumors and low-CYT tumors as well the difference in the rates (high minus low). High-CYT tumors were defined as those with CYT in the top quartile for the given tumor type. Low-CYT tumors were defined as those with CYT in the bottom quartile for the given tumor type.

To test whether the rate of Apobec-characteristic mutations (reference allele C with upstream T) was differential between high-CYT and low-CYT tumors, the count of Apobec-characteristic mutations in each tumor samples was divided by the count of all other mutations and this ratio was assessed for Spearman rank correlation with CYT. The ratio was tested for association with viral infection status and with ERV expression using Wilcoxon rank-sum test and Spearman rank correlation, respectively. For the ERV analysis, p-values were corrected by B-H method across the 18-cancer×66-ERV matrix of p-values. While several ERVs association with Apobec-characteristic mutations narrowly reached significance (p adj.<0.05) in stomach cancer (ERVH-2, ERVE-2) and breast cancer (ERVI-1), the directions of association were not consistent amongst tumor types leaving no definitive result.

Neo-Antigen Analysis

If the mutation was predicted to produce a "binder" neopeptide with affinity <500 nM and if the corresponding gene was expressed greater than 10 TPM (evaluated based on median expression in the given tumor type rather than the specific sample, as mutations may affect transcript quantification), the mutation was designated as putatively antigenic. For each tumor type, the count of total mutations and the count putatively antigenic mutations per sample was compared to the CYT. Tumor types displaying a spearman rank correlation p-value less than 0.1 (only significant positive associations were observed) are presented in FIGS. 3A and 3B. Melanoma was included regardless of significance based on prior expectation that there would be a positive relationship. For each cancer type, a local regression curve (as calculated by the R lowess( ) implementation (Cleveland, 1981), default parameters) is drawn over inner 90th percentile range of the independent variable.

To determine whether the number of neo-antigens predicted for a tumor was more or less than expected given its mutation rate, a null model for mutation was developed to control for the differing rates of mutational "spectra" observed in different tumors (a result of differing mutagenic processes). Indels and mutations in genes significantly mutated in cancer (described herein) were excluded from the analysis. 192 mutational spectra were defined based on the old base, the new base, and the identities of the nucleotides 1 base upstream and 1 base downstream (from the perspective of the coding strand). For each spectrum s, two rates were estimated empirically pan-cancer: the expected number of non-silent mutations per silent mutation, $\overline{N}_s$, and the expected number of high-affinity neo-peptide binders (not considering gene expression) per non-silent mutation, $\overline{B}_s$. Using these rates, Applicants used the silent mutational events in each tumor sample to predict the number of non-silent mutations, $N_{pred}$, and the number of neo-peptide binders, $B_{pred}$, expected for that tumor under null model in which there is no selection against mutations that yield HLA binders:

$$N_{pred} = \sum_m^{Silent\ SNVs} \overline{N}_{s(m)}$$

$$B_{pred} = \sum_m^{Silent\ SNVs} \overline{N}_{s(m)} \overline{B}_{s(m)}$$

where s(m) represents the spectrum of the given mutation. Having calculated $N_{pred}$ and $B_{pred}$ for a sample, these were compared to the actual counts in the sample, $N_{obs}$ and $B_{obs}$, to define the ratio between the observed and expected rate of neo-peptides, R:

$$R = \frac{B_{obs}/N_{obs}}{B_{pred}/N_{pred}}$$

R was characterized for the samples corresponding to each tumor type, and Wilcoxon rank sum tests were used to determine whether tumor types were significantly different from R=1. Note that since $\overline{N}_s$, and $\overline{B}_s$, were estimated empirically, they are under-estimates if strong selection against binder-yielding mutations is occurring. However, since these values are estimated pan-cancer, R can still be interpreted in a relative sense.

As a control, Applicants randomly scrambled HLA genotypes across patients and re-ran the analysis using the resulting new set of predicted neo-epitopes (but still using $\overline{N}_s$ and $\overline{B}_s$ as estimated previously).

Smoking

For the lung cancers, clinical data included the smoking history of the patients. For lung adenocarcinoma and lung squamous cell carcinoma, ever-smokers (excluding those reformed at least 15 years prior and those with an unknown number of years of reform) were compared to never-smokers in terms of CYT using the Wilcoxon rank sum test to assess significance.

Assessing Ectopic Transcription

In order to define a genes whose expression could be considers ectopic and thereby potentially immunogenic, a candidate list was first created using the list of cancer testis (CT) antigens maintained at CTdatabase (http://www.cta.lncc.br/) (Almeida et al., 2009). Using RNA-Seq data from GTEx, the 95th percentile expression value was calculated for each tissue type, including blood, as an estimate of the upper bound of the expression of the gene in that tissue type. If no tissue exceeded a threshold of 1 TPM, then the gene was included in our ectopic gene set. This filtering step was applied in order to avoid CT antigens identified genes that may be expressed stromally, which would confound association analyses. Applicants note that NY-ESO was not included because it was not quantified in some TCGA expression data sets. The degree of ectopic expression in a given tumor sample was determined by counting the number of ectopic genes expressed greater than 1 TPM. Association with CYT was determined by comparison of samples with <5 and >10 ectopic genes expressed (>1 TPM) using Wilcoxon rank-sum tests. In addition, the expression levels of individual ectopic genes were assessed for association with CYT using Spearman rank correlation.

To explore the hypothesis that CT antigens might be chromosomally deleted as a mode of immune evasion, Applicants explored several properties of their copy number alteration status. First, Applicants determined whether deletion reduced the expression of each gene in each tumor type by assessing for whether there was a significant negative Pearson correlation between the gene's GISTIC deletion signal (0-censoring values in the direction of amplification) and its log expression (using a log offset of +1 TPM). Second, Applicants determined whether high CYT was associated with deletion by looking for significant positive Pearson correlation between each gene's GISTIC deletion signal (0-censoring values in the direction of amplification) and log-scale CYT. Finally, for each tumor type, Applicants calculated the count of instances in which each gene was deleted (GISTIC score<0), divided it by the count of total alterations (GISTIC score 0), and calculated the average across all genes. Using this deletion:alteration ratio, Applicants calculated whether each CT gene was significantly more frequently deleted than amplified in comparison to genes in that tumor type in general (according to a binomial distribution). Even with loose thresholds, there were limited instances in which the three tests converged for a given gene-cancer combination.

Quantification of Endogenous Retrovirus (ERV) Transcription

The co-expression of all ERVs across the TCGA tumor samples was assessed using Spearman-rank correlation.

To define a set of tumor-specific ERVs (TSERVs), the 95th percentile expression value was calculated for each ERV in each tumor tissue type and each normal tissue type. This value was considered to represent a robust estimate of the upper limit of the expression range. If this value did not exceed 10 RPM in any normal tissue type, did exceed 10 RPM in at least one tumor tissue type, and if there existed at least one tumor tissue type with a value 5-fold greater than any normal tissue type, then the corresponding ERV was considered to be a TSERV.

Functional motifs within ERV sequences were obtained by determining the consensus sequence for each ERV (among aligning reads), translating all ORFs greater than length 75 and processing using InterProScan (Jones et al., 2014).

For each TSERV, gene set enrichment analysis was performed for the tumor type demonstrating maximum expression. This was done in the same fashion as for the viral gene set enrichment analysis, but using Spearman rank correlation to determine sign and p-value rather than Wilcoxon rank-sum test.

For all ERVs that exhibited overexpression in a given tumor type (as defined by expression exceeding that observed in normal tissues), ERV-CYT expression was assessed using Spearman rank correlation.

Correlates of Necrosis

Association between percent necrosis (based on TCGA clinical data) and various meta-genes (including CYT) was assessed using Spearman rank correlation.

Identifying Genes Significantly Point-Mutated in High-/Low-CYT Tumor Biopsies

A set of candidate genes was defined by running MutSigCV on each individual tumor type and on the entire pan-cancer.maf. MutSigCV is a tool designed to identify genes that are mutated in a non-random manner and considers variables such as the ratio of nonsynonymous to synonymous events (Lawrence et al., 2013). As described previously, the .maf contains "point mutations" (SNV, DNVs, indels and other variants that can be identified using whole exome sequencing) but excludes larger chromosomal derangements. In line with previous application of MutSigCV (Lawrence et al., 2014), genes significant at a 10% false discovery rate in any of these MutSgCV runs were deemed to be significantly mutated. Genes that were not identified in this analysis but were identified in previous pan-cancer MutSigCV application (Lawrence et al., 2014), were added to the candidate list.

To assess whether a gene's mutational status was significantly associated with CYT, rank-transformed CYT was modeled (using linear regression) as a function of the gene's mutational status (ignoring synonymous events), cancer type (encoded as a dummy variable), and the rank-transformed count of total non-synonymous mutations. The latter two variables were included to diminish confounding effects. Cancer type was defined based on the histological subtype of the tumor (indicated in the clinical data; 40 types total), and samples were excluded when the histological subtype was not defined. The p-value of the mutation status coefficient ("beta") and its sign were used a measure of enrichment for the given gene. As previously described, rank-scaling transformed data such that values were uniformly distributed between 0 and 100. It was employed as a conservative measure to avoid results driven by outliers. Thus, beta values (reported in Table 2) should be interpreted as the expected change in CYT percentile given nonsynonymous mutation, and a positive beta value implies a positive relationship between CYT and mutational status. The p-values across the 355 genes tested were corrected for multiple hypothesis testing using "method=BH" (Benjamini & Hochberg) in R's p.adjust( ) function. A set of "hits" was defined by setting an adjusted p-value cutoff of 0.1. (The pan-cancer association analysis was also conducted using synonymous mutations only and ignoring nonsynonymous events. This was to determine whether any "hits" would be discovered in a scenario in which none were expected.)

To further characterize each hit, the data was parsed into 18 subsets corresponding to each tumor type, CYT was re-rank-transformed per subset, and the linear regression (using the same covariates, excluding cancer type) was repeated on each subset (no control for histological subtype). An uncorrected p-value less than 0.05 for the (nonsynonymous) mutation status variable was considered evidence for association. The beta values can be interpreted as the expected change in CYT percentile (for the given tumor type) given mutation.

In exploring the relationship between CASP8 mutation and FASL and TRAIL expression (FIG. 5B), tumor types were analyzed if they had at least 5 instances of CASP8 mutation. For those that did, association p-values were assigned using the Wilcoxon rank sum test.

Associations between the hits and viral infection status were characterized using Fisher's exact test. For testing a given virus, uninfected samples were excluded if demonstrating non-zero transcriptional titer for any virus.

Figure 12A:
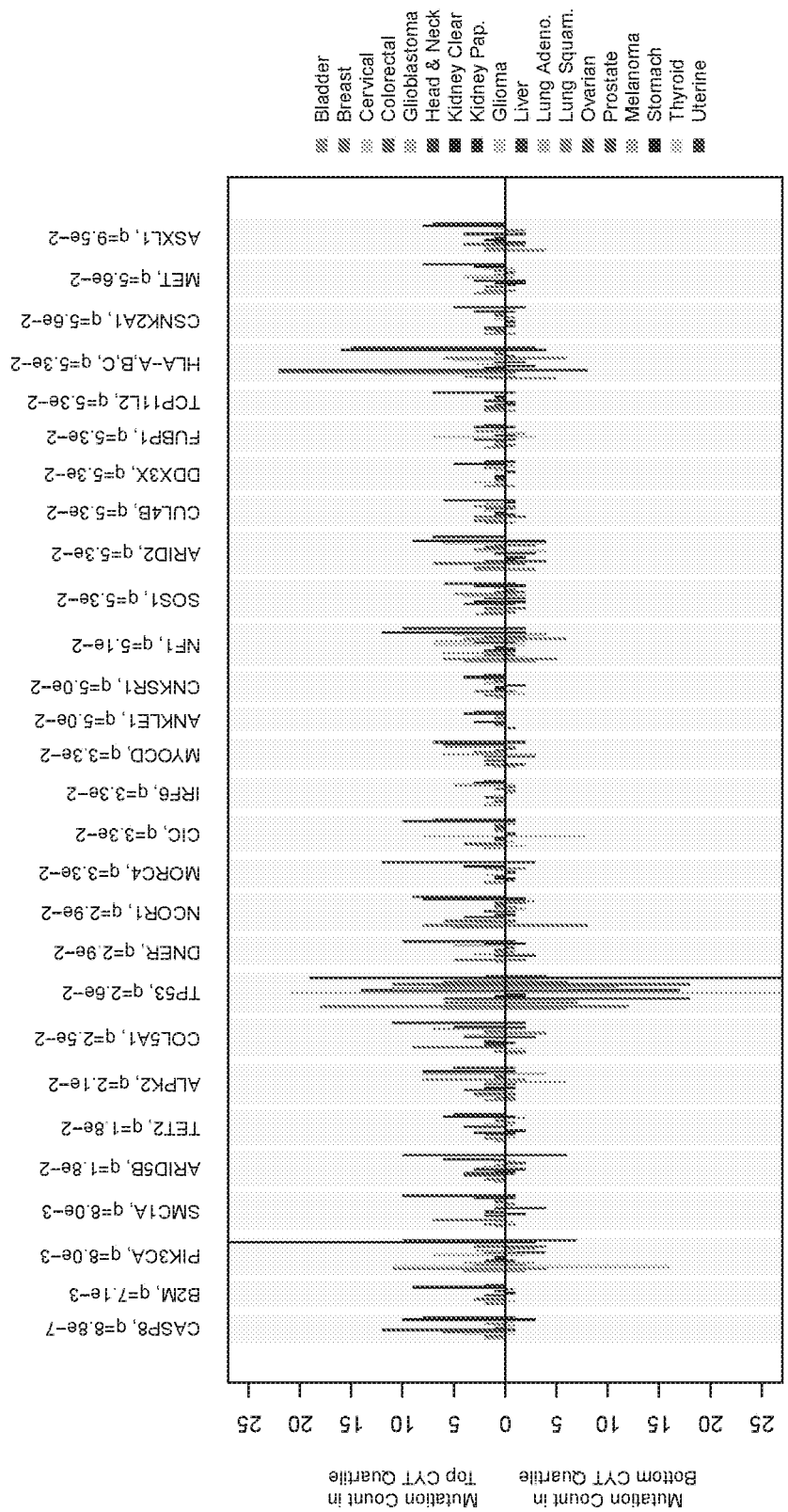
Figure 12B:
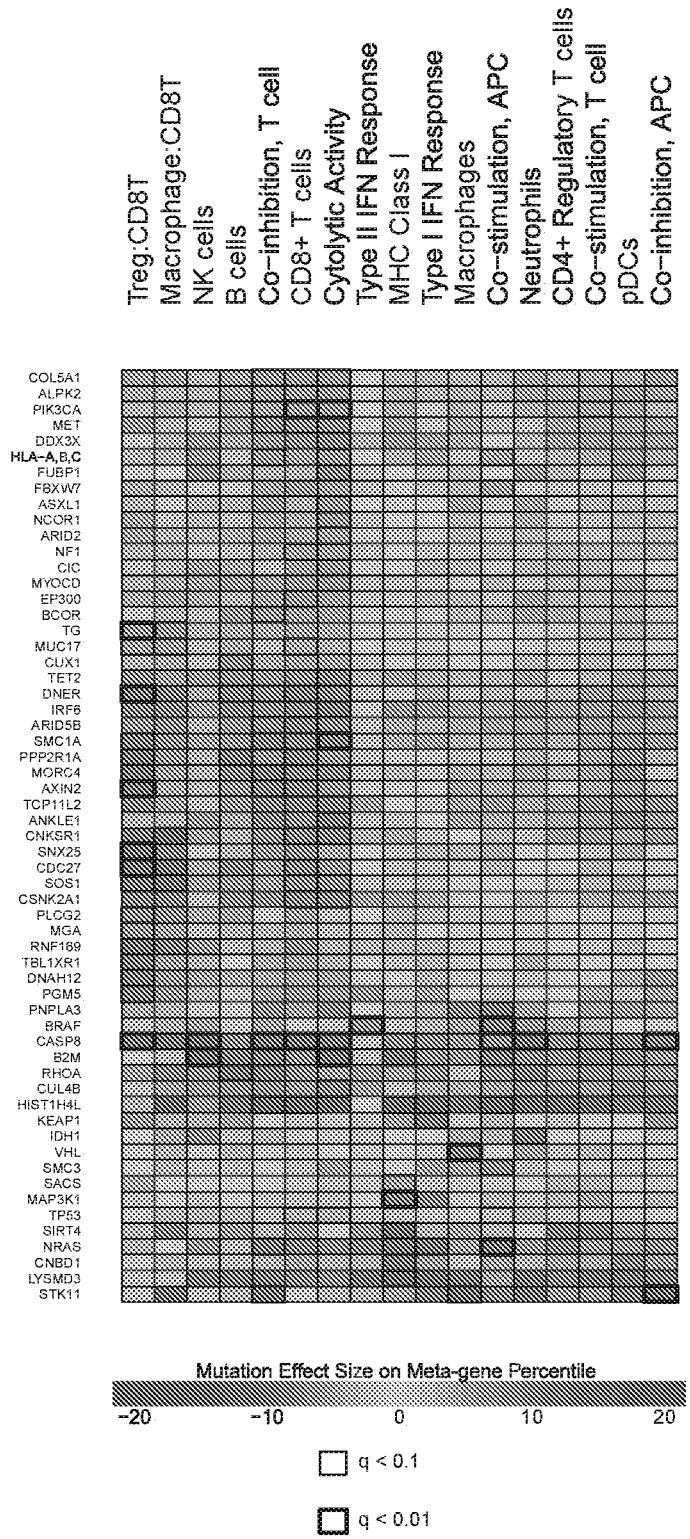
Figure 12C:
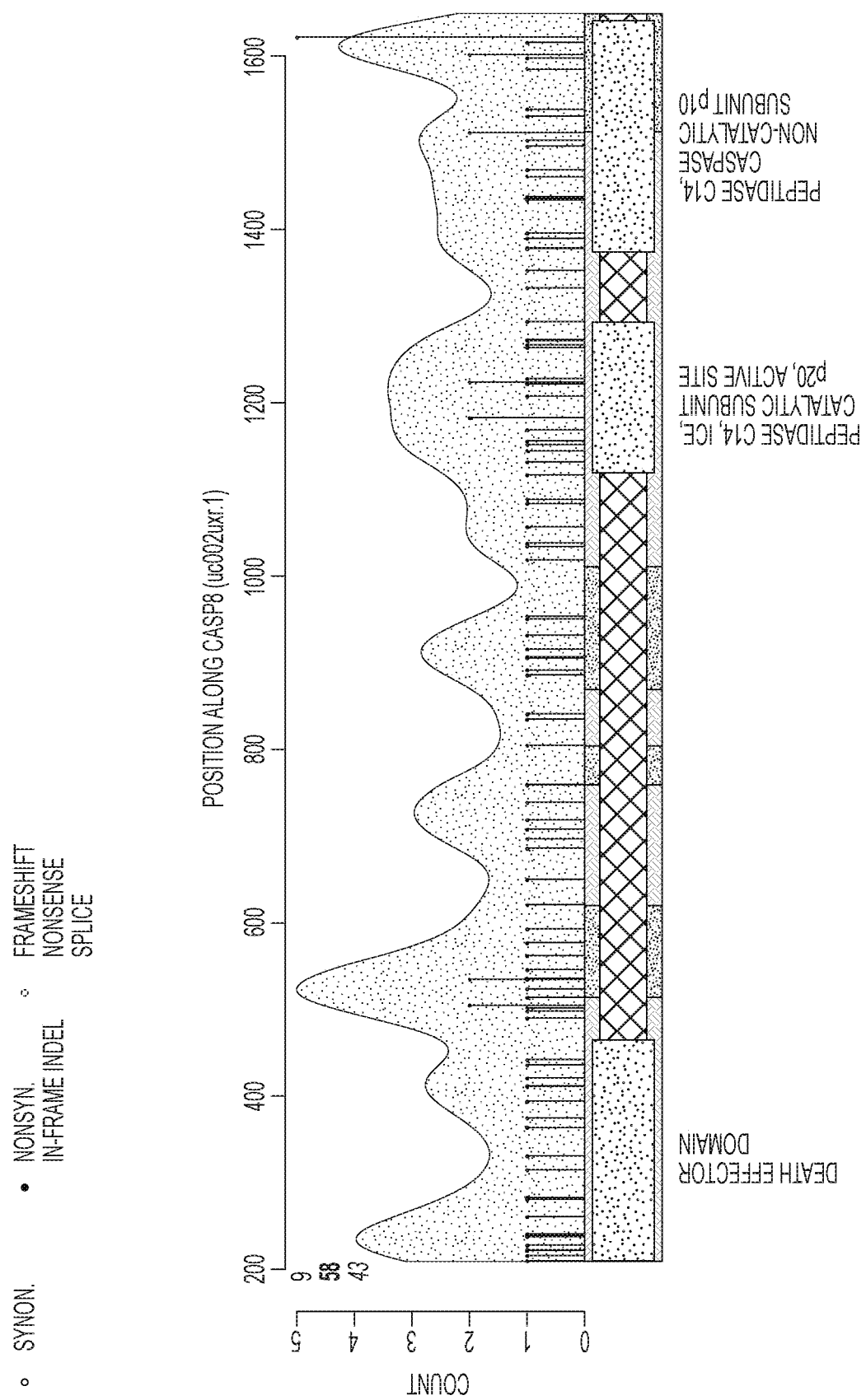
Figure 12C:
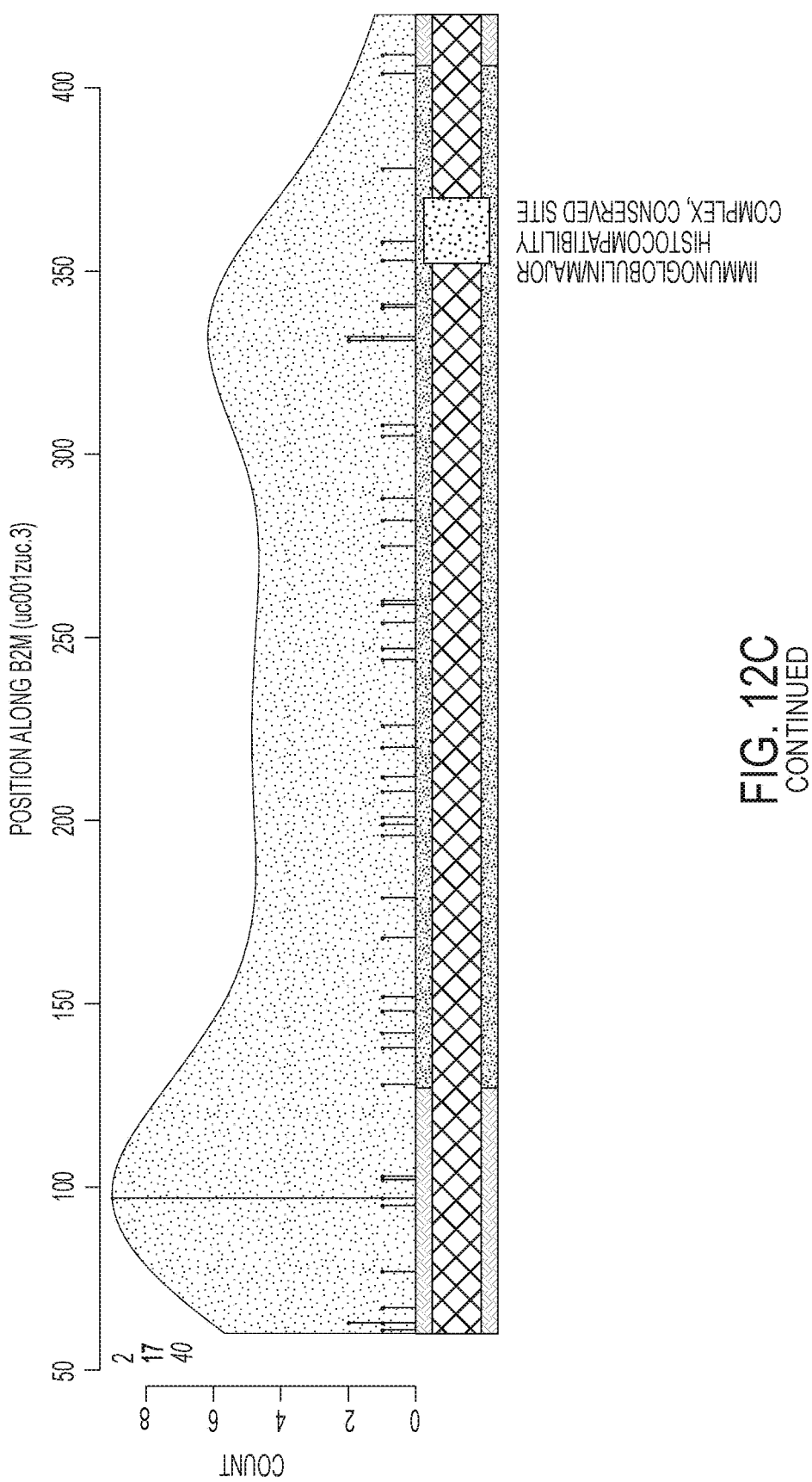
Figure 12C:
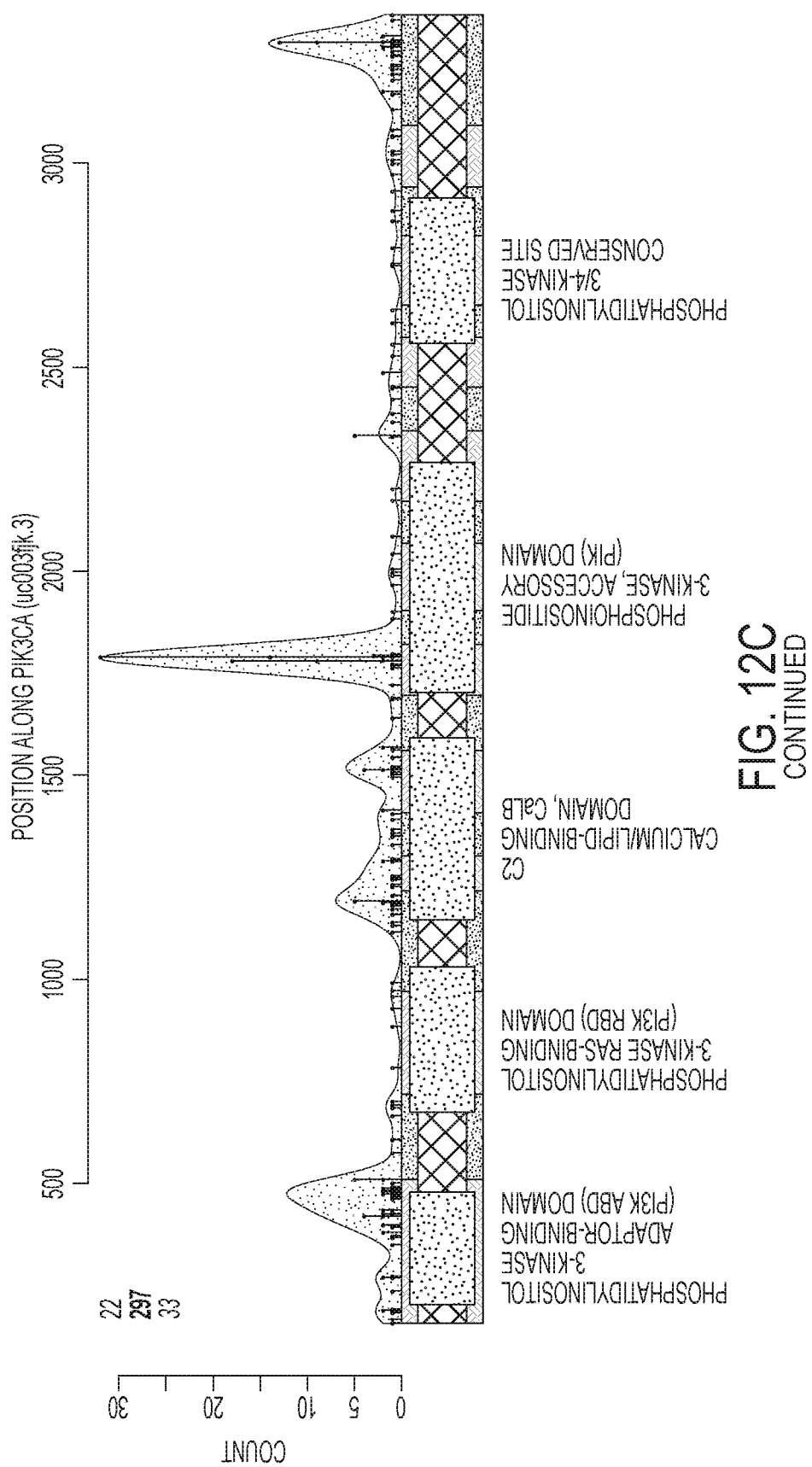
Figure 12C:
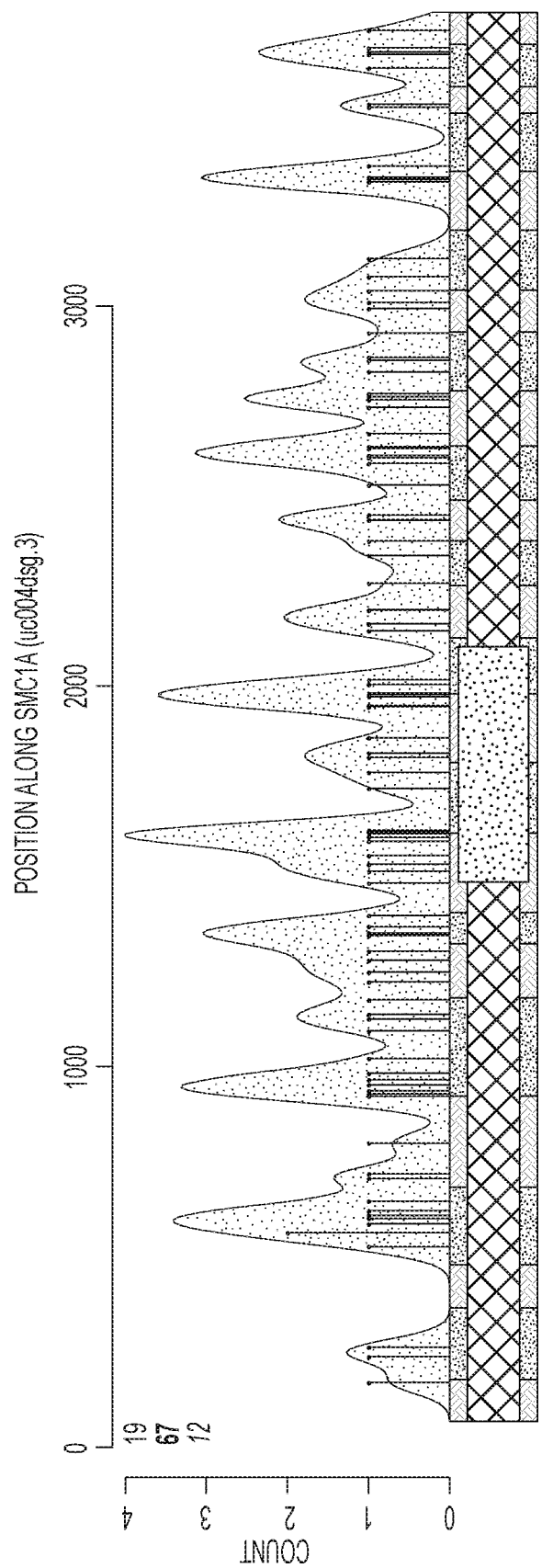
Figure 12C:
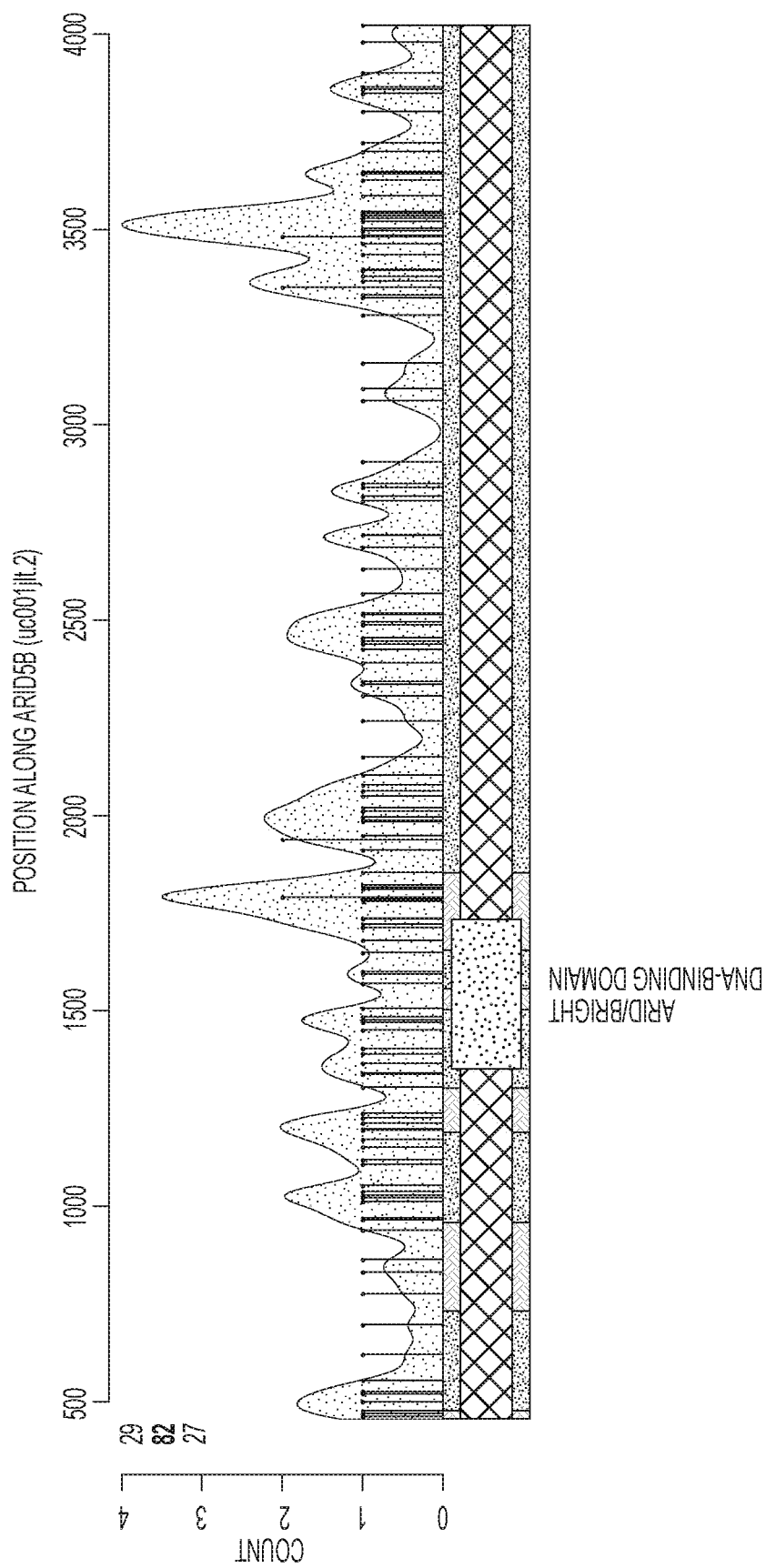
Figure 12C:
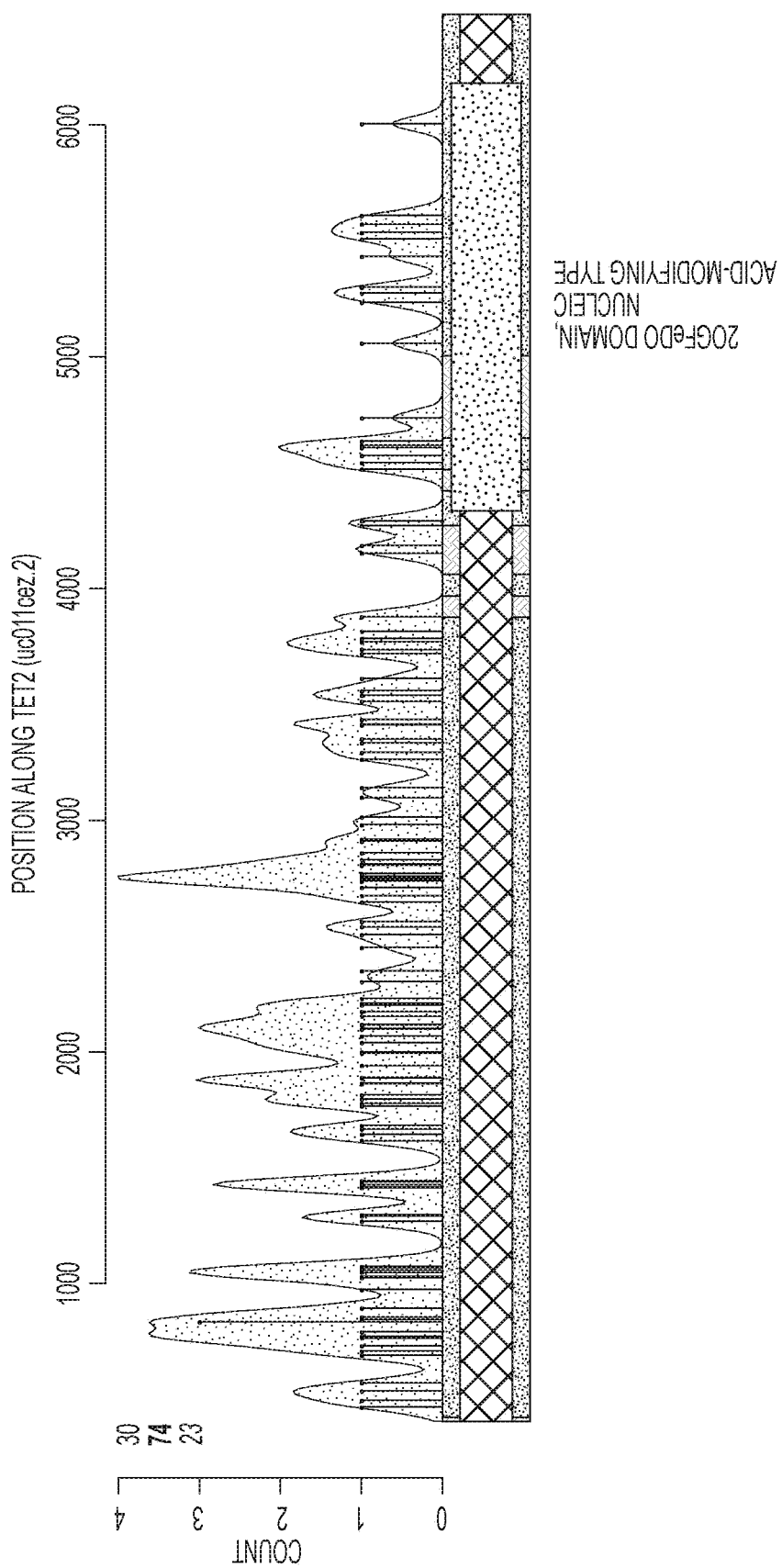
Figure 12C:
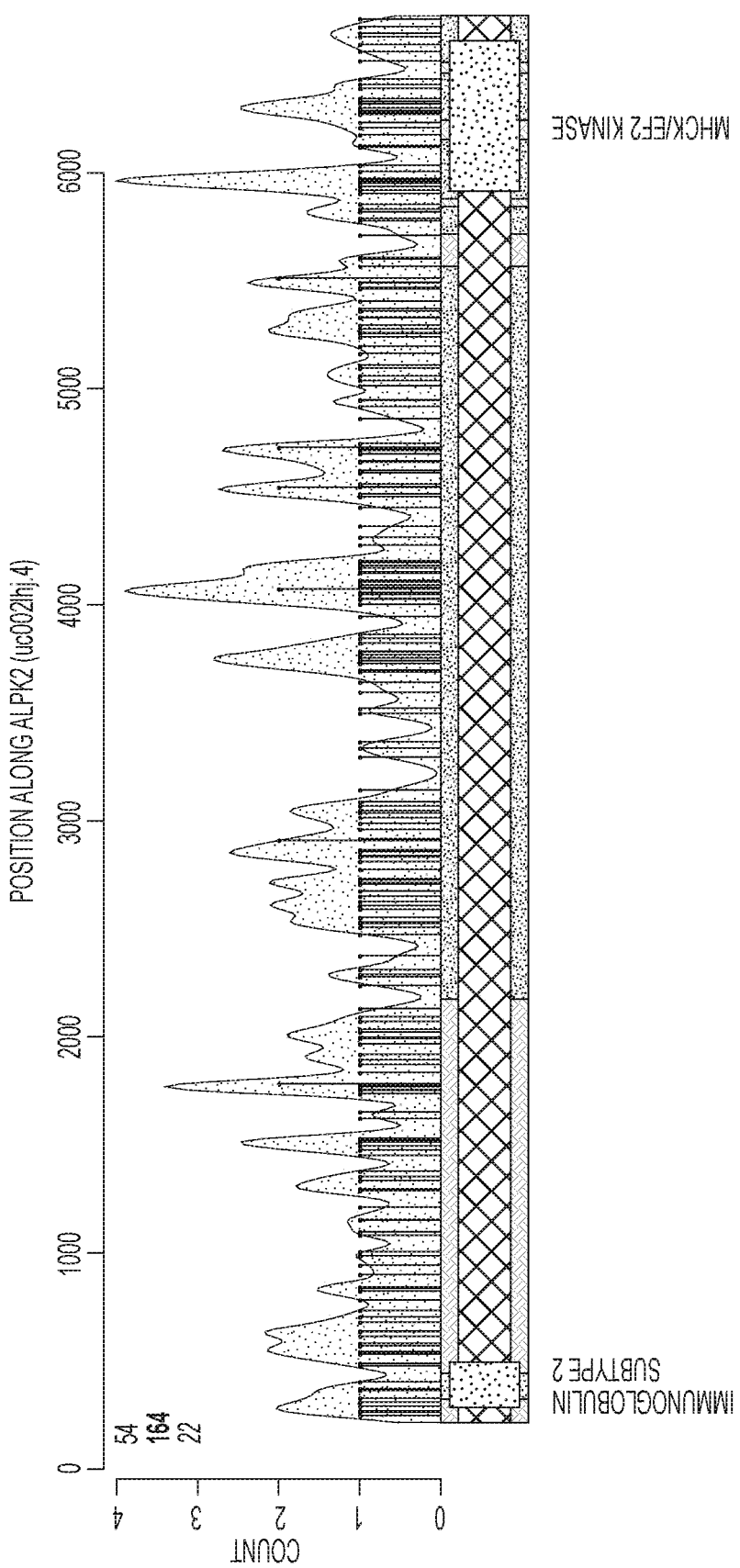
Figure 12D:
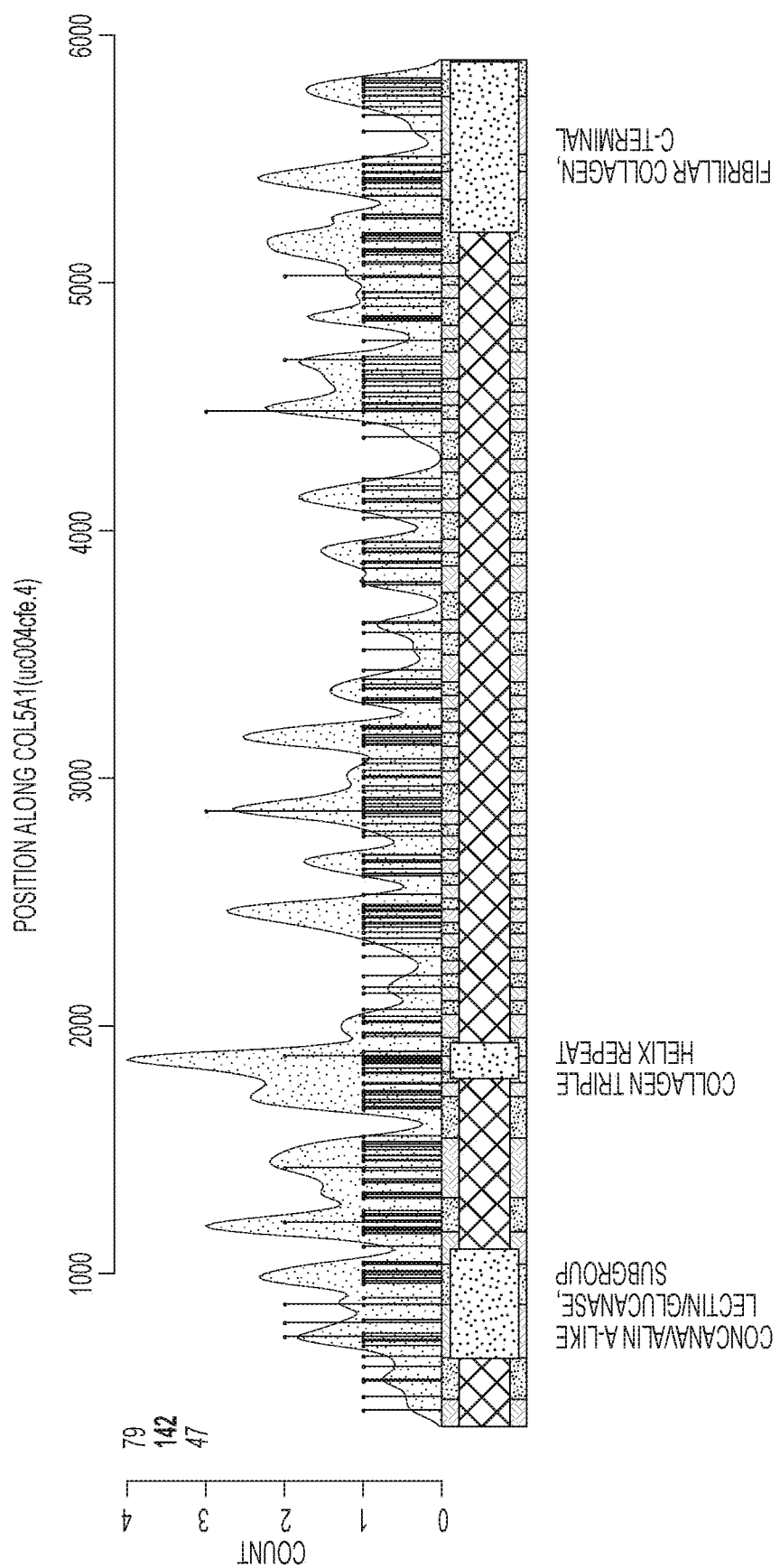
Figure 12D:
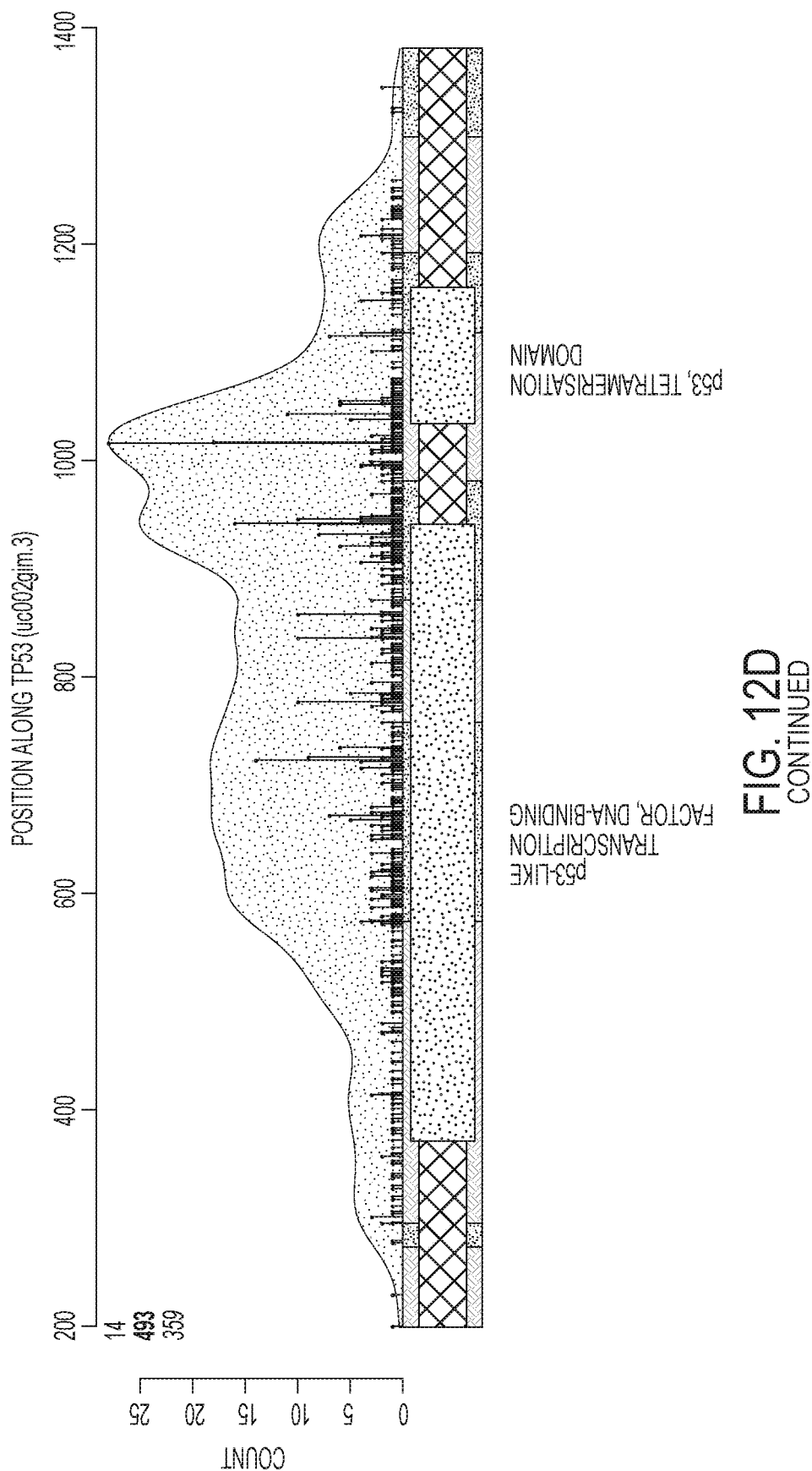
Figure 12D:
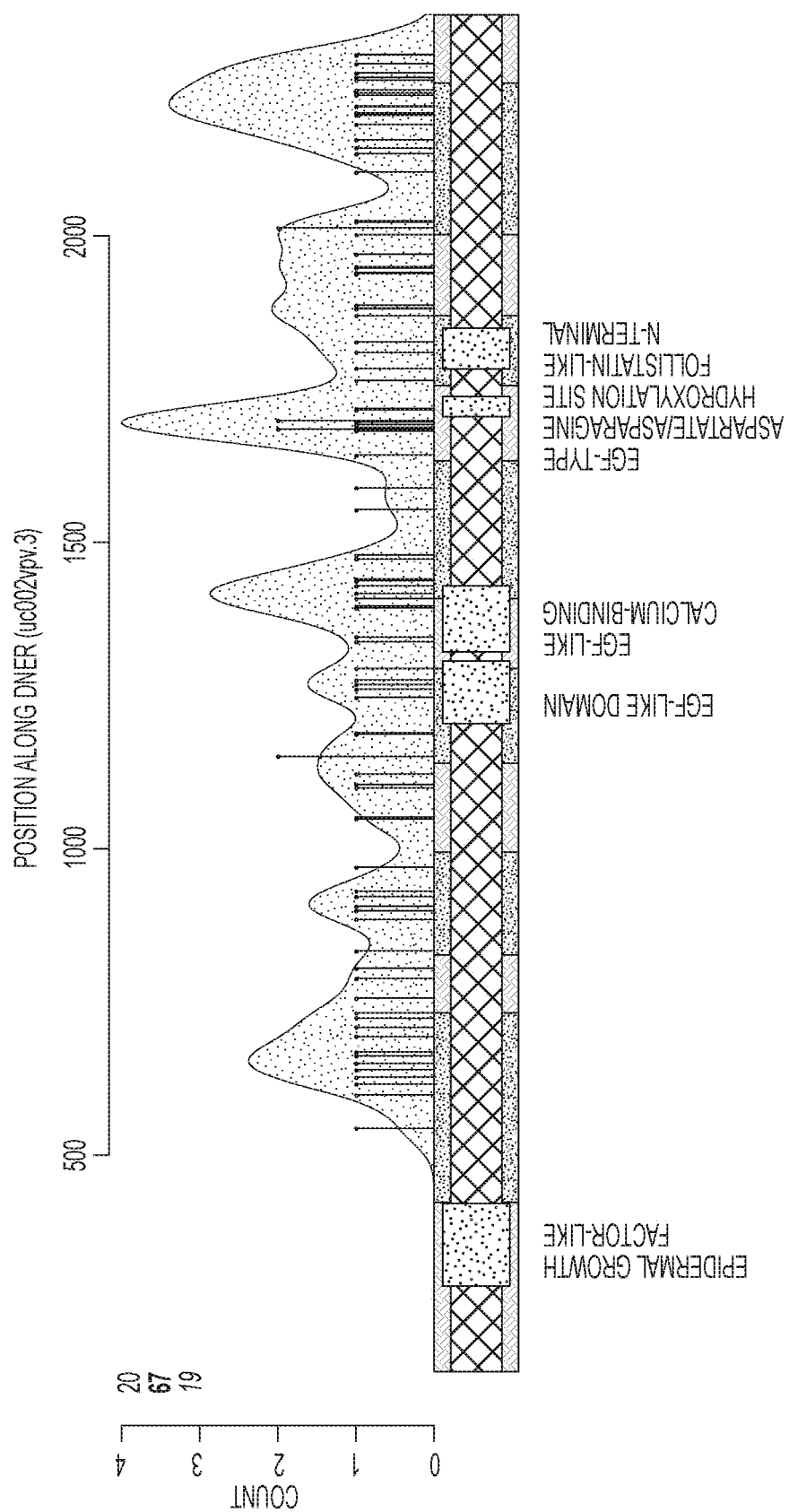
Figure 12D:
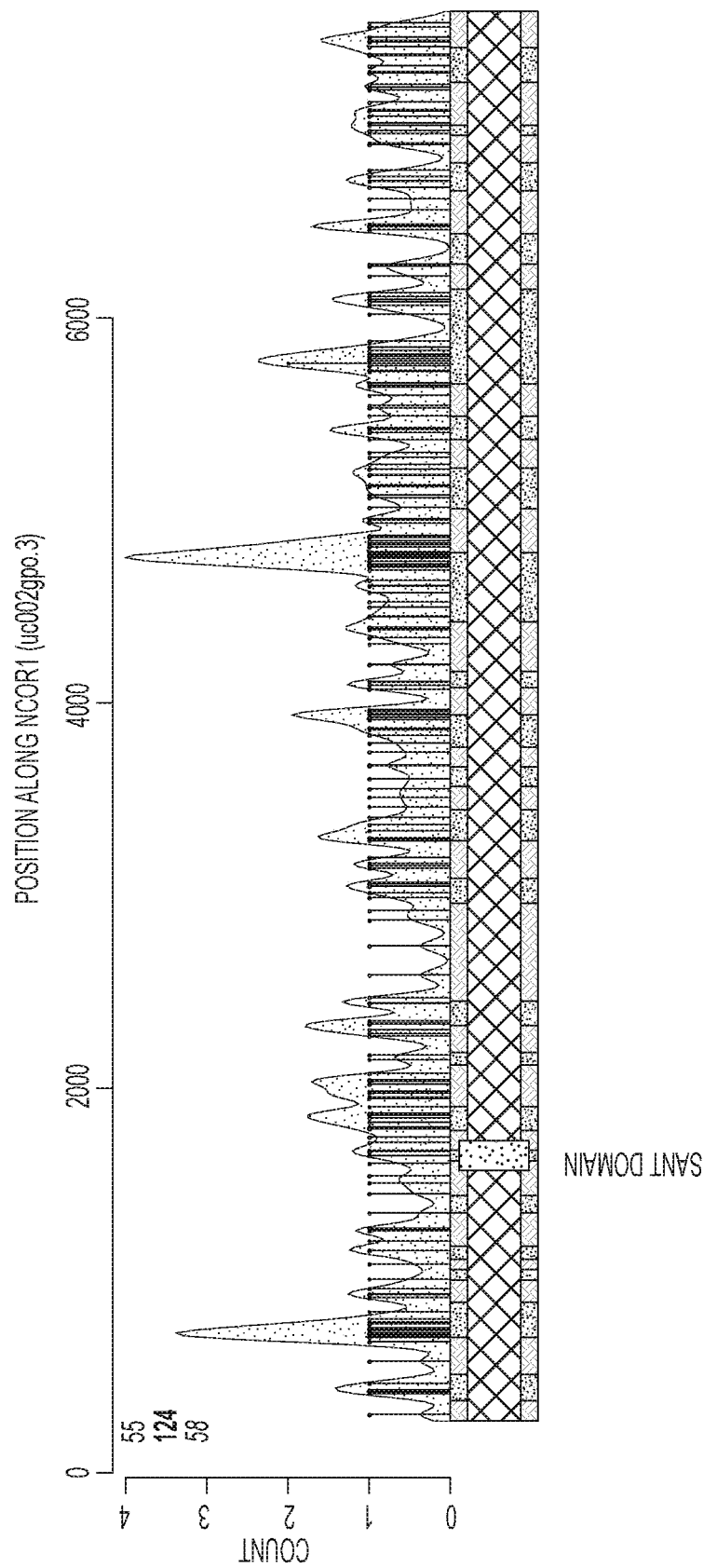
Figure 12D:
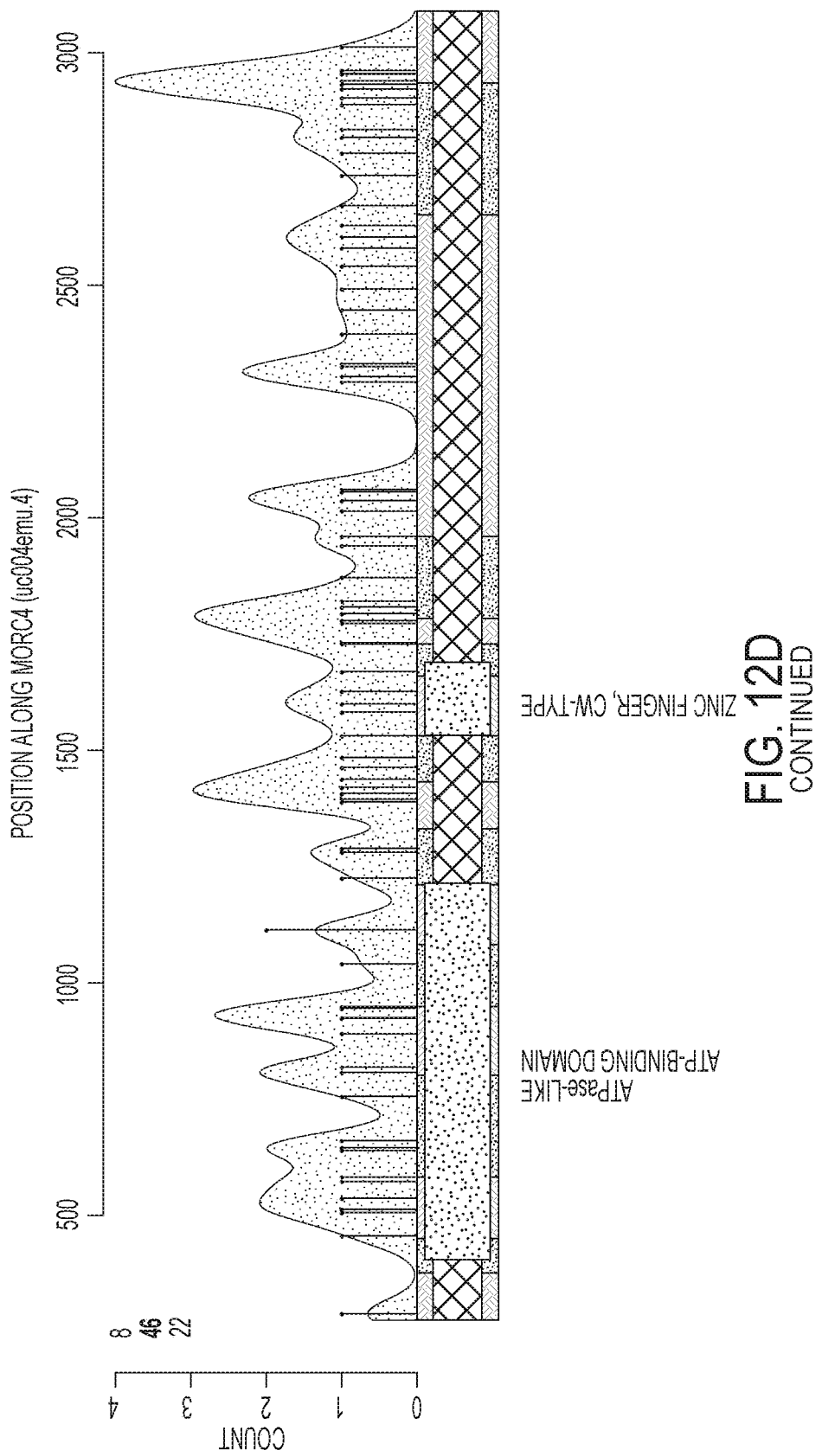
Figure 12D:
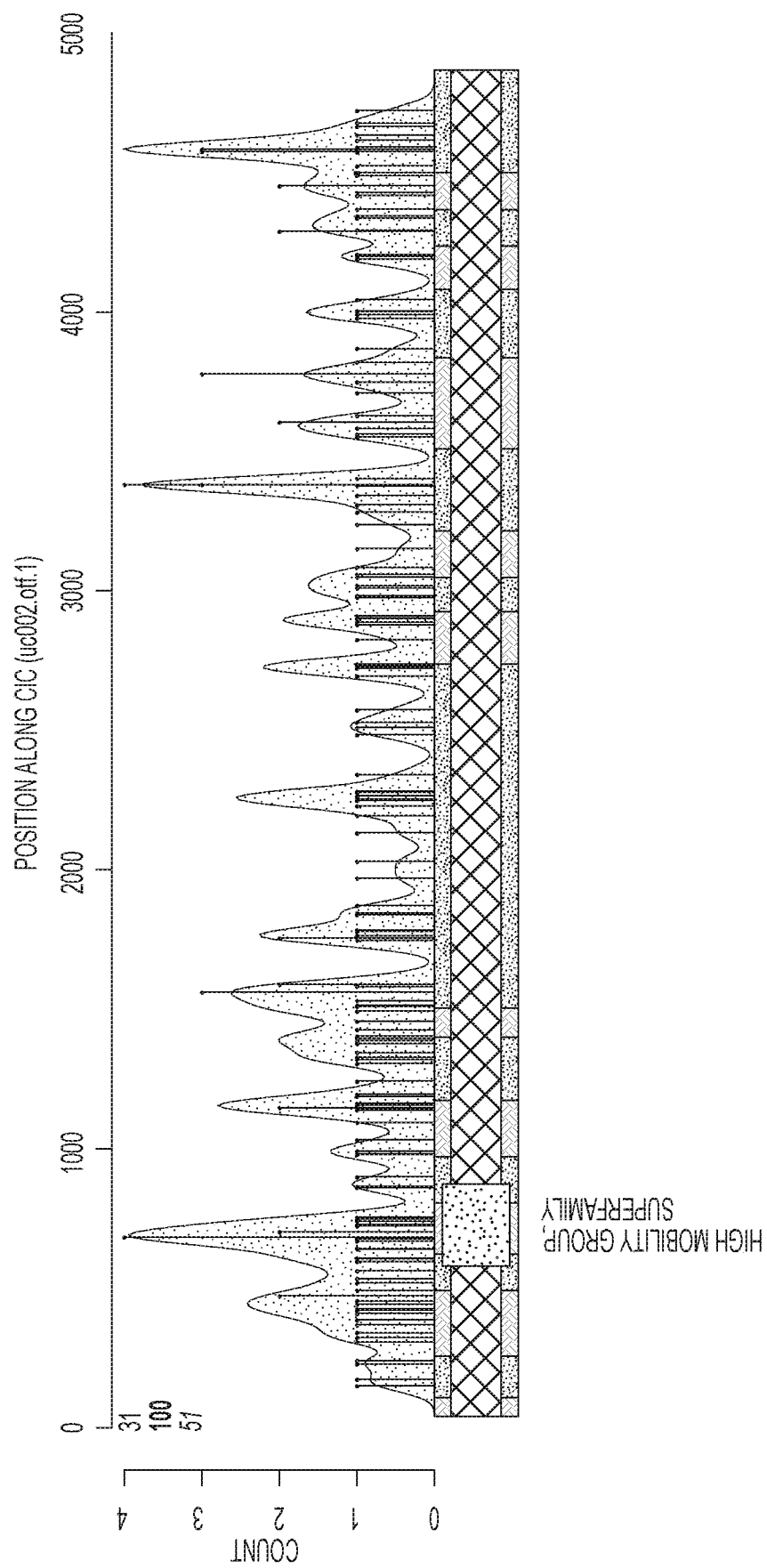
Figure 12D:
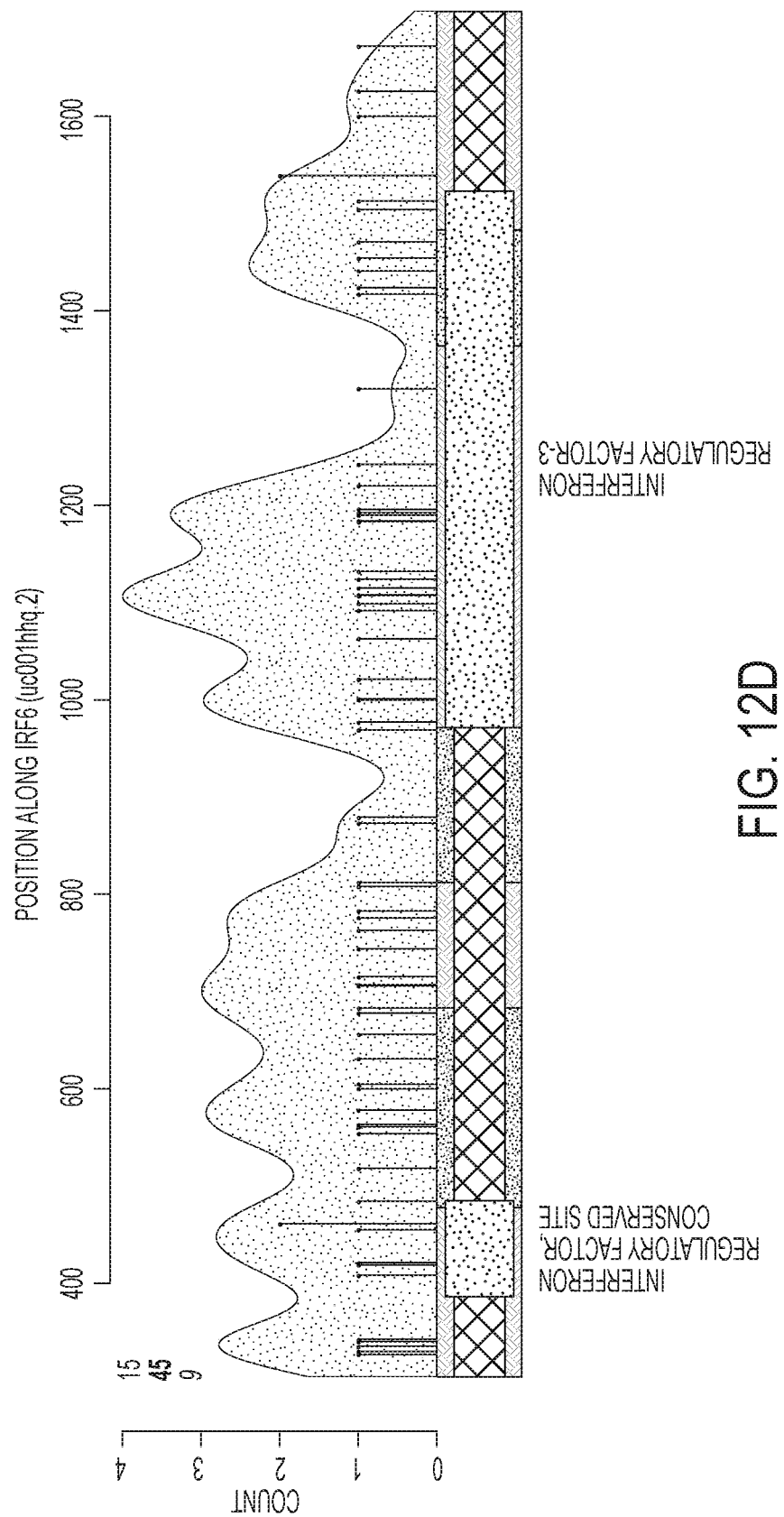
Figure 12D:
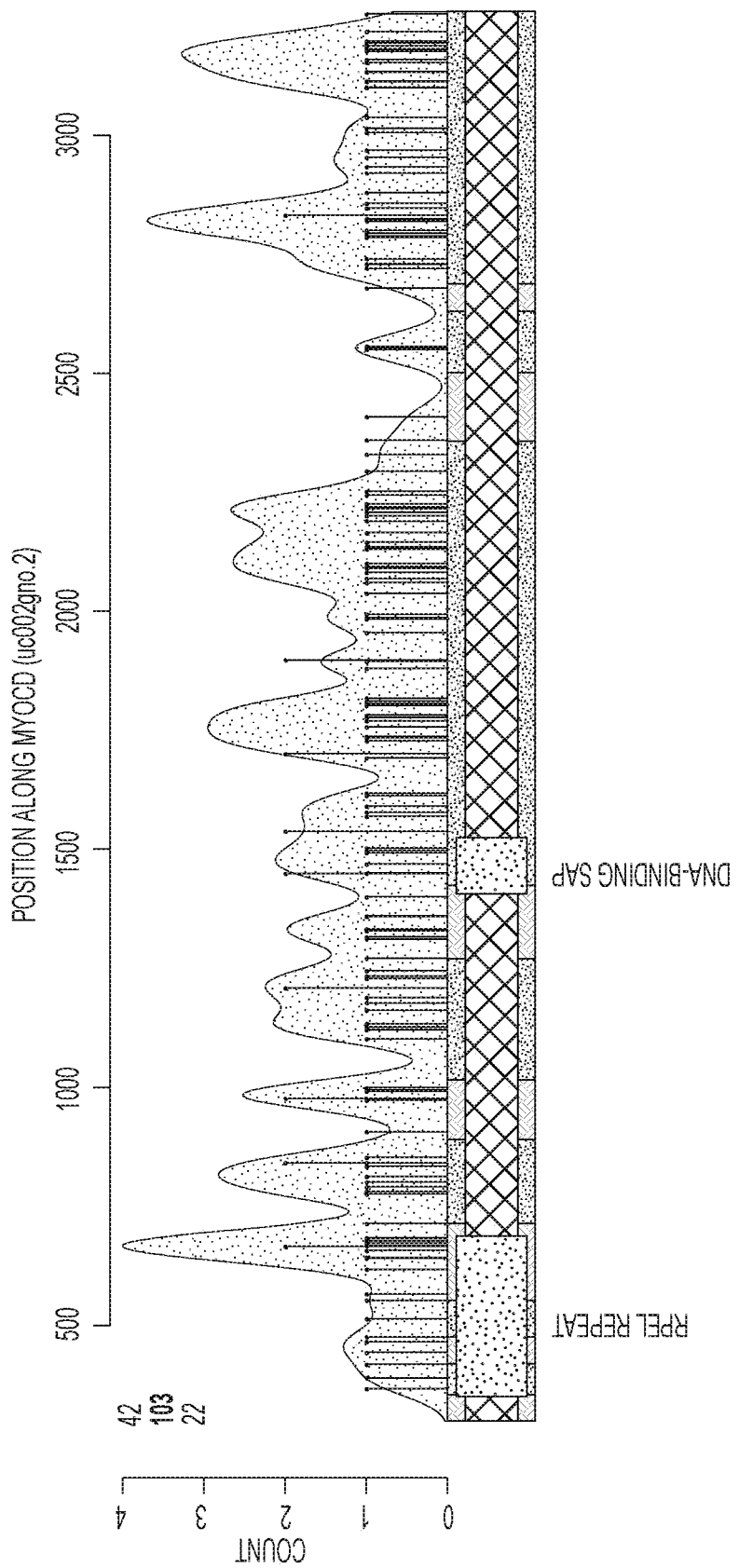
Figure 12E:
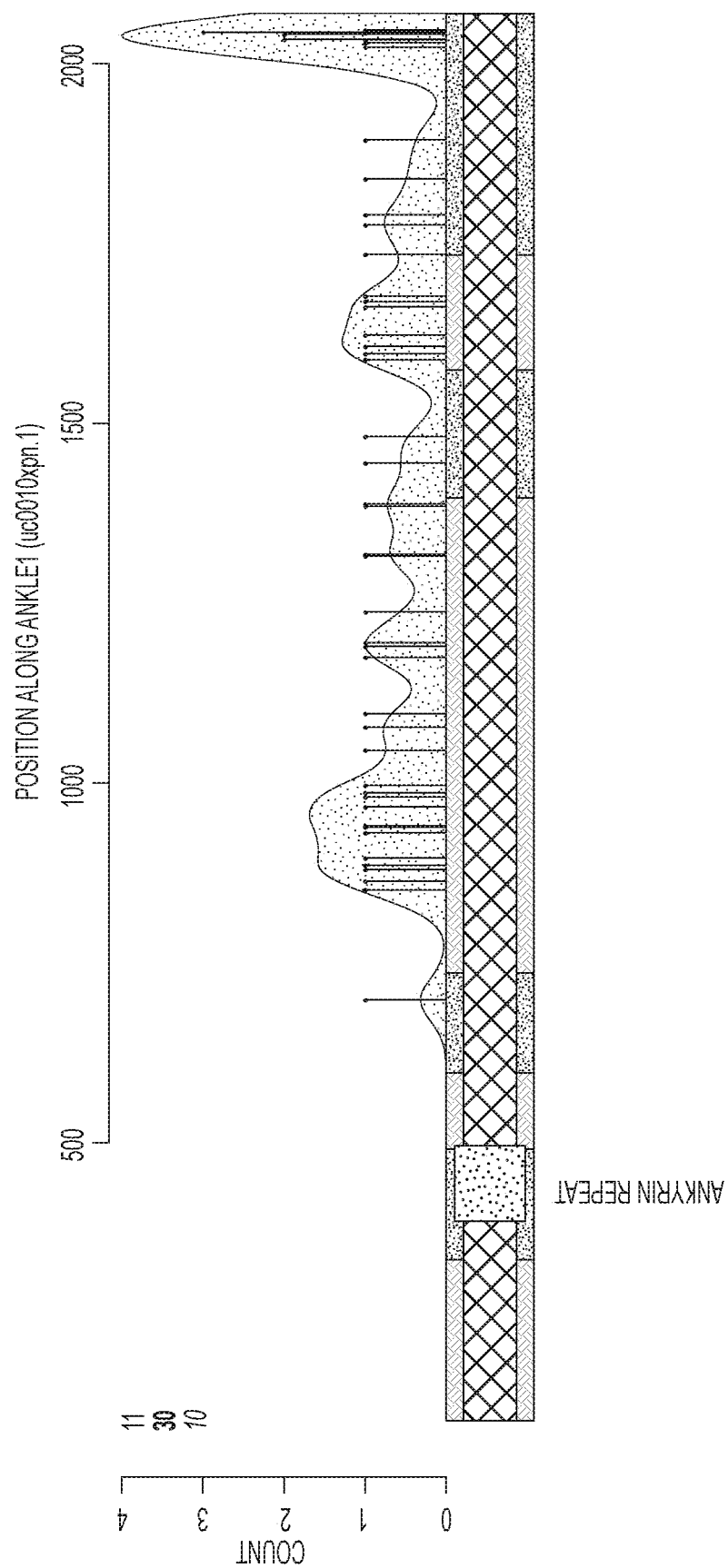
Figure 12E:
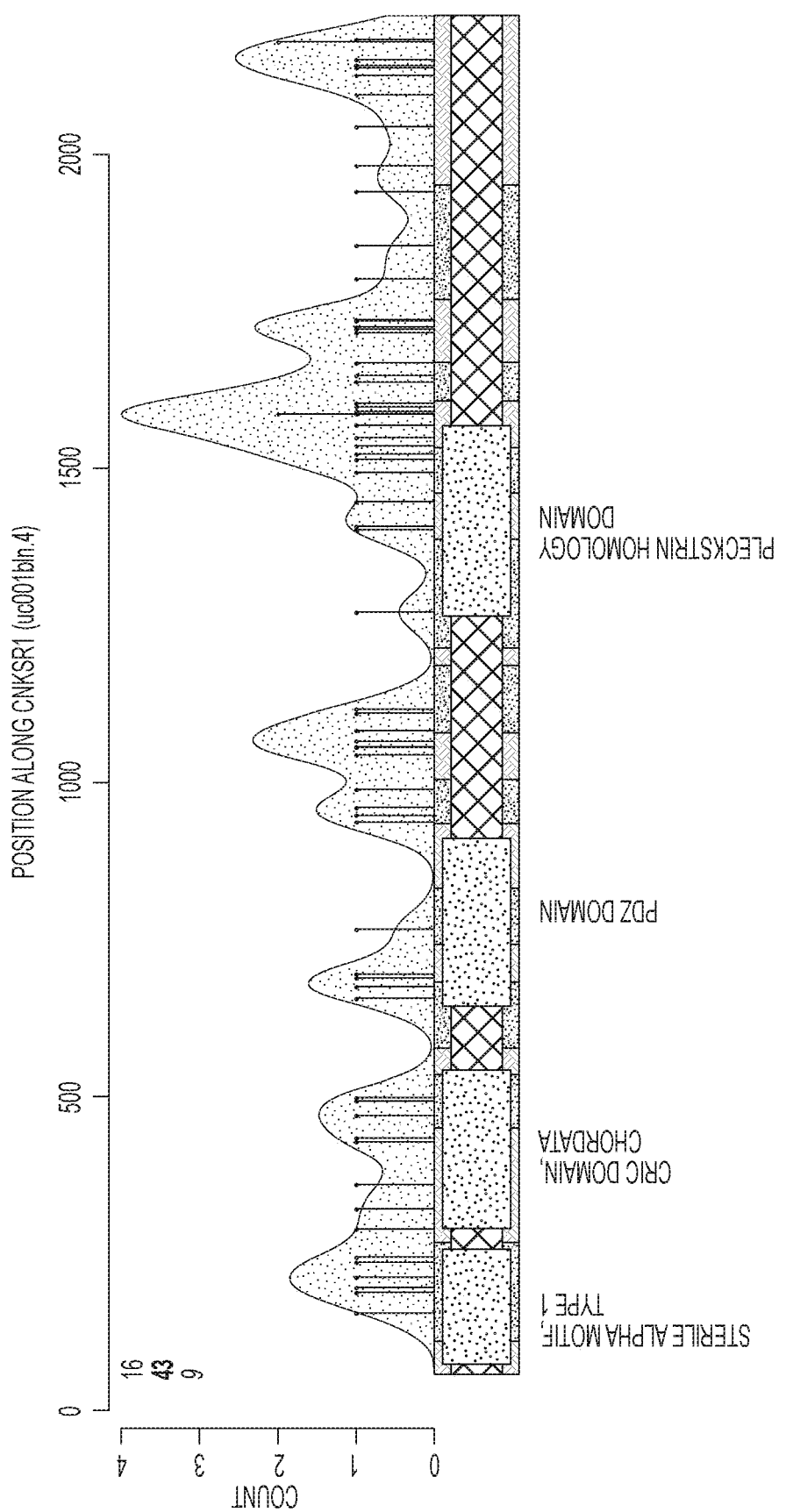
Figure 12E:
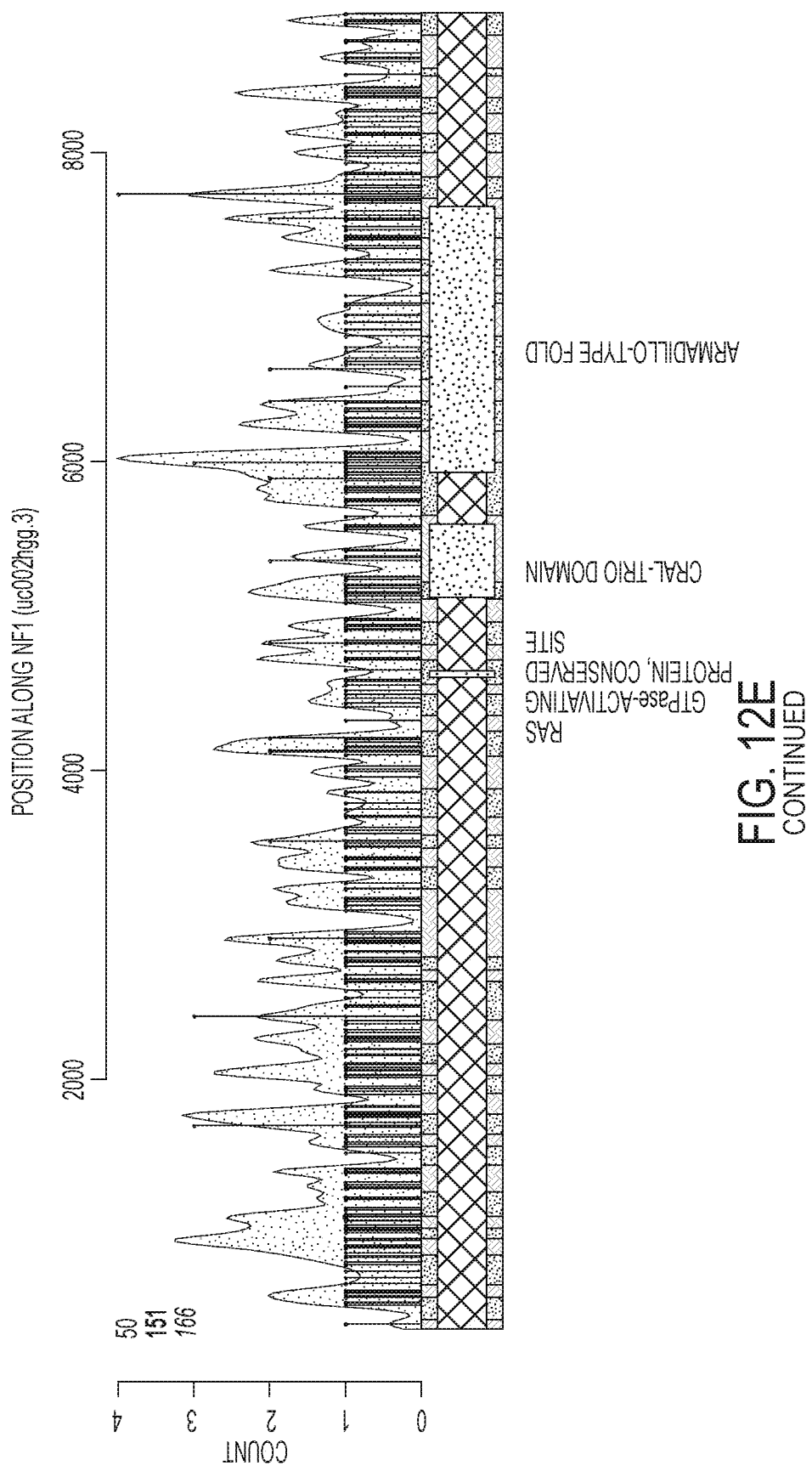
Figure 12E:
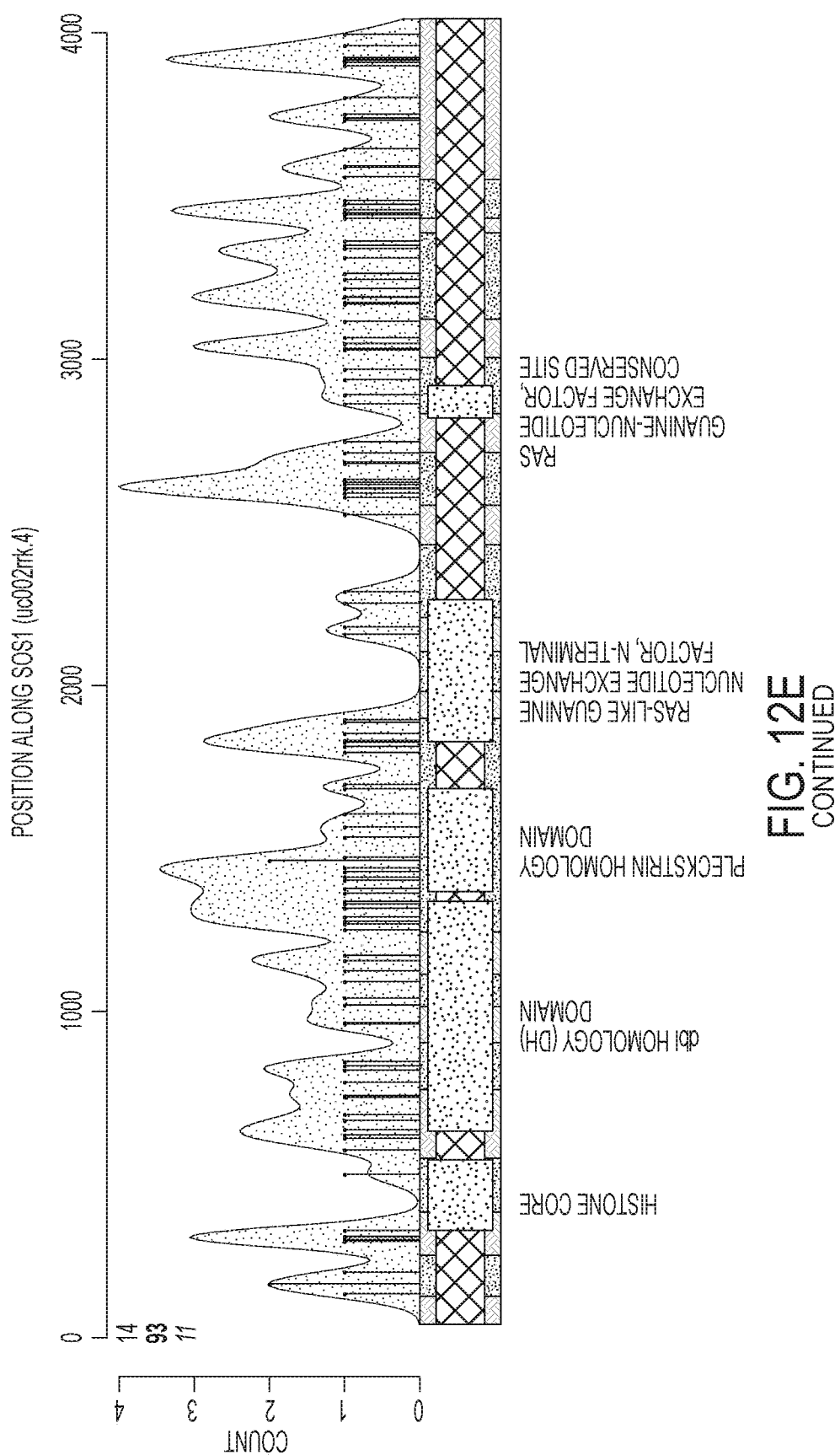
Figure 12E:
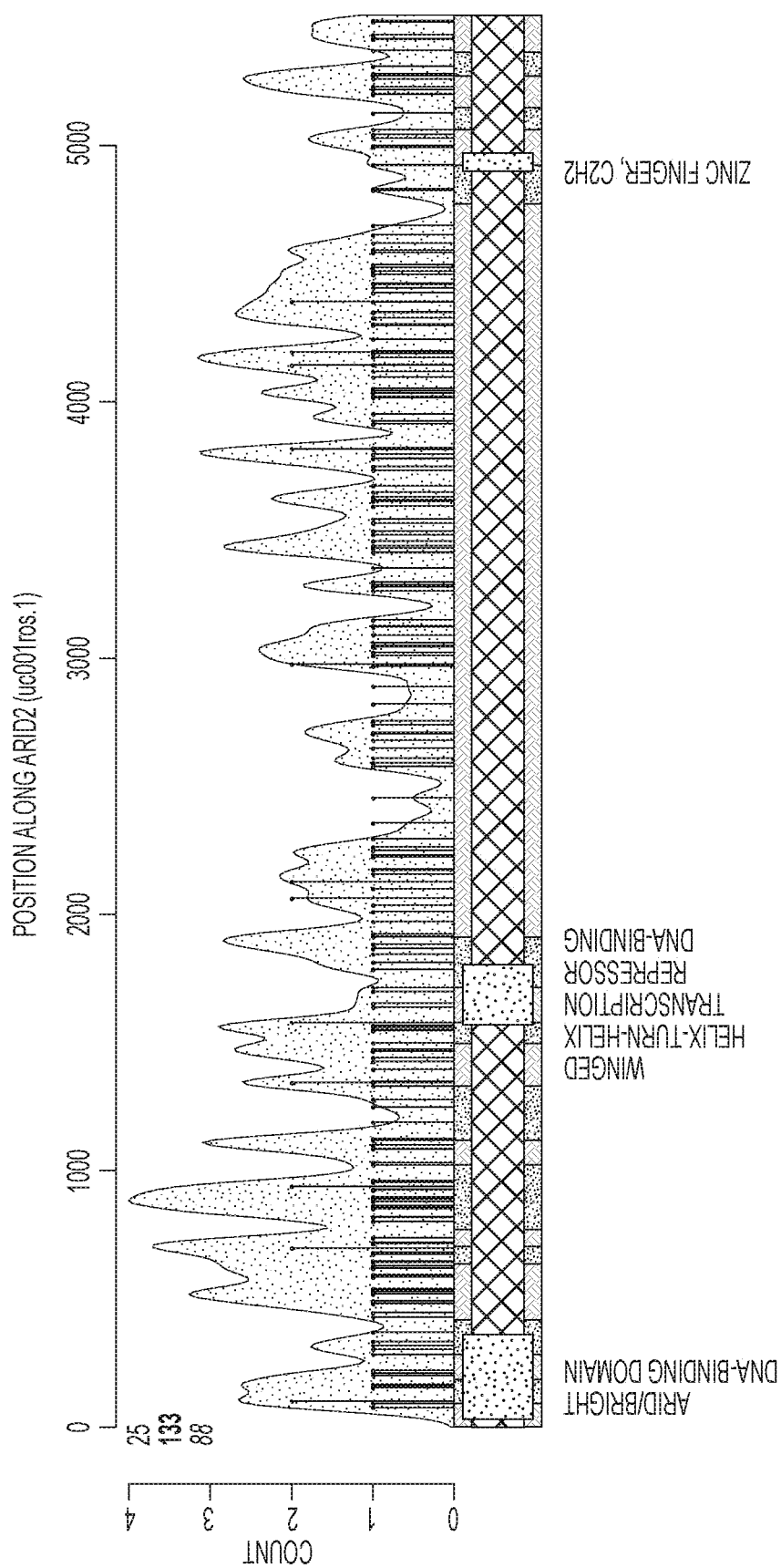
Figure 12E:
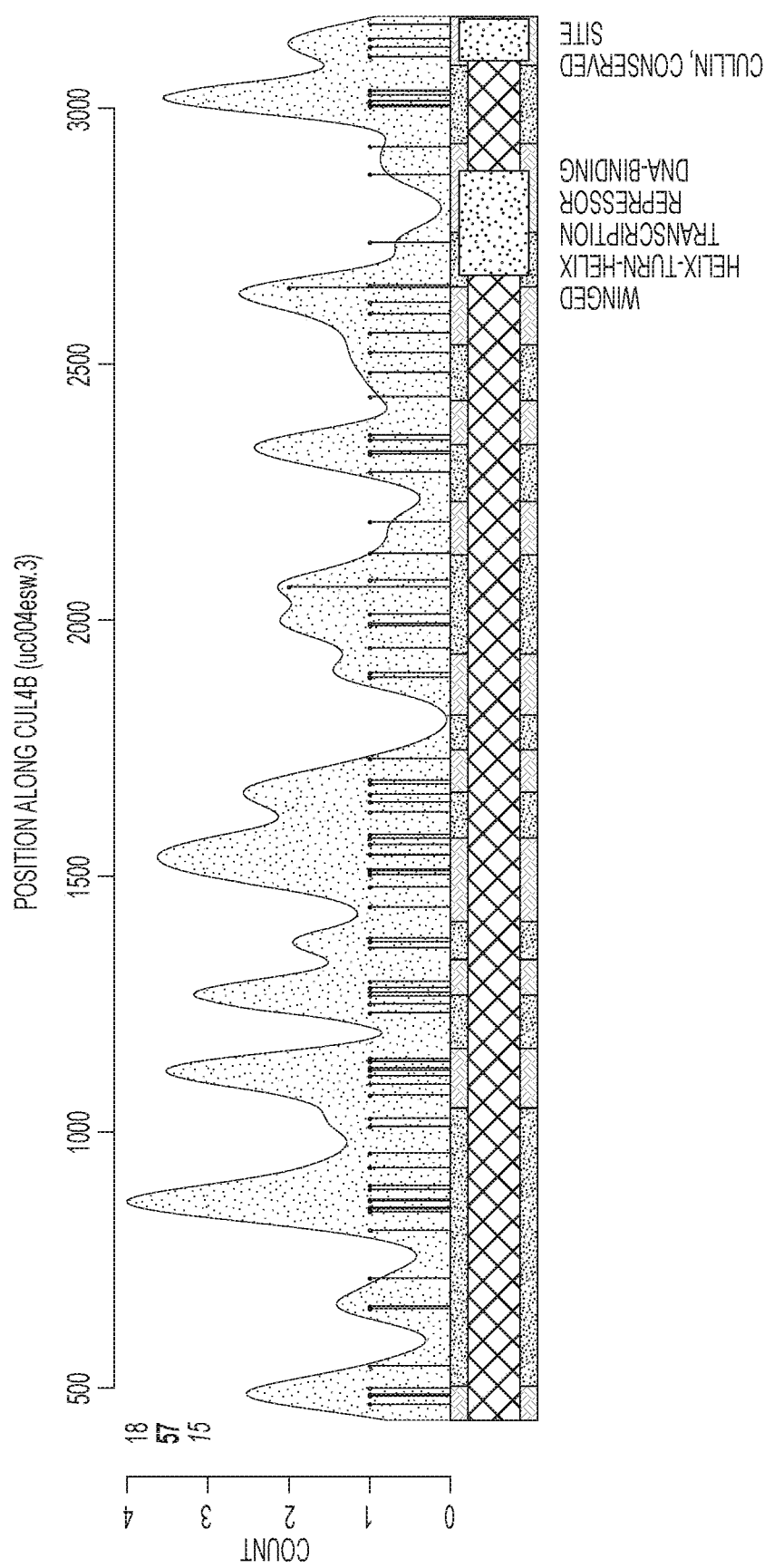
Figure 12E:
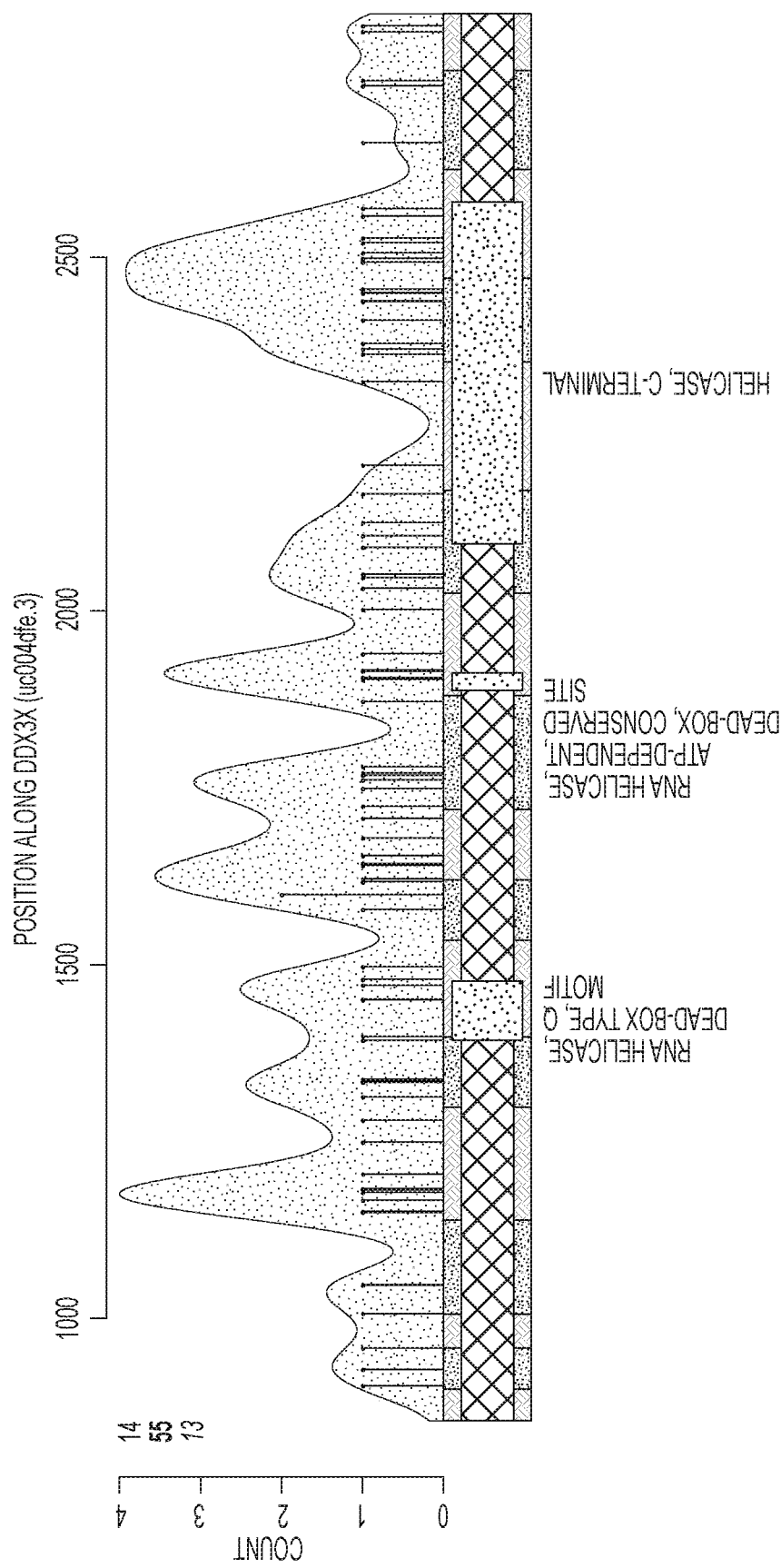
Figure 12E:
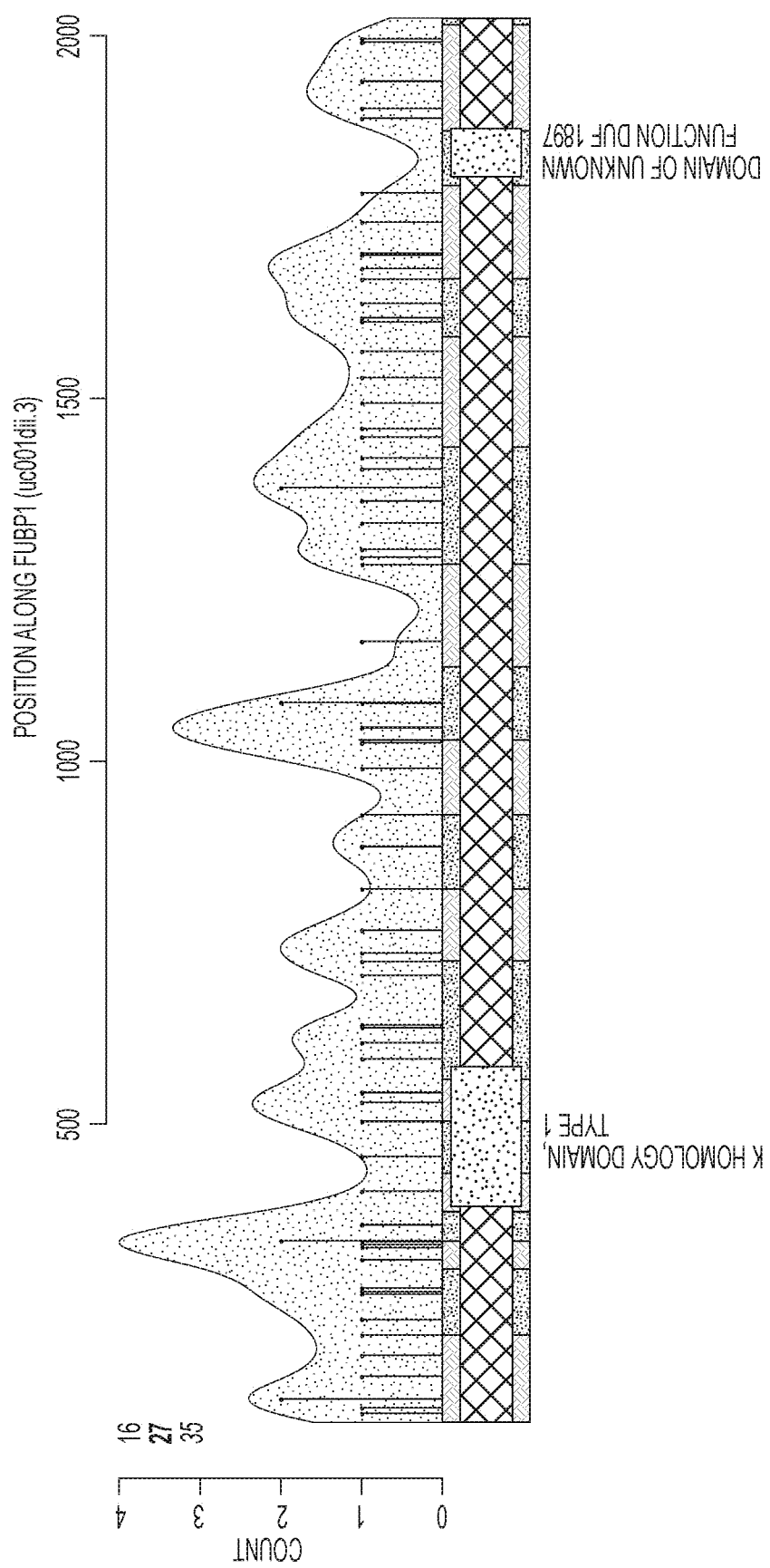
Figure 12F:
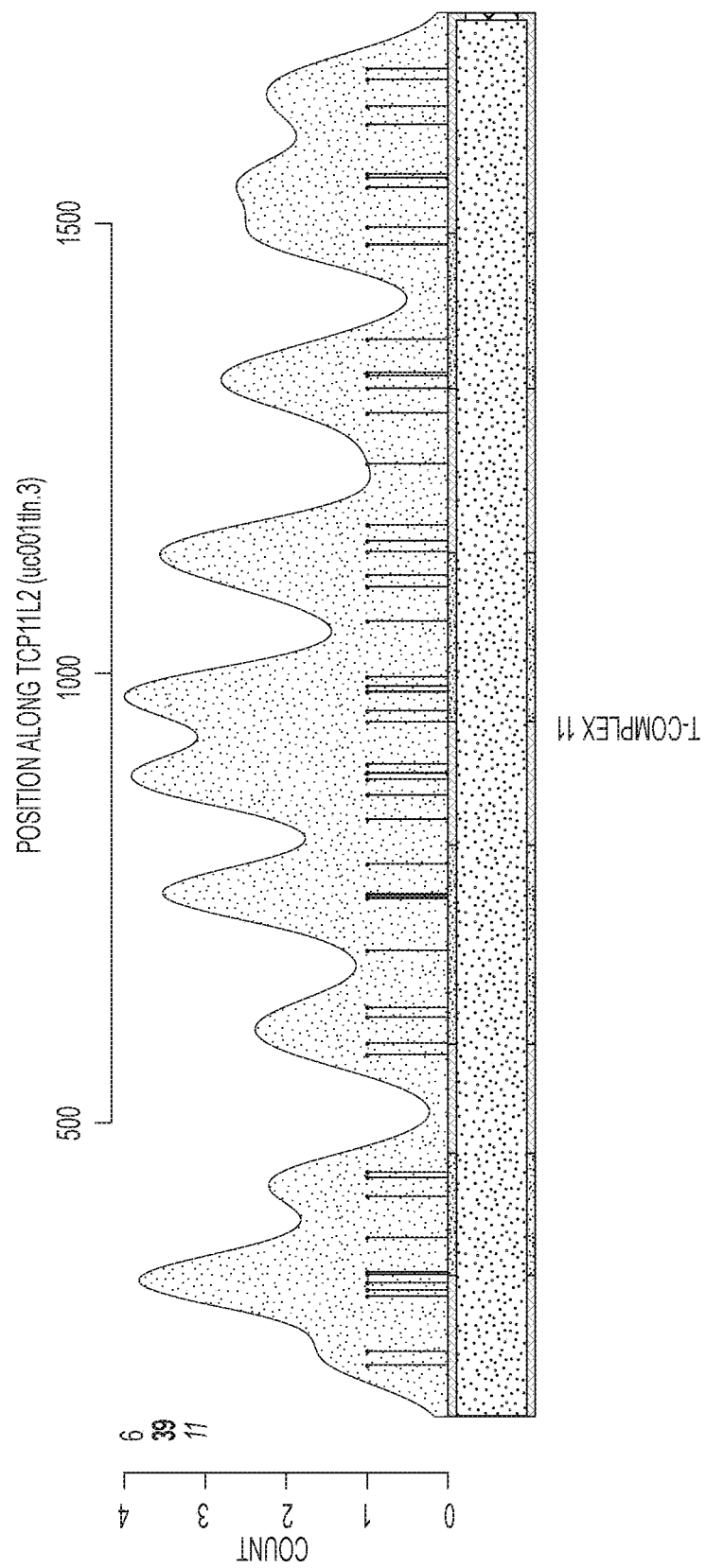
Figure 12F:
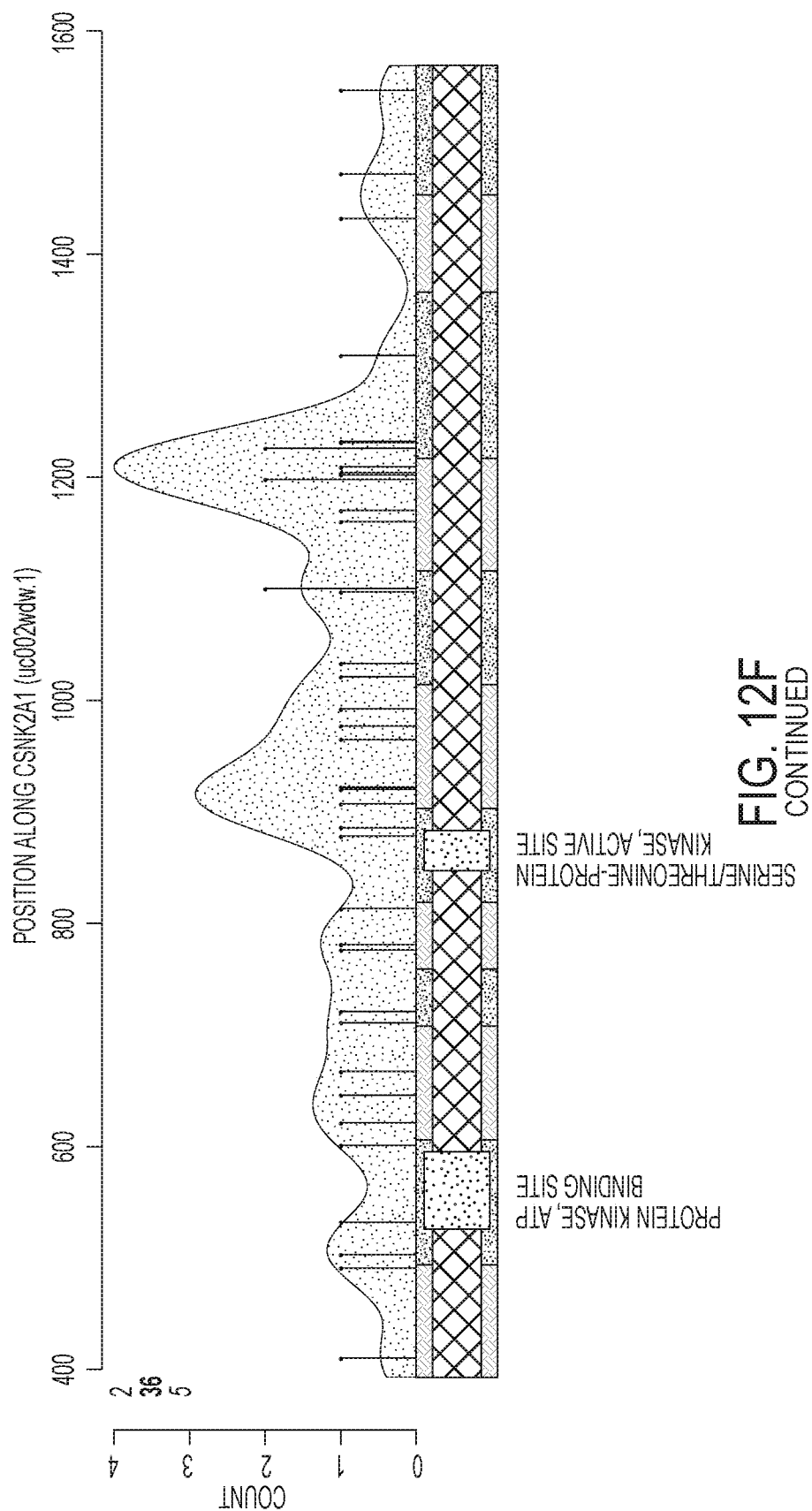
Figure 12F:
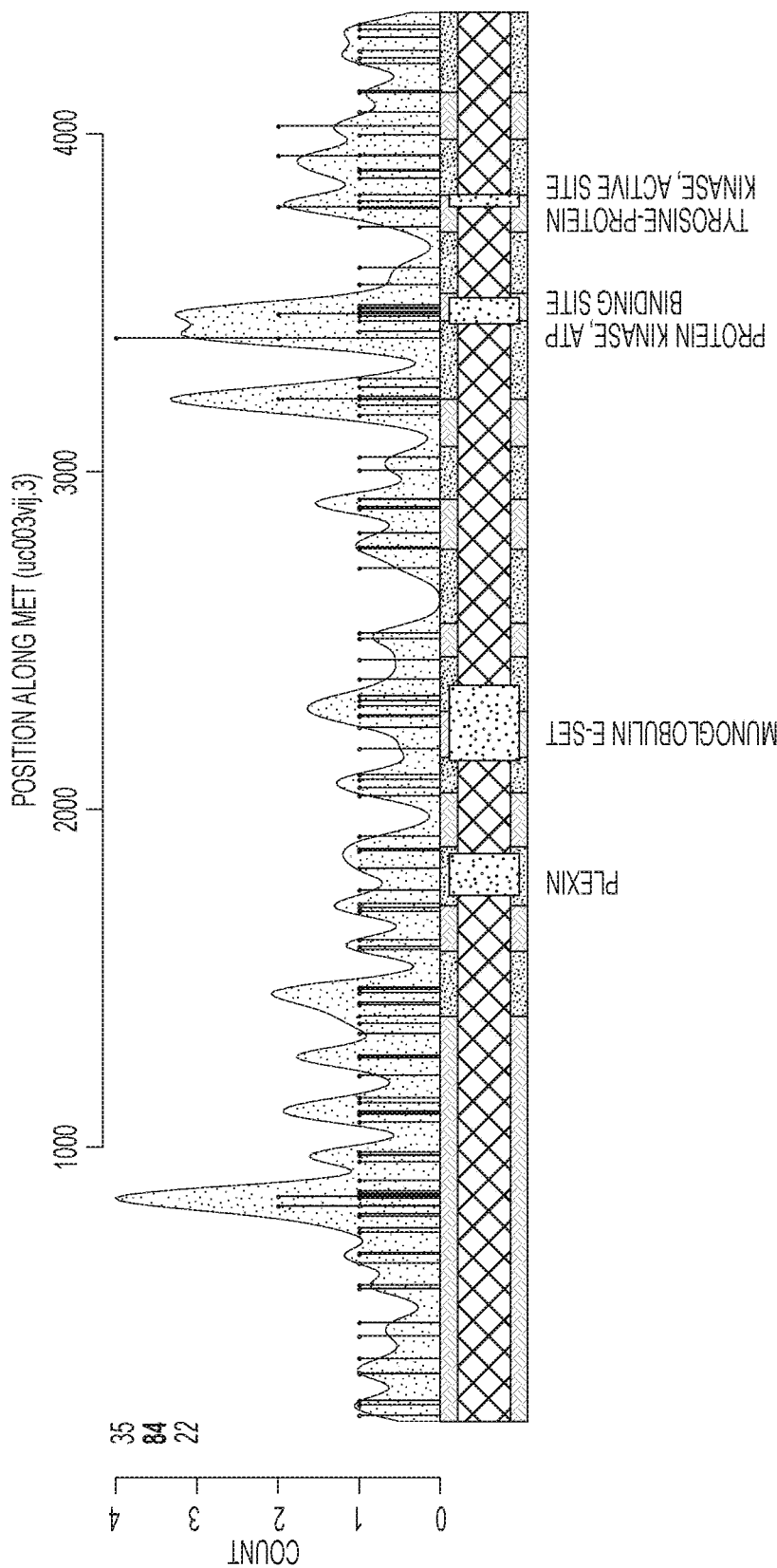
Figure 12F:
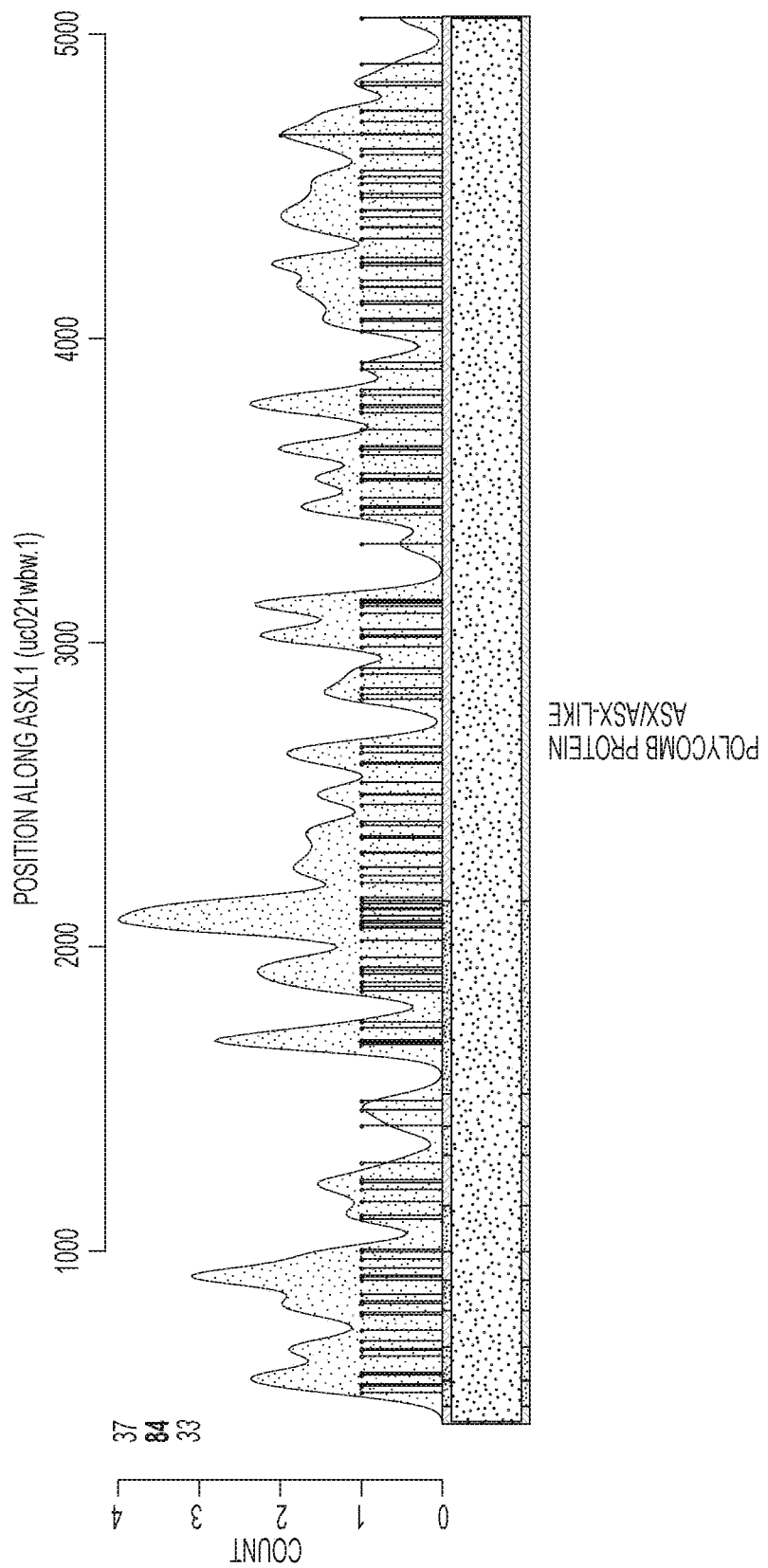

In order to visualize the mutations affecting each significantly CYT-associated gene, a representation was modeled after a popular cancer genomics tool (Gao et al., 2013) (FIG. 12C). To define the functional subdomains of each gene, the amino acid sequence was processed by InterProScan (Jones et al., 2014) which identified known motifs. When enriched domains overlapped, the smallest was selected for visual representation. In order to depict clusters of mutation, the local density of mutations was depicted using the density( ) function in R, specifying a smoothing bandwidth of 30 nucleotides.

Though CYT was the primary focus, Applicants also explored whether other cell type signatures (quantified by ssGSEA) would have mutational associations. For this, Applicants used the same "hit" identification pipeline as described above for CYT.

To identify genes specifically mutated in MSI-high vs. MSI-low/MSS tumors, Fisher's exact test was used to test for enrichment of non-silent mutation status in each of the 351 candidate genes. P-values were adjusted using the Benjamini Hochberg (BH) method.

A set of additional immune genes, which were frequently mutated in cancer but did not show mutational associations with CYT or the cell type expression markers, were assessed in terms of their gene expression correlates using an unbiased approach. To characterize the gene expression correlates of a given gene's mutation, Wilcoxon rank-sum tests were applied to all genes' expression profiles within the tumor type exhibiting the highest rate of mutation of the gene in question. Association scores were defined by multiplying the association sign by the negative log p-value, and genes were sorted by score and submitted to GOrilla (in forward and reverse order).

Identifying Copy Number Alterations (CNAs) Significantly Enriched in High-/Low-CYT Tumor Biopsies To test for CNA association, a regression approach was utilized similar to that used for the point mutation analysis. To test a given gene, rank-scaled CYT across all TCGA tumor samples was modeled as a function of the gene's copy number, cancer type (at the histological subtype level, as described previously), and three variables representing the overall copy number disruption of each tumor. These latter three variables were meant as additional controls for stromal biopsy fraction (which may negatively impact the ability to make focal amplification/deletion calls) and included 1) a rank-scaled count of genes with positive copy number signal 2) a rank-scaled count of genes with negative copy number signal and 3) a rank-scaled estimate of the number of chromosomal "events" (obtained by placing the genes in genomic order and counting the number of times the copy number signal switched between positive/zero/negative). This linear regression approach was applied twice. The first run was amplification-centric, so the copy number variable was adjusted such that negative values were set to zero (such that neutral and deleted regions are zero, and amplified regions are positive). The second run was deletion-centric, so the copy number variable was adjusted such that positive values were set to zero and the sign flipped (such that neutral and amplified regions are zero and deleted regions are positive). Thus, in both regressions, a positive copy number coefficient represented a positive association between CYT and lesion, and a negative copy number coefficient represented a negative association between copy number and lesion. The p-value of the coefficient was considered a measure of the strength of the evidence for association.

Because copy number alterations rarely affect a single gene, association signals were highly auto-correlated, meaning that genomic neighbors likely had a similar enrichment score. Because gene scores do not truly represent independent tests, standard multiple hypothesis correction procedures could not be employed at the per-gene level. Instead, an alternative approach based on permutation testing was used to assign adjusted p-values to each "peak." A "peak" was defined as a continuous stretch of genes (arranged in genomic order) with a nominal p-value less than 0.01, and the peak score was defined as the minimum p-value in the peak. To obtain the null distribution of peak scores, the CYT variable was randomly re-permuted and the entire process repeated (testing individual genes, defining peaks, and obtaining peak scores). This was repeated 500 times each for the amplification analysis and the deletion analysis yielding a peak score null distribution. The quantile of each true peak score within the peak score null distribution was taken as a peak p-value. The set of peak p-values were then subjected to standard B-H correction.

For each amplification hit, the copy number of the peak gene was then tested for association with CYT in each individual cancer type (following the same approach taken in the point mutation analysis). Cancer-specific association was defined when the uncorrected p-value was less than 0.05.

As in the point mutation analysis, the pipeline was repeated exploring for CNA associations with other cell type signatures.

Necrosis and ALOX Amplifications

The amplification of ALOX15B was tested for association with necrosis in each tumor type by using a linear regression that modeled percent necrosis as a function of ALOX15B amplification and three additional background mutation rate variables added to avoid confounding (rank-transformed count of amplified genes, rank-transformed count of deleted genes, and rank-transformed count of events, as described previously).

Example 1

A Metric for Immune Cytolytic Activity Based on Gene Expression in TCGA Tumors

To study immune effector activity in solid tumors, Applicants focused on cytotoxic T cells (CTL) and natural killer cells (NK) because of their potent ability to kill tumor cells and numerous studies showing that effector T cells at the tumor site predict favorable outcome across many cancers (Pages et al., 2005; Sato et al., 2005; Schumacher et al., 2001). Using RNA-Seq data from >7000 TCGA solid tumor biopsies, Applicants devised a simple and quantitative measure of immune cytolytic activity ('CYT') based on transcript levels of two key cytolytic effectors, granzyme A (GZMA) and perforin (PRF1), which are dramatically upregulated upon CD8+ T cell activation (Johnson et al., 2003) and during productive clinical responses to anti-CTLA-4 and anti-PD-L1 immunotherapies (Ji et al., 2012) (Herbst et al., 2014). Consistent with their coordinated roles, GZMA and PRF1 were tightly co-expressed in TCGA samples (FIG. 8A, FIG. 8B) and showed CTL-specific expression in panels of human cell types (FIG. 8C, FIG. 8D), thus serving as highly specific markers in heterogeneous tumor samples.

Figure 1A:
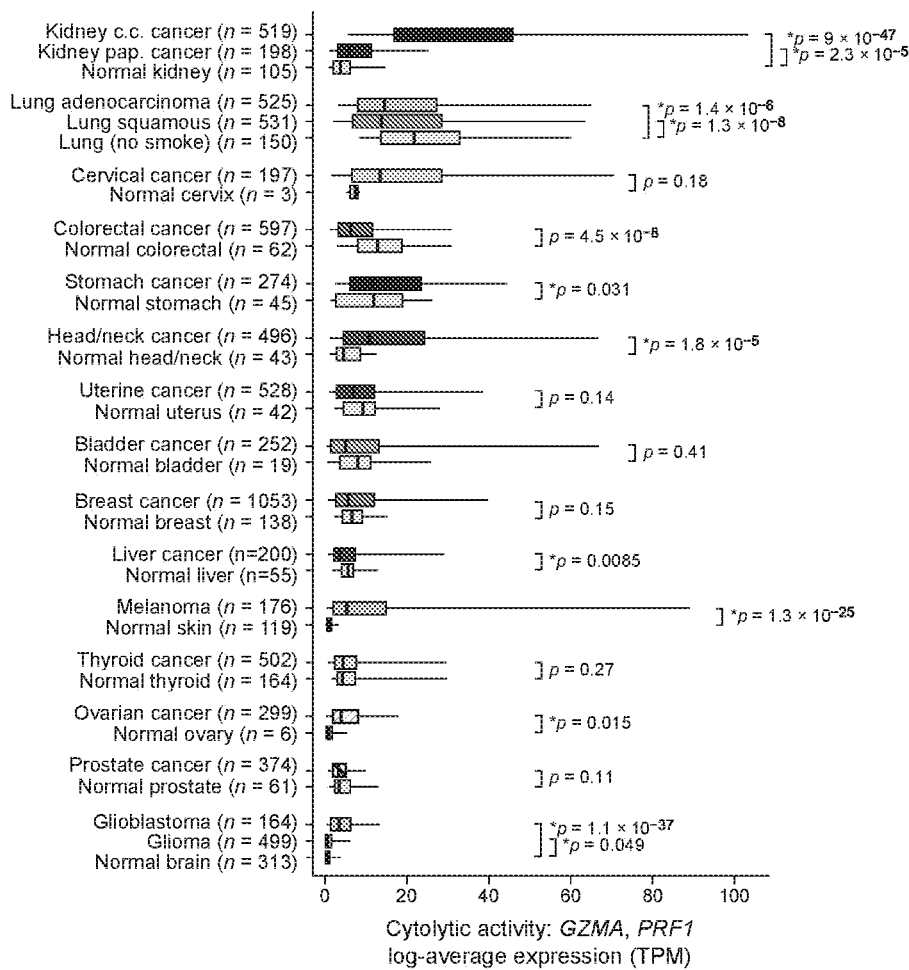
FIG. 1A-1B illustrates that immune cytolytic activity (CYT) varies across tumor types and is associated with suppressive factors. (A) Cytolytic activity (CYT), defined as the log-average (geometric mean) of GZMA and PRF1 expression in transcripts per million (TPM), is shown for each of 18 TCGA tumor types and normal tissues. Normal tissue samples include TCGA controls and GTEx samples, excluding smokers for lung tissues. Boxes in box plot represent interquartile and vertical lines $5^{th}$-$95^{th}$ percentile ranges, with a notch for the median. P-values are unadjusted and calculated by Wilcoxon rank-sum test (comparison to relevant normal), and asterisks denote events significant at 10% FDR. (B) The correlation of a gene with CYT across all tumor types is shown (X-axis) relative to it specific expression in CTL/NK cells. Top right, genes expressed in CTL/NK cells that are associated with CYT. Bottom right, non-CTL/NK genes associated with CYT. Average Spearman correlation of expression with CYT was calculated across 18 tumor types. Y-axis: for each gene, median expression in NKs and CTLs divided by median expression in non-hematopoietic cells using CAGE data from Fantom5.

Applicants found that the levels of cytolytic activity were highest in kidney clear cell carcinomas and cervical cancers, lowest in glioma and prostate cancers, and average (albeit skewed to high levels) in melanoma (FIG. 1A). Most normal tissues (from TCGA or the Genotype-Tissue Expression (GTEx) project (GTEx Consortium, 2013a)) showed definitively lower (6 tissues) or equal (7 tissues) cytolytic activity compared to their corresponding tumors, but two showed definitively higher activity (lung and colon). Of note, CYT in colorectal tumors increased considerably given high microsatellite instability (MSI) (FIG. 8E) (Schwitalle et al., 2008). The differences in cytolytic activities across tumor types and compared to normal tissues are likely to reflect a combination of tissue- and tumor-specific mechanisms that regulate local immunity.

Example 2

Figure 1B:
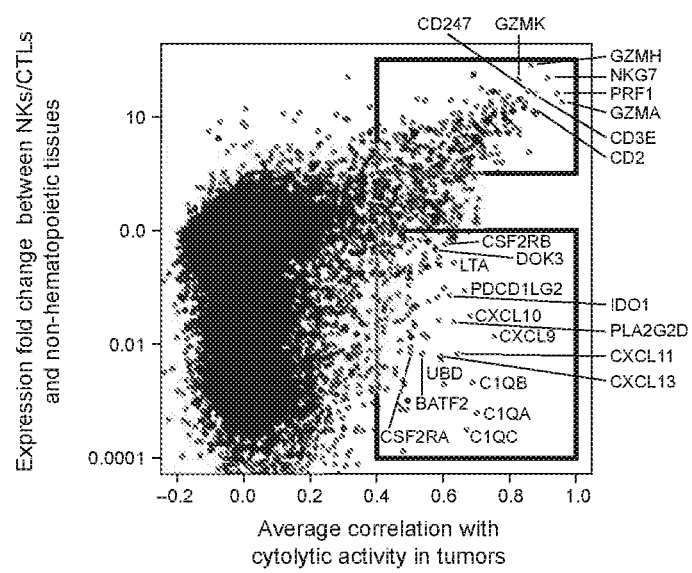

Cytolytic Activity is Associated with Counter-Regulatory Immune Responses and Improved Prognosis To determine whether cytolytic activity is associated with other immune cell types and functions, Applicants calculated the enrichment of 15 immune cell type and function gene sets in the same samples (Table 1; expression data from Fantom5 project (Fantom Consortium et al., 2014)). While CYT showed moderate correlation with B cells and weak correlation with macrophages and, it showed strong correlation with: (i) CTL markers, as expected; (ii) plasmacytoid dendritic cells; (iii) counter-regulatory Tregs and known T-cell co-inhibitory receptors, as seen in chronic inflammatory conditions (FIG. 8F) (Lund et al., 2008). Applicants note that expression of the pre-defined gene sets was similarly enriched in most tumor and normal tissues, with some notable differences (FIG. 8G)). Finally, when Applicants looked for CYT correlations with any transcript (filtering out CTL and NK genes), Applicants found that CYT was best correlated with immunosuppressive factors (Spranger et al., 2013), such as PDCD1LG2 (PDL2), IDO1/2, DOK3 (Lemay et al., 2000), GMCSF receptor (CSF2RA, CSF2RB) and the C1Q complex (FIG. 1B). In addition, it was also associated with interferon-stimulated chemokines (CXCL9, CLCL10, and CXCL11) that attract T cells, as observed previously (Bindea et al., 2013). Applicants conclude that tumors can differ dramatically in their infiltrate levels and composition, and that cytolytic activity is associated with counter-regulatory activities that limit the immune response.

Figure 8A:
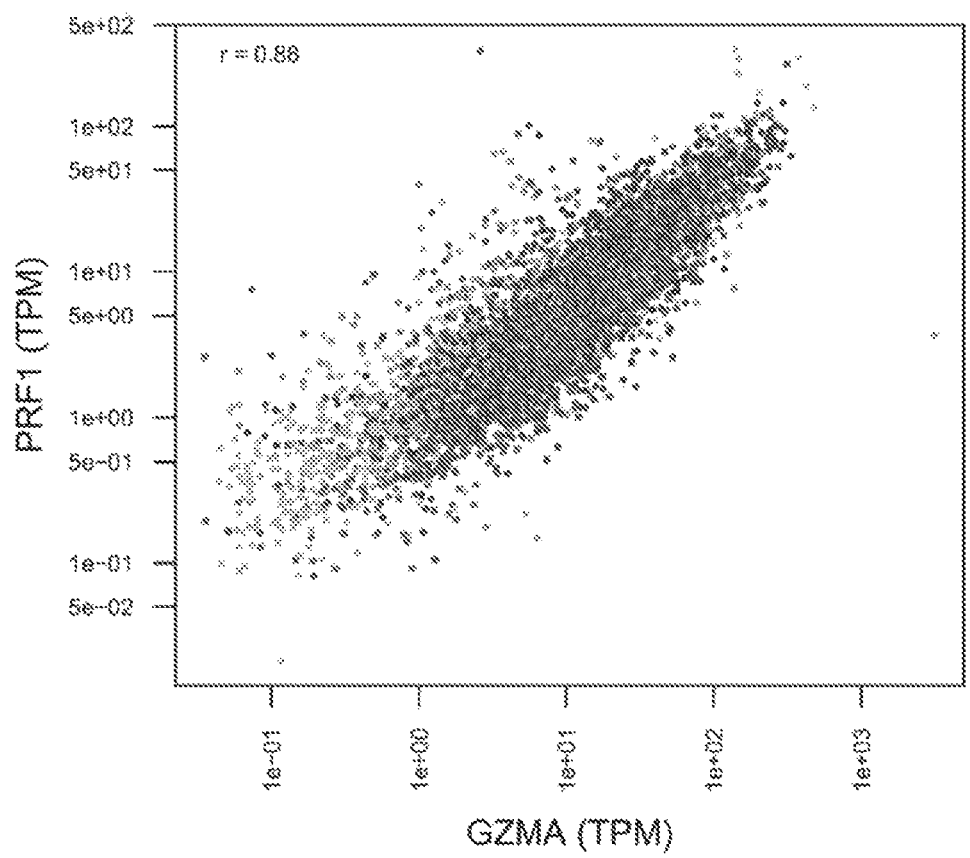
Figure 8B:
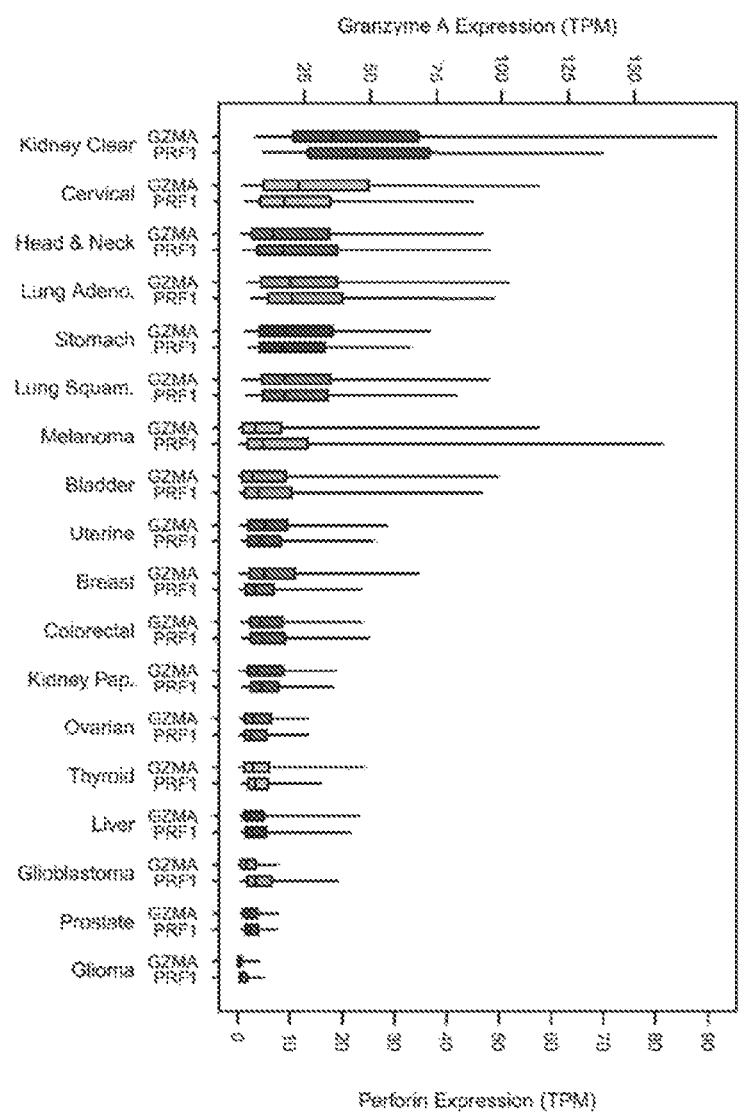
Figure 8C:
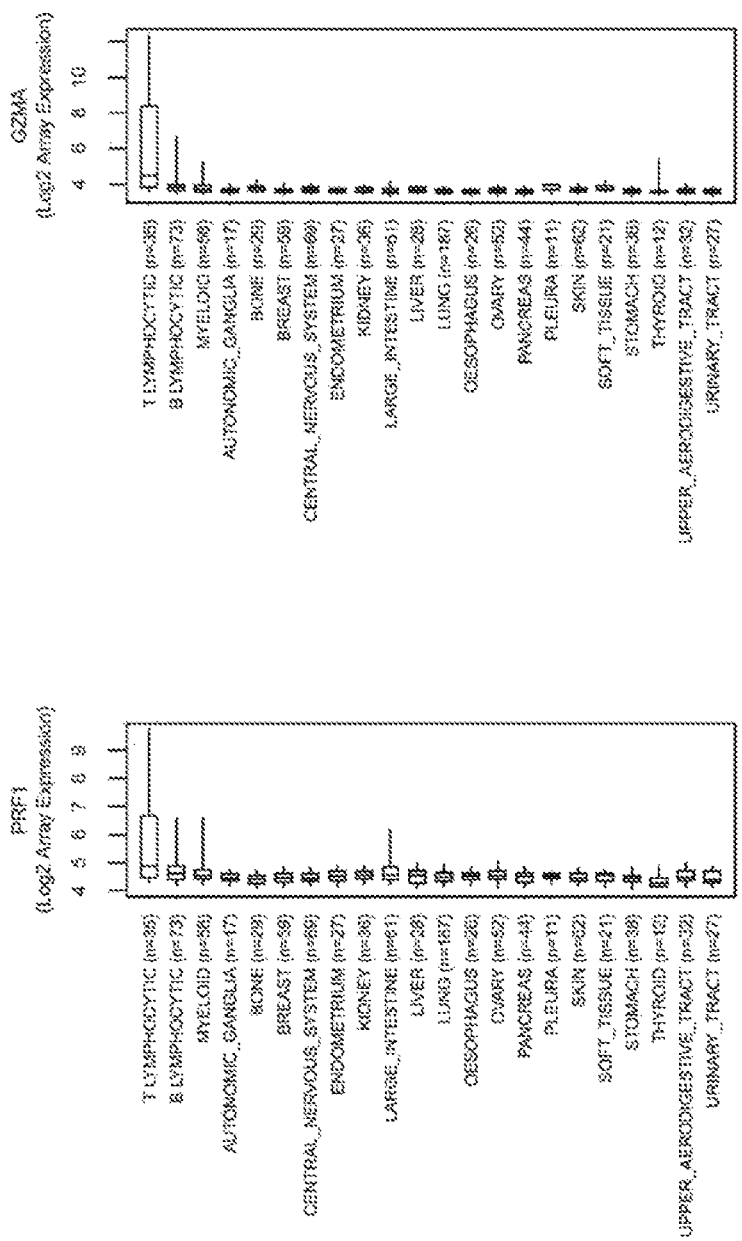
Figure 8E:
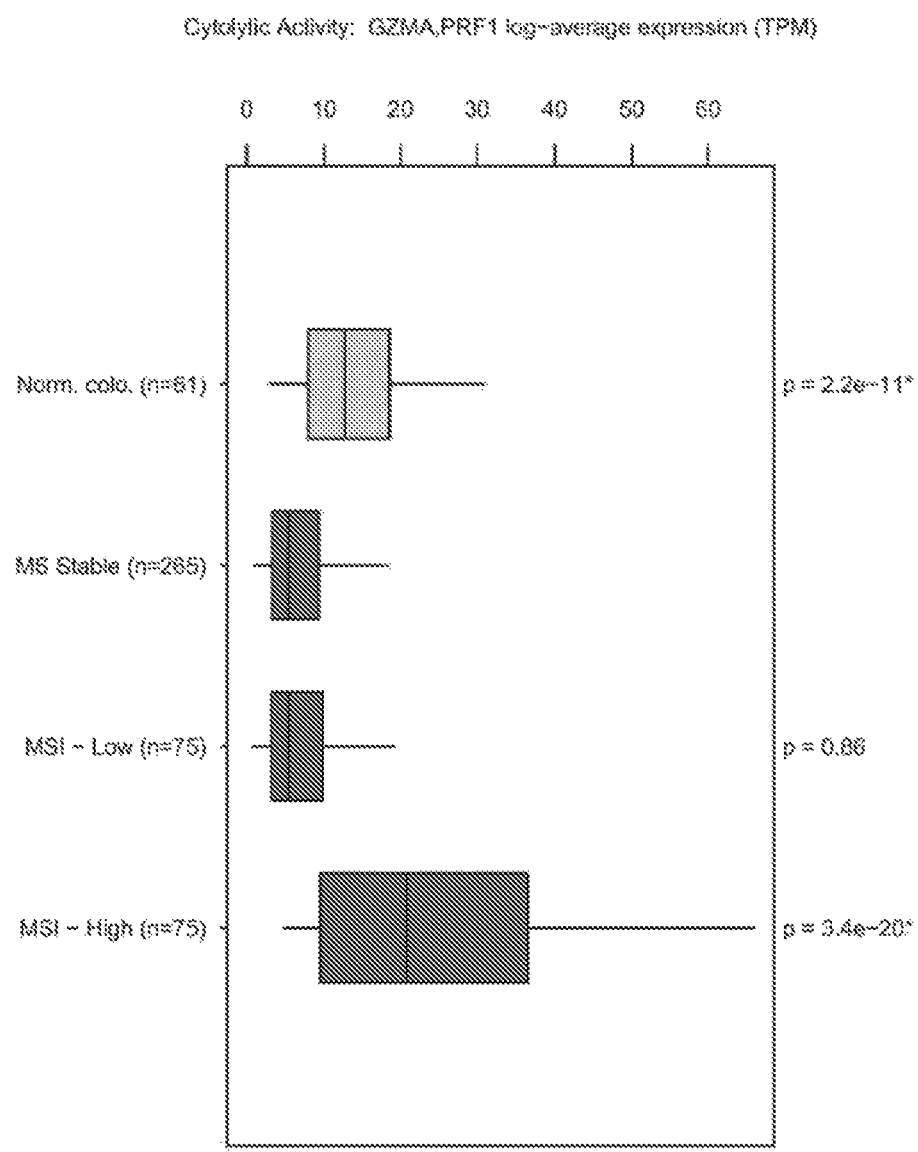
Figure 8F:
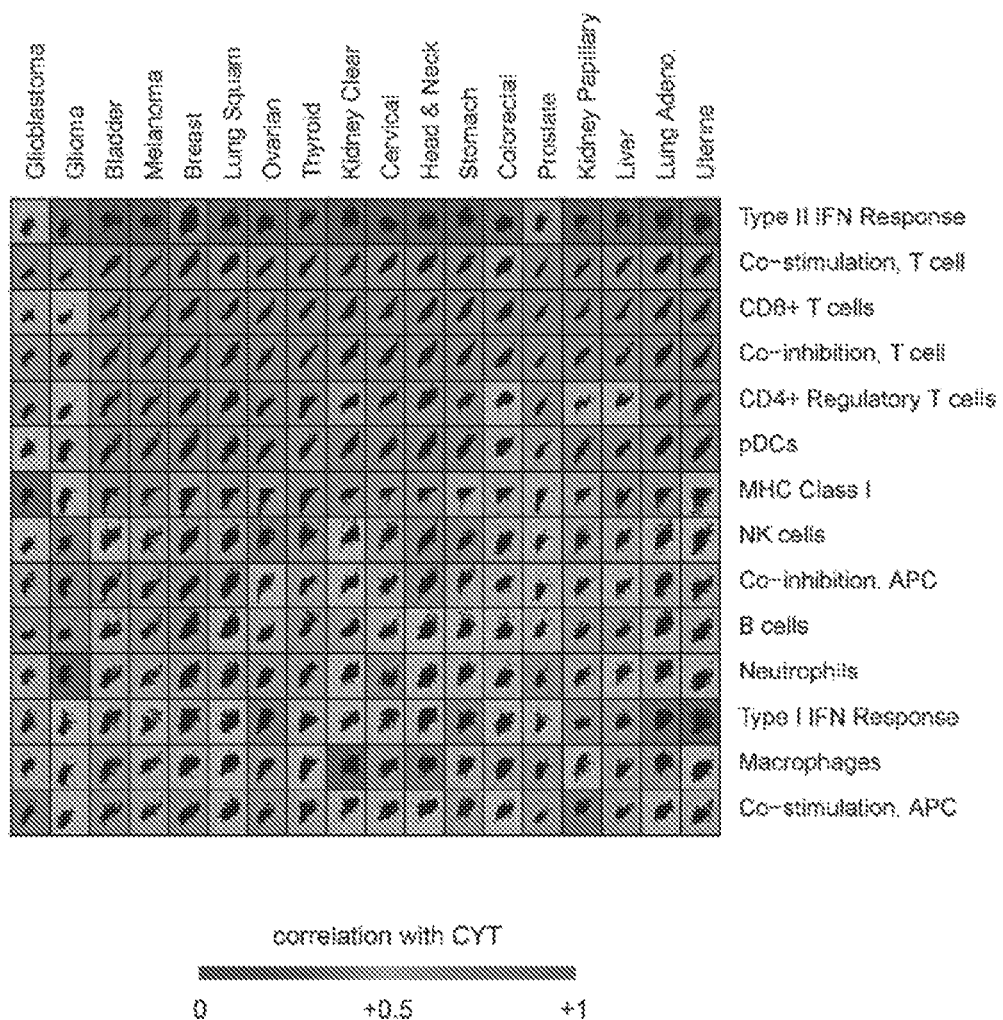
Figure 8G:
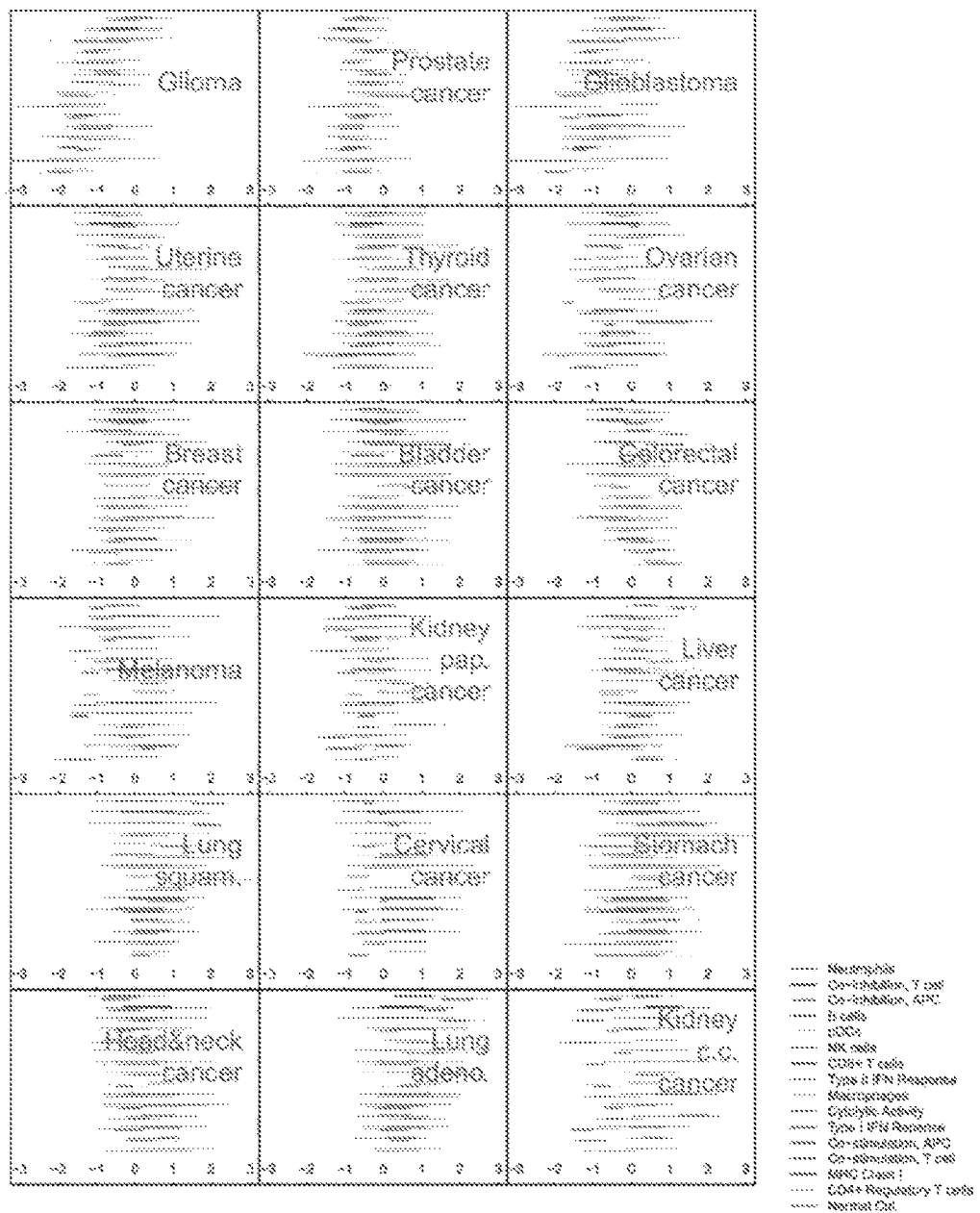
Figure 8H:
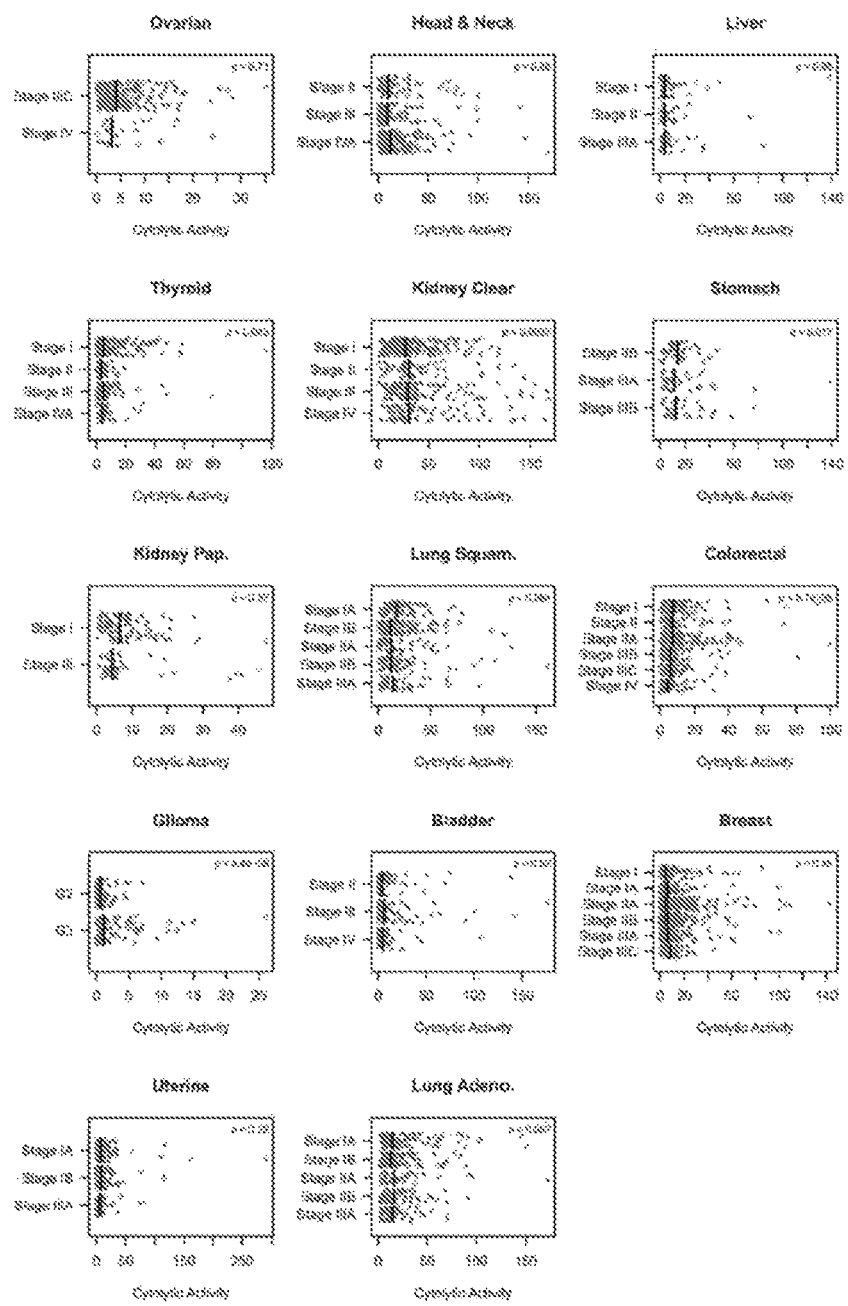
Figure 8I:
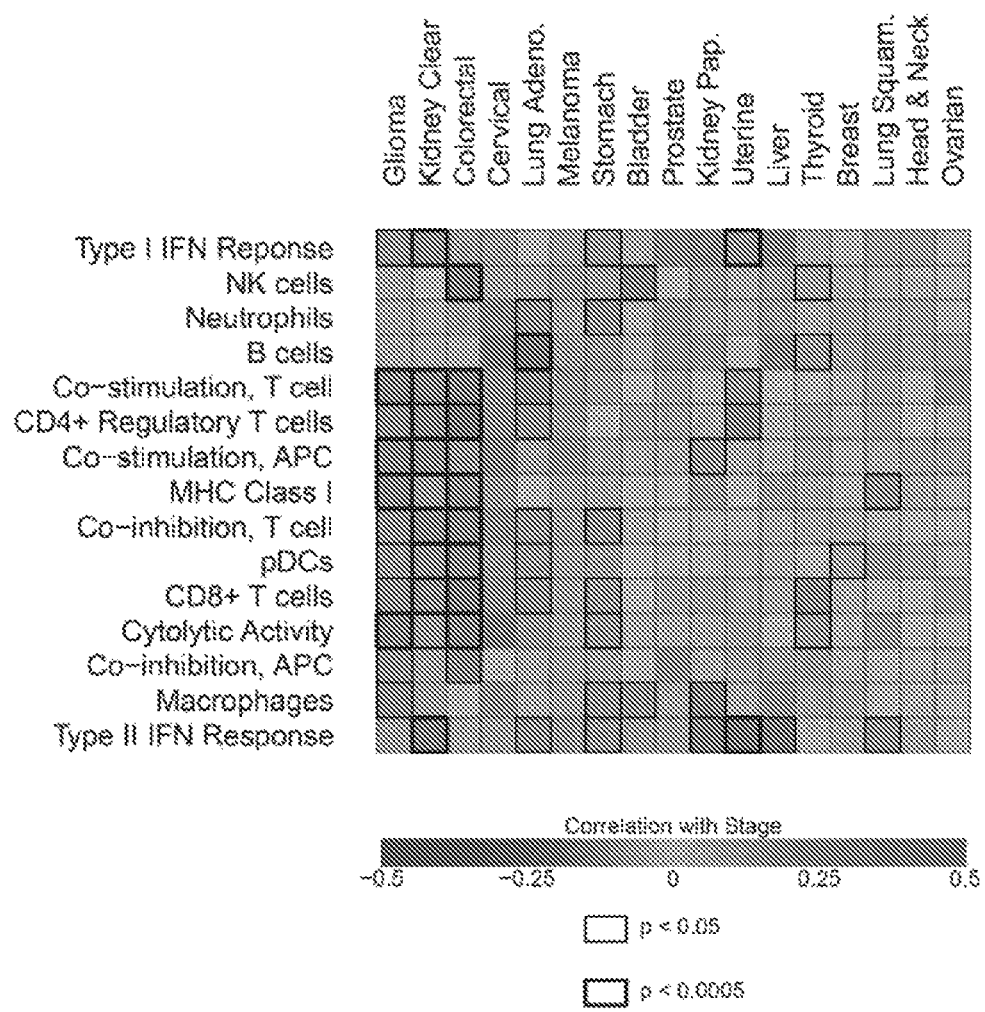
Figure 8J:
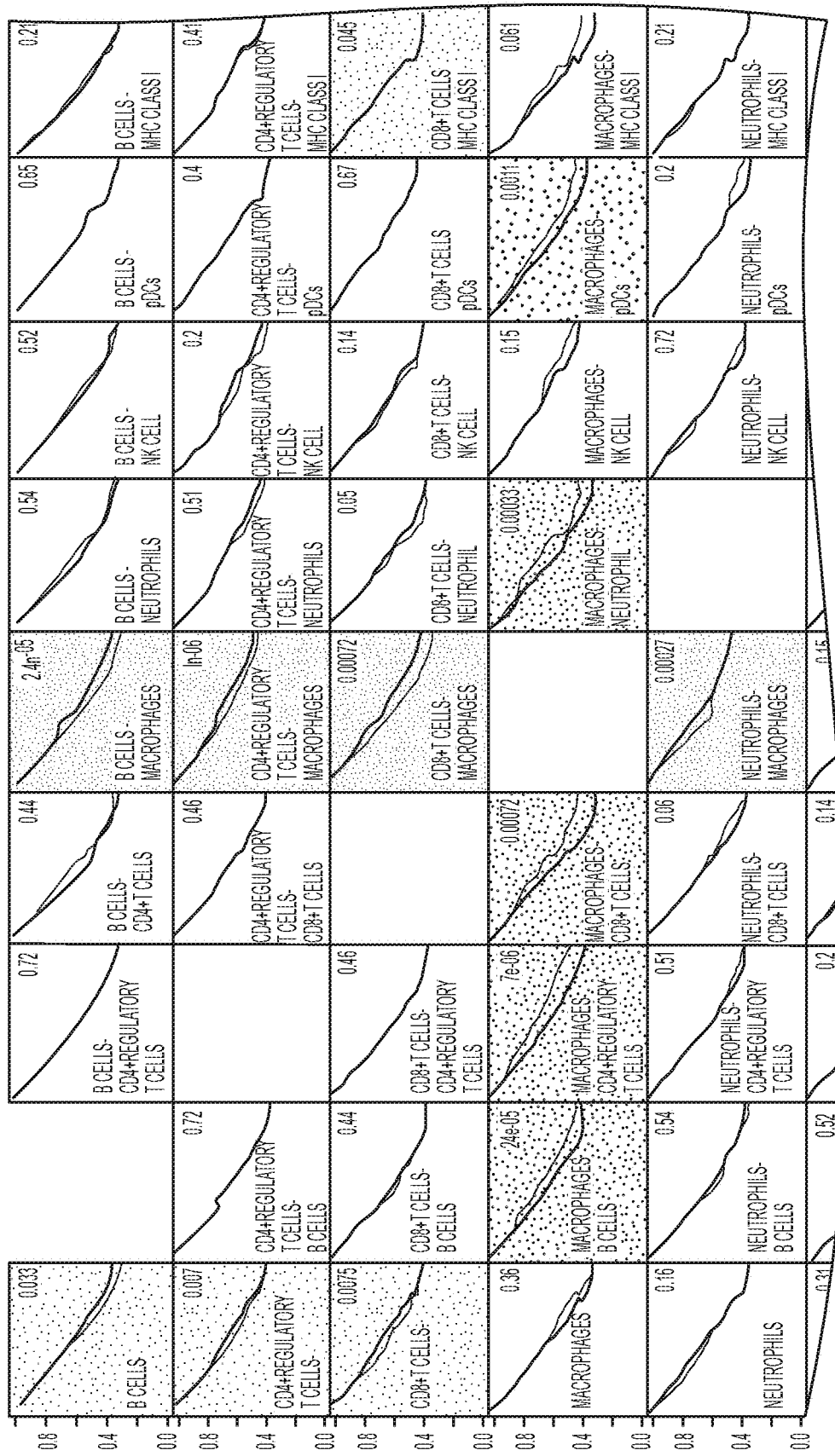
Figure 8J:
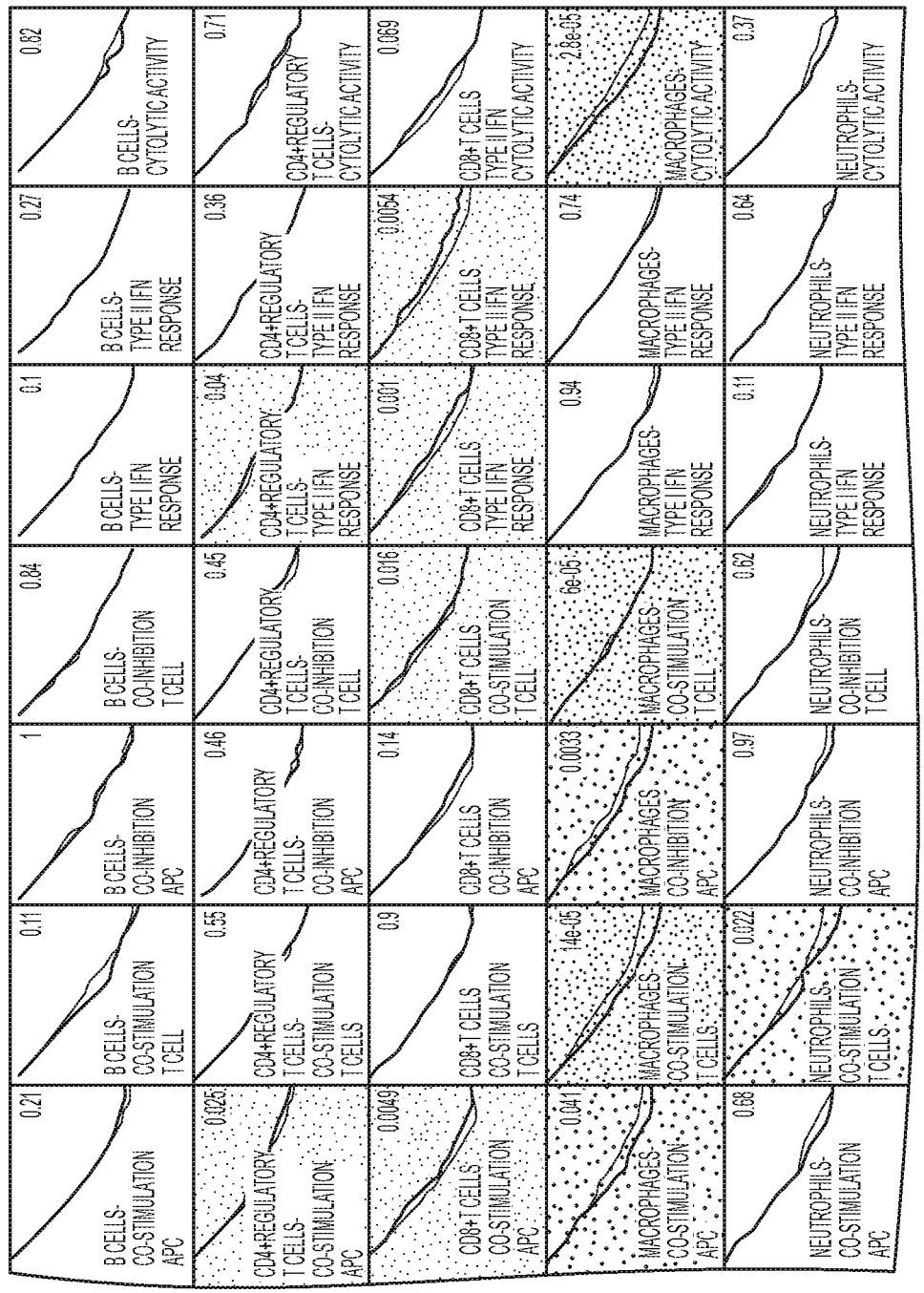
Figure 8J:
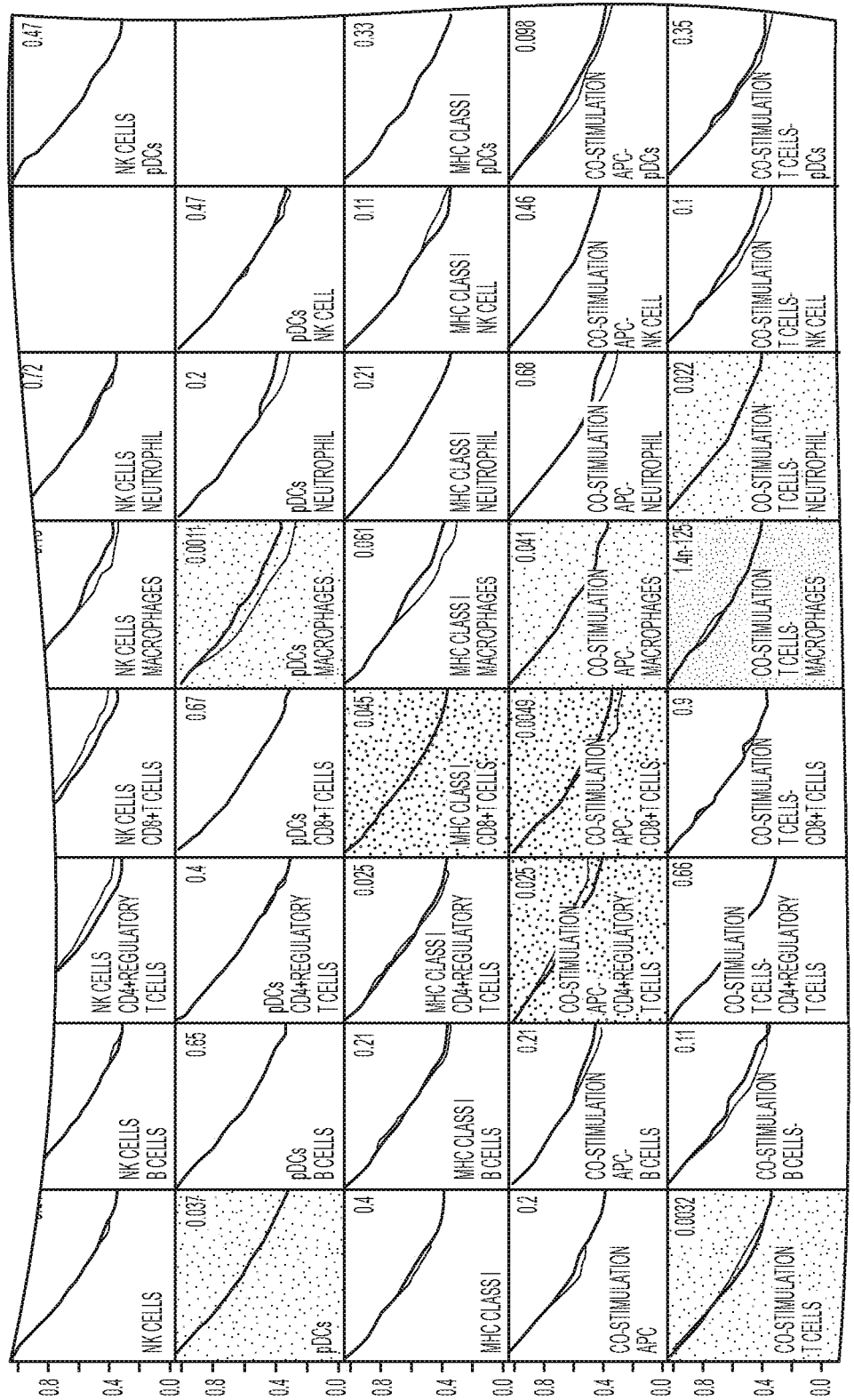
Figure 8J:
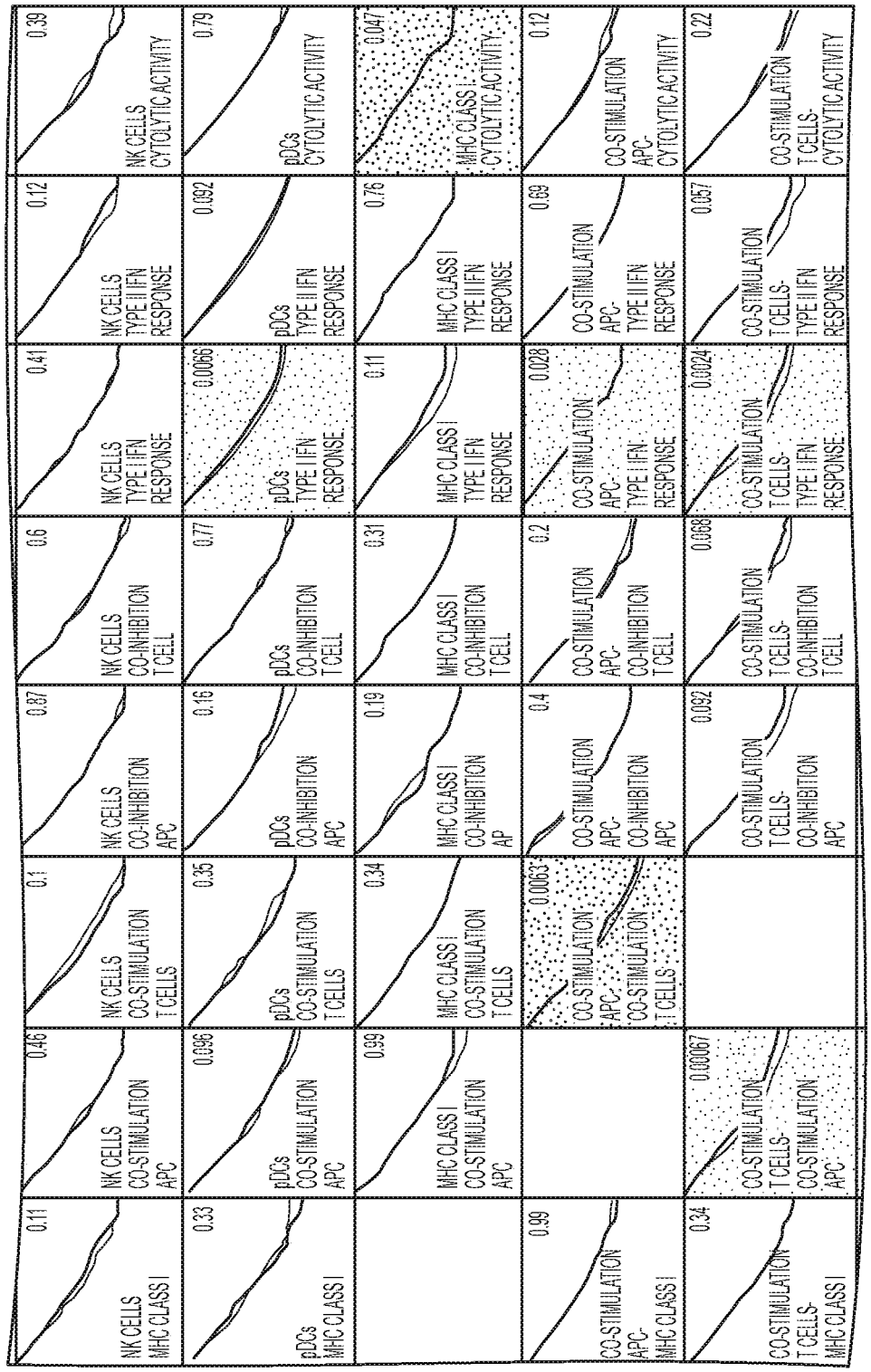
Figure 8J:
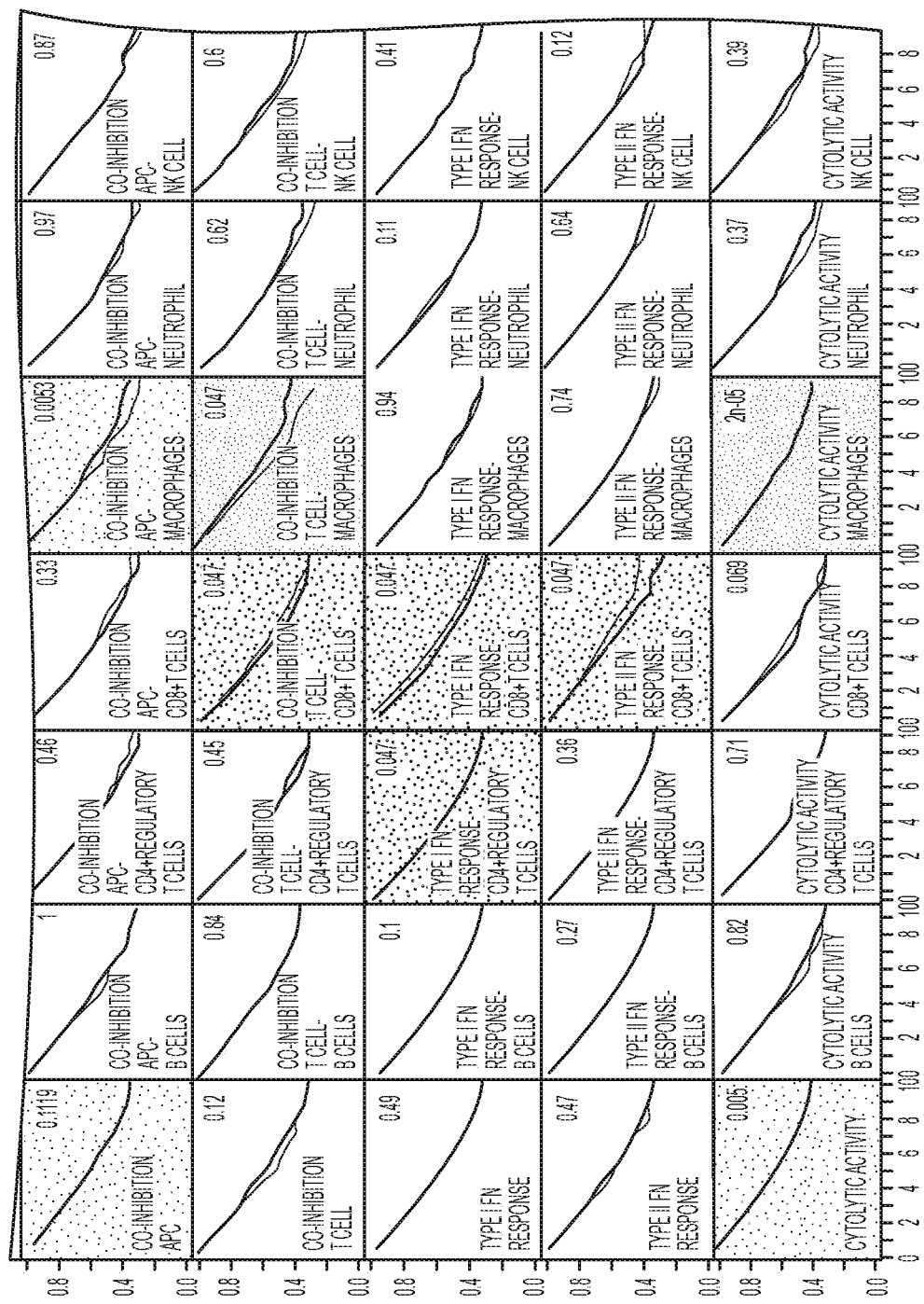
Figure 8J:
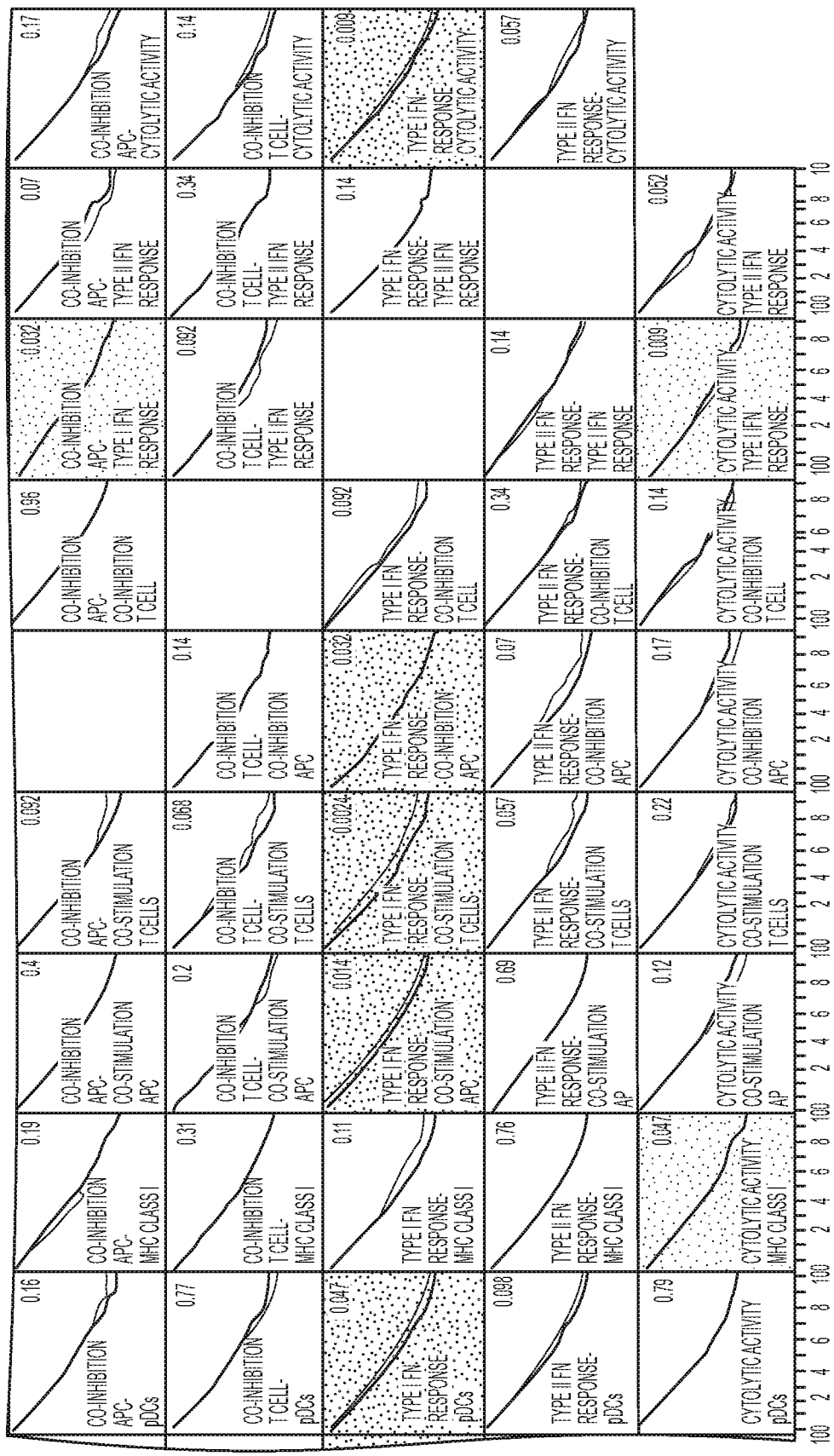

When Applicants used CYT and these other metrics to identify predictors of survival (controlling for tumor histology and stage), Applicants found that high-CYT (and other T cell markers) is associated with a modest but significant pan-cancer survival benefit (FIG. 8J). While no individual immune cell type metrics were associated with poorer prognosis, higher expression of macrophage markers relative to other markers was consistently linked with poor prognosis, while higher expression of CYT or CTL markers was correlated with improved prognosis (FIG. 8J).

Example 3

Tumor Cytolytic Activity is Associated with Oncogenic Viruses in Some Tumors

Viruses account for a subset of malignancies and are also known to activate high affinity antigen-specific CTLs against non-self viral antigens. Thus, Applicants tested for correlation of cytolytic activity levels with transcripts from oncogenic viruses—including Epstein Barr virus (EBV), hepatitis B and C (HBV and HCV), human papilloma virus (HPV), Kaposi sarcoma virus (KSV), and polyoma viruses.

Figure 2A:
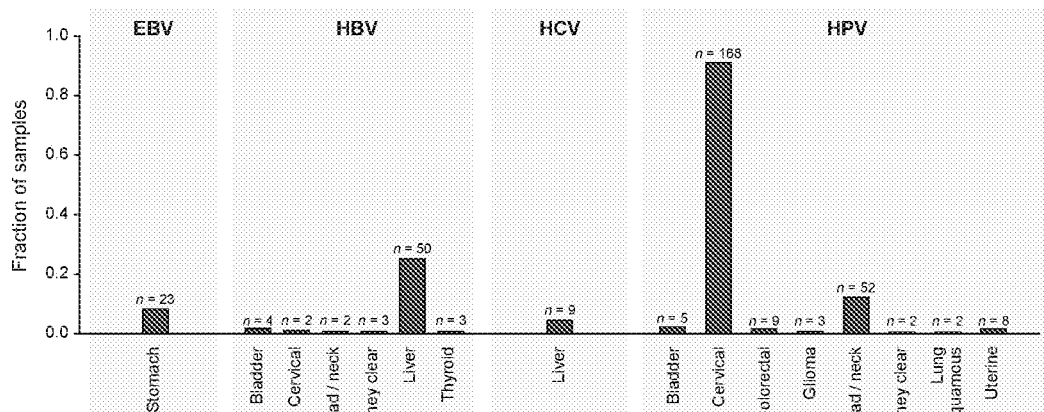
FIG. 2A-2B Viral infection is tumor-specific and associated with higher CYT in a subset of tumor types. (A) Rates of viral infection, as defined by viral RNA-Seq read counts exceeding those observed in GTEx, for tumor types exhibiting at least one case. Isolated cases of several other viruses were also observed. (B) Distribution of CYT in tumor samples with (+) or without (−) viral infection. In tumor types affected by multiple viruses, "negative" samples include only those negative for all viruses. Box plots as in FIG. 1. P-values are according to Wilcoxon rank-sum test.
Figure 2B:
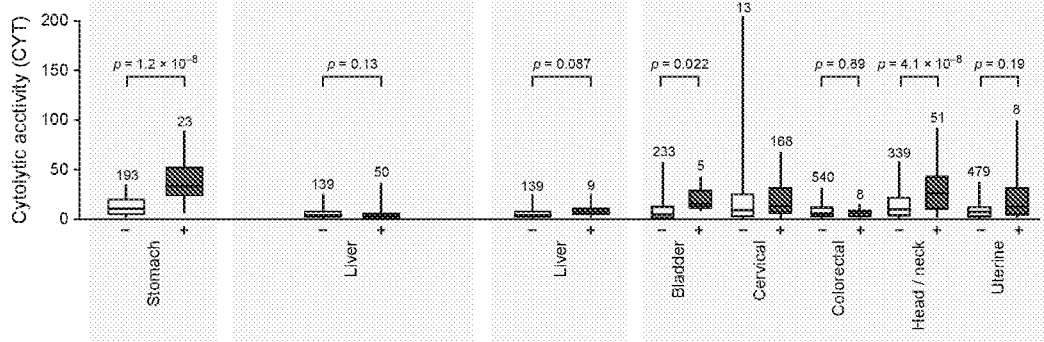

Consistent with previous analysis of TCGA data (Tang et al., 2013), HPV infection was most abundant in cervical cancer (91%), but also frequent in head and neck cancer (12%; with more men than women, OR=4.9; p=8.5e-4) and bladder cancer (2%). Applicants also observed occasional cases in colorectal, kidney clear cell, glioma, lung squamous cell carcinoma, and uterine cancer (FIG. 2A). Only stomach cancer demonstrated definitive instances of EBV infection (8%; Table S2A), which was associated with high expression of specific EBV genes EBER-1 and RPMS1 (FIG. 9A). Asian patients, known to exhibit increased rates of stomach cancer (Jemal et al., 2007), were not more likely than other stomach cancer patients to harbor EBV (p=0.63). Consistent with a role for viral infection in the induction of CTLs, >2-fold increases in cytolytic activity were observed in EBV+ vs. EBV− stomach cancers and HPV+ vs. HPV− head and neck cancers, bladder cancers, uterine cancers and possibly cervical cancers (FIG. 2B). Strikingly, all the gene sets that were most tightly associated with EBV infection in stomach cancer related to T cell activation.

HBV and HCV were primarily observed in liver cancer (25% and 5%, respectively), as expected, with occasional instances of HBV infection in diverse tumor types. The extra hepatic cases do not exhibit hepatic gene expression signatures, suggesting that these are not the result of metastases (FIG. 9B). Applicants also observed singleton cases of Kaposi sarcoma virus (lung squamous cell carcinoma and stomach cancer), BK polyoma (bladder cancer), and Merkel cell polyoma (ovarian cancer). While Applicants did observe type I interferon activation and B cell infiltration for HCV+ liver cancer (FIG. 9C), these viruses did not show an identifiable association with cytolytic activity.

These results indicate that viruses are associated with CYT based on the observation that EBV+ and HPV+ tumors have higher CYT levels. Furthermore, Applicants observed additional correlates with CYT consistent with viral infection, such as HLA association and APOBEC activity.

Example 4

Cytolytic Cells are Likely to be Targeting Tumor Neoantigens

Figures 3A, 3B, 3C:
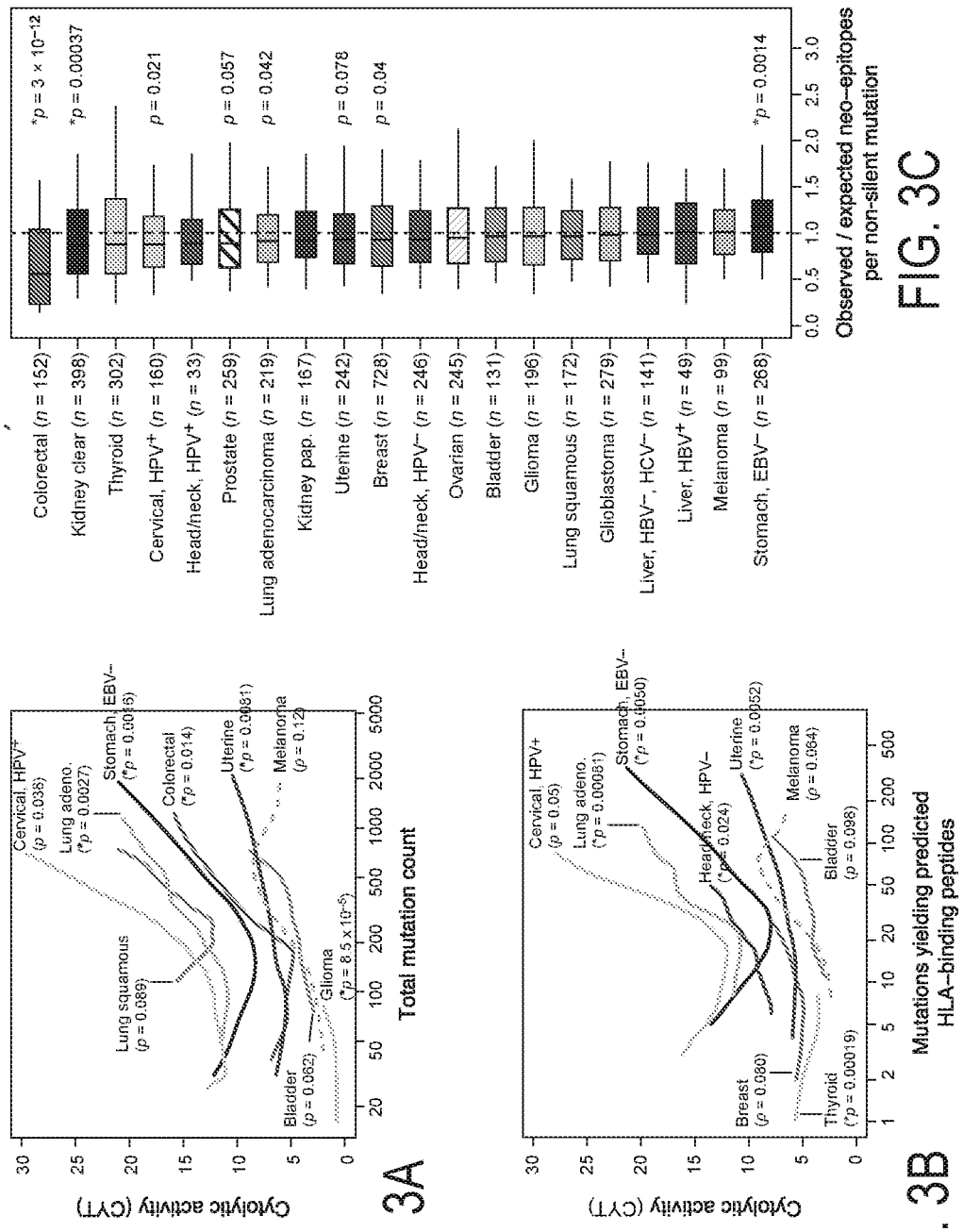
FIG. 3A-3C Count of predicted antigenic mutations per sample is linked with cytolytic activity and selectively depleted in certain tumor types. (A) Local regression curves showing the relationship between CYT and total mutation count in eight tumor types in which the relationship was significant (p<0.1, Spearman rank correlation), plus melanoma (dotted line). Curves span the $5^{th}$ to $95^{th}$ percentile of the mutation count variable. Colors correspond to tumor type and are the same as appear in FIG. 1. (B) Analogous to (a), but based on the count of point mutations predicted to yield an antigenic neo-epitope. Potential for antigenicity was defined based on gene expression and potential to bind the corresponding patient's imputed HLA with high affinity. (C) For each tumor, the count of point mutations predicted to generate neo-epitopes was divided by the total count of non-silent point mutations to yield $B_{obs}/N_{obs}$. This observed ratio was compared to an expected ratio, $B_{pred}/N_{pred}$, estimated from the mutational spectra of the silent point mutations in the given sample using an empirical model (Methods). The ratio of the observed and predicted ratios represents the relative deviation of the neo-epitope rate from expectation. P-values reflect Wilcoxon rank-sum tests for deviation from 1.
Figure 10A:
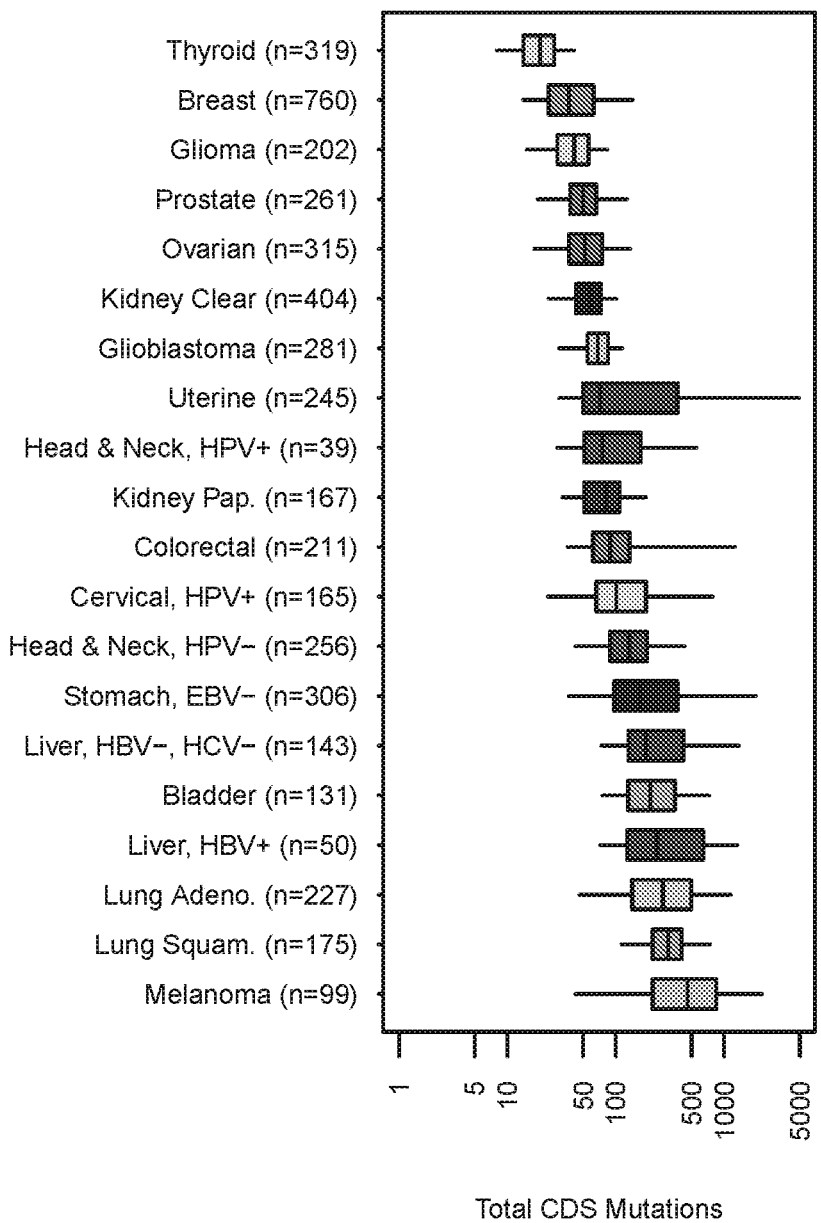
Figure 10B:
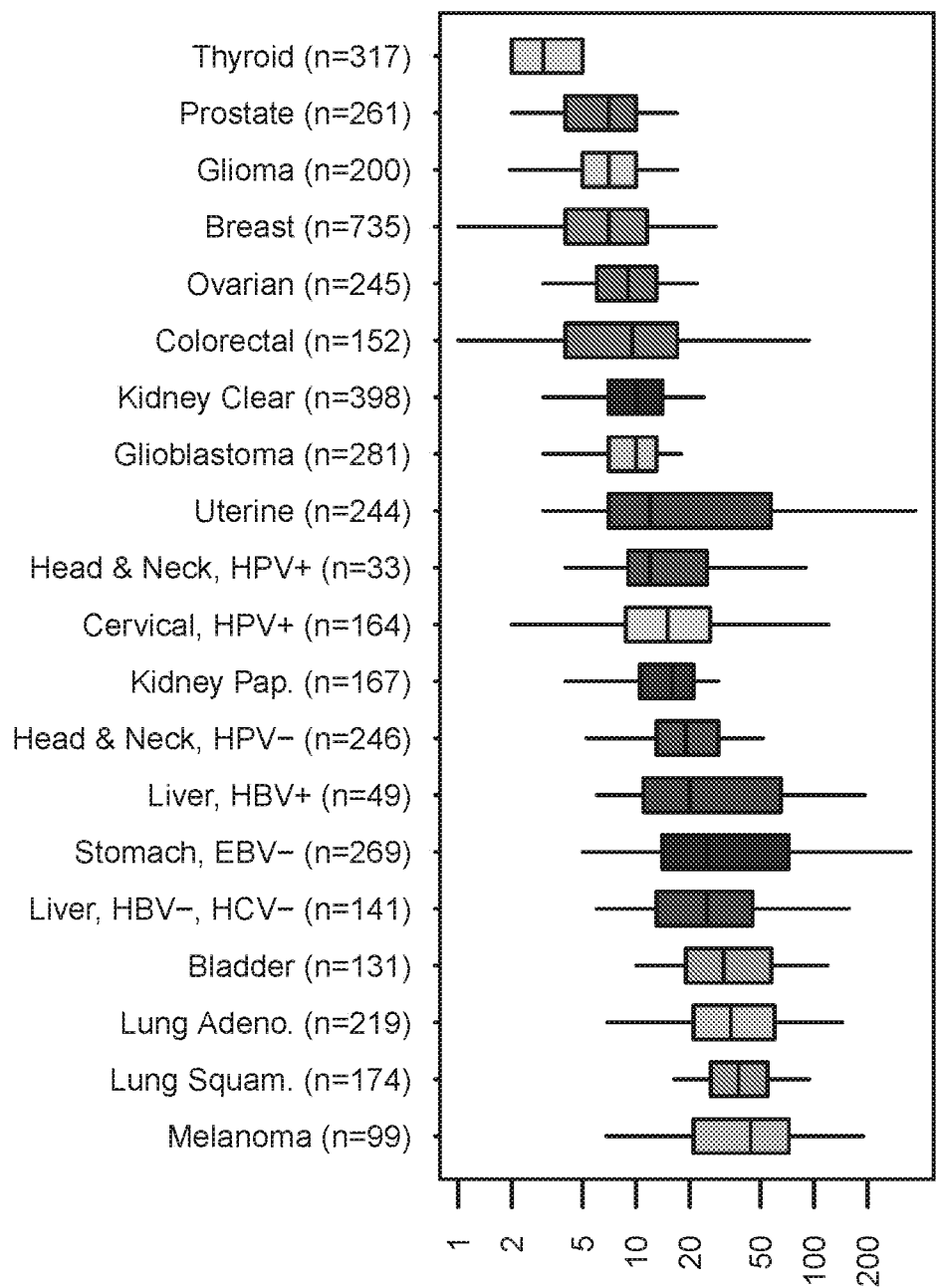
Figure 10C:
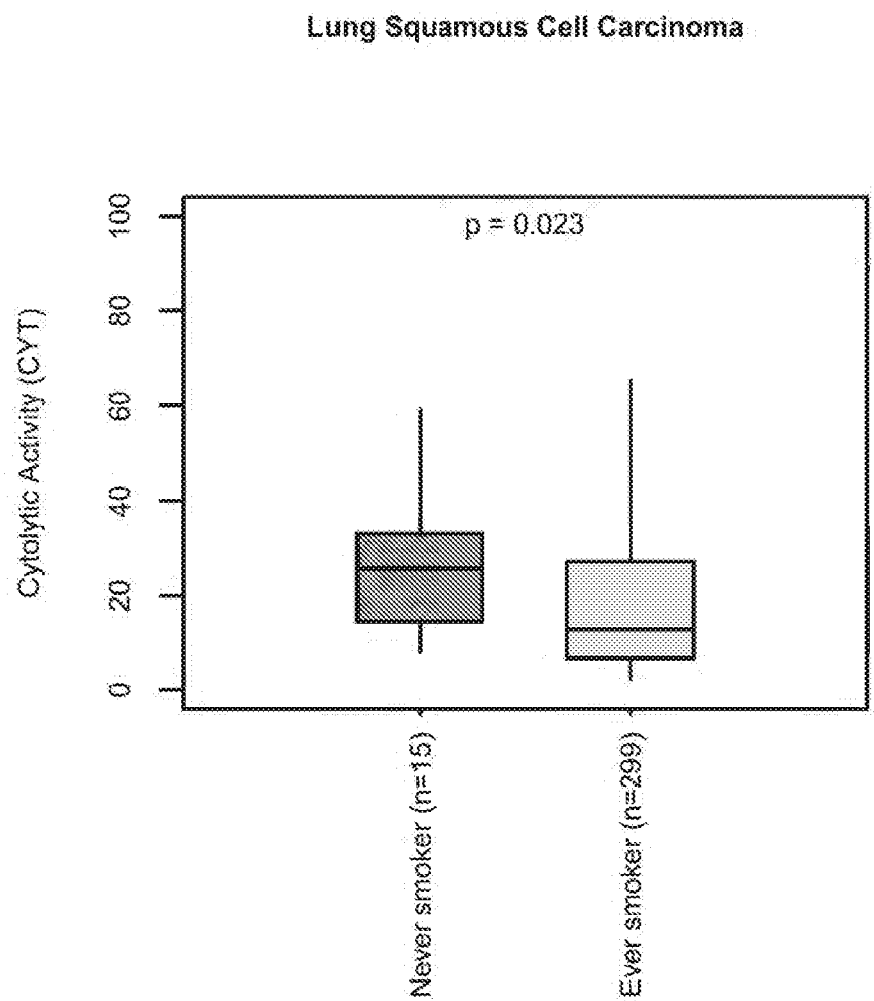
Figure 10D:
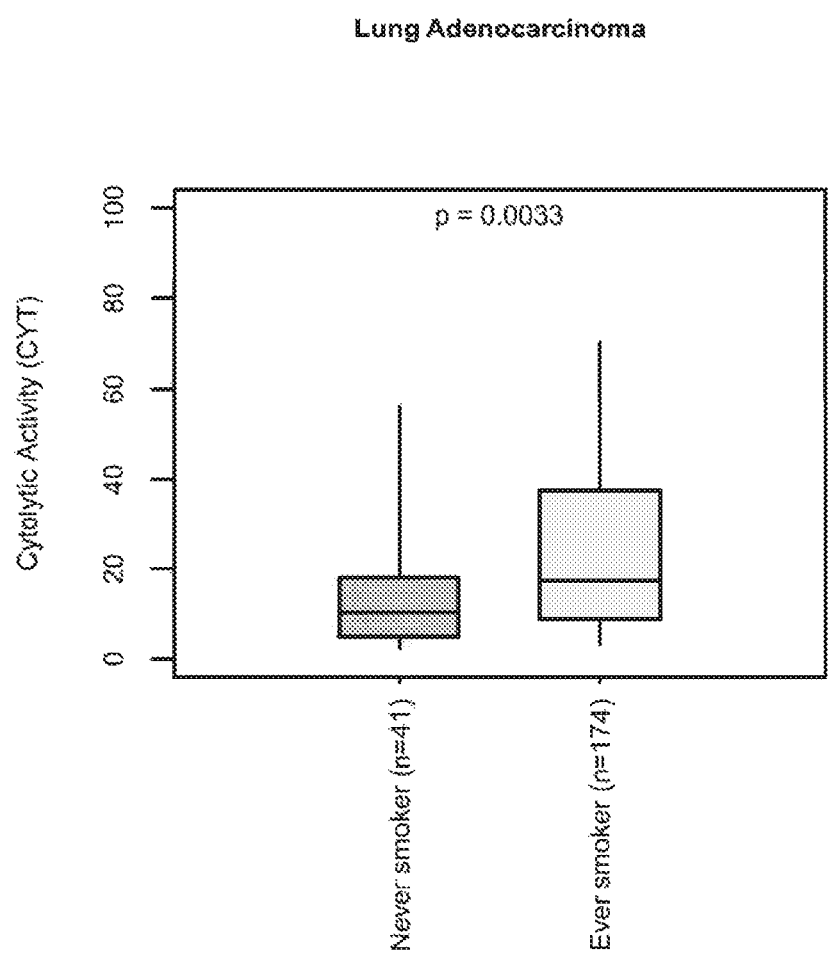
Figure 10E:
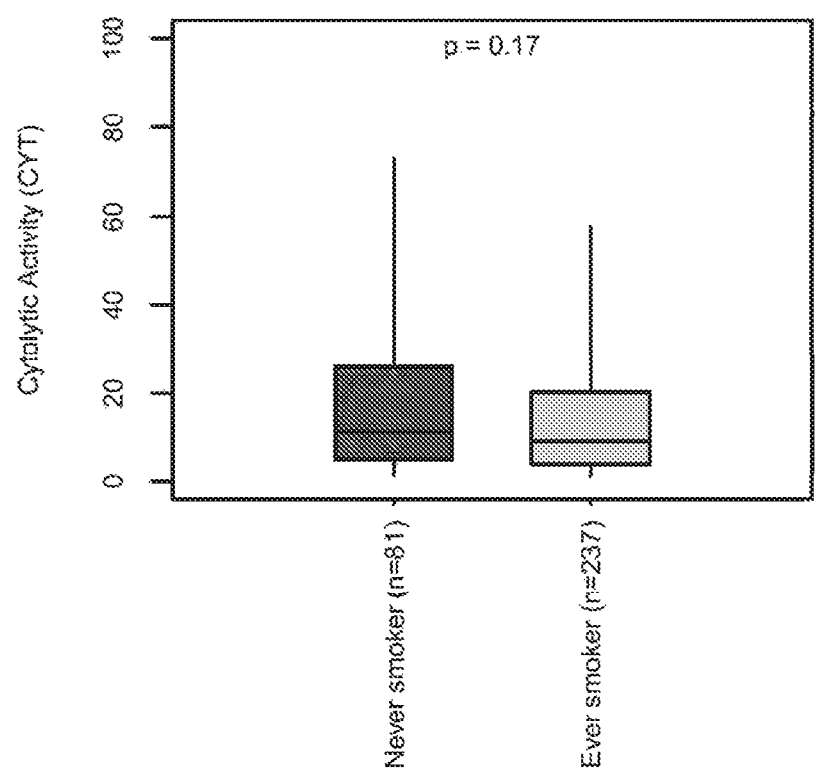

With recent studies showing the presence of neoepitope-specific T cells in patients (Fritsch et al., 2014), Applicants tested for CYT association with the overall rate of mutation and the rate of mutations predicted to yield a neoepitopes (i.e., an expressed peptide capable of binding each patient's imputed HLA alleles) (FIGS. 10A, 10B). On average, 50% of non-silent mutations yielded≥1 predicted neoepitope, and 39% of these impacted a substantially expressed gene (median expression≥10 TPM in the given tissue type). Both metrics exhibited significant positive association with CYT in multiple tumor types, most notably uterine cancer, breast cancer, stomach cancer, cervical cancer, and lung adenocarcinoma (FIG. 3A, 3B). Consistent with a smoking etiology, lung adenocarcinomas from ever-smokers demonstrated significantly higher CYT than those from never-smokers (p=0.003) (Figure S3C). Melanoma mutations exhibited a suggestive, but not definitive association, with CYT. Associations of mutations or neoepitopes with CYT were matched by correlations for other T cell markers, but less so with interferon-responsive genes (FIGS. 10D, 10E). These data are consistent with neoepitopes driving CYT for many tumor types.

Figure 10F:
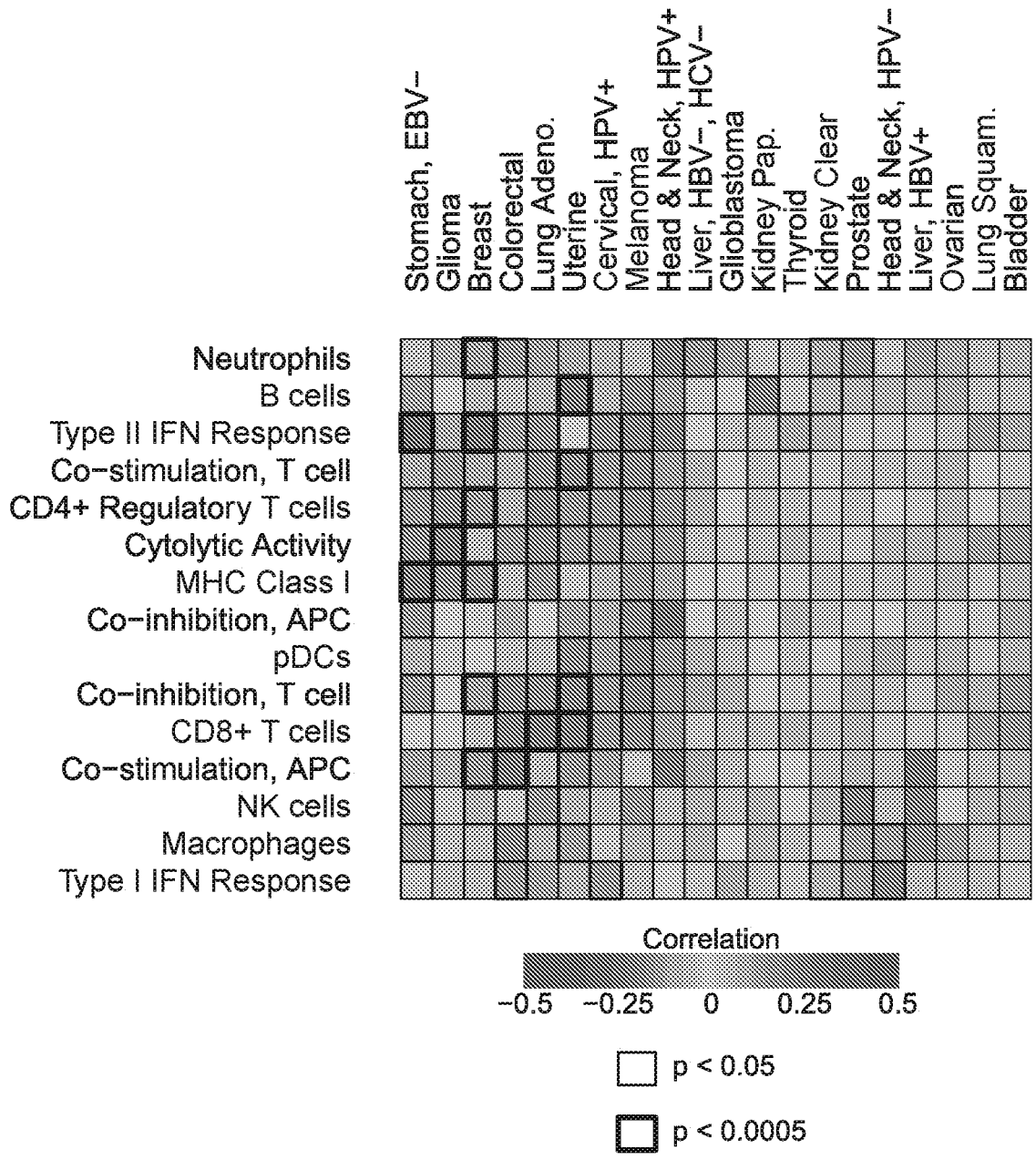
Figure 10G:
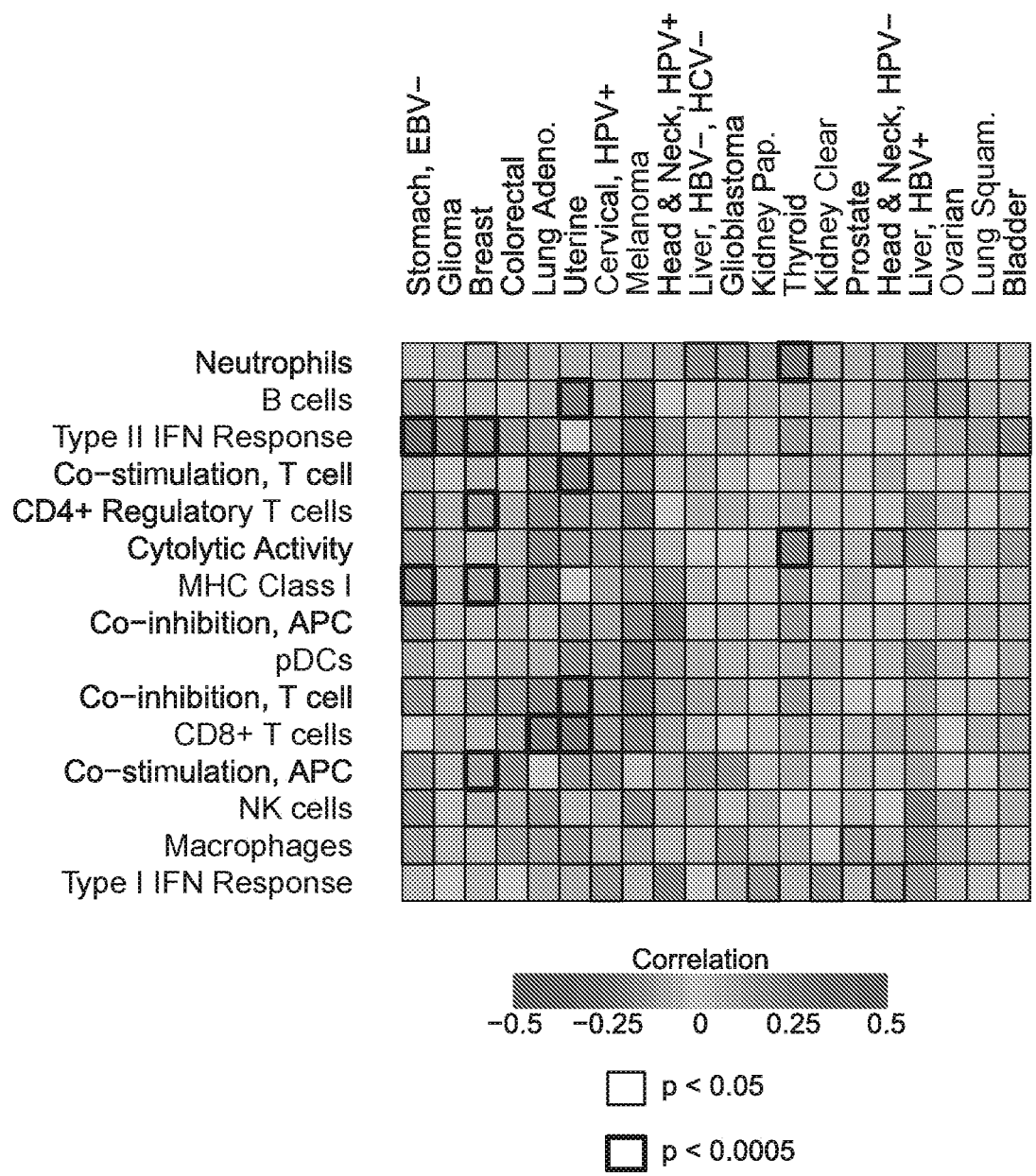
Figure 10H:
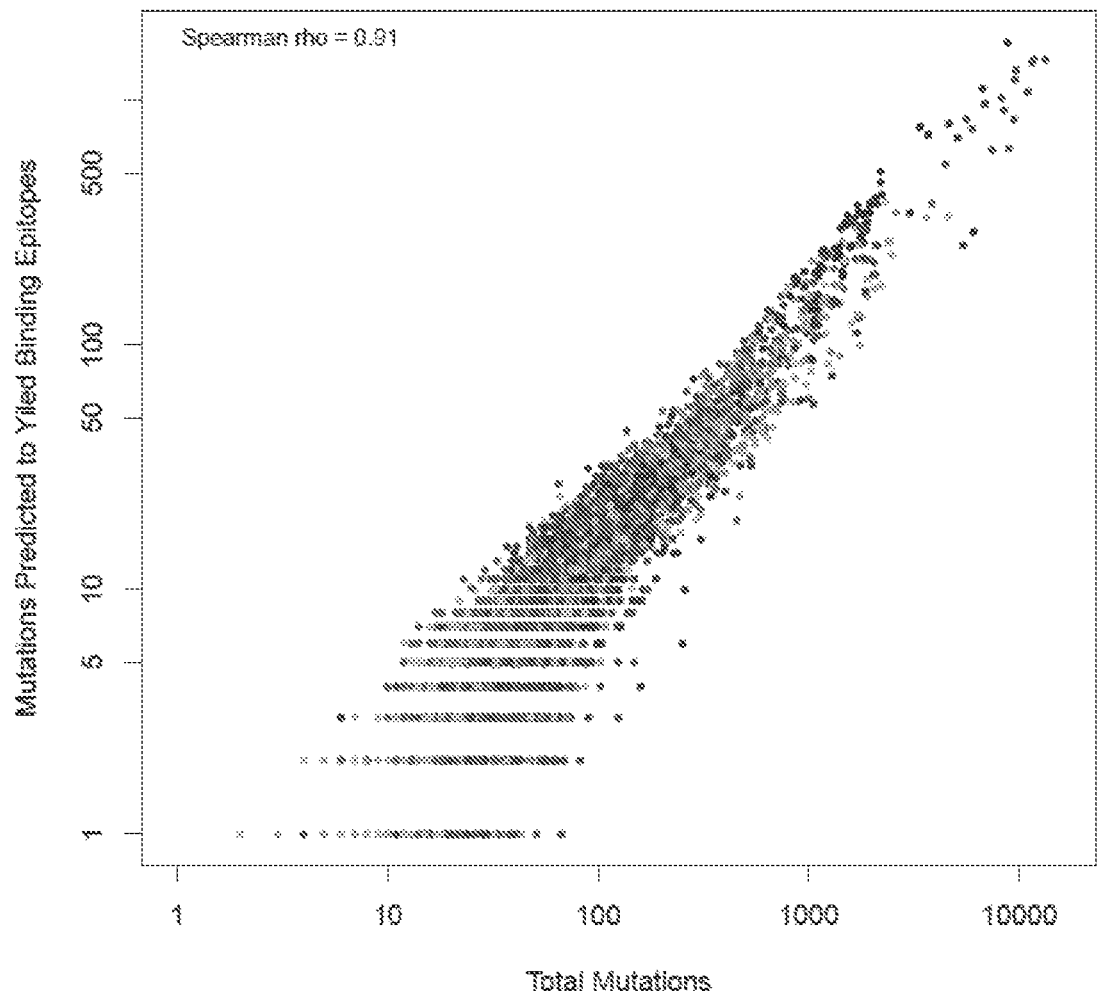
Figure 10I:
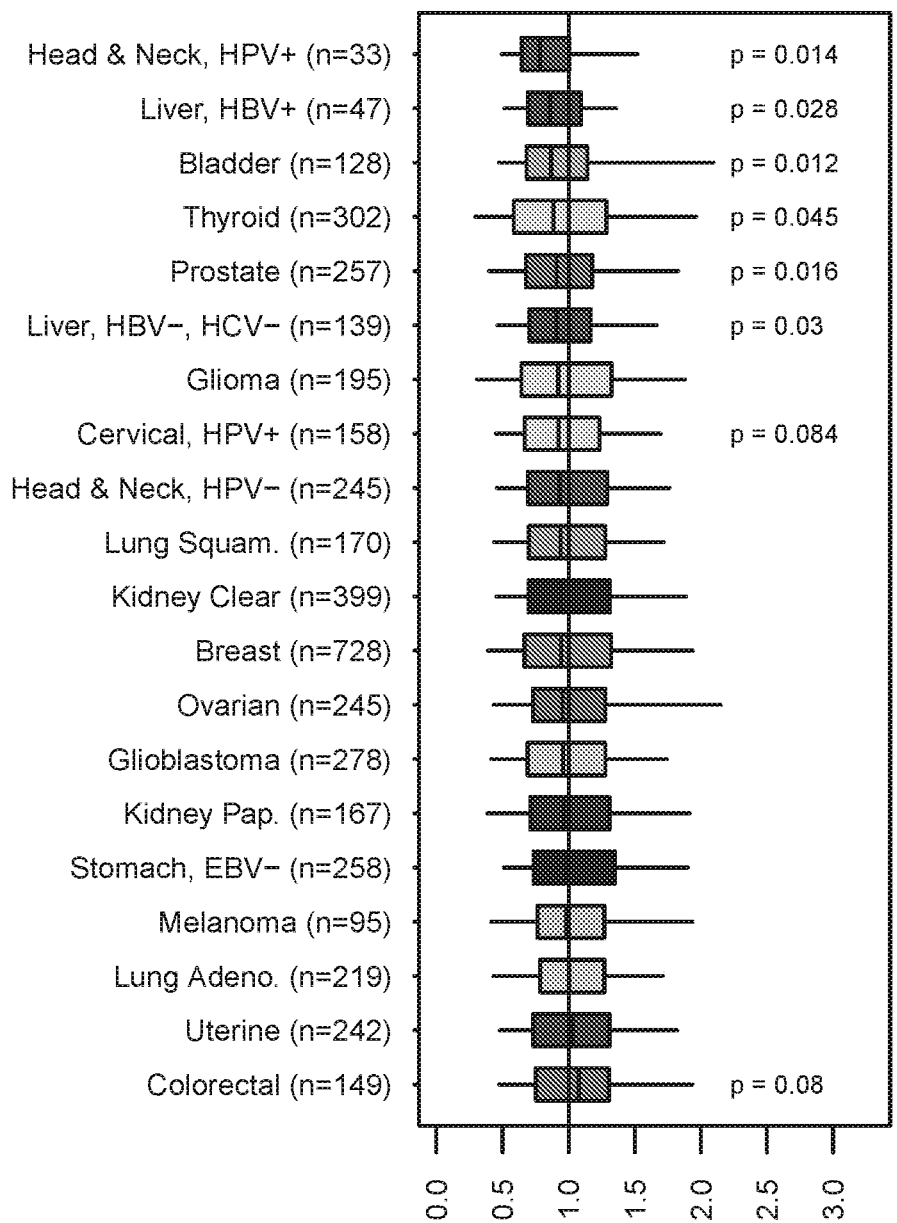

However, since the per-sample rate of neoepitope yielding mutations closely tracks with the overall rate of mutation (Spearman rho=0.91; FIG. 10F), CYT may be driven by mutation rate rather than neoepitopes. To test a role for neoepitopes, Applicants reasoned that T cell-mediated immune surveillance would lead to elimination of immunogenic sub-clones expressing neoepitopes. To quantify neoepitope depletion, Applicants determined how the rate of predicted neoepitopes generated per non-silent point mutation deviated from a null model (based on the observed mutation rate of silent point mutations). Applicants found that colorectal cancer and kidney clear cell cancer demonstrated dramatic depletions of neoepitopes (FIG. 3C; associated gene expression changes). Because neoepitope predictions are dependent on HLA genotypes, Applicants reasoned that random shuffling of HLA genotypes would abrogate the depletion signal (FIG. 10G). As expected, depletion was eliminated for colorectal cancer and kidney clear cell cancer (and Applicants note that the residual enrichment for other tumor types may reflect degeneracy of peptide binding across HLA alleles). These findings are consistent with a model in which immune surveillance programs cull subclones expressing immunogenic antigens, and may explain why CYT is better correlated with total mutation rate than neo-epitope-yielding mutations for colorectal cancer.

Applicants conclude that neoepitopes are likely to be driving cytolytic activity in a number of tumors, and that the resulting antigen-specific CTLs can eliminate tumor clones harboring these neoepitopes.

Example 5

CYT is Associated with Endogenous Retroviruses in Some Tumors

Another potential source of tumor antigens is a unique set of genes, known as cancer testis (CT) antigens, which are not expressed in healthy tissues, except germ cells, but are aberrantly expressed in tumors and associated with antigen-specific responses in patients harboring these tumors. Ectopic expression is likely due to disturbances in genomic methylation and reactivation of stem-like expression programs that may contribute to tumorigenicity (Simpson et al., 2005). Using a set of 276 known CT genes (Almeida et al., 2009), Applicants used GTEx to identify a subset of 60 that are transcriptionally silent in normal somatic tissue. Ectopic expression was observed for most tumor types, especially melanoma, head and neck, lung, liver, stomach, and ovarian cancer (FIG. 11A). The count of expressed CT antigens showed weak and typically negative association with CYT (FIG. 11B). Applicants queried individual CT antigens for correlation with CYT, and observed positive associations for CSAG2 in breast cancer (p=1.2e-15), head and neck cancer (p=1.9e-7), kidney clear cell cancer (p=9.9e-5), and other tumor types. Associations for canonical antigens, such as NY-ESO-1 (CTAG1), were less consistent. Applicants hypothesized that T cell surveillance would lead to CT antigen silencing through chromosomal deletions, but compelling evidence for this was not observed (FIG. 11C). While these findings do not disprove the notion that CT antigens can drive anti-tumor responses, it is nonetheless surprising that stronger associations are not evident.

Figure 4A:
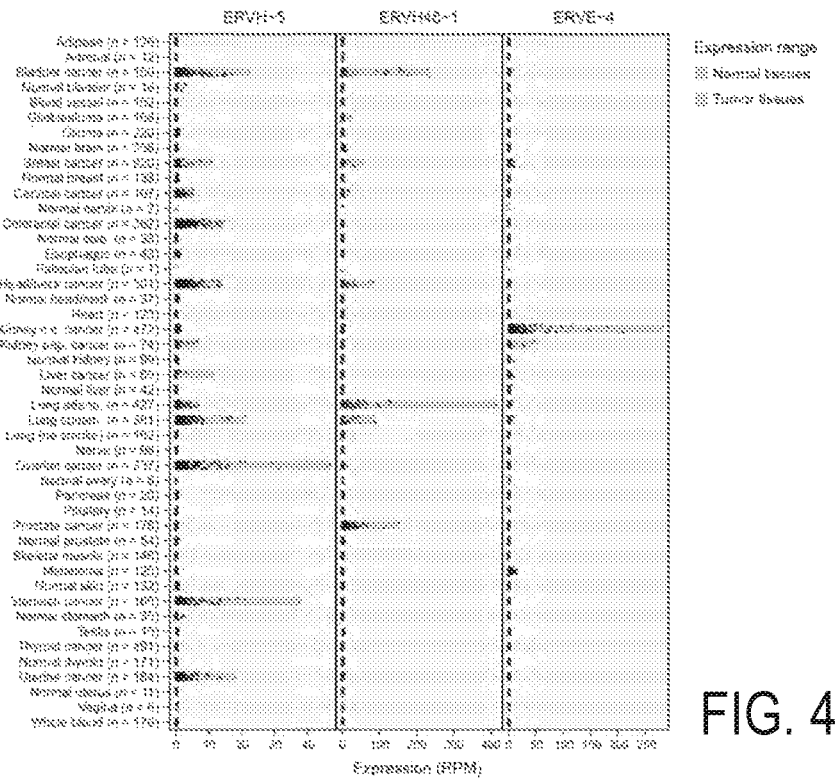
FIG. 4A-4B Endogenous retroviruses tied to local immunity (A) RNA-Seq-derived ERV expression in reads per million (RPM) across 18 TCGA tumor types and 27 non-tumor tissue types (from TCGA and GTEX) for three elements found to be tumor-specific. The expression ranges (minimum value to maximum value) are highlighted in orange (for tumor tissues) or green (for non-tumor tissues).

Endogenous retroviruses (ERVs) are another class of germline-encoded elements that may be re-activated in tumors, and Applicants considered whether these might also contribute to anti-tumor immunity. TLR7 or RAG knockouts in mice develop uncontrolled ERV expression, ERV infectivity, and ERV insertion-driven tumors (Young et al., 2012; Yu et al., 2012) yet little is known about ERV-immune and ERV-cancer interactions in humans. Given reports that these elements are transcriptionally and sometimes even translationally active in humans (Boller et al., 1997; Schmitt et al., 2013), Applicants considered the possibility that they trigger immune sensing in tumors. Therefore, Applicants mapped TCGA RNA-Seq data to a recently published annotation of 66 expressed ERV family members (FIG. 11D) and assessed associations with cytolytic activity (Mayer et al., 2011). By comparing GTEx and TCGA tissue controls to TCGA tumor samples, Applicants observed numerous instances of ERVs demonstrating re-activation in tumors, including one instance of an ERVH-2 element exceeding 2,700 reads per million in a stomach adenocarcinoma (FIG. 11E). From these data Applicants surprisingly discovered a conservative set of three tumor-specific endogenous retroviruses ('TSERVs') all with minimal to undetectable expression in normal tissues and elevated expression in tumor tissues (FIG. 4A).

Figure 4B:
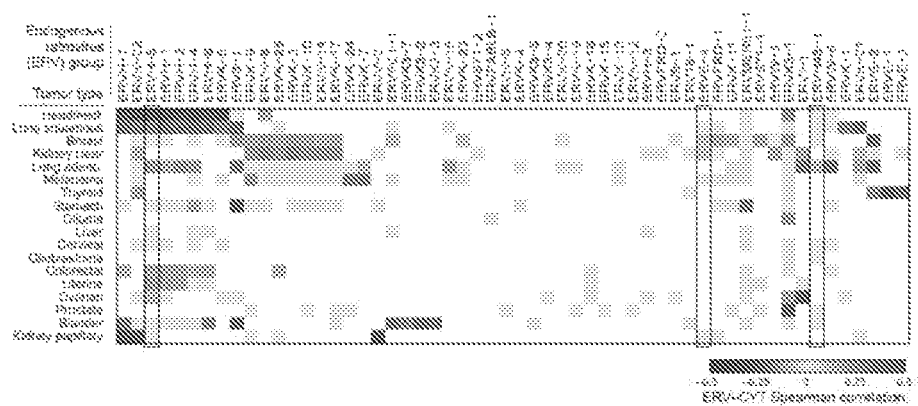

Assessing the gene expression correlates of each TSERV in the tumor type exhibiting highest expression, Applicants observed that immune pathways were typically the most significantly enriched. Many ERVs, in addition to the TSERVs, demonstrated association with CYT in multiple tumor types (FIG. 4B). While Applicants cannot determine whether ERVs activate immunity or inflammation triggers ERVs (Manghera and Douville, 2013), Applicants conclude that ERVs are highly dysregulated in tumors and may yield tumor-specific peptide epitopes (Boller et al., 1997) or act as immunological adjuvants to activate local immunity (Yu et al., 2012).

Example 6

Mutations in 28 Driver Genes were Enriched in Tumors with Higher Cytolytic Activity Applicants hypothesized that high cytolytic activity could select for tumors with somatic mutations that render them resistant to immune attack. Applicants therefore asked whether CYT is associated with mutations in 351 'driver' genes that are frequently mutated in cancer based on analysis of TCGA exome sequencing data (q<0.1 by MutSigCV (Lawrence et al., 2013). Using a regression-based approach to look for association of these mutated genes with CYT, controlling for tumor type and background mutation rate, Applicants found 28 genes (adjusted p<0.1; FIG. 5A, FIG. 12A, Table 2 A,B) across tumor types (and for most mutations within ≥2 tumor types, unadjusted p<0.05). In contrast, synonymous somatic mutations were not associated with CYT (adj. $p_{min}$=0.09). Of the top 10 CYT-associated mutations, 8 were also associated with an independent marker of CTLs (CD8a; 10% FDR), demonstrating the robustness of the CYT metric. Of the individual tumor types, uterine, stomach and colorectal had the most associations (13, 9, 6 respectively) while kidney clear cell and ovarian (which showed higher CYT compared to normal tissue) had the fewest (0 and 1). Strikingly, somatic mutations, except TP53, were all positively associated with CYT, consistent with a model in which tumors develop resistance mutations under selection pressure.

Applicants note that while it was predicted that cytolytic activity would have the strongest impact on the mutation landscape, Applicants also identified gene mutations strongly associated with other immune cell types/functions (adj. p<0.01; FIG. 12B), including STK11 and VHL with reduced macrophage signature, BRAF with increased expression of costimulatory genes, and AXIN2, SNX25 and others with the differential enrichment score of CD8+T compared to Treg.

Example 7

Higher CYT was Associated with Mutations in Genes Involved in Antigen-Presentation, Extrinsic Apoptosis and Innate Immune Sensing Several themes emerged when Applicants considered the known functions of the identified genes. First, the most enriched gene, CASP8 (q=8.8e-7), is a critical player in the extrinsic apoptosis pathway and was enriched in head and neck cancer, colorectal cancer, lung squamous cell carcinoma, and uterine cancer (where it showed a maximal mutation frequency of 7.0%). The pattern of mutation was diffuse and suggested loss of function (FIG. 12C), a potential mechanism by which a tumor cell could evade FasL- or TRAIL-induced apoptosis. Between FasL and TRAIL, FasL is most correlated with CASP8 mutations and thus more consistent with such a hypothesis (FIG. 5B). A study in mice indeed demonstrated that blockade of CASP8 results in tumor escape from CTLs (Medema et al., 1999), and our result indicates that this may be a common mechanism in human tumors (that may evade CTLs or NK cells). Interestingly, four additional genes with significant but less definitive statistical enrichment also had well-established roles in regulating extrinsic apoptosis. These include, CNKSR1 (Garimella et al., 2014), MET (Fan et al., 2001; Garofalo et al., 2009), CSNK2A1 (Ravi and Bedi, 2002) (Izeradjene et al., 2005) (Llobet et al., 2008; Wang et al., 2006), and PIK3CA (Saturno et al., 2013; Song et al., 2010). PIK3CA mutations, which were often the well-known activating alterations E545K and H1047R (Samuels and Ericson, 2006), showed their strongest enrichment in stomach cancer, demonstrating a 20% mutation rate and a strong positive association with EBV infection (p=2.9e-10). As in the case of CASP8, mutations in each of these genes were more closely associated with FASL expression than TRAIL expression. Applicants conclude that loss of the extrinsic apoptosis pathway may represent a general mechanism for tumors to escape immune cytolytic activity.

Second, the invariant chain of MHC Class I, B2M, was the second most strongly enriched gene (q=7.1e-3), showing independently significant association in uterine, breast, colorectal cancer, and stomach cancer, which exhibited the highest rate, 5.7%. The most frequent event was the same CT dinucleotide deletion observed previously in melanoma patients relapsing from T cell-based immunotherapy (Chang et al., 2005). The MHC Class I locus itself was also significant (q=5.3e-2; HLA-A, -B, -C mutations were considered jointly); q-value=1.3$e^{-11}$). HLA mutations were called through a separate pipeline and were available for a much larger number of samples; analyzed on the larger set, HLA reached a p-value of 3.0e-13 with 5 tumor types (colorectal, head and neck, uterine, stomach, and cervical cancer) independently showing this association. HLA-A and HLA-B alleles were mutated about 3 times as frequently as HLA-C alleles. No specific alleles showed strong evidence for being especially frequently mutated. The tumor types with the highest rates of HLA mutation, stomach cancer (14%), cervical cancer (12%), and head and neck cancer (11%), were also among those with frequent viral involvement. However, viral infection was not significantly associated with HLA mutation in any of them. Given the requirement of MHC Class I in presenting tumor antigens to cytotoxic CD8 T cells, Applicants consider this enrichment of MHC Class I mutations in high-CYT tumors (Khong and Restifo, 2002) as an independent and strong validation of CYT as a measure of cytolytic activity. While MHC Class II genes were not significantly mutated pan-cancer, class II gene mutations, considered collectively, were positively associated with CYT (unadj. p=0.017) with independent significance in bladder cancer (unadj. p=0.0084).

Other hits included genes with roles in innate immune sensing, including DDX3X and ARID (see Supplemental Results). Applicants also note that mutant TP53 is negatively correlated with CYT, which may be explained either by a role for p53 in regulating immunity (e.g., loss of p53-regulated stress ligands that induce cytoxicity, (Textor et al., 2011) or from absence of viral infection (consistent with p53 mutations being anti-correlated with viral infection in stomach (p=2.3e-5) and head and neck cancer (p=2.6e-4)).

Because MSI-high colorectal tumors are known to be immunogenic (Kloor et al., 2010), Applicants also considered whether MSI-high tumors were enriched for mutations in particular genes with respect to MSI-low and microsatellite stable (MSS) tumors. Mirroring the CYT analysis, CASP8 and MHC Class I mutations were the most enriched mutations in MSI-high tumors (p adj.=1.5e-5 and 1.4e-12, respectively), with COL5A1, SMC1A, CIC, ARID2 and CNKSR1 also significant (adj. p<0.05) (Table 3).

Example 8

Loci Containing Known Immune Regulators Show Copy Number Alterations Associated with CYT Applicants also considered the possibility that specific regions of the genome may be preferentially focally amplified or deleted (based on a dataset of TCGA samples profiled with SNP6.0 arrays) in high- or low-CYT tumors. As with the point mutation analysis, Applicants looked for pan-cancer CYT association with copy number alterations (CNAs) using regression and controlling for cancer subtype and background mutation rate (of amplifications and deletions). This approach yielded 13 significantly amplified regions (with 3 adjacent to each other on 6q) and 1 significantly deleted region (FDR=10%) (FIG. 6A, Table 4). Although CNAs include variable segments of a chromosomal region and do not typically identify causative genes, many of the identified regions harbored plausible candidates.

On chromosomes 9 and 8, Applicants found two well-known targets of cancer immunotherapy. First, amplification of 9p23-p24.2 (FIG. 6B), a region including PDL1 (CD274) and PDL2 (PDCD1LG2), was positively associated with CYT in lung squamous cell carcinoma, head and neck cancer, cervical cancer, stomach cancer, and colorectal cancer (FIG. 6E). PDL1 and PDL2 are critical co-stimulatory molecules that inhibit T cells through PD1, a target of numerous successful cancer immunotherapy trials. While tumor cells and tumor infiltrating leukocytes are known to express these ligands, our results suggest that tumor-expressed ligands affect tumor fitness in the presence of cytolytic activity. Second, 8p11.21-8p11.23 (FIG. 13A) showed increased probability of amplification in low-CYT tumors (pan-cancer and breast) and is adjacent to IDO1 and IDO2, enzymes that degrade extracellular tryptophan and create a potent immunosuppressive microenvironment, which may explain the associated reduction in CYT (Uyttenhove et al., 2003).

In addition, potential new targets were identified. These included 17p13.1, which was preferentially amplified in low-CYT tumors (FIG. 6D), including breast and ovarian. The peak genes, ALOX12B/ALOX15B genes (also known as 12/15-LO) that regulate immunity, for example, by blocking uptake of apoptotic cells by inflammatory monocytes in a manner that decreases antigen presentation to T cells (Uderhardt et al., 2012), consistent with the decrease in CYT. Further supporting this model, the amplification was associated with higher necrosis in breast (p=0.002) and kidney clear cell cancer (p=0.0002), though not ovarian cancer. Other peaks included ones near TNFRSF1A and TAPBPL as well as a suggestive, but not genome-wide significant enrichment at B2M (FIG. 6C).

Example 9

Tumor-Normal Differences in Immune Gene Expression

Notable differences in tumor vs. normal enrichments included the elevation of macrophage markers in ovarian cancers, the loss of neutrophils in lung cancers, and the up-regulation of MHC class I genes in glioblastoma (FIG. 8G). Most of these metrics were not correlated with stage with some possible exceptions (FIG. 8H, FIG. 8I).

Example 10

HLA-A31 is Associated with CYT in Multiple Tumor Types

As an independent approach to test potential associations of CYT with viruses, Applicants hypothesized that if CYT is driven by epitopes recurring across the patient population, as a result of viral infections, then patient HLA type would be tied to CYT. Applicants did not observe any individual tumor type for which HLA type explained a significant portion of CYT variance, with the possible exception of lung adenocarcinoma (unadjusted p=0.019; FIG. 9D). On the other hand, when Applicants considered pan-cancer association, Applicants found that HLA-A31, which has been tied to certain drug-induced hypersensitivity reactions (McCormack et al., 2011) and to HBV restriction (Missale et al., 1993), was significantly associated with CYT pan-cancer (adj. p=0.026; Wilcoxon rank-sum tests combined by Fisher's Method), showing positive association in liver cancer (both HBV+ and HBV−), glioblastoma, and melanoma and negative association in ovarian and uterine cancer (p<0.05).

The association of CYT with HLA-A31 suggests contributions of shared antigens, such as viral or CT antigens, to CYT.

Example 11

APOBEC Activity is Associated with CYT in Several Tumor Types

Since immune sensing of viral nucleic acids is known to drive both RNA- and DNA-editing activity by Apobec family enzymes (Bishop et al., 2004) (Harris et al., 2002), Applicants hypothesized that the rate of Apobec-characteristic tCx→tXx point mutations would have immunological correlates. Indeed, the rate of these mutations (relative to the overall SNV rate) is significantly positively correlated with cytolytic activity in bladder (p=0.03), head and neck (p=0.0002), cervical (p=0.002), and breast cancer (p=0.001) (FIG. 9E). Conversely, colorectal and stomach cancer demonstrated anti-correlation (p=0.0006 and p=0.00008, respectively). A significant positive association between Apobec-characteristic mutation and viral infection was observed in head and neck cancer (p=0.02), but not cervical cancer, possibly owing to the small number of HPV− cases. Therefore, while the Apobec signatures were tied to T cell activity in two virally induced tumor types, unexpected associations also existed for breast cancer, stomach cancer, and colorectal cancer pointing toward novel forms of immunity-driven mutagenesis, such as unknown viral infections (although no ERVs showed definitive association with Apobec mutation enrichments).

Example 12

Depletion of Neo-Epitope-Yielding Point Mutations

In the analysis of the depletion of mutations yielding neo-epitopes, colorectal cancer was most dramatically depleted, suggesting that mutations are rejected by T cells, and gene expression analysis showed that the degree of depletion was significantly associated with terms including "cellular response to DNA damage stimulus" (q=4.8e-26) and "antigen processing and presentation of peptide antigen via MHC Class I" (q=2.6e-18).

Example 13

Correlates of Necrosis

Given that dying cells can provide both antigens and immunostimulatory ligands, Applicants explored the potential role for necrosis in driving CYT and immune infiltration in general. Rates of necrosis (pathologist-assessed based on H&E staining; available in TCGA clinical data) are highest in glioblastoma, lung squamous cell carcinoma, and uterine cancer, and lowest in prostate, glioma, and thyroid cancer (FIG. 11F). Necrosis showed modest positive association (p<0.05) with CYT in glioblastoma, bladder, and ovarian cancer, and did not show negative association in any tumor type. Of all cell types, macrophages showed the most consistent positive associations with necrosis, with the strongest effects in glioblastoma and glioma (FIG. 11G). Nonetheless, other tumor types, particularly HPV+ head and neck cancer, lung adenocarcinoma, and EBV-stomach cancer showed overall negative relationships between necrosis and most components of the immune infiltrate, suggesting that these relationships are highly tumor type dependent.

Example 14

Genes Point-Mutated in High-CYT Tumors

Innate immune sensing emerged as another theme among the enriched genes. DDX3X is a viral RNA sensor that binds IPS-1 and drives activation of IFNβ (Oshiumi et al., 2010). While its mutations did show some positive association with HPV infection in head and neck cancer (p=0.054), they were most frequent in melanoma and uterine cancer, at about 5% in each tumor type, without apparent association with viral infection. ARID2, which appears to be important to sensing due to the effect of its knockdown on IFITM1 expression (Yan et al., 2005), showed significant negative enrichment in prostate cancer, significant positive enrichment in uterine, breast, and cervical cancer, and a notably high rate of mutation in melanoma, 18.7%. Consistent with the possible role in sensing, mutations in this gene have been observed to be enriched in HCV-associated hepatocellular carcinomas compared to non-HCV-associated cases (Li et al., 2011), though Applicants do not observe this association in our sample. NCOR1, which is a transcriptional repressor of pro-inflammatory TLR-response genes and a host target of HPV (Jennewein et al., 2008) (Pieters et al., 2013) (Powell et al., 2010), showed significant association with CYT in uterine cancer, bladder cancer, and melanoma. SOS1, a Ras guanine nucleotide exchange factor that has been connected to TLR signaling (Peng et al., 2012) showed pan-cancer enrichment. Other genes were also associated with immunity, including IRF6, systemic lupus erythematosus-associated and rheumatoid arthritis-associated ARIDSB (Yang et al., 2013) (Morozov et al., 2013), immunoglobulin domain-containing ALPK2 (FIG. 12C), and lymphoma CT-antigen MORC4 (Liggins et al., 2007).

Applicants also note that NF1, a gene previously identified as being significantly mutated in T cell-infiltrated TCGA glioblastomas (Rutledge et al., 2013), was a pan-cancer hit in our analysis.

Among the 351 genes tested were some well-characterized immune genes for which Applicants expected potential association with CYT but which Applicants did not observe. These included CD1D, CD4, CD5, CD70, CD79B, CLEC4E, IL7R, IL32, IRF4, MYD88, SELP, SLAMF7, TAP1, TNF, and TNFRSF14. Applicants tested for differential gene expression with respect to each of these mutations in the tumor type in which it was most frequent. Applicants saw evidence for increased immune activation for SLAMF7 and IRF4 mutants (6 and 8 cases, respectively) in uterine cancer and for decreased immune activation for MYD88 mutants in melanoma (3 cases). For the remaining genes, sparseness in the data may be preventing statistical identification of relevant immunological correlates—only half exceeded a mutation rate of 3% in any tumor type.

Example 15

Significant Copy Number Alterations

Amplification of 12p13.2-12p13.32, a region with homology to the MHC I locus, showed significance in lung squamous cell carcinoma and breast cancer and contained many immune-related genes including TNFRSF1A, LTBR, C1S, C1R, C1RL, APOBEC1, LAGS, CLEC4E (also implicated in the point mutation analysis), and TAPBPL, a paralog of tapesin that delays the maturation of MHC I molecules (Boyle et al., 2013; Teng et al., 2002) (FIG. 13A). A deletion peak centered near beta-catenin (CTNNB1) on 3p22.3-p21.31 also contained a large number of immune-related genes (FIG. 13A). Finally, a more challenging region to interpret was the q-arm of chromosome 6 (q16.1-q21, q22.31-q24.1, q25.1-q26) with a possible drivers including PRDM1, which may suppress interferon gamma-induced MHC Class I expression (Doody et al., 2007) and the vanin pantetheinases VNN1, VNN2, and VNN3, which are thought to be involved in leukocyte trafficking (Suzuki et al., 1999) (Yoshitake et al., 2002). For all the loci, considerable studies remain to validate drivers.

Applicants also identified potential associations of CNAs around genes involved in antigen presentation. While it did not pass false discovery rate thresholds, the region surrounding B2M demonstrated nominal pan-cancer significance (p=6.8e-4) for deletion in high-CYT tumors (FIG. 6C), mirroring the evasion pattern observed in the point mutation analysis. On the other hand, the locus containing HLA-A, —B, and —C, did not exhibit any copy number changes significantly associated with CYT. Of note, increased MHC Class I expression was associated with amplification of the MHC Class II complex (adj. p<5e-4; peak signal between HLA-DMB and TAPBP; FIG. 13B).

Discussion

Based on the notion that effective natural anti-tumor immunity requires a cytolytic immune response (FIG. 7A), Applicants quantified cytolytic activity using a simple expression metric based on the key effector molecules that mediate cytolysis. Our analysis was designed to address what genetic and environmental factors may drive tumor-associated cytolytic activity, and how this cytolytic activity may select for genetic resistance in tumors. Our results suggest that neoantigens and viruses are likely to drive cytolytic activity, and reveal known and novel mutations that enable tumors to resist immune attack.

Applicants considered several explanations for the high immune cytolytic activity observed in some tumors (FIG. 7A). First, if immunogenic antigens are required for T cells to be primed, neoepitopes would be the ideal candidates because they are absent from the thymus and thus do not induce central tolerance that deletes high-affinity T cells targeting the neoepitopes. Supporting this model, neoantigen load was strongly associated with cytolytic activity across multiple tumor types, and neoantigens appeared to be depleted in several tumor types relative to expectations based on the silent mutation rate. The observed depletion of neoantigens provides systematic evidence for the immune-editing hypothesis across many tumors (Schreiber et al., 2011). Second, when Applicants considered 60 CT antigens expressed selectively in tumors, Applicants did not observe a positive correlation between the number expressed and cytolytic activity. In addition, these genes were not contained within deletions associated with CYT as would be expected given immune pressure on CT antigens. Regardless of their role in the induction of spontaneous anti-tumor immunity, these 60 highly tumor-specific antigens are candidate targets for immunotherapy, especially adoptive T cell transfer or CAR-T therapy. Third, Applicants asked whether viruses could be inducers of immune responses. In some tumors, Applicants observed that cytolytic activity does indeed associate with the presence of exogenous or endogenous viruses, and Applicants expect that some viruses would trigger immunity through RNA and DNA sensors and generate immunogenic antigens for the adaptive immune response. Applicants note that necrosis, often considered a potential source of antigens and adjuvants, was very weakly correlated with CYT (FIG. 11E, F).

To learn more about how tumors adapt to attack by cytolytic immune cells, Applicants also searched for enrichment of somatic genetic alterations in tumors with high vs. low cytolytic activity. As expected, Applicants observed enrichment of mutations in antigen presentation machinery (thus validating our inferred cytolytic metric), including HLA and B2M, as well as extrinsic apoptosis genes, such as CASP8, that would prevent cytolytic cells from killing tumors via FasL-Fas interactions. In addition, Applicants found cytolytic activity correlating with amplifications in regions containing genes that function in immunosuppression, such as PDL1, PDL2. In total, Applicants identified >20 mutations that are likely to represent autonomous escape mechanisms (FIG. 7B). In addition, Applicants identified several mutations that correlated negatively with cytolytic activity and likely represent non-autonomous mechanisms of suppressing immunity, and include IDO1 and IDO2, p53, and the ALOX locus (FIG. 7C).

Our approach has allowed us to positively identify the subset of tumor types that are sensitive to spontaneous cytolytic activity, especially T cells targeting neoantigens (FIG. 14, Table 5). Using positive correlation of HLA or B2M mutations with CYT as a 'signature' of selection pressure by the immune system, Applicants identified colorectal, uterine, stomach, head and neck, cervical and breast cancers as tumors that are most susceptible to immune elimination. If Applicants further consider depletion of neoepitopes as an independent signature of selection, Applicants find colorectal as well as kidney clear cancer. These results suggest that for these tumor types, spontaneous tumor immunity can effectively delete tumor cells.

Applicants also found four tumors that appeared to have minimal evidence of spontaneous cytolytic activity: kidney papillary, thyroid, glioma and prostate cancers. Nevertheless, Applicants anticipate that less susceptible tumors (e.g., glioblastoma, which has no evidence of immune-mediated selection, but does have higher CYT activity than control tissues) may still be possible to treat effectively with neoantigen vaccines that may be much more potent at inducing immunity than the body's endogenous responses.

Finally, the mutations associated with cytolytic activity reveal potential biomarkers for predicting outcome and candidate targets for immunotherapy. To assess the utility of these markers, one would need to genotype tumors for the 28 identified genes at clonal or subclonal levels, and test if pre-treatment or post-treatment mutations predict refractoriness or relapse, respectively, in response to cytolytic immunotherapy. Applicants expect that some of the mutations—such as amplifications in PDL1/2 and heterozygous loss in B2M, HLA-A/B or CASP8 but not, for example, homozygous loss of B2M—would suggest that re-activating CD8 T cells would still be effective. In addition, Applicants identified new candidates for therapeutic development, including the ALOX enzymes and their products, the PIK3CA protein that is enriched in activating mutations in high-CYT stomach cancers, and FASL which may be useful to overexpress in T cells to enhance the anti-tumor activity of adoptively transferred T cells.

TCGA samples have highlighted environmental and genetic mechanisms that impact tumor-immune interactions. While Applicants chose to focus on cytolytic activity because of its central role in tumor elimination and the feasibility of monitoring its activity, Applicants did not consider other tumoricidal activities (such as antibody-dependent cell-mediated cytotoxicity) because Applicants are not aware of transcript-based markers for these activities. In addition, the CYT metric Applicants used is transcript-based and thus may not reflect changes in cytolytic activity due to post-transcriptional regulation, and is a snapshot in time that may miss previous activity that impacted tumor growth. Applicants anticipate that more accurate experimental measurements of anti-tumor immune activity will be developed and further reveal the genetic and epigenetic changes that underlie co-evolution of tumor cells and immune cells.

DESCRIPTION OF THE TABLES

Table 1. Cell type gene expression markers. Gene symbols for best transcriptomic cell type markers according to analysis of Fantom5 CAGE data.

Table 2. Analysis of significantly point-mutated genes. (A) Enrichment statistics for pan-cancer significant genes. Statistics are presented for the overall pan-cancer analysis and for tumor type-specific sub-analyses. Beta values reflect that the dependent variable (CYT) was transformed to rank values scaled from 0 to 100. The table also presents counts of mutated and total samples per tumor type/gene. Note that HLA mutations were called for a larger number of samples than general mutations. (B) Each value is a signed log 10 p-value characterizing the association between the non-silent mutation status of the gene (see row headings) and the level of cytolytic activity in the given tumor type (see column headings) according to regression analysis. For instance, the value "+2.8" for the gene BRAF in colorectal cancer indicates that BRAF mutations are positively correlated with high cytolytic activity in colorectal cancer with a pvalue of $10^{-2.8}=0.0015$. The column "PanCancer" corresponds to a meta analysis that assessed association across all 23 tumor types simultaneously. The column "PanCancer Adjusted" is identical to the "PanCancer" column, except the magnitude of the signficances has been attenuated by Benjamini Hochberg multiple hypotheses correction. This list was generated using a data set that included updated mutation calls and coverage for five additional tumor types; it displays genes that are considered hits in the updated analysis (adjusted pan-cancer p-value<0.01). Gene names are HUGO gene symbols.

Table 3. Analysis of significantly point-mutated genes. Mutations associated with microsatellite instability (MSI) in colorectal cancer (MSI-high vs. MSI-low and microsatellite stable) at 10% FDR. Table indicates odds ratios, Fisher exact test p-values and counts for virally infected vs. mutant samples, and BH-correctef p-values.

Table 4. CYT association statistics for significant copy number alterations (CNAs). Statistics are presented for the overall pancancer analysis and for tumor type-specific sub-analyses. Beta values reflect that the dependent variable (CYT) was transformed to rank values scaled from 0 to 100 and the scaling of the CNA events per sample to have a median amplitude of 1. The table also presents counts of mutated and total samples per tumor type/gene; mutant condition was based on nonzero GISTIC score.

Table 5. A Summary of Immunological Properties per Tumor Type, Related to FIG. 7. Immune attributes and associations (rows) and the corresponding tumor types in which they manifest (columns) with a "1" (highlighted in red) to mark positive instances of the trend or attribute and a "−1" (highlighted in blue) to mark cases in which the opposite trend was observed.

TABLE 1

| B cells | CD4+ Regulatory T cells | CD8+ T cells | Macrophages | Neutrophils | NK cells | pDCs | MHC Class I |
|---|---|---|---|---|---|---|---|
| CD79B | FOXP3 | CD8A | FUCA1 | KDM6B | KLRF1 | LILRA4 | HLA-A |
| BTLA | C15orf53 | | MMP9 | HSD17B11 | KLRC1 | CLEC4C | B2M |
| FCRL3 | IL5 | | LGMN | EVI2B | | PLD4 | TAP1 |
| BANK1 | CTLA4 | | HS3ST2 | MNDA | | PHEX | |
| CD79A | IL32 | | TM4SF19 | MEGF9 | | IL3RA | |
| BLK | GPR15 | | CLEC5A | SELL | | PTCRA | |
| RALGPS2 | IL4 | | GPNMB | NLRP12 | | IRF8 | |
| FCRL1 | | | C11orf45 | PADI4 | | IRF7 | |
| HVCN1 | | | CD68 | TRANK1 | | GZMB | |
| BACH2 | | | CYBB | VNN3 | | CXCR3 | |

| Co-stimulation, APC | Co-stimulation, T cell | Co-inhibition, APC | Co-inhibition, T cell | Type I IFN Reponse | Type II IFN Reponse | Cytolytic Activity |
|---|---|---|---|---|---|---|
| ICOSLG | ICOS | PDCD1LG2 | LAG3 | MX1 | GPR146 | GZMA |
| CD70 | CD28 | CD274 | CTLA4 | TNFSF10 | SELP | PRF1 |
| TNFSF14 | CD27 | C10orf54 | CD274 | RSAD2 | AHR | |
| CD40 | TNFSF14 | LGALS9 | CD160 | IFIT1 | | |
| TNFSF9 | CD40LG | PVRL3 | BTLA | IFIT3 | | |
| TNFSF4 | TNFRSF9 | | C10orf54 | IFIT2 | | |
| TNFSF15 | TNFRSF4 | | LAIR1 | IRF7 | | |
| TNFSF18 | TNFRSF25 | | HAVCR2 | DDX4 | | |
| TNFSF8 | TNFRSF18 | | CD244 | MX2 | | |
| SLAMF1 | TNFRSF8 | | TIGIT | ISG20 | | |
| CD58 | SLAMF1 | | | | | |
| | CD2 | | | | | |
| | CD226 | | | | | |

TABLE 2A

| Gene | PanCancer P | PanCancer BH adj. P | PanCancer Beta | Cancer | Count Samples | Count Mutated | Percent Mutated | Cancer P | Cancer Beta |
|---|---|---|---|---|---|---|---|---|---|
| CASP8 | 2.5E−09 | 9.2E−07 | 15.3 | HNSC | 294 | 20 | 6.8% | 1.2E−04 | 25.5 |
| CASP8 | 2.5E−09 | 9.2E−07 | 15.3 | CRC | 217 | 8 | 3.7% | 2.8E−03 | 31.7 |
| CASP8 | 2.5E−09 | 9.2E−07 | 15.3 | UCEC | 244 | 17 | 7.0% | 1.8E−02 | 18.1 |
| CASP8 | 2.5E−09 | 9.2E−07 | 15.3 | LUSC | 176 | 2 | 1.1% | 4.6E−02 | 40.8 |
| CASP8 | 2.5E−09 | 9.2E−07 | 15.3 | SKCM | 93 | 3 | 3.2% | 1.1E−01 | −27.7 |
| CASP8 | 2.5E−09 | 9.2E−07 | 15.3 | BLCA | 136 | 4 | 2.9% | 1.1E−01 | 23.3 |
| CASP8 | 2.5E−09 | 9.2E−07 | 15.3 | STAD | 263 | 18 | 6.8% | 1.3E−01 | 11.1 |
| CASP8 | 2.5E−09 | 9.2E−07 | 15.3 | CESC | 193 | 9 | 4.7% | 1.4E−01 | 17.8 |
| CASP8 | 2.5E−09 | 9.2E−07 | 15.3 | BRCA | 760 | 7 | 0.9% | 1.7E−01 | 14.9 |
| CASP8 | 2.5E−09 | 9.2E−07 | 15.3 | LUAD | 168 | 2 | 1.2% | 5.5E−01 | 12.1 |
| CASP8 | 2.5E−09 | 9.2E−07 | 15.3 | LIHC | 196 | 2 | 1.0% | 7.2E−01 | 7.5 |
| CASP8 | 2.5E−09 | 9.2E−07 | 15.3 | GBM | 147 | 0 | 0.0% | | |

TABLE 2A-continued

| Gene | PanCancer P | PanCancer BH adj. P | PanCancer Beta | Cancer | Count Samples | Count Mutated | Percent Mutated | Cancer P | Cancer Beta |
|---|---|---|---|---|---|---|---|---|---|
| CASP8 | 2.5E−09 | 9.2E−07 | 15.3 | KIRC | 406 | 0 | 0.0% | | |
| CASP8 | 2.5E−09 | 9.2E−07 | 15.3 | KIRP | 167 | 0 | 0.0% | | |
| CASP8 | 2.5E−09 | 9.2E−07 | 15.3 | LGG | 201 | 0 | 0.0% | | |
| CASP8 | 2.5E−09 | 9.2E−07 | 15.3 | OV | 188 | 0 | 0.0% | | |
| CASP8 | 2.5E−09 | 9.2E−07 | 15.3 | PRAD | 258 | 0 | 0.0% | | |
| CASP8 | 2.5E−09 | 9.2E−07 | 15.3 | THCA | 314 | 0 | 0.0% | | |
| B2M | 4.0E−05 | 7.5E−03 | 15.7 | STAD | 263 | 15 | 5.7% | 6.0E−03 | 21.8 |
| B2M | 4.0E−05 | 7.5E−03 | 15.7 | CRC | 217 | 4 | 1.8% | 3.3E−02 | 31.2 |
| B2M | 4.0E−05 | 7.5E−03 | 15.7 | BRCA | 760 | 3 | 0.4% | 3.5E−02 | 35.1 |
| B2M | 4.0E−05 | 7.5E−03 | 15.7 | UCEC | 244 | 2 | 0.8% | 4.3E−02 | 41.2 |
| B2M | 4.0E−05 | 7.5E−03 | 15.7 | LIHC | 196 | 1 | 0.5% | 1.1E−01 | 46.8 |
| B2M | 4.0E−05 | 7.5E−03 | 15.7 | KIRC | 406 | 1 | 0.2% | 1.8E−01 | −38.6 |
| B2M | 4.0E−05 | 7.5E−03 | 15.7 | HNSC | 294 | 3 | 1.0% | 2.1E−01 | 21.1 |
| B2M | 4.0E−05 | 7.5E−03 | 15.7 | CESC | 193 | 3 | 1.6% | 2.8E−01 | −18.2 |
| B2M | 4.0E−05 | 7.5E−03 | 15.7 | GBM | 147 | 2 | 1.4% | 3.1E−01 | 21.0 |
| B2M | 4.0E−05 | 7.5E−03 | 15.7 | KIRP | 167 | 1 | 0.6% | 6.1E−01 | −14.9 |
| B2M | 4.0E−05 | 7.5E−03 | 15.7 | LUSC | 176 | 2 | 1.1% | 6.2E−01 | −10.1 |
| B2M | 4.0E−05 | 7.5E−03 | 15.7 | BLCA | 136 | 1 | 0.7% | 9.2E−01 | −2.9 |
| B2M | 4.0E−05 | 7.5E−03 | 15.7 | LGG | 201 | 0 | 0.0% | | |
| B2M | 4.0E−05 | 7.5E−03 | 15.7 | LUAD | 168 | 0 | 0.0% | | |
| B2M | 4.0E−05 | 7.5E−03 | 15.7 | OV | 188 | 0 | 0.0% | | |
| B2M | 4.0E−05 | 7.5E−03 | 15.7 | PRAD | 258 | 0 | 0.0% | | |
| B2M | 4.0E−05 | 7.5E−03 | 15.7 | SKCM | 93 | 0 | 0.0% | | |
| B2M | 4.0E−05 | 7.5E−03 | 15.7 | THCA | 314 | 0 | 0.0% | | |
| PIK3CA | 8.4E−05 | 8.4E−03 | 6.3 | STAD | 263 | 52 | 19.8% | 6.6E−09 | 25.5 |
| PIK3CA | 8.4E−05 | 8.4E−03 | 6.3 | SKCM | 93 | 4 | 4.3% | 8.4E−02 | 25.3 |
| PIK3CA | 8.4E−05 | 8.4E−03 | 6.3 | KIRC | 406 | 3 | 0.7% | 1.1E−01 | 26.6 |
| PIK3CA | 8.4E−05 | 8.4E−03 | 6.3 | BRCA | 760 | 29 | 3.8% | 1.2E−01 | 8.4 |
| PIK3CA | 8.4E−05 | 8.4E−03 | 6.3 | KIRP | 167 | 2 | 1.2% | 1.8E−01 | 27.7 |
| PIK3CA | 8.4E−05 | 8.4E−03 | 6.3 | LGG | 201 | 18 | 9.0% | 2.2E−01 | 8.5 |
| PIK3CA | 8.4E−05 | 8.4E−03 | 6.3 | CESC | 193 | 54 | 28.0% | 3.0E−01 | −6.3 |
| PIK3CA | 8.4E−05 | 8.4E−03 | 6.3 | LIHC | 196 | 8 | 4.1% | 3.0E−01 | −12.6 |
| PIK3CA | 8.4E−05 | 8.4E−03 | 6.3 | LUSC | 176 | 12 | 6.8% | 3.4E−01 | −8.3 |
| PIK3CA | 8.4E−05 | 8.4E−03 | 6.3 | GBM | 147 | 10 | 6.8% | 4.4E−01 | 7.4 |
| PIK3CA | 8.4E−05 | 8.4E−03 | 6.3 | THCA | 314 | 3 | 1.0% | 4.7E−01 | 12.1 |
| PIK3CA | 8.4E−05 | 8.4E−03 | 6.3 | BLCA | 136 | 14 | 10.3% | 5.3E−01 | 5.2 |
| PIK3CA | 8.4E−05 | 8.4E−03 | 6.3 | HNSC | 294 | 8 | 2.7% | 6.1E−01 | 5.3 |
| PIK3CA | 8.4E−05 | 8.4E−03 | 6.3 | CRC | 217 | 8 | 3.7% | 6.2E−01 | 5.1 |
| PIK3CA | 8.4E−05 | 8.4E−03 | 6.3 | LUAD | 168 | 6 | 3.6% | 7.8E−01 | 3.4 |
| PIK3CA | 8.4E−05 | 8.4E−03 | 6.3 | UCEC | 244 | 33 | 13.5% | 8.2E−01 | 1.3 |
| PIK3CA | 8.4E−05 | 8.4E−03 | 6.3 | PRAD | 258 | 9 | 3.5% | 8.8E−01 | −2.1 |
| PIK3CA | 8.4E−05 | 8.4E−03 | 6.3 | OV | 188 | 0 | 0.0% | | |
| SMC1A | 9.0E−05 | 8.4E−03 | 11.3 | UCEC | 244 | 15 | 6.1% | 1.9E−03 | 24.0 |
| SMC1A | 9.0E−05 | 8.4E−03 | 11.3 | CRC | 217 | 9 | 4.1% | 3.1E−03 | 29.5 |
| SMC1A | 9.0E−05 | 8.4E−03 | 11.3 | KIRP | 167 | 2 | 1.2% | 7.7E−02 | 36.3 |
| SMC1A | 9.0E−05 | 8.4E−03 | 11.3 | LUSC | 176 | 2 | 1.1% | 1.0E−01 | −33.7 |
| SMC1A | 9.0E−05 | 8.4E−03 | 11.3 | LIHC | 196 | 7 | 3.6% | 1.1E−01 | −19.9 |
| SMC1A | 9.0E−05 | 8.4E−03 | 11.3 | HNSC | 294 | 3 | 1.0% | 1.1E−01 | 27.0 |
| SMC1A | 9.0E−05 | 8.4E−03 | 11.3 | SKCM | 93 | 1 | 1.1% | 1.6E−01 | 40.8 |
| SMC1A | 9.0E−05 | 8.4E−03 | 11.3 | KIRC | 406 | 2 | 0.5% | 2.0E−01 | −26.5 |
| SMC1A | 9.0E−05 | 8.4E−03 | 11.3 | OV | 188 | 3 | 1.6% | 2.6E−01 | 18.8 |
| SMC1A | 9.0E−05 | 8.4E−03 | 11.3 | LGG | 201 | 1 | 0.5% | 2.7E−01 | 31.1 |
| SMC1A | 9.0E−05 | 8.4E−03 | 11.3 | STAD | 263 | 7 | 2.7% | 3.4E−01 | 10.6 |
| SMC1A | 9.0E−05 | 8.4E−03 | 11.3 | BLCA | 136 | 3 | 2.2% | 3.8E−01 | 14.7 |
| SMC1A | 9.0E−05 | 8.4E−03 | 11.3 | GBM | 147 | 3 | 2.0% | 6.2E−01 | 8.4 |
| SMC1A | 9.0E−05 | 8.4E−03 | 11.3 | BRCA | 760 | 5 | 0.7% | 7.1E−01 | 4.8 |
| SMC1A | 9.0E−05 | 8.4E−03 | 11.3 | CESC | 193 | 4 | 2.1% | 7.1E−01 | 6.2 |
| SMC1A | 9.0E−05 | 8.4E−03 | 11.3 | LUAD | 168 | 2 | 1.2% | 7.7E−01 | 5.9 |
| SMC1A | 9.0E−05 | 8.4E−03 | 11.3 | PRAD | 258 | 0 | 0.0% | | |
| SMC1A | 9.0E−05 | 8.4E−03 | 11.3 | THCA | 314 | 0 | 0.0% | | |
| TET2 | 2.6E−04 | 1.9E−02 | 10.4 | UCEC | 244 | 13 | 5.3% | 1.5E−02 | 20.9 |
| TET2 | 2.6E−04 | 1.9E−02 | 10.4 | LIHC | 196 | 7 | 3.6% | 1.8E−02 | 27.2 |
| TET2 | 2.6E−04 | 1.9E−02 | 10.4 | LGG | 201 | 3 | 1.5% | 2.1E−02 | 37.4 |
| TET2 | 2.6E−04 | 1.9E−02 | 10.4 | BRCA | 760 | 4 | 0.5% | 7.2E−02 | 26.0 |
| TET2 | 2.6E−04 | 1.9E−02 | 10.4 | KIRP | 167 | 2 | 1.2% | 7.6E−02 | −36.3 |
| TET2 | 2.6E−04 | 1.9E−02 | 10.4 | STAD | 263 | 10 | 3.8% | 1.1E−01 | 15.2 |
| TET2 | 2.6E−04 | 1.9E−02 | 10.4 | OV | 188 | 1 | 0.5% | 1.3E−01 | 44.2 |
| TET2 | 2.6E−04 | 1.9E−02 | 10.4 | LUSC | 176 | 4 | 2.3% | 1.8E−01 | −19.3 |
| TET2 | 2.6E−04 | 1.9E−02 | 10.4 | SKCM | 93 | 3 | 3.2% | 1.9E−01 | −22.6 |
| TET2 | 2.6E−04 | 1.9E−02 | 10.4 | LUAD | 168 | 3 | 1.8% | 4.1E−01 | 13.5 |
| TET2 | 2.6E−04 | 1.9E−02 | 10.4 | KIRC | 406 | 7 | 1.7% | 5.5E−01 | 6.6 |
| TET2 | 2.6E−04 | 1.9E−02 | 10.4 | HNSC | 294 | 2 | 0.7% | 6.3E−01 | 9.9 |
| TET2 | 2.6E−04 | 1.9E−02 | 10.4 | CESC | 193 | 4 | 2.1% | 6.4E−01 | 13.5 |
| TET2 | 2.6E−04 | 1.9E−02 | 10.4 | BLCA | 136 | 4 | 2.9% | 7.7E−01 | 4.3 |
| TET2 | 2.6E−04 | 1.9E−02 | 10.4 | GBM | 147 | 1 | 0.7% | 9.0E−01 | −3.6 |
| TET2 | 2.6E−04 | 1.9E−02 | 10.4 | CRC | 217 | 4 | 1.8% | 9.0E−01 | 1.8 |
| TET2 | 2.6E−04 | 1.9E−02 | 10.4 | PRAD | 258 | 0 | 0.0% | | |

TABLE 2A-continued

| Gene | PanCancer P | PanCancer BH adj. P | PanCancer Beta | Cancer | Count Samples | Count Mutated | Percent Mutated | Cancer P | Cancer Beta |
|---|---|---|---|---|---|---|---|---|---|
| TET2 | 2.6E−04 | 1.9E−02 | 10.4 | THCA | 314 | 0 | 0.0% | | |
| ARID5B | 3.0E−04 | 1.9E−02 | 9.1 | CRC | 217 | 5 | 2.3% | 1.1E−02 | 33.5 |
| ARID5B | 3.0E−04 | 1.9E−02 | 9.1 | PRAD | 258 | 2 | 0.8% | 2.1E−02 | −47.3 |
| ARID5B | 3.0E−04 | 1.9E−02 | 9.1 | STAD | 263 | 11 | 4.2% | 2.9E−02 | 19.8 |
| ARID5B | 3.0E−04 | 1.9E−02 | 9.1 | BRCA | 760 | 3 | 0.4% | 1.3E−01 | 25.2 |
| ARID5B | 3.0E−04 | 1.9E−02 | 9.1 | HNSC | 294 | 11 | 3.7% | 1.4E−01 | 13.1 |
| ARID5B | 3.0E−04 | 1.9E−02 | 9.1 | BLCA | 136 | 3 | 2.2% | 1.8E−01 | 22.4 |
| ARID5B | 3.0E−04 | 1.9E−02 | 9.1 | THCA | 314 | 1 | 0.3% | 2.4E−01 | 34.2 |
| ARID5B | 3.0E−04 | 1.9E−02 | 9.1 | LIHC | 196 | 9 | 4.6% | 2.7E−01 | 12.3 |
| ARID5B | 3.0E−04 | 1.9E−02 | 9.1 | UCEC | 244 | 29 | 11.9% | 4.2E−01 | 4.7 |
| ARID5B | 3.0E−04 | 1.9E−02 | 9.1 | LUSC | 176 | 3 | 1.7% | 5.5E−01 | 10.0 |
| ARID5B | 3.0E−04 | 1.9E−02 | 9.1 | CESC | 193 | 4 | 2.1% | 6.9E−01 | 5.8 |
| ARID5B | 3.0E−04 | 1.9E−02 | 9.1 | KIRC | 406 | 3 | 0.7% | 7.2E−01 | −6.1 |
| ARID5B | 3.0E−04 | 1.9E−02 | 9.1 | SKCM | 93 | 6 | 6.5% | 7.3E−01 | −4.3 |
| ARID5B | 3.0E−04 | 1.9E−02 | 9.1 | LUAD | 168 | 4 | 2.4% | 8.4E−01 | −2.9 |
| ARID5B | 3.0E−04 | 1.9E−02 | 9.1 | GBM | 147 | 0 | 0.0% | | |
| ARID5B | 3.0E−04 | 1.9E−02 | 9.1 | KIRP | 167 | 0 | 0.0% | | |
| ARID5B | 3.0E−04 | 1.9E−02 | 9.1 | LGG | 201 | 0 | 0.0% | | |
| ARID5B | 3.0E−04 | 1.9E−02 | 9.1 | OV | 188 | 0 | 0.0% | | |
| ALPK2 | 4.2E−04 | 2.1E−02 | 7.5 | HNSC | 294 | 7 | 2.4% | 1.9E−02 | 25.9 |
| ALPK2 | 4.2E−04 | 2.1E−02 | 7.5 | THCA | 314 | 2 | 0.6% | 3.6E−02 | 43.0 |
| ALPK2 | 4.2E−04 | 2.1E−02 | 7.5 | LUSC | 176 | 16 | 9.1% | 8.8E−02 | 12.9 |
| ALPK2 | 4.2E−04 | 2.1E−02 | 7.5 | GBM | 147 | 1 | 0.7% | 1.2E−01 | −45.5 |
| ALPK2 | 4.2E−04 | 2.1E−02 | 7.5 | KIRC | 406 | 7 | 1.7% | 1.9E−01 | 14.4 |
| ALPK2 | 4.2E−04 | 2.1E−02 | 7.5 | STAD | 263 | 14 | 5.3% | 2.1E−01 | 10.4 |
| ALPK2 | 4.2E−04 | 2.1E−02 | 7.5 | LUAD | 168 | 15 | 8.9% | 2.2E−01 | −9.7 |
| ALPK2 | 4.2E−04 | 2.1E−02 | 7.5 | UCEC | 244 | 16 | 6.6% | 2.2E−01 | 9.9 |
| ALPK2 | 4.2E−04 | 2.1E−02 | 7.5 | LGG | 201 | 1 | 0.5% | 2.7E−01 | 31.1 |
| ALPK2 | 4.2E−04 | 2.1E−02 | 7.5 | OV | 188 | 1 | 0.5% | 3.2E−01 | 29.2 |
| ALPK2 | 4.2E−04 | 2.1E−02 | 7.5 | BLCA | 136 | 3 | 2.2% | 4.1E−01 | 14.2 |
| ALPK2 | 4.2E−04 | 2.1E−02 | 7.5 | BRCA | 760 | 4 | 0.5% | 4.1E−01 | 11.8 |
| ALPK2 | 4.2E−04 | 2.1E−02 | 7.5 | KIRP | 167 | 1 | 0.6% | 5.0E−01 | 19.4 |
| ALPK2 | 4.2E−04 | 2.1E−02 | 7.5 | PRAD | 258 | 4 | 1.6% | 5.5E−01 | 8.7 |
| ALPK2 | 4.2E−04 | 2.1E−02 | 7.5 | CRC | 217 | 8 | 3.7% | 5.9E−01 | 5.8 |
| ALPK2 | 4.2E−04 | 2.1E−02 | 7.5 | LIHC | 196 | 10 | 5.1% | 6.0E−01 | 5.2 |
| ALPK2 | 4.2E−04 | 2.1E−02 | 7.5 | SKCM | 93 | 22 | 23.7% | 7.2E−01 | −2.8 |
| ALPK2 | 4.2E−04 | 2.1E−02 | 7.5 | CESC | 193 | 8 | 4.1% | 9.1E−01 | 1.9 |
| LPAR2 | 4.5E−04 | 2.1E−02 | 21.9 | LUSC | 176 | 2 | 1.1% | 2.0E−02 | 47.2 |
| LPAR2 | 4.5E−04 | 2.1E−02 | 21.9 | UCEC | 244 | 6 | 2.5% | 6.5E−02 | 22.3 |
| LPAR2 | 4.5E−04 | 2.1E−02 | 21.9 | SKCM | 93 | 1 | 1.1% | 1.2E−01 | 44.7 |
| LPAR2 | 4.5E−04 | 2.1E−02 | 21.9 | KIRP | 167 | 1 | 0.6% | 1.3E−01 | 43.5 |
| LPAR2 | 4.5E−04 | 2.1E−02 | 21.9 | CESC | 193 | 1 | 0.5% | 1.5E−01 | 41.4 |
| LPAR2 | 4.5E−04 | 2.1E−02 | 21.9 | STAD | 263 | 1 | 0.4% | 6.1E−01 | −14.7 |
| LPAR2 | 4.5E−04 | 2.1E−02 | 21.9 | CRC | 217 | 2 | 0.9% | 9.6E−01 | 0.9 |
| LPAR2 | 4.5E−04 | 2.1E−02 | 21.9 | GBM | 147 | 0 | 0.0% | | |
| LPAR2 | 4.5E−04 | 2.1E−02 | 21.9 | KIRC | 406 | 0 | 0.0% | | |
| LPAR2 | 4.5E−04 | 2.1E−02 | 21.9 | LGG | 201 | 0 | 0.0% | | |
| LPAR2 | 4.5E−04 | 2.1E−02 | 21.9 | HNSC | 294 | 0 | 0.0% | | |
| LPAR2 | 4.5E−04 | 2.1E−02 | 21.9 | THCA | 314 | 0 | 0.0% | | |
| LPAR2 | 4.5E−04 | 2.1E−02 | 21.9 | LIHC | 196 | 0 | 0.0% | | |
| LPAR2 | 4.5E−04 | 2.1E−02 | 21.9 | LUAD | 168 | 0 | 0.0% | | |
| LPAR2 | 4.5E−04 | 2.1E−02 | 21.9 | OV | 188 | 0 | 0.0% | | |
| LPAR2 | 4.5E−04 | 2.1E−02 | 21.9 | PRAD | 258 | 0 | 0.0% | | |
| LPAR2 | 4.5E−04 | 2.1E−02 | 21.9 | BLCA | 136 | 0 | 0.0% | | |
| LPAR2 | 4.5E−04 | 2.1E−02 | 21.9 | BRCA | 760 | 0 | 0.0% | | |
| COL5A1 | 5.6E−04 | 2.3E−02 | 7.3 | CRC | 217 | 13 | 6.0% | 5.0E−04 | 29.2 |
| COL5A1 | 5.6E−04 | 2.3E−02 | 7.3 | UCEC | 244 | 21 | 8.6% | 2.6E−02 | 15.5 |
| COL5A1 | 5.6E−04 | 2.3E−02 | 7.3 | KIRP | 167 | 2 | 1.2% | 1.2E−01 | 32.0 |
| COL5A1 | 5.6E−04 | 2.3E−02 | 7.3 | SKCM | 93 | 17 | 18.3% | 1.5E−01 | 12.8 |
| COL5A1 | 5.6E−04 | 2.3E−02 | 7.3 | LUSC | 176 | 7 | 4.0% | 1.6E−01 | −15.7 |
| COL5A1 | 5.6E−04 | 2.3E−02 | 7.3 | THCA | 314 | 3 | 1.0% | 1.8E−01 | −22.4 |
| COL5A1 | 5.6E−04 | 2.3E−02 | 7.3 | LUAD | 168 | 13 | 7.7% | 2.3E−01 | 10.1 |
| COL5A1 | 5.6E−04 | 2.3E−02 | 7.3 | KIRC | 406 | 3 | 0.7% | 2.9E−01 | 17.7 |
| COL5A1 | 5.6E−04 | 2.3E−02 | 7.3 | PRAD | 258 | 3 | 1.2% | 3.0E−01 | 30.2 |
| COL5A1 | 5.6E−04 | 2.3E−02 | 7.3 | HNSC | 294 | 7 | 2.4% | 4.2E−01 | 9.0 |
| COL5A1 | 5.6E−04 | 2.3E−02 | 7.3 | BLCA | 136 | 7 | 5.1% | 4.4E−01 | −8.6 |
| COL5A1 | 5.6E−04 | 2.3E−02 | 7.3 | LIHC | 196 | 11 | 5.6% | 4.7E−01 | −9.0 |
| COL5A1 | 5.6E−04 | 2.3E−02 | 7.3 | BRCA | 760 | 5 | 0.7% | 4.7E−01 | −9.3 |
| COL5A1 | 5.6E−04 | 2.3E−02 | 7.3 | GBM | 147 | 1 | 0.7% | 6.1E−01 | −14.8 |
| COL5A1 | 5.6E−04 | 2.3E−02 | 7.3 | CESC | 193 | 6 | 3.1% | 6.1E−01 | 8.7 |
| COL5A1 | 5.6E−04 | 2.3E−02 | 7.3 | STAD | 263 | 21 | 8.0% | 7.7E−01 | 2.0 |
| COL5A1 | 5.6E−04 | 2.3E−02 | 7.3 | LGG | 201 | 2 | 1.0% | 9.1E−01 | −2.2 |
| COL5A1 | 5.6E−04 | 2.3E−02 | 7.3 | OV | 188 | 1 | 0.5% | 9.2E−01 | 2.7 |
| TP53 | 6.6E−04 | 2.4E−02 | −3.9 | STAD | 263 | 121 | 46.0% | 7.7E−05 | −13.9 |
| TP53 | 6.6E−04 | 2.4E−02 | −3.9 | CESC | 193 | 9 | 4.7% | 1.5E−02 | −35.6 |
| TP53 | 6.6E−04 | 2.4E−02 | −3.9 | HNSC | 294 | 54 | 18.4% | 2.4E−02 | −9.8 |
| TP53 | 6.6E−04 | 2.4E−02 | −3.9 | OV | 188 | 59 | 31.4% | 4.6E−02 | −9.0 |

TABLE 2A-continued

| Gene | PanCancer P | PanCancer BH adj. P | PanCancer Beta | Cancer | Count Samples | Count Mutated | Percent Mutated | Cancer P | Cancer Beta |
|---|---|---|---|---|---|---|---|---|---|
| TP53 | 6.6E−04 | 2.4E−02 | −3.9 | LIHC | 196 | 63 | 32.1% | 2.0E−01 | −7.3 |
| TP53 | 6.6E−04 | 2.4E−02 | −3.9 | LUSC | 176 | 40 | 22.7% | 3.2E−01 | −5.2 |
| TP53 | 6.6E−04 | 2.4E−02 | −3.9 | LGG | 201 | 104 | 51.7% | 3.7E−01 | −3.6 |
| TP53 | 6.6E−04 | 2.4E−02 | −3.9 | KIRP | 167 | 4 | 2.4% | 3.8E−01 | −15.0 |
| TP53 | 6.6E−04 | 2.4E−02 | −3.9 | UCEC | 244 | 9 | 3.7% | 3.8E−01 | −8.6 |
| TP53 | 6.6E−04 | 2.4E−02 | −3.9 | GBM | 147 | 19 | 12.9% | 3.9E−01 | −6.2 |
| TP53 | 6.6E−04 | 2.4E−02 | −3.9 | BRCA | 760 | 48 | 6.3% | 4.8E−01 | 3.0 |
| TP53 | 6.6E−04 | 2.4E−02 | −3.9 | BLCA | 136 | 24 | 17.6% | 5.9E−01 | −3.7 |
| TP53 | 6.6E−04 | 2.4E−02 | −3.9 | SKCM | 93 | 14 | 15.1% | 6.0E−01 | 4.7 |
| TP53 | 6.6E−04 | 2.4E−02 | −3.9 | KIRC | 406 | 5 | 1.2% | 6.2E−01 | −6.5 |
| TP53 | 6.6E−04 | 2.4E−02 | −3.9 | PRAD | 258 | 24 | 9.3% | 6.7E−01 | −3.1 |
| TP53 | 6.6E−04 | 2.4E−02 | −3.9 | LUAD | 168 | 40 | 23.8% | 8.8E−01 | 0.8 |
| TP53 | 6.6E−04 | 2.4E−02 | −3.9 | THCA | 314 | 3 | 1.0% | 9.3E−01 | 1.6 |
| TP53 | 6.6E−04 | 2.4E−02 | −3.9 | CRC | 217 | 24 | 11.1% | 9.8E−01 | 0.1 |
| NCOR1 | 8.7E−04 | 2.6E−02 | 6.9 | UCEC | 244 | 16 | 6.6% | 1.2E−03 | 25.8 |
| NCOR1 | 8.7E−04 | 2.6E−02 | 6.9 | BLCA | 136 | 11 | 8.1% | 3.0E−02 | 19.6 |
| NCOR1 | 8.7E−04 | 2.6E−02 | 6.9 | SKCM | 93 | 5 | 5.4% | 3.3E−02 | −28.0 |
| NCOR1 | 8.7E−04 | 2.6E−02 | 6.9 | CRC | 217 | 9 | 4.1% | 6.6E−02 | 18.6 |
| NCOR1 | 8.7E−04 | 2.6E−02 | 6.9 | HNSC | 294 | 8 | 2.7% | 1.2E−01 | 16.3 |
| NCOR1 | 8.7E−04 | 2.6E−02 | 6.9 | OV | 188 | 1 | 0.5% | 1.2E−01 | 44.8 |
| NCOR1 | 8.7E−04 | 2.6E−02 | 6.9 | STAD | 263 | 19 | 7.2% | 2.0E−01 | 9.2 |
| NCOR1 | 8.7E−04 | 2.6E−02 | 6.9 | PRAD | 258 | 6 | 2.3% | 2.3E−01 | −17.5 |
| NCOR1 | 8.7E−04 | 2.6E−02 | 6.9 | LUAD | 168 | 6 | 3.6% | 2.4E−01 | −13.8 |
| NCOR1 | 8.7E−04 | 2.6E−02 | 6.9 | BRCA | 760 | 31 | 4.1% | 4.7E−01 | 3.9 |
| NCOR1 | 8.7E−04 | 2.6E−02 | 6.9 | LGG | 201 | 2 | 1.0% | 5.0E−01 | 13.3 |
| NCOR1 | 8.7E−04 | 2.6E−02 | 6.9 | GBM | 147 | 2 | 1.4% | 6.0E−01 | 10.7 |
| NCOR1 | 8.7E−04 | 2.6E−02 | 6.9 | KIRC | 406 | 3 | 0.7% | 7.1E−01 | −6.3 |
| NCOR1 | 8.7E−04 | 2.6E−02 | 6.9 | KIRP | 167 | 4 | 2.4% | 7.1E−01 | 5.5 |
| NCOR1 | 8.7E−04 | 2.6E−02 | 6.9 | LUSC | 176 | 6 | 3.4% | 7.2E−01 | 4.4 |
| NCOR1 | 8.7E−04 | 2.6E−02 | 6.9 | CESC | 193 | 5 | 2.6% | 8.6E−01 | −3.6 |
| NCOR1 | 8.7E−04 | 2.6E−02 | 6.9 | LIHC | 196 | 8 | 4.1% | 9.4E−01 | 0.8 |
| NCOR1 | 8.7E−04 | 2.6E−02 | 6.9 | THCA | 314 | 0 | 0.0% | | |
| SSX5 | 8.8E−04 | 2.6E−02 | 13.4 | UCEC | 244 | 9 | 3.7% | 1.3E−03 | 32.2 |
| SSX5 | 8.8E−04 | 2.6E−02 | 13.4 | SKCM | 93 | 2 | 2.2% | 1.7E−01 | 28.1 |
| SSX5 | 8.8E−04 | 2.6E−02 | 13.4 | BRCA | 760 | 1 | 0.1% | 2.2E−01 | 35.4 |
| SSX5 | 8.8E−04 | 2.6E−02 | 13.4 | LGG | 201 | 2 | 1.0% | 2.2E−01 | 24.0 |
| SSX5 | 8.8E−04 | 2.6E−02 | 13.4 | CRC | 217 | 6 | 2.8% | 2.3E−01 | 14.3 |
| SSX5 | 8.8E−04 | 2.6E−02 | 13.4 | STAD | 263 | 2 | 0.8% | 2.7E−01 | 22.6 |
| SSX5 | 8.8E−04 | 2.6E−02 | 13.4 | KIRC | 406 | 1 | 0.2% | 4.5E−01 | −21.7 |
| SSX5 | 8.8E−04 | 2.6E−02 | 13.4 | LUAD | 168 | 3 | 1.8% | 4.7E−01 | −12.0 |
| SSX5 | 8.8E−04 | 2.6E−02 | 13.4 | LUSC | 176 | 1 | 0.6% | 4.9E−01 | 20.2 |
| SSX5 | 8.8E−04 | 2.6E−02 | 13.4 | HNSC | 294 | 2 | 0.7% | 6.8E−01 | −8.4 |
| SSX5 | 8.8E−04 | 2.6E−02 | 13.4 | CESC | 193 | 3 | 1.6% | 7.3E−01 | 5.9 |
| SSX5 | 8.8E−04 | 2.6E−02 | 13.4 | KIRP | 167 | 2 | 1.2% | 7.8E−01 | 5.7 |
| SSX5 | 8.8E−04 | 2.6E−02 | 13.4 | BLCA | 136 | 0 | 0.0% | | |
| SSX5 | 8.8E−04 | 2.6E−02 | 13.4 | GBM | 147 | 0 | 0.0% | | |
| SSX5 | 8.8E−04 | 2.6E−02 | 13.4 | THCA | 314 | 0 | 0.0% | | |
| SSX5 | 8.8E−04 | 2.6E−02 | 13.4 | LIHC | 196 | 1 | 0.5% | | |
| SSX5 | 8.8E−04 | 2.6E−02 | 13.4 | PRAD | 258 | 0 | 0.0% | | |
| SSX5 | 8.8E−04 | 2.6E−02 | 13.4 | OV | 188 | 0 | 0.0% | | |
| DNER | 9.0E−04 | 2.6E−02 | 9.5 | UCEC | 244 | 19 | 7.8% | 4.0E−03 | 21.2 |
| DNER | 9.0E−04 | 2.6E−02 | 9.5 | OV | 188 | 1 | 0.5% | 1.3E−01 | 44.0 |
| DNER | 9.0E−04 | 2.6E−02 | 9.5 | SKCM | 93 | 10 | 10.8% | 2.5E−01 | 11.5 |
| DNER | 9.0E−04 | 2.6E−02 | 9.5 | LGG | 201 | 1 | 0.5% | 2.7E−01 | 31.1 |
| DNER | 9.0E−04 | 2.6E−02 | 9.5 | CRC | 217 | 8 | 3.7% | 3.0E−01 | 10.9 |
| DNER | 9.0E−04 | 2.6E−02 | 9.5 | LUSC | 176 | 4 | 2.3% | 3.3E−01 | −14.3 |
| DNER | 9.0E−04 | 2.6E−02 | 9.5 | LIHC | 196 | 7 | 3.6% | 4.4E−01 | −9.5 |
| DNER | 9.0E−04 | 2.6E−02 | 9.5 | BLCA | 136 | 4 | 2.9% | 4.8E−01 | 10.4 |
| DNER | 9.0E−04 | 2.6E−02 | 9.5 | LUAD | 168 | 10 | 6.0% | 7.0E−01 | −3.6 |
| DNER | 9.0E−04 | 2.6E−02 | 9.5 | KIRC | 406 | 2 | 0.5% | 8.9E−01 | 2.9 |
| DNER | 9.0E−04 | 2.6E−02 | 9.5 | STAD | 263 | 7 | 2.7% | 9.6E−01 | −0.5 |
| DNER | 9.0E−04 | 2.6E−02 | 9.5 | BRCA | 760 | 0 | 0.0% | | |
| DNER | 9.0E−04 | 2.6E−02 | 9.5 | CESC | 193 | 1 | 0.5% | | |
| DNER | 9.0E−04 | 2.6E−02 | 9.5 | GBM | 147 | 0 | 0.0% | | |
| DNER | 9.0E−04 | 2.6E−02 | 9.5 | HNSC | 294 | 0 | 0.0% | | |
| DNER | 9.0E−04 | 2.6E−02 | 9.5 | KIRP | 167 | 0 | 0.0% | | |
| DNER | 9.0E−04 | 2.6E−02 | 9.5 | PRAD | 258 | 1 | 0.4% | | |
| DNER | 9.0E−04 | 2.6E−02 | 9.5 | THCA | 314 | 0 | 0.0% | | |
| MORC4 | 1.1E−03 | 3.0E−02 | 10.5 | UCEC | 244 | 18 | 7.4% | 1.0E−02 | 18.6 |
| MORC4 | 1.1E−03 | 3.0E−02 | 10.5 | STAD | 263 | 6 | 2.3% | 1.8E−02 | 28.3 |
| MORC4 | 1.1E−03 | 3.0E−02 | 10.5 | BLCA | 136 | 3 | 2.2% | 1.0E−01 | 27.5 |
| MORC4 | 1.1E−03 | 3.0E−02 | 10.5 | KIRP | 167 | 1 | 0.6% | 1.7E−01 | 40.4 |
| MORC4 | 1.1E−03 | 3.0E−02 | 10.5 | LGG | 201 | 2 | 1.0% | 1.7E−01 | 27.5 |
| MORC4 | 1.1E−03 | 3.0E−02 | 10.5 | LUAD | 168 | 1 | 0.6% | 2.2E−01 | 34.5 |
| MORC4 | 1.1E−03 | 3.0E−02 | 10.5 | THCA | 314 | 1 | 0.3% | 2.4E−01 | 34.2 |
| MORC4 | 1.1E−03 | 3.0E−02 | 10.5 | BRCA | 760 | 3 | 0.4% | 4.5E−01 | −12.7 |
| MORC4 | 1.1E−03 | 3.0E−02 | 10.5 | OV | 188 | 1 | 0.5% | 6.0E−01 | −15.4 |

TABLE 2A-continued

| Gene | PanCancer P | PanCancer BH adj. P | PanCancer Beta | Cancer | Count Samples | Count Mutated | Percent Mutated | Cancer P | Cancer Beta |
|---|---|---|---|---|---|---|---|---|---|
| MORC4 | 1.1E−03 | 3.0E−02 | 10.5 | LIHC | 196 | 4 | 2.0% | 6.2E−01 | 7.4 |
| MORC4 | 1.1E−03 | 3.0E−02 | 10.5 | CESC | 193 | 2 | 1.0% | 6.8E−01 | 8.4 |
| MORC4 | 1.1E−03 | 3.0E−02 | 10.5 | HNSC | 294 | 3 | 1.0% | 7.1E−01 | 6.2 |
| MORC4 | 1.1E−03 | 3.0E−02 | 10.5 | KIRC | 406 | 2 | 0.5% | 7.9E−01 | 5.6 |
| MORC4 | 1.1E−03 | 3.0E−02 | 10.5 | CRC | 217 | 3 | 1.4% | 8.3E−01 | −3.6 |
| MORC4 | 1.1E−03 | 3.0E−02 | 10.5 | LUSC | 176 | 4 | 2.3% | 8.7E−01 | −2.3 |
| MORC4 | 1.1E−03 | 3.0E−02 | 10.5 | SKCM | 93 | 0 | 0.0% | | |
| MORC4 | 1.1E−03 | 3.0E−02 | 10.5 | GBM | 147 | 0 | 0.0% | | |
| MORC4 | 1.1E−03 | 3.0E−02 | 10.5 | PRAD | 258 | 0 | 0.0% | | |
| IRF6 | 1.3E−03 | 3.1E−02 | 11.3 | HNSC | 294 | 3 | 1.0% | 8.5E−02 | 28.9 |
| IRF6 | 1.3E−03 | 3.1E−02 | 11.3 | PRAD | 258 | 1 | 0.4% | 1.2E−01 | −44.9 |
| IRF6 | 1.3E−03 | 3.1E−02 | 11.3 | UCEC | 244 | 5 | 2.0% | 1.2E−01 | 20.5 |
| IRF6 | 1.3E−03 | 3.1E−02 | 11.3 | CESC | 193 | 2 | 1.0% | 1.7E−01 | 28.3 |
| IRF6 | 1.3E−03 | 3.1E−02 | 11.3 | BLCA | 136 | 2 | 1.5% | 2.2E−01 | 25.4 |
| IRF6 | 1.3E−03 | 3.1E−02 | 11.3 | LUAD | 168 | 4 | 2.4% | 2.2E−01 | −18.1 |
| IRF6 | 1.3E−03 | 3.1E−02 | 11.3 | LGG | 201 | 1 | 0.5% | 2.7E−01 | 31.1 |
| IRF6 | 1.3E−03 | 3.1E−02 | 11.3 | SKCM | 93 | 7 | 7.5% | 2.8E−01 | 13.2 |
| IRF6 | 1.3E−03 | 3.1E−02 | 11.3 | GBM | 147 | 1 | 0.7% | 2.9E−01 | 31.2 |
| IRF6 | 1.3E−03 | 3.1E−02 | 11.3 | STAD | 263 | 5 | 1.9% | 3.3E−01 | 12.8 |
| IRF6 | 1.3E−03 | 3.1E−02 | 11.3 | CRC | 217 | 2 | 0.9% | 4.9E−01 | 14.2 |
| IRF6 | 1.3E−03 | 3.1E−02 | 11.3 | KIRP | 167 | 1 | 0.6% | 5.8E−01 | −16.0 |
| IRF6 | 1.3E−03 | 3.1E−02 | 11.3 | OV | 188 | 2 | 1.1% | 6.3E−01 | 9.8 |
| IRF6 | 1.3E−03 | 3.1E−02 | 11.3 | LIHC | 196 | 4 | 2.0% | 8.4E−01 | 3.0 |
| IRF6 | 1.3E−03 | 3.1E−02 | 11.3 | LUSC | 176 | 4 | 2.3% | 9.2E−01 | 1.5 |
| IRF6 | 1.3E−03 | 3.1E−02 | 11.3 | BRCA | 760 | 2 | 0.3% | 9.7E−01 | −0.8 |
| IRF6 | 1.3E−03 | 3.1E−02 | 11.3 | KIRC | 406 | 0 | 0.0% | | |
| IRF6 | 1.3E−03 | 3.1E−02 | 11.3 | THCA | 314 | 0 | 0.0% | | |
| MYOCD | 1.4E−03 | 3.1E−02 | 7.6 | STAD | 263 | 12 | 4.6% | 2.5E−02 | 19.2 |
| MYOCD | 1.4E−03 | 3.1E−02 | 7.6 | UCEC | 244 | 12 | 4.9% | 4.3E−02 | 17.8 |
| MYOCD | 1.4E−03 | 3.1E−02 | 7.6 | PRAD | 258 | 2 | 0.8% | 1.1E−01 | −32.8 |
| MYOCD | 1.4E−03 | 3.1E−02 | 7.6 | GBM | 147 | 3 | 2.0% | 1.1E−01 | 27.2 |
| MYOCD | 1.4E−03 | 3.1E−02 | 7.6 | SKCM | 93 | 17 | 18.3% | 2.3E−01 | 9.7 |
| MYOCD | 1.4E−03 | 3.1E−02 | 7.6 | BLCA | 136 | 2 | 1.5% | 2.4E−01 | 33.7 |
| MYOCD | 1.4E−03 | 3.1E−02 | 7.6 | LGG | 201 | 4 | 2.0% | 2.5E−01 | 16.5 |
| MYOCD | 1.4E−03 | 3.1E−02 | 7.6 | HNSC | 294 | 8 | 2.7% | 3.1E−01 | 10.6 |
| MYOCD | 1.4E−03 | 3.1E−02 | 7.6 | OV | 188 | 1 | 0.5% | 3.8E−01 | 25.8 |
| MYOCD | 1.4E−03 | 3.1E−02 | 7.6 | LUSC | 176 | 10 | 5.7% | 4.8E−01 | 6.8 |
| MYOCD | 1.4E−03 | 3.1E−02 | 7.6 | CRC | 217 | 5 | 2.3% | 5.9E−01 | −7.0 |
| MYOCD | 1.4E−03 | 3.1E−02 | 7.6 | KIRC | 406 | 1 | 0.2% | 7.0E−01 | 11.2 |
| MYOCD | 1.4E−03 | 3.1E−02 | 7.6 | LIHC | 196 | 10 | 5.1% | 7.4E−01 | −3.3 |
| MYOCD | 1.4E−03 | 3.1E−02 | 7.6 | BRCA | 760 | 2 | 0.3% | 7.4E−01 | −6.7 |
| MYOCD | 1.4E−03 | 3.1E−02 | 7.6 | LUAD | 168 | 14 | 8.3% | 8.8E−01 | −1.3 |
| MYOCD | 1.4E−03 | 3.1E−02 | 7.6 | CESC | 193 | 2 | 1.0% | 9.7E−01 | 0.9 |
| MYOCD | 1.4E−03 | 3.1E−02 | 7.6 | THCA | 314 | 0 | 0.0% | | |
| MYOCD | 1.4E−03 | 3.1E−02 | 7.6 | KIRP | 167 | 0 | 0.0% | | |
| CIC | 1.4E−03 | 3.1E−02 | 7.5 | UCEC | 244 | 20 | 8.2% | 1.2E−02 | 17.9 |
| CIC | 1.4E−03 | 3.1E−02 | 7.5 | CRC | 217 | 4 | 1.8% | 2.0E−02 | 34.1 |
| CIC | 1.4E−03 | 3.1E−02 | 7.5 | BLCA | 136 | 2 | 1.5% | 5.5E−02 | 39.2 |
| CIC | 1.4E−03 | 3.1E−02 | 7.5 | STAD | 263 | 21 | 8.0% | 9.0E−02 | 11.7 |
| CIC | 1.4E−03 | 3.1E−02 | 7.5 | GBM | 147 | 1 | 0.7% | 1.6E−01 | −40.8 |
| CIC | 1.4E−03 | 3.1E−02 | 7.5 | CESC | 193 | 8 | 4.1% | 2.5E−01 | −15.5 |
| CIC | 1.4E−03 | 3.1E−02 | 7.5 | LUAD | 168 | 3 | 1.8% | 3.1E−01 | 17.0 |
| CIC | 1.4E−03 | 3.1E−02 | 7.5 | KIRC | 406 | 3 | 0.7% | 3.3E−01 | 16.3 |
| CIC | 1.4E−03 | 3.1E−02 | 7.5 | OV | 188 | 3 | 1.6% | 4.4E−01 | 13.2 |
| CIC | 1.4E−03 | 3.1E−02 | 7.5 | HNSC | 294 | 4 | 1.4% | 7.9E−01 | 4.0 |
| CIC | 1.4E−03 | 3.1E−02 | 7.5 | LUSC | 176 | 4 | 2.3% | 7.9E−01 | 3.9 |
| CIC | 1.4E−03 | 3.1E−02 | 7.5 | LGG | 201 | 34 | 16.9% | 8.2E−01 | −1.2 |
| CIC | 1.4E−03 | 3.1E−02 | 7.5 | SKCM | 93 | 3 | 3.2% | 9.6E−01 | 0.8 |
| CIC | 1.4E−03 | 3.1E−02 | 7.5 | KIRP | 167 | 2 | 1.2% | 9.7E−01 | 0.8 |
| CIC | 1.4E−03 | 3.1E−02 | 7.5 | BRCA | 760 | 3 | 0.4% | 9.7E−01 | 0.6 |
| CIC | 1.4E−03 | 3.1E−02 | 7.5 | LIHC | 196 | 6 | 3.1% | 9.8E−01 | −0.3 |
| CIC | 1.4E−03 | 3.1E−02 | 7.5 | PRAD | 258 | 1 | 0.4% | | |
| CIC | 1.4E−03 | 3.1E−02 | 7.5 | THCA | 314 | 0 | 0.0% | | |
| SLC22A14 | 2.4E−03 | 4.7E−02 | 13.2 | HNSC | 294 | 4 | 1.4% | 1.9E−02 | 34.1 |
| SLC22A14 | 2.4E−03 | 4.7E−02 | 13.2 | UCEC | 244 | 4 | 1.6% | 4.0E−02 | 30.2 |
| SLC22A14 | 2.4E−03 | 4.7E−02 | 13.2 | LUAD | 168 | 1 | 0.6% | 1.3E−01 | −43.1 |
| SLC22A14 | 2.4E−03 | 4.7E−02 | 13.2 | BRCA | 760 | 3 | 0.4% | 1.5E−01 | 24.2 |
| SLC22A14 | 2.4E−03 | 4.7E−02 | 13.2 | STAD | 263 | 3 | 1.1% | 1.8E−01 | 22.5 |
| SLC22A14 | 2.4E−03 | 4.7E−02 | 13.2 | CESC | 193 | 1 | 0.5% | 2.2E−01 | 35.7 |
| SLC22A14 | 2.4E−03 | 4.7E−02 | 13.2 | SKCM | 93 | 4 | 4.3% | 5.5E−01 | 9.1 |
| SLC22A14 | 2.4E−03 | 4.7E−02 | 13.2 | LIHC | 196 | 3 | 1.5% | 5.6E−01 | −9.8 |
| SLC22A14 | 2.4E−03 | 4.7E−02 | 13.2 | LUSC | 176 | 1 | 0.6% | 7.1E−01 | 10.8 |
| SLC22A14 | 2.4E−03 | 4.7E−02 | 13.2 | BLCA | 136 | 1 | 0.7% | 8.2E−01 | −6.6 |
| SLC22A14 | 2.4E−03 | 4.7E−02 | 13.2 | CRC | 217 | 4 | 1.8% | 9.5E−01 | 0.9 |
| SLC22A14 | 2.4E−03 | 4.7E−02 | 13.2 | KIRC | 406 | 0 | 0.0% | | |
| SLC22A14 | 2.4E−03 | 4.7E−02 | 13.2 | KIRP | 167 | 0 | 0.0% | | |
| SLC22A14 | 2.4E−03 | 4.7E−02 | 13.2 | GBM | 147 | 0 | 0.0% | | |

TABLE 2A-continued

| Gene | PanCancer P | PanCancer BH adj. P | PanCancer Beta | Cancer | Count Samples | Count Mutated | Percent Mutated | Cancer P | Cancer Beta |
|---|---|---|---|---|---|---|---|---|---|
| SLC22A14 | 2.4E−03 | 4.7E−02 | 13.2 | THCA | 314 | 0 | 0.0% | | |
| SLC22A14 | 2.4E−03 | 4.7E−02 | 13.2 | LGG | 201 | 0 | 0.0% | | |
| SLC22A14 | 2.4E−03 | 4.7E−02 | 13.2 | PRAD | 258 | 0 | 0.0% | | |
| SLC22A14 | 2.4E−03 | 4.7E−02 | 13.2 | OV | 188 | 0 | 0.0% | | |
| CNKSR1 | 2.4E−03 | 4.7E−02 | 11.0 | SKCM | 93 | 5 | 5.4% | 6.7E−02 | 26.8 |
| CNKSR1 | 2.4E−03 | 4.7E−02 | 11.0 | BRCA | 760 | 2 | 0.3% | 8.3E−02 | 35.5 |
| CNKSR1 | 2.4E−03 | 4.7E−02 | 11.0 | HNSC | 294 | 2 | 0.7% | 1.3E−01 | 31.2 |
| CNKSR1 | 2.4E−03 | 4.7E−02 | 11.0 | OV | 188 | 1 | 0.5% | 1.4E−01 | 43.4 |
| CNKSR1 | 2.4E−03 | 4.7E−02 | 11.0 | LUAD | 168 | 5 | 3.0% | 1.6E−01 | 18.3 |
| CNKSR1 | 2.4E−03 | 4.7E−02 | 11.0 | CESC | 193 | 4 | 2.1% | 2.3E−01 | −20.1 |
| CNKSR1 | 2.4E−03 | 4.7E−02 | 11.0 | BLCA | 136 | 2 | 1.5% | 2.7E−01 | 22.5 |
| CNKSR1 | 2.4E−03 | 4.7E−02 | 11.0 | CRC | 217 | 5 | 2.3% | 2.9E−01 | 13.7 |
| CNKSR1 | 2.4E−03 | 4.7E−02 | 11.0 | KIRC | 406 | 1 | 0.2% | 3.3E−01 | 28.3 |
| CNKSR1 | 2.4E−03 | 4.7E−02 | 11.0 | UCEC | 244 | 6 | 2.5% | 3.3E−01 | 11.9 |
| CNKSR1 | 2.4E−03 | 4.7E−02 | 11.0 | STAD | 263 | 7 | 2.7% | 3.4E−01 | 10.7 |
| CNKSR1 | 2.4E−03 | 4.7E−02 | 11.0 | LIHC | 196 | 5 | 2.6% | 4.0E−01 | −12.5 |
| CNKSR1 | 2.4E−03 | 4.7E−02 | 11.0 | THCA | 314 | 1 | 0.3% | 5.5E−01 | 17.2 |
| CNKSR1 | 2.4E−03 | 4.7E−02 | 11.0 | LUSC | 176 | 1 | 0.6% | 6.5E−01 | −13.0 |
| CNKSR1 | 2.4E−03 | 4.7E−02 | 11.0 | GBM | 147 | 1 | 0.7% | 6.9E−01 | 11.8 |
| CNKSR1 | 2.4E−03 | 4.7E−02 | 11.0 | KIRP | 167 | 0 | 0.0% | | |
| CNKSR1 | 2.4E−03 | 4.7E−02 | 11.0 | LGG | 201 | 0 | 0.0% | | |
| CNKSR1 | 2.4E−03 | 4.7E−02 | 11.0 | PRAD | 258 | 0 | 0.0% | | |
| NF1 | 2.6E−03 | 4.8E−02 | 5.2 | THCA | 314 | 4 | 1.3% | 6.7E−02 | 26.5 |
| NF1 | 2.6E−03 | 4.8E−02 | 5.2 | UCEC | 244 | 20 | 8.2% | 8.4E−02 | 12.6 |
| NF1 | 2.6E−03 | 4.8E−02 | 5.2 | STAD | 263 | 22 | 8.4% | 1.2E−01 | 10.3 |
| NF1 | 2.6E−03 | 4.8E−02 | 5.2 | GBM | 147 | 13 | 8.8% | 1.4E−01 | 12.4 |
| NF1 | 2.6E−03 | 4.8E−02 | 5.2 | LGG | 201 | 12 | 6.0% | 2.4E−01 | 9.7 |
| NF1 | 2.6E−03 | 4.8E−02 | 5.2 | BRCA | 760 | 17 | 2.2% | 3.0E−01 | 7.3 |
| NF1 | 2.6E−03 | 4.8E−02 | 5.2 | LUSC | 176 | 21 | 11.9% | 3.7E−01 | −6.0 |
| NF1 | 2.6E−03 | 4.8E−02 | 5.2 | PRAD | 258 | 1 | 0.4% | 4.1E−01 | −23.7 |
| NF1 | 2.6E−03 | 4.8E−02 | 5.2 | LUAD | 168 | 17 | 10.1% | 4.7E−01 | 5.3 |
| NF1 | 2.6E−03 | 4.8E−02 | 5.2 | SKCM | 93 | 20 | 21.5% | 5.3E−01 | −5.4 |
| NF1 | 2.6E−03 | 4.8E−02 | 5.2 | HNSC | 294 | 9 | 3.1% | 5.4E−01 | 6.0 |
| NF1 | 2.6E−03 | 4.8E−02 | 5.2 | LIHC | 196 | 13 | 6.6% | 6.2E−01 | 4.5 |
| NF1 | 2.6E−03 | 4.8E−02 | 5.2 | OV | 188 | 7 | 3.7% | 6.9E−01 | 4.5 |
| NF1 | 2.6E−03 | 4.8E−02 | 5.2 | CRC | 217 | 7 | 3.2% | 8.3E−01 | 2.5 |
| NF1 | 2.6E−03 | 4.8E−02 | 5.2 | KIRP | 167 | 2 | 1.2% | 8.4E−01 | −5.7 |
| NF1 | 2.6E−03 | 4.8E−02 | 5.2 | BLCA | 136 | 11 | 8.1% | 9.0E−01 | 1.2 |
| NF1 | 2.6E−03 | 4.8E−02 | 5.2 | KIRC | 406 | 7 | 1.7% | 9.1E−01 | −1.2 |
| NF1 | 2.6E−03 | 4.8E−02 | 5.2 | CESC | 193 | 8 | 4.1% | 9.2E−01 | −1.1 |
| SOS1 | 2.9E−03 | 5.1E−02 | 7.9 | UCEC | 244 | 10 | 4.1% | 5.4E−02 | 18.5 |
| SOS1 | 2.9E−03 | 5.1E−02 | 7.9 | BLCA | 136 | 3 | 2.2% | 1.3E−01 | 26.2 |
| SOS1 | 2.9E−03 | 5.1E−02 | 7.9 | GBM | 147 | 1 | 0.7% | 1.4E−01 | 43.0 |
| SOS1 | 2.9E−03 | 5.1E−02 | 7.9 | LGG | 201 | 1 | 0.5% | 2.7E−01 | 31.1 |
| SOS1 | 2.9E−03 | 5.1E−02 | 7.9 | LUAD | 168 | 9 | 5.4% | 2.7E−01 | 10.8 |
| SOS1 | 2.9E−03 | 5.1E−02 | 7.9 | HNSC | 294 | 6 | 2.0% | 3.0E−01 | 12.3 |
| SOS1 | 2.9E−03 | 5.1E−02 | 7.9 | KIRC | 406 | 6 | 1.5% | 3.2E−01 | 11.8 |
| SOS1 | 2.9E−03 | 5.1E−02 | 7.9 | THCA | 314 | 1 | 0.3% | 3.9E−01 | 25.0 |
| SOS1 | 2.9E−03 | 5.1E−02 | 7.9 | LUSC | 176 | 11 | 6.3% | 4.0E−01 | 7.6 |
| SOS1 | 2.9E−03 | 5.1E−02 | 7.9 | SKCM | 93 | 2 | 2.2% | 4.7E−01 | 15.1 |
| SOS1 | 2.9E−03 | 5.1E−02 | 7.9 | OV | 188 | 3 | 1.6% | 5.9E−01 | −9.1 |
| SOS1 | 2.9E−03 | 5.1E−02 | 7.9 | LIHC | 196 | 9 | 4.6% | 6.0E−01 | −5.9 |
| SOS1 | 2.9E−03 | 5.1E−02 | 7.9 | CESC | 193 | 4 | 2.1% | 6.2E−01 | 10.3 |
| SOS1 | 2.9E−03 | 5.1E−02 | 7.9 | BRCA | 760 | 4 | 0.5% | 6.4E−01 | 6.7 |
| SOS1 | 2.9E−03 | 5.1E−02 | 7.9 | STAD | 263 | 7 | 2.7% | 7.8E−01 | −3.1 |
| SOS1 | 2.9E−03 | 5.1E−02 | 7.9 | KIRP | 167 | 2 | 1.2% | 8.5E−01 | 4.0 |
| SOS1 | 2.9E−03 | 5.1E−02 | 7.9 | CRC | 217 | 6 | 2.8% | 8.7E−01 | −2.0 |
| SOS1 | 2.9E−03 | 5.1E−02 | 7.9 | PRAD | 258 | 1 | 0.4% | | |
| CUL4B | 3.3E−03 | 5.2E−02 | 9.5 | BRCA | 760 | 6 | 0.8% | 2.1E−02 | 27.3 |
| CUL4B | 3.3E−03 | 5.2E−02 | 9.5 | STAD | 263 | 1 | 0.4% | 4.5E−02 | −57.2 |
| CUL4B | 3.3E−03 | 5.2E−02 | 9.5 | LGG | 201 | 3 | 1.5% | 1.6E−01 | 27.8 |
| CUL4B | 3.3E−03 | 5.2E−02 | 9.5 | LIHC | 196 | 5 | 2.6% | 1.6E−01 | 18.8 |
| CUL4B | 3.3E−03 | 5.2E−02 | 9.5 | LUSC | 176 | 5 | 2.8% | 1.7E−01 | 18.1 |
| CUL4B | 3.3E−03 | 5.2E−02 | 9.5 | BLCA | 136 | 4 | 2.9% | 2.4E−01 | 16.9 |
| CUL4B | 3.3E−03 | 5.2E−02 | 9.5 | KIRC | 406 | 1 | 0.2% | 2.6E−01 | 32.7 |
| CUL4B | 3.3E−03 | 5.2E−02 | 9.5 | UCEC | 244 | 12 | 4.9% | 2.9E−01 | 9.4 |
| CUL4B | 3.3E−03 | 5.2E−02 | 9.5 | LUAD | 168 | 3 | 1.8% | 4.9E−01 | −11.3 |
| CUL4B | 3.3E−03 | 5.2E−02 | 9.5 | SKCM | 93 | 3 | 3.2% | 5.2E−01 | 11.3 |
| CUL4B | 3.3E−03 | 5.2E−02 | 9.5 | THCA | 314 | 1 | 0.3% | 6.8E−01 | 12.0 |
| CUL4B | 3.3E−03 | 5.2E−02 | 9.5 | HNSC | 294 | 4 | 1.4% | 8.4E−01 | 3.0 |
| CUL4B | 3.3E−03 | 5.2E−02 | 9.5 | CESC | 193 | 3 | 1.6% | 9.1E−01 | 2.3 |
| CUL4B | 3.3E−03 | 5.2E−02 | 9.5 | CRC | 217 | 5 | 2.3% | 9.2E−01 | −1.4 |
| CUL4B | 3.3E−03 | 5.2E−02 | 9.5 | GBM | 147 | 0 | 0.0% | | |
| CUL4B | 3.3E−03 | 5.2E−02 | 9.5 | KIRP | 167 | 0 | 0.0% | | |
| CUL4B | 3.3E−03 | 5.2E−02 | 9.5 | OV | 188 | 0 | 0.0% | | |
| CUL4B | 3.3E−03 | 5.2E−02 | 9.5 | PRAD | 258 | 0 | 0.0% | | |
| DDX3X | 3.3E−03 | 5.2E−02 | 9.5 | STAD | 263 | 8 | 3.0% | 5.1E−02 | 20.3 |

TABLE 2A-continued

| Gene | PanCancer P | PanCancer BH adj. P | PanCancer Beta | Cancer | Count Samples | Count Mutated | Percent Mutated | Cancer P | Cancer Beta |
|---|---|---|---|---|---|---|---|---|---|
| DDX3X | 3.3E−03 | 5.2E−02 | 9.5 | LUSC | 176 | 3 | 1.7% | 9.0E−02 | 28.5 |
| DDX3X | 3.3E−03 | 5.2E−02 | 9.5 | HNSC | 294 | 3 | 1.0% | 1.5E−01 | 24.2 |
| DDX3X | 3.3E−03 | 5.2E−02 | 9.5 | CESC | 193 | 5 | 2.6% | 1.8E−01 | 22.4 |
| DDX3X | 3.3E−03 | 5.2E−02 | 9.5 | LGG | 201 | 2 | 1.0% | 2.5E−01 | 22.5 |
| DDX3X | 3.3E−03 | 5.2E−02 | 9.5 | CRC | 217 | 2 | 0.9% | 2.7E−01 | 22.8 |
| DDX3X | 3.3E−03 | 5.2E−02 | 9.5 | LIHC | 196 | 1 | 0.5% | 2.8E−01 | −31.7 |
| DDX3X | 3.3E−03 | 5.2E−02 | 9.5 | UCEC | 244 | 12 | 4.9% | 3.4E−01 | 8.3 |
| DDX3X | 3.3E−03 | 5.2E−02 | 9.5 | BRCA | 760 | 2 | 0.3% | 5.0E−01 | 13.8 |
| DDX3X | 3.3E−03 | 5.2E−02 | 9.5 | KIRC | 406 | 3 | 0.7% | 7.3E−01 | 5.8 |
| DDX3X | 3.3E−03 | 5.2E−02 | 9.5 | BLCA | 136 | 4 | 2.9% | 8.1E−01 | 3.5 |
| DDX3X | 3.3E−03 | 5.2E−02 | 9.5 | PRAD | 258 | 1 | 0.4% | 9.2E−01 | 2.8 |
| DDX3X | 3.3E−03 | 5.2E−02 | 9.5 | SKCM | 93 | 8 | 8.6% | 9.3E−01 | −1.0 |
| DDX3X | 3.3E−03 | 5.2E−02 | 9.5 | KIRP | 167 | 1 | 0.6% | 9.8E−01 | 0.6 |
| DDX3X | 3.3E−03 | 5.2E−02 | 9.5 | LUAD | 168 | 3 | 1.8% | 1.0E+00 | −0.1 |
| DDX3X | 3.3E−03 | 5.2E−02 | 9.5 | GBM | 147 | 0 | 0.0% | | |
| DDX3X | 3.3E−03 | 5.2E−02 | 9.5 | OV | 188 | 0 | 0.0% | | |
| DDX3X | 3.3E−03 | 5.2E−02 | 9.5 | THCA | 314 | 0 | 0.0% | | |
| FUBP1 | 3.5E−03 | 5.2E−02 | 9.4 | LUSC | 176 | 4 | 2.3% | 7.2E−02 | 26.2 |
| FUBP1 | 3.5E−03 | 5.2E−02 | 9.4 | SKCM | 93 | 2 | 2.2% | 1.2E−01 | 32.0 |
| FUBP1 | 3.5E−03 | 5.2E−02 | 9.4 | BLCA | 136 | 3 | 2.2% | 1.3E−01 | 26.0 |
| FUBP1 | 3.5E−03 | 5.2E−02 | 9.4 | LUAD | 168 | 3 | 1.8% | 1.7E−01 | −22.6 |
| FUBP1 | 3.5E−03 | 5.2E−02 | 9.4 | CRC | 217 | 2 | 0.9% | 2.5E−01 | 23.6 |
| FUBP1 | 3.5E−03 | 5.2E−02 | 9.4 | UCEC | 244 | 5 | 2.0% | 2.6E−01 | 15.1 |
| FUBP1 | 3.5E−03 | 5.2E−02 | 9.4 | HNSC | 294 | 5 | 1.7% | 2.7E−01 | 14.4 |
| FUBP1 | 3.5E−03 | 5.2E−02 | 9.4 | LGG | 201 | 17 | 8.5% | 4.8E−01 | 5.1 |
| FUBP1 | 3.5E−03 | 5.2E−02 | 9.4 | STAD | 263 | 7 | 2.7% | 5.7E−01 | 6.4 |
| FUBP1 | 3.5E−03 | 5.2E−02 | 9.4 | BRCA | 760 | 2 | 0.3% | 7.5E−01 | −6.6 |
| FUBP1 | 3.5E−03 | 5.2E−02 | 9.4 | LIHC | 196 | 3 | 1.5% | 7.7E−01 | 4.9 |
| FUBP1 | 3.5E−03 | 5.2E−02 | 9.4 | KIRC | 406 | 1 | 0.2% | 8.8E−01 | 4.4 |
| FUBP1 | 3.5E−03 | 5.2E−02 | 9.4 | CESC | 193 | 2 | 1.0% | 9.7E−01 | 0.9 |
| FUBP1 | 3.5E−03 | 5.2E−02 | 9.4 | GBM | 147 | 0 | 0.0% | | |
| FUBP1 | 3.5E−03 | 5.2E−02 | 9.4 | KIRP | 167 | 0 | 0.0% | | |
| FUBP1 | 3.5E−03 | 5.2E−02 | 9.4 | OV | 188 | 0 | 0.0% | | |
| FUBP1 | 3.5E−03 | 5.2E−02 | 9.4 | PRAD | 258 | 0 | 0.0% | | |
| FUBP1 | 3.5E−03 | 5.2E−02 | 9.4 | THCA | 314 | 0 | 0.0% | | |
| HLA-A, B, C | 3.7E−03 | 5.2E−02 | 6.0 | HNSC | 465 | 49 | 10.5% | 1.4E−02 | 15.0 |
| HLA-A, B, C | 3.7E−03 | 5.2E−02 | 6.0 | CESC | 189 | 22 | 11.6% | 2.1E−02 | 18.5 |
| HLA-A, B, C | 3.7E−03 | 5.2E−02 | 6.0 | STAD | 269 | 37 | 13.8% | 2.9E−02 | 12.8 |
| HLA-A, B, C | 3.7E−03 | 5.2E−02 | 6.0 | LGG | 352 | 4 | 1.1% | 4.8E−02 | 31.8 |
| HLA-A, B, C | 3.7E−03 | 5.2E−02 | 6.0 | PRAD | 333 | 1 | 0.3% | 9.9E−02 | 47.9 |
| HLA-A, B, C | 3.7E−03 | 5.2E−02 | 6.0 | UCEC | 502 | 32 | 6.4% | 1.4E−01 | 16.8 |
| HLA-A, B, C | 3.7E−03 | 5.2E−02 | 6.0 | KIRP | 195 | 4 | 2.1% | 1.4E−01 | −21.4 |
| HLA-A, B, C | 3.7E−03 | 5.2E−02 | 6.0 | BRCA | 996 | 9 | 0.9% | 1.9E−01 | −37.9 |
| HLA-A, B, C | 3.7E−03 | 5.2E−02 | 6.0 | OV | 210 | 2 | 1.0% | 2.9E−01 | −21.9 |
| HLA-A, B, C | 3.7E−03 | 5.2E−02 | 6.0 | KIRC | 471 | 7 | 1.5% | 3.6E−01 | 10.0 |
| HLA-A, B, C | 3.7E−03 | 5.2E−02 | 6.0 | LIHC | 193 | 6 | 3.1% | 3.9E−01 | −10.8 |
| HLA-A, B, C | 3.7E−03 | 5.2E−02 | 6.0 | BLCA | 250 | 13 | 5.2% | 4.2E−01 | −8.0 |
| HLA-A, B, C | 3.7E−03 | 5.2E−02 | 6.0 | CRC | 416 | 33 | 7.9% | 4.6E−01 | 12.8 |
| HLA-A, B, C | 3.7E−03 | 5.2E−02 | 6.0 | LUSC | 475 | 22 | 4.6% | 7.8E−01 | −2.5 |
| HLA-A, B, C | 3.7E−03 | 5.2E−02 | 6.0 | LUAD | 483 | 16 | 3.3% | 8.2E−01 | 3.2 |
| HLA-A, B, C | 3.7E−03 | 5.2E−02 | 6.0 | THCA | 476 | 2 | 0.4% | 9.5E−01 | −1.4 |
| HLA-A, B, C | 3.7E−03 | 5.2E−02 | 6.0 | GBM | 155 | 1 | 0.6% | | |
| HLA-A, B, C | 3.7E−03 | 5.2E−02 | 6.0 | SKCM | 159 | 2 | 1.3% | | |
| ARID2 | 3.8E−03 | 5.2E−02 | 5.9 | UCEC | 244 | 14 | 5.7% | 3.8E−03 | 23.5 |
| ARID2 | 3.8E−03 | 5.2E−02 | 5.9 | BRCA | 760 | 6 | 0.8% | 1.0E−02 | 30.4 |
| ARID2 | 3.8E−03 | 5.2E−02 | 5.9 | PRAD | 258 | 5 | 1.9% | 3.9E−02 | −30.2 |
| ARID2 | 3.8E−03 | 5.2E−02 | 5.9 | CESC | 193 | 5 | 2.6% | 4.7E−02 | 33.3 |
| ARID2 | 3.8E−03 | 5.2E−02 | 5.9 | KIRP | 167 | 4 | 2.4% | 1.1E−01 | −23.5 |
| ARID2 | 3.8E−03 | 5.2E−02 | 5.9 | CRC | 217 | 13 | 6.0% | 1.2E−01 | 13.3 |

TABLE 2A-continued

| Gene | PanCancer P | PanCancer BH adj. P | PanCancer Beta | Cancer | Count Samples | Count Mutated | Percent Mutated | Cancer P | Cancer Beta |
|---|---|---|---|---|---|---|---|---|---|
| ARID2 | 3.8E−03 | 5.2E−02 | 5.9 | THCA | 314 | 2 | 0.6% | 1.3E−01 | 31.5 |
| ARID2 | 3.8E−03 | 5.2E−02 | 5.9 | STAD | 263 | 19 | 7.2% | 2.1E−01 | 8.7 |
| ARID2 | 3.8E−03 | 5.2E−02 | 5.9 | OV | 188 | 4 | 2.1% | 2.3E−01 | 17.4 |
| ARID2 | 3.8E−03 | 5.2E−02 | 5.9 | HNSC | 294 | 11 | 3.7% | 2.3E−01 | −10.6 |
| ARID2 | 3.8E−03 | 5.2E−02 | 5.9 | LGG | 201 | 1 | 0.5% | 2.7E−01 | 31.1 |
| ARID2 | 3.8E−03 | 5.2E−02 | 5.9 | LIHC | 196 | 10 | 5.1% | 2.7E−01 | −10.9 |
| ARID2 | 3.8E−03 | 5.2E−02 | 5.9 | LUSC | 176 | 9 | 5.1% | 3.0E−01 | 10.7 |
| ARID2 | 3.8E−03 | 5.2E−02 | 5.9 | LUAD | 168 | 13 | 7.7% | 4.0E−01 | −6.9 |
| ARID2 | 3.8E−03 | 5.2E−02 | 5.9 | BLCA | 136 | 11 | 8.1% | 4.2E−01 | 7.4 |
| ARID2 | 3.8E−03 | 5.2E−02 | 5.9 | KIRC | 406 | 3 | 0.7% | 4.8E−01 | −11.7 |
| ARID2 | 3.8E−03 | 5.2E−02 | 5.9 | SKCM | 93 | 20 | 21.5% | 5.7E−01 | 4.8 |
| ARID2 | 3.8E−03 | 5.2E−02 | 5.9 | GBM | 147 | 1 | 0.7% | 7.6E−01 | −9.1 |
| TCP11L2 | 3.8E−03 | 5.2E−02 | 11.0 | UCEC | 244 | 13 | 5.3% | 5.3E−02 | 16.9 |
| TCP11L2 | 3.8E−03 | 5.2E−02 | 11.0 | BRCA | 760 | 3 | 0.4% | 6.9E−02 | 30.5 |
| TCP11L2 | 3.8E−03 | 5.2E−02 | 11.0 | LIHC | 196 | 4 | 2.0% | 2.2E−01 | 21.2 |
| TCP11L2 | 3.8E−03 | 5.2E−02 | 11.0 | OV | 188 | 1 | 0.5% | 3.8E−01 | 25.3 |
| TCP11L2 | 3.8E−03 | 5.2E−02 | 11.0 | CRC | 217 | 4 | 1.8% | 4.0E−01 | 12.2 |
| TCP11L2 | 3.8E−03 | 5.2E−02 | 11.0 | BLCA | 136 | 4 | 2.9% | 4.6E−01 | 10.8 |
| TCP11L2 | 3.8E−03 | 5.2E−02 | 11.0 | KIRP | 167 | 2 | 1.2% | 5.0E−01 | −14.1 |
| TCP11L2 | 3.8E−03 | 5.2E−02 | 11.0 | HNSC | 294 | 3 | 1.0% | 5.5E−01 | 10.1 |
| TCP11L2 | 3.8E−03 | 5.2E−02 | 11.0 | CESC | 193 | 1 | 0.5% | 5.7E−01 | −16.7 |
| TCP11L2 | 3.8E−03 | 5.2E−02 | 11.0 | LGG | 201 | 1 | 0.5% | 6.1E−01 | −14.3 |
| TCP11L2 | 3.8E−03 | 5.2E−02 | 11.0 | STAD | 263 | 4 | 1.5% | 6.1E−01 | 7.4 |
| TCP11L2 | 3.8E−03 | 5.2E−02 | 11.0 | SKCM | 93 | 1 | 1.1% | 8.8E−01 | −4.5 |
| TCP11L2 | 3.8E−03 | 5.2E−02 | 11.0 | THCA | 314 | 1 | 0.3% | | |
| TCP11L2 | 3.8E−03 | 5.2E−02 | 11.0 | PRAD | 258 | 0 | 0.0% | | |
| TCP11L2 | 3.8E−03 | 5.2E−02 | 11.0 | GBM | 147 | 0 | 0.0% | | |
| TCP11L2 | 3.8E−03 | 5.2E−02 | 11.0 | KIRC | 406 | 0 | 0.0% | | |
| TCP11L2 | 3.8E−03 | 5.2E−02 | 11.0 | LUAD | 168 | 0 | 0.0% | | |
| TCP11L2 | 3.8E−03 | 5.2E−02 | 11.0 | LUSC | 176 | 0 | 0.0% | | |
| MET | 4.3E−03 | 5.6E−02 | 7.8 | UCEC | 244 | 13 | 5.3% | 6.0E−03 | 23.8 |
| MET | 4.3E−03 | 5.6E−02 | 7.8 | STAD | 263 | 5 | 1.9% | 2.8E−02 | 28.4 |
| MET | 4.3E−03 | 5.6E−02 | 7.8 | LUAD | 168 | 11 | 6.5% | 6.6E−02 | 16.1 |
| MET | 4.3E−03 | 5.6E−02 | 7.8 | HNSC | 294 | 1 | 0.3% | 1.7E−01 | −39.9 |
| MET | 4.3E−03 | 5.6E−02 | 7.8 | BLCA | 136 | 4 | 2.9% | 1.9E−01 | 19.2 |
| MET | 4.3E−03 | 5.6E−02 | 7.8 | CRC | 217 | 4 | 1.8% | 2.1E−01 | 18.7 |
| MET | 4.3E−03 | 5.6E−02 | 7.8 | KIRC | 406 | 3 | 0.7% | 3.1E−01 | −16.9 |
| MET | 4.3E−03 | 5.6E−02 | 7.8 | OV | 188 | 3 | 1.6% | 3.2E−01 | −16.8 |
| MET | 4.3E−03 | 5.6E−02 | 7.8 | CESC | 193 | 2 | 1.0% | 3.3E−01 | 28.2 |
| MET | 4.3E−03 | 5.6E−02 | 7.8 | PRAD | 258 | 1 | 0.4% | 3.8E−01 | 25.6 |
| MET | 4.3E−03 | 5.6E−02 | 7.8 | KIRP | 167 | 12 | 7.2% | 4.8E−01 | 6.1 |
| MET | 4.3E−03 | 5.6E−02 | 7.8 | BRCA | 760 | 4 | 0.5% | 5.3E−01 | 9.1 |
| MET | 4.3E−03 | 5.6E−02 | 7.8 | LUSC | 176 | 4 | 2.3% | 5.4E−01 | 8.9 |
| MET | 4.3E−03 | 5.6E−02 | 7.8 | LIHC | 196 | 1 | 0.5% | 6.6E−01 | −12.7 |
| MET | 4.3E−03 | 5.6E−02 | 7.8 | SKCM | 93 | 7 | 7.5% | 8.4E−01 | −2.5 |
| MET | 4.3E−03 | 5.6E−02 | 7.8 | LGG | 201 | 3 | 1.5% | 9.1E−01 | 2.1 |
| MET | 4.3E−03 | 5.6E−02 | 7.8 | THCA | 314 | 0 | 0.0% | | |
| MET | 4.3E−03 | 5.6E−02 | 7.8 | GBM | 147 | 0 | 0.0% | | |
| CSNK2A1 | 4.3E−03 | 5.6E−02 | 9.8 | OV | 188 | 1 | 0.5% | 9.2E−02 | 48.7 |
| CSNK2A1 | 4.3E−03 | 5.6E−02 | 9.8 | CRC | 217 | 4 | 1.8% | 1.4E−01 | 21.5 |
| CSNK2A1 | 4.3E−03 | 5.6E−02 | 9.8 | LUAD | 168 | 1 | 0.6% | 1.7E−01 | 38.7 |
| CSNK2A1 | 4.3E−03 | 5.6E−02 | 9.8 | LIHC | 196 | 2 | 1.0% | 1.9E−01 | −38.8 |
| CSNK2A1 | 4.3E−03 | 5.6E−02 | 9.8 | BLCA | 136 | 5 | 3.7% | 1.9E−01 | 19.1 |
| CSNK2A1 | 4.3E−03 | 5.6E−02 | 9.8 | HNSC | 294 | 8 | 2.7% | 2.0E−01 | 13.3 |
| CSNK2A1 | 4.3E−03 | 5.6E−02 | 9.8 | BRCA | 760 | 1 | 0.1% | 2.2E−01 | 35.5 |
| CSNK2A1 | 4.3E−03 | 5.6E−02 | 9.8 | LGG | 201 | 1 | 0.5% | 3.4E−01 | −26.7 |
| CSNK2A1 | 4.3E−03 | 5.6E−02 | 9.8 | THCA | 314 | 1 | 0.3% | 3.9E−01 | −24.9 |
| CSNK2A1 | 4.3E−03 | 5.6E−02 | 9.8 | SKCM | 93 | 1 | 1.1% | 4.5E−01 | 22.1 |
| CSNK2A1 | 4.3E−03 | 5.6E−02 | 9.8 | UCEC | 244 | 11 | 4.5% | 4.8E−01 | 6.6 |
| CSNK2A1 | 4.3E−03 | 5.6E−02 | 9.8 | STAD | 263 | 5 | 1.9% | 5.0E−01 | 8.9 |
| CSNK2A1 | 4.3E−03 | 5.6E−02 | 9.8 | KIRP | 167 | 3 | 1.8% | 6.0E−01 | −8.8 |
| CSNK2A1 | 4.3E−03 | 5.6E−02 | 9.8 | LUSC | 176 | 3 | 1.7% | 7.9E−01 | −4.6 |
| CSNK2A1 | 4.3E−03 | 5.6E−02 | 9.8 | PRAD | 258 | 1 | 0.4% | 9.6E−01 | −1.6 |
| CSNK2A1 | 4.3E−03 | 5.6E−02 | 9.8 | CESC | 193 | 1 | 0.5% | 9.7E−01 | 0.9 |
| CSNK2A1 | 4.3E−03 | 5.6E−02 | 9.8 | GBM | 147 | 0 | 0.0% | | |
| CSNK2A1 | 4.3E−03 | 5.6E−02 | 9.8 | KIRC | 406 | 0 | 0.0% | | |
| ASXL1 | 7.5E−03 | 9.2E−02 | 6.7 | UCEC | 244 | 14 | 5.7% | 3.6E−02 | 17.6 |
| ASXL1 | 7.5E−03 | 9.2E−02 | 6.7 | KIRP | 167 | 1 | 0.6% | 8.9E−02 | 49.5 |
| ASXL1 | 7.5E−03 | 9.2E−02 | 6.7 | STAD | 263 | 13 | 4.9% | 1.0E−01 | 13.9 |
| ASXL1 | 7.5E−03 | 9.2E−02 | 6.7 | LUSC | 176 | 9 | 5.1% | 1.2E−01 | −15.3 |
| ASXL1 | 7.5E−03 | 9.2E−02 | 6.7 | LIHC | 196 | 10 | 5.1% | 1.4E−01 | 15.0 |
| ASXL1 | 7.5E−03 | 9.2E−02 | 6.7 | KIRC | 406 | 3 | 0.7% | 1.8E−01 | 22.2 |
| ASXL1 | 7.5E−03 | 9.2E−02 | 6.7 | SKCM | 93 | 2 | 2.2% | 2.1E−01 | 25.6 |
| ASXL1 | 7.5E−03 | 9.2E−02 | 6.7 | LGG | 201 | 1 | 0.5% | 2.7E−01 | 31.1 |
| ASXL1 | 7.5E−03 | 9.2E−02 | 6.7 | LUAD | 168 | 3 | 1.8% | 3.0E−01 | −17.3 |
| ASXL1 | 7.5E−03 | 9.2E−02 | 6.7 | HNSC | 294 | 8 | 2.7% | 3.2E−01 | −10.4 |
| ASXL1 | 7.5E−03 | 9.2E−02 | 6.7 | BRCA | 760 | 5 | 0.7% | 3.8E−01 | 11.3 |

TABLE 2A-continued

| Gene | PanCancer P | PanCancer BH adj. P | PanCancer Beta | Cancer | Count Samples | Count Mutated | Percent Mutated | Cancer P | Cancer Beta |
|---|---|---|---|---|---|---|---|---|---|
| ASXL1 | 7.5E−03 | 9.2E−02 | 6.7 | CRC | 217 | 10 | 4.6% | 4.2E−01 | 7.7 |
| ASXL1 | 7.5E−03 | 9.2E−02 | 6.7 | THCA | 314 | 1 | 0.3% | 6.2E−01 | −14.3 |
| ASXL1 | 7.5E−03 | 9.2E−02 | 6.7 | BLCA | 136 | 9 | 6.6% | 8.3E−01 | −2.2 |
| ASXL1 | 7.5E−03 | 9.2E−02 | 6.7 | PRAD | 258 | 2 | 0.8% | 9.0E−01 | −3.8 |
| ASXL1 | 7.5E−03 | 9.2E−02 | 6.7 | CESC | 193 | 5 | 2.6% | 9.8E−01 | 0.6 |
| ASXL1 | 7.5E−03 | 9.2E−02 | 6.7 | GBM | 147 | 0 | 0.0% | | |
| ASXL1 | 7.5E−03 | 9.2E−02 | 6.7 | OV | 188 | 0 | 0.0% | | |
| TMEM88 | 7.6E−03 | 9.2E−02 | 35.8 | SKCM | 93 | 1 | 1.1% | 9.9E−02 | 47.4 |
| TMEM88 | 7.6E−03 | 9.2E−02 | 35.8 | KIRP | 167 | 1 | 0.6% | 1.3E−01 | 44.2 |
| TMEM88 | 7.6E−03 | 9.2E−02 | 35.8 | LUAD | 168 | 1 | 0.6% | 5.2E−01 | 18.2 |
| TMEM88 | 7.6E−03 | 9.2E−02 | 35.8 | THCA | 314 | 0 | 0.0% | | |
| TMEM88 | 7.6E−03 | 9.2E−02 | 35.8 | HNSC | 294 | 0 | 0.0% | | |
| TMEM88 | 7.6E−03 | 9.2E−02 | 35.8 | KIRC | 406 | 0 | 0.0% | | |
| TMEM88 | 7.6E−03 | 9.2E−02 | 35.8 | UCEC | 244 | 0 | 0.0% | | |
| TMEM88 | 7.6E−03 | 9.2E−02 | 35.8 | GBM | 147 | 0 | 0.0% | | |
| TMEM88 | 7.6E−03 | 9.2E−02 | 35.8 | BLCA | 136 | 0 | 0.0% | | |
| TMEM88 | 7.6E−03 | 9.2E−02 | 35.8 | BRCA | 760 | 0 | 0.0% | | |
| TMEM88 | 7.6E−03 | 9.2E−02 | 35.8 | CESC | 193 | 0 | 0.0% | | |
| TMEM88 | 7.6E−03 | 9.2E−02 | 35.8 | CRC | 217 | 0 | 0.0% | | |
| TMEM88 | 7.6E−03 | 9.2E−02 | 35.8 | LGG | 201 | 0 | 0.0% | | |
| TMEM88 | 7.6E−03 | 9.2E−02 | 35.8 | LIHC | 196 | 0 | 0.0% | | |
| TMEM88 | 7.6E−03 | 9.2E−02 | 35.8 | OV | 188 | 0 | 0.0% | | |
| TMEM88 | 7.6E−03 | 9.2E−02 | 35.8 | PRAD | 258 | 0 | 0.0% | | |
| TMEM88 | 7.6E−03 | 9.2E−02 | 35.8 | LUSC | 176 | 0 | 0.0% | | |
| TMEM88 | 7.6E−03 | 9.2E−02 | 35.8 | STAD | 263 | 0 | 0.0% | | |
| DNMT3A | 8.7E−03 | 9.5E−02 | 7.7 | STAD | 263 | 8 | 3.0% | 2.4E−02 | 23.8 |
| DNMT3A | 8.7E−03 | 9.5E−02 | 7.7 | LUSC | 176 | 7 | 4.0% | 5.3E−02 | 21.6 |
| DNMT3A | 8.7E−03 | 9.5E−02 | 7.7 | CRC | 217 | 7 | 3.2% | 1.5E−01 | 16.4 |
| DNMT3A | 8.7E−03 | 9.5E−02 | 7.7 | BLCA | 136 | 1 | 0.7% | 1.9E−01 | 37.9 |
| DNMT3A | 8.7E−03 | 9.5E−02 | 7.7 | LGG | 201 | 2 | 1.0% | 2.0E−01 | 25.7 |
| DNMT3A | 8.7E−03 | 9.5E−02 | 7.7 | UCEC | 244 | 6 | 2.5% | 2.0E−01 | 15.5 |
| DNMT3A | 8.7E−03 | 9.5E−02 | 7.7 | HNSC | 294 | 6 | 2.0% | 2.4E−01 | 14.4 |
| DNMT3A | 8.7E−03 | 9.5E−02 | 7.7 | KIRP | 167 | 4 | 2.4% | 3.1E−01 | 15.0 |
| DNMT3A | 8.7E−03 | 9.5E−02 | 7.7 | CESC | 193 | 2 | 1.0% | 5.1E−01 | 19.0 |
| DNMT3A | 8.7E−03 | 9.5E−02 | 7.7 | KIRC | 406 | 5 | 1.2% | 6.2E−01 | −6.4 |
| DNMT3A | 8.7E−03 | 9.5E−02 | 7.7 | BRCA | 760 | 3 | 0.4% | 6.9E−01 | −6.7 |
| DNMT3A | 8.7E−03 | 9.5E−02 | 7.7 | PRAD | 258 | 2 | 0.8% | 8.1E−01 | −4.9 |
| DNMT3A | 8.7E−03 | 9.5E−02 | 7.7 | LUAD | 168 | 6 | 3.6% | 8.2E−01 | −2.6 |
| DNMT3A | 8.7E−03 | 9.5E−02 | 7.7 | OV | 188 | 2 | 1.1% | 8.5E−01 | 3.9 |
| DNMT3A | 8.7E−03 | 9.5E−02 | 7.7 | THCA | 314 | 5 | 1.6% | 9.1E−01 | −1.5 |
| DNMT3A | 8.7E−03 | 9.5E−02 | 7.7 | GBM | 147 | 0 | 0.0% | | |
| DNMT3A | 8.7E−03 | 9.5E−02 | 7.7 | LIHC | 196 | 2 | 1.0% | | |
| DNMT3A | 8.7E−03 | 9.5E−02 | 7.7 | SKCM | 93 | 0 | 0.0% | | |
| EP300 | 8.7E−03 | 9.5E−02 | 5.4 | HNSC | 294 | 19 | 6.5% | 7.9E−02 | 12.1 |
| EP300 | 8.7E−03 | 9.5E−02 | 5.4 | PRAD | 258 | 4 | 1.6% | 1.8E−01 | 22.8 |
| EP300 | 8.7E−03 | 9.5E−02 | 5.4 | LGG | 201 | 1 | 0.5% | 2.7E−01 | 31.1 |
| EP300 | 8.7E−03 | 9.5E−02 | 5.4 | LIHC | 196 | 8 | 4.1% | 2.9E−01 | 11.4 |
| EP300 | 8.7E−03 | 9.5E−02 | 5.4 | LUAD | 168 | 1 | 0.6% | 4.2E−01 | −23.0 |
| EP300 | 8.7E−03 | 9.5E−02 | 5.4 | UCEC | 244 | 20 | 8.2% | 4.4E−01 | 5.5 |
| EP300 | 8.7E−03 | 9.5E−02 | 5.4 | BLCA | 136 | 21 | 15.4% | 4.7E−01 | 4.9 |
| EP300 | 8.7E−03 | 9.5E−02 | 5.4 | LUSC | 176 | 7 | 4.0% | 5.4E−01 | 6.9 |
| EP300 | 8.7E−03 | 9.5E−02 | 5.4 | STAD | 263 | 17 | 6.5% | 5.7E−01 | 4.2 |
| EP300 | 8.7E−03 | 9.5E−02 | 5.4 | BRCA | 760 | 5 | 0.7% | 6.0E−01 | 6.8 |
| EP300 | 8.7E−03 | 9.5E−02 | 5.4 | CRC | 217 | 11 | 5.1% | 6.4E−01 | 4.3 |
| EP300 | 8.7E−03 | 9.5E−02 | 5.4 | KIRP | 167 | 5 | 3.0% | 8.5E−01 | −2.6 |
| EP300 | 8.7E−03 | 9.5E−02 | 5.4 | SKCM | 93 | 5 | 5.4% | 9.4E−01 | −1.1 |
| EP300 | 8.7E−03 | 9.5E−02 | 5.4 | CESC | 193 | 21 | 10.9% | 9.8E−01 | 0.2 |
| EP300 | 8.7E−03 | 9.5E−02 | 5.4 | KIRC | 406 | 6 | 1.5% | 1.0E+00 | 0.1 |
| EP300 | 8.7E−03 | 9.5E−02 | 5.4 | GBM | 147 | 0 | 0.0% | | |
| EP300 | 8.7E−03 | 9.5E−02 | 5.4 | OV | 188 | 0 | 0.0% | | |
| EP300 | 8.7E−03 | 9.5E−02 | 5.4 | THCA | 314 | 0 | 0.0% | | |
| MUC17 | 8.9E−03 | 9.5E−02 | 3.7 | KIRP | 167 | 4 | 2.4% | 8.9E−03 | −38.2 |
| MUC17 | 8.9E−03 | 9.5E−02 | 3.7 | CESC | 193 | 18 | 9.3% | 1.0E−02 | 23.3 |
| MUC17 | 8.9E−03 | 9.5E−02 | 3.7 | KIRC | 406 | 6 | 1.5% | 1.9E−02 | 27.9 |
| MUC17 | 8.9E−03 | 9.5E−02 | 3.7 | LGG | 201 | 13 | 6.5% | 2.2E−02 | 20.1 |
| MUC17 | 8.9E−03 | 9.5E−02 | 3.7 | LUSC | 176 | 30 | 17.0% | 1.0E−01 | 10.1 |
| MUC17 | 8.9E−03 | 9.5E−02 | 3.7 | UCEC | 244 | 29 | 11.9% | 1.3E−01 | 9.7 |
| MUC17 | 8.9E−03 | 9.5E−02 | 3.7 | GBM | 147 | 12 | 8.2% | 1.5E−01 | 12.6 |
| MUC17 | 8.9E−03 | 9.5E−02 | 3.7 | BLCA | 136 | 15 | 11.0% | 2.2E−01 | −10.1 |
| MUC17 | 8.9E−03 | 9.5E−02 | 3.7 | STAD | 263 | 34 | 12.9% | 3.6E−01 | 5.1 |
| MUC17 | 8.9E−03 | 9.5E−02 | 3.7 | BRCA | 760 | 23 | 3.0% | 4.3E−01 | 4.9 |
| MUC17 | 8.9E−03 | 9.5E−02 | 3.7 | LUAD | 168 | 44 | 26.2% | 6.0E−01 | 2.8 |
| MUC17 | 8.9E−03 | 9.5E−02 | 3.7 | LIHC | 196 | 27 | 13.8% | 7.1E−01 | 2.8 |
| MUC17 | 8.9E−03 | 9.5E−02 | 3.7 | OV | 188 | 6 | 3.2% | 7.4E−01 | 3.9 |
| MUC17 | 8.9E−03 | 9.5E−02 | 3.7 | CRC | 217 | 13 | 6.0% | 8.2E−01 | −2.0 |
| MUC17 | 8.9E−03 | 9.5E−02 | 3.7 | PRAD | 258 | 15 | 5.8% | 8.5E−01 | 1.8 |
| MUC17 | 8.9E−03 | 9.5E−02 | 3.7 | HNSC | 294 | 24 | 8.2% | 8.8E−01 | −1.0 |

TABLE 2A-continued

| Gene | PanCancer P | PanCancer BH adj. P | PanCancer Beta | Cancer | Count Samples | Count Mutated | Percent Mutated | Cancer P | Cancer Beta |
|---|---|---|---|---|---|---|---|---|---|
| MUC17 | 8.9E−03 | 9.5E−02 | 3.7 | THCA | 314 | 6 | 1.9% | 9.2E−01 | −1.3 |
| MUC17 | 8.9E−03 | 9.5E−02 | 3.7 | SKCM | 93 | 34 | 36.6% | 9.7E−01 | −0.3 |
| OVOL1 | 8.9E−03 | 9.5E−02 | 20.4 | STAD | 263 | 3 | 1.1% | 1.8E−02 | 39.1 |
| OVOL1 | 8.9E−03 | 9.5E−02 | 20.4 | KIRP | 167 | 1 | 0.6% | 4.3E−01 | 23.0 |
| OVOL1 | 8.9E−03 | 9.5E−02 | 20.4 | SKCM | 93 | 1 | 1.1% | 5.0E−01 | 19.9 |
| OVOL1 | 8.9E−03 | 9.5E−02 | 20.4 | LUAD | 168 | 2 | 1.2% | 5.5E−01 | 12.2 |
| OVOL1 | 8.9E−03 | 9.5E−02 | 20.4 | UCEC | 244 | 2 | 0.8% | 6.2E−01 | 10.3 |
| OVOL1 | 8.9E−03 | 9.5E−02 | 20.4 | BRCA | 760 | 0 | 0.0% | | |
| OVOL1 | 8.9E−03 | 9.5E−02 | 20.4 | CESC | 193 | 0 | 0.0% | | |
| OVOL1 | 8.9E−03 | 9.5E−02 | 20.4 | CRC | 217 | 0 | 0.0% | | |
| OVOL1 | 8.9E−03 | 9.5E−02 | 20.4 | BLCA | 136 | 0 | 0.0% | | |
| OVOL1 | 8.9E−03 | 9.5E−02 | 20.4 | PRAD | 258 | 0 | 0.0% | | |
| OVOL1 | 8.9E−03 | 9.5E−02 | 20.4 | THCA | 314 | 0 | 0.0% | | |
| OVOL1 | 8.9E−03 | 9.5E−02 | 20.4 | GBM | 147 | 0 | 0.0% | | |
| OVOL1 | 8.9E−03 | 9.5E−02 | 20.4 | HNSC | 294 | 0 | 0.0% | | |
| OVOL1 | 8.9E−03 | 9.5E−02 | 20.4 | KIRC | 406 | 0 | 0.0% | | |
| OVOL1 | 8.9E−03 | 9.5E−02 | 20.4 | LGG | 201 | 0 | 0.0% | | |
| OVOL1 | 8.9E−03 | 9.5E−02 | 20.4 | LIHC | 196 | 1 | 0.5% | | |
| OVOL1 | 8.9E−03 | 9.5E−02 | 20.4 | LUSC | 176 | 0 | 0.0% | | |
| OVOL1 | 8.9E−03 | 9.5E−02 | 20.4 | OV | 188 | 0 | 0.0% | | |

TABLE 2B

| | Adrenocorical carcinoma | Bladder Urothelial carcinoma | Breast invasive carcinoma | Cervical squamous cell carcinoma and endocervical adenocarcinoma | Colon adenocarcinoma and Rectum adenocarcinoma | Glioblastoma multiforme | Head and Neck squamous cell carcinoma | Kidney Chromophobe | Kidney renal clear cell carcinoma |
|---|---|---|---|---|---|---|---|---|---|
| DSP | 0.0 | 0.9 | 0.3 | 0.0 | 0.4 | 0.9 | 1.3 | 0.0 | −0.4 |
| SPG20 | 0.0 | 0.7 | 1.3 | 0.6 | −0.2 | 0.0 | 0.0 | 0.0 | 0.0 |
| BRAF | 4.1 | 0.0 | 0.4 | 0.1 | 2.8 | 0.7 | 0.6 | 0.0 | 0.6 |
| CCDC88A | 0.0 | 1.2 | 0.1 | 0.1 | 0.8 | 0.0 | 0.1 | −0.1 | −0.7 |
| GPR6 | 0.3 | 0.0 | 1.4 | 0.0 | 0.2 | −0.3 | 0.3 | 0.0 | 0.0 |
| USP42 | 1.7 | 1.2 | 0.3 | −0.5 | 0.2 | 0.9 | 0.4 | 0.0 | −1.3 |
| KIT | 0.0 | 0.7 | 0.4 | 0.0 | −0.3 | 0.0 | 0.3 | 0.0 | −0.4 |
| PLOD3 | 0.3 | 0.0 | 1.1 | 0.7 | 0.2 | 0.0 | 0.7 | 0.0 | −1.2 |
| CDH1 | 0.0 | 0.0 | 1.8 | 0.6 | 0.5 | −0.1 | −1.6 | 0.0 | 1.2 |
| SPTAN1 | −0.1 | 0.2 | 1.2 | 0.7 | 2.2 | −0.3 | 0.2 | 0.0 | −0.4 |
| ZMYM4 | 0.0 | −0.2 | 0.5 | 0.0 | 0.2 | 0.0 | 1.2 | 0.0 | 0.0 |
| ZC3H18 | 0.4 | 0.8 | −0.6 | 0.5 | 1.3 | 0.0 | 0.0 | 0.0 | −0.5 |

| | Kidney renal papillary cell carcinoma | Acute Myeloid Leukemia | Liver hepatocellular carcinoma | Lung adenocarcinoma | Lung squamous cell carcinoma | Ovarian serous cystadeno-carcinoma | Pancreatic adeno-carcinoma | Prostate adeno-carcinoma | Skin Cutaneous Melanoma |
|---|---|---|---|---|---|---|---|---|---|
| DSP | 0.2 | 0.0 | 0.4 | −0.5 | 1.0 | 0.0 | 0.2 | 0.4 | −0.2 |
| SPG20 | 0.0 | 0.0 | 0.0 | −0.3 | 0.7 | 0.0 | 1.1 | 0.2 | 0.7 |
| BRAF | 0.1 | 0.0 | 0.0 | 0.0 | 0.2 | 0.0 | −0.7 | 0.4 | −0.4 |
| CCDC88A | 0.6 | 0.0 | −0.2 | −0.3 | 0.1 | 0.1 | 0.0 | −0.7 | 0.3 |
| GPR6 | 0.0 | 0.2 | 0.0 | 0.6 | −0.2 | 0.0 | 2.7 | 0.0 | 0.5 |
| USP42 | 0.0 | 0.0 | 0.0 | −0.6 | 0.5 | 0.0 | 0.8 | 3.8 | 0.1 |
| KIT | 0.0 | 0.4 | −0.5 | 0.0 | 0.5 | 0.6 | 0.8 | 0.0 | 0.2 |
| PLOD3 | 0.0 | 0.0 | −0.3 | 0.5 | 1.2 | −0.6 | 0.0 | 0.2 | 0.4 |
| CDH1 | 0.8 | 0.0 | 0.3 | 0.0 | 0.5 | 0.0 | 0.8 | 0.5 | −0.8 |
| SPTAN1 | 0.2 | 0.0 | 0.1 | 0.5 | 0.0 | −0.4 | 0.7 | −0.5 | 1.0 |
| ZMYM4 | 0.0 | 0.0 | 0.0 | 0.0 | 0.2 | 0.0 | 0.7 | −0.7 | 0.4 |
| ZC3H18 | −0.5 | 0.9 | −0.2 | −0.2 | 0.7 | 0.0 | 0.8 | 1.1 | −0.1 |

| | Stomach adenocarcinoma | Testicular Cerm Cell Tumors | Thyroid carcinoma | Uterine Corpus Edometrial Carcinoma | Uterine Carcinosarcoma | PanCancer | PanCancer Adjusted |
|---|---|---|---|---|---|---|---|
| DSP | 1.0 | −1.5 | 0.0 | 2.2 | 0.1 | 4.6 | 2.7 |
| SPG20 | 2.1 | 0.0 | 0.0 | 1.1 | 0.0 | 4.6 | 2.7 |
| BRAF | 0.3 | 0.0 | 2.2 | 0.9 | 0.2 | 3.9 | 2.3 |
| CCDC88A | 1.5 | 0.0 | 1.1 | 2.2 | 0.0 | 4.0 | 2.3 |
| GPR6 | 1.4 | −0.5 | 0.0 | 1.1 | 0.0 | 4.1 | 2.3 |
| USP42 | 1.2 | 0.0 | 0.0 | 0.5 | 1.5 | 3.9 | 2.3 |
| KIT | −1.1 | 2.4 | 0.0 | 3.2 | 0.0 | 3.7 | 2.2 |
| PLOD3 | 1.9 | 0.0 | 0.0 | 1.0 | 0.0 | 3.7 | 2.1 |
| CDH1 | 1.8 | 0.0 | 0.0 | 0.8 | 0.0 | 3.5 | 2.0 |

TABLE 2B-continued

| | | | | | | | |
|---|---|---|---|---|---|---|---|
| SPTAN1 | 0.3 | −1.1 | −0.1 | 1.8 | 0.0 | 3.5 | 2.0 |
| ZMYM4 | 0.7 | 0.5 | −0.4 | 3.4 | 0.0 | 3.4 | 2.0 |
| ZC3H18 | 0.1 | 1.0 | −0.3 | 3.1 | −0.1 | 3.4 | 2.0 |

TABLE 3

| | OddsRatio | Uncorrected P | BH Adj. P |
|---|---|---|---|
| HLA-A, B, C | 35.16473 | 4.76E−15 | 1.41E−12 |
| CASP8 | Inf | 1.32E−07 | 1.46E−05 |
| CREBBP | 24.92799 | 1.48E−07 | 1.46E−05 |
| COL5A1 | 23.8067 | 2.41E−06 | 0.000179 |
| EPHA2 | Inf | 6.95E−05 | 0.003427 |
| DNMT3A | Inf | 6.95E−05 | 0.003427 |
| SMC1A | 16.45291 | 9.70E−05 | 0.0041 |
| RNF43 | 20.09593 | 0.000202 | 0.007476 |
| CIC | Inf | 0.000511 | 0.015113 |
| TRAF3 | Inf | 0.000511 | 0.015113 |
| FBXW7 | 8.115695 | 0.000994 | 0.025531 |
| EGFR | 15.92405 | 0.001159 | 0.025531 |
| BZRAP1 | 15.92405 | 0.001159 | 0.025531 |
| EPB41L3 | 9.989158 | 0.001208 | 0.025531 |
| ZC3H13 | 6.915228 | 0.001777 | 0.032876 |
| ANK3 | 6.915228 | 0.001777 | 0.032876 |
| PLEKHA6 | 24.28771 | 0.002275 | 0.036924 |
| ARID2 | 7.951178 | 0.00237 | 0.036924 |
| POLE | 7.951178 | 0.00237 | 0.036924 |
| LARP4B | 10.58883 | 0.002755 | 0.038826 |
| IDH2 | 10.58883 | 0.002755 | 0.038826 |
| MLL2 | 6.013439 | 0.002978 | 0.040065 |
| ZBTB20 | Inf | 0.003598 | 0.042605 |
| CNKSR1 | Inf | 0.003598 | 0.042605 |
| SLC1A3 | Inf | 0.003598 | 0.042605 |

TABLE 3-continued

| | OddsRatio | Uncorrected P | BH Adj. P |
|---|---|---|---|
| ZFHX3 | 6.5894 | 0.004227 | 0.048128 |
| ASXL1 | 7.909937 | 0.005521 | 0.054476 |
| AXIN2 | 7.909937 | 0.005521 | 0.054476 |
| MGA | 7.909937 | 0.005521 | 0.054476 |
| MLL | 7.909937 | 0.005521 | 0.054476 |
| GPS2 | 12.1504 | 0.006082 | 0.054553 |
| CTCF | 12.1504 | 0.006082 | 0.054553 |
| SLC4A5 | 12.1504 | 0.006082 | 0.054553 |
| ACVR1B | 5.614863 | 0.006999 | 0.059192 |
| XIRP2 | 5.614863 | 0.006999 | 0.059192 |
| ARID1A | 6.29833 | 0.009835 | 0.076609 |
| ALK | 6.29833 | 0.009835 | 0.076609 |
| EP300 | 6.29833 | 0.009835 | 0.076609 |
| MAP2K4 | 8.079521 | 0.012645 | 0.079314 |
| NCOR1 | 8.079521 | 0.012645 | 0.079314 |
| KDM5C | 8.079521 | 0.012645 | 0.079314 |
| FLG | 3.690409 | 0.012757 | 0.079314 |
| MAP3K1 | 17.43024 | 0.012862 | 0.079314 |
| RHOA | 17.43024 | 0.012862 | 0.079314 |
| CAP2 | 17.43024 | 0.012862 | 0.079314 |
| DNER | 17.43024 | 0.012862 | 0.079314 |
| ERCC2 | 17.43024 | 0.012862 | 0.079314 |
| SLC44A3 | 17.43024 | 0.012862 | 0.079314 |
| APC | 0.306996 | 0.013847 | 0.083644 |

TABLE 4

| Class | Locus | Unbiased Peak Gene | PanCancer Uncorrect Peak Gene P | PanCancer Peak BH adj. P | PanCancer Beta | Cancer | Samples with Lesion | Samples Analyzed | Percent with Lesion | Cancer Beta | Cancer P |
|---|---|---|---|---|---|---|---|---|---|---|---|
| Amplification | 6q16.1-q21 | GRIK2 | 4.7E−08 | 0.0E+00 | 4.7 | BRCA | 58 | 992 | 5.8% | 5.7 | 3.1E−04 |
| Amplification | 6q16.1-q21 | GRIK2 | 4.7E−08 | 0.0E+00 | 4.7 | UCEC | 12 | 506 | 2.4% | 8.7 | 2.5E−02 |
| Amplification | 6q16.1-q21 | GRIK2 | 4.7E−08 | 0.0E+00 | 4.7 | LIHC | 4 | 194 | 2.1% | 3.7 | 1.0E−01 |
| Amplification | 6q16.1-q21 | GRIK2 | 4.7E−08 | 0.0E+00 | 4.7 | CRC | 5 | 581 | 0.9% | 23.7 | 1.2E−01 |
| Amplification | 6q16.1-q21 | GRIK2 | 4.7E−08 | 0.0E+00 | 4.7 | BLCA | 5 | 218 | 2.3% | 6.5 | 1.3E−01 |
| Amplification | 6q16.1-q21 | GRIK2 | 4.7E−08 | 0.0E+00 | 4.7 | HNSC | 8 | 424 | 1.9% | 9.4 | 2.0E−01 |
| Amplification | 6q16.1-q21 | GRIK2 | 4.7E−08 | 0.0E+00 | 4.7 | SKCM | 1 | 81 | 1.2% | 14.9 | 2.1E−01 |
| Amplification | 6q16.1-q21 | GRIK2 | 4.7E−08 | 0.0E+00 | 4.7 | LUSC | 12 | 479 | 2.5% | 5.5 | 2.7E−01 |
| Amplification | 6q16.1-q21 | GRIK2 | 4.7E−08 | 0.0E+00 | 4.7 | CESC | 2 | 191 | 1.0% | 14.8 | 3.9E−01 |
| Amplification | 6q16.1-q21 | GRIK2 | 4.7E−08 | 0.0E+00 | 4.7 | OV | 26 | 292 | 8.9% | −1.6 | 5.7E−01 |
| Amplification | 6q16.1-q21 | GRIK2 | 4.7E−08 | 0.0E+00 | 4.7 | LGG | 3 | 262 | 1.1% | −4.1 | 6.0E−01 |
| Amplification | 6q16.1-q21 | GRIK2 | 4.7E−08 | 0.0E+00 | 4.7 | LUAD | 6 | 482 | 1.2% | 3.8 | 7.6E−01 |
| Amplification | 6q16.1-q21 | GRIK2 | 4.7E−08 | 0.0E+00 | 4.7 | STAD | 11 | 272 | 4.0% | −1.3 | 8.7E−01 |
| Amplification | 6q16.1-q21 | GRIK2 | 4.7E−08 | 0.0E+00 | 4.7 | GBM | 0 | 153 | 0.0% | | |
| Amplification | 6q16.1-q21 | GRIK2 | 4.7E−08 | 0.0E+00 | 4.7 | KIRC | 0 | 483 | 0.0% | | |
| Amplification | 6q16.1-q21 | GRIK2 | 4.7E−08 | 0.0E+00 | 4.7 | KIRP | 0 | 171 | 0.0% | | |
| Amplification | 6q16.1-q21 | GRIK2 | 4.7E−08 | 0.0E+00 | 4.7 | PRAD | 0 | 277 | 0.0% | | |

TABLE 4-continued

| Class | Locus | Unbiased Peak Gene | PanCancer Uncorrect Peak Gene P | PanCancer Peak BH adj. P | PanCancer Beta | Cancer | Samples with Lesion | Samples Analyzed | Percent with Lesion | Cancer Beta | Cancer P |
|---|---|---|---|---|---|---|---|---|---|---|---|
| Amplification | 6q16.1-q21 | GRIK2 | 4.7E−08 | 0.0E+00 | 4.7 | THCA | 0 | 488 | 0.0% | | |
| Amplification | 6q22.31-q24.1 | MIR4465 | 1.4E−06 | 3.5E−03 | 4.2 | BRCA | 65 | 992 | 6.6% | 3.0 | 1.4E−02 |
| Amplification | 6q22.31-q24.1 | MIR4465 | 1.4E−06 | 3.5E−03 | 4.2 | LGG | 1 | 262 | 0.4% | −54.0 | 4.3E−02 |
| Amplification | 6q22.31-q24.1 | MIR4465 | 1.4E−06 | 3.5E−03 | 4.2 | HNSC | 8 | 424 | 1.9% | 11.0 | 5.1E−02 |
| Amplification | 6q22.31-q24.1 | MIR4465 | 1.4E−06 | 3.5E−03 | 4.2 | LUSC | 25 | 479 | 5.2% | 8.4 | 7.2E−02 |
| Amplification | 6q22.31-q24.1 | MIR4465 | 1.4E−06 | 3.5E−03 | 4.2 | LUAD | 14 | 482 | 2.9% | 6.3 | 1.1E−01 |
| Amplification | 6q22.31-q24.1 | MIR4465 | 1.4E−06 | 3.5E−03 | 4.2 | CRC | 16 | 581 | 2.8% | 10.4 | 1.6E−01 |
| Amplification | 6q22.31-q24.1 | MIR4465 | 1.4E−06 | 3.5E−03 | 4.2 | UCEC | 16 | 506 | 3.2% | 8.9 | 1.7E−01 |
| Amplification | 6q22.31-q24.1 | MIR4465 | 1.4E−06 | 3.5E−03 | 4.2 | LIHC | 2 | 194 | 1.0% | 15.6 | 3.9E−01 |
| Amplification | 6q22.31-q24.1 | MIR4465 | 1.4E−06 | 3.5E−03 | 4.2 | OV | 15 | 292 | 5.1% | 5.6 | 4.4E−01 |
| Amplification | 6q22.31-q24.1 | MIR4465 | 1.4E−06 | 3.5E−03 | 4.2 | BLCA | 11 | 218 | 5.0% | 3.0 | 5.4E−01 |
| Amplification | 6q22.31-q24.1 | MIR4465 | 1.4E−06 | 3.5E−03 | 4.2 | PRAD | 2 | 277 | 0.7% | −14.3 | 5.8E−01 |
| Amplification | 6q22.31-q24.1 | MIR4465 | 1.4E−06 | 3.5E−03 | 4.2 | THCA | 1 | 488 | 0.2% | 15.4 | 6.0E−01 |
| Amplification | 6q22.31-q24.1 | MIR4465 | 1.4E−06 | 3.5E−03 | 4.2 | CESC | 2 | 191 | 1.0% | 5.6 | 6.0E−01 |
| Amplification | 6q22.31-q24.1 | MIR4465 | 1.4E−06 | 3.5E−03 | 4.2 | STAD | 22 | 272 | 8.1% | −1.6 | 6.7E−01 |
| Amplification | 6q22.31-q24.1 | MIR4465 | 1.4E−06 | 3.5E−03 | 4.2 | GBM | 0 | 153 | 0.0% | | |
| Amplification | 6q22.31-q24.1 | MIR4465 | 1.4E−06 | 3.5E−03 | 4.2 | KIRC | 0 | 483 | 0.0% | | |
| Amplification | 6q22.31-q24.1 | MIR4465 | 1.4E−06 | 3.5E−03 | 4.2 | KIRP | 0 | 171 | 0.0% | | |
| Amplification | 6q22.31-q24.1 | MIR4465 | 1.4E−06 | 3.5E−03 | 4.2 | SKCM | 0 | 81 | 0.0% | | |
| Amplification | 6q25.1-q26 | TMEM242 | 1.2E−06 | 3.5E−03 | 7.7 | LUSC | 26 | 479 | 5.4% | 12.6 | 5.2E−03 |
| Amplification | 6q25.1-q26 | TMEM242 | 1.2E−06 | 3.5E−03 | 7.7 | BRCA | 42 | 992 | 4.2% | 8.1 | 1.1E−02 |
| Amplification | 6q25.1-q26 | TMEM242 | 1.2E−06 | 3.5E−03 | 7.7 | OV | 24 | 292 | 8.2% | 15.5 | 2.2E−02 |
| Amplification | 6q25.1-q26 | TMEM242 | 1.2E−06 | 3.5E−03 | 7.7 | UCEC | 14 | 506 | 2.8% | 17.3 | 3.0E−02 |
| Amplification | 6q25.1-q26 | TMEM242 | 1.2E−06 | 3.5E−03 | 7.7 | LIHC | 1 | 194 | 0.5% | 60.2 | 3.9E−02 |
| Amplification | 6q25.1-q26 | TMEM242 | 1.2E−06 | 3.5E−03 | 7.7 | CRC | 17 | 581 | 2.9% | 7.9 | 1.5E−01 |
| Amplification | 6q25.1-q26 | TMEM242 | 1.2E−06 | 3.5E−03 | 7.7 | BLCA | 4 | 218 | 1.8% | 12.6 | 2.8E−01 |
| Amplification | 6q25.1-q26 | TMEM242 | 1.2E−06 | 3.5E−03 | 7.7 | GBM | 1 | 153 | 0.7% | −15.1 | 3.8E−01 |
| Amplification | 6q25.1-q26 | TMEM242 | 1.2E−06 | 3.5E−03 | 7.7 | CESC | 1 | 191 | 0.5% | −19.9 | 5.2E−01 |
| Amplification | 6q25.1-q26 | TMEM242 | 1.2E−06 | 3.5E−03 | 7.7 | HNSC | 11 | 424 | 2.6% | 4.5 | 5.4E−01 |
| Amplification | 6q25.1-q26 | TMEM242 | 1.2E−06 | 3.5E−03 | 7.7 | THCA | 1 | 488 | 0.2% | 15.4 | 6.0E−01 |
| Amplification | 6q25.1-q26 | TMEM242 | 1.2E−06 | 3.5E−03 | 7.7 | LUAD | 8 | 482 | 1.7% | −2.9 | 7.1E−01 |
| Amplification | 6q25.1-q26 | TMEM242 | 1.2E−06 | 3.5E−03 | 7.7 | STAD | 16 | 272 | 5.9% | −1.5 | 7.8E−01 |
| Amplification | 6q25.1-q26 | TMEM242 | 1.2E−06 | 3.5E−03 | 7.7 | PRAD | 3 | 277 | 1.1% | −2.0 | 9.2E−01 |
| Amplification | 6q25.1-q26 | TMEM242 | 1.2E−06 | 3.5E−03 | 7.7 | KIRC | 0 | 483 | 0.0% | | |
| Amplification | 6q25.1-q26 | TMEM242 | 1.2E−06 | 3.5E−03 | 7.7 | KIRP | 0 | 171 | 0.0% | | |
| Amplification | 6q25.1-q26 | TMEM242 | 1.2E−06 | 3.5E−03 | 7.7 | LGG | 0 | 262 | 0.0% | | |
| Amplification | 6q25.1-q26 | TMEM242 | 1.2E−06 | 3.5E−03 | 7.7 | SKCM | 0 | 81 | 0.0% | | |

TABLE 4-continued

| Class | Locus | Unbiased Peak Gene | PanCancer Uncorrect Peak Gene P | PanCancer Peak BH adj. P | PanCancer Beta | Cancer | Samples with Lesion | Samples Analyzed | Percent with Lesion | Cancer Beta | Cancer P |
|---|---|---|---|---|---|---|---|---|---|---|---|
| Amplification | 7p11.2-q11.1 | DKFZp434L192 | 5.4E−05 | 5.5E−02 | −1.8 | HNSC | 39 | 424 | 9.2% | −2.7 | 1.7E−04 |
| Amplification | 7p11.2-q11.1 | DKFZp434L192 | 5.4E−05 | 5.5E−02 | −1.8 | LUAD | 35 | 482 | 7.3% | −2.8 | 4.0E−02 |
| Amplification | 7p11.2-q11.1 | DKFZp434L192 | 5.4E−05 | 5.5E−02 | −1.8 | OV | 34 | 292 | 11.6% | 6.2 | 1.2E−01 |
| Amplification | 7p11.2-q11.1 | DKFZp434L192 | 5.4E−05 | 5.5E−02 | −1.8 | KIRC | 1 | 483 | 0.2% | −35.1 | 1.6E−01 |
| Amplification | 7p11.2-q11.1 | DKFZp434L192 | 5.4E−05 | 5.5E−02 | −1.8 | CESC | 5 | 191 | 2.6% | −4.5 | 2.5E−01 |
| Amplification | 7p11.2-q11.1 | DKFZp434L192 | 5.4E−05 | 5.5E−02 | −1.8 | SKCM | 3 | 81 | 3.7% | −10.3 | 3.8E−01 |
| Amplification | 7p11.2-q11.1 | DKFZp434L192 | 5.4E−05 | 5.5E−02 | −1.8 | LIHC | 2 | 194 | 1.0% | −15.6 | 4.8E−01 |
| Amplification | 7p11.2-q11.1 | DKFZp434L192 | 5.4E−05 | 5.5E−02 | −1.8 | UCEC | 16 | 506 | 3.2% | 1.5 | 5.5E−01 |
| Amplification | 7p11.2-q11.1 | DKFZp434L192 | 5.4E−05 | 5.5E−02 | −1.8 | LUSC | 44 | 479 | 9.2% | −0.7 | 5.9E−01 |
| Amplification | 7p11.2-q11.1 | DKFZp434L192 | 5.4E−05 | 5.5E−02 | −1.8 | CRC | 13 | 581 | 2.2% | −3.2 | 6.1E−01 |
| Amplification | 7p11.2-q11.1 | DKFZp434L192 | 5.4E−05 | 5.5E−02 | −1.8 | BRCA | 42 | 992 | 4.2% | 0.4 | 7.8E−01 |
| Amplification | 7p11.2-q11.1 | DKFZp434L192 | 5.4E−05 | 5.5E−02 | −1.8 | KIRP | 2 | 171 | 1.2% | 5.6 | 8.1E−01 |
| Amplification | 7p11.2-q11.1 | DKFZp434L192 | 5.4E−05 | 5.5E−02 | −1.8 | GBM | 16 | 153 | 10.5% | 0.6 | 8.2E−01 |
| Amplification | 7p11.2-q11.1 | DKFZp434L192 | 5.4E−05 | 5.5E−02 | −1.8 | STAD | 14 | 272 | 5.1% | −0.6 | 8.3E−01 |
| Amplification | 7p11.2-q11.1 | DKFZp434L192 | 5.4E−05 | 5.5E−02 | −1.8 | BLCA | 22 | 218 | 10.1% | 0.2 | 9.0E−01 |
| Amplification | 7p11.2-q11.1 | DKFZp434L192 | 5.4E−05 | 5.5E−02 | −1.8 | LGG | 4 | 262 | 1.5% | 0.1 | 9.6E−01 |
| Amplification | 7p11.2-q11.1 | DKFZp434L192 | 5.4E−05 | 5.5E−02 | −1.8 | PRAD | 0 | 277 | 0.0% | | |
| Amplification | 7p11.2-q11.1 | DKFZp434L192 | 5.4E−05 | 5.5E−02 | −1.8 | THCA | 0 | 488 | 0.0% | | |
| Amplification | 8p23.1 | ZNF705A | 3.4E−05 | 4.0E−02 | 3.7 | LUSC | 44 | 479 | 9.2% | 9.4 | 2.2E−03 |
| Amplification | 8p23.1 | ZNF705A | 3.4E−05 | 4.0E−02 | 3.7 | BRCA | 65 | 992 | 6.6% | 3.6 | 5.8E−02 |
| Amplification | 8p23.1 | ZNF705A | 3.4E−05 | 4.0E−02 | 3.7 | GBM | 2 | 153 | 1.3% | −14.9 | 8.6E−02 |
| Amplification | 8p23.1 | ZNF705A | 3.4E−05 | 4.0E−02 | 3.7 | KIRC | 3 | 483 | 0.6% | −16.5 | 9.9E−02 |
| Amplification | 8p23.1 | ZNF705A | 3.4E−05 | 4.0E−02 | 3.7 | CRC | 14 | 581 | 2.4% | 6.6 | 1.1E−01 |
| Amplification | 8p23.1 | ZNF705A | 3.4E−05 | 4.0E−02 | 3.7 | HNSC | 20 | 424 | 4.7% | 5.0 | 1.2E−01 |
| Amplification | 8p23.1 | ZNF705A | 3.4E−05 | 4.0E−02 | 3.7 | CESC | 2 | 191 | 1.0% | 6.4 | 1.7E−01 |
| Amplification | 8p23.1 | ZNF705A | 3.4E−05 | 4.0E−02 | 3.7 | LUAD | 25 | 482 | 5.2% | 4.7 | 3.0E−01 |
| Amplification | 8p23.1 | ZNF705A | 3.4E−05 | 4.0E−02 | 3.7 | OV | 46 | 292 | 15.8% | −2.9 | 3.2E−01 |
| Amplification | 8p23.1 | ZNF705A | 3.4E−05 | 4.0E−02 | 3.7 | UCEC | 9 | 506 | 1.8% | 6.4 | 3.9E−01 |
| Amplification | 8p23.1 | ZNF705A | 3.4E−05 | 4.0E−02 | 3.7 | LIHC | 4 | 194 | 2.1% | 11.3 | 4.7E−01 |
| Amplification | 8p23.1 | ZNF705A | 3.4E−05 | 4.0E−02 | 3.7 | BLCA | 15 | 218 | 6.9% | 2.6 | 5.0E−01 |
| Amplification | 8p23.1 | ZNF705A | 3.4E−05 | 4.0E−02 | 3.7 | LGG | 13 | 262 | 5.0% | 1.9 | 5.0E−01 |
| Amplification | 8p23.1 | ZNF705A | 3.4E−05 | 4.0E−02 | 3.7 | PRAD | 2 | 277 | 0.7% | −6.3 | 7.5E−01 |
| Amplification | 8p23.1 | ZNF705A | 3.4E−05 | 4.0E−02 | 3.7 | STAD | 9 | 272 | 3.3% | −0.5 | 9.6E−01 |
| Amplification | 8p23.1 | ZNF705A | 3.4E−05 | 4.0E−02 | 3.7 | KIRP | 0 | 171 | 0.0% | | |
| Amplification | 8p23.1 | ZNF705A | 3.4E−05 | 4.0E−02 | 3.7 | SKCM | 0 | 81 | 0.0% | | |
| Amplification | 8p23.1 | ZNF705A | 3.4E−05 | 4.0E−02 | 3.7 | THCA | 0 | 488 | 0.0% | | |
| Amplification | 8p11.23-p11.21 | ADAM2 | 1.7E−05 | 2.1E−02 | −1.7 | BRCA | 161 | 992 | 16.2% | −2.4 | 1.7E−03 |
| Amplification | 8p11.23-p11.21 | ADAM2 | 1.7E−05 | 2.1E−02 | −1.7 | CESC | 8 | 191 | 4.2% | −13.6 | 6.0E−02 |
| Amplification | 8p11.23-p11.21 | ADAM2 | 1.7E−05 | 2.1E−02 | −1.7 | LIHC | 4 | 194 | 2.1% | −15.5 | 9.0E−02 |
| Amplification | 8p11.23-p11.21 | ADAM2 | 1.7E−05 | 2.1E−02 | −1.7 | HNSC | 36 | 424 | 8.5% | −3.2 | 9.8E−02 |
| Amplification | 8p11.23-p11.21 | ADAM2 | 1.7E−05 | 2.1E−02 | −1.7 | KIRC | 2 | 483 | 0.4% | −19.1 | 1.2E−01 |
| Amplification | 8p11.23-p11.21 | ADAM2 | 1.7E−05 | 2.1E−02 | −1.7 | LUSC | 102 | 479 | 21.3% | −1.4 | 1.2E−01 |
| Amplification | 8p11.23-p11.21 | ADAM2 | 1.7E−05 | 2.1E−02 | −1.7 | CRC | 32 | 581 | 5.5% | −2.7 | 1.9E−01 |
| Amplification | 8p11.23-p11.21 | ADAM2 | 1.7E−05 | 2.1E−02 | −1.7 | PRAD | 5 | 277 | 1.8% | −6.3 | 3.2E−01 |
| Amplification | 8p11.23-p11.21 | ADAM2 | 1.7E−05 | 2.1E−02 | −1.7 | STAD | 7 | 272 | 2.6% | −1.5 | 6.3E−01 |
| Amplification | 8p11.23-p11.21 | ADAM2 | 1.7E−05 | 2.1E−02 | −1.7 | SKCM | 3 | 81 | 3.7% | −3.1 | 6.5E−01 |

TABLE 4-continued

| Class | Locus | Unbiased Peak Gene | PanCancer Uncorrect Peak Gene P | PanCancer Peak BH adj. P | PanCancer Beta | Cancer | Samples with Lesion | Samples Analyzed | Percent with Lesion | Cancer Beta | Cancer P |
|---|---|---|---|---|---|---|---|---|---|---|---|
| Amplification | 8p11.23-p11.21 | ADAM2 | 1.7E−05 | 2.1E−02 | −1.7 | LUAD | 42 | 482 | 8.7% | −0.7 | 6.6E−01 |
| Amplification | 8p11.23-p11.21 | ADAM2 | 1.7E−05 | 2.1E−02 | −1.7 | OV | 43 | 292 | 14.7% | −0.4 | 8.3E−01 |
| Amplification | 8p11.23-p11.21 | ADAM2 | 1.7E−05 | 2.1E−02 | −1.7 | LGG | 1 | 262 | 0.4% | −5.6 | 8.5E−01 |
| Amplification | 8p11.23-p11.21 | ADAM2 | 1.7E−05 | 2.1E−02 | −1.7 | BLCA | 30 | 218 | 13.8% | 0.2 | 9.3E−01 |
| Amplification | 8p11.23-p11.21 | ADAM2 | 1.7E−05 | 2.1E−02 | −1.7 | UCEC | 27 | 506 | 5.3% | 0.1 | 9.8E−01 |
| Amplification | 8p11.23-p11.21 | ADAM2 | 1.7E−05 | 2.1E−02 | −1.7 | GBM | 0 | 153 | 0.0% | | |
| Amplification | 8p11.23-p11.21 | ADAM2 | 1.7E−05 | 2.1E−02 | −1.7 | KIRP | 0 | 171 | 0.0% | | |
| Amplification | 8p11.23-p11.21 | ADAM2 | 1.7E−05 | 2.1E−02 | −1.7 | THCA | 0 | 488 | 0.0% | | |
| Amplification | 9p24.2-p23 | CD274 | 1.5E−06 | 3.5E−03 | 2.3 | HNSC | 35 | 424 | 8.3% | 4.0 | 2.5E−05 |
| Amplification | 9p24.2-p23 | CD274 | 1.5E−06 | 3.5E−03 | 2.3 | CESC | 15 | 191 | 7.9% | 5.7 | 6.4E−03 |
| Amplification | 9p24.2-p23 | CD274 | 1.5E−06 | 3.5E−03 | 2.3 | LUSC | 55 | 479 | 11.5% | 3.8 | 9.6E−03 |
| Amplification | 9p24.2-p23 | CD274 | 1.5E−06 | 3.5E−03 | 2.3 | CRC | 15 | 581 | 2.6% | 12.8 | 2.1E−02 |
| Amplification | 9p24.2-p23 | CD274 | 1.5E−06 | 3.5E−03 | 2.3 | STAD | 16 | 272 | 5.9% | 3.3 | 3.9E−02 |
| Amplification | 9p24.2-p23 | CD274 | 1.5E−06 | 3.5E−03 | 2.3 | LIHC | 7 | 194 | 3.6% | 3.2 | 6.7E−02 |
| Amplification | 9p24.2-p23 | CD274 | 1.5E−06 | 3.5E−03 | 2.3 | KIRP | 1 | 171 | 0.6% | −86.1 | 1.1E−01 |
| Amplification | 9p24.2-p23 | CD274 | 1.5E−06 | 3.5E−03 | 2.3 | SKCM | 6 | 81 | 7.4% | −8.2 | 1.7E−01 |
| Amplification | 9p24.2-p23 | CD274 | 1.5E−06 | 3.5E−03 | 2.3 | KIRC | 6 | 483 | 1.2% | 2.4 | 2.0E−01 |
| Amplification | 9p24.2-p23 | CD274 | 1.5E−06 | 3.5E−03 | 2.3 | OV | 38 | 292 | 13.0% | 4.3 | 2.5E−01 |
| Amplification | 9p24.2-p23 | CD274 | 1.5E−06 | 3.5E−03 | 2.3 | BLCA | 25 | 218 | 11.5% | 2.0 | 3.5E−01 |
| Amplification | 9p24.2-p23 | CD274 | 1.5E−06 | 3.5E−03 | 2.3 | LGG | 1 | 262 | 0.4% | −35.6 | 4.9E−01 |
| Amplification | 9p24.2-p23 | CD274 | 1.5E−06 | 3.5E−03 | 2.3 | UCEC | 20 | 506 | 4.0% | −1.5 | 4.9E−01 |
| Amplification | 9p24.2-p23 | CD274 | 1.5E−06 | 3.5E−03 | 2.3 | GBM | 3 | 153 | 2.0% | 23.6 | 5.0E−01 |
| Amplification | 9p24.2-p23 | CD274 | 1.5E−06 | 3.5E−03 | 2.3 | LUAD | 30 | 482 | 6.2% | −0.4 | 8.8E−01 |
| Amplification | 9p24.2-p23 | CD274 | 1.5E−06 | 3.5E−03 | 2.3 | BRCA | 60 | 992 | 6.0% | 0.0 | 1.0E+00 |
| Amplification | 9p24.2-p23 | CD274 | 1.5E−06 | 3.5E−03 | 2.3 | PRAD | 0 | 277 | 0.0% | | |
| Amplification | 9p24.2-p23 | CD274 | 1.5E−06 | 3.5E−03 | 2.3 | THCA | 0 | 488 | 0.0% | | |
| Amplification | 10p15.3 | DIP2C | 4.1E−05 | 4.4E−02 | 3.6 | STAD | 10 | 272 | 3.7% | 14.3 | 3.6E−02 |
| Amplification | 10p15.3 | DIP2C | 4.1E−05 | 4.4E−02 | 3.6 | CESC | 4 | 191 | 2.1% | −24.6 | 3.6E−02 |
| Amplification | 10p15.3 | DIP2C | 4.1E−05 | 4.4E−02 | 3.6 | BLCA | 34 | 218 | 15.6% | 5.0 | 6.6E−02 |
| Amplification | 10p15.3 | DIP2C | 4.1E−05 | 4.4E−02 | 3.6 | BRCA | 111 | 992 | 11.2% | 3.0 | 7.1E−02 |
| Amplification | 10p15.3 | DIP2C | 4.1E−05 | 4.4E−02 | 3.6 | CRC | 12 | 581 | 2.1% | 12.0 | 8.6E−02 |
| Amplification | 10p15.3 | DIP2C | 4.1E−05 | 4.4E−02 | 3.6 | HNSC | 14 | 424 | 3.3% | −10.2 | 8.7E−02 |
| Amplification | 10p15.3 | DIP2C | 4.1E−05 | 4.4E−02 | 3.6 | KIRP | 1 | 171 | 0.6% | −90.9 | 1.1E−01 |
| Amplification | 10p15.3 | DIP2C | 4.1E−05 | 4.4E−02 | 3.6 | PRAD | 4 | 277 | 1.4% | 20.4 | 1.2E−01 |
| Amplification | 10p15.3 | DIP2C | 4.1E−05 | 4.4E−02 | 3.6 | LUAD | 25 | 482 | 5.2% | 8.5 | 1.3E−01 |
| Amplification | 10p15.3 | DIP2C | 4.1E−05 | 4.4E−02 | 3.6 | KIRC | 2 | 483 | 0.4% | 34.0 | 2.1E−01 |
| Amplification | 10p15.3 | DIP2C | 4.1E−05 | 4.4E−02 | 3.6 | GBM | 6 | 153 | 3.9% | −13.3 | 2.5E−01 |
| Amplification | 10p15.3 | DIP2C | 4.1E−05 | 4.4E−02 | 3.6 | UCEC | 26 | 506 | 5.1% | 3.2 | 4.1E−01 |
| Amplification | 10p15.3 | DIP2C | 4.1E−05 | 4.4E−02 | 3.6 | OV | 55 | 292 | 18.8% | 1.5 | 5.8E−01 |
| Amplification | 10p15.3 | DIP2C | 4.1E−05 | 4.4E−02 | 3.6 | LIHC | 9 | 194 | 4.6% | 5.0 | 5.9E−01 |
| Amplification | 10p15.3 | DIP2C | 4.1E−05 | 4.4E−02 | 3.6 | LGG | 9 | 262 | 3.4% | −3.0 | 6.5E−01 |
| Amplification | 10p15.3 | DIP2C | 4.1E−05 | 4.4E−02 | 3.6 | SKCM | 4 | 81 | 4.9% | −1.8 | 9.0E−01 |
| Amplification | 10p15.3 | DIP2C | 4.1E−05 | 4.4E−02 | 3.6 | LUSC | 24 | 479 | 5.0% | −0.2 | 9.5E−01 |
| Amplification | 10p15.3 | DIP2C | 4.1E−05 | 4.4E−02 | 3.6 | THCA | 0 | 488 | 0.0% | | |
| Amplification | 10p15.1-p13 | SFTA1P | 3.3E−06 | 6.4E−03 | 4.0 | BRCA | 95 | 992 | 9.6% | 4.6 | 3.0E−03 |
| Amplification | 10p15.1-p13 | SFTA1P | 3.3E−06 | 6.4E−03 | 4.0 | BLCA | 30 | 218 | 13.8% | 4.1 | 3.8E−02 |

TABLE 4-continued

| Class | Locus | Unbiased Peak Gene | PanCancer Uncorrect Peak Gene P | PanCancer Peak BH adj. P | PanCancer Beta | Cancer | Samples with Lesion | Samples Analyzed | Percent with Lesion | Cancer Beta | Cancer P |
|---|---|---|---|---|---|---|---|---|---|---|---|
| Amplification | 10p15.1-p13 | SFTA1P | 3.3E−06 | 6.4E−03 | 4.0 | CESC | 5 | 191 | 2.6% | −26.9 | 3.9E−02 |
| Amplification | 10p15.1-p13 | SFTA1P | 3.3E−06 | 6.4E−03 | 4.0 | HNSC | 9 | 424 | 2.1% | −10.2 | 1.4E−01 |
| Amplification | 10p15.1-p13 | SFTA1P | 3.3E−06 | 6.4E−03 | 4.0 | LUAD | 17 | 482 | 3.5% | 8.8 | 1.7E−01 |
| Amplification | 10p15.1-p13 | SFTA1P | 3.3E−06 | 6.4E−03 | 4.0 | PRAD | 3 | 277 | 1.1% | 17.6 | 2.3E−01 |
| Amplification | 10p15.1-p13 | SFTA1P | 3.3E−06 | 6.4E−03 | 4.0 | LIHC | 3 | 194 | 1.5% | −20.4 | 2.4E−01 |
| Amplification | 10p15.1-p13 | SFTA1P | 3.3E−06 | 6.4E−03 | 4.0 | OV | 38 | 292 | 13.0% | 2.9 | 3.1E−01 |
| Amplification | 10p15.1-p13 | SFTA1P | 3.3E−06 | 6.4E−03 | 4.0 | STAD | 7 | 272 | 2.6% | 5.4 | 3.5E−01 |
| Amplification | 10p15.1-p13 | SFTA1P | 3.3E−06 | 6.4E−03 | 4.0 | LGG | 9 | 262 | 3.4% | −4.5 | 4.6E−01 |
| Amplification | 10p15.1-p13 | SFTA1P | 3.3E−06 | 6.4E−03 | 4.0 | GBM | 5 | 153 | 3.3% | −10.4 | 4.9E−01 |
| Amplification | 10p15.1-p13 | SFTA1P | 3.3E−06 | 6.4E−03 | 4.0 | SKCM | 1 | 81 | 1.2% | −25.1 | 5.5E−01 |
| Amplification | 10p15.1-p13 | SFTA1P | 3.3E−06 | 6.4E−03 | 4.0 | KIRC | 3 | 483 | 0.6% | −7.4 | 6.2E−01 |
| Amplification | 10p15.1-p13 | SFTA1P | 3.3E−06 | 6.4E−03 | 4.0 | UCEC | 14 | 506 | 2.8% | 2.2 | 7.1E−01 |
| Amplification | 10p15.1-p13 | SFTA1P | 3.3E−06 | 6.4E−03 | 4.0 | CRC | 9 | 581 | 1.5% | −2.4 | 7.8E−01 |
| Amplification | 10p15.1-p13 | SFTA1P | 3.3E−06 | 6.4E−03 | 4.0 | LUSC | 17 | 479 | 3.5% | −0.4 | 9.4E−01 |
| Amplification | 10p15.1-p13 | SFTA1P | 3.3E−06 | 6.4E−03 | 4.0 | KIRP | 0 | 171 | 0.0% | | |
| Amplification | 10p15.1-p13 | SFTA1P | 3.3E−06 | 6.4E−03 | 4.0 | THCA | 0 | 488 | 0.0% | | |
| Amplification | 11p14.1 | KCNA4 | 5.6E−05 | 5.5E−02 | 4.3 | OV | 35 | 292 | 12.0% | 6.6 | 4.8E−03 |
| Amplification | 11p14.1 | KCNA4 | 5.6E−05 | 5.5E−02 | 4.3 | LUSC | 26 | 479 | 5.4% | 6.5 | 3.7E−02 |
| Amplification | 11p14.1 | KCNA4 | 5.6E−05 | 5.5E−02 | 4.3 | CESC | 4 | 191 | 2.1% | −32.0 | 5.7E−02 |
| Amplification | 11p14.1 | KCNA4 | 5.6E−05 | 5.5E−02 | 4.3 | PRAD | 1 | 277 | 0.4% | −42.3 | 1.3E−01 |
| Amplification | 11p14.1 | KCNA4 | 5.6E−05 | 5.5E−02 | 4.3 | BRCA | 54 | 992 | 5.4% | 3.2 | 1.7E−01 |
| Amplification | 11p14.1 | KCNA4 | 5.6E−05 | 5.5E−02 | 4.3 | LUAD | 20 | 482 | 4.1% | 5.7 | 1.7E−01 |
| Amplification | 11p14.1 | KCNA4 | 5.6E−05 | 5.5E−02 | 4.3 | KIRC | 1 | 483 | 0.2% | 61.4 | 2.1E−01 |
| Amplification | 11p14.1 | KCNA4 | 5.6E−05 | 5.5E−02 | 4.3 | STAD | 7 | 272 | 2.6% | 6.4 | 2.4E−01 |
| Amplification | 11p14.1 | KCNA4 | 5.6E−05 | 5.5E−02 | 4.3 | HNSC | 11 | 424 | 2.6% | −6.2 | 3.9E−01 |
| Amplification | 11p14.1 | KCNA4 | 5.6E−05 | 5.5E−02 | 4.3 | UCEC | 9 | 506 | 1.8% | −2.1 | 4.8E−01 |
| Amplification | 11p14.1 | KCNA4 | 5.6E−05 | 5.5E−02 | 4.3 | LGG | 1 | 262 | 0.4% | 21.2 | 4.8E−01 |
| Amplification | 11p14.1 | KCNA4 | 5.6E−05 | 5.5E−02 | 4.3 | BLCA | 4 | 218 | 1.8% | −4.1 | 6.9E−01 |
| Amplification | 11p14.1 | KCNA4 | 5.6E−05 | 5.5E−02 | 4.3 | CRC | 2 | 581 | 0.3% | −3.9 | 7.9E−01 |
| Amplification | 11p14.1 | KCNA4 | 5.6E−05 | 5.5E−02 | 4.3 | SKCM | 2 | 81 | 2.5% | 4.3 | 8.6E−01 |
| Amplification | 11p14.1 | KCNA4 | 5.6E−05 | 5.5E−02 | 4.3 | GBM | 1 | 153 | 0.7% | −3.1 | 9.1E−01 |
| Amplification | 11p14.1 | KCNA4 | 5.6E−05 | 5.5E−02 | 4.3 | KIRP | 0 | 171 | 0.0% | | |
| Amplification | 11p14.1 | KCNA4 | 5.6E−05 | 5.5E−02 | 4.3 | LIHC | 0 | 194 | 0.0% | | |
| Amplification | 11p14.1 | KCNA4 | 5.6E−05 | 5.5E−02 | 4.3 | THCA | 0 | 488 | 0.0% | | |
| Amplification | 12p13.32-p13.2 | SCNN1A | 1.1E−07 | 0.0E+00 | 4.1 | LUSC | 53 | 479 | 11.1% | 5.1 | 2.3E−02 |
| Amplification | 12p13.32-p13.2 | SCNN1A | 1.1E−07 | 0.0E+00 | 4.1 | BRCA | 76 | 992 | 7.7% | 3.8 | 2.3E−02 |
| Amplification | 12p13.32-p13.2 | SCNN1A | 1.1E−07 | 0.0E+00 | 4.1 | LIHC | 8 | 194 | 4.1% | 18.0 | 4.1E−02 |
| Amplification | 12p13.32-p13.2 | SCNN1A | 1.1E−07 | 0.0E+00 | 4.1 | CESC | 5 | 191 | 2.6% | 17.1 | 6.5E−02 |
| Amplification | 12p13.32-p13.2 | SCNN1A | 1.1E−07 | 0.0E+00 | 4.1 | CRC | 22 | 581 | 3.8% | 4.0 | 9.5E−02 |
| Amplification | 12p13.32-p13.2 | SCNN1A | 1.1E−07 | 0.0E+00 | 4.1 | HNSC | 23 | 424 | 5.4% | 4.7 | 1.3E−01 |
| Amplification | 12p13.32-p13.2 | SCNN1A | 1.1E−07 | 0.0E+00 | 4.1 | GBM | 3 | 153 | 2.0% | −12.8 | 1.3E−01 |
| Amplification | 12p13.32-p13.2 | SCNN1A | 1.1E−07 | 0.0E+00 | 4.1 | KIRC | 4 | 483 | 0.8% | −14.6 | 1.4E−01 |
| Amplification | 12p13.32-p13.2 | SCNN1A | 1.1E−07 | 0.0E+00 | 4.1 | BLCA | 17 | 218 | 7.8% | 4.8 | 1.8E−01 |
| Amplification | 12p13.32-p13.2 | SCNN1A | 1.1E−07 | 0.0E+00 | 4.1 | SKCM | 1 | 81 | 1.2% | −32.4 | 2.7E−01 |
| Amplification | 12p13.32-p13.2 | SCNN1A | 1.1E−07 | 0.0E+00 | 4.1 | STAD | 15 | 272 | 5.5% | 7.1 | 2.8E−01 |
| Amplification | 12p13.32-p13.2 | SCNN1A | 1.1E−07 | 0.0E+00 | 4.1 | LUAD | 29 | 482 | 6.0% | 2.2 | 5.7E−01 |

TABLE 4-continued

| Class | Locus | Unbiased Peak Gene | PanCancer Uncorrect Peak Gene P | PanCancer Peak BH adj. P | PanCancer Beta | Cancer | Samples with Lesion | Samples Analyzed | Percent with Lesion | Cancer Beta | Cancer P |
|---|---|---|---|---|---|---|---|---|---|---|---|
| Amplification | 12p13.32-p13.2 | SCNN1A | 1.1E−07 | 0.0E+00 | 4.1 | LGG | 15 | 262 | 5.7% | 1.3 | 6.4E−01 |
| Amplification | 12p13.32-p13.2 | SCNN1A | 1.1E−07 | 0.0E+00 | 4.1 | UCEC | 24 | 506 | 4.7% | 0.5 | 8.8E−01 |
| Amplification | 12p13.32-p13.2 | SCNN1A | 1.1E−07 | 0.0E+00 | 4.1 | OV | 55 | 292 | 18.8% | 0.2 | 9.5E−01 |
| Amplification | 12p13.32-p13.2 | SCNN1A | 1.1E−07 | 0.0E+00 | 4.1 | PRAD | 3 | 277 | 1.1% | 0.1 | 1.0E+00 |
| Amplification | 12p13.32-p13.2 | SCNN1A | 1.1E−07 | 0.0E+00 | 4.1 | KIRP | 0 | 171 | 0.0% | | |
| Amplification | 12p13.32-p13.2 | SCNN1A | 1.1E−07 | 0.0E+00 | 4.1 | THCA | 0 | 488 | 0.0% | | |
| Amplification | 17p13.1 | ALOX15B | 1.2E−05 | 1.9E−02 | −8.0 | OV | 32 | 292 | 11.0% | −9.5 | 4.6E−03 |
| Amplification | 17p13.1 | ALOX15B | 1.2E−05 | 1.9E−02 | −8.0 | BRCA | 14 | 992 | 1.4% | −12.7 | 1.5E−02 |
| Amplification | 17p13.1 | ALOX15B | 1.2E−05 | 1.9E−02 | −8.0 | UCEC | 9 | 506 | 1.8% | −9.2 | 6.7E−02 |
| Amplification | 17p13.1 | ALOX15B | 1.2E−05 | 1.9E−02 | −8.0 | LUAD | 4 | 482 | 0.8% | −21.8 | 7.0E−02 |
| Amplification | 17p13.1 | ALOX15B | 1.2E−05 | 1.9E−02 | −8.0 | GBM | 1 | 153 | 0.7% | 265.7 | 7.4E−02 |
| Amplification | 17p13.1 | ALOX15B | 1.2E−05 | 1.9E−02 | −8.0 | PRAD | 1 | 277 | 0.4% | 41.1 | 1.3E−01 |
| Amplification | 17p13.1 | ALOX15B | 1.2E−05 | 1.9E−02 | −8.0 | KIRC | 1 | 483 | 0.2% | −51.4 | 1.6E−01 |
| Amplification | 17p13.1 | ALOX15B | 1.2E−05 | 1.9E−02 | −8.0 | HNSC | 2 | 424 | 0.5% | −27.2 | 1.7E−01 |
| Amplification | 17p13.1 | ALOX15B | 1.2E−05 | 1.9E−02 | −8.0 | CRC | 4 | 581 | 0.7% | 15.7 | 4.2E−01 |
| Amplification | 17p13.1 | ALOX15B | 1.2E−05 | 1.9E−02 | −8.0 | LGG | 2 | 262 | 0.8% | 19.4 | 4.2E−01 |
| Amplification | 17p13.1 | ALOX15B | 1.2E−05 | 1.9E−02 | −8.0 | BLCA | 5 | 218 | 2.3% | −8.8 | 5.7E−01 |
| Amplification | 17p13.1 | ALOX15B | 1.2E−05 | 1.9E−02 | −8.0 | STAD | 2 | 272 | 0.7% | 0.9 | 9.7E−01 |
| Amplification | 17p13.1 | ALOX15B | 1.2E−05 | 1.9E−02 | −8.0 | LUSC | 4 | 479 | 0.8% | −0.1 | 9.9E−01 |
| Amplification | 17p13.1 | ALOX15B | 1.2E−05 | 1.9E−02 | −8.0 | CESC | 0 | 191 | 0.0% | | |
| Amplification | 17p13.1 | ALOX15B | 1.2E−05 | 1.9E−02 | −8.0 | KIRP | 0 | 171 | 0.0% | | |
| Amplification | 17p13.1 | ALOX15B | 1.2E−05 | 1.9E−02 | −8.0 | LIHC | 0 | 194 | 0.0% | | |
| Amplification | 17p13.1 | ALOX15B | 1.2E−05 | 1.9E−02 | −8.0 | SKCM | 0 | 81 | 0.0% | | |
| Amplification | 17p13.1 | ALOX15B | 1.2E−05 | 1.9E−02 | −8.0 | THCA | 0 | 488 | 0.0% | | |
| Amplification | 22q11.1-q11.21 | CECR3 | 1.9E−06 | 3.5E−03 | −4.1 | LUAD | 39 | 482 | 8.1% | −9.3 | 7.5E−03 |
| Amplification | 22q11.1-q11.21 | CECR3 | 1.9E−06 | 3.5E−03 | −4.1 | BRCA | 63 | 992 | 6.4% | −4.8 | 2.3E−02 |
| Amplification | 22q11.1-q11.21 | CECR3 | 1.9E−06 | 3.5E−03 | −4.1 | LUSC | 47 | 479 | 9.8% | −6.3 | 2.6E−02 |
| Amplification | 22q11.1-q11.21 | CECR3 | 1.9E−06 | 3.5E−03 | −4.1 | SKCM | 8 | 81 | 9.9% | −9.3 | 6.0E−02 |
| Amplification | 22q11.1-q11.21 | CECR3 | 1.9E−06 | 3.5E−03 | −4.1 | PRAD | 2 | 277 | 0.7% | −14.8 | 1.9E−01 |
| Amplification | 22q11.1-q11.21 | CECR3 | 1.9E−06 | 3.5E−03 | −4.1 | LGG | 4 | 262 | 1.5% | −14.1 | 2.0E−01 |
| Amplification | 22q11.1-q11.21 | CECR3 | 1.9E−06 | 3.5E−03 | −4.1 | BLCA | 24 | 218 | 11.0% | −4.1 | 2.1E−01 |
| Amplification | 22q11.1-q11.21 | CECR3 | 1.9E−06 | 3.5E−03 | −4.1 | LIHC | 4 | 194 | 2.1% | 13.4 | 2.3E−01 |
| Amplification | 22q11.1-q11.21 | CECR3 | 1.9E−06 | 3.5E−03 | −4.1 | CRC | 15 | 581 | 2.6% | −6.1 | 2.5E−01 |
| Amplification | 22q11.1-q11.21 | CECR3 | 1.9E−06 | 3.5E−03 | −4.1 | THCA | 5 | 488 | 1.0% | −6.1 | 2.6E−01 |
| Amplification | 22q11.1-q11.21 | CECR3 | 1.9E−06 | 3.5E−03 | −4.1 | KIRP | 1 | 171 | 0.6% | −32.5 | 2.7E−01 |
| Amplification | 22q11.1-q11.21 | CECR3 | 1.9E−06 | 3.5E−03 | −4.1 | CESC | 4 | 191 | 2.1% | 11.5 | 3.5E−01 |
| Amplification | 22q11.1-q11.21 | CECR3 | 1.9E−06 | 3.5E−03 | −4.1 | HNSC | 24 | 424 | 5.7% | −2.0 | 5.6E−01 |
| Amplification | 22q11.1-q11.21 | CECR3 | 1.9E−06 | 3.5E−03 | −4.1 | UCEC | 39 | 506 | 7.7% | −0.9 | 7.4E−01 |
| Amplification | 22q11.1-q11.21 | CECR3 | 1.9E−06 | 3.5E−03 | −4.1 | STAD | 6 | 272 | 2.2% | −1.0 | 8.4E−01 |
| Amplification | 22q11.1-q11.21 | CECR3 | 1.9E−06 | 3.5E−03 | −4.1 | OV | 52 | 292 | 17.8% | −0.3 | 9.3E−01 |
| Amplification | 22q11.1-q11.21 | CECR3 | 1.9E−06 | 3.5E−03 | −4.1 | GBM | 2 | 153 | 1.3% | 0.2 | 9.9E−01 |
| Amplification | 22q11.1-q11.21 | CECR3 | 1.9E−06 | 3.5E−03 | −4.1 | KIRC | 0 | 483 | 0.0% | | |
| Deletion | 3p22.3-p21.1 | ENTPD3 | 3.0E−05 | 3.8E−02 | 5.6 | BRCA | 101 | 992 | 10.2% | 4.8 | 1.0E−01 |
| Deletion | 3p22.3-p21.1 | ENTPD3 | 3.0E−05 | 3.8E−02 | 5.6 | LUSC | 28 | 479 | 5.8% | 7.3 | 1.2E−01 |
| Deletion | 3p22.3-p21.1 | ENTPD3 | 3.0E−05 | 3.8E−02 | 5.6 | CRC | 17 | 581 | 2.9% | 11.4 | 1.2E−01 |
| Deletion | 3p22.3-p21.1 | ENTPD3 | 3.0E−05 | 3.8E−02 | 5.6 | SKCM | 2 | 81 | 2.5% | −26.7 | 2.2E−01 |

TABLE 4-continued

| Class | Locus | Unbiased Peak Gene | PanCancer Uncorrect Peak Gene P | PanCancer Peak BH adj. P | PanCancer Beta | Cancer | Samples with Lesion | Samples Analyzed | Percent with Lesion | Cancer Beta | Cancer P |
|---|---|---|---|---|---|---|---|---|---|---|---|
| Deletion | 3p22.3-p21.1 | ENTPD3 | 3.0E-05 | 3.8E-02 | 5.6 | OV | 39 | 292 | 13.4% | 4.7 | 2.9E-01 |
| Deletion | 3p22.3-p21.1 | ENTPD3 | 3.0E-05 | 3.8E-02 | 5.6 | STAD | 24 | 272 | 8.8% | 6.5 | 3.1E-01 |
| Deletion | 3p22.3-p21.1 | ENTPD3 | 3.0E-05 | 3.8E-02 | 5.6 | HNSC | 13 | 424 | 3.1% | 6.1 | 3.8E-01 |
| Deletion | 3p22.3-p21.1 | ENTPD3 | 3.0E-05 | 3.8E-02 | 5.6 | BLCA | 17 | 218 | 7.8% | 5.5 | 4.0E-01 |
| Deletion | 3p22.3-p21.1 | ENTPD3 | 3.0E-05 | 3.8E-02 | 5.6 | UCEC | 15 | 506 | 3.0% | 5.1 | 5.0E-01 |
| Deletion | 3p22.3-p21.1 | ENTPD3 | 3.0E-05 | 3.8E-02 | 5.6 | CESC | 5 | 191 | 2.6% | 5.0 | 7.0E-01 |
| Deletion | 3p22.3-p21.1 | ENTPD3 | 3.0E-05 | 3.8E-02 | 5.6 | KIRP | 2 | 171 | 1.2% | -6.0 | 7.8E-01 |
| Deletion | 3p22.3-p21.1 | ENTPD3 | 3.0E-05 | 3.8E-02 | 5.6 | LUAD | 24 | 482 | 5.0% | 1.5 | 8.2E-01 |
| Deletion | 3p22.3-p21.1 | ENTPD3 | 3.0E-05 | 3.8E-02 | 5.6 | PRAD | 1 | 277 | 0.4% | 5.0 | 8.6E-01 |
| Deletion | 3p22.3-p21.1 | ENTPD3 | 3.0E-05 | 3.8E-02 | 5.6 | GBM | 3 | 153 | 2.0% | 2.7 | 8.9E-01 |
| Deletion | 3p22.3-p21.1 | ENTPD3 | 3.0E-05 | 3.8E-02 | 5.6 | KIRC | 72 | 483 | 14.9% | -0.5 | 9.0E-01 |
| Deletion | 3p22.3-p21.1 | ENTPD3 | 3.0E-05 | 3.8E-02 | 5.6 | LGG | 5 | 262 | 1.9% | -1.2 | 9.3E-01 |
| Deletion | 3p22.3-p21.1 | ENTPD3 | 3.0E-05 | 3.8E-02 | 5.6 | LIHC | 0 | 194 | 0.0% | | |
| Deletion | 3p22.3-p21.1 | ENTPD3 | 3.0E-05 | 3.8E-02 | 5.6 | THCA | 0 | 488 | 0.0% | | |

TABLE 5

| | Thyroid | Glioblastoma | Ovarian | Glioma | Prostate | Breast | Kidney Papillary | Kidney Clear | Lung Adeno. | Lung Squam. |
|---|---|---|---|---|---|---|---|---|---|---|
| B2M mutation rate high | -1 | | -1 | -1 | -1 | | | | -1 | |
| ERVH-CYT association | | | 1 | | | | -1 | | -1 | -1 |
| CT antigen-CYT association | | | | | | | | | | -1 |
| Tumor-Normal CYT difference | | 1 | 1 | | | | | 1 | -1 | -1 |
| ALOX amp - CYT association | | | 1 | | | 1 | | | | |
| ERVK-CYT association | | | | | | 1 | | 1 | | |
| ERVE-CYT association | | | | | | 1 | | 1 | | |
| Neoantigen depletion | | | | | | | | 1 | | |
| B2M-CYT association | | | | | | 1 | | | | |
| Viral-CYT association | | | | | | | | | | |
| PDL1 rate high | | | 1 | | | 1 | | | 1 | 1 |
| CASP8-CYT association | | | | | | | | | | 1 |
| PDL1 amp - CYT association | | | | | | | | | | 1 |
| TSERV over expression | | | | | | | | 1 | 1 | 1 |
| High CYT | | -1 | | -1 | -1 | | | 1 | 1 | 1 |
| High level Neo-antigens | -1 | -1 | -1 | -1 | -1 | | | | 1 | 1 |
| CT antigen high | | | | | | 1 | | | 1 | 1 |
| Neoantigen-CYT association | -1 | | | | | 1 | | | 1 | |
| HLA-CYT association | | | | | | | | | | |
| CASP8 rate high | | | | | | | | | | |
| Viral Involvement | | | | | | | | | | |
| HLA rate high | -1 | -1 | | -1 | | | | | | |

| | Liver | Bladder | Melanoma | Cervical | Head and Neck | Stomach | Uterine | Colorectal |
|---|---|---|---|---|---|---|---|---|
| B2M mutation rate high | | -1 | | | -1 | 1 | | |
| ERVH-CYT association | | -1 | | | -1 | | 1 | 1 |
| CT antigen-CYT association | | | | | -1 | -1 | | |
| Tumor-Normal CYT difference | | | 1 | 1 | 1 | | | -1 |
| ALOX amp - CYT association | | | | | | | | |
| ERVK-CYT association | | | 1 | | | | | |
| ERVE-CYT association | | | | | | | | |
| Neoantigen depletion | | | | | | | | 1 |
| B2M-CYT association | | | | | | 1 | 1 | 1 |
| Viral-CYT association | 1 | | | | | 1 | 1 | |
| PDL1 rate high | | 1 | 1 | 1 | 1 | | | |

TABLE 5-continued

| | C1 | C2 | C3 | C4 | C5 | C6 | C7 | C8 |
|---|---|---|---|---|---|---|---|---|
| CASP8-CYT association | | | | 1 | 1 | 1 | | 1 |
| PDL1 amp - CYT association | | | | 1 | 1 | 1 | | 1 |
| TSERV over expression | | 1 | | 1 | 1 | 1 | 1 | 1 |
| High CYT | | | | 1 | 1 | 1 | | |
| High level Neo-antigens | 1 | 1 | 1 | 1 | | 1 | 1 | |
| CT antigen high | 1 | 1 | 1 | 1 | 1 | | 1 | 1 |
| Neoantigen-CYT association | | 1 | | 1 | 1 | 1 | 1 | |
| HLA-CYT association | | | | 1 | 1 | 1 | 1 | 1 |
| CASP8 rate high | | | | 1 | 1 | 1 | 1 | 1 |
| Viral Involvement | 1 | 1 | | 1 | 1 | 1 | 1 | 1 |
| HLA rate high | | 1 | | 1 | 1 | 1 | 1 | 1 |

1 = positive correlation
−1 = negative correction

REFERENCES

Almeida, L. G., Sakabe, N. J., deOliveira, A. R., Silva, M. C., Mundstein, A. S., Cohen, T., Chen, Y. T., Chua, R., Gurung, S., Gnjatic, S., et al. (2009). CTdatabase: a knowledge-base of high-throughput and curated data on cancer-testis antigens. Nucleic acids research 37, D816-819.

Barbie, D. A., Tamayo, P., Boehm, J. S., Kim, S. Y., Moody, S. E., Dunn, I. F., Schinzel, A. C., Sandy, P., Meylan, E., and Scholl, C. (2009). Systematic RNA interference reveals that oncogenic KRAS-driven cancers require TBK1. Nature 462, 108-112.

Barretina, J., Caponigro, G., Stransky, N., Venkatesan, K., Margolin, A. A., Kim, S., Wilson, C. J., Lehar, J., Kryukov, G. V., Sonkin, D., et al. (2012). The Cancer Cell Line Encyclopedia enables predictive modelling of anticancer drug sensitivity. Nature 483, 603-607.

Bindea, G., Mlecnik, B., Tosolini, M., Kirilovsky, A., Waldner, M., Obenauf, A. C., Angell, H., Fredriksen, T., Lafontaine, L., Berger, A., et al. (2013). Spatiotemporal dynamics of intratumoral immune cells reveal the immune landscape in human cancer. Immunity 39, 782-795.

Benson, G. (1999). Tandem repeats finder: a program to analyze DNA sequences. Nucleic acids research 27, 573-580.

Bishop, K. N., Holmes, R. K., Sheehy, A. M., and Malim, M. H. (2004). APOBEC-mediated editing of viral RNA. Science 305, 645.

Boyle, L. H., Hermann, C., Boname, J. M., Porter, K. M., Patel, P. A., Burr, M. L., Duncan, L. M., Harbour, M. E., Rhodes, D. A., and Skjodt, K. (2013). Tapasin-related protein TAPBPR is an additional component of the MHC class I presentation pathway. Proceedings of the National Academy of Sciences 110, 3465-3470.

Boller, K., Janssen, O., Schuldes, H., Tonjes, R. R., and Kurth, R. (1997). Characterization of the antibody response specific for the human endogenous retrovirus HTDV/HERV-K. J Virol 71, 4581-4588.

Broad Institute TCGA Genome Data Analysis Center (2014). Firehose. In Clinical Data (Broad Institute of MIT and Harvard).

Brown, S. D., Warren, R. L., Gibb, E. A., Martin, S. D., Spinelli, J. J., Nelson, B. H., and Holt, R. A. (2014). Neo-antigens predicted by tumor genome meta-analysis correlate with increased patient survival. Genome research 24, 743-750.

Cancer Genome Atlas Research Network (2014). Comprehensive molecular characterization of gastric adenocarcinoma. Nature 513, 202-209.

Chang, C. C., Campoli, M., Restifo, N. P., Wang, X., and Ferrone, S. (2005). Immune selection of hot-spot beta 2-microglobulin gene mutations, HLA-A2 allospecificity loss, and antigen-processing machinery component down-regulation in melanoma cells derived from recurrent metastases following immunotherapy. Journal of immunology 174, 1462-1471.

Chen, L., and Flies, D. B. (2013). Molecular mechanisms of T cell co-stimulation and co-inhibition. Nature reviews Immunology 13, 227-242.

Cibulskis, K., Lawrence, M. S., Carter, S. L., Sivachenko, A., Jaffe, D., Sougnez, C., Gabriel, S., Meyerson, M., Lander, E. S., and Getz, G. (2013). Sensitive detection of somatic point mutations in impure and heterogeneous cancer samples. Nature biotechnology 31, 213-219.

Cleveland, W. S. (1981). LOWESS: A program for smoothing scatterplots by robust locally weighted regression. The American Statistician 35, 54.

Doody, G. M., Stephenson, S., McManamy, C., and Tooze, R. M. (2007). PRDM1/BLIMP-1 Modulates IFN-Dependent Control of the MHC Class I Antigen-Processing and Peptide-Loading Pathway. The Journal of Immunology 179, 7614-7623.

Eden, E., Lipson, D., Yogev, S., and Yakhini, Z. (2007). Discovering motifs in ranked lists of DNA sequences. PLoS computational biology 3, e39.

Eden, E., Navon, R., Steinfeld, I., Lipson, D., and Yakhini, Z. (2009). GOrilla: a tool for discovery and visualization of enriched GO terms in ranked gene lists. BMC bioinformatics 10, 48.

Fan, S., Ma, Y. X., Gao, M., Yuan, R. Q., Meng, Q., Goldberg, I. D., and Rosen, E. M. (2001). The multisubstrate adapter Gab 1 regulates hepatocyte growth factor (scatter factor)-c-Met signaling for cell survival and DNA repair. Molecular and cellular biology 21, 4968-4984.

Fantom Consortium, Pmi, R., Clst, Forrest, A. R., Kawaji, H., Rehli, M., Baillie, J. K., de Hoon, M. J., Lassmann, T., Itoh, M., et al. (2014). A promoter-level mammalian expression atlas. Nature 507, 462-470.

Fritsch, E. F., Hacohen, N., and Wu, C. J. (2014). Personal neoantigen cancer vaccines: The momentum builds. Oncoimmunology 3, e29311.

Garimella, S. V., Gehlhaus, K., Dine, J. L., Pitt, J. J., Grandin, M., Chakka, S., Nau, M. M., Caplen, N. J., and Lipkowitz, S. (2014). Identification of novel molecular regulators of tumor necrosis factor-related apoptosis-inducing ligand (TRAIL)-induced apoptosis in breast cancer cells by RNAi screening. Breast cancer research: BCR 16, R41.

Garofalo, M., Di Leva, G., Romano, G., Nuovo, G., Suh, S. S., Ngankeu, A., Taccioli, C., Pichiorri, F., Alder, H., Secchiero, P., et al. (2009). miR-221&222 regulate TRAIL resistance and enhance tumorigenicity through PTEN and TIMP3 downregulation. Cancer cell 16, 498-509.

Gao, J., Aksoy, B. A., Dogrusoz, U., Dresdner, G., Gross, B., Sumer, S. O., Sun, Y., Jacobsen, A., Sinha, R., Larsson, E., et al. (2013). Integrative analysis of complex cancer genomics and clinical profiles using the cBioPortal. Science signaling 6, p11.

GTEx Consortium (2013a). The Genotype-Tissue Expression (GTEx) project. Nature genetics 45, 580-585.

GTEx Consortium (2013b). GTEx Portal (Broad Institute of MIT and Harvard), pp. GTEx_Analysis_RNA-seq RNA SeQCv1.1.8_gene_reads_Pilot_2013_2001_2031_patch2011.gct.

Hänzelmann, S., Castelo, R., and Guinney, J. (2013). GSVA: gene set variation analysis for microarray and RNA-Seq data. BMC bioinformatics 14, 7.

Harris, R. S., Petersen-Mahrt, S. K., and Neuberger, M. S. (2002). RNA editing enzyme APOBEC1 and some of its homologs can act as DNA mutators. Molecular cell 10, 1247-1253. Health, N.I.o. TCGA Data Portal.

Herbst, R. S., Soria, J.-C., Kowanetz, M., Fine, G. D., Hamid, O., Gordon, M. S., Sosman, J. A., McDermott, D. F., Powderly, J. D., and Gettinger, S. N. (2014). Predictive correlates of response to the anti-PD-L1 antibody MPDL3280A in cancer patients. Nature 515, 563-567.

Hinrichs, C. S., and Rosenberg, S. A. (2014). Exploiting the curative potential of adoptive T-cell therapy for cancer. Immunological reviews 257, 56-71.

Izeradjene, K., Douglas, L., Delaney, A., and Houghton, J. A. (2005). Casein kinase II (CK2) enhances death-inducing signaling complex (DISC) activity in TRAIL-induced apoptosis in human colon carcinoma cell lines. Oncogene 24, 2050-2058.

Jemal, A., Siegel, R., Ward, E., Murray, T., Xu, J., and Thun, M. J. (2007). Cancer statistics, 2007. CA: a cancer journal for clinicians 57, 43-66.

Jennewein, C., Kuhn, A. M., Schmidt, M. V., Meilladec-Jullig, V., von Knethen, A., Gonzalez, F. J., and Brune, B. (2008). Sumoylation of peroxisome proliferator-activated receptor gamma by apoptotic cells prevents lipopolysaccharide-induced NCoR removal from kappaB binding sites mediating transrepression of proinflammatory cytokines. Journal of immunology 181, 5646-5652.

Ji, R. R., Chasalow, S. D., Wang, L., Hamid, O., Schmidt, H., Cogswell, J., Alaparthy, S., Berman, D., Jure-Kunkel, M., Siemers, N. O., et al. (2012). An immune-active tumor microenvironment favors clinical response to ipilimumab. Cancer immunology, immunotherapy: CII 61, 1019-1031.

Johnson, B. J., Costelloe, E. O., Fitzpatrick, D. R., Haanen, J. B., Schumacher, T. N., Brown, L. E., and Kelso, A. (2003). Single-cell perforin and granzyme expression reveals the anatomical localization of effector CD8+ T cells in influenza virus-infected mice. Proceedings of the National Academy of Sciences of the United States of America 100, 2657-2662.

Jones, P., Binns, D., Chang, H. Y., Fraser, M., Li, W., McAnulla, C., McWilliam, H., Maslen, J., Mitchell, A., Nuka, G., et al. (2014). InterProScan 5: genome-scale protein function classification. Bioinformatics 30, 1236-1240.

Kandoth, C., McLellan, M. D., Vandin, F., Ye, K., Niu, B., Lu, C., Xie, M., Zhang, Q., McMichael, J. F., Wyczalkowski, M. A., et al. (2013). Mutational landscape and significance across 12 major cancer types. Nature 502, 333-339.

Karolchik, D., Hinrichs, A. S., Furey, T. S., Roskin, K. M., Sugnet, C. W., Haussler, D., and Kent, W. J. (2004). The UCSC Table Browser data retrieval tool. Nucleic acids research 32, D493-496.

Khong, H. T., and Restifo, N. P. (2002). Natural selection of tumor variants in the generation of "tumor escape" phenotypes. Nature immunology 3, 999-1005.

Kloor, M., Michel, S., and von Knebel Doeberitz, M. (2010). Immune evasion of microsatellite unstable colorectal cancers. International journal of cancer 127, 1001-1010.

Langmead, B., and Salzberg, S. L. (2012). Fast gapped-read alignment with Bowtie 2. Nature methods 9, 357-359.

Lawrence, M. S., Stojanov, P., Mermel, C. H., Robinson, J. T., Garraway, L. A., Golub, T. R., Meyerson, M., Gabriel, S. B., Lander, E. S., and Getz, G. (2014). Discovery and saturation analysis of cancer genes across 21 tumour types. Nature 505, 495-501.

Lawrence, M. S., Stojanov, P., Polak, P., Kryukov, G. V., Cibulskis, K., Sivachenko, A., Carter, S. L., Stewart, C., Mermel, C. H., Roberts, S. A., et al. (2013). Mutational heterogeneity in cancer and the search for new cancer-associated genes. Nature 499, 214-218.

Lemay, S., Davidson, D., Latour, S., and Veillette, A. (2000). Dok-3, a novel adapter molecule involved in the negative regulation of immunoreceptor signaling. Molecular and cellular biology 20, 2743-2754.

Li, H., Handsaker, B., Wysoker, A., Fennell, T., Ruan, J., Homer, N., Marth, G., Abecasis, G., Durbin, R., and Genome Project Data Processing, S. (2009). The Sequence Alignment/Map format and SAMtools. Bioinformatics 25, 2078-2079.

Li, M., Zhao, H., Zhang, X., Wood, L. D., Anders, R. A., Choti, M. A., Pawlik, T. M., Daniel, H. D., Kannangai, R., Offerhaus, G. J., et al. (2011). Inactivating mutations of the chromatin remodeling gene ARID2 in hepatocellular carcinoma. Nature genetics 43, 828-829.

Liggins, A. P., Cooper, C. D., Lawrie, C. H., Brown, P. J., Collins, G. P., Hatton, C. S., Pulford, K., and Banham, A. H. (2007). MORC4, a novel member of the MORC family, is highly expressed in a subset of diffuse large B-cell lymphomas. British journal of haematology 138, 479-486.

Liu, S. Y., Sanchez, D. J., Aliyari, R., Lu, S., and Cheng, G. (2012). Systematic identification of type I and type II interferon-induced antiviral factors. Proceedings of the National Academy of Sciences of the United States of America 109, 4239-4244.

Llobet, D., Eritja, N., Encinas, M., Llecha, N., Yeramian, A., Pallares, J., Sorolla, A., Gonzalez-Tallada, F. J., Matias-Guiu, X., and Dolcet, X. (2008). CK2 controls TRAIL and Fas sensitivity by regulating FLIP levels in endometrial carcinoma cells. Oncogene 27, 2513-2524.

Lund, J. M., Hsing, L., Pham, T. T., and Rudensky, A. Y. (2008). Coordination of early protective immunity to viral infection by regulatory T cells. Science 320, 1220-1224.

Manghera, M., and Douville, R. N. (2013). Endogenous retrovirus-K promoter: a landing strip for inflammatory transcription factors? Retrovirology 10, 16.

Marcais, G., and Kingsford, C. (2011). A fast, lock-free approach for efficient parallel counting of occurrences of k-mers. Bioinformatics 27, 764-770.

McCormack, M., Alfirevic, A., Bourgeois, S., Farrell, J. J., Kasperaviciute, D., Carrington, M., Sills, G. J., Marson, T., Jia, X., de Bakker, P. I., et al. (2011). HLA-A*3101 and carbamazepine-induced hypersensitivity reactions in Europeans. The New England journal of medicine 364, 1134-1143.

Mayer, J., Blomberg, J., and Seal, R. L. (2011). A revised nomenclature for transcribed human endogenous retroviral loci. Mobile DNA 2, 7.

Medema, J. P., de Jong, J., van Hall, T., Melief, C. J., and Offringa, R. (1999). Immune escape of tumors in vivo by expression of cellular FLICE-inhibitory protein. The Journal of experimental medicine 190, 1033-1038.

Mermel, C. H., Schumacher, S. E., Hill, B., Meyerson, M. L., Beroukhim, R., and Getz, G. (2011). GISTIC2.0 facilitates sensitive and confident localization of the targets of focal somatic copy-number alteration in human cancers. Genome biology 12, R41.

Missale, G., Redeker, A., Person, J., Fowler, P., Guilhot, S., Schlicht, H. J., Ferrari, C., and Chisari, F. V. (1993). HLA-A31- and HLA-Aw68-restricted cytotoxic T cell responses to a single hepatitis B virus nucleocapsid epitope during acute viral hepatitis. The Journal of experimental medicine 177, 751-762.

Morozov, V. A., Dao Thi, V. L., and Denner, J. (2013). The transmembrane protein of the human endogenous retrovirus-K (HERV-K) modulates cytokine release and gene expression. PloS one 8, e70399.

Nielsen, M., Lundegaard, C., Blicher, T., Lamberth, K., Harndahl, M., Justesen, S., Roder, G., Peters, B., Sette, A., Lund, O., et al. (2007). NetMHCpan, a method for quantitative predictions of peptide binding to any HLA-A and -B locus protein of known sequence. PloS one 2, e796.

Novershtern, N., Subramanian, A., Lawton, L. N., Mak, R. H., Haining, W. N., McConkey, M. E., Habib, N., Yosef, N., Chang, C. Y., and Shay, T. (2011). Densely interconnected transcriptional circuits control cell states in human hematopoiesis. Cell 144, 296-309.

Oshiumi, H., Sakai, K., Matsumoto, M., and Seya, T. (2010). DEAD/H BOX 3 (DDX3) helicase binds the RIG-I adaptor IPS-1 to up-regulate IFN-beta-inducing potential. European journal of immunology 40, 940-948.

Pages, F., Berger, A., Camus, M., Sanchez-Cabo, F., Costes, A., Molidor, R., Mlecnik, B., Kirilovsky, A., Nilsson, M., Damotte, D., et al. (2005). Effector memory T cells, early metastasis, and survival in colorectal cancer. The New England journal of medicine 353, 2654-2666.

Peng, Q., O'Loughlin, J. L., and Humphrey, M. B. (2012). DOK3 negatively regulates LPS responses and endotoxin tolerance. PloS one 7, e39967.

Pieters, J., Muller, P., and Jayachandran, R. (2013). On guard: coronin proteins in innate and adaptive immunity. Nature reviews Immunology 13, 510-518.

Powell, M. L., Smith, J. A., Sowa, M. E., Harper, J. W., Iftner, T., Stubenrauch, F., and Howley, P. M. (2010). NCoR1 mediates papillomavirus E8; E2C transcriptional repression. J Virol 84, 4451-4460.

Rajasagi, M., Shukla, S. A., Fritsch, E. F., Keskin, D. B., DeLuca, D., Carmona, E., Zhang, W., Sougnez, C., Cibulskis, K., Sidney, J., et al. (2014). Systematic identification of personal tumor-specific neoantigens in chronic lymphocytic leukemia. Blood 124, 453-462.

Ravi, R., and Bedi, A. (2002). Sensitization of tumor cells to Apo2 ligand/TRAIL-induced apoptosis by inhibition of casein kinase II. Cancer research 62, 4180-4185.

Rutledge, W. C., Kong, J., Gao, J., Gutman, D. A., Cooper, L. A., Appln, C., Park, Y., Scarpace, L., Mikkelsen, T., Cohen, M. L., et al. (2013). Tumor-infiltrating lymphocytes in glioblastoma are associated with specific genomic alterations and related to transcriptional class. Clinical cancer research: an official journal of the American Association for Cancer Research 19, 4951-4960.

Samuels, Y., and Ericson, K. (2006). Oncogenic PI3K and its role in cancer. Current opinion in oncology 18, 77-82.

Sato, E., Olson, S. H., Ahn, J., Bundy, B., Nishikawa, H., Qian, F., Jungbluth, A. A., Frosina, D., Gnjatic, S., Ambrosone, C., et al. (2005). Intraepithelial CD8+ tumor-infiltrating lymphocytes and a high CD8+/regulatory T cell ratio are associated with favorable prognosis in ovarian cancer. Proceedings of the National Academy of Sciences of the United States of America 102, 18538-18543.

Saturno, G., Valenti, M., De Haven Brandon, A., Thomas, G. V., Eccles, S., Clarke, P. A., and Workman, P. (2013). Combining trail with PI3 kinase or HSP90 inhibitors enhances apoptosis in colorectal cancer cells via suppression of survival signaling. Oncotarget 4, 1185-1198.

Saunders, C. T., Wong, W. S., Swamy, S., Becq, J., Murray, L. J., and Cheetham, R. K. (2012). Strelka: accurate somatic small-variant calling from sequenced tumor-normal sample pairs. Bioinformatics 28, 1811-1817.

Schmitt, K., Reichrath, J., Roesch, A., Meese, E., and Mayer, J. (2013). Transcriptional profiling of human endogenous retrovirus group HERV-K(HML-2) loci in melanoma. Genome biology and evolution 5, 307-328.

Schreiber, R. D., Old, L. J., and Smyth, M. J. (2011). Cancer immunoediting: integrating immunity's roles in cancer suppression and promotion. Science 331, 1565-1570.

Schumacher, K., Haensch, W., Roefzaad, C., and Schlag, P. M. (2001). Prognostic significance of activated CD8(+) T cell infiltrations within esophageal carcinomas. Cancer research 61, 3932-3936.

Schwitalle, Y., Kloor, M., Eiermann, S., Linnebacher, M., Kienle, P., Knaebel, H. P., Tariverdian, M., Benner, A., and von Knebel Doeberitz, M. (2008). Immune response against frameshift-induced neopeptides in HNPCC patients and healthy HNPCC mutation carriers. Gastroenterology 134, 988-997.

Sharma, P., Wagner, K., Wolchok, J. D., and Allison, J. P. (2011). Novel cancer immunotherapy agents with survival benefit: recent successes and next steps. Nature reviews Cancer 11, 805-812.

Simpson, A. J., Caballero, O. L., Jungbluth, A., Chen, Y. T., and Old, L. J. (2005). Cancer/testis antigens, gametogenesis and cancer. Nature reviews Cancer 5, 615-625.

Snyder, A., Makarov, V., Merghoub, T., Yuan, J., Zaretsky, J. M., Desrichard, A., Walsh, L. A., Postow, M. A., Wong, P., Ho, T. S., et al. (2014). Genetic basis for clinical response to CTLA-4 blockade in melanoma. The New England journal of medicine 371, 2189-2199.

Song, J. J., Kim, J. H., Sun, B. K., Alcala, M. A., Jr., Bartlett, D. L., and Lee, Y. J. (2010). c-Cbl acts as a mediator of Src-induced activation of the PI3K-Akt signal transduction pathway during TRAIL treatment. Cellular signalling 22, 377-385.

Spranger, S., Spaapen, R. M., Zha, Y., Williams, J., Meng, Y., Ha, T. T., and Gajewski, T. F. (2013). Up-regulation of PD-L1, IDO, and Tregs in the melanoma tumor microenvironment is driven by CD8+ T cells. Science translational medicine 5, 200ra116-200ra116.

Suzuki, K., Watanabe, T., Sakurai, S., Ohtake, K., Kinoshita, T., Araki, A., Fujita, T., Takei, H., Takeda, Y., Sato, Y., et al. (1999). A novel glycosylphosphatidyl inositol-anchored protein on human leukocytes: a possible role for regulation of neutrophil adherence and migration. Journal of immunology 162, 4277-4284.

Tang, K. W., Alaei-Mahabadi, B., Samuelsson, T., Lindh, M., and Larsson, E. (2013). The landscape of viral expression and host gene fusion and adaptation in human cancer. Nature communications 4, 2513.

TCGA Research Network.

Teng, M. S., Stephens, R., Pasquier, L. D., Freeman, T., Lindquist, J. A., and Trowsdale, J. (2002). A human TAPBP (TAPASIN)-related gene, TAPBP-R. European journal of immunology 32, 1059-1068.

UNC Lineberger Comprehensive Cancer Center (2013). TCGA mRNA-seq Pipeline for UNC data (CGHub).

Textor, S., Fiegler, N., Arnold, A., Porgador, A., Hofmann, T. G., and Cerwenka, A. (2011). Human NK cells are alerted to induction of p53 in cancer cells by upregulation of the NKG2D ligands ULBP1 and ULBP2. Cancer research 71, 5998-6009.

Tumeh, P. C., Harview, C. L., Yearley, J. H., Shintaku, I. P., Taylor, E. J., Robert, L., Chmielowski, B., Spasic, M., Henry, G., Ciobanu, V., et al. (2014). PD-1 blockade induces responses by inhibiting adaptive immune resistance. Nature 515, 568-571.

Uderhardt, S., Herrmann, M., Oskolkova, O. V., Aschermann, S., Bicker, W., Ipseiz, N., Sarter, K., Frey, B., Rothe, T., Voll, R., et al. (2012). 12/15-lipoxygenase orchestrates the clearance of apoptotic cells and maintains immunologic tolerance. Immunity 36, 834-846.

University of California, S. C. (2012). Cancer Genomics Hub (CGHub) (National Cancer Institute).

Uyttenhove, C., Pilotte, L., Theate, I., Stroobant, V., Colau, D., Parmentier, N., Boon, T., and Van den Eynde, B. J. (2003). Evidence for a tumoral immune resistance mechanism based on tryptophan degradation by indoleamine 2,3-dioxygenase. Nature medicine 9, 1269-1274.

Wang, G., Ahmad, K. A., and Ahmed, K. (2006). Role of protein kinase CK2 in the regulation of tumor necrosis factor-related apoptosis inducing ligand-induced apoptosis in prostate cancer cells. Cancer research 66, 2242-2249.

Yan, Z., Cui, K., Murray, D. M., Ling, C., Xue, Y., Gerstein, A., Parsons, R., Zhao, K., and Wang, W. (2005). PBAF chromatin-remodeling complex requires a novel specificity subunit, BAF200, to regulate expression of selective interferon-responsive genes. Genes & development 19, 1662-1667.

Yang, W., Tang, H., Zhang, Y., Tang, X., Zhang, J., Sun, L., Yang, J., Cui, Y., Zhang, L., Hirankarn, N., et al. (2013). Meta-analysis followed by replication identifies loci in or near CDKN1B, TET3, CD80, DRAM1, and ARID5B as associated with systemic lupus erythematosus in Asians. American journal of human genetics 92, 41-51.

Yoshihara, K., Shahmoradgoli, M., Martinez, E., Vegesna, R., Kim, H., Tones-Garcia, W., Treviño, V., Shen, H., Laird, P. W., and Levine, D. A. (2013). Inferring tumour purity and stromal and immune cell admixture from expression data. Nature communications 4.

Yoshitake, H., Takeda, Y., Nitto, T., and Sendo, F. (2002). Cross-linking of GPI-80, a possible regulatory molecule of cell adhesion, induces up-regulation of CD11b/CD18 expression on neutrophil surfaces and shedding of L-selectin. Journal of leukocyte biology 71, 205-211.

Young, G. R., Eksmond, U., Salcedo, R., Alexopoulou, L., Stoye, J. P., and Kassiotis, G. (2012). Resurrection of endogenous retroviruses in antibody-deficient mice. Nature 491, 774-778.

Yu, P., Lubben, W., Slomka, H., Gebler, J., Konert, M., Cai, C., Neubrandt, L., Prazeres da Costa, O., Paul, S., Dehnert, S., et al. (2012). Nucleic acid-sensing Toll-like receptors are essential for the control of endogenous retrovirus viremia and ERV-induced tumors. Immunity 37, 867-879.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of treating cancer in a patient in need thereof, comprising
(a) selecting a patient suffering from cancer for immunotherapy by detecting cytolytic activity in tumor tissue from the patient, wherein detecting cytolytic activity comprises measuring cytolytic activity in tumor tissue from the patient by assaying the expression of granzyme A (GZMA) and perforin (PRF1), wherein the measuring comprises sequencing RNA expressed in the tumor tissue, and comprises (i) calculating the log-average of the transcript levels of granzyme A (GZMA) and perforin (PRF1), and (ii) assigning a cytolytic activity (CYT) score to the tumor based on the log average calculated in (i); and
(b) administering to the patient an agent that stimulates the patient's preexisting immune response if the cytolytic activity detected in the tumor is at least two-fold greater than the median value observed among patients diagnosed with the same histological cancer type.

2. The method according to claim 1, further comprising:
(a) detecting a genetic alteration in the tumor, wherein the genetic alteration is a mutation in a gene selected from the group consisting of CASP8, B2M, PIK3CA, SMC1A, ARID5B, TET2, ALPK2, COL5A1, TP53, DNER, NCOR1, MORC4, CIC, IRF6, MYOCD, ANKLE1, CNKSR1, NF1, SOS1, ARID2, CUL4B, DDX3X, FUBP1, TCP11L2, HLA-A, B or C, CSNK2A1, MET, ASXL1, PD-L1, PD-L2, IDO1, IDO2, ALOX12B and ALOX15B, or copy number gain, excluding whole-chromosome events, impacting any of the following chromosomal bands: 6q16.1-q21, 6q22.31-q24.1, 6q25.1-q26, 7p11.2-q11.1, 8p23.1, 8p11.23-p11.21, 9p24.2-p23, 10p15.3, 10p15.1-p13, 11p14.1, 12p13.32-p13.2, 17p13.1 and 22q11.1-q11.21; and
(b) administering an agent that stimulates the patient's preexisting immune response if a genetic alteration associated with induction of cytolytic activity, tumor resistance to cytolytic activity and/or suppression of cytolytic activity is detected in the tumor.

3. The method according to claim 2, wherein the detecting further comprises (a) measuring expression levels of granzyme A (GZMA) and perforin (PRF1) in a sample from the tumor, and (b) assigning a cytolytic activity (CYT) score to the tumor based on the expression levels obtained in (a).

4. The method according to claim 2, wherein the genetic alteration is detected by sequencing.

5. The method according to claim 1, wherein the tumor is head and neck cancer, colon cancer, stomach cancer, lung adenocarcinoma, lung squamous cell carcinoma, uterine cancer, glioma, cervical cancer, breast cancer, bladder cancer or colorectal cancer.

6. The method according to claim 2, wherein
(a) the genetic alteration is a mutation in CASP8, and wherein the tumor is selected from the group consisting of head and neck cancer, colorectal cancer, lung squamous cell carcinoma and uterine cancer;
(b) the genetic alteration is a mutation in PIK3CA, and wherein the tumor is stomach cancer;
(c) the genetic alteration is a mutation in B2M, and wherein the tumor is uterine cancer, breast cancer, colorectal cancer or stomach cancer;
(d) the genetic alteration is a mutation in HLA-A, B or C, and wherein the tumor is colorectal cancer, head and neck cancer, uterine cancer, stomach cancer or cervical cancer; or
(e) the genetic alteration is a mutation in CNKSR1, MET or CSNK2A1.

7. The method according to claim 2, wherein the genetic alteration is the copy number gain, excluding whole-chromosome events, of any of the following chromosomal bands: 6q16.1-q21, 6q22.31-q24.1, 6q25.1-q26, 7p11.2-q11.1, 8p23.1, 8p11.23-p11.21, 9p24.2-p23 (containing PDL1, PDL2), 10p15.3, 10p15.1-p13, 11p14.1, 12p13.32-p13.2, 17p13.1, and 22q11.1-q11.21,
(a) wherein the genetic alteration is an amplification of a gene selected from PD-L1 and PD-L2, and wherein the tumor is lung squamous cell carcinoma, head and neck cancer, cervical or colorectal cancer; or
(b) wherein the genetic alteration is an amplification of a gene selected from IDO1, IDO2, ALOX12B and ALOX15B, and wherein the tumor is breast cancer or ovarian cancer.

8. The method according to claim 2, wherein the genetic alteration associated with cytolytic activity comprises a plurality of neoantigen mutations,
wherein at least 2, 3, 4, 5, 6, 7, 8, 9, 10, 15 or 20 neoantigen mutations are present in the tumor; and/or
wherein the tumor is selected from the group consisting of uterine cancer, breast cancer, stomach cancer, cervical cancer, colorectal cancer and lung adenocarcinoma.

9. The method according to claim 2, wherein induction of cytolytic activity in the tumor is associated with virus infection,
(i) wherein the virus is HPV, and wherein the tumor is cervical cancer, head and neck cancer, bladder cancer, kidney clear cell cancer, colorectal cancer, glioma, lung squamous cell cancer or uterine cancer; or
(ii) wherein the virus is EBV, and wherein the tumor is stomach cancer.

10. The method according to claim 1, wherein cytolytic activity in the tumor is associated with expression of one or more endogenous retrovirus genes.

11. The method according to claim 1, wherein the agent comprises a checkpoint inhibitor,
(a) wherein the checkpoint inhibitor is an inhibitor of the programmed death-1 (PD-1) pathway,
wherein the inhibitor of the PD-1 pathway is an anti-PD1 antibody, and wherein the inhibitor of the PD-1 pathway is nivolumab; or
(b) wherein the checkpoint inhibitor is an anti-cytotoxic T-lymphocyte-associated antigen 4 (CTLA4) antibody, and
wherein the anti-CTLA4 antibody is ipilimumab or tremelimumab.

12. The method according to claim 2, wherein the genetic alteration is a viral infection of tumor cells,
(a) wherein the virus is one of HPV, EBV, HCV, or HBV; or
(b) wherein viral infection status is detected by quantitative DNA or RNA sequencing of tumor and peripheral blood, where the tumor titer is non-zero and exceeds that observed in the non-tumor peripheral blood of the patient by at least five fold.

* * * * *